(12) United States Patent
Kettle et al.

(10) Patent No.: US 10,597,405 B2
(45) Date of Patent: Mar. 24, 2020

(54) CHEMICAL COMPOUNDS

(71) Applicant: ASTRAZENECA AB, Södertälje (SE)

(72) Inventors: Jason Grant Kettle, Cambridge (GB); Sharanjeet Bagal, Cambridge (GB); Graeme Richard Robb, Cambridge (GB); James Michael Smith, Cambridge (GB); Frederick Woolf Goldberg, Cambridge (GB); Doyle Joseph Cassar, Cambridge (GB); James Lyman Feron, Cambridge (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 16/212,063

(22) Filed: Dec. 6, 2018

(65) Prior Publication Data

US 2019/0177338 A1    Jun. 13, 2019

Related U.S. Application Data

(60) Provisional application No. 62/678,418, filed on May 31, 2018, provisional application No. 62/596,331, filed on Dec. 8, 2017.

(51) Int. Cl.
| | | |
|---|---|---|
| *C07D 498/14* | (2006.01) | |
| *C07D 471/22* | (2006.01) | |
| *C07D 471/14* | (2006.01) | |
| *A61P 35/00* | (2006.01) | |

(52) U.S. Cl.
CPC ............ *C07D 498/14* (2013.01); *A61P 35/00* (2018.01); *C07D 471/14* (2013.01); *C07D 471/22* (2013.01)

(58) Field of Classification Search
CPC ..... A61P 35/00; C07D 471/14; C07D 471/22; C07D 498/14
See application file for complete search history.

(56) References Cited

FOREIGN PATENT DOCUMENTS

| WO | 2015/054572 A1 | 4/2015 |
|---|---|---|
| WO | 2016/049524 A1 | 3/2016 |
| WO | 2016/168540 A1 | 10/2016 |
| WO | 2017/015562 A1 | 1/2017 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/087528 A1 | 5/2017 |
| WO | 2017/201161 A1 | 11/2017 |

OTHER PUBLICATIONS

Janes, et al., Cell 2018, 172, 578-89.
Zeng, et al., Cell Chemical Biology 2017, 24, 1005-16.
Ostrem, et al., Nature Reviews Drug Discovery 2016, 15, 771-785.
Fell, et al., ACS Med. Chem. Lett. 2018, 9, 1230-1234.
International Search Report for PCT/EP2018/083853 dated Feb. 5, 2019.
Written Opinion for PCT/EP2018/083853 dated Feb. 5, 2019.

*Primary Examiner* — Erich A Leeser

(57) ABSTRACT

The specification relates to compounds of Formula (I)

and pharmaceutically acceptable salts thereof. The specification also relates to processes and intermediates used for their preparation, pharmaceutical compositions containing them and their use in the treatment of cell proliferative disorders.

18 Claims, No Drawings

CHEMICAL COMPOUNDS

BACKGROUND

The KRAS, NRAS and HRAS genes encode a set of closely related small GTPase proteins KRas, NRas and HRas, collectively referred to herein as the Ras proteins or Ras, that share 82-90% overall sequence identity. The Ras proteins are critical components of signalling pathways transmitting signals from cell-surface receptors to regulate cellular proliferation, survival and differentiation. Ras functions as a molecular switch cycling between an inactive GDP-bound state and an active GTP-bound state. The GDP/GTP cycle of Ras is tightly regulated in cells by guanine nucleotide exchange factors (GEFs) such as Sos1 and Sos2, which promote the exchange of GDP for GTP, and GTPase activating proteins (GAPs) such as NF-1 and p120RasGAP which stimulate the intrinsic GTPase activity of Ras hydrolysing GTP to GDP.

The Ras proteins are 188-189 amino acids in length and have a highly conserved N-terminal G-domain containing the p-loop region, which binds nucleotide, and the switch I and switch II regions which are important for regulatory and effector protein interactions. The C-terminal region of the Ras proteins are more divergent and contain elements which regulate the association of Ras with the membrane including the conserved carboxyl terminal CAXX box motif which is necessary for post-translational prenylation modifications. On binding to GTP the switch I and switch II regions of Ras undergo a conformational change which enables its interaction and activation of effector proteins to regulate down-stream signalling pathways. The best characterised effector of Ras is the serine/threonine kinase Raf which regulates the activity of the mitogen-activate protein kinase (MAPK) pathway. The PI3K pathway is another important effector pathway down-stream of Ras with the p110 catalytic subunit of the class I phosphoinositide 3-kinases interacting with Ras. Other effectors of Ras including RalGDS, Tiam1, PLC-ε and Rassf1 have been have also been described (Cox, et al. *Nature Reviews Drug Discovery*, 2014, 13:828-851).

RAS mutations are frequently found in cancer and approximately 30% of all human cancers have a mutation in KRAS, NRAS or HRAS genes. Oncogenic Ras is typically, but not exclusively, associated with mutations at glycine 12, glycine 13 or glutamine 61 of Ras. These residues are located at the active site of Ras and mutations impair intrinsic and/or GAP-catalysed GTPase activity favouring the formation of GTP bound Ras and aberrant activation of down-stream effector pathways. KRAS is the most frequently mutated RAS gene in cancer followed by NRAS and then HRAS. There are several tumour types that exhibit a high frequency of activating mutations in KRAS including pancreatic (~90% prevalence), colorectal (~40% prevalence) and non-small cell lung cancer (~30% prevalence). KRAS mutations are also found in other cancer types including multiple myeloma, uterine cancer, bile duct cancer, stomach cancer, bladder cancer, diffuse large B cell lymphoma, rhabdomyosarcoma, cutaneous squamous cell carcinoma, cervical cancer, testicular germ cell cancer and others.

Glycine to cysteine mutations at residue 12 of Ras (the G12C mutation) is generated from a G.C to T.A base transversion at codon 12, a mutation commonly found in RAS genes that accounts for 14% of all KRAS, 2% of all NRAS and 2% of all HRAS mutations across cancer types. The G12C mutation is particularly enriched in KRAS mutant non-small cell lung cancer with approximately half carrying this mutation, which has been associated with the DNA adducts formed by tobacco smoke. The G12C mutation is not exclusively associated with lung cancer and is found in other RAS mutant cancer types including 8% of all KRAS mutant colorectal cancer.

To date there have been no inhibitors of G12C mutant Ras proteins which have been approved for therapeutic use. Hence there is a need for new inhibitors of G12C mutant Ras proteins that possess the required pharmaceutical properties to be suitable for clinical use. The compounds of the specification have been found to possess anti-tumour activity, being useful in inhibiting the uncontrolled cellular proliferation which arises from malignant disease. The compounds of the specification provide an anti-tumour effect by, as a minimum, acting as inhibitors of G12C mutant Ras proteins.

BRIEF SUMMARY

The specification relates to certain tetracyclic heteroaryl compounds and pharmaceutically acceptable salts thereof that inhibit G12C mutant RAS proteins and consequently exhibit anti-cancer activity. The specification also relates to use of said tetracyclic heteroaryl compounds and pharmaceutically acceptable salts thereof in methods of treatment of the human or animal body, for example in prevention or treatment of cancer. The specification also relates to processes and intermediate compounds involved in the preparation of said tetracyclic heteroaryl compounds and to pharmaceutical compositions containing them.

According to a first aspect of the specification there is provided a compound of the Formula (I):

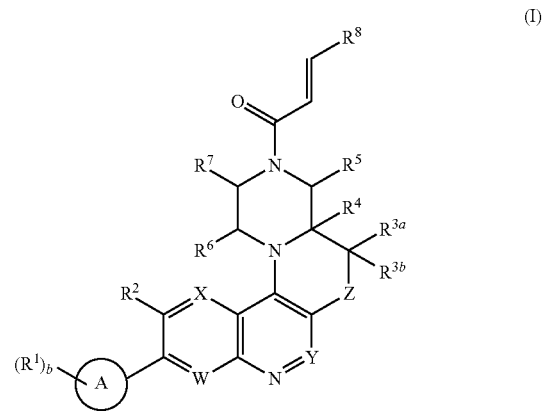

wherein:
A is selected from $C_6$-$C_{10}$ aryl, monocyclic heteroaryl and bicyclic heteroaryl;
$R^1$ is in each instance independently selected from F, Cl, Br, OH, CN, $C_1$-$C_4$ alkyl, $C_1$-$C_4$ alkoxy, $C_1$-$C_3$ fluoroalkyl, $C_1$-$C_3$ fluoroalkoxy, acetylenyl, $NR^9R^{10}$, $C(O)NR^{11}R^{12}$, $CH_2R^{13}$ and $N=S(O)Me_2$;
b is 0, 1, 2 or 3;
W is $CR^{14}$ or N;
X is $CR^{15}$ or N;
Y is CH or N;
Z is O or $NR^{16}$;
$R^2$ is H, CN, F, Cl, Br, $C_1$-$C_4$ alkyl, $C_1$-$C_4$ alkoxy, $C_1$-$C_3$ fluoroalkyl, $C_1$-$C_2$ fluoroalkoxy or acetylenyl;
$R^{3a}$ and $R^{3b}$ are each independently selected from H or Me or, in the case where Z is $NR^{16}$, can also together be =O;

$R^4$, $R^5$, $R^6$ and $R^7$ are each independently selected from H or Me;

$R^8$ is H or $CH_2NMe_2$;

$R^9$ is H, $C_1$-$C_4$ alkyl, $C(O)C_1$-$C_3$ alkyl or $CO_2C_1$-$C_3$ alkyl;

$R^{10}$, $R^{11}$ and $R^{12}$ are each independently selected from H and $C_1$-$C_4$ alkyl; or $R^9$ and $R^{10}$ together, or $R^{11}$ and $R^{12}$ together, form a 4-, 5-, 6- or 7-membered saturated heterocycle optionally incorporating O, NH or N($C_1$-$C_4$ alkyl) group;

$R^{13}$ is OH, CN, $NR^{17}R^{18}$, $C(O)NR^{19}R^{20}$ or $SO_2C_1$-$C_3$alkyl;

$R^{14}$ and $R^{15}$ are each independently selected from H, F, Cl, MeO and Me;

$R^{16}$ is H, $C_1$-$C_3$ fluoroalkyl or $CH_2R^{21}$;

$R^{17}$, $R^{18}$, $R^{19}$ and $R^{20}$ are each independently selected from H and $C_1$-$C_4$ alkyl or $R^{17}$ and $R^{18}$ together, or $R^{19}$ and $R^{20}$ together, form a 4-, 5-, 6- or 7-membered saturated heterocycle optionally incorporating O, NH or N($C_1$-$C_4$ alkyl) group;

$R^{21}$ is selected from the group consisting of:

H;

$C_1$-$C_3$ alkyl optionally substituted with 1 or 2 substituents selected from hydroxy, $C_1$-$C_3$ alkoxy, halo, $NR^{22}R^{23}$, $C(O)NR^{24}R^{25}$, $SO_2Me$, heteroaryl, $C_{3-7}$cycloalkyl or heterocyclyl, wherein said heteroaryl or $C_3$-$C_7$cycloalkyl is optionally further substituted with $C_1$-$C_4$ alkyl, hydroxy, halo, cyano, or $C_1$-$C_4$ alkoxy and said heterocyclyl is optionally further substituted with $C_1$-$C_4$ alkyl, hydroxy, halo, C(O)Me, $C_1$-$C_3$ alkoxy, $C_1$-$C_3$fluoroalkyl, $C_3$-$C_7$cycloalkyl, heterocyclyl or heteroaryl and wherein $R^{22}$, $R^{23}$, $R^{24}$ and $R^{25}$ are in each instance independently selected from H and $C_1$-$C_4$ alkyl;

$C_3$-$C_7$cycloalkyl optionally substituted with $C_1$-$C_4$ alkyl, hydroxy or halo;

heterocyclyl optionally substituted with $C_1$-$C_4$ alkyl, hydroxy, halo, C(O)Me, $C_1$-$C_3$ alkoxy, $C_1$-$C_3$ fluoroalkyl, $C_3$-$C_7$ cycloalkyl, $CH_2$cyclopropyl, heterocyclyl or heteroaryl; and heteroaryl optionally substituted with $C_1$-$C_4$ alkyl, hydroxy, halo, cyano or $C_1$-$C_4$ alkoxy;

or a pharmaceutically acceptable salt thereof.

In a further aspect there is provided a pharmaceutical composition comprising a compound of Formula (I), or a pharmaceutical acceptable salt thereof.

In a further aspect there is provided a method of treating cancer by administering to a subject suffering from cancer an effective amount of a compound of Formula (I), or a pharmaceutical acceptable salt thereof.

In a further aspect there is provided a compound of Formula (I), or a pharmaceutical acceptable salt thereof, for use in the treatment of cancer.

In a further aspect there is provided a compound of Formula (I), or a pharmaceutical acceptable salt thereof, for use in the manufacture of a medicament, for example a medicament for the treatment of cancer.

In a further aspect there is provided a kit comprising a pharmaceutical composition comprising a compound of Formula (I), or a pharmaceutical acceptable salt thereof, and instructions for its use in the treatment of cancer.

In a further aspect there is provided a method for the manufacture of a compound of Formula (I).

DETAILED DESCRIPTION

It has been found that the compounds of the present specification possess potent anti-tumour activity that, it is believed, derives from inhibition of the G12C mutant Ras proteins that are key mediators of proliferation and survival in certain tumour cells.

It is believed that the compounds of the present specification interact with, and then covalently bind to, G12C mutant Ras through the acrylamide motif located on the upper piperazine ring of Formula (I). In binding to G12C mutant Ras, the compounds of the specification (as described herein) impair or substantially eliminate the ability of the G12C Ras proteins to access their active, pro-proliferative/pro-survival confirmation.

The compounds of the present specification feature a 6-membered ring linking C-3 of the quinoline ring (and the corresponding position of ring systems in which one or more of the groups W, X and Y is N, e.g. cinnoline (Y=N), 1,5-naphthyridine (X=N), 1,8-naphthyridine (W=N), pyrido[2,3-b]pyrazine (W and X is N) and pyrazino[2,3-c]pyridazine (Y=N and W or X is N)) and the piperazine ring to which the acrylamide group is attached. Advantageously, tethering the quinoline ring, or related rings in which W, X and/or Y is N, to the piperazine ring via a tether from C-3 substantially locks the relative orientation of these two motifs and prevents free rotation of the piperazine group. Tethering through C-3 has been found to deliver compounds with Ras G12C inhibitory activity higher than that observed for compounds lacking this tether. In the untethered series, the piperazine motif to which the acrylamide is attached has a high degree of rotational freedom relative to the corresponding piperazine in the compounds of the specification.

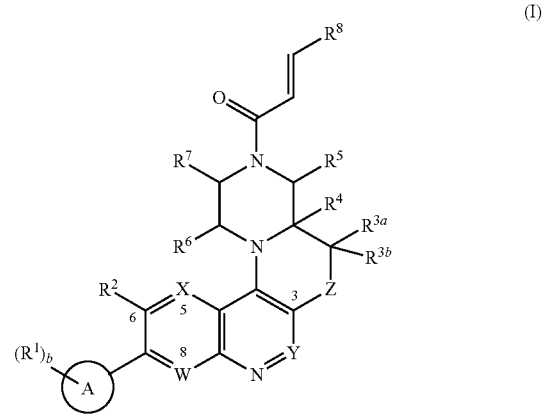

(I)

Furthermore, use of a $ZCR^{3a}R^{3b}$ tether, in which Z is O or $NR^{16}$, to form a 6-membered ring tethering the quinoline (or related ring systems) to the upper piperazine group (i.e. the piperazine to which the Michael acceptor is attached) has been found to deliver compounds that are more active than related compounds with a longer, more flexible, 7-membered tether (e.g. compounds featuring a 1,3-oxazepane between the quinoline and the piperazine). It is believed that the difference in activity between the compounds with 6- and 7-membered tethers derives from the difference in the piperazine orientation and, additionally, the increased conformational freedom of the tether and the piperazine to which the acrylamide is attached. A 6-membered tether is thus preferred as it advantageously provides greater activity against the proliferation of RasG12C mutant cells.

In addition to higher Ras G12C inhibitory activity, incorporation of a C-3 tether has advantageously been found to afford compounds with increased stability in whole blood and reduced hepatic clearance. This is significant as in the in vivo context the amount of compound available to express the desired pharmacological effect as a Ras G12C inhibitor for a given dose at the target will be increased. The improved pharmacokinetics of compounds of the specification is expected to deliver a desired therapeutic effect, e.g. an anti-tumour effect, at a lower dose level than would be possible for related non-tethered molecules. Furthermore, the increased stability of compounds of the specification in in vivo rodent models advantageously allows comparison of the anti-tumour potential of the compounds according to the specification in such models, thus facilitating development of compounds for human application. Incorporation of a methyl substituent on the piperazine ring (i.e. compounds of Formula (I) in which at least one of $R^4$ to $R^7$ is methyl) has also been found to deliver compounds with excellent pharmacokinetic properties and anti-proliferative activity against RasG12C mutant cells. In particular, compounds in which $R^7$ is methyl have been observed to be more potent RASG12C inhibitors as well as having improved transcellular permeation rates.

Accordingly, the compounds of the present specification may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of G12C mutant Ras and that are involved in the cell-signalling leading to the proliferation and survival of tumour cells.

Accordingly, there is also provided a method for providing a selective inhibitory effect on G12C mutant Ras, for example in the treatment of tumours expressing RasG12C mutant Ras, which comprises administering an effective amount of a compound of the Formula (I), or a pharmaceutically acceptable salt thereof, as defined herein, to a patient in need thereof.

Described herein are compounds that can bind to G12C mutant Ras. In biochemical and cell based assays the compounds of the present specification are shown to be potent G12C mutant Ras protein binders and may therefore be useful in the treatment of disorders mediated by KRas, NRas or HRas G12C mutations, in particular in the treatment of cancers expressing G12C mutated KRas, NRas or HRas proteins, such as pancreatic, colorectal, uterine, bile duct, stomach, bladder, cervical, testicular germ cell and non-small cell lung cancer and multiple myeloma, diffuse large B cell lymphoma, rhabdomyosarcoma and cutaneous squamous cell carcinoma.

The present specification also relates to processes for the manufacture of said compounds, to pharmaceutical compositions containing them, to methods of treatment comprising administering the said compounds to patients, for example humans, in need thereof, to use of compounds of formula (I) for the manufacture of medicaments, for example for use in the treatment of a patient suffering from a hyperproliferative disease such as cancer.

Unless defined otherwise, all technical and scientific terms used herein have the same meaning as commonly understood by one of ordinary skill in the art to which this disclosure is related. For example, the *Concise Dictionary of Biomedicine and Molecular Biology*, Juo, Pei-Show, 2nd ed., 2002, CRC Press; *The Dictionary of Cell and Molecular Biology*, 3rd ed., 1999, Academic Press; and the *Oxford Dictionary of Biochemistry and Molecular Biology*, Revised, 2000, Oxford University Press, provide one of skill with a general dictionary of many of the terms used in this disclosure.

So that the present specification may be more readily understood, certain terms are explicitly defined below. In addition, definitions are set forth as appropriate throughout the detailed description.

Units, prefixes, and symbols are denoted in their Système International de Unites (SI) accepted form. Numeric ranges are inclusive of the numbers defining the range.

The term "pharmaceutical composition" refers to a preparation which is in such form as to permit the biological activity of the active ingredient, and which contains no additional components which are unacceptably toxic to a subject to which the composition would be administered. Such compositions can be sterile. A pharmaceutical composition according to the present specification will comprise a compound of Formula (I) and at least one pharmaceutically acceptable excipient.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein the term "alkyl" refers to both straight and branched chain saturated hydrocarbon radicals having the specified number of carbon atoms. The term acetylenyl refers to an ethenyl radical i.e. a —CCH group.

In this specification the prefix $C_x$-$C_y$, as used in terms such as $C_x$-$C_y$ alkyl and the like where x and y are integers, indicates the numerical range of carbon atoms that are present in the group. For example, $C_1$-$C_4$ alkyl includes methyl, ethyl, n-propyl, i-propyl, n-butyl, s-butyl, i-butyl and t-butyl.

Examples of suitable $C_1$-$C_3$ alkyl groups include methyl, ethyl, n-propyl, and i-propyl. Examples of suitable $C_1$-$C_4$ alkoxy groups include methoxy, ethoxy, n-propoxy, i-propoxy, n-butoxy, sec-butoxy and t-butoxy. Examples of suitable $C_1$-$C_3$ alkoxy groups include methoxy, ethoxy, n-propoxy and i-propoxy.

Examples of suitable $C_1$-$C_3$ fluoroalkyl groups include fluoromethyl, difluoromethyl, trifluoromethyl and 2,2,2-trifluoroethyl. Examples of suitable $C_1$-$C_3$ fluoroalkoxy groups include fluoromethoxy, difluoromethoxy, trifluoromethoxy and 2,2,2-trifluoroethoxy.

Unless specifically stated, the bonding of an atom or group may be any suitable atom of that group; for example, propyl includes prop-1-yl and prop-2-yl.

Unless otherwise stated, halo is selected from Cl, F, Br and I.

Cycloalkyl is a non-aromatic carbocyclic ring. The carbocyclic ring may be saturated or unsaturated, and may be bridged or unbridged. $C_3$-$C_7$ cycloalkyl is any such carbocyclic ring containing 3 to 7 carbon atoms. An example of $C_3$-$C_7$ cycloalkyl is an unsaturated non-aromatic carbocyclic ring containing from 3 to 7 carbon atoms. Examples of suitable cycloalkyl groups are cyclopropyl, cyclobutyl, cyclopentyl, cyclohexyl, cycloheptyl and bicyclopentyl, such as cyclopropyl and cyclobutyl.

Heterocyclyl is a 3- to 9-membered non-aromatic, mono- or bi-cyclic ring comprising one or two heteroatoms independently selected from nitrogen, oxygen or sulphur; or an N-oxide thereof, or an S-oxide or S-dioxide thereof. The ring may be bridged or unbridged. An example of a heterocyclic ring is an unsaturated 4- to 7-membered non-aromatic, monocyclic ring comprising one or two heteroatoms independently selected from nitrogen or oxygen; or an N-oxide thereof. Examples of suitable heterocyclyl groups include oxiranyl, aziridinyl, azetidinyl, oxetanyl, tetrahydrofuranyl, pyrrolidinyl, tetrahydropyranyl, piperidinyl, morpholinyl, thiomorpholinyl, and piperazinyl, such as azetidinyl, oxetanyl, pyrrolidinyl, tetrahydropyranyl, piperidinyl or morpholinyl, for example piperidinyl or morpholinyl. For the avoidance of doubt, substituents on the heterocyclyl ring may be linked via either a carbon atom or a heteroatom (i.e. attached to a ring carbon or heteroatom as permitted by valence).

Heteroaryl is a 5-, 6-, 9- or 10-membered aromatic group comprising one ring or two fused rings and containing 1, 2, 3 or 4 N atoms, or one O atom, or one S atom, or 1 N atom and one S atom, or 1 N atom and one O atom, or 2 N atoms and one S atom, or 2 N atoms and one O atom. Examples of suitable heteroaryl groups include thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrimidinyl, pyridazinyl, pyrazinyl, indolyl, benzofuranyl, benzothienyl, benzoxazolyl, benzimidazolyl, benzotriazolyl, indazolyl, azaindolyl, azaindazolyl, quinolinyl, isoquinolinyl, quinoxalinyl, pyrrolo[1,2-b]pyridazinyl and pyrrolo[2,3-b]pyridinyl.

Monocyclic heteroaryl is an aromatic group comprising one ring and containing 1, 2, 3 or 4 N atoms, or one O atom, or one S atom, or 1 N atom and one S atom, or 1 N atom and one O atom, or 2 N atoms and one S atom, or 2 N atoms and one O atom. Examples of suitable monocyclic heteroaryl groups include thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrimidinyl, pyridazinyl and pyrazinyl.

Bicyclic heteroaryl is an aromatic group comprising two fused rings and containing 1, 2, 3 or 4 N atoms, or one O atom, or one S atom, or 1 N atom and one S atom, or 1 N atom and one O atom, or 2 N atoms and one S atom, or 2 N atoms and one O atom. Bicyclic heteroaryl groups include those groups where both fused rings are aromatic, or where one fused ring is aromatic and the other fused ring is partially or fully saturated. The said partially or fully saturated fused ring may also comprise a carbonyl group. Examples of suitable bicyclic heteroaryl groups include indolyl, benzofuranyl, benzothienyl, benzoxazolyl, benzimidazolyl, benzotriazolyl, indazolyl, azaindolyl, azaindazolyl, pyrrolo[1,2-b]pyridazinyl and pyrrolo[2,3-b]pyridinyl, quinolinyl, isoquinolinyl, quinazolinyl, cinnolinyl, phthalazinyl, quinoxalinyl and naphthyridinyl.

For the ring A, the term $C_6$-$C_{10}$ aryl, as used herein refers to a phenyl or naphthyl group. The term monocyclic heteroaryl refers to a 5- or 6-membered aromatic ring system containing at least one heteroatom selected from O or N and includes 6-membered rings in which an aromatic tautomer exists, as, for example, is the case for the 1H-pyridin-2-one system. The term bicyclic heteroaryl as used herein refers to bicyclic group with at least one aromatic ring fused to a second ring to form a 6,5- or a 6,6-ring system, wherein at least one of the rings in the bicyclic system contains at least one heteroatom selected from O or N.

For the avoidance of doubt, where multiple substituents are independently selected from a given group, the selected substituents may comprise the same substituents or different substituents from within the given group. By way of example only, where ring A is aryl substituted with $(R^1)_b$, and where b is 2, the two $R^1$ substituents could be the same, for instance both fluoro, or could be different, for instance one fluoro and one hydroxy.

For the further avoidance of doubt, the use of "⁓" in formulas of this specification denotes the point of attachment between different groups.

Where any embodiment within this specification includes a group which is said to be "optionally substituted", then a further embodiment will include that embodiment wherein the said group is unsubstituted.

As noted above, the specification provides a compound of the Formula (I):

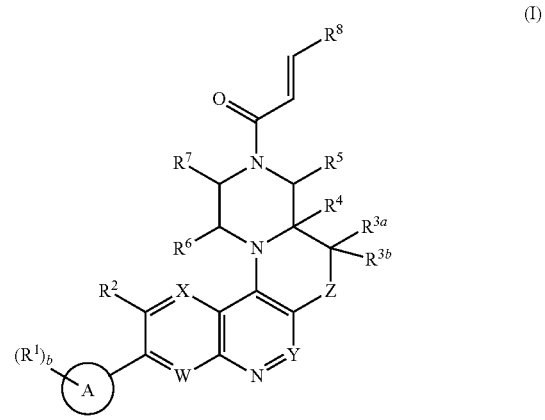

(I)

wherein:
A is selected from $C_6$-$C_{10}$ aryl, monocyclic heteroaryl and bicyclic heteroaryl;
$R^1$ is in each instance independently selected from F, Cl, Br, OH, CN, $C_1$-$C_4$ alkyl, $C_1$-$C_4$ alkoxy, $C_1$-$C_3$ fluoroalkyl, $C_1$-$C_3$ fluoroalkoxy, acetylenyl, $NR^9R^{10}$, $C(O)NR^{11}R^{12}$, $CH_2R^{13}$ and $N{=}S(O)Me_2$;
b is 0, 1, 2 or 3;
W is $CR^{14}$ or N;
X is $CR^{15}$ or N;
Y is CH or N;
Z is O or $NR^{16}$;
$R^2$ is H, CN, F, Cl, Br, $C_1$-$C_4$ alkyl, $C_1$-$C_4$ alkoxy, $C_1$-$C_3$ fluoroalkyl, $C_1$-$C_2$ fluoroalkoxy or acetylenyl;
$R^{3a}$ and $R^{3b}$ are each independently selected from H or Me or, in the case where Z is $NR^{16}$, can also together be =O;
$R^4$, $R^5$, $R^6$ and $R^7$ are each independently selected from H or Me;
$R^8$ is H or $CH_2NMe_2$;
$R^9$ is H, $C_1$-$C_4$ alkyl, $C(O)C_1$-$C_3$ alkyl or $CO_2C_1$-$C_3$ alkyl;
$R^{10}$, $R^{11}$ and $R^{12}$ are each independently selected from H and $C_1$-$C_4$ alkyl; or R⁹ and R¹⁰ together, or R¹¹ and R¹² together, form a 4-, 5-, 6- or 7-membered saturated heterocycle optionally incorporating O, NH or N($C_1$-$C_4$ alkyl) group;
R¹³ is OH, CN, NR¹⁷R¹⁸, C(O)NR¹⁹R²⁰ or $SO_2C_1$-$C_3$alkyl;
R¹⁴ and R¹⁵ are each independently selected from H, F, Cl, MeO and Me;
R¹⁶ is H, $C_1$-$C_3$ fluoroalkyl or $CH_2R^{21}$;
R¹⁷, R¹⁸, R¹⁹ and R²⁰ are each independently selected from H and $C_1$-$C_4$ alkyl or R¹⁷ and R¹⁸ together, or R¹⁹ and R²⁰ together, form a 4-, 5-, 6- or 7-membered saturated heterocycle optionally incorporating O, NH or N($C_1$-$C_4$ alkyl) group;
R²¹ is selected from the group consisting of:
H;
$C_1$-$C_3$ alkyl optionally substituted with 1 or 2 substituents selected from hydroxy, $C_1$-$C_3$ alkoxy, halo, NR²²R²³, C(O)NR²⁴R²⁵, $SO_2Me$, heteroaryl, $C_3$-$C_7$cycloalkyl or heterocyclyl, wherein said heteroaryl or $C_3$-$C_7$cycloalkyl is optionally further substituted with $C_1$-$C_4$ alkyl, hydroxy, halo, cyano, or $C_1$-$C_4$ alkoxy and said heterocyclyl is optionally further substituted with $C_1$-$C_4$ alkyl, hydroxy, halo, C(O)Me, $C_1$-$C_3$ alkoxy, $C_1$-$C_3$ fluoroalkyl, $C_3$-$C_7$cycloalkyl, heterocyclyl or heteroaryl and wherein R²², R²³, R²⁴ and R²⁵ are in each instance independently selected from H and $C_1$-$C_4$ alkyl;
$C_3$-$C_7$ cycloalkyl optionally substituted with $C_1$-$C_4$ alkyl, hydroxy or halo;
heterocyclyl optionally substituted with $C_1$-$C_4$ alkyl, hydroxy, halo, C(O)Me, $C_1$-$C_3$ alkoxy, $C_1$-$C_3$ fluoroalkyl, $C_3$-$C_7$ cycloalkyl, $CH_2$cyclopropyl, heterocyclyl or heteroaryl; and
heteroaryl optionally substituted with $C_1$-$C_4$ alkyl, hydroxy, halo, cyano or $C_1$-$C_4$ alkoxy;
or a pharmaceutically acceptable salt thereof.

In one embodiment there is provided a compound of Formula (I) as defined above.

In one embodiment there is provided a pharmaceutically acceptable salt of a compound of Formula (I).

In embodiments, the compound of Formula (I) is a compound of Formula (Ia)

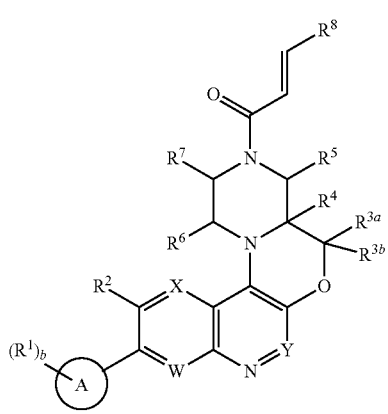

(Ia)

wherein:
A is selected from $C_6$-$C_{10}$ aryl, monocyclic heteroaryl and bicyclic heteroaryl;
R¹ is in each instance independently selected from F, Cl, Br, OH, CN, $C_1$-$C_4$alkyl, $C_1$-$C_4$alkoxy, $C_1$-$C_3$fluoroalkyl, $C_1$-$C_3$fluoroalkoxy, acetylenyl, NR⁹R¹⁰, C(O)NR¹¹R¹², $CH_2R^{13}$ and N=S(O)Me₂;
b is 0, 1, 2 or 3;
W is CR¹⁴ or N;
X is CR¹⁵ or N;
Y is CH or N;
R² is H, CN, F, Cl, Br, $C_1$-$C_4$ alkyl, $C_1$-$C_4$ alkoxy, $C_1$-$C_3$ fluoroalkyl, $C_1$-$C_2$ fluoroalkoxy or acetylenyl;
R³ᵃ, R³ᵇ, R⁴, R⁵, R⁶ and R⁷ are each independently selected from H or Me;
R⁸ is H or $CH_2NMe_2$;
R⁹ is H, $C_1$-$C_4$ alkyl, C(O)$C_1$-$C_3$alkyl or $CO_2C_1$-$C_3$alkyl;
R¹⁰, R¹¹ and R¹² are independently selected from H and $C_{1-4}$alkyl; or
R⁹ and R¹⁰ together, or R¹¹ and R¹² together, form a 4-, 5-, 6- or 7-membered saturated heterocycle optionally incorporating O, NH or N($C_1$-$C_4$ alkyl) group;
R¹³ is OH, CN, NR¹⁷R¹⁸, C(O)NR¹⁹R²⁰ or $SO_2C_1$-$C_3$alkyl;
R¹⁴ and R¹⁵ are each independently selected from H, F, Cl, MeO and Me;
R¹⁷, R¹⁸, R¹⁹ and R²⁰ are each independently selected from H and $C_1$-$C_4$alkyl or R¹⁸ and R¹⁹ together, or R¹⁹ and R²⁰ together, form a 4-, 5-, 6- or 7-membered saturated heterocycle optionally incorporating O, NH or N($C_1$-$C_4$ alkyl) group;
or a pharmaceutically acceptable salt thereof.

In embodiments, the compound of Formula (Ia) is a compound of Formula (Ib) in which Y is CH.

In embodiments, the compound of Formula (Ia) is a compound of Formula (Ic) in which Y is N.

In embodiments, the compound of Formula (Ia), (Ib) or (Ic) is a compound of Formula (Id) in which X is CR¹⁵.

In embodiments, the compound of Formula (Ia), (Ib), (Ic) or (Id) is a compound of Formula (Ie) in which W is CR¹⁴.

In embodiments, the compound of Formula (I) is a compound of Formula (If):

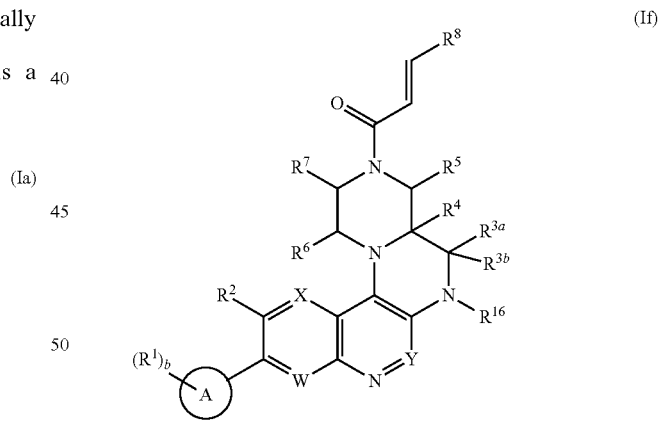

(If)

wherein:
A is selected from $C_6$-$C_{10}$ aryl, monocyclic heteroaryl and bicyclic heteroaryl;
R¹ is in each instance independently selected from F, Cl, Br, OH, CN, $C_1$-$C_4$ alkyl, $C_1$-$C_4$ alkoxy, $C_1$-$C_3$ fluoroalkyl, $C_1$-$C_3$ fluoroalkoxy, acetylenyl, NR⁹R¹⁰, C(O)NR¹¹R¹², $CH_2R^{13}$ and N=S(O)Me₂;
b is 0, 1, 2 or 3;
W is CR¹⁴ or N;
X is CR¹⁵ or N;
Y is CH or N;
R² is H, CN, F, Cl, $C_1$-$C_4$ alkyl, $C_1$-$C_4$ alkoxy, $C_1$-$C_3$ fluoroalkyl, $C_1$-$C_2$ fluoroalkoxy or acetylenyl;

$R^{3a}$ and $R^{3b}$ are each independently selected from H or Me or together are =O;

$R^4$, $R^5$, $R^6$ and $R^7$ are each independently selected from H or Me;

$R^8$ is H or $CH_2NMe_2$;

$R^9$ is H, $C_1$-$C_4$ alkyl, $C(O)C_1$-$C_3$alkyl or $CO_2C_1$-$C_3$ alkyl;

$R^{10}$, $R^{11}$ and $R^{12}$ are independently selected from H and $C_1$-$C_4$ alkyl; or $R^9$ and $R^{10}$ together, or $R^{11}$ and $R^{12}$ together, form a 4-, 5-, 6- or 7-membered saturated heterocycle optionally incorporating O, NH or $N(C_1$-$C_4$ alkyl) group;

$R^{13}$ is OH, CN, $NR^{17}R^{18}$, $C(O)NR^{19}R^{20}$ or $SO_2C_1$-$C_3$alkyl;

$R^{14}$ and $R^{15}$ are each independently selected from H, F, Cl, MeO and Me;

$R^{16}$ is H, $C_1$-$C_3$ fluoroalkyl or $CH_2R^{21}$;

$R^{17}$, $R^{18}$, $R^{19}$ and $R^{20}$ are each independently selected from H and $C_1$-$C_4$ alkyl or $R^{18}$ and $R^{19}$ together, or $R^{19}$ and $R^{20}$ together, form a 4-, 5-, 6- or 7-membered saturated heterocycle optionally incorporating O, NH or $N(C_1$-$C_4$ alkyl) group;

$R^{21}$ is selected from the group consisting of:
  H;
  $C_1$-$C_3$ alkyl optionally substituted with 1 or 2 substituents selected from hydroxy, $C_1$-$C_3$ alkoxy, halo, $NR^{22}R^{23}$, $C(O)NR^{24}R^{25}$, $SO_2Me$, heteroaryl, $C_3$-$C_7$ cycloalkyl or heterocyclyl, wherein said heteroaryl or $C_3$-$C_7$cycloalkyl is optionally further substituted with $C_1$-$C_4$ alkyl, hydroxy, halo, cyano, or $C_1$-$C_4$ alkoxy and said heterocyclyl is optionally further substituted with $C_1$-$C_4$ alkyl, hydroxy, halo, C(O)Me, $C_1$-$C_3$ alkoxy, $C_1$-$C_3$ fluoroalkyl, $C_3$-$C_7$ cycloalkyl, heterocyclyl or heteroaryl and wherein $R^{22}$, $R^{23}$, $R^{24}$ and $R^{25}$ are in each instance independently selected from H and $C_1$-$C_4$ alkyl;
  $C_3$-$C_7$ cycloalkyl optionally substituted with $C_1$-$C_4$ alkyl, hydroxy or halo;
  heterocyclyl optionally substituted with $C_1$-$C_4$ alkyl, hydroxy, halo, C(O)Me, $C_1$-$C_3$ alkoxy, $C_1$-$C_3$ fluoroalkyl, $C_3$-$C_7$ cycloalkyl, $CH_2$cyclopropyl, heterocyclyl or heteroaryl; and
  heteroaryl optionally substituted with $C_1$-$C_4$ alkyl, hydroxy, halo, cyano or $C_1$-$C_4$ alkoxy;
or a pharmaceutically acceptable salt thereof.

In embodiments, the compound of Formula (If) is a compound of Formula (Ig) in which $R^{3a}$ and $R^{3b}$ are H and H, H and Me or Me and Me.

In embodiments, the compound of Formula (If) is a compound of Formula (Ih) in which $R^{3a}$ and $R^{3b}$ together are =O.

In embodiments, the compound of Formula (If), (Ig) or (Ih) is a compound of Formula (Ii) in which Y is CH.

In embodiments, the compound of Formula (If), (Ig) or (Ih) is a compound of Formula (Ij) in which Y is N.

In embodiments, the compound of Formula (If), (Ig), (Ih), (Ii) or (Ij) is a compound of Formula (Ik) in which X is $CR^{15}$.

In embodiments, the compound of Formula (If), (Ig), (Ih), (Ii), (Ij) or (Ik) is a compound of Formula (Il) in which W is $CR^{14}$.

In embodiments, the compound of Formula (If), (Ig), (Ih), (Ii), (Ij), (Ik) or (Il) is a compound of Formula (Im) in which $R^{21}$ is selected from H and $C_1$-$C_3$ alkyl optionally substituted with 1 or 2 substituents selected from hydroxy, $C_1$-$C_3$ alkoxy, halo, $NR^{22}R^{23}$, $C(O)NR^{24}R^{25}$, $SO_2Me$ and $C_1$-$C_4$ alkoxy. In embodiments, the compound of Formula (If), (Ig), (Ih), (Ii), (Ij), (Ik) or (Il) has an $R^{21}$ group that is H (i.e. $R^{16}$ is Me).

In the embodiments below, reference to the compound of Formula (I) refers to a compound of Formula (I), (Ia), (Ib), (Ic), (Id), (Ie), (If), (Ig), (Ih), (Ii), (Ij), (Ik), (Il) or (Im) unless it is expressly indicated that this is not the case. In addition, each individual specification of a first group in an embodiment below may be combined with the individual specifications of a second group and so on. For example, a compound of Formula (I), (Ia), (Ib) . . . or (Im) may have the combination of a ring A and substituents $R^2$ and $R^8$ etc as individualised in the embodiments below. References to formulations, uses, method of use of a compound of Formula (I) herein below also specifically refer to compounds of the Formula (In), (Io) and (Ip), or a pharmaceutically acceptable salt thereof as defined below. In embodiments that relate to a compound of Formula (I), (Ia) . . . etc or a pharmaceutically acceptable salt thereof, it is to be understood that such embodiment encompass a corresponding embodiment in which compound of Formula (I), (Ia) . . . etc is provided in the free base form.

In embodiments, the compound of Formula (Ia) has the Formula (In)

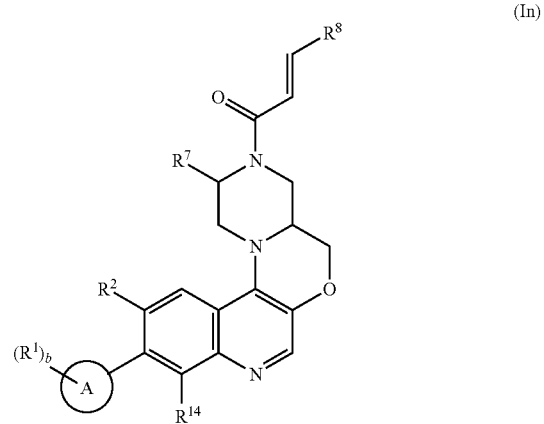

wherein:
A is selected from phenyl and bicyclic heteroaryl;
$R^1$ is in each instance independently selected from F, Cl, Br, OH, CN, $C_1$-$C_4$ alkyl, $C_1$-$C_2$ alkoxy or $C_1$-$C_2$ fluoroalkyl;
b is 0, 1, 2 or 3;
$R^2$ is CN, F, Cl, Me, Et, $CF_3$, MeO or acetylenyl;
$R^7$ is H or Me;
$R^8$ is H or $CH_2NMe_2$; and
$R^{14}$ is F, Cl, MeO and Me.

In embodiments, the compound of Formula (If) has the Formula (Io)

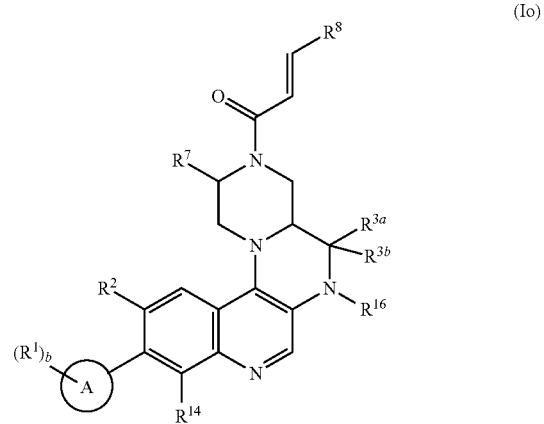

wherein:

A is selected from phenyl and bicyclic heteroaryl;
$R^1$ is in each instance independently selected from F, Cl, Br, OH, CN, $C_1$-$C_4$ alkyl, $C_1$-$C_2$ alkoxy or $C_1$-$C_2$ fluoroalkyl;
b is 0, 1, 2 or 3;
$R^2$ is CN, F, Cl, Me, Et, $CF_3$, MeO or acetylenyl;
$R^{3a}$ and $R^{3b}$ are each independently selected from H or Me or together are =O;
$R^7$ is H or Me;
$R^8$ is H or $CH_2NMe_2$;
$R^{14}$ is F, Cl, MeO and Me; and
$R^{16}$ is H or Me.

In embodiments, the compound of Formula (If) has the Formula (Ip)

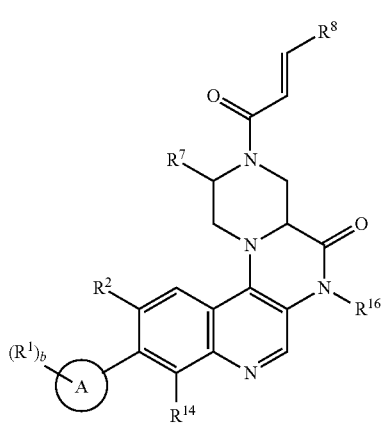

(Ip)

wherein:

A is selected from phenyl and bicyclic heteroaryl;
$R^1$ is in each instance independently selected from F, Cl, Br, OH, CN, $C_1$-$C_4$ alkyl, $C_1$-$C_2$ alkoxy or $C_1$-$C_2$ fluoroalkyl;
b is 0, 1, 2 or 3;
$R^2$ is CN, F, Cl, Me, Et, MeO or acetylenyl;
$R^7$ is H or Me;
$R^8$ is H or $CH_2NMe_2$;
$R^{14}$ is F, Cl, MeO and Me; and
$R^{16}$ is H or Me.

In embodiments, there is provided a compound of Formula (I), (In), (Io) or (Ip). In embodiments, there is provided a pharmaceutically acceptable salt of a compound of Formula (I), (In), (Io) or (Ip).

In embodiments, ring A of the compounds of Formula (I), (In), (Io) and (Ip) is phenyl.

In embodiments, ring A of the compounds of Formula (I) is naphthyl.

In embodiments, ring A of the compounds of Formula (I) is a monocyclic heteroaryl group. Monocyclic heteroaryl group, as used herein, refers to a 5- or 6-membered ring containing at least one heteroatom selected from O or N. In embodiments where a monocyclic heteroaryl group is present it is preferred that the monocyclic heteroaryl group is a 6-membered N containing heteroaromatic group.

In embodiments, ring A of the compounds of Formula (I) is a monocyclic heteroaryl group selected from the group comprising pyridinyl, 1H-pyridin-2-one, pyrimidinyl, pyrazinyl, pyridazinyl, pyrrolyl, pyrazolyl and imidazolyl.

In embodiments, ring A of the compounds of Formula (I) is 1H-pyridin-2-one,

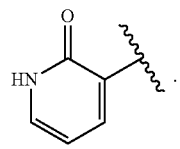 [SMILES: *c1ccc[nH]c1=O]

The wavy line as used herein indicates the site of attachment of this group to the ring containing W. In such embodiments the substituents $R^1$ may be selected from Me, $CF_3$ and F.

In embodiments, ring A of the compounds of Formula (I), (In), (Io) and (Ip) is bicyclic heteroaryl. The term bicyclic heteroaryl as used herein refers to bicyclic group with at least one aromatic ring fused to a second ring to form a 6,5-, 6,6- or 6,7-ring system, wherein at least one of the rings in the bicyclic group contains at least one heteroatom selected from O or N.

In embodiments, ring A of the compounds of Formula (I), (In), (Io) and (Ip) is a bicyclic heteroaryl group selected from the group consisting of:

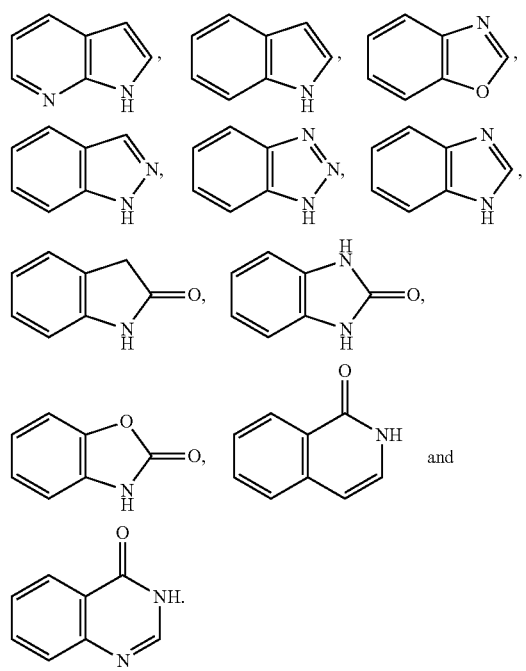

and the corresponding bicyclic heteroaryl groups in which the NH group is replaced with a N—($C_1$-$C_4$) alkyl group, for example a N-methyl group.

In embodiments, ring A of the compounds of Formula (I), (In), (Io) and (Ip) is a bicyclic heteroaryl selected from the group consisting of:

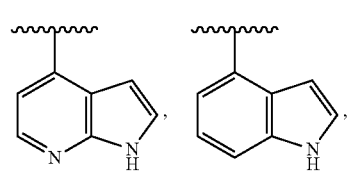

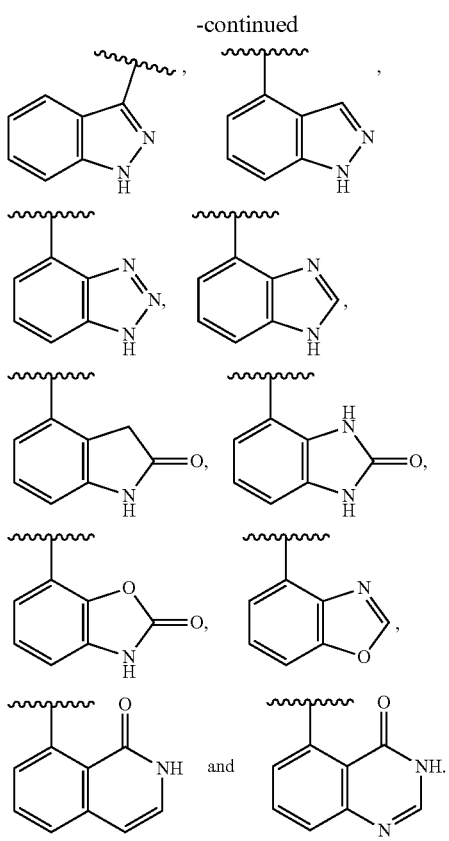

wherein the wavy line denotes the point of attachment of ring A to the rest of the molecule and wherein each NH group may be replaced with a N—($C_1$-$C_4$ alkyl) group, for example a N-methyl group.

In embodiments of the compounds of Formula (I), (In), (Io) and (Ip) wherein the ring A is phenyl or, for Formula (I) only, a monocyclic heteroaryl group, include those in which at least one substituent $R^1$ is located ortho- to the bond linking ring A to the ring containing W. In these embodiments, further $R^1$ substituents may be present, albeit in the structures below they are omitted for clarity.

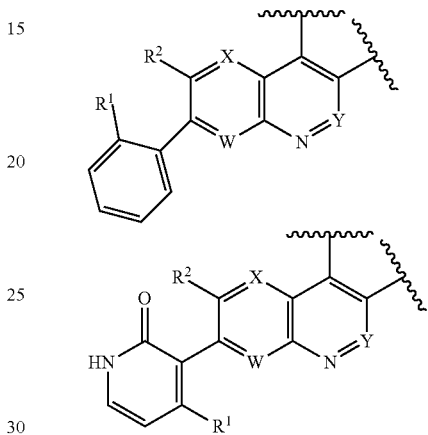

Embodiments of the compound of Formula (I), (In), (Io) and (Ip) wherein the ring A is phenyl include those in which b is 2 and the substituents $R^1$ are both ortho- to the bond linking ring A to the ring containing W. In such embodiments, the substituents $R^1$ may be independently selected from F, Cl, Me and hydroxy, for example F and hydroxy as shown below.

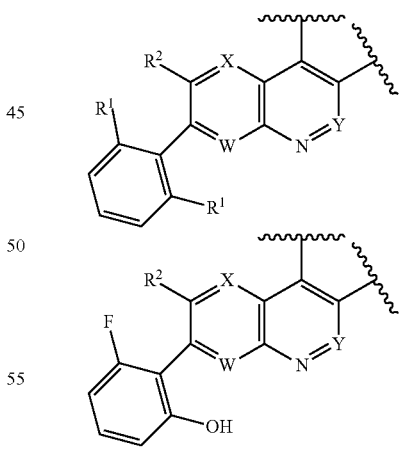

Embodiments of the compounds of Formula (I) wherein the ring A is a monocyclic heteroaryl group include those with a substituent $R^1$ that is located ortho- to the bond linking ring A to the ring containing W. For example, embodiments where the ring A is a 1H-pyridin-2-one and b=1 include those in which the substituent $R^1$ is selected from methyl or chloro and $R^1$ is located ortho- to the bond linking ring A to the ring containing W.

wherein the wavy line denotes the point of attachment of ring A to the rest of the molecule and wherein each NH group may be replaced with a N—($C_1$-$C_4$ alkyl) group, for example a N-methyl group.

In embodiments, ring A of the compounds of Formula (I), (In), (Io) and (Ip) is a bicyclic heteroaryl selected from the group consisting of:

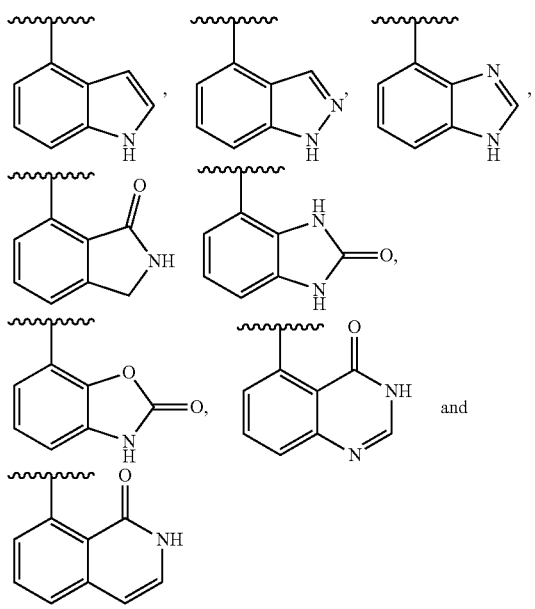

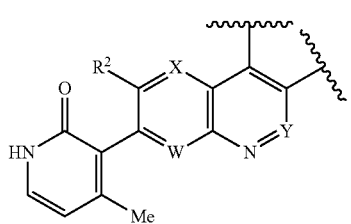

Embodiments of the compound of Formula (I), (In), (Io) and (Ip) wherein the ring A is a bicyclic heteroaryl group as defined hereinbefore include those, where possible, in which at least one substituent $R^1$ is ortho- to the bond linking ring A to the ring containing W. In such embodiments, the substituent $R^1$ that is ortho (to the biaryl bond) may be selected from methyl or F.

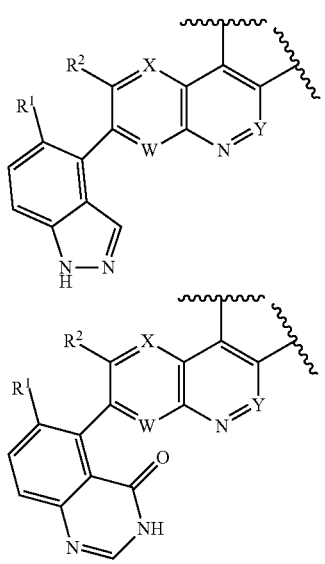

For the avoidance of doubt, a group $R^1$ may be attached to any ring N present in the ring A where chemically possible to form a neutral species, as well as the available ring carbon atoms.

In embodiments, the group $R^2$ is selected from H, CN, F, Cl, $C_1$-$C_4$ alkyl, $C_1$-$C_4$ alkoxy, $C_1$-$C_3$ fluoroalkyl, $C_1$-$C_2$ fluoroalkoxy or acetylenyl. In embodiments, the group $R^2$ is selected from Me, F, Cl, $CF_3$ and acetylene.

The compounds of Formula (I) have one or more chiral centres, for example at the bridgehead carbon between the upper piperazine to which the acrylamide is attached and the ring comprising Z, and it will be recognised that the compound of Formula (I) may be prepared, isolated and/or supplied with or without the presence, in addition, of one or more of the other possible stereoisomeric forms of the compound of Formula (I) in any relative proportions. The preparation of stereoenriched or stereopure compounds may be carried out by standard techniques of organic chemistry that are well known in the art, for example by synthesis from stereoenriched or stereopure starting materials, use of an appropriate stereoenriched or stereopure catalysts during synthesis, and/or by resolution of a racemic or partially enriched mixture of stereoisomers, for example via chiral chromatography. In preferred embodiments of the compounds of Formula (In) and (Ip) the bridgehead carbon between the upper piperazine to which the acrylamide is attached and the ring comprising Z is in the R-configuration.

Compounds of Formula (I) with the corresponding stereochemistry at this bridgehead carbon are generally preferred, albeit in the instance wherein Z=N, and $R^{3a}$ and $R^{3b}$ are H or alkyl the stereochemistry is the S-configuration. The preferred configuration of the bridgehead carbon is shown below.

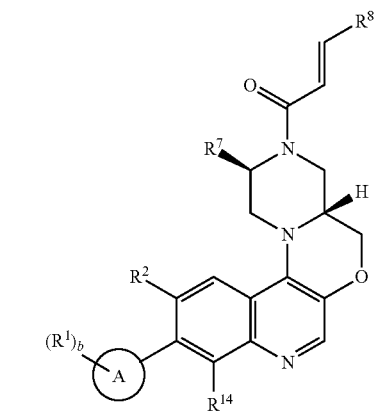

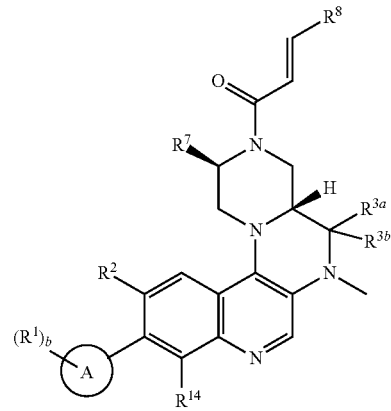

In particular, the compounds of Formula (I) may possess axial chirality, by virtue of restricted rotation around a biaryl bond and as such may exist as mixtures of atropisomers with enantiomeric excess between about 0% and >98% e.e. When a compound is a pure atropisomer, the stereochemistry at each chiral center may be specified by either aR or aS. Such designations may also be used for mixtures that are enriched in one atropisomer. By way of example only, the following moiety may exhibit atropisomerism and be capable of resolution into the aR and aS atropisomers by chiral chromatography. For illustration, the aR and aS atropisomers of a compound of Formula (I) in which the ring A is 2-F, 6-hydroxyphenyl and $R^3$-$R^7$ are not shown. The assignment of atropisomeric designator will depend on the nature of W.

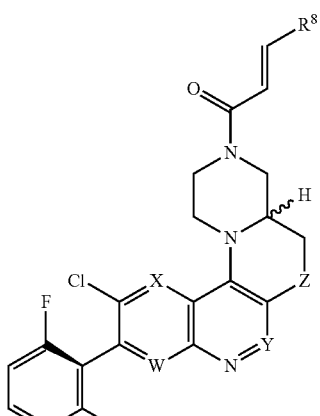

(aR) Atropisomer

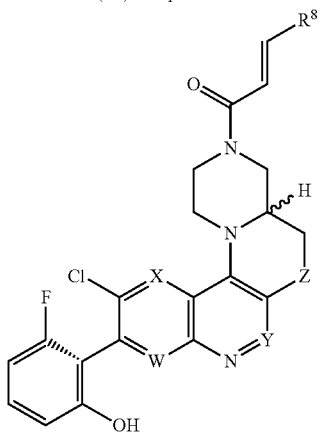

(aS) Atropisomer

Further description of atropisomerism and axial chirality and rules for assignment of configuration can be found in Eliel, E. L. & Wilen, S. H. 'Stereochemistry of Organic Compounds' John Wiley and Sons, Inc. 1994. In the compounds of the specification the groups $R^1$, $R^2$ and W may be selected to eliminate or substantially reduce the interconversion between the (aR) and (aS) atropisomers.

In more detail, the interaction between the group(s) $A(R^1)_b$ and the substituent $R^2$ may advantageously restrict the rotation around the bond between the ring A and the ring containing W. The interaction between the substituent $R^2$ and the ring A and/or the substituent(s) $R^1$ thereon may as a result be used to stabilise atropisomers of the compounds according to the present specification. This in turn may advantageously allow isolation of a stable atropisomer that exhibits higher activity as an inhibitor of G12C mutated Ras than the second atropisomer. It will be understood that the more active atropisomers are preferred embodiments.

In embodiments of the compound of Formula (I), the substituent $R^2$ is selected from the group comprising CN, F, Cl, $C_1$-$C_4$ alkyl, $C_1$-$C_4$ alkoxy, $C_1$-$C_3$fluoroalkyl, $C_1$-$C_2$fluoroalkoxy or acetylenyl. In embodiments, $R^2$ is selected from the group comprising F, Cl, $CH_3$, $CF_3$ and acetylenyl (—CCH).

In embodiments of the compound of Formula (I) wherein the group W is $CR^{14}$, the group $R^{14}$ may, similarly to the group $R^2$, be exploited to stabilise atropisomers of the compounds according to the specification. In such embodiments, the group $R^{14}$ may be selected from F, Cl, MeO and Me, for example from F, MeO and Me. Compounds with F as $R^{14}$ group have proven particularly active.

In embodiments of the compound of Formula (I) wherein the group Z is $NR^{16}$ and the groups $R^{3a}$, $R^{3b}$ are together O, the group $R^{16}$ may be selected from H or $C_1$-$C_4$ alkyl, for example H, Me and Et.

In embodiments of the compound of Formula (I) the groups $R^4$, $R^5$, $R^6$ and $R^7$ are each independently selected from H or Me. In embodiments, the groups $R^4$, $R^5$, $R^6$ and $R^7$ are H. In embodiments, the group $R^7$ of the compound of Formula (I) is Me. In embodiments, the groups $R^4$, $R^5$ and $R^6$ are H and $R^7$ is Me. The groups $R^{3a}$, $R^{3b}$, $R^4$, $R^5$, $R^6$ and $R^7$ can be used to access lipophilic interactions with Ras G12C mutant proteins and/or block or substantially reduce unwanted metabolism. In addition to its effect on activity, incorporation of a $R^7$ methyl group can advantageously improve bioavailability of compounds of Formula I. In embodiments of the compounds of Formula (I), (In), (Io) and (Ip) where $R^7$ is Me, the stereochemical configuration of the carbon atom to which the $R^7$ methyl group is attached is R.

In embodiments of the compounds of Formula (I), (In), (Io) and (Ip) $R^8$ is H.

In embodiments of the compound of Formula (I), (In), (Io) and (Ip) $R^8$ is $CH_2NMe_2$.

In embodiments, the compound of Formula (I) is selected from:
1-((4aR)-11-Chloro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one;
1-((4aR)-11-Chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one;
1-((4aS)-11-Chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one;
1-((4aR)-1-Chloro-9-fluoro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one;
(2E)-1-[(4aR)-11-Chloro-10-(2-fluoro-6-hydroxyphenyl)-1,2,4a,5-tetrahydropyrazino[1',2':4,5][1,4]oxazino[2,3-c]quinolin-3(4H)-yl]-4-(dimethylamino)but-2-en-1-one;
1-((4aR)-11-Chloro-10-(2-fluoro-6-hydroxyphenyl)-1,2,4a,5-tetrahydropyrazino[1',2':4,5][1,4]oxazino[2,3-c]cinnolin-3(4H)-yl)prop-2-en-1-one;
1-((4aS)-11-Chloro-6-(2-(dimethylamino)ethyl)-10-(2-fluoro-6-hydroxyphenyl)-1,2,4,4a,5,6-hexahydro-3H-pyrazino[1',2':4,5]pyrazino[2,3-c]quinolin-3-yl)prop-2-en-1-one;
1-[(2R,4aR)-11-Chloro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one;
1-((4aS)-11-Chloro-10-(2-fluoro-6-hydroxyphenyl)-1,2,4,4a,5,6-hexahydro-3H-pyrazino[1',2':4,5]pyrazino[2,3-c]quinolin-3-yl)prop-2-en-1-one;
1-((4aS)-11-Chloro-10-(2-fluoro-6-hydroxyphenyl)-6-methyl-1,2,4,4a,5,6-hexahydro-3H-pyrazino[1',2':4,5]pyrazino[2,3-c]quinolin-3-yl)prop-2-en-1-one;
(4aR)-3-Acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one;
(4aS)-3-Acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one;
(4aR)-11-chloro-9-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one;

(2R,4aR)-11-Chloro-9-fluoro-10-(2-fluoro-6-hydroxyphenyl)-2,6-dimethyl-3-(prop-2-enoyl)-2,3,4,4a-tetrahydro-1H-pyrazino[1',2':4,5]pyrazino[2,3-c]quinolin-5(6H)-one;

1-[(4aR)-11-Chloro-10-(2-fluoro-6-hydroxyphenyl)-9-methoxy-1,2,4a,5-tetrahydropyrazino[1',2':4,5][1,4]oxazino[2,3-c]quinolin-3(4H)-yl]prop-2-en-1-one;

(4aR)-11-Chloro-9-fluoro-6-methyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one;

(2R,4aR)-11-Chloro-9-fluoro-2,6-dimethyl-10-(5-methyl-1H-benzimidazol-4-yl)-3-(prop-2-enoyl)-2,3,4,4a-tetrahydro-1H-pyrazino[1,2:4,5]pyrazino[2,3-c]quinolin-5(6H)-one;

(2R,4aR)-11-Chloro-3-[(2E)-4-(dimethylamino)but-2-enoyl]-9-fluoro-10-(2-fluoro-6-hydroxyphenyl)-2,6-dimethyl-2,3,4,4a-tetrahydro-1H-pyrazino[1,2:4,5]pyrazino[2,3-c]quinolin-5(6H)-one;

(2R,4aR)-11-Chloro-9-fluoro-10-(2-fluoro-6-hydroxyphenyl)-2-methyl-3-(prop-2-enoyl)-2,3,4,4a-tetrahydro-1H-pyrazino[1',2':4,5]pyrazino[2,3-c]quinolin-5(6H)-one;

11-Chloro-10-(2-fluoro-6-hydroxyphenyl)-4a,6-dimethyl-3-(prop-2-enoyl)-2,3,4,4a-tetrahydro-1H-pyrazino[1',2':4,5]pyrazino[2,3-c]quinolin-5(6H)-one;

(4aR)-11-Chloro-9-fluoro-10-[2-fluoro-6-(hydroxymethyl)phenyl]-6-methyl-3-(prop-2-enoyl)-2,3,4,4a-tetrahydro-1H-pyrazino[1',2':4,5]pyrazino[2,3-c]quinolin-5(6H)-one;

(2E)-1-[(2R,4aR)-11-Chloro-9-fluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]-4-(dimethylamino)but-2-en-1-one;

1-[(4aR)-11-Chloro-10-(2-fluoro-6-hydroxyphenyl)-9-methyl-1,2,4a,5-tetrahydropyrazino[1',2':4,5][1,4]oxazino[2,3-c]quinolin-3(4H)-yl]prop-2-en-1-one;

1-[(2R,4aR)-11-Chloro-10-(2-fluoro-6-hydroxyphenyl)-2,9-dimethyl-1,2,4a,5-tetrahydropyrazino[1',2':4,5][1,4]oxazino[2,3-c]quinolin-3(4H)-yl]prop-2-en-1-one;

(4aR)-3-Acryloyl-9,11-difluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one;

(4aR)-3-Acryloyl-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one;

8-[(4aR)-11-Chloro-3-(prop-2-enoyl)-1,2,3,4,4a,5-hexahydropyrazino[1,2':4,5][1,4]oxazino[2,3-c]quinolin-10-yl]-7-fluoroisoquinolin-1(2H)-one;

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-1,3-benzoxazol-2(3H)-one;

(4aR)-11-Chloro-9-fluoro-6-methyl-10-(5-methyl-1H-indazol-4-yl)-3-(prop-2-enoyl)-2,3,4,4a-tetrahydro-1H-pyrazino[1',2:4,5]pyrazino[2,3-c]quinolin-5(6H)-one;

(4aR)-11-Chloro-10-(2-chloro-6-hydroxyphenyl)-9-fluoro-6-methyl-3-(prop-2-enoyl)-2,3,4,4a-tetrahydro-1H-pyrazino[1',2:4,5]pyrazino[2,3-c]quinolin-5(6H)-one;

(4aR)-11-Chloro-9-fluoro-10-(2-hydroxy-6-methylphenyl)-6-methyl-3-(prop-2-enoyl)-2,3,4,4a-tetrahydro-1H-pyrazino[1',2:4,5]pyrazino[2,3-c]quinolin-5(6H)-one;

(4aR)-11-Chloro-9-fluoro-10-(2-hydroxynaphthalen-1-yl)-6-methyl-3-(prop-2-enoyl)-2,3,4,4a-tetrahydro-1H-pyrazino[1',2:4,5]pyrazino[2,3-c]quinolin-5(6H)-one;

(4aR)-11-Chloro-10-(2,3-difluoro-6-hydroxyphenyl)-9-fluoro-6-methyl-3-(prop-2-enoyl)-2,3,4,4a-tetrahydro-1H-pyrazino[1',2:4,5]pyrazino[2,3-c]quinolin-5(6H)-one;

(4aR)-11-Chloro-12-fluoro-10-(2-fluoro-6-hydroxyphenyl)-6-methyl-3-(prop-2-enoyl)-2,3,4,4a-tetrahydro-1H-pyrazino[1',2:4,5]pyrazino[2,3-c]quinolin-5(6H)-one;

(4aR)-11,12-Dichloro-10-(2-fluoro-6-hydroxyphenyl)-6-methyl-3-(prop-2-enoyl)-2,3,4,4a-tetrahydro-1H-pyrazino[1',2:4,5]pyrazino[2,3-c]quinolin-5(6H)-one;

(4aR)-11-Chloro-10-[2-(difluoromethyl)-6-hydroxyphenyl]-9-fluoro-6-methyl-3-(prop-2-enoyl)-2,3,4,4a-tetrahydro-1H-pyrazino[1,2:4,5]pyrazino[2,3-c]quinolin-5(6H)-one;

1-[(2R,4aR)-9,11-Difluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one;

11-[(4aR)-11-Chloro-10-(5-methyl-1H-benzimidazol-4-yl)-1,2,4a,5-tetrahydropyrazino[1',2':4,5][1,4]oxazino[2,3-c]quinolin-3(4H)-yl]prop-2-en-1-one;

7-[(4aR)-11-Chloro-3-(prop-2-enoyl)-1,2,3,4,4a,5-hexahydropyrazino[1,2':4,5][1,4]oxazino[2,3-c]quinolin-10-yl]-1,6-dimethyl-1,3-dihydro-2H-benzimidazol-2-one;

8-[(4aR)-11-Chloro-3-(prop-2-enoyl)-1,2,3,4,4a,5-hexahydropyrazino[1,2':4,5][1,4]oxazino[2,3-c]quinolin-10-yl]-7-methylisoquinolin-1(2H)-one;

4-[(4aR)-11-Chloro-3-(prop-2-enoyl)-1,2,3,4,4a,5-hexahydropyrazino[1',2':4,5][1,4]oxazino[2,3-c]quinolin-10-yl]-5-methyl-1,3-dihydro-2H-benzimidazol-2-one;

1-[(4aS)-11-Chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinolin-3-yl]prop-2-en-1-one;

1-[(4aR)-11-Ethynyl-10-(5-methyl-1H-indazol-4-yl)-1,2,4a,5-tetrahydropyrazino[1',2':4,5][1,4]oxazino[2,3-c]quinolin-3(4H)-yl]prop-2-en-1-one;

1-[(4aR)-11-Chloro-9-fluoro-10-(5-methyl-1H-benzimidazol-4-yl)-1,2,4a,5-tetrahydropyrazino[1',2':4,5][1,4]oxazino[2,3-c]quinolin-3(4H)-yl]prop-2-en-1-one;

(4aR)-9-Chloro-11-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one;

1-[(2R,4aS)-11-Chloro-9-fluoro-10-(2-fluoro-6-hydroxyphenyl)-2-methyl-1,2,4,4a,5,6-hexahydro-3H-benzo[h]pyrazino[1,2-a][1,6]naphthyridin-3-yl]prop-2-en-1-one;

1-[(4aR)-11-Chloro-10-(2-fluoro-6-hydroxyphenyl)-12-methoxy-1,2,4a,5-tetrahydropyrazino[1',2':4,5][1,4]oxazino[2,3-c]quinolin-3(4H)-yl]prop-2-en-1-one;

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one;

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-2,3-dihydro-1H-isoindol-1-one;

(4aR)-11-Chloro-9-fluoro-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one;

(4aR)-11-Chloro-6-ethyl-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one; and (8a R)-3-(2-Fluoro-6-hydroxyphenyl)-2,4,7-trimethyl-10-(prop-2-enoyl)-9,10,11,12-tetrahydro-7H-pyrazino[1',2':4,5]pyrazino[2,3-c][1,5]naphthyridin-8(8aH)-one;

or a pharmaceutically acceptable salt thereof, and each individual stereoisomer, for example atropisomer, thereof.

In embodiments of the present specification there is also provided an intermediate (Iq), or a derivative thereof protected at the piperazine NH (marked with *) useful for the preparation of a compound of Formula (I) wherein the groups and substituents are as defined for any of compounds of Formula (I) to Formula (Ip) above.

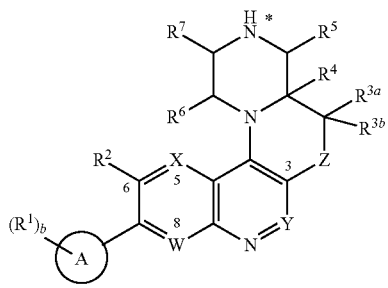

(Iq)

In a related embodiment, there is provided a method for synthesising a compound of Formula (I) involving reaction of a compound of Formula (Iq) with i) acryloyl chloride, or an equivalent thereof such as acryloyl anhydride, and a base or ii) acrylic acid or an ester thereof and a coupling reagent.

In embodiments of the present specification there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with a diastereomeric excess (% d.e.) of ≥90%.

In embodiments of the present specification there is provided a pharmaceutical composition which comprises a compound of the Formula (I) or a pharmaceutically acceptable salt thereof, in association with a pharmaceutically acceptable excipient, optionally further comprising one or more of the other stereoisomeric forms of the compound of Formula (I) or pharmaceutically acceptable salt thereof, wherein the compound of Formula (I) or pharmaceutically acceptable salt thereof is present within the composition with an enantiomeric excess (% ee) of ≥90% and a diastereomeric excess (% de) of ≥90%.

The compounds of Formula (I) and pharmaceutically acceptable salts thereof may be prepared, used or supplied in amorphous form, crystalline form, or semi-crystalline form and any given compound of Formula (I) or pharmaceutically acceptable salt thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I) and pharmaceutically acceptable salts thereof.

In further embodiments of the present specification there is provided a compound of Formula (I), which is obtainable by the methods described in the 'Examples' section hereinafter.

The present specification is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. Isotopically labelled compounds of Formula (I) can generally be prepared by conventional techniques known to those skilled in the art or by processes analogous to those described in the accompanying Examples using appropriate isotopically labelled reagents in place of the non-labelled reagents previously employed.

A suitable pharmaceutically acceptable salt of a compound of the Formula (I) is, for example, an acid addition salt. A suitable pharmaceutically acceptable salt of a compound of the Formula (I) may be, for example, an acid-addition salt of a compound of the Formula (I), for example an acid-addition salt with an inorganic or organic acid.

A further suitable pharmaceutically acceptable salt of a compound of the Formula (I) is, for example, a salt formed within the human or animal body after administration of a compound of the Formula (I) to said human or animal body.

The compound of Formula (I) or pharmaceutically acceptable salt thereof may be prepared as a co-crystal solid form. It is to be understood that a pharmaceutically acceptable co-crystal of a compound of the Formula (I) or pharmaceutically acceptable salts thereof, form an aspect of the present specification.

For use in a pharmaceutical context it may be preferable to provide a compound of Formula (I) or a pharmaceutically acceptable salt thereof without large amounts of the other stereoisomeric forms being present.

The compound of Formula (I), or a pharmaceutically acceptable salt thereof, will normally be administered via the oral route though parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form may be possible. Depending upon the disorder and patient to be treated and the route of administration, the compositions may be administered at varying doses.

The pharmaceutical formulations of the compound of Formula (I) described above may be prepared e.g. for parenteral, subcutaneous, intramuscular or intravenous administration The pharmaceutical formulations of the compound of Formula (I) described above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985).

Pharmaceutical formulations suitable for oral administration may comprise one or more physiologically compatible carriers and/or excipients and may be in solid or liquid form. Tablets and capsules may be prepared with binding agents; fillers; lubricants; and surfactants. Liquid compositions may contain conventional additives such as suspending agents; emulsifying agents; and preservatives Liquid compositions may be encapsulated in, for example, gelatin to provide a unit dosage form. Solid oral dosage forms include tablets, two-piece hard shell capsules and soft elastic gelatin (SEG) capsules. An exemplary oral composition would comprise a compound of Formula (I) and at least one pharmaceutically acceptable excipient filled into a two-piece hard shell capsule or a soft elastic gelatin (SEG) capsule.

According to a further embodiment there is provided a compound of the Formula (I), or a pharmaceutically acceptable salt thereof, as defined hereinbefore, for use as a medicament in a warm-blooded animal such as man.

According to a further embodiment, there is provided a compound of the Formula (I), or a pharmaceutically acceptable salt thereof, as defined hereinbefore for use in the production of an anti-proliferative effect in a warm-blooded animal such as man.

According to a further embodiment, there is provided a compound of the Formula (I), or a pharmaceutically acceptable salt thereof, as defined hereinbefore for use in a warm-blooded animal such as man as an anti-invasive agent in the containment and/or treatment of solid tumour disease.

According to a further embodiment, there is provided the use of a compound of the Formula (I), or a pharmaceutically acceptable salt thereof, as defined hereinbefore, for the production of an anti-proliferative effect in a warm-blooded animal such as man.

According to a further embodiment, there is provided the use of a compound of the Formula (I), or a pharmaceutically acceptable salt thereof, as defined hereinbefore, in the manufacture of a medicament for use in the production of an anti-proliferative effect in a warm-blooded animal such as man.

According to a further embodiment, there is provided the use of a compound of the Formula (I), or a pharmaceutically acceptable salt thereof, as defined hereinbefore, in the manufacture of a medicament for use in a warm-blooded animal such as man as an anti-invasive agent in the containment and/or treatment of solid tumour disease.

According to a further embodiment, there is provided a method for producing an anti-proliferative effect in a warm-blooded animal, such as man, in need of such treatment which comprises administering to said animal an effective amount of a compound of the Formula (I), or a pharmaceutically acceptable salt thereof, as defined hereinbefore.

In this specification, unless otherwise stated, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. The effective amount will generally be in the range of 0.1 mg to 1,000 mg.

According to a further embodiment, there is provided a method for producing an anti-invasive effect by the containment and/or treatment of solid tumour disease in a warm-blooded animal, such as man, in need of such treatment which comprises administering to said animal an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore, for use in the prevention or treatment of cancer in a warm-blooded animal such as man.

According to a further embodiment, there is provided the use of a compound of the Formula (I), or a pharmaceutically acceptable salt thereof, as defined hereinbefore in the manufacture of a medicament for use in the prevention or treatment of cancer in a warm-blooded animal such as man.

According to a further embodiment, there is provided a method for the prevention or treatment of cancer in a warm-blooded animal, such as man, in need of such treatment which comprises administering to said animal an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore for use in the prevention or treatment of solid tumour disease in a warm-blooded animal such as man.

According to a further embodiment, there is provided the use of a compound of the Formula (I), or a pharmaceutically acceptable salt thereof, as defined hereinbefore, in the manufacture of a medicament for use in the prevention or treatment of solid tumour disease in a warm-blooded animal such as man.

According to a further embodiment, there is provided a method for the prevention or treatment of solid tumour disease in a warm-blooded animal, such as man, in need of such treatment which comprises administering to said animal an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore, for use in the prevention or treatment of tumours which are sensitive to inhibition of G12C mutant Ras.

According to a further embodiment, there is provided the use of a compound of the Formula (I), or a pharmaceutically acceptable salt thereof, as defined hereinbefore, in the manufacture of a medicament for use in the prevention or treatment of those tumours which are sensitive to inhibition of G12C mutant Ras.

According to a further embodiment, there is provided a method for the prevention or treatment of those tumours which are sensitive to inhibition of G12C mutant RAS, which comprises administering to a patient in need thereof an effective amount of a compound of the Formula (I), or a pharmaceutically acceptable salt thereof, as defined hereinbefore.

According to a further embodiment, there is provided a compound of the Formula (I), or a pharmaceutically acceptable salt thereof, as defined hereinbefore for use in providing an inhibitory effect on G12C mutant Ras.

According to a further embodiment, there is provided the use of a compound of the Formula (I), or a pharmaceutically acceptable salt thereof, as defined hereinbefore in the manufacture of a medicament for use in providing an inhibitory effect on G12C mutant Ras.

According to a further embodiment, there is also provided a method for providing an inhibitory effect on G12C mutant RAS which comprises administering an effective amount of a compound of the Formula (I), or a pharmaceutically acceptable salt thereof, as defined hereinbefore, to a patient in need thereof.

According to a further embodiment, there is provided a compound of the Formula (I), or a pharmaceutically acceptable salt thereof, as defined hereinbefore, for use in providing a selective inhibitory effect on G12C mutant Ras.

According to a further embodiment, there is provided the use of a compound of the Formula (I), or a pharmaceutically acceptable salt thereof, as defined hereinbefore, in the manufacture of a medicament for use in providing a selective inhibitory effect on G12C mutant Ras.

According to a further embodiment, there is also provided a method for providing a selective inhibitory effect on G12C mutant Ras which comprises administering an effective amount of a compound of the Formula (I), or a pharmaceutically acceptable salt thereof, to a patient in need thereof.

Described herein are compounds that can bind to G12C mutant Ras. In biochemical and cell based assays the compounds of the present specification are shown to be potent G12C mutant Ras protein binders and may therefore be useful in the treatment of disorders mediated by KRas, NRas or HRas G12C mutations, in particular in the treatment of cancers expressing G12C mutated KRas, NRas or HRas proteins, such as pancreatic, colorectal, uterine, bile duct, stomach, bladder, cervical, testicular germ cell and non-small cell lung cancer and multiple myeloma, diffuse large B cell lymphoma, rhabdomyosarcoma and cutaneous squamous cell carcinoma.

According to a further embodiment, there is provided a compound of the Formula (I), or a pharmaceutically acceptable salt thereof, as defined hereinbefore, for use in the treatment of disorders mediated by KRas, NRas or HRas G12C mutations.

According to a further embodiment, there is provided a method for treating disorders mediated by KRas, NRas or HRas G12C mutations, which comprises administering an effective amount of a compound of the Formula (I), or a pharmaceutically acceptable salt thereof, as defined hereinbefore.

According to a further embodiment, there is provided the use of a compound of the Formula (I), or a pharmaceutically acceptable salt thereof, as defined hereinbefore, in the manufacture of a medicament for use in the treatment of disorders mediated by KRas, NRas or HRas G12C mutations.

According to a further embodiment, there is provided a compound of the Formula (I), or a pharmaceutically acceptable salt thereof, as defined hereinbefore, for use in the treatment of pancreatic cancer, non-small cell lung cancer or colorectal cancer.

According to a further embodiment, there is provided a compound of the Formula (I), or a pharmaceutically acceptable salt thereof, as defined hereinbefore, for use in the treatment of non-small cell lung cancer.

According to a further embodiment, there is provided a method for treating pancreatic cancer, non-small cell lung cancer or colorectal cancer, which comprises administering an effective amount of a compound of the Formula (I), or a pharmaceutically acceptable salt thereof, as defined hereinbefore to a patient in need thereof.

According to a further embodiment, there is provided a method for treating non-small cell lung cancer, which comprises administering an effective amount of a compound of the Formula (I), or a pharmaceutically acceptable salt thereof, to a patient in need thereof.

According to a further embodiment, there is provided the use of a compound of the Formula (I), or a pharmaceutically acceptable salt thereof, as defined hereinbefore, in the manufacture of a medicament for use in the treatment of breast or gynaecological cancers.

According to a further embodiment, there is provided the use of a compound of the Formula (I), or a pharmaceutically acceptable salt thereof, as defined hereinbefore, in the manufacture of a medicament for use in the treatment of pancreatic cancer, non-small cell lung cancer or colorectal cancer.

According to a further aspect of the specification, there is provided the use of a compound of the Formula (I), or a pharmaceutically acceptable salt thereof, as defined hereinbefore, in the manufacture of a medicament for use in the treatment of non-small cell lung cancer.

The anti-cancer treatment defined herein may be applied as a sole therapy or may involve, in addition to the compounds of the specification, conventional surgery or radiotherapy or chemotherapy.

Accordingly, in one embodiment, there is provided a compound of Formula (I), or a pharmaceutically acceptable salt thereof, and an additional anti-tumour substance for the conjoint treatment of cancer.

According to an embodiment of the specification there is provided a combination suitable for use in the treatment of cancer comprising a compound of the Formula (I) or a pharmaceutically acceptable salt thereof and another anti-tumour agent.

In a further embodiment of the specification there is provided a compound of the Formula (I), or a pharmaceutically acceptable salt thereof, in combination with another anti-tumour agent.

Although the compounds of the Formula (I) are primarily of value as therapeutic agents for use in warm-blooded animals (including man), they are also useful whenever it is required to inhibit G12C mutant Ras. Thus, they are useful as pharmacological standards for use in the development of new biological tests and in the search for new pharmacological agents.

Another embodiment is based on identifying a link between the G12C KRas, HRas or NRas mutation status of a patient and potential susceptibility to treatment with a compound of Formula (I). A Ras inhibitor, such as a compound of Formula (I), may then advantageously be used to treat patients with G12C KRas, HRas or NRas mutations who may be resistant to other therapies. This therefore provides opportunities, methods and tools for selecting patients for treatment with a compound of Formula (I), particularly cancer patients. The selection is based on whether the tumour cells to be treated possess wild-type or G12C mutant KRAS, HRAS or NRAS gene. The G12C KRAS, HRAS or NRAS gene status could therefore be used as a biomarker to indicate that selecting treatment with a compound of Formula (I) may be advantageous.

According to one embodiment, there is provided a method for selecting a patient for treatment with a compound of Formula (I), the method comprising providing a tumour cell-containing sample from a patient; determining whether the RAS gene in the patient's tumour cell-containing sample encodes for wild-type (glycine at position 12) or mutant (cysteine at position 12) KRas, HRas or NRas protein; and selecting a patient for treatment with a compound of Formula (I) based thereon.

The method may include or exclude the actual patient sample isolation step. Thus, according to one embodiment there is provided a method for selecting a patient for treatment with a compound of Formula (I), the method comprising determining whether the RAS gene in a tumour cell-containing sample previously isolated from the patient encodes for wild-type (glycine at position 12) or mutant (cysteine at position 12) KRas, HRas or NRas protein; and selecting a patient for treatment with a compound of Formula (I) based thereon.

In embodiments, the patient is selected for treatment with a compound of Formula (I) if the tumour cell DNA has a G12C mutant KRAS gene.

In embodiments, the patient is selected for treatment with a compound of Formula (I) if the tumour cell DNA has a G12C mutant HRAS gene.

In embodiments, the patient is selected for treatment with a compound of Formula (I) if the tumour cell DNA has a G12C mutant NRAS gene.

According to another embodiment, there is provided a compound of Formula (I), or a pharmaceutically acceptable salt thereof, for use in treating cancers with tumour cells identified as harbouring a G12C mutant KRAS gene.

According to another embodiment, there is provided a compound of Formula (I), or a pharmaceutically acceptable salt thereof, for use in treating cancers with tumour cells identified as harbouring a G12C mutant HRAS gene.

According to another aspect of the specification there is provided a compound of Formula (I), or a pharmaceutically acceptable salt thereof, for use in treating cancers with tumour cells identified as harbouring a G12C mutant NRAS gene.

According to another embodiment, there is provided a method of treating cancers with tumour cells identified as harbouring a G12C mutant KRAS, HRAS or NRAS gene comprising administering an effective amount of a compound of Formula (I) or a pharmaceutically acceptable salt thereof.

According to another embodiment, there is provided a pharmaceutical composition comprising a compound of Formula (I) for use in the prevention and treatment of cancer with tumour cells identified as harbouring a G12C mutant KRAS, HRAS or NRAS gene.

EXAMPLES

It will be appreciated that the following examples are provided so that the nature of the invention may be fully understood. It will also be appreciated that the following examples are not intended to limit the scope of the description in any way.

Biological Assays

The following assays were used to measure the effects of the compounds of the present specification.

KRasG12C Functional Assay

The inactive GDP loaded biotinylated $KRas^{G12C}$ protein was expressed, purified and GDP loaded in house. All enzyme and substrate solutions were prepared in assay buffer containing 20 mM HEPES (pH 7.5), 5 mM MgCl2, 150 mM NaCl, and 0.01% Tween 20. 10 nM GDP loaded biotinylated $KRas^{G12C}$ and 37.5 ng/ml Streptavidin Europium Cryptate (Cisbio) were prepared in assay buffer, 5 μl was dispensed into each well of a 384 polystyrene, Hibase, medium binding white assay plate (Greiner, #784075) containing test and reference samples prepared in DMSO and the samples incubated for 4 hrs. In a separate mix 20 nM GST-Raf Ras binding domain (GST-Raf RBD, purified in house) and 4 μg/ml anti-GST XL665 antibody (Cisbio) was prepared in assay buffer containing 50 mM Potassium Fluoride and 0.05 mg/ml BSA and equilibrated for 4 hours before adding 0.6 μM Guanosine 5′-[γ-thio]triphosphate (GTPγS, Sigma) and 0.08 μM SOS (purified in house). 5 μl of the GST-RAF RBD mix was then dispensed into each well of the assay plate. This addition initiates the nucleotide exchange reaction and transition of inactive GDP loaded $KRas^{G12C}$ to active GTPγS $KRas^{G12C}$. This is detected simultaneously via the specific binding interaction between active GTPγS $KRas^{G12C}$ with GST-Raf RBD which brings the europium and XL665 into close proximity enabling an increased FRET signal to be detected on a Pherastar (BMG) plate reader equipped with the HTRF filter module. Any compound which prevents the activation of KRas via inhibiting the nucleotide exchange process, or inhibits the active KRas:Raf RBD binding interaction, will result in a reduced FRET signal. $IC_{50}$ values were calculated from normalised dose-response response FRET data curve fitted in Genedata screener (Basel, Switzerland).

KRasG12C Mass Spectrometry Adducting Assay

The inactive GDP loaded biotinylated $KRas^{G12C}$ protein was expressed, purified and GDP loaded in house. Enzyme solutions were prepared in assay buffer containing 20 mM HEPES (pH 7.5), 5 mM MgCl2, and 150 mM NaCl. 4 μM GDP loaded biotinylated $KRas^{G12C}$ was prepared in assay buffer and 50 μl added into each well of a 96 well polypropylene assay plate (Greiner, #651201) containing 500 nl of 1 mM test compounds (final concentration 10 μM), this was allowed to react for 4 hours before the addition of 50 μl 1% Formic acid to quench the reaction. The plate was sealed before reading on a Xevo G2 QTOF (Waters) and Acquity LC system (Waters). 10 μl of sample was injected onto a Xbridge BEH300; C4; 3.5 um; 2.1×50 mm column (Waters) running a 3 minute gradient. Blank samples were run in between each test sample.

Data was analysed in Mass Lynx software (Waters), the Total ion count (TIC) trace was used and the eluted protein peak data combined. Using the combined spectrum the data was deconvoluted using MaxEnt1 method. The peak area for apo-protein $KRas^{G12C}$ (APO) and KRAS+relative cmpd mass (adduct) were measured, and a percentage adduct was calculated using the following calculation:

Percent adduct=100*(area of adduct peak/(sum of APO+adduct peaks)

The data shown in Table A were generated for the Examples (the data below may be a result from a single experiment or an average of two or more experiments).

TABLE A

| Example No | KRasG12C functional assay $IC_{50}$ value (μM) | KRasG12C M.S. Binding Mean adduct % |
| --- | --- | --- |
| 1† | 0.186 | 96 |
| 2† | 0.281 | 87 |
| Mixture of 1 & 2 | 0.211 | ND |
| 3 | 0.081 | 93 |
| 4 | 1.7 | ND |
| 5 | 5.8 | ND |
| 6 | 0.662 | ND |
| 7 | 0.02 | 95 |
| 8 | 8.5 | ND |
| 9* | 0.341 | 74 |
| 10* | 0.135 | 81 |
| 11* | 0.047 | 93 |
| 12* | 0.231 | 75 |
| 13* | 0.387 | 86 |
| 14* | 0.132 | 91 |
| 15* | 0.145 | 100 |
| 16* | 2.7 | 18 |
| 17 | 0.018 | 100 |
| 18 | 3.5 | 3 |
| 19 | >9.2 | 3 |
| 20 | 0.63 | 51 |
| 21 | 9.5 | 15 |
| 22 | 0.005 | 100 |
| 23 | 4.2 | ND |
| 24 | 0.070 | 96 |
| 25 | 0.028 | ND |
| 26 | 0.446 | ND |
| 27 | 8.8 | ND |
| 28 | 0.003 | ND |
| 29 | 0.025 | ND |
| 30 | 4.6 | ND |
| 31 | 0.004 | ND |
| 32 | 2.2 | ND |
| 33 | 0.745 | 87 |
| 34 | 9.8 | ND |

TABLE A-continued

| Example No | KRasG12C functional assay IC$_{50}$ value (µM) | KRasG12C M.S. Binding Mean adduct % |
|---|---|---|
| 35 | 0.133 | ND |
| 36 | 28.1 | ND |
| 37 | 0.021 | ND |
| 38 | 9.7 | 7 |
| 39 | 0.097 | 94 |
| 40 | 0.062 | 96 |
| 41 | 1.5 | ND |
| 42 | 0.077 | ND |
| 43 | >100 | ND |
| 44 | 0.142 | ND |
| 45 | 0.026 | 96 |
| 46 | 1.1 | ND |
| 47 | 0.031 | ND |
| 48 | 3.6 | ND |
| 49 | 0.047 | 95 |
| 50 | 9.6 | ND |
| 51 | >100 | ND |
| 52 | 0.014 | ND |
| 53 | 37.6 | ND |
| 54 | 0.040 | ND |
| 55 | 5.9 | ND |
| 56 | 0.056 | ND |
| 57 | 8.9 | ND |
| 58 | 0.020 | ND |
| 59 | 0.202 | ND |
| 60 | 0.501 | ND |
| 61 | 38.7 | ND |
| 62 | 0.037 | ND |
| 63 | 1.9 | ND |
| 64 | 0.020 | ND |
| 65 | 0.047 | 95 |
| 66 | 0.654 | 25 |
| 67 | 0.047 | 97 |
| 68 | 11.4 | 4 |
| 69 | 2.7 | 12 |
| 70 | 0.049 | 94 |
| 71 | 0.047 | 94 |
| 72 | 8.3 | ND |
| 73 | 0.057 | ND |
| 74 | 13.1 | ND |
| 75 | 0.096 | 96 |
| 76 | 0.931 | ND |
| 77 | 0.028 | 60 |
| 78 | 7.143 | ND |
| 79 | 0.141 | ND |
| 80 | 14.7 | ND |
| 81 | 4.5 | ND |
| 82 | 0.005 | 100 |
| 83 | 0.257 | 77 |
| 84 | 2.4 | ND |
| 85 | 0.010 | ND |
| 86 | 0.041 | 95 |
| 87 | 8.6 | ND |
| 88 | 0.014 | 96 |
| 89 | 3.6 | ND |
| 90 | 0.333 | ND |
| 91 | 35.2 | ND |
| 92 | 0.082 | 97 |

*compound tested as a mixture of atropisomers;
†atropisomers of compound separated but interconvert prior to assay;
ND = not determined.

As can be seen from Table A, the compounds of the specification prevent the activation of KRas via inhibiting the nucleotide exchange process, or via inhibiting the active KRas:Raf RBD binding interaction, as seen from the reduced FRET signal in the KRasG12C functional assay. In addition, the compounds of the specification proved to be effective covalently binders to KRasG12C in the KRasG12C Mass Spectrometry adducting assay.

It can also be seen that the difference in activity between the various atropisomeric pairs is usually pronounced, for example 10- or 20-fold or more (e.g. cf 3 and 4, and 5 and 6). The exception to this observation is the case of Compounds 1 and 2 wherein the difference in activity observed for the atropisomeric pair was less than 2-fold. It was suspected that the lack of a profound difference in this case was due to the propensity of this atropisomeric pair to interconvert. A mixture of compounds 1 and 2 was thus assayed and, as the activity displayed by the mixture proved intermediate to that of the two atropisomers as separated then assayed, it would appear that the modest difference in activity between atropisomers 1 and 2 may well be attributable a lack of atropisomeric stability (i.e. a degree of interconversion between the two atropsomeric forms likely occurs prior to testing).

As observed above, in addition to high activity against RasG12C, compounds of Formula (I) have been found to possess good pharmacokinetic properties. For example, examples 17 and 22 show low reactivity to glutathione with respective $t_{1/2}$ values of 585 and 929 minutes being observed when these compounds were co-incubated with glutathione in buffer as well as low turnover in incubations with hepatic systems. These assays reflect the good metabolic stability of compound of Formula (I) in general and suggests that there will be limited off-target reactivity in the therapeutic context. In addition, in vivo studies demonstrated that the observed in vitro stability translated well to the in vivo context with compounds of Formula (I) exhibiting good oral bioavailability and low clearance. For example, the F value for example 40 was determined at 43%, while the corresponding $R^7$ methyl derivative, example 39, had a clearance in rat of just 6 ml/min/kg and complete F.

SYNTHETIC EXAMPLES

The specification will now be illustrated in the following Examples in which, unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work up procedures were carried out after removal of residual solids by filtration;

(iii) flash column chromatography was performed on Merck Kieselgel silica (Art. 9385) or on reversed phase silica (Fluka silica gel 90 C18) or on Silicycle cartridges (40-63 µm silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 µm silica) or on Interchim puri-Flash cartridges (50 µm silica, 4-800 g) either manually or automated using an Isco CombiFlash Companion system or similar system;

(iv) preparative reverse phase HPLC was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm or 50 mm diameter, 100 mm length, flow rate of 40 mL/minute) using decreasingly polar mixtures of water (containing 1% ammonia) and acetonitrile or decreasingly polar mixtures of water (containing 0.1% formic acid) and acetonitrile as eluents;

(vi) yields, where present, are not necessarily the maximum attainable;

(vii) in general, the structures of end products of the Formula I were confirmed by nuclear magnetic resonance (NMR) spectroscopy; NMR chemical shift values were measured on the delta scale [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;

(viii) in general, end products of the Formula I were also characterized by mass spectroscopy following liquid chromatography (LCMS or UPLC); in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B. The reported molecular ion corresponds to the [M+H]+ unless otherwise specified;

(ix) ion exchange purification was generally performed using an SCX-2 (Biotage) cartridge;

(x) where reactions refer to the use of a microwave, one of the following microwave reactors were used: Biotage Initiator, Personal Chemistry Emrys Optimizer, Personal Chemistry Smithcreator or CEM Explorer;

(xi) intermediate purity was assessed by thin layer chromatographic, mass spectroscopy, LCMS, UPLC/MS, HPLC and/or NMR analysis;

(xii) the following abbreviations have been used:

BPR—back pressure regulator; DCM—dichloromethane; DEA—diethylamine; DIPEA—N,N-diisopropylethylamine; DMA—N,N-dimethylacetamide; DMF—N,N-dimethylformamide; DMSO—dimethylsulfoxide; d.e.—diastereomeric excess; EDC—N-Ethyl-N'-(3-dimethylaminopropyl)carbodiimide hydrochloride; EtOAc—ethyl acetate; EtOH—ethanol; h—hour; HATU—N-[(Dimethylamino)-1H-1,2,3-triazolo-[4,5-b]pyridin-1-ylmethylene]-N-methylmethanaminium hexafluorophosphate N-oxide; HCl—hydrochloric acid; Hex—hexane; HPLC—high performance liquid chromatography; IPA/iPrOH Isopropanol; MeCN acetonitrile; MeOH—methanol; NMR—nuclear magnetic resonance; NMP—N-methyl pyrrolidine; RuPhos dicyclohexyl(2',6'-diisopropoxy-[1,1'-biphenyl]-2-yl)phosphane; RuPhos Pd G3—(2-dicyclohexylphosphino-2',6'-diisopropoxy-1,1'-biphenyl)[2-(2'-amino-1,1'-biphenyl)]palladium(II) methanesulfonate; Pd-100—trans dichloro bis(triphenylphosphine)palladium(II); Pd-118—dichloro [1,1'-bis(di-tertbutylphosphino)ferrocene] palladium(II); rt room termperature; scCO2—supercritical CO2; SCX—strong cation exchange; SFC—supercritical fluid chromatography; SPhos Pd G2—chloro(2-dicyclohexylphosphino-2',6'-dimethoxy-1,1'-biphenyl)[2-(2'-amino-1,1'-biphenyl)]palladium(II); TBME—tert-butyl methyl ether; TEA—triethylamine; TFA—trifluoroacetic acid; THF—tetrahydrofuran; tR—retention time; and XPhos-Pd-G2—chloro(2-dicyclohexyl phosphino-2',4',6'-triisopropyl-1,1'-biphenyl)[2-(2'-amino-1,1'-biphenyl)]palladium(II).

Compounds are otherwise referred to by their IUPAC names or were named using ACD/ChemSketch 2015 or 2017 versions (commercially available from ACD Labs).

EXPERIMENTAL

Diethyl 2-(((3-bromo-4-chlorophenyl)amino)methylene)malonate

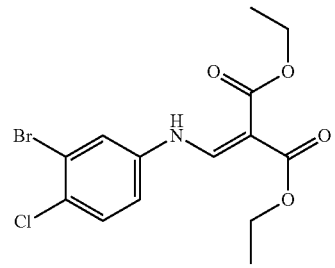 [SMILES: CCOC(=O)C(=CNc1ccc(Cl)c(Br)c1)C(=O)OCC]

Diethyl 2-(ethoxymethylene)malonate (11.69 ml, 57.83 mmol) was added to 3-bromo-4-chloroaniline (9.95 g, 48.19 mmol) in EtOH (100 ml). The resulting solution was stirred at 80° C. for 16 hours. The reaction mixture was concentrated and the residue diluted with heptane (75 ml). The mixture was stirred for 20 minutes at ambient temperature, by which time a solid had precipitated from solution. The solid was collected by filtration, washed with heptane and dried under vacuum to give diethyl 2-(((3-bromo-4-chlorophenyl)amino)methylene)malonate (15.34 g, 85%) as a white solid. 1H NMR (500 MHz, DMSO, 27° C.) 1.24 (6H, t), 4.06-4.27 (4H, m), 7.43 (1H, dd), 7.58 (1H, d), 7.88 (1H, d), 8.30 (1H, s), 10.57 (1H, s). m/z: ES− [M−H]− 374.

Ethyl 7-bromo-6-chloro-4-hydroxyquinoline-3-carboxylate

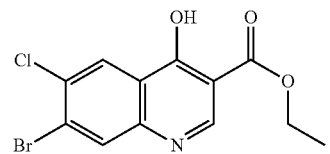 [SMILES: CCOC(=O)c1cnc2cc(Br)c(Cl)cc2c1O]

Diethyl 2-(((3-bromo-4-chlorophenyl)amino)methylene) malonate (5 g, 13.28 mmol) was added to DOWTHERM™ (35 ml) at 260° C. The resulting solution was stirred at 260° C. for 4 hours under reflux. The reaction was cooled to 40° C. with stirring. The resulting solid was collected by filtration, washed with diethyl ether (3×50 ml) and dried under vacuum to afford crude ethyl 7-bromo-6-chloro-4-hydroxyquinoline-3-carboxylate (3.94 g, 90%) as a beige solid which was used without purification. m/z: ES+ [M+H]+ 330.

7-Bromo-6-chloro-4-hydroxyquinoline-3-carboxylic acid

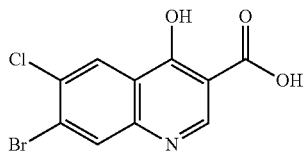 [SMILES: O=C(O)c1cnc2cc(Br)c(Cl)cc2c1O]

2M Sodium hydroxide solution (15.13 ml, 30.25 mmol) was added to a suspension of ethyl 7-bromo-6-chloro-4-hydroxyquinoline-3-carboxylate (2 g, 6.05 mmol) in EtOH (20 ml). The mixture was heated at 100° C. for 30 minutes. The mixture was cooled to ambient temperature, diluted with water (70 ml) and adjusted to pH3 with 2N HCl solution. The resulting precipitate was collected by filtration, washed with water and dried under vacuum at 65° C. to afford 7-bromo-6-chloro-4-hydroxyquinoline-3-carboxylic acid (1.72 g, 94%) as a pale pink solid, which was used without purification. 1H NMR (500 MHz, DMSO, 27° C.) 8.18 (1H, s), 8.32 (1H, s), 8.94 (1H, s), 13.38 (1H, br s), (1 exchangeable proton not seen). m/z: ES+ [M+H]+ 302.

7-Bromo-6-chloroquinolin-4-ol

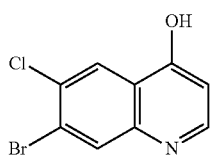 [SMILES: Oc1ccnc2cc(Br)c(Cl)cc12]

7-Bromo-6-chloro-4-hydroxyquinoline-3-carboxylic acid (8.52 g, 28.16 mmol) in sulfolane (2 ml) was heated at 250° C. for 2 hours. The mixture was cooled to 60° C. and added to stirred water (50 ml). The resulting precipitate was collected by filtration, washed with water and dried under vacuum to afford 7-bromo-6-chloroquinolin-4-ol (6.89 g, 95%) as a beige solid, which was used without further purification. 1H NMR (500 MHz, DMSO, 27° C.) 6.08 (1H, d), 7.94 (1H, s), 7.96 (1H, d), 8.13 (1H, s), 11.86 (1H, s). m/z: ES+ [M+H]+ 258.

7-Bromo-6-chloro-3-nitroquinolin-4(1H)-one

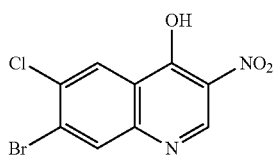 [SMILES: O=[N+]([O-])c1cnc2cc(Br)c(Cl)cc2c1O]

7-Bromo-6-chloroquinolin-4(1H)-one (4.2 g, 16.25 mmol) was added to stirred propionic acid (30 ml, 487.43 mmol) and the mixture was heated at 125° C. with stirring. Fuming nitric acid (1.36 ml, 32.5 mmol) was added dropwise, and the solution was stirred for a further 90 minutes at 125° C. before being allowed to cool to room temperature. Water (30 ml) was added, and the mixture was filtered. The solid collected was washed with water (2×1 ml) and EtOH (2 ml) then dried in a vacuum oven to give 7-bromo-6-chloro-3-nitroquinolin-4(1H)-one (2.8 g, 57%) as a yellow solid. 1H NMR (500 MHz, DMSO, 27° C.) 8.10 (1H, s), 8.29 (1H, s), 9.26 (1H, s), 13.03 (1H, s). m/z: ES+ [M+H]+ 302.

7-Bromo-4,6-dichloro-3-nitroquinoline

Phosphoryl trichloride (2.57 ml, 27.68 mmol) was added to 7-bromo-6-chloro-3-nitroquinolin-4(1H)-one (2.8 g, 9.23 mmol) in toluene (25 ml). After heating with stirring at 105° C., DMF (0.1 ml) was added and the mixture was stirred at 105° C. for 5 h, then allowed to cool to room temperature. The solvents were removed by evaporation. Toluene (10 ml) was added and the solvents evaporated. The residue was taken up in DCM (100 ml) and poured into ice-cold saturated aq. NaHCO$_3$ (100 ml). The mixture was extracted with DCM (4×100 ml). The combined organic layers were washed with water (100 ml), brine, dried and evaporated to give 7-bromo-4,6-dichloro-3-nitroquinoline (2.8 g, 94%) as a pale yellow solid. 1H NMR (500 MHz, DMSO, 27° C.) 8.59 (1H, d), 8.70 (1H, s), 9.42 (1H, s).

Tert-Butyl (R)-4-(7-bromo-6-chloro-3-nitroquinolin-4-yl)-3-(hydroxymethyl)piperazine-1-carboxylate

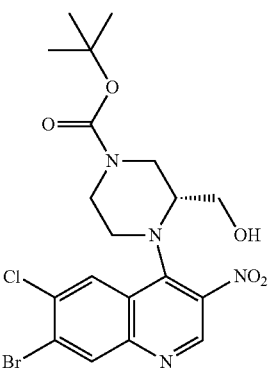 [SMILES: CC(C)(C)OC(=O)N1CCN(c2c([N+](=O)[O-])cnc3cc(Br)c(Cl)cc23)[C@@H](CO)C1]

Tert-butyl (R)-3-(hydroxymethyl)piperazine-1-carboxylate (384 mg, 1.78 mmol) was added to a mixture of 7-bromo-4,6-dichloro-3-nitroquinoline (260 mg, 0.81 mmol) and DIPEA (0.316 ml, 1.78 mmol) in NMP (4 ml). The mixture was heated at 75° C. for 2 hours, then allowed to cool to room temperature. The mixture was partitioned between ethyl acetate (100 ml) and water (100 ml). The aqueous layer was extracted with ethyl acetate (100 ml) and the extracts combined with the organic layer. The combined organics were washed sequentially with water (2×100 ml) and saturated brine (50 ml), then dried and evaporated to dryness to give a brown gum. The crude product was purified by flash silica chromatography, elution gradient 20 to 40% EtOAc in heptane. Pure fractions were evaporated to dryness to afford tert-butyl (R)-4-(7-bromo-6-chloro-3-nitroquinolin-4-yl)-3-(hydroxymethyl)piperazine-1-carboxylate (218 mg, 54%) as a yellow solid. 1H NMR (500 MHz, DMSO, 27° C.) 1.43 (9H, s), 3.34-3.53 (5H, m), 3.64 (3H, d), 4.34-4.42 (1H, m), 4.58 (1H, t), 8.38 (1H, d), 8.49 (1H, s), 9.05 (1H, s). m/z: ES+ [M+H]+ 501.

Tert-Butyl (R)-10-bromo-11-chloro-1,2,4a,5-tetrahydropyrazino[1',2':4,5][1,4]oxazino[2,3-c]quinoline-3(4H)-carboxylate

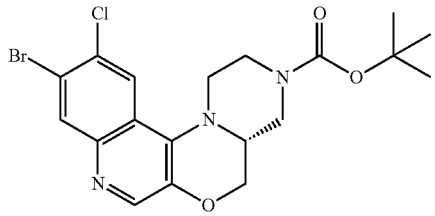 [SMILES: CC(C)(C)OC(=O)N1CCN2c3c(cnc4cc(Br)c(Cl)cc34)OC[C@H]2C1]

Tert-butyl (R)-4-(7-bromo-6-chloro-3-nitroquinolin-4-yl)-3-(hydroxymethyl)piperazine-1-carboxylate (460 mg, 0.92 mmol) was dissolved in DMF (24 ml) under nitrogen at room temperature. The solution was split into 3 equal portions in screw cap vials. To each vial was added sodium hydride (37 mg, 60% in mineral oil) (total across the 3 vials 110 mg, 2.75 mmol), then each vial was sealed and stirred at 95° C. for 84 hrs, then allowed to cool to room temperature. The reaction mixture was concentrated to remove most DMF solvent to give a liquid residue. To this was added DCM (200 ml), and the organic layer washed with water (3×100 ml), brine, and evaporated to give a gum residue. The crude product was purified by flash silica chromatography, elution gradient 10 to 25% EtOAc in heptane. Pure fractions were evaporated to dryness to afford tert-butyl (R)-10-bromo-11-chloro-1,2,4a,5-tetrahydropyrazino[1',2':4,5][1,4]oxazino[2,3-c]quinoline-3(4H)-carboxylate (200 mg, 48%) as a yellow gum. 1H NMR (500 MHz, DMSO, 27° C.) 1.42 (9H, s), 3.16 (1H, d), 3.33 (1H, s), 3.38-3.55 (2H, m), 3.61 (1H, d), 3.74 (2H, s), 4.19 (1H, t), 4.35 (1H, dd), 8.11 (1H, s), 8.29 (1H, s), 8.52 (1H, s). m/z: ES+ [M+H]+ 454.

Tert-Butyl (4aR)-11-chloro-10-(2-fluoro-6-hydroxyphenyl)-1,2,4a,5-tetrahydropyrazino[1',2':4,5][1,4]oxazino[2,3-c]quinoline-3(4H)-carboxylate

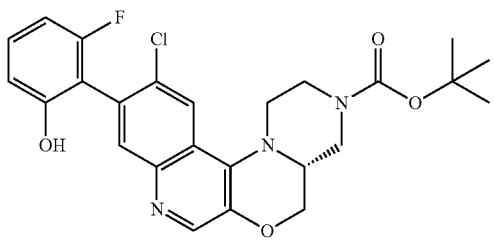 [SMILES: CC(C)(C)OC(=O)N1CCN2c3c(cnc4cc(-c5c(O)cccc5F)c(Cl)cc34)OC[C@H]2C1]

Pd-100 (PdCl$_2$(PPh$_3$)$_2$) (21 mg, 0.03 mmol) was added to a degassed mixture of tert-butyl (R)-10-bromo-11-chloro-1,2,4a,5-tetrahydropyrazino[1',2':4,5][1,4]oxazino[2,3-c]quinoline-3(4H)-carboxylate (136 mg, 0.3 mmol), (2-fluoro-6-hydroxyphenyl)boronic acid (117 mg, 0.75 mmol) and potassium carbonate (124 mg, 0.9 mmol) in 1,4-dioxane (2.5 ml) and water (1 ml). The mixture was sealed in a microwave tube and heated at 100° C. for 6 hours then allowed to cool to room temperature. 1,1'-Bis(di-tert-butylphosphino) ferrocene palladium dichloride (19.5 mg, 0.03 mmol), potassium carbonate (41.3 mg, 0.3 mmol) and (2-fluoro-6-hydroxyphenyl)boronic acid (46.6 mg, 0.3 mmol) were added. The vial was resealed under nitrogen, and heated at 110° C. in the microwave for 2 hours then cooled to room temperature. The reaction mixture was diluted with water (60 ml) and extracted with DCM (3×60 ml). The combined organic layers were washed with brine, dried and evaporated to give a crude residue. The crude product was purified by flash silica chromatography, elution gradient 10 to 50% EtOAc in heptane. Pure fractions were evaporated to dryness to afford tert-butyl (4aR)-11-chloro-10-(2-fluoro-6-hydroxyphenyl)-1,2,4a,5-tetrahydropyrazino[1',2':4,5][1,4]oxazino[2,3-c]quinoline-3(4H)-carboxylate (53 mg, 37%) as a white solid. 1H NMR (500 MHz, DMSO, 27° C.) 1.43 (9H, s), 3.19 (1H, s), 3.33 (1H, s), 3.46 (2H, d), 3.63 (1H, d), 3.79 (2H, s), 4.17-4.26 (1H, m), 4.36 (1H, dd), 6.74 (1H, t), 6.81 (1H, d), 7.27 (1H, td), 7.81 (1H, d), 8.05 (1H, s), 8.53 (1H, s), 9.97 (1H, d). m/z: ES+ [M+H]+ 486.

2-((4aR)-11-Chloro-1,2,3,4,4a,5-hexahydropyrazino[1',2':4,5][1,4]oxazino[2,3-c]quinolin-10-yl)-3-fluorophenol

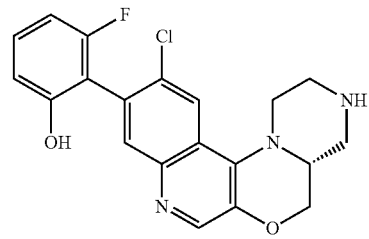 [SMILES: Oc1cccc(F)c1-c1cc2ncc3c(c2cc1Cl)N1CCNC[C@@H]1CO3]

TFA (0.5 ml, 6.53 mmol) was added to tert-butyl (4aR)-11-chloro-10-(2-fluoro-6-hydroxyphenyl)-1,2,4a,5-tetrahydropyrazino[1',2':4,5][1,4]oxazino[2,3-c]quinoline-3(4H)-carboxylate (51 mg, 0.1 mmol) in DCM (2 ml) at room temperature and the mixture was stirred at room temperature for 1 hour. The solution was evaporated to give a gum. The residue was purified by ion exchange chromatography, using an SCX2 column (5 g). The desired product was eluted from the column using 1M NH$_3$/MeOH. Pure fractions were evaporated to dryness to afford 2-((4aR)-11-chloro-1,2,3,4,4a,5-hexahydropyrazino[1',2':4,5][1,4]oxazino[2,3-c]quinolin-10-yl)-3-fluorophenol (41 mg, 101%) as a white solid. 1H NMR (500 MHz, CDCl$_3$, 27° C.) 2.75-2.83 (1H, m), 2.94 (1H, dt), 3.02-3.35 (6H, m), 3.41-3.47 (1H, m), 4.25 (1H, ddd), 4.32 (1H, dd), 6.65-6.74 (1H, m), 6.86-6.92 (1H, m), 7.22-7.31 (1H, m), 7.68 (1H, s), 7.89 (1H, s), 8.23 (1H, s). m/z: ES+ [M+H]+ 386.

1-((4aR)-11-Chloro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one Atropisomer 1, Example 1 and Atropisomer 2, Example 2

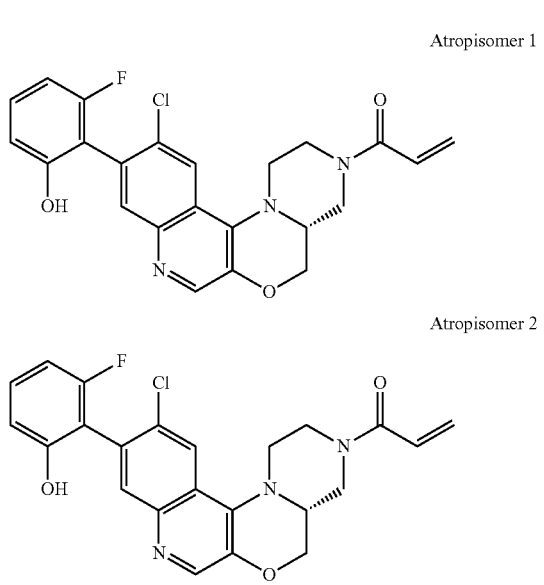

Acryloyl chloride (8.88 µl, 0.11 mmol) in THF (0.5 ml) was added dropwise over 3 minutes to a mixture of 2-((4aR)-11-chloro-1,2,3,4,4a,5-hexahydropyrazino[1',2':4,5][1,4]oxazino[2,3-c]quinolin-10-yl)-3-fluorophenol (40 mg, 0.1 mmol) and DIPEA (0.022 ml, 0.12 mmol) in THF (2 ml) at −15° C., and the resultant mixture was stirred at −15° C. for 2 hours, warming to 0° C. over this time. To the reaction mixture was added DCM (50 ml), and the organic layer was washed with water (30 ml), brine, dried and evaporated to give a crude residue. To this residue was added DMSO (1.5 ml) and the mixture filtered. The crude products were purified from this solution by preparative LCMS (Waters XSelect CSH C18 column, 5µ silica, 30 mm diameter, 100 mm length), using decreasingly polar mixtures of water (containing 1% $NH_3$) and MeCN as eluents. Fractions containing the desired compounds were evaporated then extracted with DCM (3×150 ml). The combined organic layers were washed with brine (150 ml), dried and evaporated to give 1-((4aR)-11-chloro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one atropisomer 1 (9 mg, 20%) as a white solid. 1H NMR (500 MHz, $CDCl_3$, 27° C.) 1.59 (1H, s), 3.11 (1H, s), 3.36 (1H, s), 3.42 (1H, s), 3.71 (3H, d), 4.20 (3H, d), 5.74 (1H, d), 6.34 (1H, d), 6.49 (1H, d), 6.64 (1H, t), 6.84 (1H, d), 7.2-7.24 (1H, m), 7.70 (1H, s), 7.90 (1H, s), 8.20 (1H, s). m/z: ES+ [M+H]+ 440, followed by 1-((4aR)-11-chloro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one atropisomer 2 (9 mg, 20%) as a white solid. 1H NMR (500 MHz, $CDCl_3$, 27° C.) 3.29 (1H, d), 3.39 (2H, s), 3.42 (1H, s), 3.80 (2H, s), 4.11-4.24 (3H, m), 5.73 (1H, d), 6.3-6.35 (1H, m), 6.50 (1H, dd), 6.69 (1H, d), 6.82 (1H, t), 6.93-6.96 (1H, m), 7.23-7.3 (1H, m), 7.92 (1H, s), 7.99 (1H, s), 8.39 (1H, s). m/z: ES+ [M+H]+ 440.

Tert-Butyl (4aR)-11-chloro-10-(5-methyl-1H-indazol-4-yl)-1,2,4a,5-tetrahydropyrazino[1',2':4,5][1,4]oxazino[2,3-c]quinoline-3(4H)-carboxylate

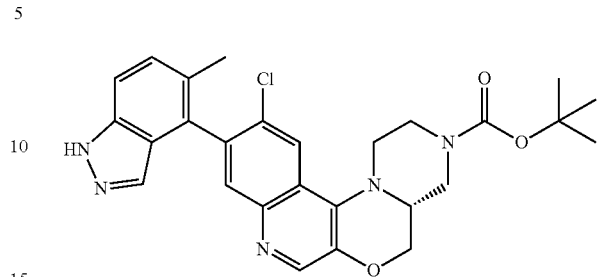

Pd-100 (30.1 mg, 0.04 mmol) was added to a degassed mixture of tert-butyl (R)-10-bromo-11-chloro-1,2,4a,5-tetrahydropyrazino[1',2':4,5][1,4]oxazino[2,3-c]quinoline-3(4H)-carboxylate (195 mg, 0.43 mmol), (5-methyl-1H-indazol-4-yl)boronic acid (189 mg, 1.07 mmol) and potassium carbonate (178 mg, 1.29 mmol) in 1,4-dioxane (4 ml) and water (1.5 ml). The mixture was sealed in a microwave tube and heated at 105° C. for 8 hours then allowed to cool to room temperature. The reaction mixture was diluted with water (60 ml) and extracted with DCM (3×60 ml). The combined organic layers were washed with brine, dried and evaporated to give a crude residue. The crude product was purified by flash silica chromatography, elution gradient 20 to 60% EtOAc in heptane. Pure fractions were evaporated to dryness to afford tert-butyl (4aR)-11-chloro-10-(5-methyl-1H-indazol-4-yl)-1,2,4a,5-tetrahydropyrazino[1',2':4,5][1,4]oxazino[2,3-c]quinoline-3(4H)-carboxylate (213 mg, 98%) as a white solid. 1H NMR (500 MHz, DMSO, 27° C.) 1.44 (9H, s), 2.15 (3H, d), 3.27 (1H, s), 3.35 (1H, d), 3.52 (2H, d), 3.64 (1H, d), 3.80 (2H, d), 4.24 (1H, t), 4.38 (1H, dt), 7.35 (1H, dd), 7.42-7.55 (2H, m), 7.83 (1H, d), 8.14 (1H, s), 8.55 (1H, d), 13.09 (1H, s). m/z: ES+ [M+H]+ 506.

(4aR)-11-Chloro-10-(5-methyl-1H-indazol-4-yl)-1,2,3,4,4a,5-hexahydropyrazino[1',2':4,5][1,4]oxazino[2,3-c]quinoline

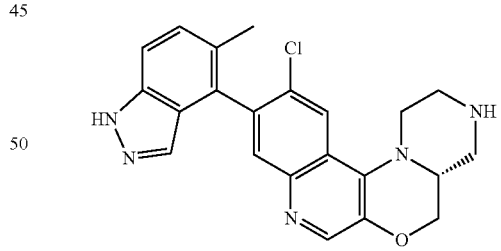

TFA (2 ml, 26.14 mmol) was added to tert-butyl (4aR)-11-chloro-10-(5-methyl-1H-indazol-4-yl)-1,2,4a,5-tetrahydropyrazino[1',2':4,5][1,4]oxazino[2,3-c]quinoline-3(4H)-carboxylate (210 mg, 0.42 mmol) in DCM (6 ml) at room temperature and the mixture was stirred at room temperature for 18 hours. The solution was evaporated to give a gum. The residue was purified by ion exchange chromatography, using an SCX2 column (10 g). The desired product was eluted from the column using 1M $NH_3$/MeOH. Pure fractions were evaporated to dryness to afford (4aR)-11-chloro-10-(5-methyl-1H-indazol-4-yl)-1,2,3,4,4a,5-hexahydropyrazino[1',2':4,5][1,4]oxazino[2,3-c]quinoline (153 mg, 91%)

as a white solid. 1H NMR (500 MHz, DMSO, 27° C.) 2.15 (3H, d), 2.5-2.51 (1H, m), 2.93 (1H, s), 2.96-3.06 (2H, m), 3.1-3.25 (3H, m), 3.44 (1H, dd), 4.28 (1H, dt), 4.49 (1H, td), 7.35 (1H, dd), 7.43-7.54 (2H, m), 7.82 (1H, d), 8.09 (1H, d), 8.54 (1H, d), 13.06 (1H, d). m/z: ES+ [M+H]+ 406.

1-((4aR)-11-Chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one Atropisomer 1, Example 3 and Atropisomer 2, Example 4

Atropisomer 1

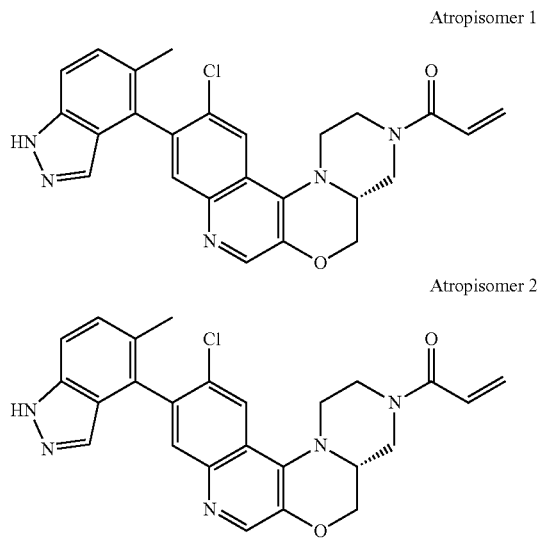

Atropisomer 2

Acryloyl chloride (0.036 ml, 0.44 mmol) in DMA (0.5 ml) was added dropwise over 3 minutes to a mixture of (4aR)-11-chloro-10-(5-methyl-1H-indazol-4-yl)-1,2,3,4,4a,5-hexahydropyrazino[1',2':4,5] [1,4]oxazino[2,3-c]quinoline (150 mg, 0.37 mmol) and DIPEA (0.077 ml, 0.44 mmol) in DMA (2.5 ml) at −15° C., and the resultant mixture was stirred at −15° C. for 60 minutes. To the reaction mixture was added DCM (70 ml), and the organic layer was washed with water (2×40 ml), brine, dried and evaporated to give a crude residue. To this residue was added DMSO (2.5 ml) and the mixture filtered. The crude products were purified from this solution by preparative LCMS (Waters XSelect CSH C18 column, 5μ silica, 30 mm diameter, 100 mm length), using decreasingly polar mixtures of water (containing 1% NH₃) and MeCN as eluents. Fractions containing the desired compounds were evaporated to dryness to afford 1-((4aR)-11-chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one atropisomer 1 (26 mg, 15%) as a white solid 1H NMR (500 MHz, DMSO, 27° C.) 2.23 (3H, s), 3.3-3.36 (1H, m), 3.52 (1H, s), 3.68 (1H, d), 3.72-3.92 (1H, m), 4.02 (1H, d), 4.11-4.35 (3H, m), 4.44 (1H, d), 5.81 (1H, s), 6.25 (1H, d), 6.86-7 (1H, m), 7.41 (1H, d), 7.52 (1H, s), 7.59 (1H, d), 7.91 (1H, s), 8.25 (1H, s), 8.63 (1H, s), 13.17 (1H, s). m/z: ES+ [M+H]+ 460 followed by 1-((4aR)-11-chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one atropisomer 2 (24 mg, 14%) as a white solid. 1H NMR (500 MHz, DMSO, 27° C.) 2.21 (3H, s), 3.34 (1H, s), 3.52 (1H, s), 3.63-3.71 (1H, m), 3.77 (1H, d), 3.88 (1H, s), 4.03 (1H, d), 4.21 (1H, d), 4.31 (1H, d), 4.46 (1H, dd), 5.82 (1H, s), 6.25 (1H, d), 6.86-7 (1H, m), 7.41 (1H, d), 7.55 (1H, s), 7.59 (1H, d), 7.91 (1H, s), 8.25 (1H, s), 8.63 (1H, s), 13.17 (1H, s). m/z: ES+ [M+H]+ 460.

Tert-butyl (S)-4-(7-bromo-6-chloro-3-nitroquinolin-4-yl)-3-(hydroxymethyl) piperazine-1-carboxylate

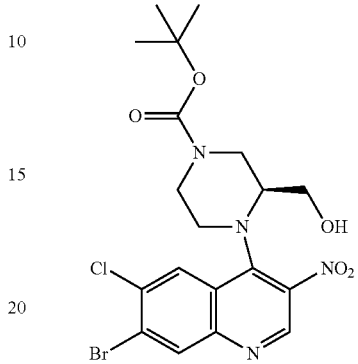

Tert-butyl (S)-3-(hydroxymethyl)piperazine-1-carboxylate (887 mg, 4.1 mmol) was added to 7-bromo-4,6-dichloro-3-nitroquinoline (600 mg, 1.86 mmol), and DIPEA (0.664 ml, 3.73 mmol) in NMP (4.5 ml) in a microwave tube, which was sealed and heated at 80° C. in a microwave reactor for 60 mins. To the reaction mixture was added DCM (150 ml), and the organic layer was washed with water (3×100 ml), brine, dried and evaporated to give a crude residue. The crude product was purified by flash silica chromatography, elution gradient 10 to 30% EtOAc in heptane. Pure fractions were evaporated to dryness to afford tert-butyl (S)-4-(7-bromo-6-chloro-3-nitroquinolin-4-yl)-3-(hydroxymethyl) piperazine-1-carboxylate (365 mg, 39%) as a yellow solid. 1H NMR (500 MHz, DMSO, 27° C.) 1.44 (9H, s), 3.43-3.48 (2H, m), 3.76 (1H, s), 3.85-3.9 (1H, m), 3.96-4.05 (1H, m), 4.07-4.31 (3H, m), 4.58 (1H, t), 8.38 (1H, s), 8.50 (1H, s), 9.05 (1H, s), 11.15 (1H, s). m/z: ES+ [M+H]+ 501.

Tert-butyl (S)-10-bromo-11-chloro-1,2,4a,5-tetrahydropyrazino[1',2':4,5][1,4]oxazino[2,3-c]quinoline-3(4H)-carboxylate

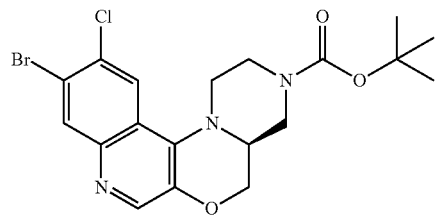 [SMILES: CC(C)(C)OC(=O)N1CCN2c3c(cnc4cc(Br)c(Cl)cc34)OC[C@@H]2C1]

Sodium hydride (60% in mineral oil) (102 mg, 2.55 mmol) was added to a stirred mixture of tert-butyl (S)-4-(7-bromo-6-chloro-3-nitroquinolin-4-yl)-3-(hydroxymethyl)piperazine-1-carboxylate (320 mg, 0.64 mmol) in dry DMF (18 ml) at room temperature, and the resultant mixture was split into 2 portions and each portion sealed in a vial and stirred at 95° C. for 72 hours then allowed to cool to room temperature. The reaction mixture was concentrated to give a liquid. To this was added DCM (200 ml), and the organic layer washed with water (3×100 ml), brine, and evaporated to give a liquid. The crude product was purified by flash silica chromatography, elution gradient 10 to 25% EtOAc in heptane. Pure fractions were evaporated to dryness to afford tert-butyl (S)-10-bromo-11-chloro-1,2,4a,5-tetrahydropyrazino[1',2':4,5][1,4]oxazino[2,3-c]quinoline-3(4H)-carboxylate (138 mg, 48%) as a yellow gum. 1H NMR (500 MHz, DMSO, 27° C.) 1.42 (9H, s), 3.18 (1H, s), 3.33 (1H, s), 3.36-3.57 (2H, m), 3.61 (1H, d), 3.74 (2H, s), 4.19 (1H, t), 4.35 (1H, dd), 8.11 (1H, s), 8.30 (1H, s), 8.53 (1H, s). m/z: ES+ [M+H]+ 454.

Tert-butyl (4aS)-11-chloro-10-(5-methyl-1H-indazol-4-yl)-1,2,4a,5-tetrahydropyrazino[1',2':4,5][1,4]oxazino[2,3-c]quinoline-3(4H)-carboxylate

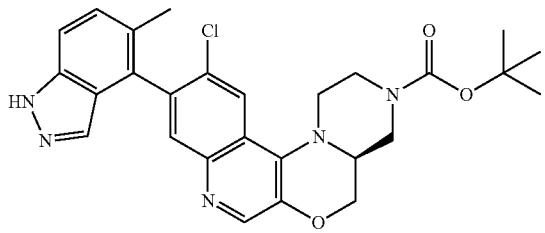 [SMILES: Cc1ccc2[nH]ncc2c1-c1cc2ncc3c(c2cc1Cl)N1CCN(C(=O)OC(C)(C)C)C[C@H]1CO3]

Pd-100 (40 mg, 0.06 mmol) and Pd-118 (38 mg, 0.06 mmol) were added to a mixture of tert-butyl (S)-10-bromo-11-chloro-1,2,4a,5-tetrahydropyrazino[1',2':4,5][1,4]oxazino[2,3-c]quinoline-3(4H)-carboxylate (130 mg, 0.29 mmol), (5-methyl-1H-indazol-4-yl)boronic acid (276 mg, 1.55 mmol) and potassium carbonate (240 mg, 1.72 mmol) in 1,4-dioxane (3 ml) and water (1 ml). The mixture was sealed in a microwave tube and heated at 105° C. for a total of 8 hours then allowed to cool to room temperature. The reaction mixture was diluted with water (60 ml) and extracted with DCM (3×60 ml). The combined organic layers were washed with brine, dried and evaporated to give a crude residue. The crude product was purified by flash silica chromatography, elution gradient 20 to 60% EtOAc in heptane. Pure fractions were evaporated to dryness to afford tert-butyl (4aS)-11-chloro-10-(5-methyl-1H-indazol-4-yl)-1,2,4a,5-tetrahydropyrazino[1',2':4,5][1,4]oxazino[2,3-c]quinoline-3(4H)-carboxylate as a mixture of atropisomers (102 mg, 71%) as a white solid. 1H NMR (500 MHz, DMSO, 27° C.) 1.44 (9H, s), 2.15 (3H, d), 3.28 (1H, d), 3.37 (1H, s), 3.52 (2H, d), 3.64 (1H, d), 3.78 (2H, s), 4.24 (1H, t), 4.38 (1H, dt), 7.33-7.38 (1H, m), 7.43-7.48 (1H, m), 7.51 (1H, t), 7.83 (1H, d), 8.14 (1H, s), 8.55 (1H, d), 13.06 (1H, d). m/z: ES+ [M+H]+ 506.

(4aS)-11-Chloro-10-(5-methyl-1H-indazol-4-yl)-1,2,3,4,4a,5-hexahydropyrazino[1',2':4,5][1,4]oxazino[2,3-c]quinoline

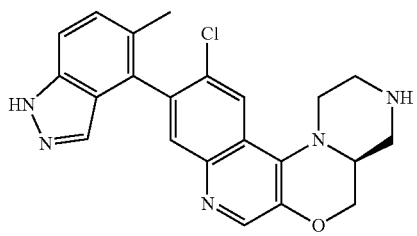 [SMILES: Cc1ccc2[nH]ncc2c1-c1cc2ncc3c(c2cc1Cl)N1CCNC[C@H]1CO3]

TFA (1 ml, 13.07 mmol) was added to tert-butyl (4aS)-11-chloro-10-(5-methyl-1H-indazol-4-yl)-1,2,4a,5-tetrahydropyrazino[1',2':4,5][1,4]oxazino[2,3-c]quinoline-3(4H)-carboxylate (98 mg, 0.19 mmol) in DCM (3 ml) at room temperature and the mixture was stirred for 24 hours. The solution was evaporated to give a gum. The residue was purified by ion exchange chromatography, using an SCX2 column. The desired product was eluted from the column using 1M NH3/MeOH. Pure fractions were evaporated to dryness to afford (4aS)-11-chloro-10-(5-methyl-1H-indazol-4-yl)-1,2,3,4,4a,5-hexahydropyrazino[1',2':4,5][1,4]oxazino[2,3-c]quinoline as a mixture of atropisomers (80 mg, 102%) as a white solid. 1H NMR (500 MHz, DMSO, 27° C.) 2.15 (3H, d), 2.5-2.51 (1H, m), 2.93 (1H, s), 2.98-3.06 (2H, m), 3.12-3.25 (3H, m), 3.42-3.48 (1H, m), 4.28 (1H, dt), 4.47-4.53 (1H, m), 7.35 (1H, dd), 7.43-7.54 (2H, m), 7.82 (1H, d), 8.09 (1H, d), 8.54 (1H, d), 13.06 (1H, d). m/z: ES+ [M+H]+ 406.

1-((4aS)-11-chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one Atropisomer 1, Example 5 and Atropisomer 2, Example 6

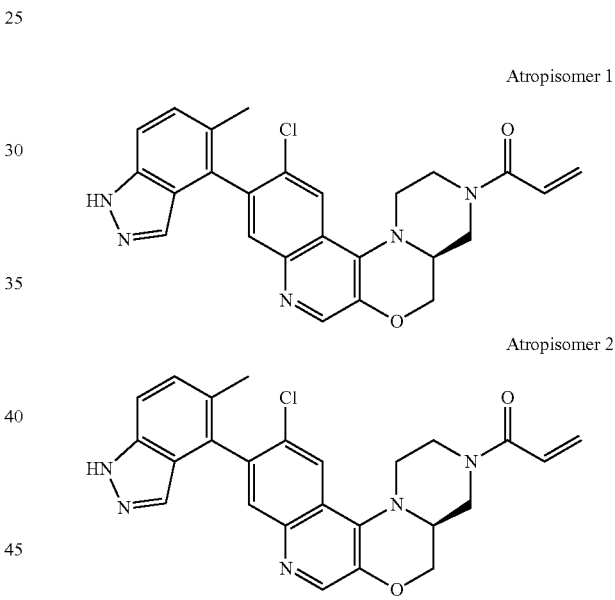

Acryloyl chloride (0.016 ml, 0.19 mmol) in DMA (0.5 ml) was added dropwise over 2 mins to a mixture of (4aS)-11-chloro-10-(5-methyl-1H-indazol-4-yl)-1,2,3,4,4a,5-hexahydropyrazino[1',2':4,5][1,4] oxazino[2,3-c]quinoline (78 mg, 0.19 mmol) and DIPEA (0.04 ml, 0.23 mmol) in DMA (1 ml) at −15° C., and the resultant mixture was stirred at −15° C. for 20 mins. To the reaction mixture was added DCM (50 ml), and the organic layer was washed with water (2×25 ml), brine, dried and evaporated to give a crude residue. To this residue was added DMSO (1 ml) and the mixture filtered. The crude products were purified from this solution by preparative LCMS (Waters XSelect CSH C18 column, 5μ silica, 30 mm diameter, 100 mm length), using decreasingly polar mixtures of water (containing 1% NH3) and MeCN as eluents. Fractions containing the desired compounds were evaporated to dryness to afford 1-((4aS)-11-chloro-10-(5-methyl-1H-indazol-4-yl)-1,2,4a,5-tetrahydropyrazino[1',2':4,5][1,4]oxazino [2,3-c]quinolin-3(4H)-yl)prop-2-en-1-one atropisomer 1 (10 mg, 11%) as a white solid 1H NMR (500

MHz, DMSO, 27° C.) 2.16 (3H, s), 3.45 (1H, s), 3.61 (1H, d), 3.70 (1H, s), 3.80 (1H, s), 3.97 (1H, s), 4.03-4.29 (3H, m), 4.41 (1H, s), 5.75 (1H, s), 6.18 (1H, d), 6.85 (1H, s), 7.34 (1H, d), 7.45 (1H, s), 7.52 (1H, d), 7.84 (1H, s), 8.18 (1H, s), 8.56 (1H, s), 13.09 (1H, s). m/z: ES+ [M+H]+ 460 and 1-((4aS)-11-chloro-10-(5-methyl-1H-indazol-4-yl)-1,2,4a, 5-tetrahydropyrazino[1',2':4,5][1,4]oxazino[2,3-c]quinolin-3(4H)-yl)prop-2-en-1-one atropisomer 2 (9 mg, 10%) as a white solid 1H NMR (500 MHz, DMSO, 27° C.) 2.14 (3H, s), 3.50 (1H, s), 3.64 (2H, d), 3.85 (1H, s), 4.00 (3H, d), 4.25 (1H, d), 4.38 (1H, d), 5.75 (1H, s), 6.18 (1H, d), 6.86 (1H, s), 7.34 (1H, d), 7.48 (1H, s), 7.53 (1H, d), 7.84 (1H, s), 8.20 (1H, s), 8.57 (1H, s), 13.11 (1H, s). m/z: ES+ [M+H]+ 460.

3-Bromo-4-chloro-2-fluoroaniline

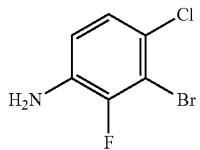

To a solution of 3-bromo-2-fluoroaniline (10 g, 52.63 mmol) in DMF (50 ml) was added 1-chloropyrrolidine-2,5-dione (7.38 g, 55.26 mmol) portionwise, and the resultant mixture stirred at room temperature for 3 hours. NOTE: delayed exotherm, after 1 hour temperature had risen to ca 50° C. Mixture was poured onto ice-water (300 ml) then extracted with ethyl acetate (200 ml) then organics were washed with water (2×200 ml) then brine. Organic extracts were dried and evaporated and the crude product purified by flash silica chromatography, elution gradient 0 to 5% EtOAc in heptane. Pure fractions were evaporated to dryness to afford 3-bromo-4-chloro-2-fluoroaniline (5.69 g, 48%) as a brown oil which solidified on standing. 1H NMR (400 MHz, DMSO) 5.58 (2H, s), 6.73-6.82 (1H, m), 7.12 (1H, dd).

7-Bromo-6-chloro-8-fluoroquinolin-4(1H)-one

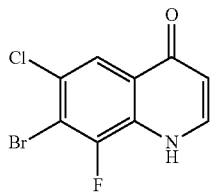 [SMILES: O=c1cc[nH]c2c(F)c(Br)c(Cl)cc12]

2,2-Dimethyl-1,3-dioxane-4,6-dione (4.94 g, 34.3 mmol) was added to trimethoxymethane (17.06 ml, 155.93 mmol), warmed at 110° C. (reflux) over a period of 10 minutes under nitrogen. The resulting solution was stirred at 85° C. for 1.5 hours under nitrogen. 3-Bromo-4-chloro-2-fluoroaniline (7 g, 31.19 mmol) was added, and the solution stirred at 85° C. for another 60 minutes. The mixture was cooled to room temperature, and the solid formed in the mixture was collected by filtration, and washed with i-PrOH (2×1 ml) and diethyl ether (2×2 ml) to give a pale orange solid. This solid was added to stirred DOWTHERM™ (200 ml) at 210° C.—vigorous evolution of gas. The orange solution was stirred for another 40 minutes at 210° C. then cooled to room temperature and stirred for 10 mins. To the mixture was added heptane (200 ml), and the mixture was filtered, with the solid collected washed on the filter with heptane then diethyl ether and dried on the filter to give 7-bromo-6-chloro-8-fluoroquinolin-4(1H)-one (5.6 g, 65%) as a tan solid. 1H NMR (400 MHz, DMSO, 30° C.) 6.15 (1H, d), 7.90 (1H, d), 8.01 (1H, d), 12.11 (1H, s). m/z: ES+ [M+H]+ 276.

7-Bromo-6-chloro-8-fluoro-3-nitroquinolin-4(1H)-one

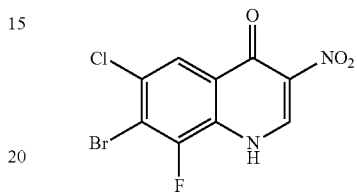

7-Bromo-6-chloro-8-fluoroquinolin-4(1H)-one (5.6 g, 20.25 mmol) was added to stirred propionic acid (55 ml, 607.62 mmol) and the mixture was heated at 125° C. with stirring. Nitric acid (fuming) (1.697 ml, 40.51 mmol) was added dropwise, and the solution was stirred for 2 hours at 125° C. before being allowed to cool to room temperature. Water (50 ml) was added, and the mixture was filtered. The solid collected was washed with water (2×20 ml) and diethyl ether (20 ml) then dried to give 7-bromo-6-chloro-8-fluoro-3-nitroquinolin-4(1H)-one (4.81 g, 74%) as a pale solid which was not purified further. 1H NMR (400 MHz, DMSO, 30° C.) 8.15 (1H, d), 8.96 (1H, s), 13.32 (1H, s). m/z: ES+ [M+H]+ 321.

7-Bromo-4,6-dichloro-8-fluoro-3-nitroquinoline

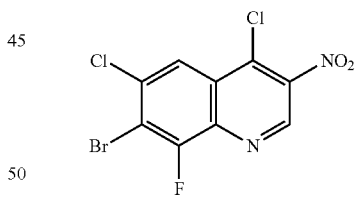

Phosphoryl trichloride (1.62 ml, 17.42 mmol) was added to 7-bromo-6-chloro-8-fluoro-3-nitroquinolin-4(1H)-one (1.4 g, 4.35 mmol) in toluene (25 ml) at room temperature. The mixture was heated at 100° C. with stirring, at which point DMF (0.1 ml) was added and the mixture was stirred at 105° C. overnight. The solvents were removed by evaporation. Toluene (20 ml) was added and the solvents evaporated. The residue was taken up in DCM (100 ml) and poured into ice-cold sat NaHCO₃ (200 ml). The mixture was extracted with DCM (3×100 ml). The combined organic layers were washed with brine, dried and evaporated to give 7-bromo-4,6-dichloro-8-fluoro-3-nitroquinoline (1.2 g, 81%) as a light brown solid. 1H NMR (400 MHz, DMSO, 30° C.) 8.51 (1H, d), 9.48 (1H, d).

Tert-butyl (R)-4-(7-bromo-6-chloro-8-fluoro-3-nitroquinolin-4-yl)-3-(hydroxymethyl)piperazine-1-carboxylate

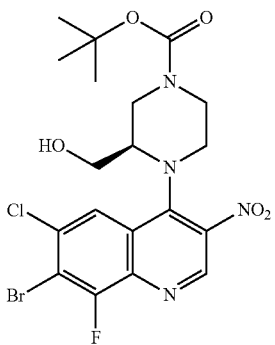 [SMILES: CC(C)(C)OC(=O)N1CCN(c2c([N+](=O)[O-])cnc3c(F)c(Br)c(Cl)cc23)[C@@H](CO)C1]

Tert-butyl (R)-3-(hydroxymethyl)piperazine-1-carboxylate (1.68 g, 7.77 mmol) was added to 7-bromo-4,6-dichloro-8-fluoro-3-nitroquinoline (1.2 g, 3.53 mmol), and DIPEA (1.571 ml, 8.83 mmol) in NMP (10 ml) under nitrogen, and the resulting solution was stirred at room temperature for 3 hours. The mixture was partitioned between ethyl acetate and water then the organic layer was washed with water (×2) then brine, dried and evaporated then purified by flash silica chromatography, elution gradient 10 to 40% EtOAc in heptane. Pure fractions were evaporated to dryness to afford tert-butyl (R)-4-(7-bromo-6-chloro-8-fluoro-3-nitroquinolin-4-yl)-3-(hydroxymethyl)piperazine-1-carboxylate (0.96 g, 52%) as a yellow solid. m/z: ES+ [M+H]+ 521.

Tert-butyl (3R)-4-(6-chloro-8-fluoro-7-(2-fluoro-6-methoxyphenyl)-3-nitroquinolin-4-yl)-3-(hydroxymethyl) piperazine-1-carboxylate

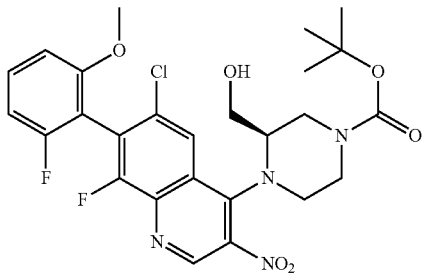 [SMILES: COc1cccc(F)c1-c1c(Cl)cc2c(N3CCN(C(=O)OC(C)(C)C)C[C@@H]3CO)c([N+](=O)[O-])cnc2c1F]

Tert-butyl (R)-4-(7-bromo-6-chloro-8-fluoro-3-nitroquinolin-4-yl)-3-(hydroxymethyl)piperazine-1-carboxylate (0.85 g, 1.64 mmol), (2-fluoro-6-methoxyphenyl)boronic acid (0.42 g, 2.45 mmol), 2M aqueous potassium carbonate (1.64 ml, 3.27 mmol), RuPhos Pd G3 (0.137 g, 0.16 mmol) and RuPhos (0.076 g, 0.16 mmol) were stirred in 1,4-dioxane (15 ml) and degassed by bubbling nitrogen. The mixture was heated at 80° C. for 1 hour under nitrogen then cooled to room temperature and partitioned between ethyl acetate and water, then the organic layer was dried and evaporated. The crude product was purified by flash silica chromatography, elution gradient 0 to 50% EtOAc in heptane. Pure fractions were evaporated to dryness to afford tert-butyl (3R)-4-(6-chloro-8-fluoro-7-(2-fluoro-6-methoxyphenyl)-3-nitroquinolin-4-yl)-3-(hydroxymethyl)piperazine-1-carboxylate (0.55 g, 60%) as a yellow solid. m/z: ES+ [M+H]+ 565.

Tert-butyl (4aR)-11-chloro-9-fluoro-10-(2-fluoro-6-methoxyphenyl)-1,2,4a,5-tetrahydropyrazino[1',2':4,5][1,4]oxazino[2,3-c]quinoline-3(4H)-carboxylate (Atropisomer 1 and 2)

Atropisomer 1

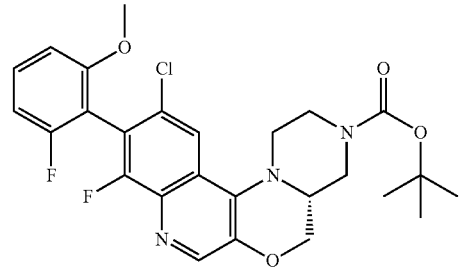

Atropisomer 2

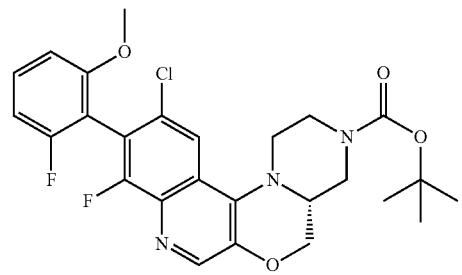

Tert-butyl (3R)-4-(6-chloro-8-fluoro-7-(2-fluoro-6-methoxyphenyl)-3-nitroquinolin-4-yl)-3-(hydroxymethyl)piperazine-1-carboxylate (0.53 g, 0.94 mmol) was dissolved in NMP (20 ml) under nitrogen at room temperature. Lithium bis(trimethylsilyl)amide (1.03 ml, 1.03 mmol) was added and the mixture was heated at 120° C. overnight. The mixture was partitioned between ethyl acetate and water then the organic layer washed with water (×2), dried and evaporated to afford a brown solid. The sample was dissolved in MeOH and separated using the SFC conditions detailed below: Column: Chiralpak IC, 30×250 mm, 5 micron Mobile phase: 40% MeOH+0.1% NH$_3$/60% scCO$_2$ Flow rate: 90 ml/min BPR: 120 bar Column temperature: 40° C. to afford atropisomer 1 of tert-butyl (4aR)-11-chloro-9-fluoro-10-(2-fluoro-6-methoxyphenyl)-1,2,4a,5-tetrahydropyrazino[1',2':4,5][1,4]oxazino[2,3-c]quinoline-3(4H)-carboxylate as a colourless glass (0.117 g, 24%, d.e.>99%). 1H NMR (400 MHz, DMSO, 30° C.) 1.45 (9H, s), 3.26 (1H, d), 3.38 (1H, s), 3.49 (2H, d), 3.65 (1H, d), 3.77 (5H, d), 4.25 (1H, t), 4.40 (1H, dd), 7.00 (1H, t), 7.07 (1H, d), 7.5-7.6 (1H, m), 7.94 (1H, s), 8.58 (1H, s). m/z: ES+ [M+H]+ 518. 1H NMR (400 MHz, DMSO, 30° C.) 1.45 (9H, s), 3.22 (1H, d), 3.34-3.56 (3H, m), 3.77 (6H, s), 4.25 (1H, t), 4.40 (1H, dd), 7.00 (1H, t), 7.07 (1H, d), 7.5-7.61 (1H, m), 7.94 (1H, s), 8.58 (1H, s). m/z: ES+ [M+H]+ 518, followed by atropisomer 2 of tert-butyl (4aR)-11-chloro-9-fluoro-10-(2-fluoro-6-methoxyphenyl)-1,2,4a,5-tetrahydropyrazino[1',2':4,5][1,4]oxazino[2,3-c]quinoline-3(4H)-carboxylate as a colourless glass (0.135 g, 27%, d.e.>99%). 1H NMR (400 MHz, DMSO) 1.45 (s, 9H), 3.26 (d, J=9.6 Hz, 1H), 3.38 (s, 1H), 3.49 (d, J=13.8 Hz, 2H), 3.65 (d, J=9.6 Hz, 1H), 3.77

(d, J=3.7 Hz, 5H), 4.25 (t, J=10.1 Hz, 1H), 4.40 (dd, J=2.7, 10.8 Hz, 1H), 7.00 (t, J=8.6 Hz, 1H), 7.07 (d, J=8.5 Hz, 1H), 7.5-7.6 (m, 1H), 7.94 (s, 1H), 8.58 (s, 1H). m/z: ES+ [M+H]+ 518.

2-((4aR)-11-Chloro-9-fluoro-1,2,3,4,4a,5-hexahydropyrazino[1',2':4,5][1,4]oxazino[2,3-c]quinolin-10-yl)-3-fluorophenol Atropisomer 1

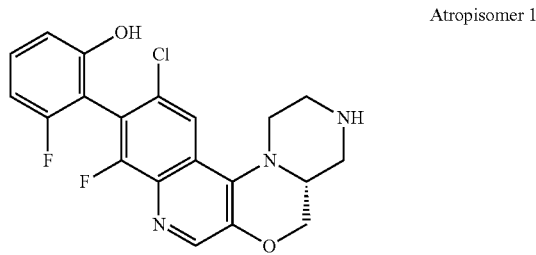 [SMILES: Oc1cccc(F)c1-c1c(Cl)cc2c3c(cnc2c1F)OC[C@H]1CNCCN31]

Tert-butyl (4aR)-11-chloro-9-fluoro-10-(2-fluoro-6-methoxyphenyl)-1,2,4a,5-tetrahydropyrazino[1',2':4,5][1,4]oxazino[2,3-c]quinoline-3(4H)-carboxylate (0.117 g, 0.23 mmol) was dissolved in DCM (3 ml) and the mixture was cooled at −78° C. under nitrogen then tribromoborane (1.807 ml, 1.81 mmol) was added dropwise. The mixture was stirred for 30 minutes then warmed to −10° C. and stirred for 2 hours. The mixture was quenched by addition of water (1 ml) then diluted with methanol and absorbed onto 10 g SCX cartridge. Washed with methanol then eluted with 2M ammonia in methanol then evaporated to afford 2-((4aR)-11-chloro-9-fluoro-1,2,3,4,4a,5-hexahydropyrazino [1',2':4,5][1,4]oxazino[2,3-c]quinolin-10-yl)-3-fluorophenol (0.078 g, 86%) as a colourless oily solid that was used without further purification. 1H NMR (400 MHz, CDCl$_3$, 30° C.) 3.00-3.12 (2H, m), 3.19 (1H, ddd), 3.28-3.41 (4H, m), 3.49 (1H, s), 4.26 (1H, dd), 4.39-4.52 (1H, m), 6.78 (1H, t), 6.85 (1H, d), 7.32 (1H, td), 7.77 (1H, d), 8.44 (1H, s), (1 exchangeable proton not seen). m/z: ES+ [M+H]+ 404.

2-((4aR)-11-Chloro-9-fluoro-1,2,3,4,4a,5-hexahydropyrazino[1',2':4,5][1,4]oxazino[2,3-c]quinolin-10-yl)-3-fluorophenol Atropisomer 2

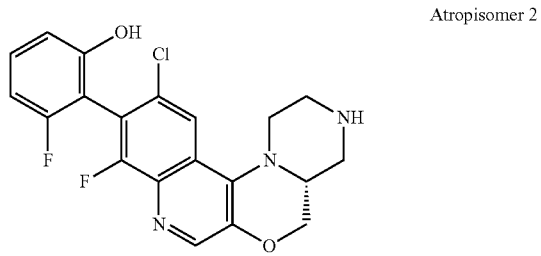 [SMILES: Oc1cccc(F)c1-c1c(Cl)cc2c3c(cnc2c1F)OC[C@H]1CNCCN31]

Tert-butyl (4aR)-11-chloro-9-fluoro-10-(2-fluoro-6-methoxyphenyl)-1,2,4a,5-tetrahydropyrazino [1',2':4,5][1,4]oxazino[2,3-c]quinoline-3(4H)-carboxylate (0.132 g, 0.25 mmol) was dissolved in DCM (3 ml) and the mixture was cooled to −78° C. under nitrogen then tribromoborane (2.039 ml, 2.04 mmol) was added dropwise. The mixture was stirred for 30 minutes then warmed to −10° C. and stirred for 2 hours. The mixture was quenched by addition of water (1 ml) then diluted with methanol and absorbed onto a 10 g SCX cartridge. This was washed with methanol, then eluted with 2M ammonia in methanol to afford 2-((4aR)-11-chloro-9-fluoro-1,2,3,4,4a,5-hexahydropyrazino[1',2':4,5][1,4]oxazino[2,3-c]quinolin-10-yl)-3-fluorophenol (0.082 g, 80%) as a colourless oily solid which was used without further purification. m/z: ES+ [M+H]+ 404.

1-((4aR)-11-Chloro-9-fluoro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one Atropisomer 1, Example 7

Atropisomer 1

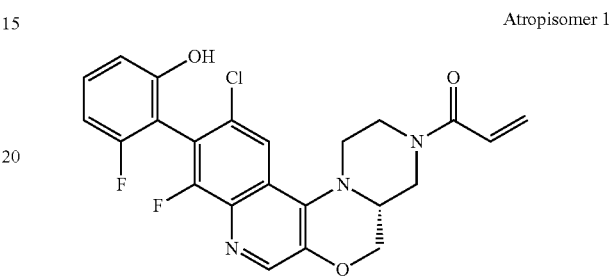

To a solution of 2-((4aR)-11-chloro-9-fluoro-1,2,3,4,4a,5-hexahydropyrazino[1',2':4,5][1,4]oxazino[2,3-c]quinolin-10-yl)-3-fluorophenol (76 mg, 0.19 mmol) in DCM (4 ml), i-PrOH (2 ml) and triethylamine (0.052 ml, 0.38 mmol) at −78° C. was added a solution of acryloyl chloride (18 mg, 0.2 mmol) in DCM (1 ml, added slowly dropwise over 5 min) and the reaction mixture stirred at −78° C. for ten minutes. The reaction mixture was brought up to room temperature and the DCM was removed in vacuo. 1M Methanolic ammonia (1 ml) was added and the crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents. Pure fractions were evaporated to afford 1-((4aR)-11-chloro-9-fluoro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one (18 mg, 21%, d.e.>99%) as a white solid. 1H NMR (400 MHz, DMSO, 30° C.) 3.44 (2H, d), 3.57 (1H, d), 3.76 (2H, d), 3.88-4.2 (3H, m), 4.24 (1H, t), 4.39 (1H, d), 5.75 (1H, s), 6.19 (1H, d), 6.69-6.98 (3H, m), 7.24-7.42 (1H, m), 7.96 (1H, d), 8.58 (1H, s). m/z: ES+ [M+H]+ 458.

1-((4aR)-11-Chloro-9-fluoro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one Atropisomer 2, Example 8

Atropisomer 2

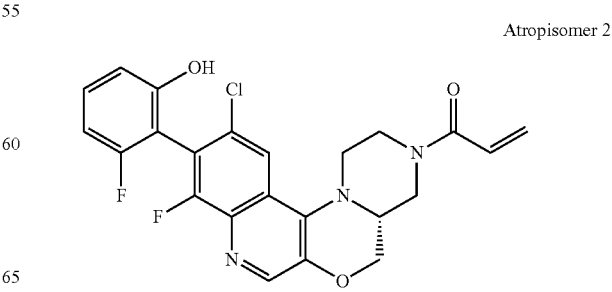

To a solution of 2-((4aR)-11-chloro-9-fluoro-1,2,3,4,4a,5-hexahydropyrazino[1',2':4,5][1,4]oxazino[2,3-c]quinolin-10-yl)-3-fluorophenol (73 mg, 0.18 mmol) in DCM (4 ml), i-PrOH (1.25 ml) and pyridine (28.6 mg, 0.36 mmol) at −78° C. was added a solution of acryloyl chloride (17 mg, 0.19 mmol) in DCM (1 ml, added slowly dropwise over 5 min) and the reaction mixture stirred at −78° C. for ten minutes. The reaction mixture was brought up to room temperature and the DCM was removed in vacuo. 1M Methanolic ammonia (1 ml) was added and the crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents. Pure fractions were evaporated to afford 1-((4aR)-11-chloro-9-fluoro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one (31 mg, d.e.>99%, 38%) as a white solid. 1H NMR (400 MHz, DMSO, 30° C.) 3.47 (1H, s), 3.51-3.66 (2H, m), 3.67-4.18 (4H, m), 4.24 (1H, t), 4.41 (1H, d), 5.77 (1H, s), 6.18 (1H, d), 6.71-6.98 (3H, m), 7.33 (1H, q), 7.95 (1H, d), 8.58 (1H, s), 10.18 (1H, s). m/z: ES+ [M+H]+ 458.

(2E)-1-[(4aR)-11-Chloro-10-(2-fluoro-6-hydroxyphenyl)-1,2,4a,5-tetrahydropyrazino[1',2':4,5][1,4]oxazino[2,3-c]quinolin-3(4H)-yl]-4-(dimethylamino)but-2-en-1-one, Example 9

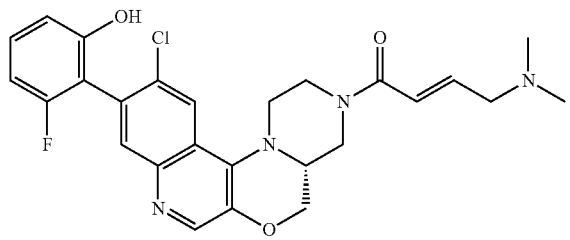 [SMILES: CN(C)C/C=C/C(=O)N1CCN2c3c(cnc4cc(-c5c(O)cccc5F)c(Cl)cc34)OC[C@H]2C1]

DIPEA (0.724 ml, 4.15 mmol) was added to 2-[(4aR)-11-chloro-1,2,3,4,4a,5-hexahydropyrazino[1',2':4,5][1,4]oxazino[2,3-c]quinolin-10-yl]-3-fluorophenol (400 mg, 1.04 mmol), (E)-4-(dimethylamino)but-2-enoic acid hydrochloride (172 mg, 1.04 mmol) and 1-ethyl-3-(3-dimethylaminopropyl)carbodiimide (397 mg, 2.07 mmol) in DMF (5 ml). The resulting solution was stirred at room temperature for 2 hours. The reaction mixture was purified by flash C18-flash chromatography, elution gradient 0 to 36% MeCN in water (0.2% NH$_4$OH). Pure fractions were evaporated to dryness to afford (E)-1-((4aR)-11-chloro-10-(2-fluoro-6-hydroxyphenyl)-1,2,4a,5-tetrahydropyrazino[1',2':4,5][1,4]oxazino[2,3-c]quinolin-3(4H)-yl)-4-(dimethylamino)but-2-en-1-one (98 mg, 19%) as a white solid. 1H NMR (300 MHz, DMSO-d6) 2.14 (6H, s), 2.94-3.26 (3H, m), 3.39-3.83 (3H, m), 3.84-4.25 (4H, m), 4.26-4.40 (1H, m), 6.62-6.75 (2H, m), 6.78 (2H, dd), 7.19-7.34 (1H, m), 7.81 (1H, d), 8.07 (1H, s), 8.52 (1H, s), 10.00 (1H, s). m/z (ES+), [M+H]+=497.

2-Amino-4-bromo-5-chloro-N-methoxy-N-methylbenzamide

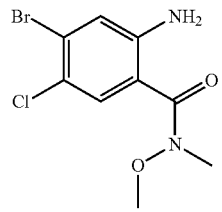

2-Amino-4-bromo-5-chlorobenzoic acid (2 g, 7.98 mmol) was added to thionyl chloride (0.58 ml, 7.98 mmol). The resulting mixture was stirred at 100° C. for 2 hours. The solvent was removed under reduced pressure and dissolved in DCM then added to a stirred mixture of N,O-dimethylhydroxylamine (0.975 g, 15.97 mmol), and DIPEA (4.18 ml, 23.95 mmol) in DCM (20 ml). The resulting mixture was stirred at 25° C. for 4 hours. The solvent was removed under reduced pressure. The crude product was purified by flash C18-flash chromatography, elution gradient 2 to 30% EtOAc in petroleum ether. Pure fractions were evaporated to dryness to afford 2-amino-4-bromo-5-chloro-N-methoxy-N-methylbenzamide (1.5 g, 64%) as a yellow oil. 1H NMR (DMSO-d6, 400 MHz) 3.23 (3H, s), 3.55 (3H, s), 7.11 (1H, s), 7.35 (1H, s), 7.96 (2H, s). m/z (ES+), [M+H]+=293.

1'-(2-Amino-4-bromo-5-chlorophenyl)ethan-1-one

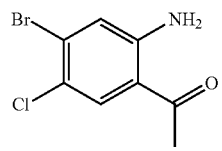

Methylmagnesium bromide (3.0 M in THF, 5.96 ml, 17.88 mmol) was added to 2-amino-4-bromo-5-chloro-N-methoxy-N-methylbenzamide (1.5 g, 5.11 mmol) in THF (20 ml). The resulting mixture was stirred at 25° C. for 4 hours. The reaction mixture was quenched with saturated aqueous NH$_4$Cl (50 ml), extracted with EtOAc (3×50 ml), the organic layer was dried, filtered and evaporated to afford yellow oil. The crude product was purified by flash silica chromatography, elution gradient 5 to 30% EtOAc in petroleum ether. Pure fractions were evaporated to dryness to afford 1-(2-amino-4-bromo-5-chlorophenyl)ethan-1-one (0.7 g, 55%) as a yellow solid. 1H NMR (DMSO-d6, 400 MHz) 2.51 (3H, d), 7.19 (1H, s), 7.36 (2H, s), 7.90 (1H, s). m/z (ES+), [M+H]+=248.

7-Bromo-6-chlorocinnolin-4-ol

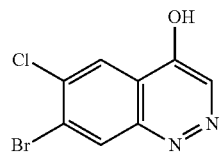 [SMILES: Oc1cnnc2cc(Br)c(Cl)cc12]

A solution of sodium nitrite (194 mg, 2.82 mmol) in water (1 ml) was added to a stirred mixture of 1-(2-amino-4-bromo-5-chlorophenyl)ethan-1-one (700 mg, 2.82 mmol) and HCl (3 ml, 3 mmol) in water (1 ml) cooled at 0° C., over a period of 10 minutes. The resulting mixture was stirred at 25° C. for 4 hours. The reaction mixture was poured into ice water. The precipitate was collected by filtration, washed with water (20 ml) and dried under vacuum to afford 7-bromo-6-chlorocinnolin-4-ol (300 mg, 41%) as a yellow solid. 1H NMR (DMSO-d6, 300 MHz) 7.78 (1H, s), 7.94 (1H, s), 8.09 (1H, s), 13.60 (1H, s).

7-bromo-6-chloro-3-nitrocinnolin-4-ol

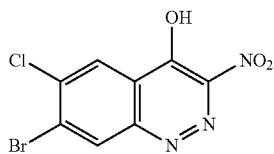 [SMILES: O=[N+]([O-])c1nnc2cc(Br)c(Cl)cc2c1O]

Nitric acid (1 ml, 1.16 mmol) was added to 7-bromo-6-chlorocinnolin-4-ol (300 mg, 1.16 mmol), in $H_2SO_4$ (2 ml) cooled at 0° C. The resulting mixture was stirred at 60° C. for 1 hour. The reaction mixture was poured into ice water. The precipitate was collected by filtration, washed with water (20 ml) and dried under vacuum to afford 7-bromo-6-chloro-3-nitrocinnolin-4-ol (200 mg, 57%) as a yellow solid. 1H NMR (DMSO-$d_6$, 300 MHz) 8.12 (1H, s), 8.30 (1H, s), (1 exchangeable proton not seen). m/z (ES+), [M+H]+=304.

7-Bromo-4,6-dichloro-3-nitrocinnoline

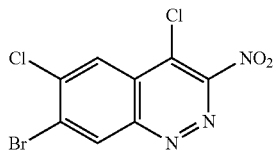

Phosphorus(V)oxychloride (0.06 ml, 0.66 mmol) was added to 7-bromo-6-chloro-3-nitrocinnolin-4-ol (100 mg, 0.33 mmol), in DMF (1 ml). The resulting mixture was stirred at 25° C. for 3 hours. The reaction mixture was poured into ice water. The precipitate was collected by filtration, washed with water (10 ml) and dried under vacuum to afford 7-bromo-4,6-dichloro-3-nitrocinnoline (40 mg, 38%) as a yellow solid. 1H NMR (DMSO-d6, 400 MHz) 8.47 (1H, s), 9.12 (1H, s). m/z (ES+), [M+H]+=324.

Tert-butyl (3R)-4-(7-bromo-6-chloro-3-nitrocinnolin-4-yl)-3-({[tert-butyl(dimethyl)silyl]oxy}methyl)piperazine-1-carboxylate

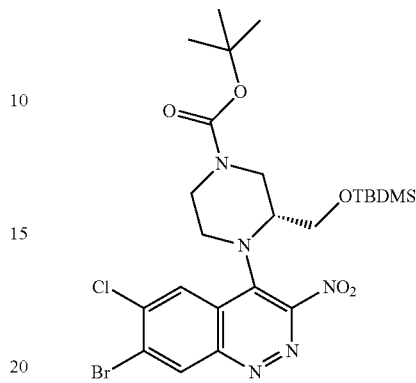

DIPEA (0.065 ml, 0.37 mmol) was added to 7-bromo-4,6-dichloro-3-nitrocinnoline (40 mg, 0.12 mmol) and tert-butyl (R)-3-(((tert-butyldimethylsilyl)oxy)methyl)piperazine-1-carboxylate (61 mg, 0.19 mmol) in i-PrOH (1 ml). The resulting mixture was stirred at 80° C. for 4 hours. The solvent was removed under reduced pressure. The crude product was purified by flash silica chromatography, elution gradient 2 to 10% EtOAc in petroleum ether. Pure fractions were evaporated to dryness to afford tert-butyl (R)-4-(7-bromo-6-chloro-3-nitrocinnolin-4-yl)-3-(((tert-butyldimethylsilyl)oxy)methyl) piperazine-1-carboxylate (30 mg, 39%) as a yellow solid. m/z (ES+), [M+H]+=618.

Tert-butyl (3R)-4-(7-bromo-6-chloro-3-nitrocinnolin-4-yl)-3-(hydroxymethyl)piperazine-1-carboxylate

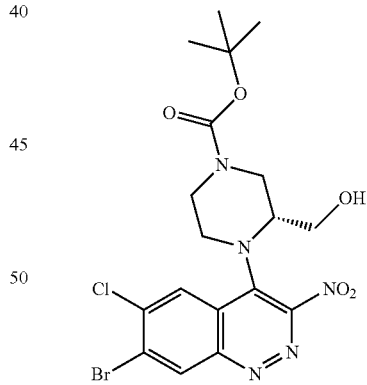

TBAF (1.0 M in THF, 0.146 ml, 0.15 mmol) was added to tert-butyl (3R)-4-(7-bromo-6-chloro-3-nitrocinnolin-4-yl)-3-({[tert-butyl(dimethyl)silyl]oxy}methyl)piperazine-1-carboxylate (30 mg, 0.05 mmol) in THF (1 ml). The resulting mixture was stirred at 25° C. for 5 hours. The solvent was removed under reduced pressure. The crude product was purified by flash silica chromatography, elution gradient 10 to 30% EtOAc in petroleum ether. Pure fractions were evaporated to dryness to afford tert-butyl (R)-4-(7-bromo-6-chloro-3-nitrocinnolin-4-yl)-3-(hydroxymethyl)piperazine-1-carboxylate (20 mg, 82%) as a yellow solid. m/z (ES+), [M+H]+=502.

Tert-butyl (4aR)-10-bromo-11-chloro-1,2,4a,5-tetrahydropyrazino[1',2':4,5][1,4]oxazino[2,3-c]cinnoline-3(4H)-carboxylate

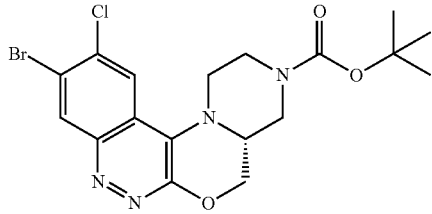 [SMILES: CC(C)(C)OC(=O)N1CCN2c3c(nnc4cc(Br)c(Cl)cc34)OC[C@H]2C1]

Lithium bis(trimethylsilyl)amide (1.19 ml, 1.19 mmol) was added to tert-butyl (3R)-4-(7-bromo-6-chloro-3-nitrocinnolin-4-yl)-3-(hydroxymethyl)piperazine-1-carboxylate (200 mg, 0.4 mmol) in DMF (10 ml). The resulting mixture was stirred at 100° C. for 8 hours. The solvent was removed under reduced pressure. The crude product was purified by flash silica chromatography, elution gradient 2 to 10% MeOH in DCM. Pure fractions were evaporated to dryness to afford tert-butyl (R)-10-bromo-11-chloro-1,2,4a,5-tetrahydropyrazino[1',2':4,5][1,4]oxazino[2,3-c]cinnoline-3(4H)-carboxylate (120 mg, 66%) as a yellow solid. m/z (ES+), [M+H]+=455.

Tert-butyl (4aR)-11-chloro-10-(2-fluoro-6-hydroxyphenyl)-1,2,4a,5-tetrahydropyrazino[1',2':4,5][1,4]oxazino[2,3-c]cinnoline-3(4H)-carboxylate

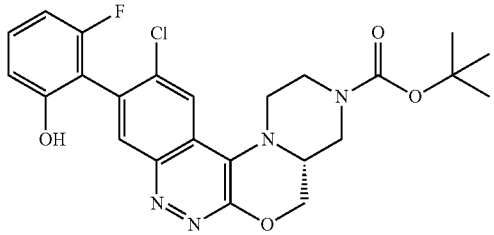 [SMILES: CC(C)(C)OC(=O)N1CCN2c3c(nnc4cc(-c5c(O)cccc5F)c(Cl)cc34)OC[C@H]2C1]

RuPhos Pd G3 (15 mg, 0.02 mmol) was added to tert-butyl (4aR)-10-bromo-11-chloro-1,2,4a,5-tetrahydropyrazino[1',2':4,5][1,4]oxazino[2,3-c]cinnoline-3(4H)-carboxylate (80 mg, 0.18 mmol), (2-fluoro-6-hydroxyphenyl)boronic acid (68.4 mg, 0.44 mmol), Ruphos (8 mg, 0.02 mmol) and potassium carbonate (61 mg, 0.44 mmol) in 1,4-dioxane (2 ml) and water (0.5 ml) under nitrogen. The resulting mixture was stirred at 100° C. for 3 hours. The solvent was removed under reduced pressure. The crude product was purified by flash silica chromatography, elution gradient 20 to 50% EtOAc in petroleum ether. Pure fractions were evaporated to dryness to afford tert-butyl (4aR)-11-chloro-10-(2-fluoro-6-hydroxyphenyl)-1,2,4a,5-tetrahydropyrazino[1',2':4,5][1,4]oxazino[2,3-c]cinnoline-3(4H)-carboxylate (26 mg, 30%) as a yellow solid. m/z (ES+), [M+H]+=487.

2-((4aR)-11-Chloro-1,2,3,4,4a,5-hexahydropyrazino[1',2':4,5][1,4]oxazino[2,3-c]cinnolin-10-yl)-3-fluorophenol

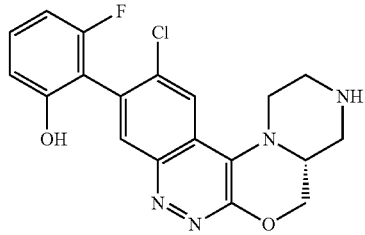 [SMILES: Oc1cccc(F)c1-c1cc2nnc3c(c2cc1Cl)N1CCNC[C@@H]1CO3]

TFA (0.2 ml, 2.60 mmol) was added to tert-butyl (4aR)-11-chloro-10-(2-fluoro-6-hydroxyphenyl)-1,2,4a,5-tetrahydropyrazino[1',2':4,5][1,4]oxazino[2,3-c]cinnoline-3(4H)-carboxylate (26 mg, 0.05 mmol) in DCM (1 ml). The resulting mixture was stirred at 25° C. for 4 hours. The solvent was removed under reduced pressure. The product, 2-((4aR)-11-chloro-1,2,3,4,4a,5-hexahydropyrazino[1',2':4,5][1,4]oxazino[2,3-c]cinnolin-10-yl)-3-fluorophenol (28 mg, >100%) was isolated as a yellow oil which was used in the next step directly without further purification. m/z (ES+), [M+H]+=387.

1-((4aR)-11-Chloro-10-(2-fluoro-6-hydroxyphenyl)-1,2,4a,5-tetrahydropyrazino[1',2':4,5][1,4]oxazino[2,3-c]cinnolin-3(4H)-yl)prop-2-en-1-one, Example 10

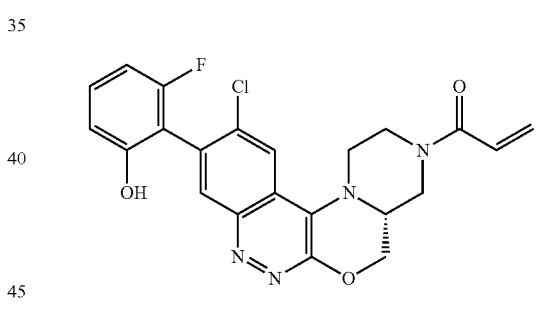

Acryloyl chloride (140 mg, 1.55 mmol) was added to 2-((4aR)-11-chloro-1,2,3,4,4a,5-hexahydropyrazino[1',2':4,5][1,4]oxazino[2,3-c]cinnolin-10-yl)-3-fluorophenol (200 mg, 0.52 mmol) in DMF (5 ml) cooled at −40° C. The resulting mixture was stirred at −40° C. for 0.5 hours. The crude product was purified by preparative HPLC Column: XBridge C18 OBD Prep Column, 100 Å, 5 μm, 19 mm×250 mm; Mobile Phase A: Water (0.05% NH$_3$ in H$_2$O), Mobile Phase B: ACN; Flow rate: 25 ml/min; Gradient: 19% B to 30% B in 7 min; 254/220 nm; Rt: 6.65 min. Fractions containing the desired compound were evaporated to dryness to afford 1-((4aR)-11-chloro-10-(2-fluoro-6-hydroxyphenyl)-1,2,4a,5-tetrahydropyrazino[1',2':4,5][1,4]oxazino[2,3-c]cinnolin-3(4H)-yl)prop-2-en-1-one (30 mg, 13%) as a yellow solid. 1H NMR (DMSO-d6, 400 MHz) 3.10-3.15 (1H, m), 3.52-3.59 (2H, m), 3.71-3.76 (1H, m), 4.08-4.37 (4H, m), 4.46-4.54 (1H, m), 5.74-5.79 (1H, m), 6.19 (1H, d), 6.74-6.88 (3H, m), 7.26-7.37 (1H, m), 8.06 (1H, s), 8.14 (1H, s), 10.11 (1H, s). m/z (ES+), [M+H]+=441.

Tert-butyl (2R,5R)-5-(((tert-butyldimethylsilyl)oxy)methyl)-2-methylpiperazine-1-carboxylate

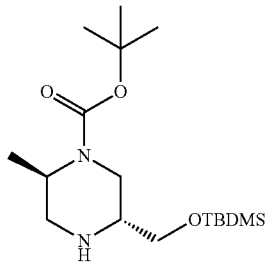 [SMILES: C[C@@H]1CN[C@@H](CO[Si](C)(C)C(C)(C)C)CN1C(=O)OC(C)(C)C]

Tert-butyl (2R,5R)-5-(hydroxymethyl)-2-methylpiperazine-1-carboxylate (770 mg, 3.34 mmol), tert-butylchlorodimethylsilane (756 mg, 5.02 mmol), triethylamine (677 mg, 6.69 mmol) and N,N-dimethylpyridin-4-amine (41 mg, 0.33 mmol) were dissolved in DCM (6 ml) and the mixture was stirred at room temperature for 2 hours. The reaction was quenched with saturated aqueous NH$_4$Cl and extracted with DCM (3×30 ml). The organic phase was washed with brine and dried. The solvent was removed under reduced pressure and the crude product was purified by flash chromatography on a silica gel, eluting from 0-30% (EtOAc in petroleum ether). The fractions containing the desired product were evaporated to dryness to afford tert-butyl (2R,5R)-5-(((tert-butyldimethylsilyl)oxy)methyl)-2-methylpiperazine-1-carboxylate (1.04 g, 90%) as a colourless oil. 1H NMR (Chloroform-d, 400 MHz) 0.08 (6H, d), 0.91 (9H, s), 1.30 (3H, d), 1.47 (9H, s), 2.56 (1H, dd), 2.96-3.05 (1H, m), 3.10 (1H, dd), 3.30 (1H, dd), 3.55 (1H, dd), 3.68-3.82 (2H, m), 4.15-4.25 (1H, m), (1 exchangeable proton not seen). m/z (ES+), [M+H]+=345.

Tert-butyl (2R,5R)-4-(7-bromo-6-chloro-3-nitroquinolin-4-yl)-5-(((tert-butyldimethylsilyl)oxy)methyl)-2-methylpiperazine-1-carboxylate

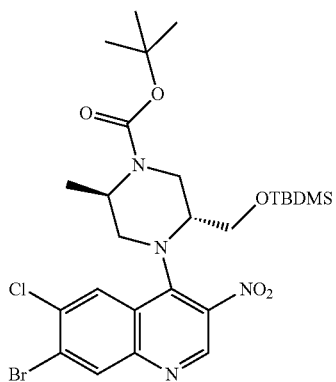 [SMILES: C[C@@H]1CN(c2c([N+](=O)[O-])cnc3cc(Br)c(Cl)cc23)[C@@H](CO[Si](C)(C)C(C)(C)C)CN1C(=O)OC(C)(C)C]

7-Bromo-4,6-dichloro-3-nitroquinoline (841 mg, 2.61 mmol), tert-butyl (2R,5R)-5-(((tert-butyldimethylsilyl)oxy)methyl)-2-methylpiperazine-1-carboxylate (750 mg, 2.18 mmol) and DIPEA (338 mg, 2.61 mmol) were dissolved in i-PrOH (20 ml) and the mixture was stirred at 80° C. for two hours. The solvent was removed under reduced pressure and DCM was added, then washed with water and brine. The organic phase was dried and evaporated to dryness to afford tert-butyl (2R,5R)-4-(7-bromo-6-chloro-3-nitroquinolin-4-yl)-5-(((tert-butyldimethylsilyl)oxy)methyl)-2-methylpiperazine-1-carboxylate (1.5 g, >100%). The crude product was used for next step without any further purification. m/z (ES+), [M+H]+=629.

Tert-butyl (2R,5R)-4-(7-bromo-6-chloro-3-nitroquinolin-4-yl)-5-(hydroxymethyl)-2-methylpiperazine-1-carboxylate

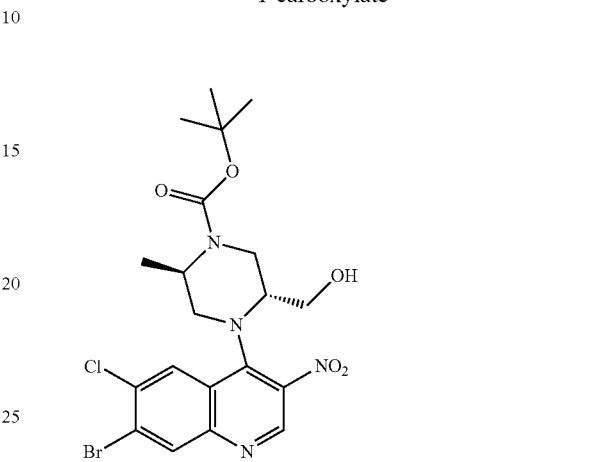

Tert-butyl (2R,5R)-4-(7-bromo-6-chloro-3-nitroquinolin-4-yl)-5-(((tert-butyldimethylsilyl)oxy)methyl)-2-methylpiperazine-1-carboxylate (1644 mg, 2.61 mmol) was dissolved in THF (10 ml) followed by adding tetra-n-butylammonium fluoride (2047 mg, 7.83 mmol). The mixture was stirred at 25° C. overnight. After removing the solvent under reduced pressure, the crude was purified by flash chromatography eluting with EtOAc in petroleum ether to give tert-butyl (2R,5R)-4-(7-bromo-6-chloro-3-nitroquinolin-4-yl)-5-(hydroxymethyl)-2-methylpiperazine-1-carboxylate (880 mg, 65%) as a yellow solid. 1H NMR (DMSO-d6, 400 MHz) 1.21 (3H, d), 1.44 (9H, s), 3.50-3.69 (3H, m), 3.76 (2H, s), 3.98 (1H, d), 4.29 (1H, s), 4.66 (1H, t), 8.32 (1H, s), 8.48 (1H, s), 9.01 (1H, s), (1 exchangeable proton not seen). m/z (ES+), [M+H]+=515.

Tert-butyl (2R,4aR)-10-bromo-11-chloro-2-methyl-1,2,4a,5-tetrahydropyrazino[1',2':4,5][1,4]oxazino[2,3-c]quinoline-3(4H)-carboxylate

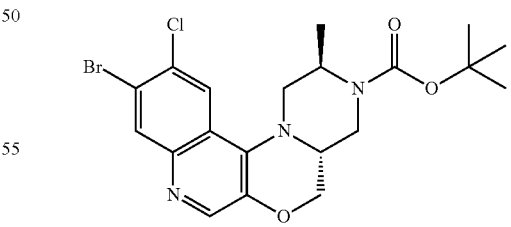

Tert-butyl (2R,5R)-4-(7-bromo-6-chloro-3-nitroquinolin-4-yl)-5-(hydroxymethyl)-2-methylpiperazine-1-carboxylate (312 mg, 0.6 mmol) was dissolved in DMA, followed by adding lithium bis(trimethylsilyl)amide (0.73 ml, 0.73 mmol) under nitrogen. The mixture was stirred for 48 hours then purified by flash chromatography on a C18 column, eluent from 0-80%, MeOH in water (0.1% TFA). The fraction containing the product was collected and evaporated to dryness to afford tert-butyl (2R,4aR)-10-bromo-11-chloro-2-methyl-1,2,4a,5-tetrahydropyrazino[1',2':4,5][1,4]oxazino[2,3-c]quinoline-3(4H)-carboxylate (147 mg, 52%) as a yellow solid. 1H NMR (DMSO-d6, 400 MHz) 1.44 (9H, s), 1.48 (3H, d), 3.17 (1H, m), 3.40 (1H, m), 3.95 (2H, m), 4.22-4.39 (4H, m), 8.03 (1H, s), 8.35 (1H, s), 8.60 (1H, s), (1 exchangeable proton not seen). m/z (ES+), [M+H]+=468.

Tert-butyl (2R,4aR)-10-bromo-11-chloro-2-methyl-1,2,4a,5-tetrahydropyrazino[1',2':4,5][1,4]oxazino[2,3-c]quinoline-3(4H)-carboxylate

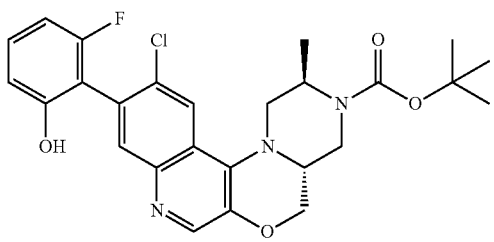 [SMILES: C[C@@H]1CN2c3c(cnc4cc(-c5c(O)cccc5F)c(Cl)cc34)OC[C@H]2CN1C(=O)OC(C)(C)C]

Tert-butyl (2R,4aR)-10-bromo-11-chloro-2-methyl-1,2,4a,5-tetrahydropyrazino[1',2':4,5][1,4]oxazino [2,3-c]quinoline-3(4H)-carboxylate (147 mg, 0.31 mmol), (2-fluoro-6-hydroxyphenyl)boronic acid (122 mg, 0.78 mmol), sodium carbonate (100 mg, 0.94 mmol) and Pd(PPh3)4 (362 mg, 0.31 mmol) were added to a mixture of water (1 ml) and 1,4-dioxane (4 ml). After degassing, the mixture was stirred at 100° C. for 1 hour. After removing the solvents, the crude was purified by flash on C18 column, elution from 0% to 80% (MeOH in 0.1% aqueous TFA). The fraction containing the product was collected and evaporated to dryness to afford the tert-butyl (2R,4aR)-11-chloro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (90 mg, 57%) as a yellow solid. m/z (ES+), [M+H]+=500.

2-[(2R,4aR)-11-Chloro-2-methyl-1,2,3,4,4a,5-hexahydropyrazino[1',2':4,5][1,4]oxazino[2,3-c]quinolin-10-yl]-3-fluorophenol

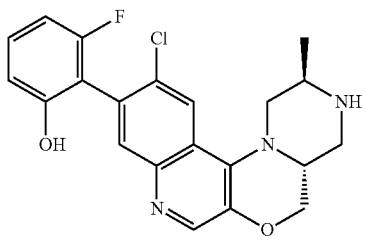 [SMILES: C[C@@H]1CN2c3c(cnc4cc(-c5c(O)cccc5F)c(Cl)cc34)OC[C@H]2CN1]

Tert-butyl (2R,4aR)-11-chloro-10-(2-fluoro-6-hydroxyphenyl)-2-methyl-1,2,4a,5-tetrahydropyrazino [1',2':4,5][1,4]oxazino[2,3-c]quinoline-3(4H)-carboxylate (80 mg, 0.16 mmol) was dissolved in DCM (2 ml), followed by adding TFA (0.5 ml). The mixture was stirred at room temperature for 1 hour. The mixture was evaporated to dryness to afford 2-((2R,4aR)-11-chloro-2-methyl-1,2,3,4,4a,5-hexahydropyrazino[1',2':4,5][1,4]oxazino[2,3-c]quinolin-10-yl)-3-fluorophenol (105 mg, >100%) that was used in the next step without further purification. m/z (ES+), [M+H]+=400.

1-[(2R,4aR)-11-Chloro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one, Example 11

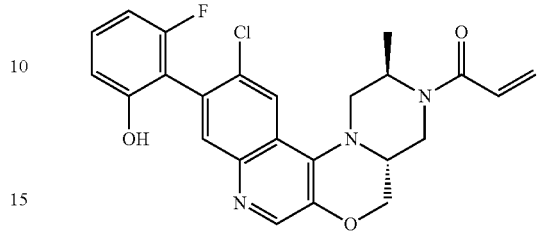

2-[(2R,4aR)-11-Chloro-2-methyl-1,2,3,4,4a,5-hexahydropyrazino[1',2':4,5][1,4]oxazino[2,3-c] quinolin-10-yl]-3-fluorophenol (80 mg, 0.16 mmol) was dissolved in THF (2 ml) and the mixture was cooled at 0° C., followed by adding acryloyl chloride (14.8 mg, 0.16 mmol) and DIPEA (40 mg, 0.31 mmol). The mixture was stirred for 2 hours at 0° C. After removing the solvent under reduced pressure, the crude product was purified by flash chromatography on a C-18 column, elution gradient 0 to 40% MeCN in water (0.5% HCOOH). Pure fractions were evaporated to dryness to afford 1-((2R,4aR)-11-chloro-10-(2-fluoro-6-hydroxyphenyl)-2-methyl-1,2,4a,5-tetrahydropyrazino[1',2':4,5][1,4]oxazino [2,3-c]quinolin-3(4H)-yl)prop-2-en-1-one (20 mg, 28%) as a white solid. 1H NMR (DMSO-d6, 400 MHz) 1.59 (3H, d), 3.06 (1H, m), 3.54 (1H, m), 4.36 (6H, m), 5.75 (1H, d), 6.19 (1H, d), 6.67-6.98 (3H, m), 7.29 (1H, q), 7.86 (1H, d), 7.99 (1H, d), 8.59 (1H, s), 10.04 (1H, s). m/z (ES+), [M+H]+=454.

Tert-butyl (3R)-4-(6-bromo-7-chloro-3-nitroquinolin-4-yl)-3-(hydroxymethyl)piperazine-1-carboxylate

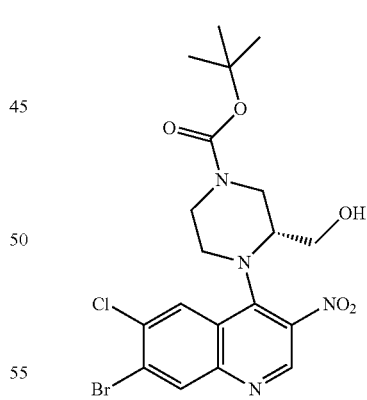

DIPEA (84 ml, 480.94 mmol) was added to 7-bromo-4,6-dichloro-3-nitroquinoline (60 g, 186.37 mmol) and tert-butyl (R)-3-(hydroxymethyl)piperazine-1-carboxylate (89 g, 410.02 mmol) in i-PrOH (600 ml). The resulting mixture was stirred at 80° C. for 2 hours. The solvent was removed under reduced pressure. The crude product was purified by flash silica chromatography, elution gradient 0 to 20% EtOAc in petroleum ether. Pure fractions were evaporated to dryness to afford tert-butyl (3R)-4-(6-bromo-7-chloro-3-nitroquinolin-4-yl)-3-(hydroxymethyl)piperazine-1-carboxylate (54 g, 58%) as a yellow solid. 1H NMR (DMSO, 300 MHz) 1.16 (1H, t), 1.31-1.46 (9H, m), 1.97 (1H, s), 2.10-2.27 (1H, m), 2.36 (1H, d), 2.66 (1H, s), 3.47 (1H, s), 3.77 (1H, s), 4.01 (1H, q), 4.14 (1H, s), 7.50-7.64 (1H, m), 8.52 (1H, d), 8.62 (1H, s), 11.16 (1H, s). m/z (ES+), [M+H]+=503.

Tert-butyl (3R)-4-(7-bromo-6-chloro-3-nitroquinolin-4-yl)-3-(chloromethyl)piperazine-1-carboxylate

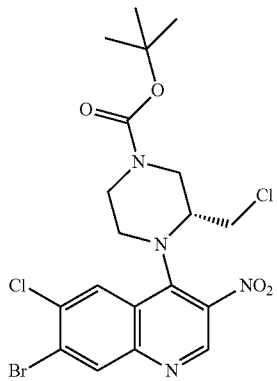 [SMILES: CC(C)(C)OC(=O)N1CCN(c2c([N+](=O)[O-])cnc3cc(Br)c(Cl)cc23)[C@@H](CCl)C1]

Tetrachloromethane (1.2 ml, 12.44 mmol) was added to triphenylphosphine (3.14 g, 11.96 mmol) and tert-butyl (3R)-4-(7-bromo-6-chloro-3-nitroquinolin-4-yl)-3-(hydroxymethyl)piperazine-1-carboxylate (2 g, 3.99 mmol) in 1,2-dichloroethane (20 ml). The resulting mixture was stirred at 80° C. for 18 hours. The solvent was removed under reduced pressure. The crude product was purified by flash silica chromatography, elution gradient 5 to 30% EtOAc in petroleum ether. Pure fractions were evaporated to dryness to afford tert-butyl (3R)-4-(7-bromo-6-chloro-3-nitroquinolin-4-yl)-3-(chloromethyl)piperazine-1-carboxylate (1.2 g, 58%) as a yellow solid. 1H NMR (DMSO, 300 MHz) 1.46 (9H, s), 2.86-3.34 (2H, m), 3.35-4.39 (7H, m), 8.36 (1H, s), 8.53 (1H, s), 9.10 (1H, s). m/z (ES+), [M+H]+=521.

Tert-butyl (3R)-4-(3-amino-7-bromo-6-chloroquinolin-4-yl)-3-(chloromethyl)piperazine-1-carboxylate

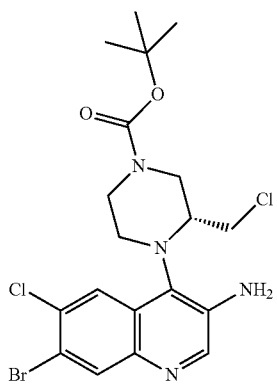 [SMILES: CC(C)(C)OC(=O)N1CCN(c2c(N)cnc3cc(Br)c(Cl)cc23)[C@@H](CCl)C1]

5% Platinum on carbon (45 mg, 0.12 mmol) was added to tert-butyl (3R)-4-(7-bromo-6-chloro-3-nitroquinolin-4-yl)-3-(chloromethyl)piperazine-1-carboxylate (1.2 g, 2.31 mmol) in EtOAc (20 ml). The resulting mixture was stirred at 25° C. for 1 hour. The mixture was filtered through a Celite pad. The solvent was removed under reduced pressure. The product, tert-butyl (3R)-4-(3-amino-7-bromo-6-chloroquinolin-4-yl)-3-(chloromethyl)piperazine-1-carboxylate (1.16 g, >100%) was used in the next step directly without further purification. 1H NMR (DMSO, 400 MHz) 1.46 (9H, d), 2.90 (1H, s), 3.14 (1H, s), 3.44-3.52 (1H, m), 3.79 (2H, d), 4.03 (1H, q), 4.11 (1H, s), 5.79 (1H, s), 5.90 (1H, s), 8.17 (1H, d), 8.26 (1H, s), 8.55 (1H, d), (2 exchangeable protons not seen). m/z (ES+), [M+H]+=491.

Tert-butyl (4aS)-10-bromo-11-chloro-1,2,4,4a,5,6-hexahydro-3H-pyrazino[1',2':4,5]pyrazino[2,3-c]quinoline-3-carboxylate

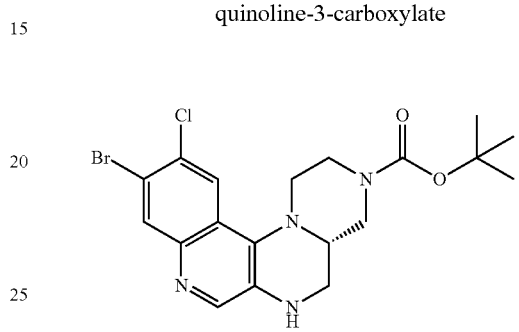

DIPEA (1 ml, 5.73 mmol) was added to tert-butyl (3R)-4-(3-amino-7-bromo-6-chloroquinolin-4-yl)-3-(chloromethyl)piperazine-1-carboxylate (1.16 g, 2.37 mmol), in DMF (20 ml). The resulting mixture was stirred at 120° C. for 5 hours. The solvent was removed under reduced pressure. The crude product was purified by flash silica chromatography, elution gradient 2 to 10% MeOH in DCM. Pure fractions were evaporated to dryness to afford tert-butyl (4aS)-10-bromo-11-chloro-1,2,4,4a,5,6-hexahydro-3H-pyrazino[1',2':4,5]pyrazino[2,3-c]quinoline-3-carboxylate (1.4 g, >100%) as a yellow solid. 1H NMR (DMSO, 300 MHz) 1.41 (9H, s), 2.87 (1H, s), 2.97-3.29 (4H, m), 3.50-3.67 (2H, m), 3.83 (1H, s), 3.95 (1H, d), 7.94 (1H, d), 8.12 (1H, s), 8.36 (1H, s), (1 exchangeable proton not seen). m/z (ES+), [M+H]+=455.

Tert-butyl (4aS)-10-bromo-11-chloro-6-(2-(dimethylamino)ethyl)-1,2,4,4a,5,6-hexahydro-3H-pyrazino[1',2':4,5]pyrazino[2,3-c]quinoline-3-carboxylate

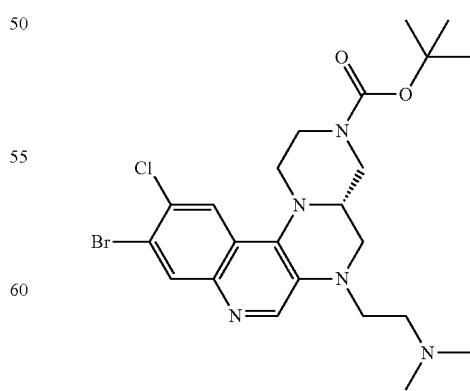

Sodium hydride (176 mg, 4.41 mmol) was added to tert-butyl (4aS)-10-bromo-11-chloro-1,2,4,4a,5,6-hexahydro-3H-pyrazino[1',2':4,5]pyrazino[2,3-c]quinoline-3-carboxylate (500 mg, 1.10 mmol) in DMF (20 ml) at 0° C. under nitrogen. After 20 minutes, 2-chloro-N,N-dimethyl-ethan-1-amine, HCl (159 mg, 1.1 mmol) was added to the mixture. The resulting suspension was stirred at room temperature for 3 hours. The reaction mixture was quenched with water (5 ml). The reaction mixture was diluted with EtOAc (200 ml), and washed sequentially with saturated ammonium chloride (200 ml), saturated brine (200 ml×2) and the organic layer was dried, filtered and evaporated to afford crude product. The crude product was purified by flash silica chromatography, elution gradient 0 to 20% MeOH in DCM. Pure fractions were evaporated to dryness to afford tert-butyl (4aS)-10-bromo-11-chloro-6-(2-(dimethylamino)ethyl)-1,2,4,4a,5,6-hexahydro-3H-pyrazino[1',2':4,5]pyrazino[2,3-c]quinoline-3-carboxylate (225 mg, 39%) as an orange solid. 1H NMR (300 MHz, DMSO-d6) 1.44 (9H, s), 2.23 (6H, s), 2.41-2.49 (1H, m), 2.67-2.81 (1H, m), 3.03-3.22 (3H, m), 3.23-3.39 (3H, m), 3.40-3.67 (2H, m), 3.74-4.10 (3H, m), 8.00 (1H, s), 8.16 (1H, s), 8.70 (1H, s). m/z (ES+), [M+H]+=524.

Tert-butyl (4aS)-11-chloro-6-(2-(dimethylamino)ethyl)-10-(2-fluoro-6-hydroxyphenyl)-1,2,4,4a,5,6-hexahydro-3H-pyrazino[1',2':4,5]pyrazino[2,3-c]quinoline-3-carboxylate

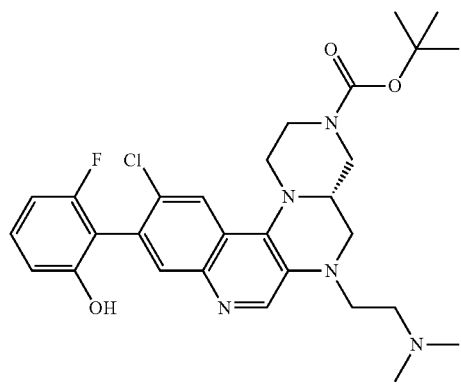 [SMILES: CN(C)CCN1C[C@H]2CN(C(=O)OC(C)(C)C)CCN2c2c1cnc1cc(-c3c(O)cccc3F)c(Cl)cc21]

RuPhos Pd G3 (33.4 mg, 0.04 mmol) was added to tert-butyl (4aS)-10-bromo-11-chloro-6-(2-(dimethylamino)ethyl)-1,2,4,4a,5,6-hexahydro-3H-pyrazino[1',2':4,5]pyrazino[2,3-c]quinoline-3-carboxylate (210 mg, 0.40 mmol), (2-fluoro-6-hydroxyphenyl)boronic acid (125 mg, 0.80 mmol), K$_2$CO$_3$ (111 mg, 0.80 mmol) and Ruphos (18.7 mg, 0.04 mmol) were stirred in 1,4-dioxane/H$_2$O (15 ml, 3:1 ratio) at room temperature under nitrogen. The resulting suspension was stirred at 100° C. for 1 hour. The solvent was removed under reduced pressure. The crude product was purified by flash C18-flash chromatography, elution gradient 0 to 100%, 20 minutes, 46% MeCN in water (0.1% HCOOH). Pure fractions were evaporated to dryness to afford tert-butyl (4aS)-10-(2,6-dihydroxyphenyl)-6-(2-(dimethylamino)ethyl)-1,2,4,4a,5,6-hexahydro-3H-pyrazino[1',2':4,5]pyrazino [2,3-c]quinoline-3-carboxylate (206 mg, 93%) as an orange solid. 1H NMR (300 MHz, DMSO-d6) 1.45 (9H, s), 2.27 (6H, s), 2.55-2.66 (2H, m), 2.71-2.85 (1H, m), 3.07-3.17 (2H, m), 3.19-3.36 (2H, m), 3.45-3.70 (3H, m), 3.77-3.93 (2H, m), 4.00 (1H, d), 6.68-6.86 (2H, m), 7.26 (1H, dd), 7.69 (1H, d), 7.95 (1H, s), 8.71 (1H, s), (1 exchangeable proton not seen). m/z (ES+), [M+H]+=556.

2-((4aR)-11-Chloro-6-(2-(dimethylamino)ethyl)-2,3,4,4a,5,6-hexahydro-1H-pyrazino[1',2':4,5]pyrazino[2,3-c]quinolin-10-yl)-3-fluorophenol

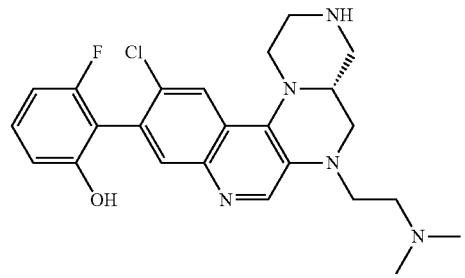 [SMILES: CN(C)CCN1C[C@H]2CNCCN2c2c1cnc1cc(-c3c(O)cccc3F)c(Cl)cc21]

HCl (4M in 1,4-dioxane) (4 ml, 16 mmol) was added to tert-butyl (4aS)-11-chloro-6-(2-(dimethylamino)ethyl)-10-(2-fluoro-6-hydroxyphenyl)-1,2,4,4a,5,6-hexahydro-3H-pyrazino[1',2':4,5] pyrazino[2,3-c]quinoline-3-carboxylate (200 mg, 0.36 mmol) in MeOH (4 ml) at room temperature. The resulting mixture was stirred at room temperature for 1 hour. The solvent was removed under reduced pressure to afford product 2-((4aR)-11-chloro-6-(2-(dimethylamino)ethyl)-2,3,4,4a,5,6-hexahydro-1H-pyrazino[1',2':4,5]pyrazino[2,3-c]quinolin-10-yl)-3-fluorophenol (203 mg, >100%) as an orange solid. The product was used in the next step directly without further purification. m/z (ES+), [M+H]+=456.

1-((4aS)-11-Chloro-6-(2-(dimethylamino)ethyl)-10-(2-fluoro-6-hydroxyphenyl)-1,2,4,4a,5,6-hexahydro-3H-pyrazino[1',2':4,5]pyrazino[2,3-c]quinolin-3-yl)prop-2-en-1-one, Example 12

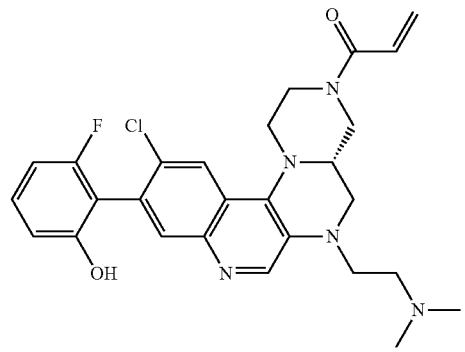 [SMILES: C=CC(=O)N1CCN2c3c(cnc4cc(-c5c(O)cccc5F)c(Cl)cc34)N(CCN(C)C)C[C@H]2C1]

Acryloyl chloride (38 mg, 0.42 mmol, in DMF) was added to 2-((4aR)-11-chloro-6-(2-(dimethylamino)ethyl)-2,3,4,4a,5,6-hexahydro-1H-pyrazino[1',2':4,5]pyrazino[2,3-c]quinolin-10-yl)-3-fluorophenol (190 mg, 0.42 mmol) and DIPEA (0.218 ml, 1.25 mmol) in DMF (4 ml) at −10° C. under nitrogen. The reaction mixture was allowed to warm to room temperature, then was stirred at room temperature for 1 hour and then purified by flash C18-flash chromatography, elution gradient 0 to 100%, 20 minutes, 65% MeCN in water (0.1% NH$_4$HCO$_3$). Pure fractions were evaporated to dryness to afford 1-((4aS)-11-chloro-6-(2-(dimethylamino)ethyl)-10-(2-fluoro-6-hydroxyphenyl)-1,2,4,4a,5,6-hexahydro-3H-pyrazino[1',2':4,5]pyrazino[2,3-c]quinolin-3-yl)prop-2-en-1-one (66 mg, 31%) as a yellow solid. 1H NMR (300 MHz, DMSO-d6) 2.21 (6H, s), 2.38-2.48 (2H, m), 2.71-2.91 (1H, m), 3.13-3.28 (3H, m), 3.43-3.63 (3H, m), 3.64-3.83 (2H, m), 4.17 (1H, dd), 4.44 (1H, dd), 5.77 (1H, d), 6.19 (1H, d), 6.69-6.87 (2H, m), 6.87-6.94 (1H, m), 7.20-7.34 (1H, m), 7.70 (1H, d), 7.99 (1H, s), 8.70 (1H, s), 9.92 (1H, s). m/z (ES+), [M+H]+=510.

Tert-butyl (4aS)-11-chloro-10-(2-fluoro-6-hydroxyphenyl)-1,2,4,4a,5,6-hexahydro-3H-pyrazino[1',2':4,5]pyrazino[2,3-c]quinoline-3-carboxylate

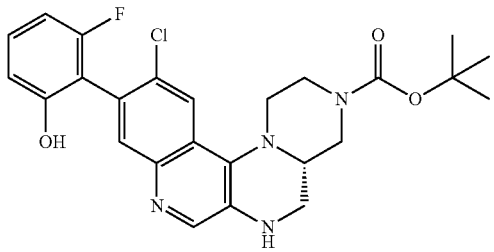 [SMILES: CC(C)(C)OC(=O)N1CCN2c3c(cnc4cc(-c5c(O)cccc5F)c(Cl)cc34)NC[C@H]2C1]

Tetrakis(triphenylphosphine)palladium(0) (50.9 mg, 0.04 mmol) was added to tert-butyl (4aS)-10-bromo-11-chloro-1,2,4,4a,5,6-hexahydro-3H-pyrazino[1',2':4,5]pyrazino[2,3-c]quinoline-3-carboxylate (200 mg, 0.44 mmol), (2-fluoro-6-hydroxyphenyl)boronic acid (172 mg, 1.10 mmol), and Cs$_2$CO$_3$ (431 mg, 1.32 mmol) in 1,4-dioxane (5 ml) and water (1.25 ml) under nitrogen. The resulting mixture was stirred at 100° C. for 16 hours and then purified by flash C18-flash chromatography, elution gradient 2 to 70% MeCN in water. Pure fractions were evaporated to dryness to afford tert-butyl (4aS)-11-chloro-10-(2-fluoro-6-hydroxyphenyl)-1,2,4,4a,5,6-hexahydro-3H-pyrazino[1',2':4,5]pyrazino[2,3-c]quinoline-3-carboxylate (120 mg, 56%) yellow solid. 1H NMR (DMSO-d6, 400 MHz) 1.44 (9H, s), 2.61-2.84 (1H, m), 2.91-3.13 (1H, m), 3.37-3.45 (2H, m), 3.43-3.75 (2H, m), 3.79-4.19 (2H, m), 6.58 (2H, s), 6.71 (1H, s), 7.14 (1H, d), 7.62-7.64 (1H, m), 7.64-7.67 (1H, m), 7.88 (1H, s), 8.37 (1H, s), (1 exchangeable proton not seen). m/z (ES+), [M+H]+=485.

2-((4aR)-11-Chloro-2,3,4,4a,5,6-hexahydro-1H-pyrazino[1',2':4,5]pyrazino[2,3-c]quinolin-10-yl)-3-fluorophenol

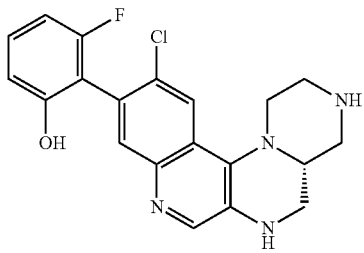 [SMILES: Oc1cccc(F)c1-c1cc2ncc3c(c2cc1Cl)N1CCNC[C@@H]1CN3]

Tert-butyl (4aS)-11-chloro-10-(2-fluoro-6-hydroxyphenyl)-1,2,4,4a,5,6-hexahydro-3H-pyrazino[1',2':4,5]pyrazino[2,3-c]quinoline-3-carboxylate (120 mg, 0.25 mmol) in 4M HCl in dioxane (2 ml). The resulting mixture was stirred at 25° C. for 4 hours. The solvent was removed under reduced pressure to give 2-((4aR)-11-chloro-2,3,4,4a,5,6-hexahydro-1H-pyrazino[1',2':4,5]pyrazino[2,3-c]quinolin-10-yl)-3-fluorophenol (150 mg, >100%) as a yellow solid (HCl salt). m/z (ES+), [M+H]+=385.

1-((4aS)-11-Chloro-10-(2-fluoro-6-hydroxyphenyl)-1,2,4,4a,5,6-hexahydro-3H-pyrazino[1',2':4,5]pyrazino[2,3-c]quinolin-3-yl)prop-2-en-1-one, Example 13

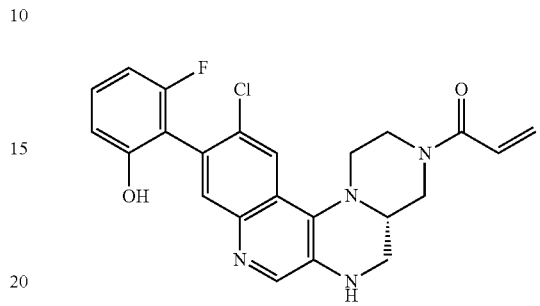

Acryloyl chloride (29.6 mg, 0.33 mmol) was added to 2-((4aR)-11-chloro-2,3,4,4a,5,6-hexahydro-1H-pyrazino[1',2':4,5]pyrazino[2,3-c]quinolin-10-yl)-3-fluorophenol (140 mg, 0.36 mmol) in DMF (0.5 ml). The resulting mixture was stirred at −20° C. for 0.5 hours. The crude product was purified by preparative Column: Xbridge Phenyl OBD Column, 5 um, 19*150 mm; Mobile Phase A: Water (0.05% NH$_3$ in H$_2$O), Mobile Phase B: ACN; Flow rate: 25 ml/min; Gradient: 23% B to 35% B in 9 min; 254/220 nm; Rt: 6.83/7.95 min. Fractions containing the desired compound were evaporated to dryness to afford 1-((4aS)-11-chloro-10-(2-fluoro-6-hydroxyphenyl)-1,2,4,4a,5,6-hexahydro-3H-pyrazino[1',2':4,5] pyrazino [2,3-c]quinolin-3-yl)prop-2-en-1-one (30 mg, 19%) as a yellow solid. 1H NMR (400 MHz, DMSO-d6) 2.63-3.01 (1H, m), 2.94-3.16 (1H, m), 3.16-3.30 (2H, m), 3.31-3.50 (2H, m), 3.50-3.88 (1H, m), 4.00-4.34 (1H, m), 4.36-4.57 (1H, m), 5.55-5.93 (1H, m), 6.04-6.39 (1H, m), 6.65 (1H, s), 6.69-6.77 (1H, m), 6.80 (1H, d), 6.83-6.96 (1H, m), 7.25 (1H, t), 7.66 (1H, d), 7.93 (1H, s), 8.38 (1H, s), 9.91 (1H, s). m/z (ES+), [M+H]+=439.

Tert-butyl (4aS)-10-bromo-11-chloro-6-methyl-1,2,4,4a,5,6-hexahydro-3H-pyrazino[1',2':4,5]pyrazino[2,3-c] quinoline-3-carboxylate

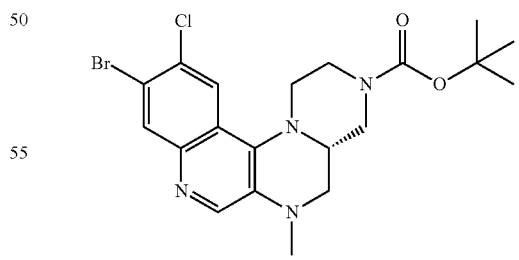

Sodium hydride (42.3 mg, 1.76 mmol) was added slowly to tert-butyl (4aS)-10-bromo-11-chloro-1,2,4,4a,5,6-hexahydro-3H-pyrazino[1',2':4,5]pyrazino[2,3-c]quinoline-3-carboxylate (400 mg, 0.88 mmol) and iodomethane (125 mg, 0.88 mmol) in THF (3 ml) at 0° C. over a period of 5 minutes under nitrogen. The resulting suspension was stirred at room temperature for 1 hour. The reaction mixture was poured into water (100 ml), extracted with EtOAc (3×100 ml), the organic layer was dried, filtered and evaporated to afford the crude product. The crude product was purified by flash silica chromatography, elution gradient 0 to 33% petroleum ether in EtOAc. Pure fractions were evaporated to dryness to afford tert-butyl (4aS)-10-bromo-11-chloro-6-methyl-1,2,4,4a,5,6-hexahydro-3H-pyrazino[1',2':4,5]pyrazino[2,3-c]quinoline-3-carboxylate (200 mg, 49%) as a yellow solid. 1H NMR (DMSO, 300 MHz) 1.41 (9H, s), 2.47 (1H, s), 2.50 (1H, s), 2.82 (1H, s), 3.07 (3H, s), 3.17 (3H, d), 3.41 (1H, t), 3.78 (1H, s), 3.88 (1H, d), 7.98 (1H, s), 8.16 (1H, s), 8.63 (1H, s). m/z (ES+), [M+H]+=469.

Tert-butyl (4aS)-11-chloro-10-(2-fluoro-6-methoxyphenyl)-6-methyl-1,2,4,4a,5,6-hexahydro-3H-pyrazino[1',2':4,5]pyrazino[2,3-c]quinoline-3-carboxylate

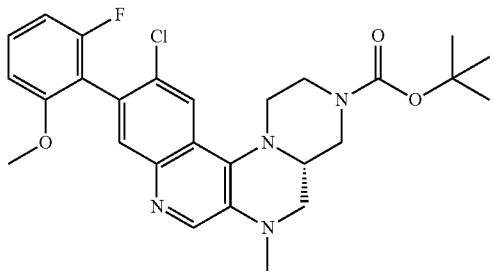 [SMILES: COc1cccc(F)c1-c1cc2ncc3c(c2cc1Cl)N1CCN(C(=O)OC(C)(C)C)C[C@@H]1CN3C]

Pd(PPh$_3$)$_4$ (47 mg, 0.04 mmol) was added to tert-butyl (4aS)-10-bromo-11-chloro-6-methyl-1,2,4,4a,5,6-hexahydro-3H-pyrazino[1',2':4,5]pyrazino[2,3-c]quinoline-3-carboxylate (190 mg, 0.41 mmol), (2-fluoro-6-methoxyphenyl)boronic acid (76 mg, 0.45 mmol) and Cs$_2$CO$_3$ (265 mg, 0.81 mmol) in 1,4-dioxane/H$_2$O (10 ml), (3:1 ratio) at room temperature under nitrogen. The resulting suspension was stirred at 100° C. for 3 hours. The solvent was removed under reduced pressure. The crude product was purified by flash C18-flash chromatography, elution gradient 0 to 100%, 20 minutes, 85% MeCN in water (0.1% TFA). Pure fractions were evaporated to dryness to afford tert-butyl (4aS)-11-chloro-10-(2-fluoro-6-methoxyphenyl)-6-methyl-1,2,4,4a,5,6-hexahydro-3H-pyrazino[1',2':4,5]pyrazino[2,3-c]quinoline-3-carboxylate (164 mg, 79%) as bright green solid. 1H NMR (300 MHz, DMSO-d6) 1.45 (9H, s), 2.97-3.13 (4H, m), 3.20 (1H, dd), 3.26-3.49 (4H, m), 3.53-3.64 (1H, m), 3.75 (3H, d), 3.79-3.91 (2H, m), 6.89-7.06 (2H, m), 7.59-7.63 (1H, m), 7.98 (1H, s), 8.14 (1H, s), 8.63 (1H, s). m/z (ES+), [M+H]+=513.

2-((4aR)-11-Chloro-6-methyl-2,3,4,4a,5,6-hexahydro-1H-pyrazino[1',2':4,5]pyrazino[2,3-c]quinolin-10-yl)-3-fluorophenol

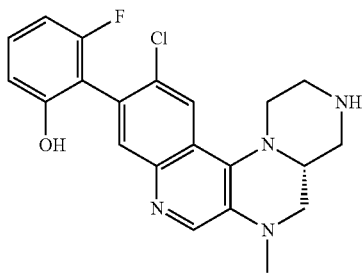 [SMILES: CN1C[C@H]2CNCCN2c2c1cnc1cc(-c3c(O)cccc3F)c(Cl)cc21]

Boron tribromide in DCM (6 ml, 6 mmol) was added to tert-butyl (4aS)-11-chloro-10-(2-fluoro-6-methoxyphenyl)-6-methyl-1,2,4,4a,5,6-hexahydro-3H-pyrazino[1',2':4,5]pyrazino[2,3-c]quinoline-3-carboxylate (150 mg, 0.29 mmol) at room temperature. The resulting suspension was stirred at room temperature for 1 hour. The reaction mixture was quenched with MeOH (2 ml). The solvent was removed under reduced pressure. The crude product was purified by ion exchange chromatography, using an SCX column. The desired product was eluted from the column using 7M NH$_3$/MeOH and pure fractions were evaporated to dryness to afford 2-((4aR)-11-chloro-6-methyl-2,3,4,4a,5,6-hexahydro-1H-pyrazino[1',2':4,5]pyrazino[2,3-c]quinolin-10-yl)-3-fluorophenol (86 mg, 74%) as an orange solid. 1H NMR (300 MHz, DMSO-d6) 3.10 (3H, s), 3.17 (3H, s), 3.19-3.26 (1H, m), 3.26-3.54 (5H, m), 3.67-3.83 (1H, m), 4.14 (1H, s), 6.74 (1H, t), 6.85 (1H, d), 7.19-7.33 (1H, m), 7.71 (1H, d), 7.94 (1H, s), 8.65 (1H, s). m/z (ES+), [M+H]+=399.

1-((4aS)-11-chloro-10-(2-fluoro-6-hydroxyphenyl)-6-methyl-1,2,4,4a,5,6-hexahydro-3H-pyrazino[1',2':4,5]pyrazino[2,3-c]quinolin-3-yl)prop-2-en-1-one, Example 14

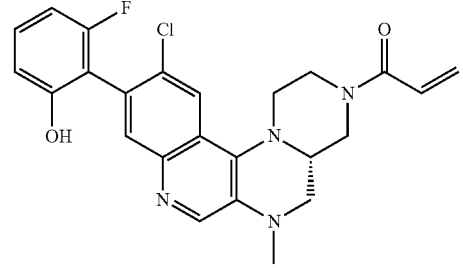 [SMILES: C=CC(=O)N1CCN2c3c(cnc4cc(-c5c(O)cccc5F)c(Cl)cc34)N(C)C[C@H]2C1]

Acryloyl chloride (12.5 mg, 0.14 mmol in DMF) was added to 2-((4aR)-11-chloro-6-methyl-2,3,4,4a,5,6-hexahydro-1H-pyrazino[1',2':4,5]pyrazino[2,3-c]quinolin-10-yl)-3-fluorophenol (55 mg, 0.14 mmol) and DIPEA (0.048 ml, 0.28 mmol) in DMF (3 ml) at −10° C. under nitrogen. The resulting mixture was stirred at room temperature for 1 hour. The crude product was purified by flash C18-flash chromatography, elution gradient 0 to 100%, 20 minutes, 54% MeCN in water (0.1% NH$_4$HCO$_3$). Pure fractions were evaporated to dryness to afford 1-((4as)-11-chloro-10-(2-fluoro-6-hydroxyphenyl)-6-methyl-1,2,4,4a,5,6-hexahydro-3H-pyrazino[1',2':4,5]pyrazino[2,3-c]quinolin-3-yl)prop-2-en-1-one (31 mg, 49%) as a yellow solid. 1H NMR (300 MHz, DMSO-d6) 2.90 (1H, d), 3.10 (3H, s), 3.16-3.28 (2H, m), 3.35-3.57 (3H, m), 3.63-3.91 (1H, m), 4.12 (1H, dd), 4.34 (1H, dd), 5.75 (1H, t), 6.19 (1H, dd), 6.69-6.97 (3H, m), 7.19-7.33 (1H, m), 7.70 (1H, d), 7.98 (1H, s), 8.67 (1H, s), 9.96 (1H, s). m/z (ES+), [M+H]+=453.

1-(Tert-butyl) 3-methyl 4-(7-bromo-6-chloro-3-nitroquinolin-4-yl)piperazine-1,3-dicarboxylate

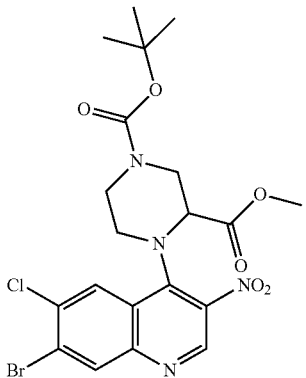 [SMILES: COC(=O)C1CN(C(=O)OC(C)(C)C)CCN1c1c([N+](=O)[O-])cnc2cc(Br)c(Cl)cc12]

To a solution of 7-bromo-4,6-dichloro-3-nitroquinoline (2.07 g, 6.43 mmol) in THF (50 ml) was added 1-(tert-butyl) 3-methyl piperazine-1,3-dicarboxylate (2.356 g, 9.64 mmol) followed by DIPEA (3.36 ml, 19.29 mmol) under nitrogen. The reaction was then heated at reflux overnight, cooled and evaporated, taken up in water and extracted with DCM then dried by passing through a phase separator cartridge. Evaporation afforded an orange gum which was purified by flash silica chromatography, elution gradient 0 to 50% EtOAc in heptane. Pure fractions were evaporated to dryness to afford 1-(tert-butyl) 3-methyl-4-(7-bromo-6-chloro-3-nitroquinolin-4-yl)piperazine-1,3-dicarboxylate (1.66 g, 49%) as a yellow foam. 1H NMR (400 MHz, DMSO, 30° C.) 1.45 (9H, s), 3.30 (1H, s), 3.55 (3H, s), 3.59-3.69 (1H, m), 3.72 (1H, d), 3.75 (1H, d), 3.84 (1H, s), 4.11 (1H, s), 4.35 (1H, s), 8.50 (1H, s), 8.54 (1H, s), 9.12 (1H, s). m/z: ES+ [M+H]+ 529.

1-(3-Amino-7-bromo-6-chloroquinolin-4-yl)-4-(tert-butoxycarbonyl)piperazine-2-carboxylic acid

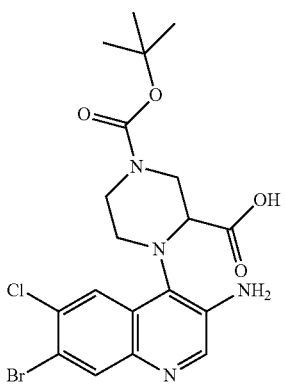 [SMILES: CC(C)(C)OC(=O)N1CCN(c2c(N)cnc3cc(Br)c(Cl)cc23)C(C(=O)O)C1]

1-(Tert-butyl) 3-methyl 4-(7-bromo-6-chloro-3-nitroquinolin-4-yl)piperazine-1,3-dicarboxylate (1.66 g, 3.13 mmol) and 10% platinum on carbon (0.061 g, 0.31 mmol) in EtOAc (100 ml) were stirred at room temperature under 1 atm of hydrogen over 72 hours. The reaction was filtered through celite, washed with ethyl acetate, and evaporation afforded 1-(3-amino-7-bromo-6-chloroquinolin-4-yl)-4-(tert-butoxycarbonyl)piperazine-2-carboxylic acid (1.4 g, 92%) as a solid which was used without further purification. m/z: ES+ [M+H]+ 485.

Tert-butyl 10-bromo-11-chloro-5-oxo-1,2,4,4a,5,6-hexahydro-3H-pyrazino[1',2':4,5]pyrazino[2,3-c]quinoline-3-carboxylate

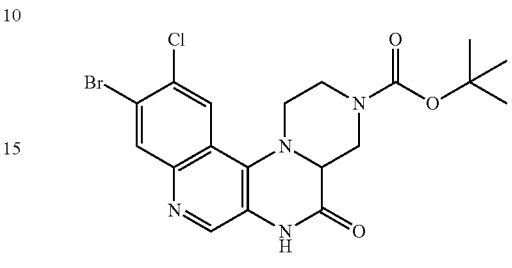

HATU (1.205 g, 3.17 mmol) was added to a suspension of 1-(3-amino-7-bromo-6-chloroquinolin-4-yl)-4-(tert-butoxycarbonyl)piperazine-2-carboxylic acid (1.4 g, 2.88 mmol) and DIPEA (1.095 ml, 6.34 mmol) in THF (30 ml) at room temperature under nitrogen. The reaction was stirred at room temperature for 10 minutes then evaporated, taken up in DCM/MeOH and extracted with water, then pre-absorbed onto silica and purified by flash silica chromatography, elution gradient 0 to 100% EtOAc in heptane then 10% MeOH/EtOAc. Pure fractions were evaporated to dryness to afford tert-butyl 10-bromo-11-chloro-5-oxo-1,2,4,4a,5,6-hexahydro-3H-pyrazino[1',2':4,5]pyrazino[2,3-c]quinoline-3-carboxylate (1.29 g, 96%) as a yellow solid. 1H NMR (400 MHz, DMSO, 30° C.) 1.52 (9H, s), 3.30 (4H, s), 3.83 (2H, s), 4.69 (1H, d), 8.04 (1H, s), 8.22 (1H, s), 8.36 (1H, s), 10.94 (1H, s). m/z: ES+ [M+H]+ 467.

Tert-butyl 10-bromo-11-chloro-6-methyl-5-oxo-1,2,4,4a,5,6-hexahydro-3H-pyrazino [1',2':4,5]pyrazino [2,3-c]quinoline-3-carboxylate

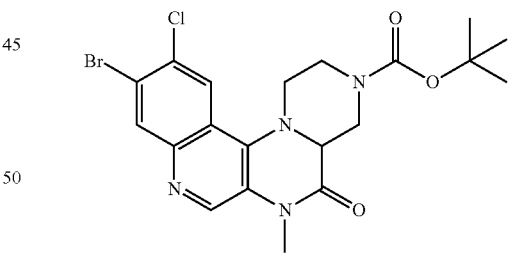

To a solution of tert-butyl 10-bromo-1-chloro-5-oxo-1,2,4,4a,5,6-hexahydro-3H-pyrazino[1',2':4,5]pyrazino[2,3-c]quinoline-3-carboxylate (1.29 g, 2.76 mmol) in DMF (20 ml) at 0° C. under nitrogen was added sodium hydride (0.121 g, 3.03 mmol) and the reaction was stirred at 0° C. for 30 minutes. Iodomethane (0.172 ml, 2.76 mmol) was added and the reaction mixture was stirred at room temperature overnight. The reaction was evaporated, taken up in DCM and extracted with water then dried by passing through a phase separator column. The mixture was purified by flash silica chromatography, elution gradient 0 to 100% EtOAc in heptane then 10% MeOH/EtOAc. Pure fractions were evaporated to dryness to afford tert-butyl 10-bromo-11- chloro-6-methyl-5-oxo-1,2,4,4a,5,6-hexahydro-3H-pyrazino[1',2':4,5]pyrazino[2,3-c]quinoline-3-carboxylate (0.58 g, 44%) as a yellow solid. 1H NMR (400 MHz, DMSO, 30° C.) 1.45 (9H, s), 3.19 (2H, d), 3.48 (3H, s), 3.76-4.1 (4H, m), 4.74 (1H, d), 8.27 (1H, s), 8.43 (1H, s), 8.96 (1H, s). m/z: ES+ [M+H]+ 483.

Tert-butyl 11-chloro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate

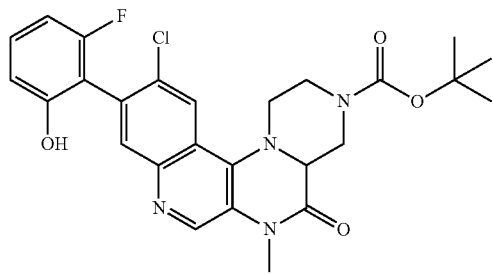 [SMILES: CN1C(=O)C2CN(C(=O)OC(C)(C)C)CCN2c2c1cnc1cc(-c3c(O)cccc3F)c(Cl)cc21]

A mixture of tert-butyl 10-bromo-11-chloro-6-methyl-5-oxo-1,2,4,4a,5,6-hexahydro-3H-pyrazino[1',2':4,5]pyrazino[2,3-c]quinoline-3-carboxylate (0.58 g, 1.20 mmol), (2-fluoro-6-hydroxyphenyl)boronic acid (0.422 g, 2.71 mmol) and potassium carbonate (0.499 g, 3.61 mmol) in 1,4-dioxane (20 ml) and water (3 ml) was degassed for 15 minutes then RuPhos (0.056 g, 0.12 mmol) and RuPhos Pd G3 (0.101 g, 0.12 mmol) was added. The reaction was heated at 102° C. for 30 minutes then evaporated, taken up in saturated ammonium chloride and extracted with DCM. The solution was dried by passing through a phase separator cartridge. Evaporation afforded tert-butyl 11-chloro-10-(2-fluoro-6-hydroxyphenyl)-6-methyl-5-oxo-1,2,4,4a,5,6-hexahydro-3H-pyrazino[1',2':4,5] pyrazino[2,3-c]quinoline-3-carboxylate (0.618 g, 100%) as a foam. m/z: ES+ [M+H]+ 513.

(4aR)-11-Chloro-10-(2-fluoro-6-hydroxyphenyl)-6-methyl-2,3,4,4a-tetrahydro-1H-pyrazino [1',2':4,5]pyrazino[2,3-c]quinolin-5(6H)-one and (4aS)-11-Chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one

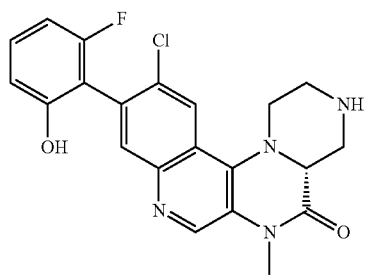

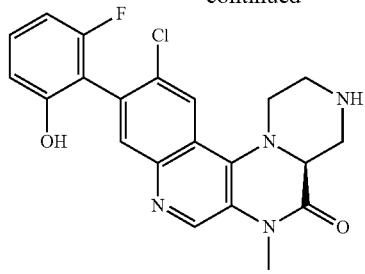

A solution of tert-butyl 11-chloro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (0.62 g, 1.20 mmol) and HCl (6N in i-PrOH) (8.03 ml, 48.19 mmol) in MeOH (5 ml) was stirred at ambient temperature for 1 hr. The reaction mixture was purified by ion exchange chromatography, using an SCX 50 g column, the desired product was eluted from the column using 7N NH₃/MeOH and pure fractions were evaporated to dryness to afford a foam. Further purification was performed by preparative HPLC (Waters CSH C18 OBD column, 30×100 mm id, 5 micron particle size), using decreasingly polar mixtures of water (containing 1% by volume of NH₄OH (28-30% in H₂O)) and MeCN (10 to 40%) as eluent. Detection UV @ 268 nm. This gave (4aR)-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one (57 mg, 12%) as a yellow foam. 1H NMR (400 MHz, DMSO1H NMR (400 MHz, DMSO, 30° C.) 2.63 (1H, q), 2.90 (1H, d), 3.01 (2H, dd), 3.11 (1H, d), 3.52 (4H, s), 3.60 (1H, s), 3.67 (1H, d), 6.77 (1H, t), 6.84 (1H, d), 7.30 (1H, td), 7.93 (1H, d), 8.19 (1H, s), 8.95 (1H, s), 10.05 (1H, s). m/z: ES+ [M+H]+ 413. This was followed by (4aS)-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one (47 mg, 10%) as a yellow foam. 1H NMR (400 MHz, DMSO, 30° C.) 2.63 (1H, q), 2.90 (1H, d), 3.01 (2H, dd), 3.11 (1H, d), 3.52 (4H, s), 3.60 (1H, s), 3.67 (1H, d), 6.77 (1H, t), 6.84 (1H, d), 7.30 (1H, td), 7.93 (1H, d), 8.19 (1H, s), 8.95 (1H, s), 10.05 (1H, s). m/z: ES+ [M+H]+ 413.

(4aR)-3-Acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one, Example 15

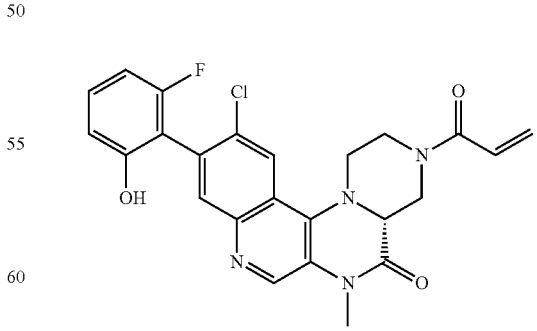

To a solution of (4aR)-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one (0.055 g, 0.13 mmol) and DIPEA (0.035 ml, 0.20 mmol) in DCM (5 ml) under nitrogen at 0° C. was added acryloyl chloride (10.14 μl, 0.13 mmol). The reaction was stirred at room temperature for 10 minutes then evaporated to a gum and purified by preparative HPLC (Waters CSH C18 OBD column, 30×100 mm id, 5 micron particle size), using decreasingly polar mixtures of water (containing 1% by volume of $NH_4OH$ (28-30% in $H_2O$)) and MeCN as eluents. Shallow gradient: 20 to 50% MeCN. Detection UV @ 220 nm. Fractions containing the desired compound were evaporated to dryness to afford (4aR)-3-acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6)-one (0.038 g, 60%) as a solid. 1H NMR (400 MHz, DMSO, 30° C.) 2.56-2.72 (1H, m), 3.08-3.45 (2H, m), 3.42-3.57 (3H, m), 3.63 (1H, d), 3.94 (1H, s), 4.46 (1H, d), 4.78 (1H, d), 5.76 (1H, d), 6.15 (1H, dd), 6.69 (1H, t), 6.79 (1H, dd), 7.08 (1H, dd), 7.25 (1H, q), 7.93 (1H, d), 8.26 (1H, s), 8.96 (1H, s), (1 exchangeable proton not seen). m/z: ES+ [M+H]+ 467.

(4aS)-3-Acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one, Example 16

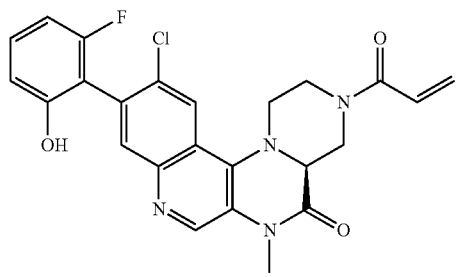 [SMILES: C=CC(=O)N1CCN2c3c(cnc4cc(-c5c(O)cccc5F)c(Cl)cc34)N(C)C(=O)[C@@H]2C1]

To a solution of (4aS)-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one (0.047 g, 0.12 mmol) and DIPEA (0.03 ml, 0.17 mmol) in DCM (5 ml) under nitrogen at 0° C. was added acryloyl chloride (8.68 μl, 0.11 mmol). The reaction was stirred at room temperature for 10 minutes then evaporated to a gum and purified by preparative HPLC (Waters CSH C18 OBD column, 30×100 mm id, 5 micron particle size), using decreasingly polar mixtures of water (containing 1% by volume of $NH_4OH$ (28-30% in $H_2O$)) and MeCN as eluents. Shallow gradient: 20 to 50% MeCN. Detection UV @ 220 nm. Fractions containing the desired compound were evaporated to dryness to afford (4aS)-3-acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one (0.029 g, 54%) as a solid. 1H NMR (400 MHz, DMSO, 30° C.) 2.56-2.72 (1H, m), 3.08-3.45 (2H, m), 3.42-3.57 (3H, m), 3.63 (1H, d), 3.94 (1H, s), 4.46 (1H, d), 4.78 (1H, d), 5.76 (1H, d), 6.15 (1H, dd), 6.69 (1H, t), 6.79 (1H, dd), 7.08 (1H, dd), 7.25 (1H, q), 7.93 (1H, d), 8.26 (1H, s), 8.96 (1H, s), (1 exchangeable proton not seen). m/z: ES+ [M+H]+ 467.

7-bromo-4,6-dichloro-8-fluoro-3-nitroquinoline

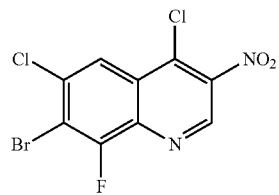 [SMILES: O=[N+]([O-])c1cnc2c(F)c(Br)c(Cl)cc2c1Cl]

To a stirred suspension of 7-bromo-6-chloro-8-fluoro-3-nitroquinolin-4-ol (25 g, 77.76 mmol) in DMF (200 ml) was added phosphoryl trichloride (9.42 ml, 101.1 mmol) and the reaction mixture was heated at 100° C. for one hour then cooled to room temperature. The reaction mixture was poured onto ice (700 g), the solid filtered off, washed thoroughly with water and dried to afford 7-bromo-4,6-dichloro-8-fluoro-3-nitroquinoline (26.3 g, 99%) as a pale brown solid. 1H NMR (400 MHz, DMSO, 30° C.) 8.49 (1H, d), 9.47 (1H, s).

1-Tert-butyl 3-methyl (3R)-4-(7-bromo-6-chloro-8-fluoro-3-nitroquinolin-4-yl)piperazine-1,3-dicarboxylate

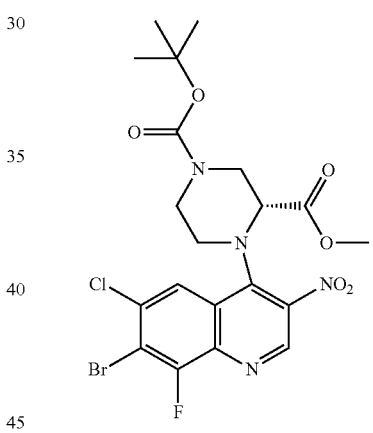

To a de-gassed solution of THF (325 ml) and DIPEA (12.74 ml, 73.14 mmol) under a nitrogen atmosphere was added 7-bromo-4,6-dichloro-8-fluoro-3-nitroquinoline (26.59 g, 66.49 mmol) and 1-(tert-butyl) 3-methyl (R)-piperazine-1,3-dicarboxylate (17.05 g, 69.81 mmol). The resultant brown solution was heated at 61° C. (internal temperature) under a nitrogen atmosphere for 18 hours. Additional DIPEA (5.8 ml, 33.24 mmol) and 1-(tert-butyl) 3-methyl (R)-piperazine-1,3-dicarboxylate (8.12 g, 33.24 mmol) was then added and the resultant reaction mixture was heated at 61° C. (internal) for 4 hours. The reaction mixture was concentrated in vacuo, and the crude product was purified by flash silica chromatography, elution gradient 0 to 50% ethyl acetate in heptane. Pure fractions were evaporated to dryness to afford 1-tert-butyl 3-methyl (3R)-4-(7-bromo-6-chloro-8-fluoro-3-nitroquinolin-4-yl)piperazine-1,3-dicarboxylate (32.1 g, 88%) as an orange solid. 1H NMR (400 MHz, DMSO, 30° C.) 1.45 (9H, s), 2.52-2.53 (1H, m), 3.29-3.34 (1H, m), 3.56 (3H, s), 3.61-3.77 (2H, m), 3.78-3.93 (1H, m), 4.04-4.21 (1H, m), 4.33-4.4 (1H, m), 8.36 (1H, d), 9.16 (1H, s). m/z: ES+ [M+H]+ 547. 97% ee.

Tert-butyl (4aR)-10-bromo-11-chloro-9-fluoro-5-oxo-1,2,4,4a,5,6-hexahydro-3H-pyrazino[1',2':4,5]pyrazino[2,3-c]quinoline-3-carboxylate

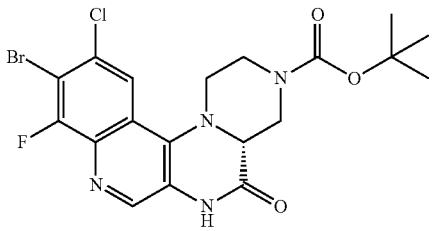 [SMILES: CC(C)(C)OC(=O)N1CCN2c3c(cnc4c(F)c(Br)c(Cl)cc34)NC(=O)[C@H]2C1]

To a stirred solution of 1-tert-butyl 3-methyl (3R)-4-(7-bromo-6-chloro-8-fluoro-3-nitroquinolin-4-yl)piperazine-1,3-dicarboxylate (28.21 g, 51.50 mmol) in acetic acid (400 ml) at room temperature under a nitrogen atmosphere was added iron powder (10.07 g, 180.25 mmol) and the resultant reaction mixture was stirred at 80° C. for 30 minutes. The reaction mixture was concentrated in vacuo, the crude residue was suspended in DCM and was basified with aqueous saturated NaHCO₃ to pH>8. The resulting suspension was filtered through celite, washing with DCM. The layers were separated, the organics were dried by passing through a phase separating cartridge and concentrated in vacuo to afford tert-butyl (4aR)-10-bromo-11-chloro-9-fluoro-5-oxo-1,2,4,4a,5,6-hexahydro-3H-pyrazino[1',2':4,5]pyrazino[2,3-c]quinoline-3-carboxylate (24.21 g, 97%) as a light yellow solid. 1H NMR (400 MHz, DMSO, 30° C.) 1.44 (9H, s), 2.61-2.77 (1H, m), 3.08-3.33 (3H, m), 3.85 (2H, s), 4.68 (1H, d), 8.09 (1H, d), 8.64 (1H, s), 11.03 (1H, s). m/z: ES+ [M+H]+ 485. >99% ee.

Tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate

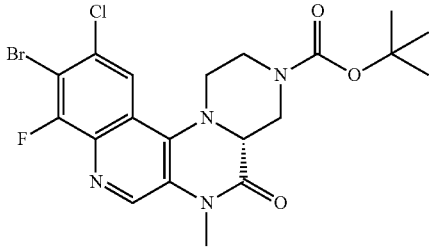 [SMILES: CN1C(=O)[C@H]2CN(C(=O)OC(C)(C)C)CCN2c2c1cnc1c(F)c(Br)c(Cl)cc21]

To a stirred suspension of tert-butyl (4aR)-10-bromo-11-chloro-9-fluoro-5-oxo-1,2,4,4a,5,6-hexahydro-3H-pyrazino[1',2':4,5]pyrazino[2,3-c]quinoline-3-carboxylate (26.6 g, 54.76 mmol) and potassium carbonate (15.14 g, 109.52 mmol) in acetone (350 ml) at room temperature was added iodomethane (34.1 ml, 547.62 mmol). The resultant suspension was heated at 40° C. (internal temperature) for 18 hours. The reaction mixture was concentrated in vacuo and the crude residue was dissolved in DCM, washed with water and aqueous saturated brine. The aqueous layers were back extracted with DCM and the combined organic layers were dried with a phase separating cartridge, concentrated in vacuo to afford the crude product as a dark red foam. The crude product was slurried in diethyl ether for 30 minutes and was concentrated in vacuo to afford tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (27.2 g, 100%) as an orange solid. 1H NMR (400 MHz, DMSO, 30° C.) 1.45 (9H, s), 2.62-2.75 (1H, m), 3.15-3.31 (3H, m), 3.49 (3H, s), 3.79-3.98 (2H, m), 4.73 (1H, d), 8.15 (1H, d), 9.00 (1H, s). m/z: ES+ [M+H]+ 499. 99% ee.

Tert-butyl (4aR)-11-chloro-9-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate

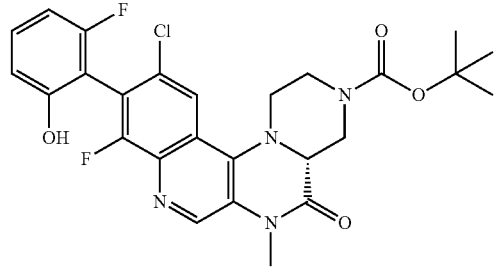 [SMILES: CN1C(=O)[C@H]2CN(C(=O)OC(C)(C)C)CCN2c2c1cnc1c(F)c(-c3c(O)cccc3F)c(Cl)cc21]

A stirred suspension of tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (10 g, 20 mmol), (2-fluoro-6-hydroxyphenyl)boronic acid (6.24 g, 40.02 mmol) and potassium carbonate (8.30 g, 60.03 mmol) in dioxane (120 ml) and water (40 ml) was de-gassed for 15 minutes. RuPhos-Pd-G3 (1.67 g, 2 mmol) and Ruphos (0.93 g, 2 mmol) were added, the reaction mixture was further de-gassed for approximately 5 minutes before the flask was lowered into a preheated hotplate at 80° C. The resultant dark reaction mixture was heated at 80° C. for 2 hours. Additional (2-fluoro-6-hydroxyphenyl)boronic acid (1.56 g, 10 mmol) was added and the reaction mixture was further heated at 80° C. for 1 hour. The reaction mixture was cooled to room temperature and the organic solvent was removed in vacuo, diluted with DCM and was washed with aqueous saturated NH₄Cl. The aqueous phase was back-extracted with DCM and the combined organic layers were dried by passing through a phase separating cartridge. The filtrate was concentrated in vacuo and the crude product was purified by flash silica chromatography, elution gradient 0 to 100% ethyl acetate in heptane. Pure fractions were evaporated to dryness to afford the crude product which was triturated with diethyl ether (150 ml), the solid residue was washed with copious amounts of diethyl ether and the filtrate was concentrated in vacuo to afford tert-butyl (4aR)-11-chloro-9-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (5.5 g, 52%) as a yellow solid (a 29:71 mixture of atropisomers). 1H NMR (400 MHz, DMSO, 30° C.) 1.46 (9H, s), 2.64-2.77 (1H, m), 3.19-3.3 (3H, m), 3.51 (3H, s), 3.8-4 (2H, m), 4.76 (1H, d), 6.81 (1H, t), 6.87 (1H, d), 7.36 (1H, q), 8.08 (1H, s), 9.00 (1H, s), 10.18 (1H, s). m/z: ES+ [M+H]+ 531.

(4aR)-11-chloro-9-fluoro-1-(2-fluoro-6-hydroxyphenyl)-6-methyl-2,3,4,4a-tetrahydro-1H-pyrazino[1',2':4,5]pyrazino[2,3-c]quinolin-5(6H)-one

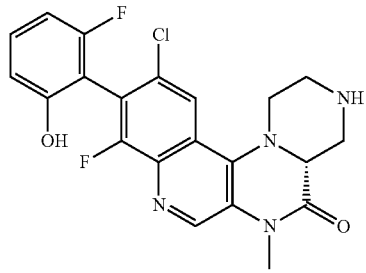 [SMILES: CN1C(=O)[C@H]2CNCCN2c2c1cnc1c(F)c(-c3c(O)cccc3F)c(Cl)cc21]

To a stirred yellow suspension of tert-butyl (4aR)-11-chloro-9-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (15 g, 28.25 mmol) in MeOH (300 ml) was added HCl (6N in i-PrOH) (94 ml, 565 mmol) (on addition the reaction mixture turned into an orange solution). The resultant solution was stirred at room temperature for 3 hours after which a suspension had formed and the reaction mixture was concentrated in vacuo. The crude residue was dissolved in a mixture of MeOH (300 ml) and water (15 ml) and purified by ion exchange chromatography using loose SCX (300 g, 483.87 mmol). The pad of SCX was washed with MeOH (3.5 l) and the desired product was eluted using 1M $NH_3$/MeOH (2.5 l). Pure fractions were evaporated to dryness and was azeotroped with DCM and diethyl ether to afford (4aR)-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (11.35 g, 93%) as a pale yellow solid. 1H NMR (400 MHz, DMSO, 30° C.) 2.56-2.66 (1H, m), 2.84-2.93 (1H, m), 2.94-3.06 (3H, m), 3.07-3.14 (1H, m), 3.52 (3H, s), 3.57-3.72 (2H, m), 6.81 (1H, t), 6.86 (1H, d), 7.35 (1H, q), 8.04 (1H, s), 8.98 (1H, s), 10.16 (1H, s). m/z: ES+ [M+H]+ 431.

(4aR)-11-Chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (Atropisomer 1 and 2)

atropisomer 1

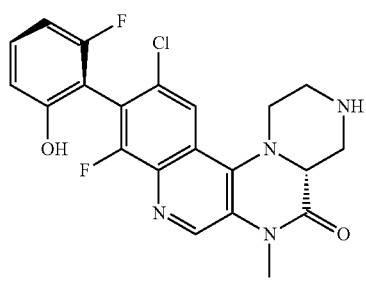

atropisomer 2

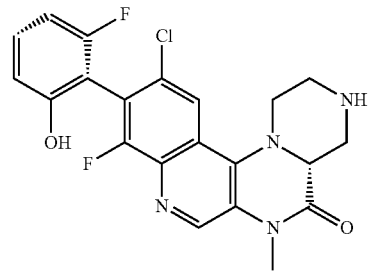

(4aR)-11-chloro-9-fluoro-10-(2-fluoro-6-hydroxyphenyl)-6-methyl-2,3,4,4a-tetrahydro-1H-pyrazino [1',2':4,5]pyrazino[2,3-c]quinolin-5(6H)-one (7.46 g, 17.32 mmol) was dissolved in MeOH/2-methyltetrahydrofuran (30 ml, 4:1 ratio) and purified using SFC conditions: Column Phenomenex C4, 30×250 mm, 5 micron Mobile phase: 45% MeOH+0.1% $NH_3$/55% $scCO_2$, Flow rate: 90 ml/min, BPR: 120 bar Column temperature: 40° C. Fractions containing the desired compounds were concentrated in vacuo to afford (4aR)-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one, atropisomer 1 (1.74 g, 23%) as a pale yellow solid. 1H NMR (400 MHz, DMSO, 30° C.) 2.57-2.67 (1H, m), 2.84-2.94 (1H, m), 2.96-3.06 (2H, m), 3.07-3.15 (1H, m), 3.53 (3H, s), 3.62 (1H, s), 3.67 (1H, d), 6.81 (1H, t), 6.87 (1H, d), 7.36 (1H, q), 8.05 (1H, s), 8.99 (1H, s), 10.19 (1H, s) exchangeable NH not seen. m/z: ES+ [M+H]+ 431, 99% ee, followed by (4aR)-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one, atropisomer 2 (3.7 g, 50%) as a pale yellow solid. 1H NMR (400 MHz, DMSO, 30° C.) 2.57-2.66 (1H, m), 2.85-2.93 (1H, m), 2.95-3.06 (2H, m), 3.07-3.15 (1H, m), 3.53 (3H, s), 3.61 (1H, d), 3.67 (1H, d), 6.81 (1H, t), 6.86 (1H, d), 7.32-7.4 (1H, m), 8.04 (1H, d), 8.99 (1H, s), 10.18 (1H, s) exchangeable NH not seen. m/z: ES+ [M+H]+ 431. 99% ee. NB the atropisomeric configuration presented is believed to be correct but has not yet been confirmed by X-ray crystallography.

(4aR)-11-Chloro-9-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one, Example 17

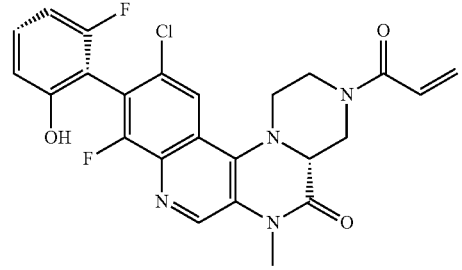

To a stirred solution of (4aR)-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one, atropisomer 2 (0.73 g, 1.69 mmol) and DIPEA (0.33 ml, 1.86 mmol) in DCM (15 ml) under nitrogen at 0° C. was added acryloyl chloride (0.12 ml, 1.52 mmol) and the reaction mixture was stirred at 0° C. for 15 minutes. The reaction mixture was washed with cold water and dried by passing through a phase separator cartridge. The filtrate was concentrated in vacuo and the crude product was triturated with diethyl ether to afford a yellow solid which was purified by flash silica chromatography, elution gradient 0 to 100% ethyl acetate in heptane. Pure fractions were evaporated to dryness to afford a white solid which was dissolved in a mixture of MeOH (5 ml) and 7N $NH_3$/MeOH (10 ml). The resulting solution was stirred at room temperature for 5 minutes and the reaction mixture was concentrated in vacuo and then triturated with diethyl ether to afford (4aR)-11-chloro-9-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one as a white solid (0.30 g, 36%). 1H NMR (400 MHz, DMSO, 30° C.) 2.63-2.74 (1H, m), 3.18 (1H, d), 3.35 (1H, d), 3.50 (3H, s), 3.63 (1H, d), 3.96 (1H, s), 4.44 (1H, d), 4.78 (1H, d), 5.76 (1H, d), 6.15 (1H, dd), 6.75-6.91 (2H, m), 7.07 (1H, dd), 7.37 (1H, td), 8.13 (1H, s), 9.01 (1H, s), 10.18 (1H, s). m/z: ES+ [M+H]+ 485. >99% ee. NB the atropisomeric configuration presented is believed to be correct but has not yet been confirmed by X-ray crystallography.

Example 17, also known as 3-acryloyl-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5 (6H)-one, was also obtained from an achiral synthesis as detailed below. Example 17 was isolated along with the 3 other possible stereochemical forms of the molecule (2 enantiomers, each in 2 atropisomeric forms) by preparative HPLC and chiral SFC.

3-Acryloyl-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (2 Enantiomers and 2 Atropisomers, Examples 17, 18, 19 and 20)

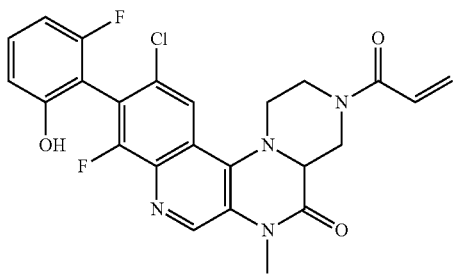 [SMILES: C=CC(=O)N1CCN2c3c(cnc4c(F)c(-c5c(O)cccc5F)c(Cl)cc34)N(C)C(=O)C2C1]

To a solution of racemic 11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (0.121 g, 0.28 mmol) and DIPEA (0.073 ml, 0.42 mmol) in DCM (5 ml) under nitrogen at 0° C. was added acryloyl chloride (0.021 ml, 0.27 mmol) and the reaction mixture stirred at 0° C. for 10 mins. The reaction mixture was extracted with cold water then saturated brine and dried by passing through a phase separator cartridge. Evaporation afforded a gum which was purified by preparative HPLC (Waters XSelect CSH C18 column, 30×100 mm id, 5 micron particle size), using decreasingly polar mixtures of water (containing 0.1% formic acid) and MeCN as eluents. Shallow gradient: 30 to 60% MeCN. Detection UV @ 271 nm. Fractions containing the desired compounds were evaporated to dryness to afford Sample 1 (i.e. peak 1) and Sample 2 (i.e. peak 2). Each sample was separately dissolved in MeOH (2 ml) and 2-methyltetrahydrofuran (1 ml) and then purified using SFC—conditions: Column: Chiralpak ID, 30×250 mm, 5 micron Mobile phase: 40 MeOH+0.1% $NH_3$/60% scCO2, Flow rate: 90 ml/min, BPR: 120 bar, Column temperature: 40° C. Individual peak fractions were combined then QC analysed using the following conditions: Column: Chiralpak ID, 3.0×100 mm, 3 micron Mobile phase: 40 MeOH+0.1% $NH_3$/60% scCO2 Flow rate: 2.0 ml/min BPR: 120 bar. Temperature: 40° C. Evaporation afforded firstly 3-acryloyl-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (13 mg, 10%), sample 1, rotational isomer 1 (Example 18) as a solid (atropisomer 1 from sample 1). 1H NMR (400 MHz, DMSO, 30° C.) 2.68 (1H, s), 3.20 (1H, d), 3.35 (1H, d), 3.50 (3H, s), 3.63 (1H, d), 3.96 (1H, s), 4.44 (1H, d), 4.78 (1H, d), 5.76 (1H, d), 6.15 (1H, dd), 6.84 (2H, dd), 7-7.17 (1H, m), 7.36 (1H, q), 8.13 (1H, s), 9.01 (1H, s), 10.19 (1H, s). m/z: ES+ [M+H]+ 485. >99% ee, followed by 3-acryloyl-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (14 mg, 11%) sample 1, rotational isomer 2 (Example 17) as a solid (atropisomer 2 from sample 1). 1H NMR (400 MHz, DMSO, 30° C.) 2.68 (1H, s), 3.14-3.24 (1H, m), 3.35 (1H, d), 3.50 (3H, s), 3.63 (1H, d), 3.96 (1H, s), 4.44 (1H, d), 4.78 (1H, d), 5.76 (1H, d), 6.15 (1H, dd), 6.76-6.91 (2H, m), 6.99-7.18 (1H, m), 7.37 (1H, q), 8.13 (1H, s), 9.01 (1H, s), 10.18 (1H, s). m/z: ES+ [M+H]+ 485. >99% ee.

Sample 2 was similarly chirally separated to give 3-acryloyl-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (7 mg, 5%), sample 2, rotational isomer 1 (Example 19) as a solid (atropisomer 1 from sample 2). 1H NMR (400 MHz, DMSO, 30° C.) 2.68 (1H, s), 3.20 (1H, d), 3.35 (1H, s), 3.50 (3H, s), 3.63 (1H, d), 3.97 (1H, s), 4.46 (1H, s), 4.78 (1H, d), 5.76 (1H, d), 6.15 (1H, d), 6.73-6.94 (2H, m), 7.07 (1H, s), 7.36 (1H, q), 8.13 (1H, s), 9.01 (1H, s), 10.21 (1H, s). m/z: ES+ [M+H]+ 485. >99% ee, followed by 3-acryloyl-11-chloro-9-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (6 mg, 5%), sample 2, rotational isomer 2 (Example 20) as a solid (atropisomer 2 from sample 2). 1H NMR (400 MHz, DMSO, 30° C.) 2.67 (1H, s), 3.16-3.26 (1H, m), 3.30 (1H, s), 3.50 (3H, s), 3.62 (1H, s), 3.97 (1H, s), 4.47 (1H, s), 4.78 (1H, d), 5.76 (1H, d), 6.15 (1H, d), 6.76-6.9 (2H, m), 7.08 (1H, s), 7.36 (1H, q), 8.13 (1H, s), 9.00 (1H, s), 10.21 (1H, s). m/z: ES+ [M+H]+ 485. >96.3% ee.

Methyl N-[(benzyloxy)carbonyl]-L-seryl-D-alaninate

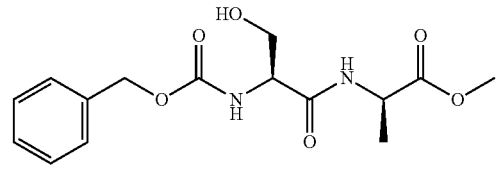 [SMILES: COC(=O)[C@@H](C)NC(=O)[C@H](CO)NC(=O)OCc1ccccc1]

A suspension of methyl D-alaninate hydrochloride (25 g, 179.11 mmol) and N-[(benzyloxy)carbonyl]-L-serine (42.8 g, 179.11 mmol) in dichloromethane (786 ml) was cooled in an ice-bath to 0° C. and EDC (41.2 g, 214.93 mmol) was added. DIPEA (109 ml, 626.89 mmol) was added dropwise over 20 minutes and then the resulting solution was stirred at room temperature overnight. The reaction mixture was concentrated under reduced pressure to give a colourless residue. The residue was dissolved in ethyl acetate (500 ml) and washed with 1:1 water/aqueous saturated sodium hydrogen carbonate solution (600 ml). The organic portion was collected and the aqueous was washed with a further portion of ethyl acetate (500 ml). The combined organic extracts were washed with aqueous 2 M hydrochloric acid solution (300 ml), brine (300 ml), dried over magnesium sulphate, filtered and concentrated to give methyl N-[(benzyloxy)carbonyl]-L-seryl-D-alaninate (44.9 g, 77%) as a colourless solid. 1H NMR (400 MHz, CD₃OD, 30° C.): 1.38 (3H, d), 3.71 (3H, s), 3.76 (2H, d), 4.24 (1H, t), 4.37-4.48 (1H, m), 5.11 (2H, s), 7.21-7.47 (5H, m). m/z: ES+ [M+H]+=325.1.

(3S,6R)-3-(Hydroxymethyl)-6-methylpiperazine-2,5-dione

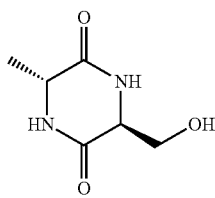

Methyl N-[(benzyloxy)carbonyl]-L-seryl-D-alaninate (44.9 g, 138.44 mmol) was dissolved in methanol (140 ml) and cyclohexene (90 ml, 888.54 mmol). 10% Palladium on carbon (2.25 g, 10.90 mmol) was added in one portion and the resultant mixture was heated to reflux overnight. A further portion of methanol (120 ml) was added and the mixture was stirred at reflux for one hour. The reaction mixture was filtered (whilst hot) through celite and the celite was washed with hot methanol (2×300 ml). The filtrate was concentrated to give a grey semi-solid. The solid was triturated with acetonitrile (200 ml), filtered and washed with acetonitrile (100 ml). The solid was dried under vacuum at 40° C. for one hour to give (3S,6R)-3-(hydroxymethyl)-6-methylpiperazine-2,5-dione (19.22 g, 88%) as a grey solid. 1H NMR (400 MHz, DMSO, 30° C.): 1.24 (3H, d), 3.52 (1H, ddd), 3.68 (1H, q), 3.74 (1H, ddd), 3.92 (1H, q), 5.09 (1H, t), 7.87 (1H, s), 8.06 (1H, s).

[(2R,5R)-5-Methylpiperazin-2-yl]methanol dihydrochloride

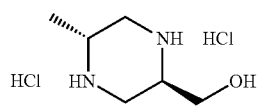

A vessel charged with (3S,6R)-3-(hydroxymethyl)-6-methylpiperazine-2,5-dione (10 g, 63.23 mmol) was cooled in an ice-bath and 1 M borane in THF (474 ml, 474.21 mmol) was added slowly. On addition, the mixture was brought to room temperature and then heated to 70° C. overnight. The reaction mixture was allowed to cool to room temperature and then cooled in an ice-bath to 0° C. Methanol (125 ml) was added dropwise and then aqueous 5 M hydrochloric acid solution (34 ml, 170 mmol) was added dropwise. The resultant solution was heated at 70° C. for 2 hours. The mixture was cooled to room temperature and then in an ice-bath. The precipitate formed was filtered off and the filter cake was washed with THF (60 ml). The solid was dried over vacuum to give [(2R,5R)-5-methylpiperazin-2-yl]methanol (12.11 g, 94%) as a grey solid (as the dihydrochloride salt). 1H NMR (400 MHz, DMSO, 30° C.): 1.32 (3H, d), 3.11 (2H, q), 3.37-3.78 (6H, m), 5.58 (1H, s), 9.98 (4H, s).

Tert-butyl (2R,5R)-5-(hydroxymethyl)-2-methylpiperazine-1-carboxylate

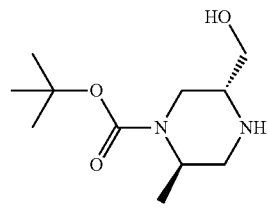 [SMILES: C[C@@H]1CN[C@@H](CO)CN1C(=O)OC(C)(C)C]

[(2R,5R)-5-Methylpiperazin-2-yl]methanol dihydrochloride (19.1 g, 94.04 mmol) was suspended in methanol (92 ml) and cooled in an ice-bath to 0° C. Triethylamine (40.6 ml, 291.52 mmol) was added and then a solution of di-tert-butyl dicarbonate (49.3 g, 225.69 mmol) in methanol (138 ml) was added dropwise over 30 minutes (keeping internal reaction temperature <10° C.). The resultant solution was stirred in the ice-bath for one hour before being brought to room temperature and then heated to 50° C. overnight. The reaction mixture was cooled to room temperature and concentrated under reduced pressure. The resultant residue was dissolved in ethanol (313 ml) and aqueous 1.5 M sodium hydroxide solution (313 ml, 470.20 mmol) and the solution was heated to 100° C. overnight. The reaction mixture was cooled to room temperature and brought to pH 9 using aqueous 2 M hydrochloric acid solution. The solution was extracted with chloroform (2×600 ml) and the combined organic extracts were dried over magnesium sulphate, filtered and concentrated under reduced pressure to give a pale yellow oil. The oil was re-dissolved in methanol, concentrated and dried under vacuum overnight to give tert-butyl (2R,5R)-5-(hydroxymethyl)-2-methylpiperazine-1-carboxylate (21.45 g, 99%) as an oil which solidified on standing to a pale yellow waxy solid. 1H NMR (400 MHz, CD3OD, 30° C.): 1.24 (3H, d), 1.46 (9H, s), 2.57 (1H, dd), 2.93-3.02 (1H, m), 3.07 (1H, dd), 3.24 (1H, dd), 3.54 (1H, dd), 3.59-3.68 (1H, m), 3.78 (1H, dd), 4.09-4.2 (1H, m). m/z: ES+ [M+H]+=231.1.

1-Benzyl 4-tert-butyl (2R,5R)-2-(hydroxymethyl)-5-methylpiperazine-1,4-dicarboxylate

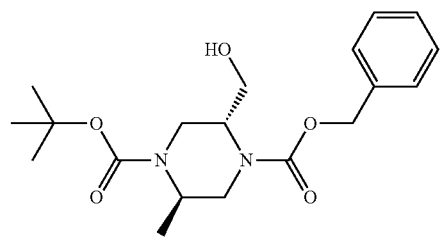 [SMILES: C[C@@H]1CN(C(=O)OCc2ccccc2)[C@@H](CO)CN1C(=O)OC(C)(C)C]

A solution of tert-butyl (2R,5R)-5-(hydroxymethyl)-2-methylpiperazine-1-carboxylate (18.5 g, 80.33 mmol) in THF (190 ml) was cooled in an ice-bath to 0° C. Aqueous 1M sodium hydroxide solution (88 ml, 88.36 mmol) was added, followed by benzyl chloroformate (11.99 ml, 84.34 mmol) (internal reaction temperature kept <10° C.). The mixture was stirred in the ice-bath for 60 minutes before being brought to room temperature and stirred. After one hour, the phases were separated and the aqueous was washed with ethyl acetate (2×50 ml). The combined organics were washed with brine (100 ml), dried over magnesium sulphate, filtered and concentrated under reduced pressure to give a pale yellow oil. The crude product was purified by flash silica chromatography, elution gradient 0 to 100% ethyl acetate in heptane. Pure fractions were evaporated to dryness to afford 1-benzyl 4-tert-butyl (2R,5R)-2-(hydroxymethyl)-5-methylpiperazine-1,4-dicarboxylate (25.4 g, 87%) as a colourless oil. 1H NMR (400 MHz, CD$_3$OD, 30° C.): 1.12 (3H, dd), 1.46 (9H, s), 3.1-3.29 (2H, m), 3.53-3.66 (2H, m), 3.81 (1H, d), 3.88-4.02 (1H, m), 4.15-4.38 (2H, m), 5.06-5.26 (2H, m), 7.21-7.51 (5H, m). One exchangeable proton not seen. m/z: ES+ [M-Boc]=265.1.

(2R,5R)-1-[(Benzyloxy)carbonyl]-4-(tert-butoxycarbonyl)-5-methylpiperazine-2-carboxylic acid

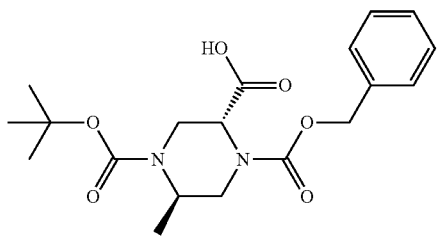

Sodium periodate (29.8 g, 139.39 mmol) was dissolved in water (174 ml) and acetonitrile/dimethyl carbonate (93 ml, 1:1 ratio) and then ruthenium(III) chloride hydrate (157 mg, 0.70 mmol) was added. The solution was cooled in an ice-bath to 0° C. and a solution of 1-benzyl 4-tert-butyl (2R,5R)-2-(hydroxymethyl)-5-methylpiperazine-1,4-dicarboxylate (25.4 g, 69.70 mmol) in acetonitrile/dimethyl carbonate (232 ml, 1:1 ratio) was added slowly over 15 minutes (solution precipitates). On addition, the solution was brought to room temperature and stirred. After 45 minutes the reaction mixture was diluted with water (300 ml) and extracted with ethyl acetate (3×300 ml). The combined organics were washed with brine (500 ml) and dried over magnesium sulphate. The mixture was filtered through a short pad of celite and concentrated under reduced pressure to give a pale brown residue. The residue was dissolved in diethyl ether (100 ml) and slowly concentrated and dried to give a pale brown solid. The solid was triturated with heptane (100 ml) to give a fine solid which was filtered, washed with heptane (100 ml) and dried under vacuum at 45° C. to give (2R,5R)-1-[(benzyloxy)carbonyl]-4-(tert-butoxycarbonyl)-5-methylpiperazine-2-carboxylic acid (23.30 g, 88%) as a beige solid. 1H NMR (400 MHz, DMSO, 30° C.): 1.07 (3H, dd), 1.38 (9H, s), 3.17-3.4 (2H, m), 3.55-3.71 (1H, m), 4.04-4.32 (2H, m), 4.56 (1H, s), 5.01-5.23 (2H, m), 7.19-7.51 (5H, m), 13.02 (1H, s). m/z: ES− [M−H]−=377.2.

1-Benzyl 4-tert-butyl 2-methyl (2R,5R)-5-methylpiperazine-1,2,4-tricarboxylate

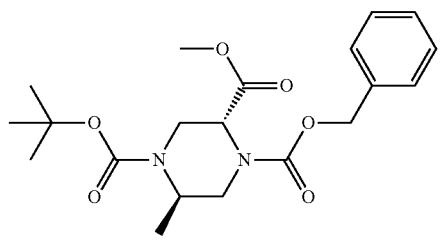 [SMILES: COC(=O)[C@H]1CN(C(=O)OC(C)(C)C)[C@H](C)CN1C(=O)OCc1ccccc1]

A solution of (2R,5R)-1-[(benzyloxy)carbonyl]-4-(tert-butoxycarbonyl)-5-methylpiperazine-2-carboxylic acid (23.3 g, 61.57 mmol) in acetonitrile (400 ml) was placed in a water bath and potassium carbonate (12.76 g, 92.36 mmol) was added. Iodomethane (5.75 ml, 92.36 mmol) was added dropwise and the suspension was heated to 60° C. After 2 hours, the reaction mixture was cooled to room temperature and concentrated under reduced pressure to give a pale yellow residue. The residue was dissolved in ethyl acetate (300 ml) and water (300 ml). The organic portion was collected and the aqueous was extracted with ethyl acetate (300 ml). The combined organic extracts were washed with brine (300 ml), dried over magnesium sulphate, filtered and concentrated to give a pale brown oil (27 g). The crude product was purified by flash silica chromatography, elution gradient 0 to 70% ethyl acetate in heptane. Pure fractions were evaporated to dryness to afford 1-benzyl 4-tert-butyl 2-methyl (2R,5R)-5-methylpiperazine-1,2,4-tricarboxylate (21.70 g, 90%) as a colourless oil. 1H NMR (400 MHz, DMSO, 30° C.): 1.08 (3H, d), 1.39 (9H, s), 3.30 (3H, s), 3.64 (3H, t), 4.02-4.31 (2H, m), 4.69 (1H, s), 5.02-5.23 (2H, m), 7.23-7.5 (5H, m). m/z: ES+ [M+H]+=393.3.

1-Tert-butyl 3-methyl (3R,6R)-6-methylpiperazine-1,3-dicarboxylate

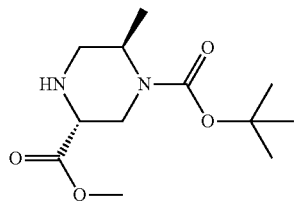 [SMILES: COC(=O)[C@H]1CN(C(=O)OC(C)(C)C)[C@H](C)CN1]

1-Benzyl 4-tert-butyl 2-methyl (2R,5R)-5-methylpiperazine-1,2,4-tricarboxylate (21.7 g, 55.29 mmol) was dissolved in methanol (276 ml) and 10% palladium on carbon (4.34 g, 40.78 mmol) was added. The mixture was stirred at room temperature under a hydrogen atmosphere (0.5 bar) overnight. The reaction mixture was filtered through a short pad of celite, washing with methanol (200 ml) and the filtrate was concentrated under reduced pressure to give a grey residue. The residue was dissolved in methanol (100 ml) and passed through a syringe filter. The resultant colourless solution was concentrated under reduced pressure and dried under vacuum at 45° C. to give 1-tert-butyl 3-methyl (3R,6R)-6-methylpiperazine-1,3-dicarboxylate (14.1 g, 99%) as a pale yellow oil. 1H NMR (400 MHz, DMSO, 30° C.) 1.13 (3H, d), 1.37 (9H, s), 2.46 (1H, dd), 2.66 (1H, s), 2.93 (1H, dd), 3.15 (1H, dd), 3.56 (1H, d), 3.63 (3H, s), 3.95-4.07 (1H, m), 4.07-4.16 (1H, m). m/z: ES+ [M-Boc]=158.9.

1-Tert-butyl 3-methyl (3R,6R)-4-(7-bromo-6-chloro-8-fluoro-3-nitroquinolin-4-yl)-6-methylpiperazine-1,3-dicarboxylate

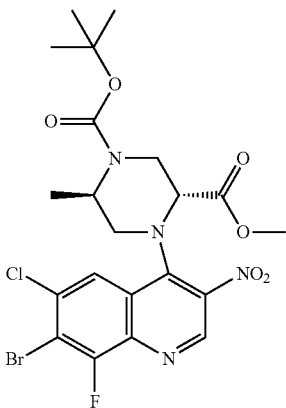 [SMILES: COC(=O)[C@H]1CN(C(=O)OC(C)(C)C)[C@H](C)CN1c1c([N+](=O)[O-])cnc2c(F)c(Br)c(Cl)cc12]

A solution of 1-tert-butyl 3-methyl (3R,6R)-6-methylpiperazine-1,3-dicarboxylate (310 mg, 1.20 mmol) in THF (4.56 ml) and DIPEA (0.226 ml, 1.30 mmol) was degassed with nitrogen for 5 minutes. 7-Bromo-4,6-dichloro-8-fluoro-3-nitroquinoline (400 mg, 1.00 mmol) was added and the mixture was heated to 60° C. After three hours, the reaction mixture was cooled to room temperature and concentrated in vacuo. The brown residue was dissolved in dichloromethane (20 ml) and washed with aqueous 1 M citric acid solution (20 ml). The organic portion was collected and the aqueous extract was washed with a further portion of dichloromethane (20 ml). The combined organic extracts were washed with brine (10 ml), passed through a hydrophobic frit and concentrated to give an orange solid. The solid was triturated with diethyl ether (30 ml), filtered and dried in air over vacuum to give 1-tert-butyl 3-methyl (3R,6R)-4-(7-bromo-6-chloro-8-fluoro-3-nitroquinolin-4-yl)-6-methylpiperazine-1,3-dicarboxylate (430 mg, 77%) as a yellow solid. 1H NMR (400 MHz, DMSO, 30° C.): 1.19 (3H, d), 1.43 (9H, s), 3.29 (1H, s), 3.58 (3H, s), 3.66 (1H, d), 3.87 (1H, dd), 4.32 (2H, d), 4.47 (1H, d), 8.36 (1H, d), 9.16 (1H, s). 19F NMR (376 MHz, DMSO, 30° C.): −107.64. m/z: ES+ [M+H]+=560.8.

Tert-butyl (2R,4aR)-10-bromo-11-chloro-9-fluoro-2-methyl-5-oxo-1,2,4,4a,5,6-hexahydro-3H-pyrazino[1',2':4,5]pyrazino[2,3-c]quinoline-3-carboxylate

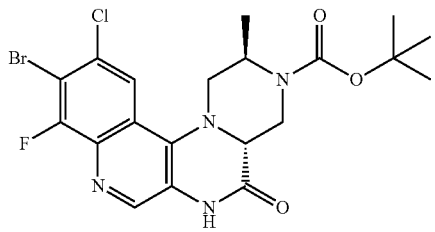 [SMILES: C[C@@H]1CN2c3c(cnc4c(F)c(Br)c(Cl)cc34)NC(=O)[C@H]2CN1C(=O)OC(C)(C)C]

To a stirred solution of 1-tert-butyl 3-methyl (3R,6R)-4-(7-bromo-6-chloro-8-fluoro-3-nitroquinolin-4-yl)-6-methylpiperazine-1,3-dicarboxylate (430 mg, 0.77 mmol) in acetic acid (7.5 ml) at room temperature was added iron powder (150 mg, 2.68 mmol). The resultant suspension was stirred at 80° C. After 1 hour, the reaction mixture was concentrated under reduced pressure to give a brown solid. The solid was suspended in dichloromethane (30 ml) and aqueous saturated sodium hydrogen carbonate solution was added until the solution was at pH 8. The mixture was filtered through celite (washing with dichloromethane). The phases were separated and the aqueous was washed with dichloromethane (30 ml). The combined organic extracts were washed with brine (30 ml), passed through a hydrophobic frit and concentrated to give tert-butyl (2R,4aR)-10-bromo-11-chloro-9-fluoro-2-methyl-5-oxo-1,2,4,4a,5,6-hexahydro-3H-pyrazino[1',2':4,5]pyrazino[2,3-c]quinoline-3-carboxylate (371 mg, 97%) as a pale brown solid. 1H NMR (400 MHz, DMSO, 30° C.): 1.44 (12H, s), 2.88 (1H, dd), 2.95-3.11 (1H, m), 3.35-3.48 (1H, m), 3.77-3.92 (1H, m), 4.09-4.3 (1H, m), 4.55-4.69 (1H, m), 7.94 (1H, d), 8.64 (1H, s), 11.06 (1H, s). 19F NMR (376 MHz, DMSO, 30° C.): −108.63. m/z: ES+ [M+H]+=500.9.

Tert-butyl (2R,4aR)-10-bromo-11-chloro-9-fluoro-2,6-dimethyl-5-oxo-1,2,4,4a,5,6-hexahydro-3H-pyrazino[1',2':4,5]pyrazino[2,3-c]quinoline-3-carboxylate

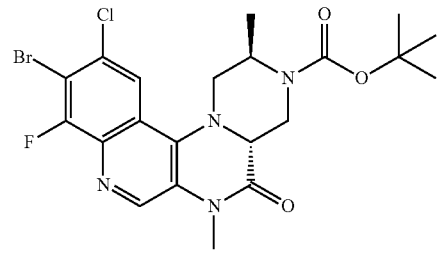 [SMILES: C[C@@H]1CN2c3c(cnc4c(F)c(Br)c(Cl)cc34)N(C)C(=O)[C@H]2CN1C(=O)OC(C)(C)C]

To a stirred suspension of tert-butyl (2R,4aR)-10-bromo-11-chloro-9-fluoro-2-methyl-5-oxo-1,2,4,4a,5,6-hexahydro-3H-pyrazino[1',2':4,5]pyrazino[2,3-c]quinoline-3-carboxylate (371 mg, 0.74 mmol) and potassium carbonate (205 mg, 1.48 mmol) in acetone (6.96 ml) was stirred at room temperature. Iodomethane (0.462 ml, 7.42 mmol) was added and the resultant mixture was stirred at 40° C. overnight. The reaction mixture was cooled to room temperature and evaporated to dryness. The crude residue was dissolved in dichloromethane (20 ml), extracted with water (10 ml) and washed with brine (10 ml). The organic extract was passed through a hydrophobic frit and concentrated to give a red foam. The crude product was purified by flash silica chromatography, elution gradient 0 to 80% ethyl acetate in dichloromethane. Pure fractions were evaporated to dryness to afford tert-butyl (2R,4aR)-10-bromo-11-chloro-9-fluoro-2,6-dimethyl-5-oxo-1,2,4,4a,5,6-hexahydro-3H-pyrazino[1',2':4,5]pyrazino[2,3-c]quinoline-3-carboxylate (248 mg, 65%) as a pale yellow solid. 1H NMR (400 MHz, CDCl3, 30° C.): 1.43-1.67 (12H, m), 2.97 (2H, s), 3.51-3.59 (5H, m), 4.51 (1H, s), 4.94 (1H, d), 8.00 (1H, d), 8.79 (1H, s). 19F NMR (376 MHz, CDCl3, 30° C.): −107.72. m/z: ES+ [M+H]+=512.9.

87

Tert-butyl (2R,4aR)-11-chloro-9-fluoro-10-(2-fluoro-6-hydroxyphenyl)-2,6-dimethyl-5-oxo-1,2,4,4a,5,6-hexahydro-3H-pyrazino[1',2':4,5]pyrazino[2,3-c]quinoline-3-carboxylate

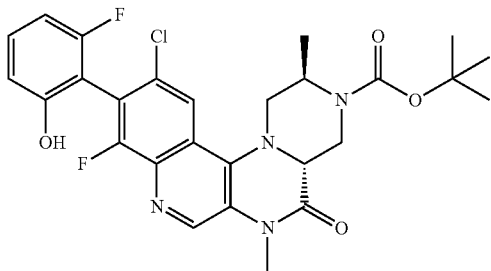 [SMILES: C[C@@H]1CN2c3c(cnc4c(F)c(-c5c(O)cccc5F)c(Cl)cc34)N(C)C(=O)[C@H]2CN1C(=O)OC(C)(C)C]

A stirred suspension of tert-butyl (2R,4aR)-10-bromo-11-chloro-9-fluoro-2,6-dimethyl-5-oxo-1,2,4,4a,5,6-hexahydro-3H-pyrazino[1',2':4,5]pyrazino[2,3-c]quinoline-3-carboxylate (248 mg, 0.48 mmol), (2-fluoro-6-hydroxyphenyl)boronic acid (151 mg, 0.97 mmol) and potassium carbonate (200 mg, 1.45 mmol) in dioxane/water (4 ml, 3:1 ratio) was de-gassed with nitrogen for 10 minutes. RuPhos Pd G3 (40.4 mg, 0.05 mmol) and RuPhos (22.52 mg, 0.05 mmol) were added and the mixture was heated to 80° C. After 1.5 hours, the reaction mixture was cooled to room temperature and diluted with ethyl acetate (30 ml). The solution was washed with water (30 ml) and the aqueous portion was extracted with ethyl acetate (30 ml). The combined organic extracts were washed with brine (30 ml), dried over magnesium sulphate, filtered and concentrated in vacuo to give a yellow residue. The crude product was purified by flash silica chromatography, elution gradient 0 to 100% ethyl acetate in heptane. Pure fractions were evaporated to dryness to afford tert-butyl (2R,4aR)-11-chloro-9-fluoro-10-(2-fluoro-6-hydroxyphenyl)-2,6-dimethyl-5-oxo-1,2,4,4a,5,6-hexahydro-3H-pyrazino[1',2':4,5]pyrazino[2,3-c]quinoline-3-carboxylate (223 mg, 85%) as a yellow dry film (as a 1:1.2 mixture of atropisomers). 1H NMR (400 MHz, CDCl$_3$, 30° C.): 1.45-1.67 (12H, m), 2.86-3.08 (2H, m), 3.43-3.61 (5H, m), 4.25-4.58 (1H, m), 4.84-5.03 (1H, m), 5.74-6.28 (1H, m), 6.83 (2H, dt), 7.26-7.42 (1H, m), 7.82-8.13 (1H, m), 8.64-8.92 (1H, m). 19F NMR (376 MHz, CDCl$_3$, 30° C.): −116.77, −116.29, −112.15, −112.03. m/z: ES+ [M+H]+=545.0.

(2R,4aR)-11-Chloro-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one (Atropisomer 1 and Atropisomer 2)

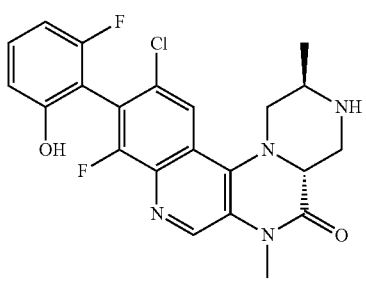 [SMILES: C[C@@H]1CN2c3c(cnc4c(F)c(-c5c(O)cccc5F)c(Cl)cc34)N(C)C(=O)[C@H]2CN1]

88

Tert-butyl (2R,4aR)-11-chloro-9-fluoro-10-(2-fluoro-6-hydroxyphenyl)-2,6-dimethyl-5-oxo-1,2,4,4a,5,6-hexahydro-3H-pyrazino[1',2':4,5]pyrazino[2,3-c]quinoline-3-carboxylate (223 mg, 0.41 mmol) was dissolved in methanol (2 ml) and hydrochloric acid (6N in isopropanol) (2.73 ml, 16.37 mmol) was added. The resultant solution was stirred at room temperature. After 35 minutes, the reaction mixture was purified using ion exchange chromatography, using a SCX-2 cartridge, eluting first with methanol and then 1 M ammonia in methanol. Pure fractions were collected and concentrated to give (2R,4aR)-11-chloro-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one (162 mg) as a yellow foam (as a mixture of atropisomers). The atropisomers were separated using supercritical fluid chromatography (SFC) (Column: Phenomenex C4, 30×250 mm, 5 micron; Mobile phase A: 45% methanol (+0.1% NH$_3$)/Mobile Phase B: scCO2; flow rate: 100 ml/min; BPR: 120 bar; Column temperature: 40° C.). Fractions containing the desired products were evaporated to dryness to afford atropisomer 1 of (2R,4aR)-11-chloro-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one (56 mg, 34%). 1H NMR (400 MHz, CDCl$_3$, 30° C.): 1.60 (3H, d), 3.06 (2H, d), 3.24 (1H, dd), 3.47-3.6 (5H, m), 3.63-3.74 (1H, m), 6.83 (2H, t), 7.35 (1H, td), 8.03 (1H, d), 8.76 (1H, s). Two exchangeable protons not seen. 19F NMR (376 MHz, CDCl$_3$, 30° C.): −116.58, −112.03--111.57. m/z: ES+ [M+H]+=445.0. This was followed by atropisomer 2 of (2R,4aR)-11-chloro-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one (70 mg, 43%). 1H NMR (400 MHz, CDCl$_3$, 30° C.): 1.55 (3H, d), 3.06 (2H, d), 3.21 (1H, dd), 3.54 (5H, d), 3.67 (1H, dd), 6.79 (1H, t), 6.85 (1H, d), 7.27-7.38 (1H, m), 7.88 (1H, d), 8.67 (1H, s). Two exchangeable protons not seen. 19F NMR (376 MHz, CDCl$_3$, 30° C.): −116.07, −113.08--112.15. m/z: ES+ [M+H]+=445.0.

(2R,4aR)-11-Chloro-9-fluoro-10-(2-fluoro-6-hydroxyphenyl)-2,6-dimethyl-3-(prop-2-enoyl)-2,3,4,4a-tetrahydro-1H-pyrazino[1',2':4,5]pyrazino[2,3-c]quinolin-5(6H)-one Atropisomer 1, Example 21

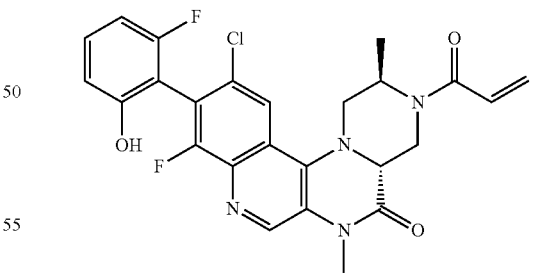

A solution of (2R,4aR)-11-chloro-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one atropisomer 1 (56 mg, 0.13 mmol) and triethylamine (23 μL, 0.16 mmol) in dichloromethane (1.19 ml) was cooled in an ice-bath to 0° C. Acryloyl chloride (11 μL, 0.14 mmol) was added and the resultant mixture was stirred at 0° C. After 45 minutes a further portion of acryloyl chloride (11 μL, 0.14 mmol) was added and the mixture was stirred at 0° C. After a further 15 minutes, the mixture was quenched by addition of water (5 ml) and extracted with dichloromethane (2×10 ml). The combined organics were passed through a hydrophobic frit and concentrated under reduced pressure to give a yellow dry film. The film was dissolved in 1 M ammonia in methanol (10 ml) and the suspension was stirred at room temperature. After 10 minutes the reaction mixture was concentrated under reduced pressure to give a yellow dry film (70 mg). The crude product was purified by flash silica chromatography, elution gradient 0 to 100% ethyl acetate in heptane. Pure fractions were evaporated to dryness to afford (2R,4aR)-11-chloro-9-fluoro-10-(2-fluoro-6-hydroxyphenyl)-2,6-dimethyl-3-(prop-2-enoyl)-2,3,4,4a-tetrahydro-1H-pyrazino[1',2':4,5]pyrazino[2,3-c]quinolin-5(6H)-one (7.8 mg, 12%) as a colourless solid. 1H NMR (400 MHz, CDCl$_3$, 30° C.): 1.56 (3H, d), 2.85-3.1 (2H, m), 3.48 (3H, s), 3.56-3.66 (1H, m), 3.74 (1H, d), 4.74 (1H, d), 4.79-4.92 (1H, m), 5.74 (1H, d), 6.30 (1H, dd), 6.73 (1H, t), 6.79 (1H, d), 6.86-7.01 (1H, m), 7.26 (1H, td), 7.94 (1H, d), 8.71 (1H, s). One exchangeable proton not seen. 19F NMR (376 MHz, CDCl$_3$, 30° C.): −116.62, −112.24. m/z: ES+ [M+H]+=499.1.

(2R,4aR)-11-Chloro-9-fluoro-10-(2-fluoro-6-hydroxyphenyl)-2,6-dimethyl-3-(prop-2-enoyl)-2,3,4,4a-tetrahydro-1H-pyrazino[1',2':4,5]pyrazino[2,3-c]quinolin-5(6H)-one Atropisomer 2, Example 22

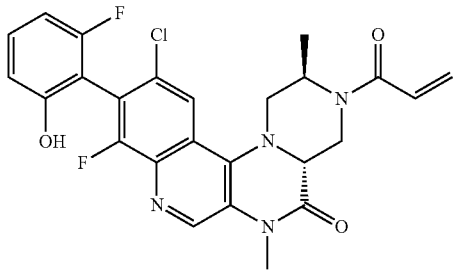 [SMILES: C=CC(=O)N1C[C@@H]2C(=O)N(C)c3cnc4c(F)c(-c5c(O)cccc5F)c(Cl)cc4c3N2C[C@H]1C]

A solution of (2R,4aR)-11-chloro-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one atropisomer 2 (70 mg, 0.16 mmol) and triethylamine (29 µL, 0.20 mmol) in dichloromethane (1.53 ml) was cooled in an ice-bath to 0° C. Acryloyl chloride (14 µL, 0.17 mmol) was added and the resultant mixture was stirred at 0° C. After 10 minutes a further portion of acryloyl chloride (14.06 µL, 0.17 mmol) was added and the mixture was stirred at 0° C. After a further 10 minutes, the mixture was quenched by addition of water (5 ml) and extracted with dichloromethane (2×10 ml). The combined organics were passed through a hydrophobic frit and concentrated under reduced pressure to give a yellow dry film. The film was dissolved in 1 M ammonia in methanol (10 ml) and the suspension was stirred at room temperature. After 15 minutes the reaction mixture was concentrated under reduced pressure to give a yellow dry film. The crude product was purified by preparative HPLC (Column: Waters CSH C18 OBD, 30×100 mm id, 5 micron particle size), using decreasingly polar mixtures of water (containing 1% by volume of NH$_4$OH (28-30% in H2O)) and acetonitrile as eluents (using a shallow gradient of 20 to 35% acetonitrile). Fractions containing the desired compound were evaporated to dryness to afford (2R,4aR)-11-chloro-9-fluoro-10-(2-fluoro-6-hydroxyphenyl)-2,6-dimethyl-3-(prop-2-enoyl)-2,3,4,4a-tetrahydro-1H-pyrazino[1',2':4,5]pyrazino[2,3-c]quinolin-5(6H)-one (29.1 mg, 37%) as a colourless solid. 1H NMR (400 MHz, CDCl$_3$, 30° C.): 1.57 (1H, s), 1.66 (3H, d), 3.01 (1H, d), 3.15 (1H, d), 3.56 (3H, s), 3.65 (1H, s), 3.81 (1H, d), 4.81 (1H, d), 5.00 (1H, s), 5.80 (1H, d), 6.36 (1H, d), 6.75-6.9 (2H, m), 6.93-7.1 (1H, m), 7.35 (1H, td), 8.02 (1H, s), 8.80 (1H, s). 19F NMR (376 MHz, CDCl$_3$, 30° C.): −112.04, −116.25. m/z: ES+ [M+H]+=499.

tert-Butyl (4aR)-10-bromo-11-chloro-9-methoxy-1,2,4a,5-tetrahydropyrazino[1',2':4,5][1,4]oxazino[2,3-c]quinoline-3(4H)-carboxylate

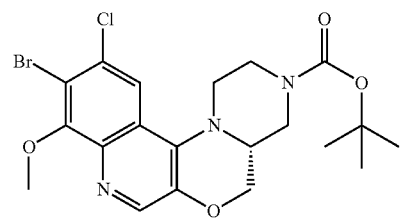 [SMILES: COc1c(Br)c(Cl)cc2c3c(cnc12)OC[C@H]1CN(C(=O)OC(C)(C)C)CCN31]

Sodium methoxide (25 wt % solution in methanol, 0.278 mL, 1.22 mmol) was added to a stirred solution of tert-butyl (4aR)-10-bromo-11-chloro-9-fluoro-1,2,4a,5-tetrahydropyrazino[1',2':4,5][1,4]oxazino[2,3-c]quinoline-3(4H)-carboxylate (576 mg, 1.22 mmol) in dioxane (10 mL). The resulting solution was stirred at 100° C. for 2 h. The reaction mixture was allowed to cool, diluted with water (50 mL), and extracted with EtOAc (2×75 mL), the organic extracts were combined, washed with brine (50 mL), dried with MgSO$_4$, filtered and concentrated in vacuo to afford crude product. This was purified by flash silica chromatography (0 to 50% EtOAc in heptane) to give tert-butyl (4aR)-10-bromo-11-chloro-9-methoxy-1,2,4a,5-tetrahydropyrazino[1',2':4,5][1,4]oxazino[2,3-c]quinoline-3(4H)-carboxylate (389 mg, 72%) as a yellow foam; $^1$H NMR (400 MHz, CDCl$_3$, 30° C.) 1.49 (9H, s), 3.08-3.18 (1H, m), 3.32 (1H, s), 3.42 (2H, d), 3.65 (1H, dd), 3.96 (2H, dd), 4.15 (3H, s), 4.28 (2H, d), 7.81 (1H, s), 8.55 (1H, s), m/z ES$^+$ [M+H]$^+$ 484.

tert-Butyl (4aR)-11-chloro-10-(2-fluoro-6-hydroxyphenyl)-9-methoxy-1,2,4a,5-tetrahydropyrazino[1',2':4,5][1,4]oxazino[2,3-c]quinoline-3(4H)-carboxylate

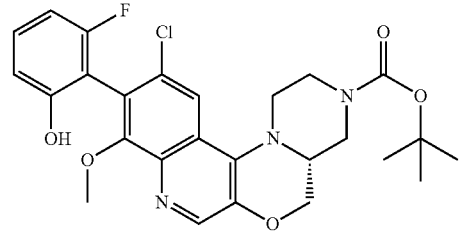 [SMILES: COc1c(-c2c(O)cccc2F)c(Cl)cc2c3c(cnc12)OC[C@H]1CN(C(=O)OC(C)(C)C)CCN31]

RuPhos Pd G3 (67 mg, 0.08 mmol), RuPhos (37.4 mg, 0.08 mmol), K$_2$CO$_3$ (222 mg, 1.60 mmol) and (2-fluoro-6-hydroxyphenyl)boronic acid (250 mg, 1.60 mmol) were added to a stirred and degassed solution of tert-butyl (4aR)-

10-bromo-11-chloro-9-methoxy-1,2,4a,5-tetrahydropyrazino[1',2':4,5][1,4]oxazino[2,3-c]quinoline-3(4H)-carboxylate (389 mg, 0.80 mmol) in dioxane (6 mL) and water (1.5 mL). The resulting mixture was stirred at 80° C. for 17 h. The reaction mixture was diluted with water (25 mL), and extracted with EtOAc (50 mL), the aq. layer was adjusted to pH 5 with 1N citric acid, extracted with EtOAc (75 mL). The organic extracts were combined, washed with brine (50 mL), dried (MgSO₄), filtered and concentrated in vacuo to afford crude product. This was purified by flash silica chromatography (0 to 70% EtOAc in heptane) to give the title compound (175 mg) as a yellow gum. This purified by SFC (Column: Phenomenex A1, 30×250 mm, 5 μm, Mobile phase: 35% IPA+0.1% DEA/55% scCO2, Flow rate: 80 mL/min, BPR: 120 bar, Column temperature: 40° C., UV max 226 nm) to afford atropisomer 1 of tert-butyl (4aR)-11-chloro-10-(2-fluoro-6-hydroxyphenyl)-9-methoxy-1,2,4a,5-tetrahydropyrazino[1',2':4,5][1,4]oxazino[2,3-c]quinoline-3(4H)-carboxylate (51 mg, 12%, 98.4% ee), as a pale yellow solid; 1H NMR (400 MHz, CDCl₃, 30° C.) 1.50 (9H, s), 3.23-3.46 (4H, m), 3.5-3.62 (1H, m), 3.71 (1H, dd), 3.88 (1H, dd), 3.93 (3H, s), 4.29 (2H, d), 6.81 (1H, t), 6.88 (1H, d), 7.32 (1H, td), 7.84 (1H, s), 8.55 (1H, s), OH not seen, m/z ES+ [M+H]+ 516. This was followed atropisomer 2 of tert-butyl (4aR)-11-chloro-10-(2-fluoro-6-hydroxyphenyl)-9-methoxy-1,2,4a,5-tetrahydropyrazino[1',2':4,5][1,4]oxazino[2,3-c]quinoline-3(4H)-carboxylate (56 mg, 14%, 99.4% ee), as a pale yellow solid; ¹H NMR (400 MHz, CDCl₃, 30° C.) 1.50 (9H, s), 3.04-3.14 (1H, m), 3.33-3.54 (3H, m), 3.61 (1H, dd), 3.86 (3H, s), 3.86-3.95 (1H, m), 4.04 (1H, d), 4.29 (2H, q), 6.76 (1H, t), 6.90 (1H, d), 6.90-7.00 (1H, brs), 7.31 (1H, td), 7.66 (1H, s), 8.42 (1H, s), m/z ES⁺ [M+H]⁺ 516.

2-[(4aR)-11-Chloro-9-methoxy-1,2,3,4,4a,5-hexahydropyrazino[1',2':4,5][1,4]oxazino[2,3-c]quinolin-10-yl]-3-fluorophenol Atropisomer 1

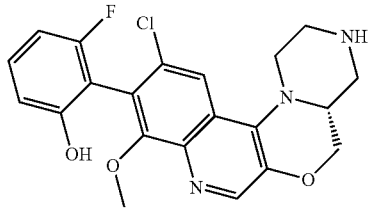 [SMILES: COc1c(-c2c(O)cccc2F)c(Cl)cc2c3c(cnc12)OC[C@H]1CNCCN31]

4M HCl in dioxane (1.1 mL, 4.15 mmol) in MeOH (1 mL) was added to a stirred solution of atropisomer 1 of tert-butyl (4aR)-11-chloro-10-(2-fluoro-6-hydroxyphenyl)-9-methoxy-1,2,4a,5-tetrahydropyrazino[1',2':4,5][1,4]oxazino[2,3-c]quinoline-3(4H)-carboxylate (51 mg, 0.10 mmol) in MeOH (1 mL). The resulting solution was stirred at rt for 3 h. The reaction mixture was purified, using an SCX column (1M NH₃/MeOH) to give atropisomer 1 of 2-[(4aR)-11-chloro-9-methoxy-1,2,3,4,4a,5-hexahydropyrazino[1',2':4,5][1,4]oxazino[2,3-c]quinolin-10-yl]-3-fluorophenol (42 mg, 100%) as a beige solid; 1H NMR (400 MHz, DMSO, 30° C.) 2.96-3.22 (6H, m), 3.43 (1H, d), 3.88 (3H, s), 4.25-4.34 (1H, m), 4.51 (1H, t), 6.73 (1H, t), 6.80 (1H, d), 7.26 (1H, q), 7.80 (1H, s), 8.53 (1H, s), 9.85 (1H, s), NH not observed, m/z ES⁺ [M+H]⁺ 416.

2-[(4aR)-11-Chloro-9-methoxy-1,2,3,4,4a,5-hexahydropyrazino[1',2':4,5][1,4]oxazino[2,3-c]quinolin-10-yl]-3-fluorophenol Atropisomer 2

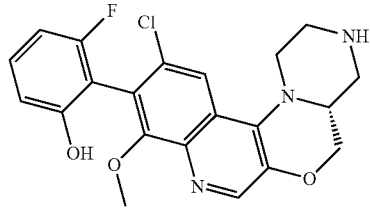 [SMILES: COc1c(-c2c(O)cccc2F)c(Cl)cc2c3c(cnc12)OC[C@H]1CNCCN31]

4M HCl in dioxane (1.1 mL, 4.34 mmol) in MeOH (1 mL) was added to a stirred solution of atropisomer 2 of tert-butyl (4aR)-11-chloro-10-(2-fluoro-6-hydroxyphenyl)-9-methoxy-1,2,4a,5-tetrahydropyrazino[1',2':4,5][1,4]oxazino[2,3-c]quinoline-3(4H)-carboxylate (56 mg, 0.11 mmol) in MeOH (1 mL). The resulting solution was stirred at rt for 3 h. The reaction mixture was purified by SCX (1M NH₃/MeOH) to afford atropisomer 2 of 2-[(4aR)-11-chloro-9-methoxy-1,2,3,4,4a,5-hexahydropyrazino[1',2':4,5][1,4]oxazino[2,3-c]quinolin-10-yl]-3-fluorophenol (47 mg, 100%) as a beige solid; ¹H NMR (400 MHz, DMSO, 30° C.) 2.86-3.15 (6H, m), 3.38 (1H, d), 3.88 (3H, s), 4.23-4.32 (1H, m), 4.50 (1H, t), 6.74 (1H, t), 6.80 (1H, d), 7.26 (1H, q), 7.78 (1H, s), 8.52 (1H, s), 9.82 (1H, s); m/z ES⁺ [M+H]⁺ 416.

1-[(4aR)-11-Chloro-10-(2-fluoro-6-hydroxyphenyl)-9-methoxy-1,2,4a,5-tetrahydropyrazino[1',2':4,5][1,4]oxazino[2,3-c]quinolin-3(4H)-yl]prop-2-en-1-one (Atropisomer 1, Compound 23)

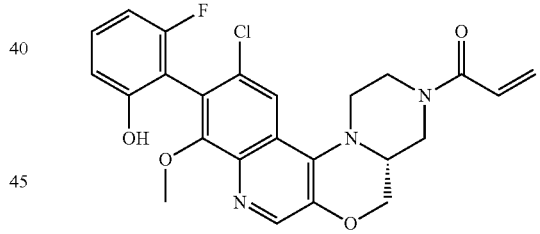

Acryloyl chloride (7.81 μl, 0.10 mmol) was added to a stirred solution of atropisomer 1 of 2-[(4aR)-11-chloro-9-methoxy-1,2,3,4,4a,5-hexahydropyrazino[1',2':4,5][1,4]oxazino[2,3-c]quinolin-10-yl]-3-fluorophenol (40 mg, 0.10 mmol) and NEt₃ (0.027 mL, 0.19 mmol) in DCM (2 mL) cooled to −70° C. The resulting solution was stirred at −70° C. for 20 min. The reaction mixture was concentrated in vacuo, redissolved in THF (1 mL) and a solution of lithium hydroxide hydrate (8.1 mg, 0.19 mmol) in water (0.5 mL) was added. The resulting solution was stirred at rt for 30 min. The reaction mixture was adjusted to pH 4 with 2M HCl, concentrated and purified by preparative HPLC (Waters CSH C18 OBD column, 30×100 mm id, 5 μm particle size), using water (containing 1% by volume of NH₄OH (28-30% in H₂O)) and MeCN as eluents. This gave atropisomer 1 of 1-[(4aR)-11-chloro-10-(2-fluoro-6-hydroxyphenyl)-9-methoxy-1,2,4a,5-tetrahydropyrazino[1',2':4,5][1,4]oxazino[2,3-c]quinolin-3(4H)-yl]prop-2-en-1-one (6 mg, 13%) as a white solid; 1H NMR (400 MHz, DMSO, 30° C.)

3.52-3.69 (3H, m), 3.77 (1H, s), 3.86 (3H, s), 3.97 (1H, s), 4.07-4.5 (4H, m), 5.76 (1H, s), 6.18 (1H, d), 6.57 (1H, s), 6.70 (1H, d), 6.86 (1H, s), 7.11-7.25 (1H, m), 7.84 (1H, s), 8.53 (1H, s); m/z ES+ [M+H]+ 470.

1-[(4aR)-11-Chloro-10-(2-fluoro-6-hydroxyphenyl)-9-methoxy-1,2,4a,5-tetrahydropyrazino[1',2':4,5][1,4]oxazino[2,3-c]quinolin-3(4H)-yl]prop-2-en-1-one (Atropisomer 2, Compound 24)

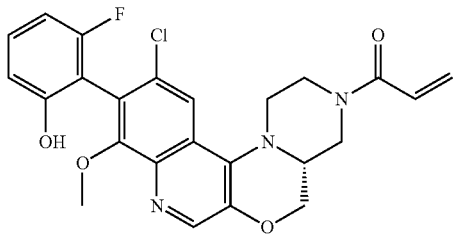 [SMILES: C=CC(=O)N1CCN2c3c(cnc4c(OC)c(-c5c(O)cccc5F)c(Cl)cc34)OC[C@H]2C1]

A solution of acryloyl chloride (8.79 µl, 0.11 mmol) in DCM (0.5 mL) was added slowly to a stirred solution of atropisomer 2 of 2-[(4aR)-11-chloro-9-methoxy-1,2,3,4,4a,5-hexahydropyrazino[1',2':4,5][1,4]oxazino[2,3-c]quinolin-10-yl]-3-fluorophenol (45 mg, 0.11 mmol) and NEt₃ (0.030 mL, 0.22 mmol) in DCM (2 mL) at −70° C. The resulting solution was stirred at −70° C. for 20 min. The reaction mixture was concentrated in vacuo and the residue was purified by preparative HPLC (Waters CSH C18 OBD column, 30×100 mm id, 5 µm particle size), using water (containing 1% by volume of NH₄OH (28-30% in H₂O)) and MeCN as eluents. This gave atropisomer 2 of 1-[(4aR)-11-chloro-10-(2-fluoro-6-hydroxyphenyl)-9-methoxy-1,2,4a,5-tetrahydropyrazino[1',2':4,5][1,4]oxazino[2,3-c]quinolin-3(4H)-yl]prop-2-en-1-one (20 mg, 40%) as a white solid; 1H NMR (400 MHz, DMSO, 30° C.) 3.44-3.58 (3H, m), 3.70 (1H, s), 3.84-4.02 (1H, m), 3.88 (3H, s), 4.06-4.28 (3H, m), 4.37 (1H, d), 5.76 (1H, s), 6.18 (1H, d), 6.64-6.95 (3H, m), 7.2-7.28 (1H, m), 7.85 (1H, s), 8.54 (1H, s); m/z ES+ [M+H]+ 470.

4-Bromo-5-methyl-1H-benzimidazole

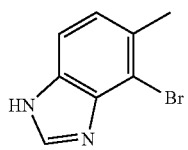

3-Bromo-4-methylbenzene-1,2-diamine (2.0 g, 9.95 mmol) was dissolved in formic acid (20 mL, 530.15 mmol) and the resulting mixture was stirred at 100° C. for 75 mins. The reaction was cooled to rt and the solvent was removed in vacuo. The reaction mixture was purified using a SCX-2 cartridge (1M then 7M NH₃/MeOH) to give 4-bromo-5-methyl-1H-benzimidazole (2.1 g, 100%) as a brown solid; ¹H NMR (400 MHz, CDCl₃, 30° C.) 2.54 (3H, s), 7.19 (1H, d), 7.57 (1H, s), 8.03 (1H, s), 9.25 (1H, s); m/z: ES+ [M+H]+=211.0.

4-Bromo-5-methyl-1-(oxan-2-yl)-1H-benzimidazole

A mixture of 4-bromo-5-methyl-1H-benzimidazole (2.1 g, 9.94 mmol), 3,4-dihydro-2H-pyran (4.54 mL, 49.68 mmol) and 4-methylbenzenesulfonic acid hydrate (0.283 g, 1.49 mmol) in THF (80 mL) was stirred at 65° C. for 23 h. The reaction mixture was cooled to rt and concentrated in vacuo. The resultant residue was dissolved in EtOAc (150 mL) and washed sequentially with aq. sat. NaHCO₃ (75 mL) and brine (50 mL). The organic layer was passed through a hydrophobic frit and concentrated in vacuo to afford the crude product. This was purified by flash silica chromatography, (0 to 80% EtOAc in heptane) to give 4-bromo-5-methyl-1-(oxan-2-yl)-1H-benzimidazole (2.2 g, 75%) as an orange solid; 1H NMR (400 MHz, CDCl₃, 30° C.): 1.63-1.85 (3H, m), 2.04-2.21 (3H, m), 2.54 (3H, s), 3.74 (1H, td), 4.10 (1H, d), 5.46 (1H, dd), 7.17 (1H, d), 7.36 (1H, d), 8.06 (1H, s); m/z: ES+ [M+H]+ 297.1.

[5-Methyl-1-(oxan-2-yl)-1H-benzimidazol-4-yl]boronic acid

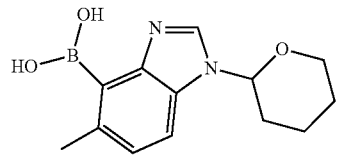 [SMILES: Cc1ccc2c(ncn2C2CCCCO2)c1B(O)O]

Dichlorobis(tricyclohexylphosphine)palladium(II) (525 mg, 0.71 mmol), 4,4,4',4',5,5,5',5'-octamethyl-2,2'-bi(1,3,2-dioxaborolane, 1.81 g, 7.11 mmol), 4-bromo-5-methyl-1-(oxan-2-yl)-1H-benzimidazole (2.1 g, 7.11 mmol) and potassium acetate (1.75 g, 17.79 mmol) were dissolved in DMA (20 mL). The resulting solution was stirred at 155° C. for 105 min. The reaction mixture was cooled to rt and diluted with water (80 mL). The aqueous was extracted with EtOAc (3×80 mL) and the combined organic extracts were washed with water (80 mL) and brine (80 mL). The organic portion was passed through a hydrophobic frit and concentrated in vacuo to afford a crude brown solid. The solid was purified by preparative HPLC (RediSepRF C18 GOLD, 150 gram HP C18), eluting with water (containing 0.1% by volume of formic acid) and MeCN (10-100% gradient) to give [5-methyl-1-(oxan-2-yl)-1H-benzimidazol-4-yl]boronic acid (1.87 g, >100%) as an orange solid which was used without further purification; ¹H NMR (400 MHz, DMSO, 30° C.): 1.75 (2H, d), 2.13-2.25 (2H, m), 2.60 (3H, s), 2.63-2.69 (2H, m), 3.75 (2H, td), 5.68 (1H, dd), 7.13 (1H, d), 7.61 (1H, d), 8.46 (1H, s), 8.95 (2H, s); m/z: ES+ [M+H]+ 261.1.

tert-Butyl (4aR)-11-chloro-9-fluoro-6-methyl-10-[5-methyl-1-(oxan-2-yl)-1H-benzimidazol-4-yl]-5-oxo-1,2,4,4a,5,6-hexahydro-3H-pyrazino[1',2':4,5]pyrazino[2,3-c]quinoline-3-carboxylate

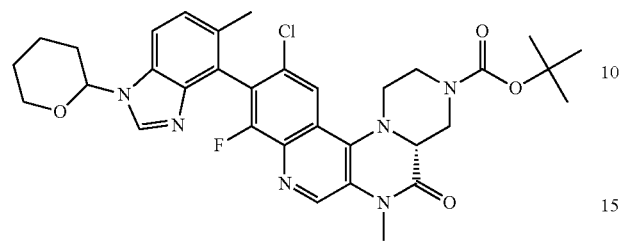

A degassed mixture of RuPhos Pd G3 (111 mg, 0.13 mmol), RuPhos (62.1 mg, 0.13 mmol), K₂CO₃ (460 mg, 3.33 mmol), tert-butyl (R)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (665 mg, 1.33 mmol) and [5-methyl-1-(oxan-2-yl)-1H-benzimidazol-4-yl] boronic acid (989 mg, 2.66 mmol) in 1,4-dioxane (50 mL) and water (12.5 mL) was stirred at 100° C. overnight. The reaction mixture was cooled and concentrated in vacuo. EtOAc (100 mL) was added and the mixture washed with water (40 mL) and brine (40 mL). The organic phase was passed through a phase separator cartridge and dried in vacuo to give the crude product. This was purified using the reverse phase chromatography (Column: Waters CSH C18 OBD column, 30×100 mm id, 5 μm particle size), using d water (+0.1% formic acid) and MeCN as eluents to give tert-butyl (4aR)-11-chloro-9-fluoro-6-methyl-10-[5-methyl-1-(oxan-2-yl)-1H-benzimidazol-4-yl]-5-oxo-1,2,4,4a,5,6-hexahydro-3H-pyrazino[1',2':4,5]pyrazino[2,3-c]quinoline-3-carboxylate (53 mg, 6%, as a 1:1.8 mixture of atropisomers); $^1$H NMR (400 MHz, DMSO, 30° C.): 1.25 (2H, s), 1.47 (9H, s), 1.70 (4H, d), 1.96-2.1 (3H, m), 2.19 (2H, s), 2.22 (2H, s), 3.52 (3H, s), 3.78 (1H, s), 3.90 (2H, s), 4.02 (1H, d), 4.77 (1H, d), 5.71 (1H, d), 7.32 (1H, d), 7.70 (1H, d), 8.12 (1H, s), 8.27 (1H, s), 9.01 (1H, s); m/z: ES⁺ [M+H]⁺ 635.2.

(4aR)-11-Chloro-9-fluoro-6-methyl-10-(5-methyl-1H-benzimidazol-4-yl)-2,3,4,4a-tetrahydro-1H-pyrazino[1',2':4,5]pyrazino[2,3-c]quinolin-5(6H)-one

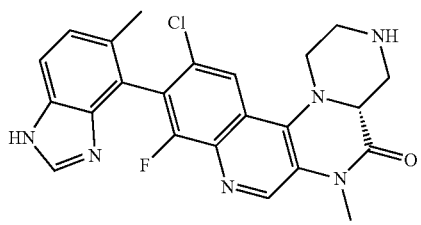 [SMILES: Cc1ccc2[nH]cnc2c1-c1c(Cl)cc2c3c(cnc2c1F)N(C)C(=O)[C@H]1CNCCN31]

tert-Butyl (4aR)-11-chloro-9-fluoro-6-methyl-10-(5-methyl-1-(tetrahydro-2H-pyran-2-yl)-1H-benzo[d]imidazol-4-yl)-5-oxo-1,2,4,4a,5,6-hexahydro-3H-pyrazino[1',2':4,5]pyrazino[2,3-c]quinoline-3-carboxylate (50 mg, 0.08 mmol) was dissolved in hydrogen chloride (6 M in IPA, 525 μL, 3.15 mmol) and was heated at 60° C. After 3 hs, the mixture was cooled to rt and concentrated in vacuo. The resultant residue was purified using a SCX-2 cartridge (1M NH₃/MeOH) to give (4aR)-11-chloro-9-fluoro-6-methyl-10-(5-methyl-1H-benzimidazol-4-yl)-2,3,4,4a-tetrahydro-1H-pyrazino[1',2':4,5]pyrazino[2,3-c]quinolin-5(6H)-one (31 mg, 87%) as a pale yellow dry film (as a 1.9:1 mixture of atropisomers); m/z: ES⁺ [M+H]⁺=451.0.

(4aR)-11-Chloro-9-fluoro-6-methyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one (Atropisomer 1, Compound 25; Atropisomer 2, Compound 26)

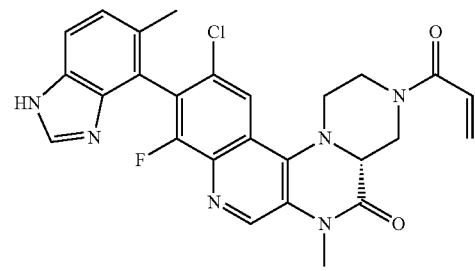 [SMILES: C=CC(=O)N1CCN2c3c(cnc4c(F)c(-c5c(C)ccc6[nH]cnc56)c(Cl)cc34)N(C)C(=O)[C@H]2C1]

To a solution of (4aR)-11-chloro-9-fluoro-6-methyl-10-(5-methyl-1H-benzimidazol-4-yl)-2,3,4,4a-tetrahydro-1H-pyrazino[1',2':4,5]pyrazino[2,3-c]quinolin-5(6H)-one (31 mg, 0.07 mmol) and NEt₃ (15 μL, 0.11 mmol) in DCM (1 mL) at −78° C. was added acryloyl chloride (5.83 μL, 0.07 mmol). The reaction mixture stirred at −78° C. for 20 min. The mixture was quenched at −78° C. with MeOH (0.2 mL) and concentrated in vacuo to give a pale brown solid (60 mg). The atropisomers were separated using reverse phase chromatography (Column: Waters CSH C18 OBD column, 30×100 mm id, 5 μm particle size), using water (containing 0.3% by volume of NH₄OH (28-30% in H₂O)) and MeCN as eluents to give atropisomer 1 of (4aR)-11-chloro-9-fluoro-6-methyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one (3 mg, 8%) as a colourless solid; $^1$H NMR (400 MHz, CDCl₃, 30° C.): 2.27 (3H, s), 2.76-2.89 (1H, m), 3.16 (1H, s), 3.29 (1H, d), 3.49-3.69 (5H, m), 4.74 (1H, s), 4.93 (1H, s), 5.81 (1H, d), 6.38 (1H, dd), 7.02 (1H, d), 7.30 (1H, d), 7.66 (1H, d), 8.00 (2H, s), 8.73 (1H, s); $^{19}$F NMR (376 MHz, CDCl3, 30° C.): −118.57--117.59; m/z: ES⁺ [M+H]⁺=505.0. This was followed by atropisomer 2 of (4aR)-11-chloro-9-fluoro-6-methyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one (6 mg, 16%) as a colourless solid; $^1$H NMR (400 MHz, CDCl₃, 30° C.): 2.27 (3H, s), 2.61 (1H, s), 2.92-3.16 (2H, m), 3.5-3.73 (5H, m), 4.57-4.72 (1H, m), 4.84-5.03 (1H, m), 5.80 (1H, d), 6.36 (1H, dd), 6.95-7.1 (1H, m), 7.29 (1H, d), 7.60 (1H, d), 7.94 (1H, s), 8.02 (1H, s), 8.82 (1H, s). $^{19}$F NMR (376 MHz, CDCl₃, 30° C.): −118.9--118.21; m/z: ES+ [M+H]+=505.1.

tert-Butyl (2R,4aR)-11-chloro-9-fluoro-2,6-dimethyl-1-[5-methyl-1-(oxan-2-yl)-1H-benzimidazol-4-yl]-5-oxo-1,2,4,4a,5,6-hexahydro-3H-pyrazino[1',2':4,5]pyrazino[2,3-c]quinoline-3-carboxylate

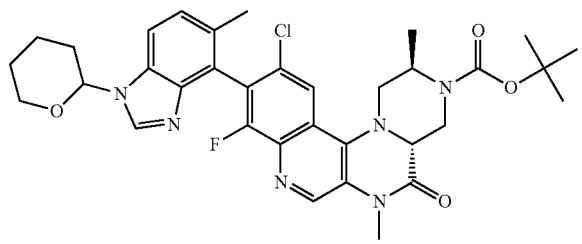 [SMILES: Cc1ccc2c(ncn2C2CCCCO2)c1-c1c(Cl)cc2c3c(cnc2c1F)N(C)C(=O)[C@H]1CN(C(=O)OC(C)(C)C)[C@H](C)CN31]

A stirred suspension of tert-butyl (2R,4aR)-10-bromo-11-chloro-9-fluoro-2,6-dimethyl-5-oxo-1,2,4,4a,5,6-hexahydro-3H-pyrazino[1',2':4,5]pyrazino[2,3-c]quinoline-3-carboxylate (332 mg, 0.65 mmol), [5-methyl-1-(oxan-2-yl)-1H-benzimidazol-4-yl]boronic acid (467 mg, 1.62 mmol) and K$_2$CO$_3$ (268 mg, 1.94 mmol) in dioxane (4.85 mL) and water (1.62 mL) was de-gassed with nitrogen for 10 mins. RuPhos Pd G3 (54 mg, 0.06 mmol) and RuPhos (30 mg, 0.06 mmol) were added and the mixture was heated at 90° C. overnight. The cooled reaction mixture was diluted with EtOAc (20 mL) and washed with water (10 mL). The aqueous was extracted with a further portion of EtOAc (20 mL) and the combined organics were washed with brine (10 mL), dried (MgSO$_4$), filtered and concentrated in vacuo to give a yellow residue. This was purified by flash silica chromatography (0 to 100% EtOAc in heptane and then 0 to 1 M NH$_3$/MeOH in DCM) to give tert-butyl (2R,4aR)-11-chloro-9-fluoro-2,6-dimethyl-10-[5-methyl-1-(oxan-2-yl)-1H-benzimidazol-4-yl]-5-oxo-1,2,4,4a,5,6-hexahydro-3H-pyrazino[1',2':4,5]pyrazino[2,3-c]quinoline-3-carboxylate (398 mg, 95%) as a brown dry film (as a 1:1 mixture of atropisomers); m/z: ES+ [M+H]+=649.1.

(2R,4aR)-11-Chloro-9-fluoro-2,6-dimethyl-10-(5-methyl-1H-benzimidazol-4-yl)-2,3,4,4a-tetrahydro-1H-pyrazino[1',2':4,5]pyrazino[2,3-c]quinolin-5(6H)-one Atropisomer 1 and 2

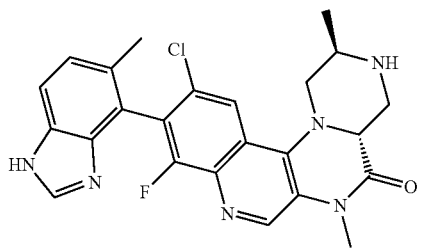 [SMILES: Cc1ccc2[nH]cnc2c1-c1c(Cl)cc2c3c(cnc2c1F)N(C)C(=O)[C@H]1CN[C@H](C)CN31]

tert-Butyl (2R,4aR)-11-chloro-9-fluoro-2,6-dimethyl-10-[5-methyl-1-(oxan-2-yl)-1H-benzimidazol-4-yl]-5-oxo-1,2,4,4a,5,6-hexahydro-3H-pyrazino[1',2':4,5]pyrazino[2,3-c]quinoline-3-carboxylate (398 mg, 0.61 mmol) was dissolved in HCl (6 M in IPA, 4.09 mL, 24.52 mmol) and the resultant solution was heated at 60° C. for 2.5 h. The mixture was cooled to rt and concentrated in vacuo. The resultant residue was purified using a SCX-2 cartridge (1M NH$_3$/MeOH) to give the title compound as a pale red dry film (as a mixture of atropisomers). The atropisomers were separated by SFC (Column: Chiralpak OD, 20×250 mm, 5 μm; Mobile phase A: 45% MeOH (+0.1% NH$_3$)/Mobile Phase B: 55% scCO2; flow rate: 60 mL/min; BPR: 120 bar; Column temperature: 40° C.) to afford atropisomer 1 of (2R,4aR)-11-chloro-9-fluoro-2,6-dimethyl-10-(5-methyl-1H-benzimidazol-4-yl)-2,3,4,4a-tetrahydro-1H-pyrazino[1',2':4,5]pyrazino[2,3-c]quinolin-5(6H)-one (74 mg, 26%) as a pale brown dry film; $^1$H NMR (400 MHz, DMSO, 30° C.): 1.43 (3H, dd), 2.17 (3H, s), 3-3.18 (3H, m), 3.36 (2H, s), 3.52 (3H, s), 3.76 (1H, dd), 7.24 (1H, dd), 7.55 (1H, d), 7.67 (1H, d), 8.03-8.15 (2H, m), 8.93 (1H, d), 12.19 (0.5H, s), 12.49 (0.5H, s); $^{19}$F NMR (376 MHz, DMSO, 30° C.): −119.49, −119.36; m/z: ES+ [M+H]+=465.0. This was followed by atropisomer 2 of (2R,4aR)-11-chloro-9-fluoro-2,6-dimethyl-10-(5-methyl-1H-benzimidazol-4-yl)-2,3,4,4a-tetrahydro-1H-pyrazino[1',2':4,5]pyrazino[2,3-c]quinolin-5(6H)-one (51 mg, 18%) as a pale brown dry film; $^1$H NMR (400 MHz, DMSO, 30° C.): 1.43 (3H, t), 2.19 (3H, s), 3.08 (3H, p), 3.33-3.39 (2H, m), 3.51 (3H, d), 3.68 (0.5H, d), 3.74 (0.5H, d), 7.23 (1H, dd), 7.55 (1H, d), 7.66 (1H, d), 8-8.13 (2H, m), 8.92 (1H, d), 12.19 (0.5H, s), 12.47 (0.5H, s); $^{19}$F NMR (376 MHz, DMSO, 30° C.): −119.45, −119.22; m/z: ES+ [M+H]+=465.0.

(2R,4aR)-11-Chloro-9-fluoro-2,6-dimethyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one (Atropisomer 1, Compound 27)

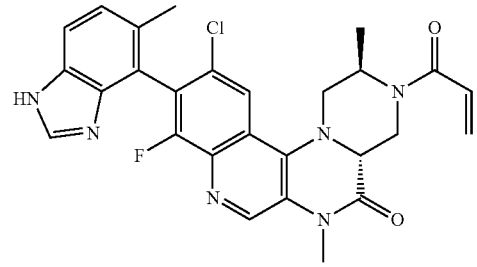 [SMILES: C=CC(=O)N1C[C@@H]2C(=O)N(C)c3cnc4c(F)c(-c5c(C)ccc6[nH]cnc56)c(Cl)cc4c3N2C[C@H]1C]

A solution of atropisomer 1 of (2R,4aR)-11-chloro-9-fluoro-2,6-dimethyl-10-(5-methyl-1H-benzimidazol-4-yl)-2,3,4,4a-tetrahydro-1H-pyrazino[1',2':4,5]pyrazino[2,3-c]quinolin-5(6H)-one (74 mg, 0.16 mmol) and NEt$_3$ (43 μL, 0.32 mmol) in DCM (1.5 mL) was cooled to −78° C. Acryloyl chloride (13.5 μL, 0.17 mmol) was added and the reaction mixture was stirred at −78° C. for 20 min. The mixture was quenched at −78° C. with MeOH (0.3 mL) and the solvent was removed in vacuo to give a pale brown solid. The crude product was purified by preparative HPLC (Column: Waters CSH C18 OBD, 30×100 mm id, 5 μm particle size), using water (containing 0.3% by volume of NH$_4$OH (28-30% in H$_2$O)) and MeCN as eluents (using a shallow gradient of 30 to 60% MeCN), to afford atropisomer 1 of (2R,4aR)-11-chloro-9-fluoro-2,6-dimethyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one (20 mg, 25%) as a colourless solid; $^1$H NMR (400 MHz, DMSO, 100° C.): 1.58 (3H, d), 2.20 (3H, s), 2.97-3.01 (1H, m), 3.20 (1H, d), 3.53 (3H, s), 3.59-3.78 (1H, m), 3.97 (1H, d), 4.64-4.92 (2H, m), 5.72 (1H, dd), 6.13 (1H, dd), 6.84-7.01 (1H, m), 7.24 (1H, d), 7.55-7.67 (1H, m), 8.01

(1H, s), 8.08 (1H, d), 8.99 (1H, s), 11.94 (1H, s); $^{19}$F NMR (376 MHz, DMSO, 30° C.): −119.46, −119.23; m/z: ES$^+$ [M+H]$^+$=519.0.

(2R,4aR)-11-Chloro-9-fluoro-2,6-dimethyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one (Atropisomer 2, Compound 28)

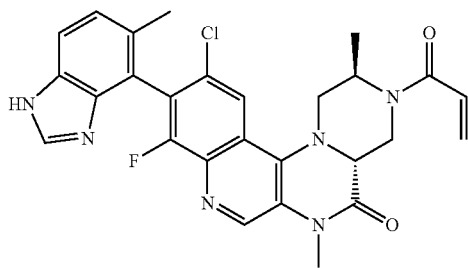

A solution of atropisomer 2 of (2R,4aR)-11-chloro-9-fluoro-2,6-dimethyl-10-(5-methyl-1H-benzimidazol-4-yl)-2,3,4,4a-tetrahydro-1H-pyrazino[1',2':4,5]pyrazino[2,3-c]quinolin-5(6H)-one (51 mg, 0.11 mmol) and NEt$_3$ (30 μL, 0.22 mmol) in DCM (1 mL) was cooled to −78° C. Acryloyl chloride (9.31 μL, 0.12 mmol) was added and the reaction mixture was stirred at −78° C. for 10 min. The reaction mixture was quenched at −78° C. with MeOH (0.3 mL) and the solvent was removed in vacuo to give a pale brown solid. The crude product was purified by preparative HPLC (Column: Waters CSH C18 OBD, 30×100 mm id, 5 μm particle size), using water (containing 0.3% by volume of NH$_4$OH (28-30% in H$_2$O)) and MeCN as eluents, to afford atropisomer 2 of (2R,4aR)-11-chloro-9-fluoro-2,6-dimethyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one (15 mg, 27%) as a colourless solid; $^1$H NMR (400 MHz, DMSO, 100° C.): 1.57 (3H, d), 2.22 (3H, s), 2.99 (1H, d), 3.23 (1H, d), 3.53 (3H, s), 3.65-3.78 (1H, m), 3.93 (1H, s), 4.58-4.92 (2H, m), 5.72 (1H, dd), 6.13 (1H, dd), 6.91 (1H, s), 7.24 (1H, d), 7.61 (1H, s), 8.01 (1H, s), 8.08 (1H, s), 8.99 (1H, s), 11.8-12.41 (1H, m); $^{19}$F NMR (376 MHz, DMSO, 30° C.): −119.42, −119.35, −119.22, −119.14; m/z: ES$^+$ [M+H]$^+$=519.0.

(2R,4aR)-11-Chloro-3-[(2E)-4-(dimethylamino)but-2-enoyl]-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one (Atropisomer 2, Compound 29)

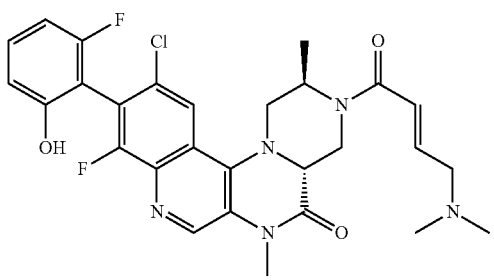 [SMILES: C[C@@H]1CN2c3c(cnc4c(F)c(-c5c(O)cccc5F)c(Cl)cc34)N(C)C(=O)[C@H]2CN1C(=O)/C=C/CN(C)C]

Atropisomer 2 of (2R,4aR)-11-chloro-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one (265 mg, 0.6 mmol) and (E)-4-(dimethylamino)but-2-enoic acid hydrochloride (109 mg, 0.66 mmol) were dissolved in DCM (5.6 mL) and DIPEA (0.42 mL, 2.38 mmol). O-(7-Azabenzotriazol-1-yl)-N,N,N',N'-tetramethyluronium hexafluorophosphate (272 mg, 0.71 mmol) was added and the solution was stirred at rt. After 30 min, the reaction mixture was diluted with DCM (10 mL) washed with aq. sat. NaHCO$_3$ (5 mL). The organic portion was washed with brine (10 mL), dried (phase separator) and concentrated in vacuo to give an orange residue. The crude product was purified by preparative HPLC (Column: Waters CSH C18 OBD, 30×100 mm id, 5 μm particle size), using water (containing 0.1% 0.1% formic acid) and MeCN as eluents to afford 120.9 mg of product as the formate salt. The material was dissolved in 10% MeOH in DCM (20 mL) and washed with aq. sat. NaHCO$_3$ (10 mL). The organic portion was dried (phase separator) and concentrated in vacuo. The sample was dried overnight at 50° C. in a vacuum oven to give atropisomer 2 of (2R,4aR)-11-chloro-3-[(2E)-4-(dimethylamino)but-2-enoyl]-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one (92 mg, 28%) as a pale yellow solid; $^1$H NMR (400 MHz, CDCl$_3$, 30° C.): 1.67 (4H, d), 2.49-2.75 (6H, m), 2.9-3 (1H, m), 3.07-3.2 (2H, m), 3.45-3.63 (5H, m), 3.76-3.87 (1H, m), 4.82 (1H, d), 4.93-5.07 (1H, m), 6.78-6.93 (3H, m), 7.08 (1H, d), 7.37 (1H, td), 8.01 (1H, d), 8.79 (1H, s). 19F NMR (376 MHz, CDCl$_3$, 30° C.): −116.40, −112.18; m/z: ES$^+$ [M+H]$^+$=556.0.

6-Chloro-8-fluoro-7-(2-fluoro-6-methoxyphenyl)-3-nitroquinolin-4(1H)-one

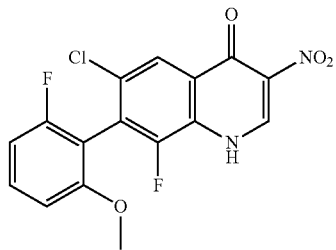 [SMILES: COc1cccc(F)c1-c1c(Cl)cc2c(=O)c([N+](=O)[O-])c[nH]c2c1F]

RuPhos (1.45 g, 3.11 mmol) and RuPhos Pd G3 (2.60 g, 3.11 mmol) were added to a degassed mixture of 7-bromo-6-chloro-8-fluoro-3-nitroquinolin-4(1H)-one (10 g, 31.11 mmol), (2-fluoro-6-methoxyphenyl)boronic acid (10.57 g, 62.21 mmol) and K$_2$CO$_3$ (12.90 g, 93.32 mmol) in dioxane (400 mL) and water (100 mL). The reaction mixture was stirred at 70° C. for 1 h and then a further portion of (2-fluoro-6-methoxyphenyl)boronic acid (5 g) was added and stirring continued. After 2 h, a further portion of (2-fluoro-6-methoxyphenyl)boronic acid (2.5 g) was added. After 1 h another portion of (2-fluoro-6-methoxyphenyl) boronic acid (2.5 g) was added. After 1 h, a final portion of (2-fluoro-6-methoxyphenyl)boronic acid (2 g) was added and the stirring was continued for 1 h and then allowed to cool to rt overnight. The reaction mixture was diluted with EtOAc (500 mL) and the organic layer was washed with aq. 2N NaOH (2×250 mL). The aqueous was combined and back extracted with EtOAc (250 mL) and the combined organic layers were washed with brine (500 mL), then dried and concentrated in vacuo. The residue was stirred overnight in diethyl ether and the resultant solid filtered off, washing thoroughly with fresh diethyl ether, and then dried to afford 6-chloro-8-fluoro-7-(2-fluoro-6-methoxyphenyl)-3-nitroquinolin-4(1H)-one (13.84 g, >100%) as a yellow solid which was used without further purification; $^1$H NMR (400 MHz, DMSO, 30° C.): 3.78 (3H, d), 6.98 (1H, t), 7.05 (1H, d), 7.48-7.57 (1H, m), 8.08 (1H, d), 8.94 (1H, d); m/z: ES$^+$ [M+H]$^+$ 367.

4,6-Dichloro-8-fluoro-7-(2-fluoro-6-methoxyphenyl)-3-nitroquinoline

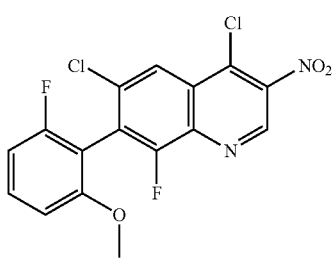 [SMILES: COc1cccc(F)c1-c1c(Cl)cc2c(Cl)c([N+](=O)[O-])cnc2c1F]

To a stirred solution of 6-chloro-8-fluoro-7-(2-fluoro-6-methoxyphenyl)-3-nitroquinolin-4(1H)-one (11.41 g, 31.11 mmol) in DMF (80 mL) was added phosphoryl trichloride (3.19 mL, 34.22 mmol) and the reaction mixture was heated at 100° C. for 1 h then further phosphoryl trichloride (1 mL) was added. After 1 h, phosphoryl trichloride (0.5 mL) was added and the reaction mixture was stirred for 1 h then allowed to cool to rt. The reaction mixture was poured onto ice (800 g), and the solid was filtered off. The filter cake was washed with water and dried in vacuo to afford a pale brown solid. This was purified by flash silica chromatography (0 to 20% EtOAc in heptane) to afford 4,6-dichloro-8-fluoro-7-(2-fluoro-6-methoxyphenyl)-3-nitroquinoline (4.13 g, 33%) as a white solid; $^1$H NMR (400 MHz, DMSO, 30° C.): 3.80 (3H, s), 7.03-7.09 (1H, m), 7.13 (1H, d), 7.57-7.66 (1H, m), 8.47 (1H, d), 9.48 (1H, s); m/z: ES$^+$ [M+H]$^+$ 385.

1-tert-Butyl 3-methyl (3R,6R)-4-[6-chloro-8-fluoro-7-(2-fluoro-6-methoxyphenyl)-3-nitroquinolin-4-yl]-6-methylpiperazine-1,3-dicarboxylate

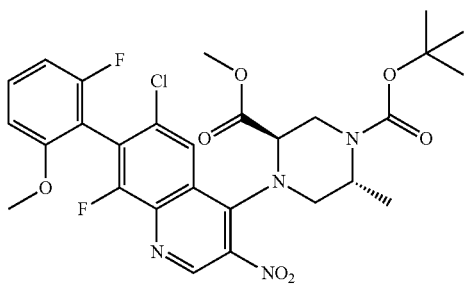 [SMILES: COC(=O)[C@H]1CN(C(=O)OC(C)(C)C)[C@H](C)CN1c1c([N+](=O)[O-])cnc2c(F)c(-c3c(F)cccc3OC)c(Cl)cc12]

A solution of 1-tert-butyl 3-methyl (3R,6R)-6-methylpiperazine-1,3-dicarboxylate (724 mg, 2.80 mmol) in THF (11 mL) and DIPEA (0.53 mL, 3.04 mmol) was degassed. 4,6-Dichloro-8-fluoro-7-(2-fluoro-6-methoxyphenyl)-3-nitroquinoline (900 mg, 2.34 mmol) was added and the mixture was heated at 60° C. overnight. The reaction mixture was cooled to rt and concentrated in vacuo to give a brown residue. The residue was dissolved in DCM (50 mL) and washed with aq. 1 M citric acid solution (30 mL). The organic portion was collected and the aqueous was washed with DCM (20 mL). The combined organics were washed with brine (30 mL), dried (phase separator) and concentrated in vacuo to give a red residue. This was purified by flash silica chromatography (0 to 20% EtOAc in DCM) to afford 1-tert-butyl 3-methyl (3R,6R)-4-[6-chloro-8-fluoro-7-(2-fluoro-6-methoxyphenyl)-3-nitroquinolin-4-yl]-6-methylpiperazine-1,3-dicarboxylate (1.31 g, 92%) as a yellow foam; $^1$H NMR (400 MHz, CDCl$_3$, 30° C.): 1.34 (3H, d), 1.50 (9H, s), 3.19 (1H, d), 3.73 (3H, s), 3.74-3.79 (1H, m), 3.81 (3H, d), 4.16 (1H, d), 4.24 (1H, s), 4.53 (2H, d), 6.87 (2H, td), 7.42-7.51 (1H, m), 8.33 (1H, d), 9.00 (1H, d); $^{19}$F NMR: (376 MHz, CDCl3, 30° C.) −115.67, −115.46, −112.26 (J=7.5), −111.81 (J=11.9); m/z: ES$^+$ [M+H]$^+$=607.0.

tert-Butyl (2R,4aR)-11-chloro-9-fluoro-10-(2-fluoro-6-methoxyphenyl)-2-methyl-5-oxo-1,2,4,4a,5,6-hexahydro-3H-pyrazino[1',2':4,5]pyrazino[2,3-c]quinoline-3-carboxylate

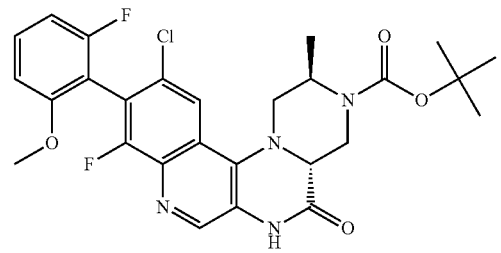 [SMILES: COc1cccc(F)c1-c1c(Cl)cc2c3c(cnc2c1F)NC(=O)[C@H]1CN(C(=O)OC(C)(C)C)[C@H](C)CN31]

To a stirred solution of 1-tert-butyl 3-methyl (3R,6R)-4-[6-chloro-8-fluoro-7-(2-fluoro-6-methoxyphenyl)-3-nitroquinolin-4-yl]-6-methylpiperazine-1,3-dicarboxylate (1.3 g, 2.14 mmol) in acetic acid (21 mL) at rt was added iron powder (419 mg, 7.50 mmol) and the resultant reaction mixture stirred at 80° C. After 45 min, the reaction mixture was concentrated in vacuo to give a brown solid. This was suspended in DCM (50 mL) and aq. sat. NaHCO$_3$ was added until the solution was at pH 8. The mixture was filtered through CELITE™ (washing with DCM). The phases were separated and the aqueous was washed with DCM (50 mL). The combined organics were washed with brine (50 mL), dried (phase separator) and concentrated in vacuo to give a pale yellow residue. This was dissolved in DCM (10 mL) and heptane (10 mL) and concentrated in vacuo and dried under vacuum to give tert-butyl (2R,4aR)-11-chloro-9-fluoro-10-(2-fluoro-6-methoxyphenyl)-2-methyl-5-oxo-1,2,4,4a,5,6-hexahydro-3H-pyrazino[1',2':4,5]pyrazino[2,3-c]quinoline-3-carboxylate (1.05 g, 90%) as a pale yellow solid; $^1$H NMR (400 MHz, DMSO, 30° C.): 1.38-1.5 (12H, m), 2.86-2.96 (1H, m), 3.01-3.18 (1H, m), 3.38-3.48 (1H, m), 3.77 (3H, d), 3.81-3.92 (1H, m), 4.1-4.35 (1H, m), 4.56-4.73 (1H, m), 7.01 (1H, td), 7.07 (1H, dd), 7.56 (1H, q), 7.92 (1H, s), 8.65 (1H, s), 11.04 (1H, s); $^{19}$F NMR (376 MHz, DMSO, 30° C.): −118.37, −113.54 (J=7.8), −113.46; m/z: ES$^+$ [M+H]$^+$=545.

(2R,4aR)-11-Chloro-9-fluoro-10-(2-fluoro-6-hydroxyphenyl)-2-methyl-2,3,4,4a-tetrahydro-1H-pyrazino[1',2':4,5]pyrazino[2,3-c]quinolin-5(6H)-one Atropisomer 1 and 2

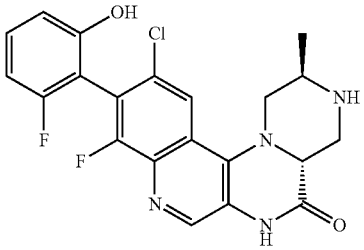 [SMILES: C[C@@H]1CN2c3c(cnc4c(F)c(-c5c(O)cccc5F)c(Cl)cc34)NC(=O)[C@H]2CN1]

tert-Butyl (2R,4aR)-11-chloro-9-fluoro-10-(2-fluoro-6-methoxyphenyl)-2-methyl-5-oxo-1,2,4,4a,5,6-hexahydro-3H-pyrazino[1',2':4,5]pyrazino[2,3-c]quinoline-3-carboxylate (600 mg, 1.1 mmol) was dissolved in DCM (11 mL) and the mixture was cooled to 0° C. then tribromoborane (11.01 mL of a 1 M solution in DCM, 11.01 mmol) was added dropwise. The suspension was brought to rt and stirred. After 5 h, a further portion of tribromoborane (11.01 mL of a 1 M solution in DCM, 11.01 mmol) was added dropwise at rt. After a further 1 h, the reaction mixture was cooled in an ice-bath and water (5 mL) was added dropwise. MeOH (20 mL) was added and the volatiles were removed in vacuo. The resultant residue was purified using a SCX-2 cartridge (1M NH$_3$/MeOH) to give (2R,4aR)-11-chloro-9-fluoro-10-(2-fluoro-6-hydroxyphenyl)-2-methyl-2,3,4,4a-tetrahydro-1H-pyrazino[1',2':4,5]pyrazino[2,3-c]quinolin-5(6H)-one (458 mg) as an orange solid (as a mixture of atropisomers). The atropisomers were separated by SFC (Column: Chiralpak IC, 20×250 mm, 5 μm; Mobile phase A: 45% MeOH (+0.1% NH$_3$)/Mobile Phase B: 55% scCO2; flow rate: 60 mL/min; BPR: 120 bar; Column temperature: 40° C.) to afford atropisomer 1 of (2R,4aR)-11-chloro-9-fluoro-10-(2-fluoro-6-hydroxyphenyl)-2-methyl-2,3,4,4a-tetrahydro-1H-pyrazino[1',2':4,5]pyrazino[2,3-c]quinolin-5(6H)-one (155 mg, 34%) as a tan solid; $^1$H NMR (400 MHz, DMSO, 30° C.): 1.34 (3H, d), 2.22 (1H, s), 2.95-3.09 (2H, m), 3.22 (1H, dd), 3.3-3.38 (2H, m), 3.77 (1H, t), 6.79 (1H, t), 6.85 (1H, d), 7.34 (1H, q), 8.00 (1H, d), 8.51 (1H, s), 10.15 (1H, s), 10.93 (1H, s); $^{19}$F NMR (376 MHz, DMSO, 30° C.): −118.15, −113.59 (J=6.8); m/z: ES$^+$ [M+H]$^+$=431.0. This was followed by atropisomer 2 of (2R,4aR)-11-chloro-9-fluoro-10-(2-fluoro-6-hydroxyphenyl)-2-methyl-2,3,4,4a-tetrahydro-1H-pyrazino[1',2':4,5]pyrazino[2,3-c]quinolin-5(6H)-one (172 mg, 38%) as a tan solid; $^1$H NMR (400 MHz, DMSO, 30° C.): 1.33 (3H, d), 2.22 (1H, s), 2.94-3.1 (2H, m), 3.22 (1H, dd), 3.36 (2H, dd), 3.72-3.83 (1H, m), 6.74-6.88 (2H, m), 7.34 (1H, td), 7.99 (1H, d), 8.51 (1H, s), 10.13 (1H, s), 10.92 (1H, s). 19F NMR (376 MHz, DMSO, 30° C.): −118.00, −113.62 (J=7.1); m/z: ES$^+$ [M+H]$^+$=431.0.

(2R,4aR)-11-Chloro-9-fluoro-10-(2-fluoro-6-hydroxyphenyl)-2-methyl-3-(prop-2-enoyl)-2,3,4,4a-tetrahydro-1H-pyrazino[1',2':4,5]pyrazino[2,3-c]quinolin-5(6H)-one (Atropisomer 1, Compound 30)

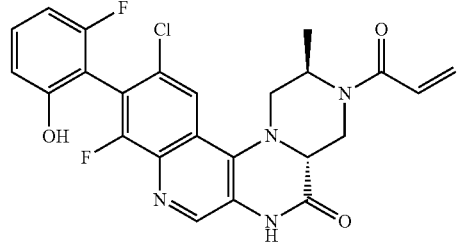 [SMILES: C=CC(=O)N1C[C@@H]2C(=O)Nc3cnc4c(F)c(-c5c(O)cccc5F)c(Cl)cc4c3N2C[C@H]1C]

To a solution of atropisomer 1 of (2R,4aR)-11-chloro-9-fluoro-10-(2-fluoro-6-hydroxyphenyl)-2-methyl-2,3,4,4a-tetrahydro-1H-pyrazino[1',2':4,5]pyrazino[2,3-c]quinolin-5(6H)-one (155 mg, 0.36 mmol) and NEt$_3$ (65 μL, 0.47 mmol) in DCM (3.5 mL) at 0° C. was added acryloyl chloride (32 μL, 0.40 mmol). The resultant mixture was stirred at 0° C. After 5 min, a further portion of acryloyl chloride (16 μL, 0.20 mmol) was added. After a further 5 min, the mixture was quenched by addition of water (5 mL) and extracted with DCM (2×10 mL). The combined organics were dried (phase separator) and concentrated in vacuo to give a yellow dry film. The film was dissolved in 7 M ammonia in MeOH (10 mL) and the suspension was stirred at rt. After 2 min, the reaction mixture was concentrated in vacuo to give a yellow dry film (175 mg). The crude product was purified by SFC (Column: Chiralpak IC, 20×250 mm, 5 μm; Mobile phase A: 25-45% MeOH (+0.1% NH$_3$)/Mobile Phase B: 75-55% scCO2; flow rate: 100 mL/min; BPR: 120 bar; Column temperature: 40° C.) to afford atropisomer 1 of (2R,4aR)-11-chloro-9-fluoro-10-(2-fluoro-6-hydroxyphenyl)-2-methyl-3-(prop-2-enoyl)-2,3,4,4a-tetrahydro-1H-pyrazino[1',2':4,5]pyrazino[2,3-c]quinolin-5(6H)-one (73 mg, 42%) as a colourless solid; $^1$H NMR (400 MHz, DMSO, 30° C.) 1.53 (3H, dd), 2.91 (1H, dd), 3.18 (1H, s), 3.75 (1H, dd), 3.92-4 (1H, m), 4.63 (1H, d), 4.74 (1H, s), 5.76 (1H, dd), 6.14 (1H, dd), 6.75-6.89 (2H, m), 6.99 (1H, dd), 7.27-7.43 (1H, m), 7.94 (1H, s), 8.66 (1H, s), 10.22 (1H, s), 11.09 (1H, s); $^{19}$F NMR (376 MHz, DMSO, 30° C.): −113.68, −118.23; m/z: ES$^+$ [M+H]$^+$=485.

(2R,4aR)-11-Chloro-9-fluoro-10-(2-fluoro-6-hydroxyphenyl)-2-methyl-3-(prop-2-enoyl)-2,3,4,4a-tetrahydro-1H-pyrazino[1',2':4,5]pyrazino[2,3-c]quinolin-5(6H)-one (Atropisomer 2, Compound 31)

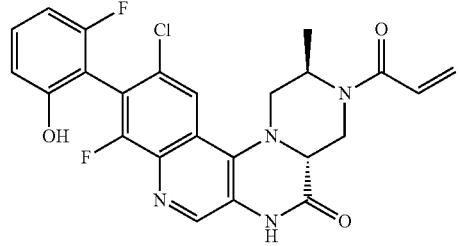 [SMILES: C=CC(=O)N1C[C@@H]2C(=O)Nc3cnc4c(F)c(-c5c(O)cccc5F)c(Cl)cc4c3N2C[C@H]1C]

To a solution of atropisomer 2 of (2R,4aR)-11-chloro-9-fluoro-10-(2-fluoro-6-hydroxyphenyl)-2-methyl-2,3,4,4a-tetrahydro-1H-pyrazino[1',2':4,5]pyrazino[2,3-c]quinolin-5(6H)-one (172 mg, 0.40 mmol) and NEt₃ (72 µL, 0.52 mmol) in DCM (3.9 mL) at 0° C. was added acryloyl chloride (35.7 µL, 0.44 mmol). The resultant mixture was stirred at 0° C. After 5 min, a further portion of acryloyl chloride (18 µL, 0.44 mmol) was added. After a further 10 min, the mixture was quenched by addition of water (5 mL) and extracted with DCM (2×10 mL). The combined organics were passed through a hydrophobic frit and concentrated in vacuo to give a yellow dry film. The film was dissolved in 7 N ammonia in MeOH (5 mL) and the suspension was stirred at rt. After 4 min, the reaction mixture was concentrated in vacuo to give a yellow dry film (228 mg). The crude product was purified by SFC (Column: Chiralpak IC, 20×250 mm, 5 µm; Mobile phase A: 25-45% MeOH (+0.1% NH₃)/Mobile Phase B: 75-55% scCO2; flow rate: 100 mL/min; BPR: 120 bar; Column temperature: 40° C.) to give atropisomer 2 of (2R,4aR)-11-chloro-9-fluoro-10-(2-fluoro-6-hydroxyphenyl)-2-methyl-3-(prop-2-enoyl)-2,3,4,4a-tetrahydro-1H-pyrazino[1',2':4,5]pyrazino[2,3-c]quinolin-5(6H)-one (125 mg, 65%) as a colourless solid; ¹H NMR (400 MHz, DMSO, 30° C.): 1.52 (3H, dd), 2.86-3.02 (1H, m), 3.18 (1H, d), 3.74 (1H, dd), 3.88-4.01 (1H, m), 4.63 (1H, d), 4.72 (1H, s), 5.75 (1H, dd), 6.14 (1H, dd), 6.74-6.91 (2H, m), 6.98 (1H, dd), 7.28-7.42 (1H, m), 7.93 (1H, s), 8.65 (1H, s), 10.20 (1H, s), 11.08 (1H, s). 19F NMR (376 MHz, DMSO, 30° C.): −113.66, −118.06, −118.12; m/z: ES⁺ [M+H]⁺=485.0.

tert-Butyl 10-bromo-11-chloro-4a,6-dimethyl-5-oxo-1,2,4,4a,5,6-hexahydro-3H-pyrazino[1',2':4,5]pyrazino[2,3-c]quinoline-3-carboxylate Enantiomer 1 and 2

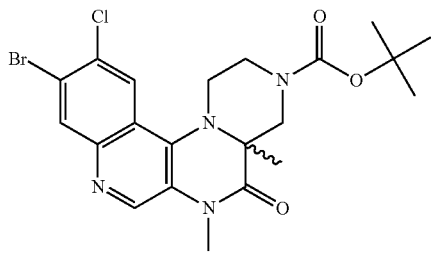 [SMILES: CN1C(=O)C2(C)CN(C(=O)OC(C)(C)C)CCN2c2c1cnc1cc(Br)c(Cl)cc21]

Sodium hydride (159 mg, 3.98 mmol) was added to tert-butyl (4aR)-10-bromo-11-chloro-5-oxo-1,2,4,4a,5,6-hexahydro-3H-pyrazino[1',2':4,5]pyrazino[2,3-c]quinoline-3-carboxylate (620 mg, 1.33 mmol) in DMF (10 mL) at 0° C. and the resulting suspension was stirred for 30 min. Iodomethane (0.495 mL, 7.95 mmol) was then added and the reaction mixture was stirred at rt for 1 h. The reaction mixture was quenched with water and extracted with EtOAc. The organic phase was dried (phase separator) and concentrated in vacuo. The crude product was purified by flash silica chromatography (0 to 100% EtOAc in heptane) to give tert-butyl 10-bromo-1-chloro-4a,6-dimethyl-5-oxo-1,2,4,4a,5,6-hexahydro-3H-pyrazino[1',2':4,5]pyrazino[2,3-c]quinoline-3-carboxylate (450 mg, 69%) as a yellow solid. The enantiomers were separated by SFC (Column Lux C4, 20×250 mm, 5 µm. Mobile phase: 40% MeOH+0.1% DEA/60% scCO₂. Flow rate: 100 mL/min, BPR: 120 bar. Column temperature: 40° C.) to give tert-butyl 10-bromo-11-chloro-4a,6-dimethyl-5-oxo-1,2,4,4a,5,6-hexahydro-3H-pyrazino[1',2':4,5]pyrazino[2,3-c]quinoline-3-carboxylate enantiomer 1 (183 mg, 28%) as a yellow solid; ¹H NMR (400 MHz, DMSO, 30° C.) 0.96 (3H, s), 1.45 (9H, s), 2.66-2.79 (1H, m), 3.03 (1H, d), 3.25 (1H, s), 3.32 (1H, s), 3.50 (3H, s), 3.78 (1H, s), 4.71 (1H, d), 8.27 (1H, s), 8.45 (1H, s), 8.95 (1H, s); m/z: ES⁺ [M+H]⁺ 495. Further elution gave tert-butyl 10-bromo-11-chloro-4a,6-dimethyl-5-oxo-1,2,4,4a,5,6-hexahydro-3H-pyrazino[1',2':4,5]pyrazino[2,3-c]quinoline-3-carboxylate enantiomer 2 (198 mg, 30%) as a yellow solid; ¹H NMR (400 MHz, DMSO, 30° C.) 0.96 (3H, s), 1.45 (9H, s), 2.66-2.77 (1H, m), 2.99 (1H, s), 3.25 (1H, s), 3.32 (1H, s), 3.50 (3H, s), 3.78 (1H, s), 4.71 (1H, d), 8.27 (1H, s), 8.44 (1H, s), 8.95 (1H, s); m/z: ES⁺ [M+H]⁺ 495.

tert-Butyl 11-chloro-10-(2-fluoro-6-hydroxyphenyl)-4a,6-dimethyl-5-oxo-1,2,4,4a,5,6-hexahydro-3H-pyrazino[1',2':4,5]pyrazino[2,3-c]quinoline-3-carboxylate Enantiomer 1

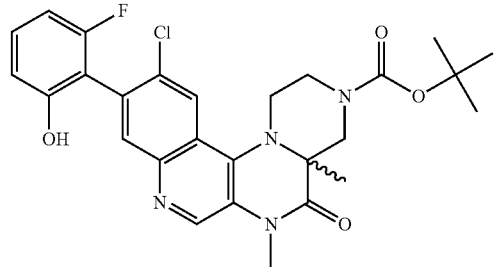 [SMILES: CN1C(=O)C2(C)CN(C(=O)OC(C)(C)C)CCN2c2c1cnc1cc(-c3c(O)cccc3F)c(Cl)cc21]

RuPhos (16.94 mg, 0.04 mmol) and RuPhos Pd G3 (30.4 mg, 0.04 mmol) were added to a degassed suspension of tert-butyl 10-bromo-1-chloro-4a,6-dimethyl-5-oxo-1,2,4,4a,5,6-hexahydro-3H-pyrazino[1',2':4,5]pyrazino[2,3-c]quinoline-3-carboxylate enantiomer 1 (180 mg, 0.36 mmol), (2-fluoro-6-hydroxyphenyl)boronic acid (127 mg, 0.82 mmol) and K₂CO₃ (151 mg, 1.09 mmol) in dioxane (4 mL) and water (1 mL). The reaction mixture was heated at 80° C. for 10 min. The reaction mixture was allowed to cool, diluted with EtOAc, then washed with water and brine. The organic phase was dried (phase separator) and concentrated in vacuo. The crude product was purified by flash silica chromatography (0 to 100% EtOAc in heptane) to give tert-butyl 11-chloro-10-(2-fluoro-6-hydroxyphenyl)-4a,6-dimethyl-5-oxo-1,2,4,4a,5,6-hexahydro-3H-pyrazino[1',2':4,5]pyrazino[2,3-c]quinoline-3-carboxylate enantiomer 1 (170 mg, 89%) as a pale yellow solid; 1H NMR (400 MHz, DMSO, 30° C.) 1.00 (3H, s), 1.46 (9H, s), 2.71 (1H, d), 3.02 (1H, s), 3.30 (1H, s), 3.31-3.39 (1H, m), 3.52 (3H, s), 3.84 (1H, s), 4.74 (1H, d), 6.74-6.87 (2H, m), 7.27-7.36 (1H, m), 7.94 (1H, d), 8.22 (1H, s), 8.95 (1H, s), 10.03 (1H, s); m/z: ES⁺ [M+H]⁺ 527.

11-Chloro-10-(2-fluoro-6-hydroxyphenyl)-4a,6-dimethyl-2,3,4,4a-tetrahydro-1H-pyrazino[1',2':4,5]pyrazino[2,3-c]quinolin-5(6H)-one Enantiomer 1

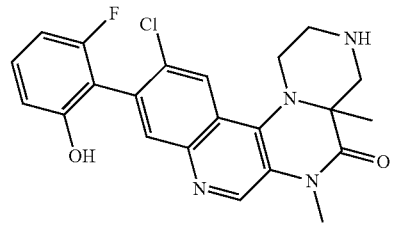 [SMILES: CN1C(=O)C2(C)CNCCN2c2c1cnc1cc(-c3c(O)cccc3F)c(Cl)cc21]

HCl (4M in dioxane, 0.806 mL, 3.23 mmol) was added to enantiomer 1 of tert-butyl 11-chloro-10-(2-fluoro-6-hydroxyphenyl)-4a,6-dimethyl-5-oxo-1,2,4,4a,5,6-hexahydro-3H-pyrazino[1',2':4,5]pyrazino[2,3-c]quinoline-3-carboxylate (170 mg, 0.32 mmol) in MeOH (1 mL) at 20° C. The resulting solution was stirred at rt for 3 h. The reaction mixture was purified using SCX (1M NH$_3$/MeOH) to give enantiomer 1 of 11-chloro-10-(2-fluoro-6-hydroxyphenyl)-4a,6-dimethyl-2,3,4,4a-tetrahydro-1H-pyrazino[1',2':4,5]pyrazino[2,3-c]quinolin-5(6H)-one (120 mg, 87%) as an orange solid; $^1$H NMR (400 MHz, DMSO, 30° C.) 0.91 (3H, s), 2.04 (1H, d), 2.64 (1H, d), 2.89 (1H, d), 2.99 (1H, t), 3.10 (1H, d), 3.18 (1H, d), 3.54 (3H, s), 3.68 (1H, d), 6.72-6.89 (2H, m), 7.30 (1H, q), 7.94 (1H, s), 8.22 (1H, s), 8.96 (1H, s), 9.88 (1H, s); m/z: ES$^+$ [M+H]$^+$ 427.

11-Chloro-10-(2-fluoro-6-hydroxyphenyl)-4a,6-dimethyl-3-(prop-2-enoyl)-2,3,4,4a-tetrahydro-1H-pyrazino[1',2':4,5]pyrazino[2,3-c]quinolin-5(6H)-one (Enantiomer 1, Compound 32)

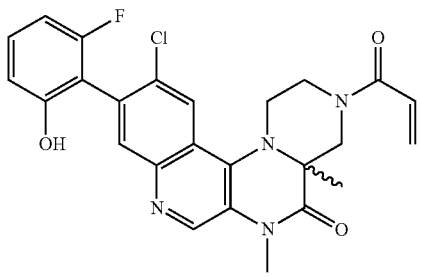 [SMILES: C=CC(=O)N1CCN2c3c(cnc4cc(-c5c(O)cccc5F)c(Cl)cc34)N(C)C(=O)C2(C)C1]

To a solution of enantiomer 1 of 11-chloro-10-(2-fluoro-6-hydroxyphenyl)-4a,6-dimethyl-2,3,4,4a-tetrahydro-1H-pyrazino[1',2':4,5]pyrazino[2,3-c]quinolin-5(6H)-one (110 mg, 0.26 mmol) and NEt$_3$ (0.216 mL, 1.55 mmol) in DCM (2 mL) at 0° C. was added acryloyl chloride (0.063 mL, 0.77 mmol). The reaction mixture was brought up to rt and concentrated in vacuo. 7M NH$_3$/MeOH (1 mL) was added and the reaction mixture was stirred at rt for 1 h. The crude reaction mixture was purified by preparative HPLC (Waters CSH C18 OBD column, 30×100 mm id, 5 μm particle size), using water (containing 1% by volume of NH$_4$OH (28-30% in H$_2$O)) and MeCN as eluents, to give enantiomer 1 of 11-chloro-10-(2-fluoro-6-hydroxyphenyl)-4a,6-dimethyl-3-(prop-2-enoyl)-2,3,4,4a-tetrahydro-1H-pyrazino[1',2':4,5]pyrazino[2,3-c]quinolin-5(6H)-one (32 mg, 26%) as a pale yellow solid; $^1$H NMR (500 MHz, DMSO, 27° C.) 1.05 (3H, s), 2.61-2.72 (1H, m), 3.21 (1H, t), 3.35 (1H, s), 3.36-3.45 (1H, m), 3.51 (3H, s), 4.36 (1H, d), 4.81 (1H, d), 5.76 (1H, d), 6.15 (1H, dd), 6.78 (1H, t), 6.85 (1H, dd), 7.09 (1H, dd), 7.26-7.36 (1H, m), 7.95 (1H, d), 8.27 (1H, s), 8.96 (1H, s), 10.05 (1H, s); m/z: ES$^+$ [M+H]$^+$ 481.

tert-Butyl 11-chloro-10-(2-fluoro-6-hydroxyphenyl)-4a,6-dimethyl-5-oxo-1,2,4,4a,5,6-hexahydro-3H-pyrazino[1',2':4,5]pyrazino[2,3-c]quinoline-3-carboxylate Enantiomer 2

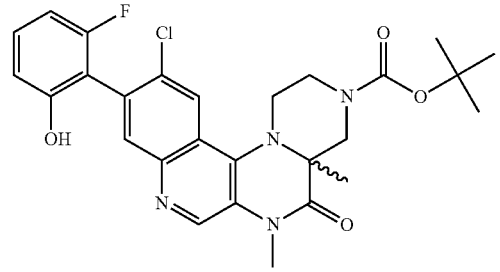 [SMILES: CN1C(=O)C2(C)CN(C(=O)OC(C)(C)C)CCN2c2c1cnc1cc(-c3c(O)cccc3F)c(Cl)cc21]

RuPhos (17.88 mg, 0.04 mmol) and RuPhos Pd G3 (32.1 mg, 0.04 mmol) were added to a de-gassed suspension of enantiomer 2 of tert-butyl 10-bromo-11-chloro-4a,6-dimethyl-5-oxo-1,2,4,4a,5,6-hexahydro-3H-pyrazino[1',2':4,5]pyrazino[2,3-c]quinoline-3-carboxylate (190 mg, 0.38 mmol), (2-fluoro-6-hydroxyphenyl)boronic acid (134 mg, 0.86 mmol) and K$_2$CO$_3$ (159 mg, 1.15 mmol) in dioxane (4 mL) and water (1 mL). The reaction mixture was heated to 80° C. for 10 min. The reaction mixture was allowed to cool, diluted with EtOAc, then washed with water and brine. The organic phase was dried (phase separator) and concentrated in vacuo. The crude product was purified by flash silica chromatography (0 to 100% EtOAc in heptane) to give enantiomer 2 of tert-butyl 11-chloro-10-(2-fluoro-6-hydroxyphenyl)-4a,6-dimethyl-5-oxo-1,2,4,4a,5,6-hexahydro-3H-pyrazino[1',2':4,5]pyrazino[2,3-c]quinoline-3-carboxylate (180 mg, 89%) as a pale yellow solid; $^1$H NMR (400 MHz, DMSO, 30° C.) 1.00 (3H, s), 1.46 (9H, s), 2.71 (1H, d), 3.02 (1H, s), 3.26 (1H, s), 3.31-3.39 (1H, m), 3.52 (3H, s), 3.84 (1H, s), 4.74 (1H, d), 6.74-6.88 (2H, m), 7.26-7.34 (1H, m), 7.94 (1H, d), 8.22 (1H, s), 8.95 (1H, s), 10.03 (1H, s); m/z: ES$^+$ [M+H]$^+$ 527.

11-Chloro-10-(2-fluoro-6-hydroxyphenyl)-4a,6-dimethyl-2,3,4,4a-tetrahydro-1H-pyrazino[1',2':4,5]pyrazino[2,3-c]quinolin-5(6H)-one Enantiomer 2

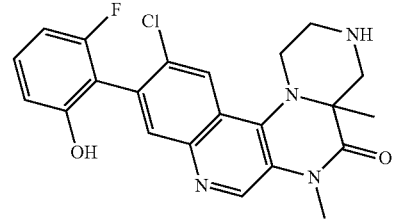 [SMILES: CN1C(=O)C2(C)CNCCN2c2c1cnc1cc(-c3c(O)cccc3F)c(Cl)cc21]

HCl (4M in dioxane, 0.806 mL, 3.23 mmol) was added to enantiomer 2 of tert-butyl 11-chloro-10-(2-fluoro-6-hydroxyphenyl)-4a,6-dimethyl-5-oxo-1,2,4,4a,5,6-hexahydro-3H-pyrazino[1',2':4,5]pyrazino[2,3-c]quinoline-3-carboxylate (170 mg, 0.32 mmol) in MeOH (1 mL) at 20° C. The resulting solution was stirred at rt for 3 h. The reaction mixture was purified using SCX (1M NH$_3$/MeOH) to give enantiomer 2 of 11-chloro-10-(2-fluoro-6-hydroxyphenyl)-4a,6-dimethyl-2,3,4,4a-tetrahydro-1H-pyrazino[1',2':4,5]

pyrazino[2,3-c]quinolin-5(6H)-one (130 mg, 94%) as an orange solid; $^1$H NMR (400 MHz, DMSO, 30° C.) 0.91 (3H, s), 2.11 (1H, d), 2.64 (1H, d), 2.89 (1H, d), 2.99 (1H, t), 3.10 (1H, d), 3.18 (1H, d), 3.54 (3H, s), 3.69 (1H, d), 6.71-6.89 (2H, m), 7.30 (1H, q), 7.94 (1H, s), 8.22 (1H, s), 8.96 (1H, s), 10.02 (1H, s); m/z: ES$^+$ [M+H]$^+$ 427.

11-Chloro-10-(2-fluoro-6-hydroxyphenyl)-4a,6-dimethyl-3-(prop-2-enoyl)-2,3,4,4a-tetrahydro-1H-pyrazino[1',2':4,5]pyrazino[2,3-c]quinolin-5(6H)-one (Enantiomer 2, Compound 33)

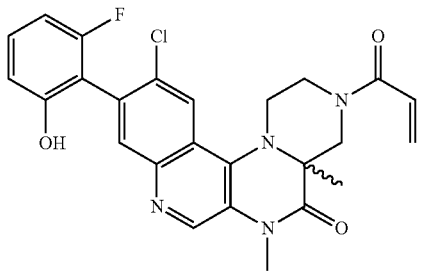 [SMILES: C=CC(=O)N1CCN2c3c(cnc4cc(-c5c(O)cccc5F)c(Cl)cc34)N(C)C(=O)C2(C)C1]

To a solution of enantiomer 2 of 11-chloro-10-(2-fluoro-6-hydroxyphenyl)-4a,6-dimethyl-2,3,4,4a-tetrahydro-1H-pyrazino[1',2':4,5]pyrazino[2,3-c]quinolin-5(6H)-one (120 mg, 0.28 mmol) and NEt$_3$ (0.235 mL, 1.69 mmol) in DCM (2 mL) at 0° C. was added acryloyl chloride (0.069 mL, 0.84 mmol). The reaction mixture was brought up to rt and concentrated in vacuo. 7M NH$_3$/MeOH (1 mL) was added and the reaction mixture was stirred at rt for 1 h. The crude reaction mixture was purified by preparative HPLC (Waters CSH C18 OBD column, 30×100 mm id, 5 μm particle size), using water (containing 1% by volume of NH$_4$OH (28-30% in H$_2$O)) and MeCN as eluents, to give enantiomer 2 of 11-chloro-10-(2-fluoro-6-hydroxyphenyl)-4a,6-dimethyl-3-(prop-2-enoyl)-2,3,4,4a-tetrahydro-1H-pyrazino[1',2':4,5]pyrazino[2,3-c]quinolin-5(6H)-one (48 mg, 36%) as a pale yellow solid; $^1$H NMR (500 MHz, DMSO, 27° C.) 1.05 (3H, s), 2.61-2.71 (1H, m), 3.21 (1H, t), 3.35 (1H, s), 3.37-3.44 (1H, m), 3.51 (3H, s), 4.35 (1H, d), 4.81 (1H, d), 5.76 (1H, d), 6.15 (1H, dd), 6.78 (1H, t), 6.85 (1H, dd), 7.09 (1H, dd), 7.25-7.35 (1H, m), 7.95 (1H, d), 8.27 (1H, s), 8.96 (1H, s), 10.00 (1H, s); m/z: ES$^+$ [M+H]$^+$ 481.

tert-Butyl (4aR)-11-chloro-9-fluoro-10-[2-fluoro-6-(hydroxymethyl)phenyl]-6-methyl-5-oxo-1,2,4,4a,5,6-hexahydro-3H-pyrazino[1',2':4,5]pyrazino[2,3-c]quinoline-3-carboxylate Atropisomer 1 and 2

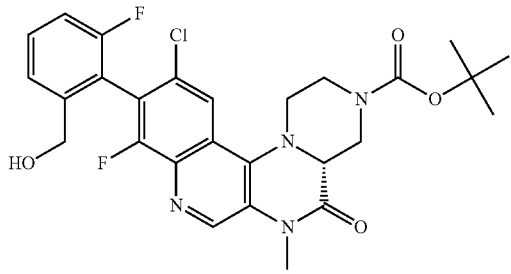 [SMILES: CN1C(=O)[C@H]2CN(C(=O)OC(C)(C)C)CCN2c2c1cnc1c(F)c(-c3c(F)cccc3CO)c(Cl)cc21]

A stirred suspension of tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (500 mg, 1 mmol), (2-fluoro-6-(hydroxymethyl)phenyl)boronic acid (340 mg, 2 mmol) and K$_2$CO$_3$ (830 mg, 6 mmol) in 2-methyltetrahydrofuran (7.5 mL) and water (2.5 mL) was degassed. RuPhos Pd G3 (84 mg, 0.10 mmol) and RuPhos (46.7 mg, 0.10 mmol) were added and the reaction mixture was heated at 60° C. for 2.25 h. The reaction mixture was allowed to cool to rt and was diluted with EtOAc and water. The layers were separated and the organic layer was washed with water and brine. The aqueous layers were extracted with EtOAc and the combined organic layers were dried (phase separator) and concentrated in vacuo to afford the crude product. This was purified by flash silica chromatography (0 to 100% EtOAc in heptane) to give tert-butyl (4aR)-11-chloro-9-fluoro-10-[2-fluoro-6-(hydroxymethyl)phenyl]-6-methyl-5-oxo-1,2,4,4a,5,6-hexahydro-3H-pyrazino[1',2':4,5]pyrazino[2,3-c]quinoline-3-carboxylate (507 mg, 93%) as a brown foam. This was purified using SFC (Column YMC Amylose C, 20×250 mm, 5 μm Mobile phase: 30% IPA+0.1% diethylamine/70% scCO$_2$, Flow rate: 60 mL/min, BPR: 120 bar, Column temperature: 40° C., UV max 267 nm) to give atropisomer 1 of tert-butyl (4aR)-11-chloro-9-fluoro-10-[2-fluoro-6-(hydroxymethyl)phenyl]-6-methyl-5-oxo-1,2,4,4a,5,6-hexahydro-3H-pyrazino[1',2':4,5]pyrazino[2,3-c]quinoline-3-carboxylate (227 mg, 42%, >99% de) as a white solid; $^1$H NMR (400 MHz, DMSO, 30° C.) 1.46 (9H, s), 2.68-2.78 (1H, m), 3.18-3.29 (3H, m), 3.51 (3H, s), 3.84-3.99 (2H, m), 4.27 (2H, t), 4.76 (1H, d), 5.26 (1H, t), 7.30 (1H, t), 7.51 (1H, d), 7.60 (1H, td), 8.13 (1H, s), 9.02 (1H, s); m/z: ES$^+$ [M+H]$^+$ 545. This was followed by atropisomer 2 of tert-butyl (4aR)-11-chloro-9-fluoro-10-[2-fluoro-6-(hydroxymethyl)phenyl]-6-methyl-5-oxo-1,2,4,4a,5,6-hexahydro-3H-pyrazino[1',2':4,5]pyrazino[2,3-c]quinoline-3-carboxylate (228 mg, 42%, >99% de) as a white solid; $^1$H NMR (400 MHz, DMSO, 30° C.) 1.46 (9H, s), 2.69-2.78 (1H, m), 3.19-3.3 (3H, m), 3.51 (3H, s), 3.83-3.99 (2H, m), 4.26 (2H, dd), 4.76 (1H, d), 5.26 (1H, t), 7.31 (1H, t), 7.51 (1H, d), 7.60 (1H, td), 8.13 (1H, s), 9.02 (1H, s); m/z: ES$^+$ [M+H]$^+$ 545.

(4aR)-11-Chloro-9-fluoro-10-[2-fluoro-6-(hydroxymethyl)phenyl]-6-methyl-2,3,4,4a-tetrahydro-1H-pyrazino[1',2':4,5]pyrazino[2,3-c]quinolin-5(6H)-one Atropisomer 1

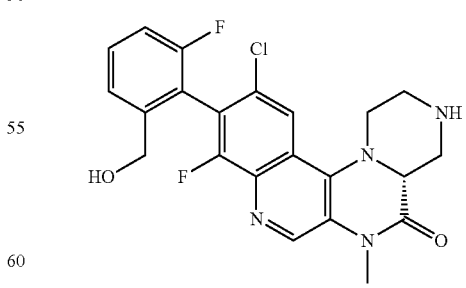

To a stirred solution of atropisomer 1 of tert-butyl (4aR)-11-chloro-9-fluoro-10-[2-fluoro-6-(hydroxymethyl)phenyl]-6-methyl-5-oxo-1,2,4,4a,5,6-hexahydro-3H-pyrazino[1',2':4,5]pyrazino[2,3-c]quinoline-3-carboxylate (227 mg, 0.42 mmol) in MeOH (2 mL) was added HCl (6M in IPA, 1.388 mL, 8.33 mmol) dropwise. The resultant reaction mixture was stirred at rt for 1 h. The crude product was purified by SCX (1M NH$_3$/MeOH) to give atropisomer 1 of (4aR)-11-chloro-9-fluoro-10-[2-fluoro-6-(hydroxymethyl)phenyl]-6-methyl-2,3,4,4a-tetrahydro-1H-pyrazino[1',2':4,5]pyrazino[2,3-c]quinolin-5(6H)-one (176 mg, 95%) as a white solid; $^1$H NMR (400 MHz, DMSO, 30° C.) 2.62-2.73 (1H, m), 2.9-2.98 (1H, m), 3.03-3.14 (2H, m), 3.14-3.2 (1H, m), 3.54 (3H, s), 3.66-3.77 (2H, m), 4.27 (2H, t), 5.27 (1H, t), 7.30 (1H, t), 7.51 (1H, d), 7.60 (1H, td), 8.12 (1H, d), 9.02 (1H, s); m/z: ES$^+$ [M+H]$^+$ 445.

(4aR)-11-Chloro-9-fluoro-10-[2-fluoro-6-(hydroxymethyl)phenyl]-6-methyl-3-(prop-2-enoyl)-2,3,4,4a-tetrahydro-1H-pyrazino[1',2':4,5]pyrazino[2,3-c]quinolin-5(6H)-one, (Atropisomer 1, Compound 34)

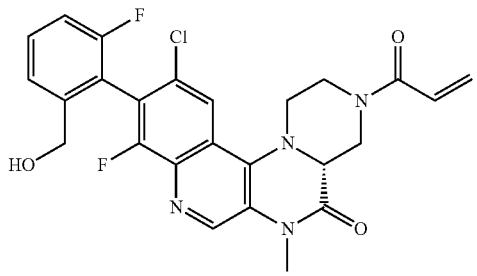 [SMILES: C=CC(=O)N1CCN2c3c(cnc4c(F)c(-c5c(F)cccc5CO)c(Cl)cc34)N(C)C(=O)[C@H]2C1]

To a stirred solution of atropisomer 1 of (4aR)-11-chloro-9-fluoro-10-[2-fluoro-6-(hydroxymethyl)phenyl]-6-methyl-2,3,4,4a-tetrahydro-1H-pyrazino[1',2':4,5]pyrazino[2,3-c]quinolin-5(6H)-one (176 mg, 0.4 mmol) and DIPEA (0.090 mL, 0.51 mmol) in DCM (4 mL) at 0° C. was added acryloyl chloride (0.033 mL, 0.42 mmol) dropwise and the reaction mixture was stirred at 0° C. for 15 min. The reaction mixture was diluted with DCM and was quenched at 0° C. with water. The layers were separated, the organic phase was washed with water and brine, dried (phase separating cartridge), filtered and concentrated in vacuo to afford the crude product. This was dissolved in cold 7N NH$_3$/MeOH (20 mL) and was stirred at rt for 1.5 h. The reaction mixture was concentrated in vacuo and the crude product was dissolved in DCM. The organic was washed with water and brine, dried (phase separating cartridge), filtered and concentrated in vacuo to afford the crude product. This was purified by preparative HPLC (Waters CSH C18 OBD column, 30×100 mm id, 5 μm particle size), using water (containing 1% by volume of NH$_4$OH (28-30% in water)) and MeCN as eluents, to give atropisomer 1 of (4aR)-11-chloro-9-fluoro-10-[2-fluoro-6-(hydroxymethyl)phenyl]-6-methyl-3-(prop-2-enoyl)-2,3,4,4a-tetrahydro-1H-pyrazino[1',2':4,5]pyrazino[2,3-c]quinolin-5(6H)-one (113 mg, 57%, >99% de) as a white solid; $^1$H NMR (400 MHz, DMSO, 30° C.) 2.64-2.74 (1H, m), 3.16-3.27 (1H, m), 3.33-3.4 (1H, m), 3.50 (3H, s), 3.57-3.69 (1H, m), 3.98 (1H, s), 4.19-4.34 (2H, m), 4.39-4.5 (1H, m), 4.78 (1H, d), 5.27 (1H, t), 5.76 (1H, d), 6.15 (1H, dd), 7.01-7.14 (1H, m), 7.31 (1H, t), 7.51 (1H, d), 7.56-7.65 (1H, m), 8.19 (1H, s), 9.03 (1H, s); m/z: ES$^+$ [M+H]$^+$ 499.

(4aR)-11-Chloro-9-fluoro-10-[2-fluoro-6-(hydroxymethyl)phenyl]-6-methyl-2,3,4,4a-tetrahydro-1H-pyrazino[1',2':4,5]pyrazino[2,3-c]quinolin-5(6H)-one Atropisomer 2

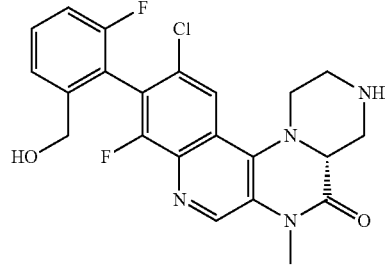 [SMILES: CN1C(=O)[C@H]2CNCCN2c2c1cnc1c(F)c(-c3c(F)cccc3CO)c(Cl)cc21]

To a stirred solution of atropisomer 2 of tert-butyl (4aR)-11-chloro-9-fluoro-10-[2-fluoro-6-(hydroxymethyl)phenyl]-6-methyl-5-oxo-1,2,4,4a,5,6-hexahydro-3H-pyrazino[1',2':4,5]pyrazino[2,3-c]quinoline-3-carboxylate (228 mg, 0.42 mmol) in MeOH (2 mL) was added HCl (6M in IPA, 1.388 mL, 8.33 mmol) dropwise. The resultant reaction mixture was stirred at rt for 1.5 h, then purified by SCX (1M NH$_3$/MeOH) to give atropisomer 2 of (4aR)-11-chloro-9-fluoro-10-[2-fluoro-6-(hydroxymethyl)phenyl]-6-methyl-2,3,4,4a-tetrahydro-1H-pyrazino[1',2':4,5]pyrazino[2,3-c]quinolin-5(6H)-one (180 mg, 97%) as a white solid; $^1$H NMR (400 MHz, DMSO, 30° C.) 2.59-2.7 (1H, m), 2.87-2.95 (1H, m), 2.98-3.08 (2H, m), 3.11-3.19 (1H, m), 3.53 (3H, s), 3.64-3.73 (2H, m), 4.25 (2H, dd), 5.26 (1H, t), 7.30 (1H, t), 7.48-7.55 (1H, m), 7.60 (1H, td), 8.10 (1H, d), 9.01 (1H, s); m/z: ES$^+$ [M+H]$^+$ 445.

(4aR)-11-Chloro-9-fluoro-10-[2-fluoro-6-(hydroxymethyl)phenyl]-6-methyl-3-(prop-2-enoyl)-2,3,4,4a-tetrahydro-1H-pyrazino[1',2':4,5]pyrazino[2,3-c]quinolin-5(6H)-one, (Atropisomer 2, Compound 35)

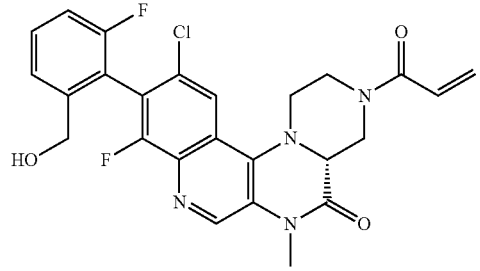 [SMILES: C=CC(=O)N1CCN2c3c(cnc4c(F)c(-c5c(F)cccc5CO)c(Cl)cc34)N(C)C(=O)[C@H]2C1]

To a stirred solution of atropisomer 2 of (4aR)-11-chloro-9-fluoro-10-[2-fluoro-6-(hydroxymethyl)phenyl]-6-methyl-2,3,4,4a-tetrahydro-1H-pyrazino[1',2':4,5]pyrazino[2,3-c]quinolin-5(6H)-one (180 mg, 0.4 mmol) and DIPEA (0.092 mL, 0.53 mmol) in DCM (4 mL) at 0° C. was added acryloyl chloride (0.034 mL, 0.42 mmol) dropwise and the reaction mixture was stirred at 0° C. for 15 min. The reaction mixture was diluted with DCM and was quenched at 0° C. with water. The layers were separated, the organic phase was washed with water and brine, dried (phase separating cartridge), filtered and concentrated in vacuo to afford the crude product. This was dissolved in cold 7N NH₃/MeOH (20 mL) and was stirred at rt for 1.5 h. The reaction mixture was concentrated in vacuo and the crude product was dissolved in DCM. The organic was washed with water and brine, dried (phase separating cartridge), filtered and concentrated in vacuo to afford the crude product. This was purified by preparative HPLC (Waters CSH C18 OBD column, 30×100 mm id, 5 μm particle size), using water (containing 1% by volume of NH₄OH (28-30% in water)) and MeCN as eluents, to give atropisomer 2 of (4aR)-11-chloro-9-fluoro-10-[2-fluoro-6-(hydroxymethyl)phenyl]-6-methyl-3-(prop-2-enoyl)-2,3,4,4a-tetrahydro-1H-pyrazino[1',2':4,5]pyrazino[2,3-c]quinolin-5(6H)-one (120 mg, 60%, >99% de) as a white solid; ¹H NMR (400 MHz, DMSO, 30° C.) 2.63-2.74 (1H, m), 3.14-3.27 (1H, m), 3.33-3.42 (1H, m), 3.51 (3H, s), 3.62 (1H, d), 3.97 (1H, s), 4.18-4.33 (2H, m), 4.44 (1H, d), 4.78 (1H, d), 5.27 (1H, t), 5.76 (1H, d), 6.15 (1H, dd), 7.01-7.14 (1H, m), 7.31 (1H, t), 7.51 (1H, d), 7.60 (1H, td), 8.19 (1H, s), 9.03 (1H, s); m/z: ES⁺ [M+H]⁺ 499.

tert-Butyl (2R,5R)-4-(7-bromo-6-chloro-8-fluoro-3-nitroquinolin-4-yl)-5-(hydroxymethyl)-2-methylpiperazine-1-carboxylate

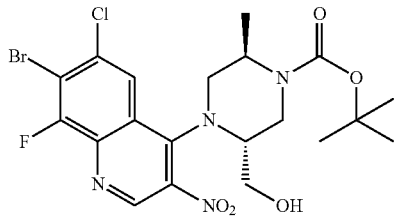 [SMILES: C[C@@H]1CN(c2c([N+](=O)[O-])cnc3c(F)c(Br)c(Cl)cc23)[C@@H](CO)CN1C(=O)OC(C)(C)C]

A stirred solution of 7-bromo-4,6-dichloro-8-fluoro-3-nitroquinoline (2 g, 5.88 mmol) and tert-butyl (2R,5R)-5-(hydroxymethyl)-2-methylpiperazine-1-carboxylate (1.355 g, 5.88 mmol) in MeCN (30 mL) was treated with DIPEA (1.025 mL, 5.88 mmol) and the reaction mixture stirred at 80° C. for 75 min. The reaction mixture was concentrated in vacuo and purified by flash silica chromatography (0 to 40% EtOAc in heptane) to give tert-butyl (2R,5R)-4-(7-bromo-6-chloro-8-fluoro-3-nitroquinolin-4-yl)-5-(hydroxymethyl)-2-methylpiperazine-1-carboxylate (2.6 g, 83%) as a yellow solid; m/z: ES⁺ [M+H]⁺ 533/535.

tert-Butyl (2R,4aR)-10-bromo-11-chloro-9-fluoro-2-methyl-1,2,4a,5-tetrahydropyrazino[1',2':4,5][1,4]oxazino[2,3-c]quinoline-3(4H)-carboxylate

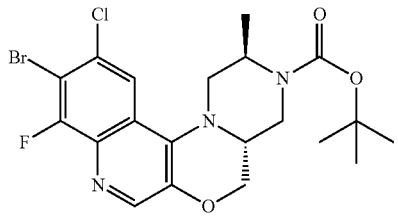 [SMILES: C[C@@H]1CN2c3c(cnc4c(F)c(Br)c(Cl)cc34)OC[C@H]2CN1C(=O)OC(C)(C)C]

To a solution of tert-butyl (2R,5R)-4-(7-bromo-6-chloro-8-fluoro-3-nitroquinolin-4-yl)-5-(hydroxymethyl)-2-methylpiperazine-1-carboxylate (2.6 g, 4.87 mmol) in anhydrous DMA (50 mL) was added 4 Å molecular sieves (3 g) and the mixture stirred for 0.5 h. Lithium bis(trimethylsilyl)amide (1M in THF, 4.87 mL, 4.87 mmol) was added and the reaction mixture stirred at rt for 0.5 h then at 120° C. for 40 h then allowed to cool. The sieves were filtered off, washing with EtOAc (100 mL) and the organic layer was washed with water (200 mL) which was back extracted with EtOAc (2×50 mL). The combined organic layer was washed with water (4×100 mL) then dried (MgSO₄) and concentrated in vacuo. The residue was purified by flash silica chromatography (0 to 20% EtOAc/heptane) to give tert-butyl (2R,4aR)-10-bromo-11-chloro-9-fluoro-2-methyl-1,2,4a,5-tetrahydropyrazino[1',2':4,5][1,4]oxazino[2,3-c]quinoline-3(4H)-carboxylate (0.816 g, 34%) as a pale yellow solid; ¹H NMR (400 MHz, DMSO, 30° C.) 1.43 (9H, s), 1.49 (3H, dd), 3.05 (1H, dd), 3.3-3.39 (2H, m), 3.61 (1H, dd), 3.97 (1H, d), 4.25 (1H, s), 4.3-4.39 (2H, m), 7.84 (1H, d), 8.62 (1H, s); m/z: ES⁺ [M+H]⁺ 486/488.

tert-Butyl (2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate Atropisomer 1 and 2

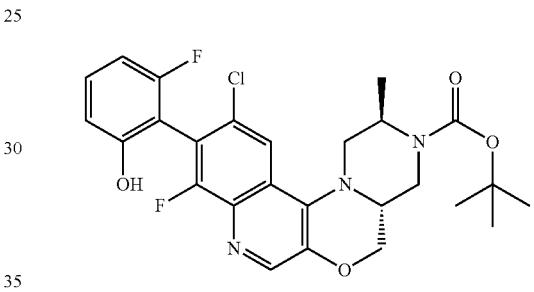

tert-Butyl (2R,4aR)-10-bromo-11-chloro-9-fluoro-2-methyl-1,2,4a,5-tetrahydropyrazino[1',2':4,5][1,4]oxazino[2,3-c]quinoline-3(4H)-carboxylate (800 mg, 1.64 mmol), Na₂CO₃ (348 mg, 3.29 mmol) and (2-fluoro-6-hydroxyphenyl)boronic acid (384 mg, 2.47 mmol) were combined in a degassed mixture of dioxane (24 mL) and water (4 mL). SPhos Pd G2 (118.6 mg, 0.16 mmol) was added and the reaction was degassed then heated at 80° C. for 1.5 h. Additional (2-fluoro-6-hydroxyphenyl)boronic acid (100 mg) was added and the reaction mixture stirred for 1.5 min then allowed to cool. The reaction mixture was diluted with EtOAc (200 mL) and the organic layer was washed with water (2×100 mL) and brine (100 mL) then dried (MgSO₄) and concentrated in vacuo. The residue was purified by flash silica chromatography (0 to 50% EtOAc/heptane) to give tert-butyl (2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (794 mg, 93%) as a pale brown solid. This was purified by SFC (Column: Chiralpak IC, 20×250 mm, 5 μm, Mobile phase: 40% MeOH 0.1% NH₃/60% scCO₂, Flow rate: 60 mL/min, BPR: 120 bar, Column temperature: 40° C., UV max 265 nm) to afford atropisomer 1 of tert-butyl (2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (0.182 g, 23%, 99% d.e.) as a white solid; ¹H NMR (400 MHz, DMSO, 30° C.) 1.45 (9H, s), 1.52 (3H, d), 3.08 (1H, dd), 3.31-3.35 (1H, m), 3.41 (1H, dd), 3.64 (1H, d), 4.00 (1H, d), 4.21-4.49 (3H, m), 6.71-6.94 (2H, m), 7.26-7.46 (1H, m), 7.82 (1H, d), 8.62 (1H, s), 10.16 (1H, s); m/z: ES⁺ [M+H]⁺ 518/520. This was followed by atropisomer 2 of tert-butyl (2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (0.293 g, 38%, 99% d.e.) as a white solid; $^1$H NMR (400 MHz, DMSO, 30° C.) 1.45 (9H, s), 1.52 (3H, d), 3.08 (1H, dd), 3.34 (1H, d), 3.43 (1H, dd), 3.64 (1H, d), 4.00 (1H, d), 4.19-4.49 (3H, m), 6.71-6.99 (2H, m), 7.35 (1H, td), 7.82 (1H, d), 8.62 (1H, s), 10.13 (1H, d); m/z: ES$^+$ [M+H]$^+$ 518/520.

2-[(2R,4aR)-11-Chloro-9-fluoro-2-methyl-1,2,3,4,4a,5-hexahydropyrazino[1',2':4,5][1,4]oxazino[2,3-c]quinolin-10-yl]-3-fluorophenol Atropisomer 1

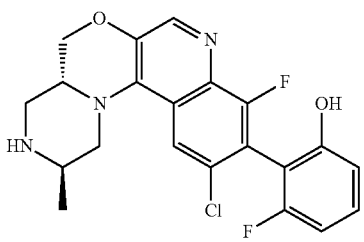

To a solution of atropisomer 1 of tert-butyl (2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (175 mg, 0.34 mmol) in DCM (4 mL) at 0° C. was added TFA (2 mL, 26.1 mmol) and the reaction mixture stirred for 2 h, then concentrated in vacuo. The residue was purified using SCX (1M NH$_3$/MeOH) to give atropisomer 1 of 2-[(2R,4aR)-11-chloro-9-fluoro-2-methyl-1,2,3,4,4a,5-hexahydropyrazino[1',2':4,5][1,4]oxazino[2,3-c]quinolin-10-yl]-3-fluorophenol (146 mg, >100%) as an off-white solid that was used without further purification; m/z: ES$^+$ [M+H]$^+$ 418/420.

(2E)-1-[(2R,4aR)-11-Chloro-9-fluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]-4-(dimethylamino)but-2-en-1-one (Atropisomer 1, Compound 36)

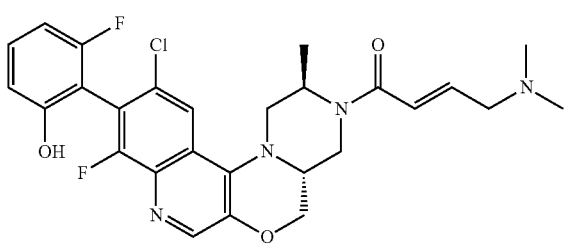 [SMILES: C[C@@H]1CN2c3c(cnc4c(F)c(-c5c(O)cccc5F)c(Cl)cc34)OC[C@H]2CN1C(=O)/C=C/CN(C)C]

Atropisomer 1 of 2-[(2R,4aR)-11-chloro-9-fluoro-2-methyl-1,2,3,4,4a,5-hexahydropyrazino[1',2':4,5][1,4]oxazino[2,3-c]quinolin-10-yl]-3-fluorophenol (146 mg, 0.35 mmol) and (E)-4-(dimethylamino)but-2-enoic acid (64 mg, 0.38 mmol) were dissolved in DCM (5 mL) and DIPEA (0.243 mL, 1.40 mmol). O-(7-Azabenzotriazol-1-yl)-N,N,N',N'-tetramethyluronium hexafluorophosphate (159 mg, 0.42 mmol) was added and the solution was stirred at rt for 1.5 h. The reaction mixture was diluted with DCM (50 mL), washed with aq. sat. NaHCO$_3$ (25 mL) and brine (25 mL) then the organic layer dried and concentrated in vacuo. The residue was purified by preparative HPLC (Waters CSH C18 OBD column, 30×100 mm id, 5-µm particle size), using water (containing 1% by volume of N H$_4$OH (28-30% in H$_2$O)) and MeCN as eluents, to give atropisomer 1 of (2E)-1-[(2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]-4-(dimethylamino)but-2-en-1-one (117 mg, 63%) as a white solid; $^1$H NMR (400 MHz, CDCl$_3$, 30° C.) 1.66 (3H, d), 2.30 (6H, s), 2.92 (1H, d), 3.14 (2H, q), 3.22-3.46 (2H, m), 3.61 (1H, s), 4.08-4.43 (3H, m), 4.64 (1H, s), 6.46 (1H, d), 6.7-6.84 (2H, m), 6.91 (1H, dt), 7.30 (1H, td), 7.82 (1H, s), 8.54 (1H, s); m/z: ES$^+$ [M+H]$^+$ 529/531.

2-[(2R,4aR)-11-Chloro-9-fluoro-2-methyl-1,2,3,4,4a,5-hexahydropyrazino[1',2':4,5][1,4]oxazino[2,3-c]quinolin-10-yl]-3-fluorophenol Atropisomer 2

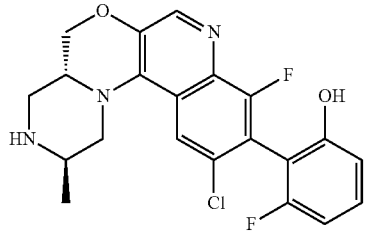 [SMILES: C[C@@H]1CN2c3c(cnc4c(F)c(-c5c(O)cccc5F)c(Cl)cc34)OC[C@H]2CN1]

To a solution of atropisomer 2 of tert-butyl (2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (288 mg, 0.56 mmol) in DCM (6 mL) at 0° C. was added TFA (3 mL, 39.18 mmol). The reaction mixture stirred for 2 h, then concentrated in vacuo. The residue was purified by SCX (1M NH$_3$/MeOH) to give atropisomer 2 of 2-[(2R,4aR)-11-chloro-9-fluoro-2-methyl-1,2,3,4,4a,5-hexahydropyrazino[1',2':4,5][1,4]oxazino[2,3-c]quinolin-10-yl]-3-fluorophenol (241 mg, >100%) as an off-white solid that was used without further purification; $^1$H NMR (400 MHz, DMSO, 30° C.) 0.89-1.21 (3H, m), 2.74 (1H, dd), 2.81-2.95 (2H, m), 3.06 (1H, dd), 3.48 (1H, td), 3.96 (1H, t), 4.11 (1H, dd), 4.26 (1H, dd), 6.64-7.02 (2H, m), 7.34 (1H, td), 7.79 (1H, d), 8.40 (1H, s), 10.12 (1H, s); m/z: ES$^+$ [M+H]$^+$ 418/420.

(2E)-1-[(2R,4aR)-11-Chloro-9-fluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]-4-(dimethylamino)but-2-en-1-one (Atropisomer 2, Compound 37)

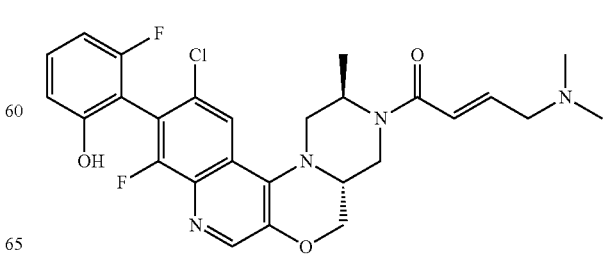

Atropisomer 2 of 2-[(2R,4aR)-11-chloro-9-fluoro-2-methyl-1,2,3,4,4a,5-hexahydropyrazino [1',2':4,5][1,4]oxazino[2,3-c]quinolin-10-yl]-3-fluorophenol (241 mg, 0.58 mmol) and (E)-4-(dimethylamino)but-2-enoic acid.HCl (105 mg, 0.63 mmol) were dissolved in DCM (5 mL) and DIPEA (0.402 mL, 2.31 mmol). O-(7-Azabenzotriazol-1-yl)-N,N,N',N'-tetramethyluronium hexafluorophosphate (263 mg, 0.69 mmol) was added and the solution was stirred at rt for 1.5 h. The reaction mixture was diluted with DCM (50 mL), washed with aq. sat. NaHCO₃ (25 mL) and brine (25 mL) then the organic layer dried and concentrated in vacuo. The residue was purified by preparative HPLC (Waters CSH C18 OBD column, 30×100 mm id, 5-μm particle size), using water (containing 1% by volume of N H₄OH (28-30% in H₂O)) and MeCN as eluents, to give atropisomer 2 of (2E)-1-[(2R,4aR)-11-chloro-9-fluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]-4-(dimethylamino)but-2-en-1-one (178 mg, 58%) as a white solid; ¹H NMR (400 MHz, CDCl₃, 30° C.) 1.64 (3H, s), 2.29 (6H, s), 2.81-3.44 (5H, m), 3.55 (1H, dd), 3.80 (1H, s), 4.24 (2H, s), 4.81 (1H, d), 6.41 (1H, d), 6.63-6.99 (3H, m), 7.27-7.36 (1H, m), 7.72 (1H, s), 8.47 (1H, s). m/z: ES⁺ [M+H]⁺ 529/531.

3-Bromo-4-chloro-2-methylaniline

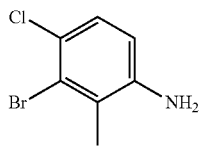

To a solution of 3-bromo-2-methylaniline (19.9 g, 106.96 mmol) in DMF (107 ml) was added N-chlorosuccinimide (15 g, 112.31 mmol) portionwise, and the resultant mixture stirred at 50° C. for 3 h. The mixture was diluted with EtOAc (500 ml) and washed with water (4×400 ml) followed by brine (300 ml). The solvent was removed in vacuo to afford 3-bromo-4-chloro-2-methylaniline as a dark brown oil which was used in the next step without further purification.

5-[(3-Bromo-4-chloro-2-methylanilino)methylidene]-2,2-dimethyl-1,3-dioxane-4,6-dione

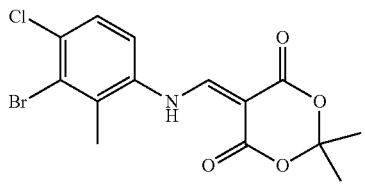 [SMILES: Cc1c(NC=C2C(=O)OC(C)(C)OC2=O)ccc(Cl)c1Br]

A mixture of 2,2-dimethyl-1,3-dioxane-4,6-dione (16.95 g, 117.64 mmol) in trimethoxymethane (58.5 ml, 534.71 mmol) was heated at 85° C. and stirred for 1.5 h. 3-Bromo-4-chloro-2-methylaniline (23.58 g, 106.94 mmol) in ethanol (80 ml) was added and the reaction mixture was stirred at 85° C. for 3 h. The mixture was cooled to rt and the resulting solid was filtered, washed with IPA (2×50 ml) and diethyl ether (4×50 ml), and dried in a vacuum oven to afford 5-[(3-bromo-4-chloro-2-methylanilino)methylidene]-2,2-dimethyl-1,3-dioxane-4,6-dione (19.01 g, 48%) as a beige solid; m/z: ES⁻ [M−H]⁻ 373.0.

7-Bromo-6-chloro-8-methylquinolin-4(1H)-one

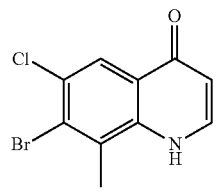

5-[(3-Bromo-4-chloro-2-methylanilino)methylidene]-2,2-dimethyl-1,3-dioxane-4,6-dione (19.09 g, 50.96 mmol) was added to stirring DOWTHERM™ A (350 ml) preheated at 220° C. After addition the mixture was stirred for 40 min and then left to cool to rt. The resulting solid was filtered under vacuum and washed with diethyl ether (5×100 ml). The solid was dried under vacuum to afford 7-bromo-6-chloro-8-methylquinolin-4(1H)-one (12.16 g, 88%) as a beige solid; ¹H NMR (400 MHz, DMSO, 30° C.) 2.66 (3H, s), 6.13 (1H, d), 7.88 (1H, d), 8.09 (1H, s), 11.32 (1H, s); m/z: ES⁺ [M+H]⁺ 272.0.

7-Bromo-6-chloro-8-methyl-3-nitroquinolin-4(1H)-one

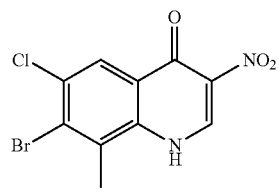

7-Bromo-6-chloro-8-methylquinolin-4(1H)-one (12.16 g, 44.62 mmol) was added to stirred propionic acid (110 ml, 1474.51 mmol) and the mixture was heated at 120° C. Nitric acid (fuming) (3.92 ml, 89.24 mmol) was added dropwise, and the solution was stirred for 1 h at 120° C. before being allowed to cool to rt. Water (250 ml) was added and the mixture was filtered, washing with water (100 ml) and diethyl ether (2×50 ml). The solid was dried under vacuum to afford 7-bromo-6-chloro-8-methyl-3-nitroquinolin-4(1H)-one (9.62 g, 68%) as a pale brown solid; ¹H NMR (400 MHz, DMSO, 30° C.) 2.71 (3H, s), 8.22 (1H, s), 8.89 (1H, s), 12.42 (1H, s); m/z: ES⁺ [M+H]⁺ 317.0.

7-Bromo-4,6-dichloro-8-methyl-3-nitroquinoline

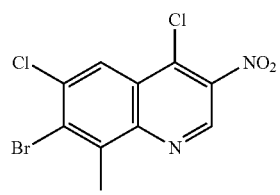 [SMILES: Cc1c(Br)c(Cl)cc2c(Cl)c([N+](=O)[O-])cnc12]

Phosphoryl trichloride (2.025 mL, 21.79 mmol) was added to 7-bromo-6-chloro-8-methyl-3-nitroquinolin-4 (1H)-one (1.73 g, 5.45 mmol) in toluene (25 mL) at rt. The mixture was heated at 105° C. with stirring, at which point DMF (0.1 mL) was added and the mixture was stirred at 105° C. overnight. The mixture was allowed to cool and concentrated in vacuo. The residue was taken up in DCM (100 mL) and poured into ice-cold sat. aq. NaHCO₃ (200 mL). The organic layer was washed with brine, dried and concentrated in vacuo to give 7-bromo-4,6-dichloro-8-methyl-3-nitroquinoline (1.57 g, 86%) as a light brown solid; ¹H NMR (400 MHz, DMSO, 30° C.) 2.88 (3H, s), 8.41 (1H, s), 9.37 (1H, s); m/z: ES⁻ [M−H]⁻ 331.

tert-Butyl (3R)-4-(7-bromo-6-chloro-8-methyl-3-nitroquinolin-4-yl)-3-(hydroxymethyl)piperazine-1-carboxylate

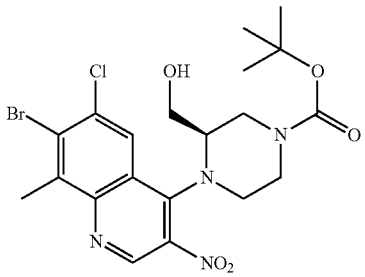 [SMILES: Cc1c(Br)c(Cl)cc2c(N3CCN(C(=O)OC(C)(C)C)C[C@@H]3CO)c([N+](=O)[O-])cnc12]

tert-Butyl (R)-3-(hydroxymethyl)piperazine-1-carboxylate (2.224 g, 10.28 mmol) was added to 7-bromo-4,6-dichloro-8-methyl-3-nitroquinoline (1.57 g, 4.67 mmol) and DIPEA (2.08 mL, 11.68 mmol) in NMP (10 mL) and the resulting solution was stirred at rt for 3 h. The mixture was partitioned between EtOAc and water then the organic layer was washed with water (×2) then brine. The organic layer was dried and concentrated in vacuo then purified by flash silica chromatography (10 to 40% EtOAc in heptane) to give tert-butyl (3R)-4-(7-bromo-6-chloro-8-methyl-3-nitroquinolin-4-yl)-3-(hydroxymethyl)piperazine-1-carboxylate (1.55 g, 64%) as a yellow solid; ¹H NMR (400 MHz, DMSO, 30° C.) 1.45 (9H, s), 2.92 (3H, s), 3.08 (1H, s), 3.33-3.5 (4H, m), 3.58 (1H, s), 3.71 (3H, d), 4.56 (1H, t), 7.79 (OH, s), 8.31 (1H, s), 8.37 (OH, s), 9.11 (1H, s); m/z: ES⁺ [M+H]⁺ 517.3.

tert-Butyl (4aR)-10-bromo-11-chloro-9-methyl-1,2,4a,5-tetrahydropyrazino[1',2':4,5][1,4]oxazino[2,3-c]quinoline-3(4H)-carboxylate

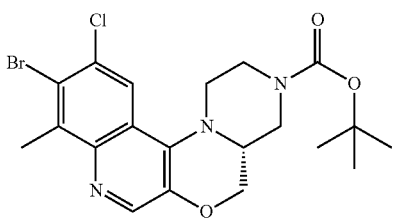 [SMILES: Cc1c(Br)c(Cl)cc2c3c(cnc12)OC[C@H]1CN(C(=O)OC(C)(C)C)CCN31]

tert-Butyl (3R)-4-(7-bromo-6-chloro-8-methyl-3-nitroquinolin-4-yl)-3-(hydroxymethyl)piperazine-1-carboxylate (0.5 g, 0.97 mmol) was dissolved in NMP (10 mL) at rt.

Lithium bis(trimethylsilyl)amide (1M in THF, 0.969 mL, 0.97 mmol) was added and the mixture was heated at 120° C. for 7 h. The mixture was cooled to rt, partitioned between EtOAc and water, and the organic layer washed with water (×2) then brine, dried and concentrated in vacuo to afford a brown oil. This was purified by flash silica chromatography (0 to 40% EtOAc in heptane) to give tert-butyl (4aR)-10-bromo-11-chloro-9-methyl-1,2,4a,5-tetrahydropyrazino[1',2':4,5][1,4]oxazino[2,3-c]quinoline-3(4H)-carboxylate (0.269 g, 59%) as a yellow solid; ¹H NMR (400 MHz, DMSO, 30° C.) 1.44 (9H, s), 2.86 (3H, s), 3.07-3.2 (1H, m), 3.33-3.53 (2H, m), 3.61 (1H, d), 3.80 (2H, s), 4.22 (1H, t), 4.36 (1H, dd), 8.02 (1H, s), 8.57 (1H, s), 9.04 (1H, s); m/z: ES⁺ [M+H]⁺ 470.

tert-Butyl (4aR)-11-chloro-10-(2-fluoro-6-methoxyphenyl)-9-methyl-1,2,4a,5-tetrahydropyrazino[1',2':4,5][1,4]oxazino[2,3-c]quinoline-3(4H)-carboxylate

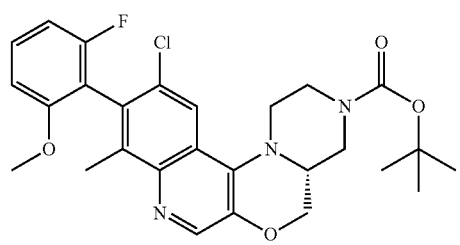 [SMILES: COc1cccc(F)c1-c1c(Cl)cc2c3c(cnc2c1C)OC[C@H]1CN(C(=O)OC(C)(C)C)CCN31]

tert-Butyl (4aR)-10-bromo-11-chloro-9-methyl-1,2,4a,5-tetrahydropyrazino[1',2':4,5][1,4]oxazino[2,3-c]quinoline-3 (4H)-carboxylate (0.22 g, 0.47 mmol), (2-fluoro-6-methoxyphenyl)boronic acid (0.120 g, 0.70 mmol), Ruphos Pd G3 (0.039 g, 0.05 mmol), RuPhos (0.022 g, 0.05 mmol) and 2M aq. K₂CO₃ (0.469 mL, 0.94 mmol) were dissolved in dioxane (5 mL) and degassed. The mixture was heated at 80° C. overnight then partitioned between EtOAc and water, then the organic layer dried and concentrated in vacuo. The crude product was purified by flash silica chromatography (0 to 100% EtOAc in heptane) to give tert-butyl (4aR)-11-chloro-10-(2-fluoro-6-methoxyphenyl)-9-methyl-1,2,4a,5-tetrahydropyrazino[1',2':4,5][1,4]oxazino[2,3-c]quinoline-3(4H)-carboxylate (0.12 g, 50%) as a yellow oil; ¹H NMR (400 MHz, DMSO, 30° C.) 1.45 (9H, s), 2.40 (3H, s), 3.14 (1H, s), 3.35 (1H, s), 3.46 (2H, d), 3.64 (1H, s), 3.72-3.92 (5H, m), 4.25 (1H, t), 4.37 (1H, dd), 6.97 (1H, t), 7.05 (1H, d), 7.45-7.56 (1H, m), 7.94 (1H, s), 8.57 (1H, s); m/z: ES⁺ [M+H]⁺ 514.

2-[(4aR)-11-Chloro-9-methyl-1,2,3,4,4a,5-hexahydropyrazino[1',2':4,5][1,4]oxazino[2,3-c]quinolin-10-yl]-3-fluorophenol

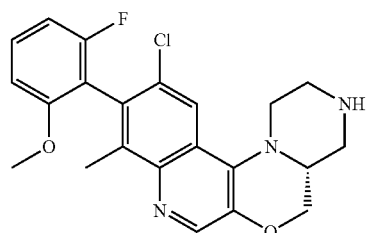

tert-Butyl (4aR)-1-chloro-10-(2-fluoro-6-methoxyphenyl)-9-methyl-1,2,4a,5-tetrahydropyrazino[1',2':4,5][1,4]oxazino[2,3-c]quinoline-3(4H)-carboxylate (0.12 g, 0.23 mmol) was dissolved in DCM (4 mL) and mixture was cooled to 0° C. and tribromoborane (1.868 mL, 1.87 mmol) was added dropwise. The mixture was stirred at 0° C. for 2 h then purified by SCX (2M NH$_3$/MeOH) to give 2-[(4aR)-11-chloro-9-methyl-1,2,3,4,4a,5-hexahydropyrazino[1',2':4,5][1,4]oxazino[2,3-c]quinolin-10-yl]-3-fluorophenol (0.055 g, 59%) as a yellow oil; m/z: ES$^+$ [M+H]$^+$ 400.

1-[(4aR)-11-Chloro-10-(2-fluoro-6-hydroxyphenyl)-9-methyl-1,2,4a,5-tetrahydropyrazino[1',2':4,5][1,4]oxazino[2,3-c]quinolin-3(4H)-yl]prop-2-en-1-one (Atropisomer 1, Compound 38; Atropisomer 2, Compound 39)

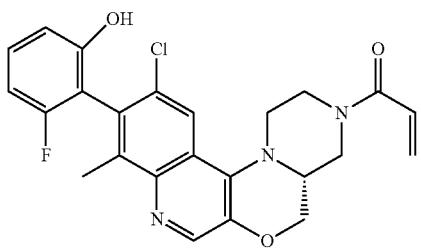 [SMILES: C=CC(=O)N1CCN2c3c(cnc4c(C)c(-c5c(O)cccc5F)c(Cl)cc34)OC[C@H]2C1]

To a stirring solution of 2-[(4aR)-11-chloro-9-methyl-1,2,3,4,4a,5-hexahydropyrazino[1',2':4,5][1,4]oxazino[2,3-c]quinolin-10-yl]-3-fluorophenol (85 mg, 0.21 mmol), IPA (0.5 mL) and pyridine (0.034 mL, 0.43 mmol) in DCM (2 mL) at −78° C. was added a solution of acryloyl chloride (0.018 mL, 0.22 mmol) in DCM (1 mL, added slowly dropwise over 5 min) and the reaction mixture stirred at −78° C. for 10 min. The mixture was warmed to rt. The mixture was cooled to −78° C. then a further portion of acryloyl chloride (5 µL) was added and the mixture was stirred for 10 min then allowed to warm to rt. The mixture was concentrated in vacuo, then purified by preparative LCMS (Waters XSelect CSH C18 column, 5µ silica, 50 mm diameter, 150 mm length), using water (containing 1% AcOH) and MeCN as eluents, to give 1-[(4aR)-11-chloro-10-(2-fluoro-6-hydroxyphenyl)-9-methyl-1,2,4a,5-tetrahydropyrazino[1',2':4,5][1,4]oxazino[2,3-c]quinolin-3(4H)-yl]prop-2-en-1-one (75 mg, 78%) as a white solid. The atropisomers were separated using SFC (Column Chiralcel OJ-H, 20×250 mm, 5 µm. Mobile phase: 22% MeOH+0.1% NH$_3$/78% scCO2. Flow rate: 60 mL/min, BPR: 120 bar. Column temperature: 40° C.) to give atropisomer 1 of 1-[(4aR)-11-chloro-10-(2-fluoro-6-hydroxyphenyl)-9-methyl-1,2,4a,5-tetrahydropyrazino[1',2':4,5][1,4]oxazino[2,3-c]quinolin-3(4H)-yl]prop-2-en-1-one (19 mg, 20%, 99% d.e.) as a white solid; $^1$H NMR (400 MHz, DMSO, 30° C.) 2.44 (3H, s), 3.17 (1H, s), 3.43 (1H, s), 3.49-4.29 (6H, m), 4.36 (1H, d), 5.76 (1H, s), 6.18 (1H, d), 6.7-6.97 (3H, m), 7.23-7.37 (1H, m), 7.97 (1H, s), 8.57 (1H, s), 9.88 (1H, s); m/z: ES$^+$ [M+H]$^+$ 454. This was followed by atropisomer 2 of 1-[(4aR)-11-chloro-10-(2-fluoro-6-hydroxyphenyl)-9-methyl-1,2,4a,5-tetrahydropyrazino[1',2':4,5][1,4]oxazino[2,3-c]quinolin-3(4H)-yl]prop-2-en-1-one (17 mg, 18%, 95% de.) as a white solid; $^1$H NMR (400 MHz, DMSO, 30° C.) 2.44 (3H, s), 3.18 (1H, d), 3.35-3.61 (2H, m), 3.6-4.27 (5H, m), 4.36 (1H, d), 5.76 (1H, s), 6.18 (1H, d), 6.68-7.02 (3H, m), 7.22-7.35 (1H, m), 7.96 (1H, s), 8.57 (1H, s), 9.87 (1H, d); m/z: ES$^+$ [M+H]$^+$ 454.

tert-Butyl (2R,5R)-4-(7-bromo-6-chloro-8-methyl-3-nitroquinolin-4-yl)-5-(hydroxymethyl)-2-methylpiperazine-1-carboxylate

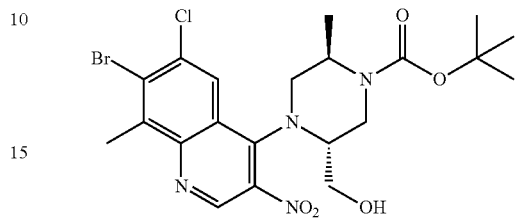

DIPEA (7.7 ml, 44.2 mmol) was added slowly to a stirred solution of 7-bromo-4,6-dichloro-8-methyl-3-nitroquinoline (9.9 g, 29.47 mmol) and tert-butyl (2R,5R)-5-(hydroxymethyl)-2-methylpiperazine-1-carboxylate (8.82 g, 38.31 mmol) in DCM (100 ml) at rt. The resulting solution was stirred at rt for 64 h and then concentrated in vacuo to afford crude product, which was purified by flash silica chromatography (0 to 40% EtOAc in heptane) to give tert-butyl (2R,5R)-4-(7-bromo-6-chloro-8-methyl-3-nitroquinolin-4-yl)-5-(hydroxymethyl)-2-methylpiperazine-1-carboxylate (8.9 g, 57%) as an orange solid; $^1$H NMR (400 MHz, DMSO, 30° C.) 1.22 (3H, d), 1.45 (9H, s), 2.91 (3H, s), 2.93-3.02 (1H, m), 3.46-3.68 (3H, m), 3.68-3.81 (2H, m), 4.02 (1H, d), 4.22-4.38 (1H, m), 4.62 (1H, t), 8.22 (1H, s), 9.05 (1H, s); m/z: ES$^+$ [M+H]$^+$ 529.2.

tert-Butyl (2R,4aR)-10-bromo-11-chloro-2,9-dimethyl-1,2,4a,5-tetrahydropyrazino[1',2':4,5][1,4]oxazino[2,3-c]quinoline-3(4H)-carboxylate

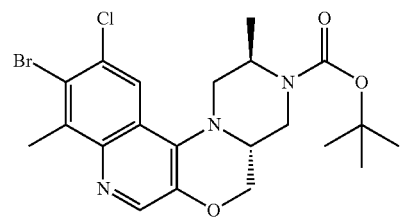

To a solution of tert-butyl (2R,5R)-4-(7-bromo-6-chloro-8-methyl-3-nitroquinolin-4-yl)-5-(hydroxymethyl)-2-methylpiperazine-1-carboxylate (500 mg, 0.94 mmol) in anhydrous DMA (10 ml) was added 4 Å molecular sieves (0.5 g) and lithium bis(trimethylsilyl)amide (1M in THF, 0.944 ml, 0.94 mmol) and the reaction mixture was stirred at rt for 2 min then heated at 120° C. and stirred for 20 h. The reaction was left to cool to rt and filtered. The filtrate was diluted with EtOAc (100 ml) and was washed with water (3×100 ml) and brine (100 ml). The organic layer was dried (phase separator) and concentrated in vacuo to afford a brown oil. The oil was purified by flash silica chromatography (0 to 30% EtOAc/heptane) to give tert-butyl (2R,4aR)-10-bromo-11-chloro-2,9-dimethyl-1,2,4a,5-tetrahydropyrazino[1',2':4,5][1,4]oxazino[2,3-c]quinoline-3(4H)-carboxylate (168 mg, 37%) as a pale yellow foam; $^1$H NMR (400 MHz, DMSO, 30° C.) 1.44 (9H, s), 1.51 (3H, d), 2.87 (3H, s), 2.95-3.07

(1H, m), 3.31-3.37 (2H, m), 3.62 (1H, d), 3.97 (1H, d), 4.22-4.42 (3H, m), 7.92 (1H, s), 8.61 (1H, s); m/z: ES+ [M+H]+ 482.2.

tert-Butyl (2R,4aR)-11-chloro-10-(2-fluoro-6-hydroxyphenyl)-2,9-dimethyl-1,2,4a,5-tetrahydropyrazino[1',2':4,5][1,4]oxazino[2,3-c]quinoline-3(4H)-carboxylate

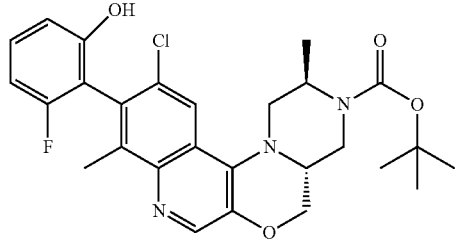 [SMILES: Cc1c(-c2c(O)cccc2F)c(Cl)cc2c3c(cnc12)OC[C@H]1CN(C(=O)OC(C)(C)C)[C@H](C)CN31]

A mixture of (2-fluoro-6-hydroxyphenyl)boronic acid (108.6 mg, 0.70 mmol), tert-butyl (2R,4aR)-10-bromo-11-chloro-2,9-dimethyl-1,2,4a,5-tetrahydropyrazino[1',2':4,5][1,4]oxazino[2,3-c]quinoline-3(4H)-carboxylate (168 mg, 0.35 mmol) and K$_2$CO$_3$ (289 mg, 2.09 mmol) in 2-methyltetrahydrofuran (1.555 ml) and water (0.518 ml) was degassed. SPhos G2 (25.08 mg, 0.03 mmol) was added at 25° C. and heated at 60° C. for 16 h. The reaction was cooled to rt and diluted with EtOAc (150 ml) and washed with water (2×100 ml) and brine (100 ml). The organic layer was dried (phase separator) and concentrated in vacuo to afford a brown oil. This was purified by flash silica chromatography (0 to 50% EtOAc in heptane) to give tert-butyl (2R,4aR)-11-chloro-10-(2-fluoro-6-hydroxyphenyl)-2,9-dimethyl-1,2,4a,5-tetrahydropyrazino[1',2':4,5][1,4]oxazino[2,3-c]quinoline-3(4H)-carboxylate (69 mg, 39%) as a yellow dry film; m/z: ES+ [M+H]+ 514.0.

2-[(2R,4aR)-11-Chloro-2,9-dimethyl-1,2,3,4,4a,5-hexahydropyrazino[1',2':4,5][1,4]oxazino[2,3-c]quinolin-10-yl]-3-fluorophenol

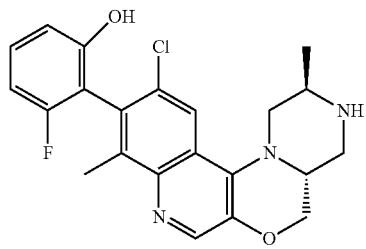 [SMILES: Cc1c(-c2c(O)cccc2F)c(Cl)cc2c3c(cnc12)OC[C@H]1CN[C@H](C)CN31]

A solution of tert-butyl (2R,4aR)-11-chloro-10-(2-fluoro-6-hydroxyphenyl)-2,9-dimethyl-1,2,4a,5-tetrahydropyrazino[1',2':4,5][1,4]oxazino[2,3-c]quinoline-3(4H)-carboxylate (69 mg, 0.13 mmol) and HCl (6M in IPA, 0.895 ml, 5.37 mmol) in MeOH (0.569 ml) was stirred at rt for 5 h. The reaction mixture was then purified by SCX (1M NH$_3$/MeOH) to give 2-[(2R,4aR)-11-chloro-2,9-dimethyl-1,2,3,4,4a,5-hexahydropyrazino[1',2':4,5][1,4]oxazino[2,3-c]quinolin-10-yl]-3-fluorophenol (47 mg, 85%) as a yellow film; m/z: ES+ [M+H]+ 414.2.

1-[(2R,4aR)-11-Chloro-10-(2-fluoro-6-hydroxyphenyl)-2,9-dimethyl-1,2,4a,5-tetrahydropyrazino[1',2':4,5][1,4]oxazino[2,3-c]quinolin-3(4H)-yl]prop-2-en-1-one (Atropisomer 1, Compound 40; Atropisomer 2, Compound 41)

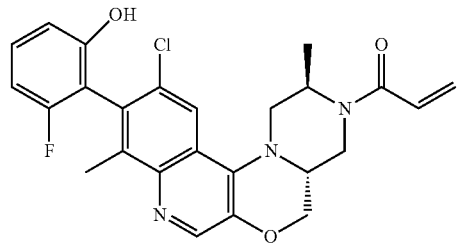 [SMILES: C=CC(=O)N1C[C@@H]2COc3cnc4c(C)c(-c5c(O)cccc5F)c(Cl)cc4c3N2C[C@H]1C]

To a solution of 2-[(2R,4aR)-11-chloro-2,9-dimethyl-1,2,3,4,4a,5-hexahydropyrazino[1',2':4,5][1,4]oxazino[2,3-c]quinolin-10-yl]-3-fluorophenol (47 mg, 0.11 mmol) and DIPEA (0.026 ml, 0.15 mmol) in DCM (3.588 ml) at 0° C. was added acryloyl chloride (9.92 µl, 0.12 mmol) and the solution was stirred at 0° C. for 2 h. The reaction mixture was washed with water (5 ml), dried (phase separator) and concentrated in vacuo to afford a white solid. The solid was dissolved in MeOH (1 ml) and 7N NH$_3$/MeOH (2 ml) was added. The resulting solution was stirred at rt for 60 min. The solvent was removed in vacuo to afford a yellow film. This was purified by preparative HPLC (Waters XSelect CSH C18 ODB column, 5µ silica, 30 mm diameter, 100 mm length), using water (containing 1% NH$_3$) and MeCN as eluents, to afford atropisomer 1 of 1-[(2R,4aR)-11-chloro-10-(2-fluoro-6-hydroxyphenyl)-2,9-dimethyl-1,2,4a,5-tetrahydropyrazino[1',2':4,5][1,4]oxazino[2,3-c]quinolin-3(4H)-yl]prop-2-en-1-one (4 mg, 8%) as a dry film; $^1$H NMR (400 MHz, CD$_3$CN, 30° C.) 1.69 (3H, s), 2.51 (3H, s), 3.03-3.15 (1H, m), 3.32-3.46 (1H, m), 3.46-3.55 (1H, m), 3.56-3.76 (1H, m), 3.93-4.2 (1H, m), 4.21-4.33 (1H, m), 4.33-4.5 (2H, m), 4.5-4.71 (1H, m), 5.73 (1H, dd), 6.21 (1H, dd), 6.65-6.79 (1H, m), 6.79-6.85 (1H, m), 6.85-6.9 (1H, m), 7.26-7.45 (1H, m), 8.03 (1H, s), 8.58 (1H, s); m/z: ES+ [M+H]+ 468.3. This was followed by atropisomer 2 of 1-[(2R,4aR)-11-chloro-10-(2-fluoro-6-hydroxyphenyl)-2,9-dimethyl-1,2,4a,5-tetrahydropyrazino[1',2':4,5][1,4]oxazino[2,3-c]quinolin-3(4H)-yl]prop-2-en-1-one (2 mg, 4%) as a dry film; $^1$H NMR (400 MHz, CD$_3$CN, 30° C.) 1.69 (3H, s), 2.51 (3H, s), 3.09 (1H, dd), 3.41 (1H, s), 3.50 (1H, dd), 4.04 (1H, s), 4.28 (1H, d), 4.41 (2H, t), 4.59 (1H, s), 5.73 (1H, dd), 6.21 (1H, dd), 6.73 (1H, dd), 6.79-6.91 (2H, m), 7.36 (1H, td), 8.03 (1H, s), 8.58 (1H, s); m/z: ES+ [M+H]+ 468.3.

5-[(3-Bromo-2,4-difluoroanilino)methylidene]-2,2-dimethyl-1,3-dioxane-4,6-dione

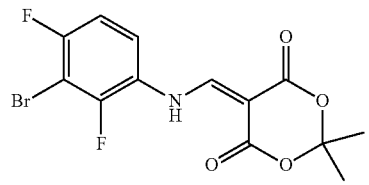

A mixture of 2,2-dimethyl-1,3-dioxane-4,6-dione (7.62 g, 52.88 mmol) in trimethoxymethane (26.3 mL, 240.38 mmol) was heated at 85° C. and stirred for 1.5 h. 3-Bromo-2,4-difluoroaniline (10 g, 48.08 mmol) in ethanol (42.4 mL) was added and the reaction mixture was stirred at 85° C. for 3 h. The mixture was cooled with the resulting solid was filtered and washed with IPA (2×50 mL) and diethyl ether (4×50 mL). The solid was dried under vacuum overnight to afford 5-[(3-bromo-2,4-difluoroanilino)methylidene]-2,2-dimethyl-1,3-dioxane-4,6-dione (14.62 g, 84%) as a beige solid; $^1$H NMR (400 MHz, DMSO, 30° C.) 1.69 (6H, s), 7.33-7.43 (1H, m), 7.86-7.97 (1H, m), 8.56-8.64 (1H, m), 11.24 (1H, s); m/z: ES$^+$ [M+H]$^+$ 362.0.

7-Bromo-6,8-difluoroquinolin-4(1H)-one

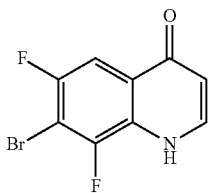 [SMILES: O=c1cc[nH]c2c(F)c(Br)c(F)cc12]

5-[(3-Bromo-2,4-difluoroanilino)methylidene]-2,2-dimethyl-1,3-dioxane-4,6-dione (14.62 g, 40.37 mmol) was added to stirring DOWTHERM™ A (99 mL) preheated to 210° C. After addition the mixture was stirred for 1 h and then left to cool to rt. Diethyl ether (100 mL) was added and the solid was filtered, washed with diethyl ether (3×100 mL) and dried under vacuum for 4 h to afford 7-bromo-6,8-difluoroquinolin-4(1H)-one (9.05 g, 86%) as a brown solid; $^1$H NMR (400 MHz, DMSO, 30° C.) 6.12 (1H, d), 7.74 (1H, dd), 7.90 (1H, t), 12.09 (1H, s); m/z: ES$^+$ [M+H]$^+$ 260.1.

7-Bromo-6,8-difluoro-3-nitroquinolin-4(1H)-one

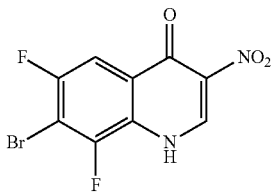

7-Bromo-6,8-difluoroquinolin-4(1H)-one (9.05 g, 34.80 mmol) was added to stirred propionic acid (83 mL) and the mixture was heated at 120° C. Nitric acid (fuming) (3.06 mL) was added dropwise and the solution was stirred for 4 h at 120° C. before cooling to rt. Water (100 mL) was added and the mixture was filtered. The solid was washed with water (3×50 mL) and dried under vacuum for 16 h to afford 7-bromo-6,8-difluoro-3-nitroquinolin-4(1H)-one (6.41 g, 60%) as a light brown solid; $^1$H NMR (400 MHz, DMSO, 30° C.) 7.93 (1H, dd), 8.97 (1H, s), 13.43 (1H, s); m/z: ES$^+$ [M+H]$^+$ 304.9.

7-Bromo-4-chloro-6,8-difluoro-3-nitroquinoline

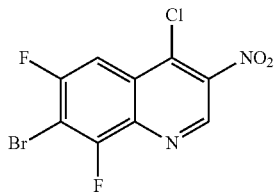

To a stirred suspension of 7-bromo-6,8-difluoro-3-nitroquinolin-4(1H)-one (6.41 g, 21.01 mmol) in DMF (39.5 mL) at rt was added phosphoryl trichloride (2.55 mL, 27.32 mmol) and the reaction mixture was heated to 100° C. for 1 h. After cooling to rt the resulting pale yellow solid was poured onto ice (200 mL) and filtered. The solid was washed with water (100 mL) and dried under vacuum to afford 7-bromo-4-chloro-6,8-difluoro-3-nitroquinoline (6.6 g, 97%) as a beige solid; $^1$H NMR (400 MHz, DMSO, 30° C.) 8.25 (1H, d), 9.44 (1H, s).

1-tert-Butyl 3-methyl (3R)-4-(7-bromo-6,8-difluoro-3-nitroquinolin-4-yl)piperazine-1,3-dicarboxylate

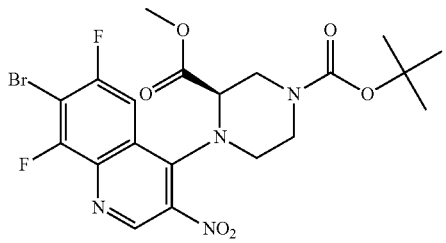 [SMILES: COC(=O)[C@H]1CN(C(=O)OC(C)(C)C)CCN1c1c([N+](=O)[O-])cnc2c(F)c(Br)c(F)cc12]

To degassed solution of 1,4-dioxane (71.6 mL) and DIPEA (5.65 mL, 32.46 mmol) at rt was added 7-bromo-4-chloro-6,8-difluoro-3-nitroquinoline (3.5 g, 10.82 mmol) followed by 1-tert-butyl 3-methyl (3R)-piperazine-1,3-dicarboxylate (3.96 g, 16.23 mmol). The reaction was heated at 100° C. for 16 h. The reaction was cooled to rt and the solvent removed in vacuo. The resulting residue was diluted with EtOAc (300 mL), washed with water (2×250 mL) and brine (100 mL). The organic layer was dried (phase separator) and concentrated in vacuo to afford crude material which was purified by flash silica chromatography (0 to 50% EtOAc in heptane) to give 1-tert-butyl 3-methyl (3R)-4-(7-bromo-6,8-difluoro-3-nitroquinolin-4-yl)piperazine-1,3-dicarboxylate (3.89 g, 68%) as an orange dry film; $^1$H NMR (400 MHz, DMSO, 30° C.) 1.45 (9H, s), 3.18-3.29 (2H, m), 3.54 (3H, s), 3.57-3.66 (1H, m), 3.72-3.95 (2H, m), 4.05 (1H, s), 4.33 (1H, s), 8.06 (1H, dd), 9.13 (1H, s); m/z: ES$^+$ [M+H]$^+$ 530.9.

tert-Butyl (4aR)-10-bromo-9,11-difluoro-5-oxo-1,2,4,4a,5,6-hexahydro-3H-pyrazino[1',2':4,5]pyrazino[2,3-c]quinoline-3-carboxylate

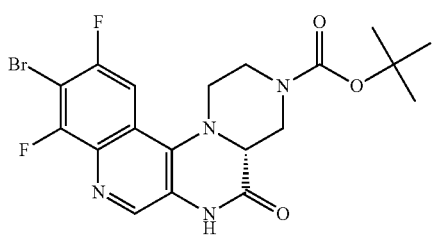 [SMILES: CC(C)(C)OC(=O)N1CCN2c3c(cnc4c(F)c(Br)c(F)cc34)NC(=O)[C@H]2C1]

To a stirred solution of 1-tert-butyl 3-methyl (3R)-4-(7-bromo-6,8-difluoro-3-nitroquinolin-4-yl)piperazine-1,3-dicarboxylate (3.89 g, 7.32 mmol) in acetic acid (73.2 mL) at rt was added iron powder (1.022 g, 18.30 mmol) and the resulting reaction mixture was stirred at 80° C. for 1 h. The reaction mixture was cooled to rt and diluted with citric acid (0.5M, 100 mL) followed by water (300 mL). The solid was filtered and dried in a vacuum oven for 16 h to afford tert-butyl (4aR)-10-bromo-9,11-difluoro-5-oxo-1,2,4,4a,5,6-hexahydro-3H-pyrazino[1',2':4,5]pyrazino[2,3-c]quinoline-3-carboxylate (3.13 g, 91%) as a pale yellow solid; $^1$H NMR (400 MHz, DMSO, 30° C.) 1.44 (9H, s), 2.67 (1H, s), 3.04-3.25 (3H, m), 3.74-3.98 (2H, m), 4.69 (1H, d), 7.81 (1H, d), 8.61 (1H, s), 11.02 (1H, s); m/z: ES$^+$ [M+H]$^+$ 469.0.

tert-Butyl (4aR)-10-bromo-9,11-difluoro-6-methyl-5-oxo-1,2,4,4a,5,6-hexahydro-3H-pyrazino[1',2':4,5]pyrazino[2,3-c]quinoline-3-carboxylate

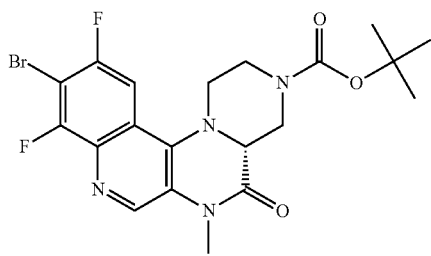 [SMILES: CN1C(=O)[C@H]2CN(C(=O)OC(C)(C)C)CCN2c2c1cnc1c(F)c(Br)c(F)cc21]

To a stirred suspension of tert-butyl (4aR)-10-bromo-9,11-difluoro-5-oxo-1,2,4,4a,5,6-hexahydro-3H-pyrazino[1',2':4,5]pyrazino[2,3-c]quinoline-3-carboxylate (3.1 g, 6.61 mmol) and K$_2$CO$_3$ (1.826 g, 13.21 mmol) in acetone (100 mL) at rt was added iodomethane (12.33 mL, 198.18 mmol) and the mixture was heated at reflux for 16 h. The reaction mixture was concentrated in vacuo and dissolved in EtOAc (500 mL), washed with water (400 mL), brine (100 mL), dried (phase separator) and concentrated in vacuo to give tert-butyl (4aR)-10-bromo-9,11-difluoro-6-methyl-5-oxo-1,2,4,4a,5,6-hexahydro-3H-pyrazino[1',2':4,5]pyrazino[2,3-c]quinoline-3-carboxylate (3 g, 94%) as an orange solid; $^1$H NMR (400 MHz, DMSO, 30° C.) 1.45 (9H, s), 2.62-2.69 (1H, m), 3.12-3.27 (3H, m), 3.49 (3H, s), 3.78-3.98 (2H, m), 4.74 (1H, d), 7.86 (1H, d), 8.97 (1H, s); m/z: ES$^+$ [M+H]$^+$ 483.0.

tert-Butyl (4aR)-9,11-difluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate

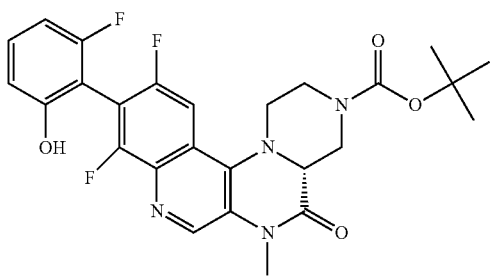 [SMILES: CN1C(=O)[C@H]2CN(C(=O)OC(C)(C)C)CCN2c2c1cnc1c(F)c(-c3c(O)cccc3F)c(F)cc21]

A mixture of tert-butyl (4aR)-10-bromo-9,11-difluoro-6-methyl-5-oxo-1,2,4,4a,5,6-hexahydro-3H-pyrazino[1',2':4,5]pyrazino[2,3-c]quinoline-3-carboxylate (500 mg, 1.03 mmol), (2-fluoro-6-hydroxyphenyl)boronic acid (363 mg, 2.33 mmol) and K$_2$CO$_3$ (429 mg, 3.1 mmol) in 1,4-dioxane (10 mL) and water (2.5 mL) was degassed. RuPhos (97 mg, 0.21 mmol) and RuPhos Pd G3 (173 mg, 0.21 mmol) was then added and the reaction mixture heated at 80° C. for 2 h. The reaction was left to cool to rt and the solvent was removed in vacuo. EtOAc (200 mL) was added and the reaction mixture washed with water (2×100 mL) and brine (100 mL), dried (phase separator) and concentrated in vacuo to afford a brown oil. The crude product was purified by flash silica chromatography (0 to 100% EtOAc in heptane) to give tert-butyl (4aR)-9,11-difluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (587 mg, >100%) as a yellow oil; m/z: ES$^+$ [M+H]$^+$ 515.1.

(4aR)-9,11-Difluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one

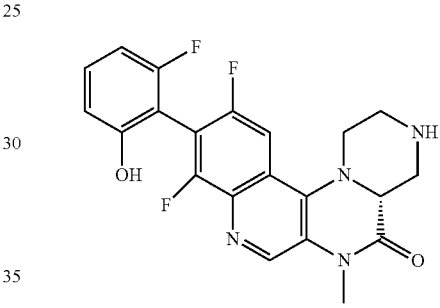

A solution of tert-butyl (4aR)-9,11-difluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (587 mg, 1.14 mmol) and HCl (6M in IPA, 7.61 mL, 45.64 mmol) in MeOH (5 mL) was stirred at rt for 6 h. The reaction mixture was then purified by SCX (1M NH$_3$/MeOH) to give (4aR)-9,11-difluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (153 mg, 32%) as an orange solid; m/z: ES$^+$ [M+H]$^+$ 414.9.

(4aR)-3-Acryloyl-9,11-difluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (Compound 42)

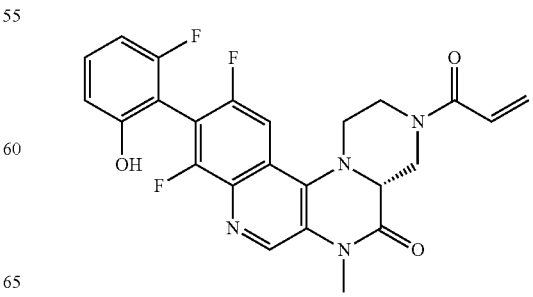

To a solution of (4aR)-9,11-difluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (150 mg, 0.36 mmol) and DIPEA (82 μl, 0.47 mmol) in DCM (3.5 mL) at 0° C. was added acryloyl chloride (31.6 μl, 0.4 mmol) and the reaction mixture was stirred at 0° C. for 30 min. The reaction mixture was washed with water (5 mL), dried (phase separator) and concentrated in vacuo. The residue was diluted with MeOH (1 mL) and 7N NH₃/MeOH (1 mL). The resulting solution was stirred at rt for 5 min then concentrated in vacuo. The crude product was purified by preparative HPLC (Waters XSelect CSH C18 ODB column, 5μ silica, 30 mm diameter, 100 mm length), using water (containing 1% NH₃) and MeCN as eluents, to give (4aR)-3-acryloyl-9,11-difluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (30 mg, 18%) as a white solid; $^1$H NMR (400 MHz, DMSO, 30° C.) 2.58-2.66 (1H, m), 3.12-3.26 (1H, m), 3.32-3.39 (1H, m), 3.50 (3H, s), 3.55-3.67 (1H, m), 3.89-4.04 (1H, m), 4.37-4.53 (1H, m), 4.72-4.87 (1H, m), 5.71-5.82 (1H, m), 6.04-6.22 (1H, m), 6.82 (1H, t), 6.88 (1H, d), 6.98-7.17 (1H, m), 7.3-7.45 (1H, m), 7.82 (1H, d), 8.97 (1H, s), 10.23 (1H, s); m/z: ES⁺ [M+H]⁺ 469.0.

5-[(3-Bromo-2,4-dimethylanilino)methylidene]-2,2-dimethyl-1,3-dioxane-4,6-dione

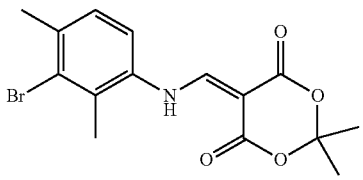 [SMILES: Cc1ccc(NC=C2C(=O)OC(C)(C)OC2=O)c(C)c1Br]

A mixture of 2,2-dimethyl-1,3-dioxane-4,6-dione (4.24 g, 29.41 mmol) in trimethoxymethane (14.63 ml, 133.70 mmol) was heated at 85° C. and stirred for 1.5 h. 3-Bromo-2,4-dimethylaniline (5.35 g, 26.74 mmol) in ethanol (23.57 ml) was added and the reaction mixture was stirred at 85° C. for 3 h. The mixture was cooled with the resulting solid filtered and washed with IPA (2×50 ml) and diethyl ether (4×50 ml). The solid was dried under vacuum overnight to afford 5-[(3-bromo-2,4-dimethylanilino)methylidene]-2,2-dimethyl-1,3-dioxane-4,6-dione (7.74 g, 82%) as a beige solid; $^1$H NMR (400 MHz, DMSO, 30° C.) 1.69 (6H, s), 2.39 (3H, s), 2.42 (3H, s), 7.32 (1H, d), 7.55 (1H, d), 8.48 (1H, d), 11.33 (1H, d); m/z: ES⁺ [M+H]⁺ 354.1.

7-Bromo-6,8-dimethylquinolin-4(1H)-one

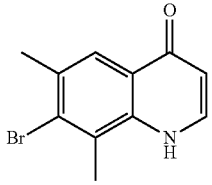

5-[(3-Bromo-2,4-dimethylanilino)methylidene]-2,2-dimethyl-1,3-dioxane-4,6-dione (7.74 g, 21.85 mmol) was added to stirred DOWTHERM™ A (50 ml) preheated at 210° C. After addition the mixture was stirred for 40 min and then left to cool to rt. The resulting solid was filtered and washed with diethyl ether (5×100 ml). The solid was dried under vacuum overnight to afford 7-bromo-6,8-dimethylqui-nolin-4(1H)-one (4.71 g, 85%) as a brown solid; $^1$H NMR (400 MHz, DMSO, 30° C.) 2.47 (3H, s), 2.61 (3H, s), 6.08 (1H, d), 7.82 (1H, s), 7.93 (1H, s), 11.14 (1H, s); m/z: ES⁺ [M+H]⁺ 252.1.

7-Bromo-6,8-dimethyl-3-nitroquinolin-4(1H)-one

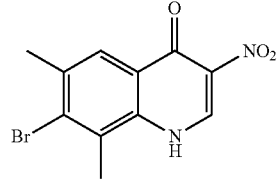 [SMILES: Cc1cc2c(=O)c([N+](=O)[O-])c[nH]c2c(C)c1Br]

7-Bromo-6,8-dimethylquinolin-4(1H)-one (4.71 g, 18.68 mmol) was added to stirred propionic acid (44.6 ml) and the mixture was heated at 120° C. Nitric acid (70%, 2.347 ml) was added dropwise, and the solution was stirred for 4 h at 120° C. before cooling to rt. Water (100 ml) was added, and the mixture was filtered. The resulting solid was washed with water (3×50 ml) and dried under vacuum for 16 h to afford 7-bromo-6,8-dimethyl-3-nitroquinolin-4(1H)-one (3.53 g, 64%) as a beige solid; $^1$H NMR (400 MHz, DMSO, 30° C.) 2.67 (3H, s), 8.10 (1H, s), 8.85 (1H, s), 12.26 (1H, s); m/z: ES⁺ [M+H]⁺ 296.8.

7-Bromo-4-chloro-6,8-dimethyl-3-nitroquinoline

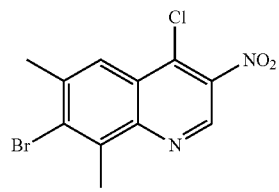 [SMILES: Cc1cc2c(Cl)c([N+](=O)[O-])cnc2c(C)c1Br]

To a stirred suspension of 7-bromo-6,8-dimethyl-3-nitroquinolin-4(1H)-one (3.53 g, 11.88 mmol) in DMF (22.32 ml) at rt was added phosphoryl trichloride (1.44 ml, 15.45 mmol) and the reaction mixture was heated at 100° C. for 1 h and then left to cool to rt. The resulting pale yellow solid was poured onto ice (200 ml) and filtered. The solid was washed with water (100 ml) and dried under vacuum to afford 7-bromo-4-chloro-6,8-dimethyl-3-nitroquinoline (3.54 g, 94%) as a beige solid; $^1$H NMR (400 MHz, DMSO, 30° C.) 2.68 (3H, s), 2.93 (3H, s), 8.29 (1H, s), 9.38 (1H, s); m/z: ES⁺ [M+H]⁺ 314.7.

1-tert-Butyl 3-methyl (3R)-4-(7-bromo-6,8-dimethyl-3-nitroquinolin-4-yl)piperazine-1,3-dicarboxylate

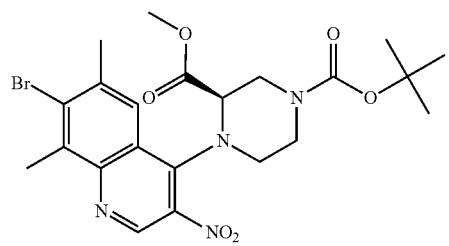 [SMILES: COC(=O)[C@H]1CN(C(=O)OC(C)(C)C)CCN1c1c([N+](=O)[O-])cnc2c(C)c(Br)c(C)cc12]

To degassed mixture of 1,4-dioxane (74.3 ml) and DIPEA (5.86 ml, 33.66 mmol) at rt was added 7-bromo-4-chloro-6,8-dimethyl-3-nitroquinoline (3.54 g, 11.22 mmol) followed by 1-tert-butyl 3-methyl (3R)-piperazine-1,3-dicarboxylate (4.11 g, 16.83 mmol). The reaction was heated at 100° C. for 48 h. The reaction was then cooled to rt and the solvent was removed in vacuo. The residue was diluted with EtOAc (300 ml) and washed with water (2×250 ml) and brine (100 ml). The organic layer was dried (phase separator) and concentrated in vacuo. The crude product was purified by flash silica chromatography (0 to 50% EtOAc in heptane) to give 1-tert-butyl 3-methyl (3R)-4-(7-bromo-6,8-dimethyl-3-nitroquinolin-4-yl)piperazine-1,3-dicarboxylate (4.79 g, 82%) as an orange oil; $^1$H NMR (400 MHz, DMSO, 30° C.) 1.45 (9H, s), 2.64 (3H, s), 2.88 (3H, s), 3.13-3.21 (1H, m), 3.51 (3H, s), 3.51-3.62 (2H, m), 3.8-3.89 (2H, m), 4.03 (1H, s), 4.31 (1H, s), 8.13 (1H, s), 9.06 (1H, s); m/z: ES$^+$ [M+H]$^+$ 524.9.

tert-Butyl (4aR)-10-bromo-9,11-di methyl-5-oxo-1,2,4,4a,5,6-hexahydro-3H-pyrazino[1',2':4,5]pyrazino[2,3-c]quinoline-3-carboxylate

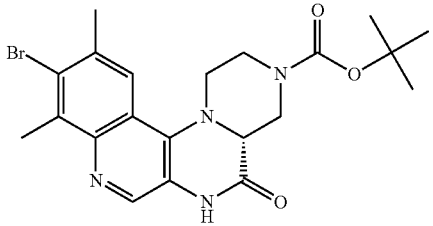 [SMILES: Cc1cc2c3c(cnc2c(C)c1Br)NC(=O)[C@H]1CN(C(=O)OC(C)(C)C)CCN31]

To a stirred solution of 1-tert-butyl 3-methyl (3R)-4-(7-bromo-6,8-dimethyl-3-nitroquinolin-4-yl)piperazine-1,3-dicarboxylate (4.79 g, 9.15 mmol) in acetic acid (92 ml) at rt was added iron powder (1.278 g, 22.88 mmol) and the resulting reaction mixture was stirred at 80° C. for 1 h. The reaction mixture was allowed to cool to rt and was diluted with citric acid (0.5M, 100 ml) followed by water (300 ml). The solid was filtered and dried in a vacuum oven for 16 h to afford tert-butyl (4aR)-10-bromo-9,11-dimethyl-5-oxo-1,2,4,4a,5,6-hexahydro-3H-pyrazino[1',2':4,5]pyrazino[2,3-c]quinoline-3-carboxylate (3.3 g, 78%) as a yellow solid; $^1$H NMR (400 MHz, DMSO, 30° C.) 1.45 (9H, s), 2.58 (3H, s), 2.63-2.69 (1H, m), 2.84 (3H, s), 3.09-3.26 (3H, m), 3.78 (1H, s), 3.91 (1H, s), 4.72 (1H, d), 7.91 (1H, s), 8.57 (1H, s), 10.83 (1H, s); m/z: ES$^+$ [M+H]$^+$ 461.0.

tert-Butyl (4aR)-10-bromo-6,9,11-trimethyl-5-oxo-1,2,4,4a,5,6-hexahydro-3H-pyrazino[1',2':4,5]pyrazino[2,3-c]quinoline-3-carboxylate

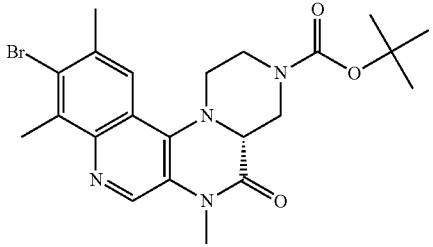 [SMILES: Cc1cc2c3c(cnc2c(C)c1Br)N(C)C(=O)[C@H]1CN(C(=O)OC(C)(C)C)CCN31]

To a stirred suspension of tert-butyl (4aR)-10-bromo-9,11-dimethyl-5-oxo-1,2,4,4a,5,6-hexahydro-3H-pyrazino[1',2':4,5]pyrazino[2,3-c]quinoline-3-carboxylate (3.3 g, 7.15 mmol) and K$_2$CO$_3$ (1.977 g, 14.31 mmol) in acetone (100 ml) at rt was added iodomethane (4.45 ml, 71.53 mmol) and the reaction mixture was stirred at 40° C. for 16 h. The reaction mixture was concentrated in vacuo and dissolved in EtOAc (500 ml), washed with water (400 ml), brine (100 ml), dried (phase separator) and concentrated in vacuo to give tert-butyl (4aR)-10-bromo-6,9,11-trimethyl-5-oxo-1,2,4,4a,5,6-hexahydro-3H-pyrazino[1',2':4,5]pyrazino[2,3-c]quinoline-3-carboxylate (3.34 g, 98%) as a yellow solid; 1H NMR (400 MHz, DMSO, 30° C.) 1.45 (9H, s), 2.56-2.64 (4H, m), 2.87 (3H, s), 3.1-3.27 (3H, m), 3.47 (3H, s), 3.75-3.86 (1H, m), 3.87-4.02 (1H, m), 4.75 (1H, d), 7.96 (1H, s), 8.90 (1H, s); m/z: ES$^+$ [M+H]$^+$ 475.0.

tert-Butyl (4aR)-10-(2-fluoro-6-hydroxyphenyl)-6,9,11-trimethyl-5-oxo-1,2,4,4a,5,6-hexahydro-3H-pyrazino[1',2':4,5]pyrazino[2,3-c]quinoline-3-carboxylate

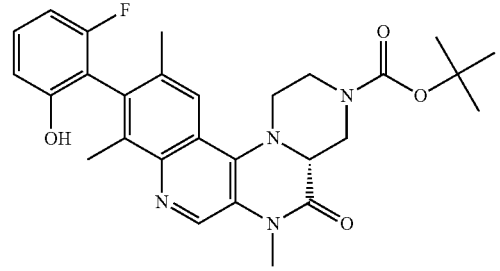 [SMILES: Cc1cc2c3c(cnc2c(C)c1-c1c(O)cccc1F)N(C)C(=O)[C@H]1CN(C(=O)OC(C)(C)C)CCN31]

A mixture of tert-butyl (4aR)-10-bromo-6,9,11-trimethyl-5-oxo-1,2,4,4a,5,6-hexahydro-3H-pyrazino[1',2':4,5]pyrazino[2,3-c]quinoline-3-carboxylate (1 g, 2.10 mmol), (2-fluoro-6-hydroxyphenyl)boronic acid (738 mg, 4.73 mmol) and K$_2$CO$_3$ (872 mg, 6.31 mmol) in 1,4-dioxane (20 ml) and water (5.00 ml) was degassed. RuPhos (196 mg, 0.42 mmol) and RuPhos Pd G3 (352 mg, 0.42 mmol) was then added and heated at 80° C. for 2 h. The reaction was left to cool to rt and the solvent was removed in vacuo. EtOAc (200 ml) was added and the solution was washed with water (2×100 ml) and brine (100 ml). The organic layer was dried (phase separator) and concentrated in vacuo to afford an orange oil. This was purified by flash silica chromatography (0 to 60% EtOAc in heptane) to give tert-butyl (4aR)-10-(2-fluoro-6-hydroxyphenyl)-6,9,11-trimethyl-5-oxo-1,2,4,4a,5,6-hexahydro-3H-pyrazino[1',2':4,5]pyrazino[2,3-c]quinoline-3-carboxylate (1.49 g, >100%) as a yellow solid; m/z: ES$^+$ [M+H]$^+$ 507.1.

(4aR)-10-(2-Fluoro-6-hydroxyphenyl)-6,9,11-trimethyl-2,3,4,4a-tetrahydro-1H-pyrazino[1',2':4,5]pyrazino[2,3-c]quinolin-5(6H)-one Atropisomer 1 and 2

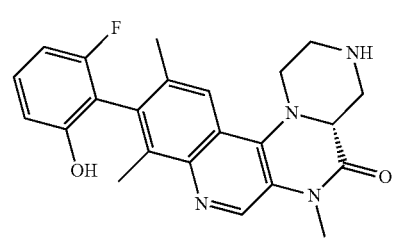 [SMILES: Cc1cc2c3c(cnc2c(C)c1-c1c(O)cccc1F)N(C)C(=O)[C@H]1CNCCN31]

A solution of tert-butyl (4aR)-10-(2-fluoro-6-hydroxyphenyl)-6,9,11-trimethyl-5-oxo-1,2,4,4a,5,6-hexahydro-3H-pyrazino[1',2':4,5]pyrazino[2,3-c]quinoline-3-carboxylate (1.07 g, 2.10 mmol) and HCl (6N in IPA, 14.03 ml, 84.17 mmol) in MeOH (7.014 ml) was stirred at rt for 4 h. The reaction mixture was then purified by SCX (1M NH$_3$/MeOH) to give (4aR)-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (260 mg, 30%) as a transparent film that solidified. The sample was purified using SFC (Column: Chiralpak IC, 20×250 mm, 5 μm Mobile phase: 35% MeOH+0.1% NH$_3$/65% scCO$_2$ Flow rate: 60 ml/min BPR: 120 bar Column temperature: 40° C.) to afford atropisomer 1 of (4aR)-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (260 mg, 30%) as a white solid; $^1$H NMR (400 MHz, DMSO, 30° C.) 2.18 (3H, s), 2.42 (3H, s), 2.55-2.63 (1H, m), 2.86-3.21 (4H, m), 3.48-3.56 (4H, m), 3.68 (1H, d), 6.7-6.83 (1H, m), 6.85 (1H, d), 7.21-7.34 (1H, m), 7.86 (1H, s), 8.87 (1H, s), 9.76 (1H, s); m/z: ES$^+$ [M+H]$^+$ 407.3. This was followed by atropisomer 2 of (4aR)-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (355 mg, 42%) as a white solid; $^1$H NMR (400 MHz, DMSO, 30° C.) 2.18 (3H, s), 2.43 (3H, s), 2.52-2.63 (1H, m), 2.82-3.16 (4H, m), 3.46-3.6 (4H, m), 3.69 (1H, d), 6.72-6.82 (1H, m), 6.85 (1H, d), 7.15-7.39 (1H, m), 7.86 (1H, s), 8.87 (1H, s), 9.76 (1H, s); m/z: ES$^+$ [M+H]$^+$ 407.3.

(4aR)-3-Acryloyl-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (Atropisomer 1, Compound 43)

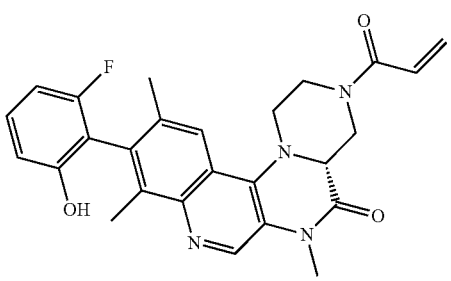 [SMILES: C=CC(=O)N1CCN2c3c(cnc4c(C)c(-c5c(O)cccc5F)c(C)cc34)N(C)C(=O)[C@H]2C1]

To a solution of atropisomer 1 of (4aR)-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (260 mg, 0.64 mmol), IPA (1.289 ml) and pyridine (0.155 ml, 1.92 mmol) in DCM (3.8 ml) at −78° C. was added acryloyl chloride (0.052 ml, 0.64 mmol) dropwise and the reaction mixture was stirred for 20 min. The reaction mixture was concentrated in vacuo and purified by reverse phase chromatography (Column: Waters XSelect CSH C18 column, 30×100 mm id, 5 μm particle size Gradient: 25 to 55% MeCN/75 to 45% water (+0.1% ammonium hydroxide)) to afford atropisomer 1 of (4aR)-3-acryloyl-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (3.6 mg, 1%) as a transparent film; $^1$H NMR (400 MHz, CD$_3$CN, 30° C.) 2.36 (3H, s), 2.55-2.67 (1H, m), 2.99-3.14 (1H, m), 3.15-3.26 (1H, m), 3.40 (3H, s), 3.46-3.54 (1H, m), 3.62-3.72 (1H, m), 4.49 (1H, d), 4.76 (1H, d), 5.64 (1H, d), 6.11 (1H, dd), 6.61 (1H, t), 6.68 (1H, d), 6.93-7.05 (1H, m), 7.05-7.21 (1H, m), 7.87 (1H, s), 8.69 (1H, s); m/z: ES$^+$ [M+H]$^+$ 461.1.

(4aR)-3-Acryloyl-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (Atropisomer 2, Compound 44)

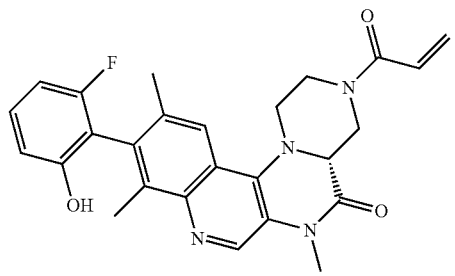 [SMILES: C=CC(=O)N1CCN2c3c(cnc4c(C)c(-c5c(O)cccc5F)c(C)cc34)N(C)C(=O)[C@H]2C1]

To a solution of atropisomer 2 of (4aR)-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (355 mg, 0.87 mmol)), IPA (1.29 ml) and pyridine (0.212 ml, 2.62 mmol) in DCM (3.87 ml) at −78° C. was added acryloyl chloride (0.071 ml, 0.87 mmol) dropwise and the reaction mixture was stirred for 20 min. The reaction mixture was concentrated in vacuo, dissolved in 1 M NH$_3$/MeOH and purified by reverse phase chromatography (Column: Waters XSelect CSH C18 column, 30×100 mm id, 5 μm particle size Gradient: 25 to 55% MeCN/75 to 45% water (+0.1% ammonium hydroxide)) to afford atropisomer 2 of (4aR)-3-acryloyl-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one (19 mg, 5%) as a white solid; $^1$H NMR (400 MHz, DMSO, 30° C.) 2.20 (3H, s), 2.37-2.46 (4H, m), 3.06-3.23 (2H, m), 3.49 (3H, s), 3.54-3.74 (1H, m), 3.83-4.02 (1H, m), 4.48 (1H, d), 4.79 (1H, d), 5.65-5.85 (1H, m), 6.03-6.22 (1H, m), 6.59-6.76 (1H, m), 6.77-6.9 (1H, m), 7.03-7.15 (1H, m), 7.17-7.33 (1H, m), 7.83-7.94 (1H, m), 8.88 (1H, s); m/z: ES$^+$ [M+H]$^+$ 461.1.

8-Bromo-7-fluoroisoquinoline

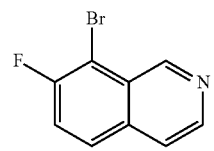 [SMILES: Fc1ccc2ccncc2c1Br]

2,2-Diethoxyethan-1-amine (6.07 mL, 41.77 mmol) was added to a stirred solution of 2-bromo-3-fluorobenzaldehyde (8.479 g, 41.77 mmol) in anhydrous toluene (20 mL) and the mixture was stirred at 100° C. for 18 h. The reaction mixture was allowed to cool to rt and concentrated in vacuo. The crude residue was dissolved in DCM (30 mL) and cooled to 0° C. Aluminum trichloride (18.38 g, 137.83 mmol) was added portionwise and the resultant dark red suspension was left to stir at 0° C. for 30 mins and then allowed to slowly warm to rt over 1 h and stirred at rt for 16 h. The reaction mixture was poured into ice water and was diluted with DCM. The reaction mixture was basified with 2M aq. NaOH solution and the phases separated. The aqueous phase was extracted with DCM, the combined organic extracts were dried (phase separator) and concentrated in vacuo. The crude product was purified by flash silica chromatography (0 to 40% EtOAc in heptane) to give 8-bromo-7-fluoroisoquinoline (2.23 g, 24%) as a brown solid; $^1$H NMR (400 MHz, CDCl$_3$, 30° C.) 7.52 (1H, t), 7.64 (1H, d), 7.81 (1H, dd), 8.62 (1H, d), 9.63 (1H, s); m/z: ES$^+$ [M+H]$^+$ 228.

8-Bromo-7-fluoroisoquinoline 2-oxide

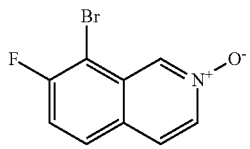

3-Chloroperoxybenzoic acid (0.523 g, 2.34 mmol) was added to a stirred solution of 8-bromo-7-fluoroisoquinoline (0.44 g, 1.95 mmol) in DCM (10 mL) at rt and the reaction stirred for 2 h. The mixture was diluted with DCM (100 mL) and washed with sat. NaHCO$_3$ (2×100 mL). The organic layer was dried (phase separator) and concentrated in vacuo to give 8-bromo-7-fluoroisoquinoline 2-oxide (0.466 g, 99%) as a pale yellow solid; $^1$H NMR (400 MHz, CDCl$_3$, 30° C.) 7.38 (1H, dd), 7.66 (1H, d), 7.76 (1H, dd), 8.16 (1H, dd), 9.09-9.2 (1H, m); m/z: ES$^+$ [M+H]$^+$ 242.

8-Bromo-7-fluoro-1-methoxyisoquinoline

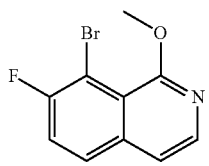

NEt$_3$ (0.924 mL, 6.63 mmol) was added to a stirred suspension of 8-bromo-7-fluoroisoquinoline 2-oxide (0.802 g, 3.31 mmol) and methyl chloroformate (0.333 mL, 4.31 mmol) at 0° C. The reaction was stirred overnight, with warming to rt. Further methyl chloroformate (0.333 mL, 4.31 mmol) and NEt$_3$ (0.924 mL, 6.63 mmol) were added and the reaction stirred for a further 2 h. Volatiles were removed in vacuo and the residue was dissolved in DCM (50 mL) and washed with water (50 mL) then brine (50 mL). The organic layer was dried (phase separator) and concentrated in vacuo. The crude product was purified by flash silica chromatography (0 to 25% EtOAc in heptane) to give 8-bromo-7-fluoro-1-methoxyisoquinoline (0.386 g, 46%) as a white solid; $^1$H NMR (400 MHz, CDCl3, 30° C.) 4.11 (3H, s), 7.21 (1H, d), 7.42 (1H, dd), 7.67 (1H, dd), 7.99 (1H, d); m/z: ES$^+$ [M+H]$^+$ 258.

tert-Butyl (4aR)-11-chloro-10-(4,4,5,5-tetra methyl-1,3,2-dioxaborolan-2-yl)-1,2,4a,5-tetrahydropy-razino[1',2':4,5][1,4]oxazino[2,3-c]quinoline-3(4H)-carboxylate

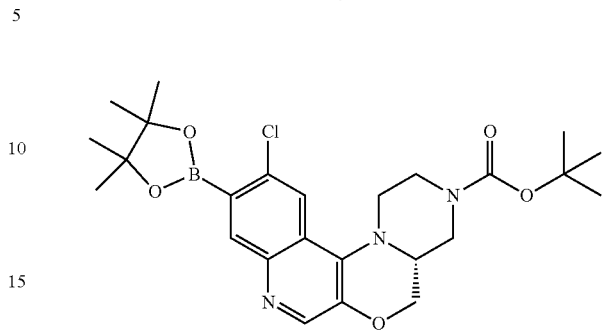

[1,1'-Bis(diphenylphosphino)ferrocene]dichloropalladium(II) complex with DCM (145 mg, 0.18 mmol), 4,4,4',4',5,5,5',5'-octamethyl-2,2'-bi(1,3,2-dioxaborolane) (1357 mg, 5.34 mmol) and potassium acetate (350 mg, 3.56 mmol) were added to a stirred and degassed solution of tert-butyl (R)-10-bromo-11-chloro-1,2,4a,5-tetrahydropyrazino[1',2':4,5][1,4]oxazino[2,3-c]quinoline-3(4H)-carboxylate (810 mg, 1.78 mmol) in dioxane (25 mL). The resulting mixture was stirred at 90° C. for 17 h. The reaction mixture was allowed to cool, concentrated in vacuo and partitioned between EtOAc (125 mL), and water (75 mL), the organic layer was separated, washed with brine (50 mL), dried (MgSO$_4$) and concentrated in vacuo to afford crude tert-butyl (4aR)-11-chloro-10-(4,4,5,5-tetramethyl-1,3,2-dioxaborolan-2-yl)-1,2,4a,5-tetrahydropyrazino[1',2':4,5][1,4]oxazino[2,3-c]quinoline-3(4H)-carboxylate (2 g); m/z: ES$^+$ [M+H]$^+$ 420 (boronic acid).

tert-Butyl (4aR)-11-chloro-10-(7-fluoro-1-methoxy-isoquinolin-8-yl)-1,2,4a,5-tetrahydropyrazino[1',2':4,5][1,4]oxazino[2,3-c]quinoline-3(4H)-carboxylate Atropisomer 1 and 2

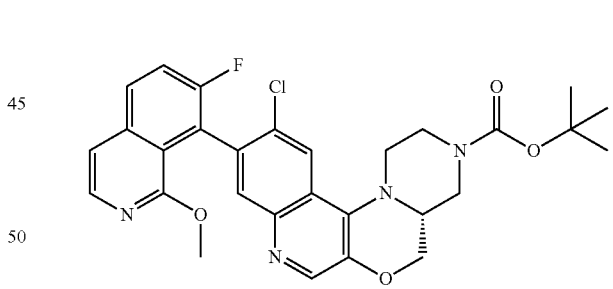

RuPhos Pd G3 (100 mg, 0.12 mmol), RuPhos (55.8 mg, 0.12 mmol), K$_2$CO$_3$ (330 mg, 2.39 mmol), 8-bromo-7-fluoro-1-methoxyisoquinoline (306 mg, 1.20 mmol) and tert-butyl (4aR)-11-chloro-10-(4,4,5,5-tetra methyl-1,3,2-dioxaborolan-2-yl)-1,2,4a,5-tetrahydropyrazino[1',2':4,5][1,4]oxazino[2,3-c]quinoline-3(4H)-carboxylate (600 mg, 1.2 mmol) were combined and dioxane (12 mL) and water (3 mL) were then added. The reaction mixture was stirred at 80° C. for 2 h. The reaction mixture was allowed to cool and concentrated in vacuo. The resulting residue was partitioned between EtOAc (20 mL) and water (10 mL) and the layers were separated. The aqueous layer was extracted with EtOAc (2×15 mL). The combined organic extracts were dried (phase separator) and concentrated in vacuo to afford crude product. This was purified by flash silica chromatography (0 to 50% EtOAc in heptane) to give a pale tan gum (570 mg). The gum was purified by reverse phase chromatography (150 gram C18 cartridge, 30% to 100% MeCN in water (containing formic acid (0.1%) as a modifier)) to give tert-butyl (4aR)-1-chloro-10-(7-fluoro-1-methoxyisoquinolin-8-yl)-1,2,4a,5-tetrahydropyrazino[1',2':4,5][1,4]oxazino[2,3-c]quinoline-3(4H)-carboxylate (200 mg, 30%) as a mixture of atropisomers; $^1$H NMR (400 MHz, CDCl$_3$, 30° C.) 1.51 (9H, s), 3.16-3.47 (2H, m), 3.57 (5H, d), 3.71 (1H, dd), 3.86-4.05 (2H, m), 4.25-4.36 (2H, m), 7.29 (1H, d), 7.49-7.59 (1H, m), 7.84 (1H, dd), 7.91 (1H, s), 8.00 (1H, d), 8.02 (1H, s), 8.57 (1H, s); m/z (ES$^+$), [M+H]$^+$ 551, 553. This was separated using SFC (Column: Chiralpak ID, 3.0×100 mm, 3 µm, Mobile phase: 45% IPA+0.1% DEA/55% scCO$_2$, Flow rate: 2 mL/min, 120 bar, Column temp: 40° C.) to give atropisomer 1 of tert-butyl (4aR)-11-chloro-10-(7-fluoro-1-methoxyisoquinolin-8-yl)-1,2,4a,5-tetrahydropyrazino[1',2':4,5][1,4]oxazino[2,3-c]quinoline-3(4H)-carboxylate (87 mg, 26%, d.e. 99%) as a beige foam. This was followed by atropisomer 2 of tert-butyl (4aR)-11-chloro-10-(7-fluoro-1-methoxyisoquinolin-8-yl)-1,2,4a,5-tetrahydropyrazino[1',2':4,5][1,4]oxazino[2,3-c]quinoline-3(4H)-carboxylate (46 mg, 14%, d.e. 98.8%).

8-[(4aR)-11-Chloro-1,2,3,4,4a,5-hexahydropyrazino[1',2':4,5][1,4]oxazino[2,3-c]quinolin-10-yl]-7-fluoroisoquinolin-1(2H)-one Atropisomer 1

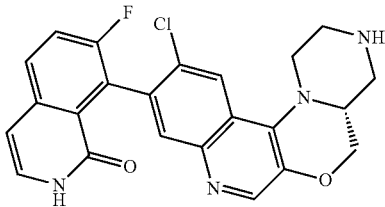 [SMILES: O=c1[nH]ccc2ccc(F)c(-c3cc4ncc5c(c4cc3Cl)N3CCNC[C@@H]3CO5)c12]

A microwave vial was charged with atropisomer 1 of tert-butyl (4aR)-11-chloro-10-(7-fluoro-1-methoxyisoquinolin-8-yl)-1,2,4a,5-tetrahydropyrazino[1',2':4,5][1,4]oxazino[2,3-c]quinoline-3(4H)-carboxylate atropisomer 1 (87 mg, 0.16 mmol), lithium chloride (33.5 mg, 0.79 mmol), 4-methylbenzenesulfonic acid hydrate (150 mg, 0.79 mmol) and DMF (2.5 mL) and irradiated with stirring at 120° C. for 30 min. The crude reaction mixture was purified by SCX (1M NH$_3$/MeOH) to give atropisomer 1 of 8-[(4aR)-11-chloro-1,2,3,4,4a,5-hexahydropyrazino[1',2':4,5][1,4]oxazino[2,3-c]quinolin-10-yl]-7-fluoroisoquinolin-1(2H)-one (67 mg, 97%) as a pale brown gum; m/z (ES$^+$), [M+H]$^+$ 437.

8-[(4aR)-11-Chloro-1,2,3,4,4a,5-hexahydropyrazino[1',2':4,5][1,4]oxazino[2,3-c]quinolin-10-yl]-7-fluoroisoquinolin-1(2H)-one Atropisomer 2

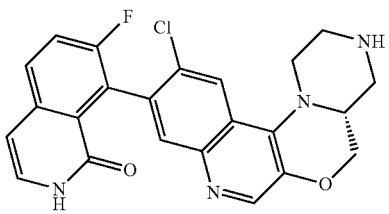 [SMILES: O=c1[nH]ccc2ccc(F)c(-c3cc4ncc5c(c4cc3Cl)N3CCNC[C@@H]3CO5)c12]

The title compound was prepared in an analogous fashion to corresponding atropisomer 1 starting from atropisomer 2 of tert-butyl (4aR)-11-chloro-10-(7-fluoro-1-methoxyisoquinolin-8-yl)-1,2,4a,5-tetrahydropyrazino[1',2':4,5][1,4]oxazino[2,3-c]quinoline-3(4H)-carboxylate. The title compound was isolated as a pale brown gum (33 mg, 89%); m/z (ES+), [M$^+$H]$^+$ 437, 439.

8-[(4aR)-11-Chloro-3-(prop-2-enoyl)-1,2,3,4,4a,5-hexahydropyrazino[1',2':4,5][1,4]oxazino[2,3-c]quinolin-10-yl]-7-fluoroisoquinolin-1(2H)-one (Atropisomer 1, Compound 45)

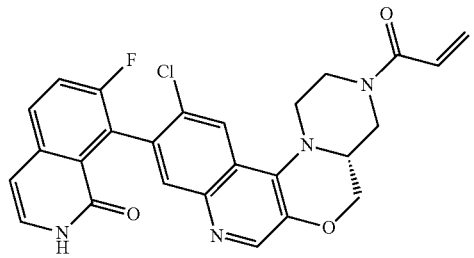 [SMILES: C=CC(=O)N1CCN2c3c(cnc4cc(-c5c(F)ccc6cc[nH]c(=O)c56)c(Cl)cc34)OC[C@H]2C1]

To a solution of atropisomer 1 of 8-[(4aR)-11-chloro-1,2,3,4,4a,5-hexahydropyrazino[1',2':4,5][1,4]oxazino[2,3-c]quinolin-10-yl]-7-fluoroisoquinolin-1(2H)-one (0.067 g, 0.15 mmol), IPA (1.3 mL) and NEt$_3$ (0.021 mL, 0.15 mmol) in DCM (4 mL) at −78° C. was added dropwise a solution of acryloyl chloride (0.013 mL, 0.16 mmol) in DCM (1 mL), and the reaction mixture stirred at −78° C. for 10 min. The reaction mixture was brought up to rt, diluted with DCM (20 mL) and washed with water (10 mL). The organic layer was separated, dried (phase separator) and concentrated in vacuo to give crude the product. This was purified by preparative HPLC (Waters XSelect CSH C18 column, 5µ silica, 30 mm diameter, 100 mm length), using water (containing 1% NH$_3$) and MeCN (gradient of 25 to 50%) as eluents, to give atropisomer 1 of 8-[(4aR)-11-chloro-3-(prop-2-enoyl)-1,2,3,4,4a,5-hexahydropyrazino[1',2':4,5][1,4]oxazino[2,3-c]quinolin-10-yl]-7-fluoroisoquinolin-1(2H)-one (11 mg, 14%, d.e. 99%) as a white solid; $^1$H NMR (400 MHz, DMSO, 30° C.) 3.25 (1H, s), 3.46 (1H, s), 3.59 (1H, d), 4.05 (4H, d), 4.24 (1H, d), 4.34 (1H, s), 5.77 (1H, s), 6.19 (1H, d), 6.64 (1H, d), 6.87 (1H, s), 7.16 (1H, t), 7.67-7.78 (2H, m), 7.81-7.89 (1H, m), 8.03 (1H, s), 8.53 (1H, d), 11.04 (1H, s); m/z (ES+), [M+H]+ 491, 493.

8-[(4aR)-11-Chloro-3-(prop-2-enoyl)-1,2,3,4,4a,5-hexahydropyrazino[1',2':4,5][1,4]oxazino[2,3-c]quinolin-10-yl]-7-fluoroisoquinolin-1(2H)-one (Atropisomer 2, Compound 46)

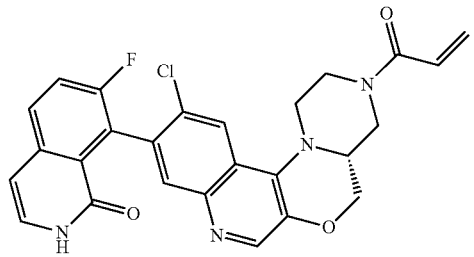 [SMILES: C=CC(=O)N1CCN2c3c(cnc4cc(-c5c(F)ccc6cc[nH]c(=O)c56)c(Cl)cc34)OC[C@H]2C1]

The title compound was prepared in an analogous fashion to the corresponding atropisomer 1, starting from atropisomer 2 of 8-[(4aR)-11-chloro-1,2,3,4,4a,5-hexahydropyrazino[1',2':4,5][1,4]oxazino[2,3-c]quinolin-10-yl]-7-fluoroisoquinolin-1(2H)-one. The title compound was isolated as a white solid (20 mg, 51%, d.e. 97%); $^1$H NMR (400 MHz, DMSO, 30° C.) 3.45 (1H, s), 3.52-3.64 (2H, m), 3.66-3.87 (1H, m), 4.05-4.33 (3H, m), 4.34 (1H, s), 5.76 (1H, d), 6.19 (1H, d), 6.65 (1H, d), 6.76-6.99 (1H, m), 7.17 (1H, d), 7.68-7.82 (2H, m), 7.86 (1H, dd), 8.03 (1H, s), 8.53 (1H, s), 11.01 (1H, s); m/z (ES$^+$), [M+H]$^+$ 491, 493.

2-Bromo-3-methyl-6-nitrophenol

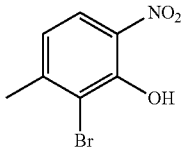

5-Methyl-2-nitrophenol (10 g, 65.30 mmol), DIPEA (18.61 mL, 130.60 mmol) and 1-bromopyrrolidine-2,5-dione (9.30 g, 52.24 mmol) were dissolved in DCM (200 mL) and stirred at rt for 24 h. Concentration in vacuo afforded crude product which was purified by C18-flash chromatography (0 to 90% MeCN in water (0.1% TFA)) to give 2-bromo-3-methyl-6-nitrophenol (11.8 g, 78%) as a yellow solid; $^1$H NMR (400 MHz, DMSO, 30° C.) 2.34-2.43 (3H, m), 6.88 (1H, d), 7.88 (1H, d).

2-(Benzyloxy)-3-bromo-4-methyl-1-nitrobenzene

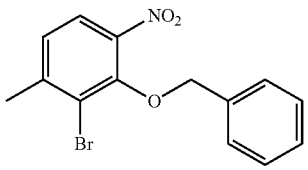 [SMILES: Cc1ccc([N+](=O)[O-])c(OCc2ccccc2)c1Br]

2-Bromo-3-methyl-6-nitrophenol (2 g, 8.62 mmol), benzyl bromide (1.23 mL, 10.34 mmol) and K$_2$CO$_3$ (1.549 g, 11.21 mmol) in MeCN (20 mL) were stirred at 80° C. for 12 h. The reaction mixture was filtered and the filtrate concentrated in vacuo to afford crude product. This was purified by flash silica chromatography (0 to 20% EtOAc in petroleum ether) to afford 2-(benzyloxy)-3-bromo-4-methyl-1-nitrobenzene (1.7 g, 61%) as a white solid; $^1$H NMR (400 MHz, CDCl$_3$, 30° C.) 2.55 (3H, s), 5.20 (2H, s), 7.19 (1H, d), 7.35-7.49 (3H, m), 7.56-7.64 (2H, m), 7.78 (1H, d).

2-(Benzyloxy)-3-bromo-4-methylaniline

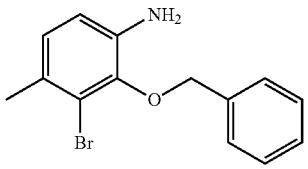 [SMILES: Cc1ccc(N)c(OCc2ccccc2)c1Br]

Iron (173 mg, 3.10 mmol) was added to 2-(benzyloxy)-3-bromo-4-methyl-1-nitrobenzene (200 mg, 0.62 mmol) and NH$_4$Cl (66.4 mg, 1.24 mmol) in EtOH (5 mL) at rt. The resulting mixture was stirred at 80° C. for 2 h and the solvent removed in vacuo. The crude product was purified by flash silica chromatography (0 to 20% EtOAc in petroleum ether) to afford 2-(benzyloxy)-3-bromo-4-methylaniline (184 mg, >100%) as a white solid; m/z: ES$^+$ [M+H]$^+$=292.

2-(Benzyloxy)-4-methyl-3-(4,4,5,5-tetramethyl-1,3,2-dioxaborolan-2-yl)aniline

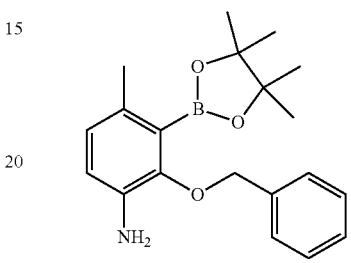

Bis(triphenylphosphine)palladium(II) dichloride (230 mg, 0.31 mmol) was added to 2-(benzyloxy)-3-bromo-4-methylaniline (911 mg, 3.12 mmol), 4,4,4',4',5,5,5',5'-octamethyl-2,2'-bi-1,3,2-dioxaborolane (1584 mg, 6.24 mmol) and potassium acetate (918 mg, 9.35 mmol) in DMA (5 mL) at rt. The resulting solution was stirred at 155° C. for 0.5 h. The reaction mixture was diluted with EtOAc (200 mL) then washed sequentially with brine (200 mL) and water (100 mL). The organic layer was dried (Na$_2$SO$_4$) and concentrated in vacuo to afford crude product. This was purified by flash silica chromatography (20 to 40% EtOAc in petroleum ether) to afford 2-(benzyloxy)-4-methyl-3-(4,4,5,5-tetramethyl-1,3,2-dioxaborolan-2-yl)aniline (955 mg, 90%) as a white solid; $^1$H NMR (300 MHz, CDCl$_3$, 30° C.) 1.33 (12H, s), 2.32 (3H, s), 4.96 (2H, s), 6.73 (2H, m), 7.35 (3H, m), 7.49 (2H, d); m/z: ES$^+$ [M+H]$^+$=340.

tert-Butyl (4aR)-10-[3-amino-2-(benzyloxy)-6-methylphenyl]-11-chloro-9-fluoro-1,2,4a,5-tetrahydropyrazino[1',2':4,5][1,4]oxazino[2,3-c]quinoline-3(4H)-carboxylate

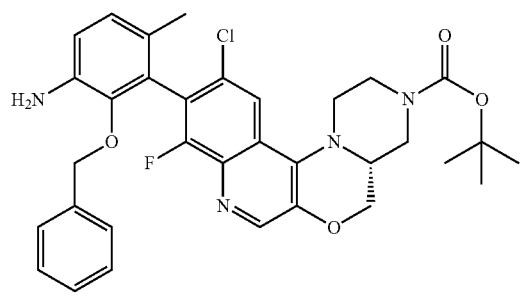 [SMILES: Cc1ccc(N)c(OCc2ccccc2)c1-c1c(Cl)cc2c3c(cnc2c1F)OC[C@H]1CN(C(=O)OC(C)(C)C)CCN31]

tert-Butyl (4aR)-10-bromo-11-chloro-9-fluoro-1,2,4a,5-tetrahydropyrazino[1',2':4,5][1,4]oxazino[2,3-c]quinoline-3 (4H)-carboxylate (1 g, 2.12 mmol), 2-(benzyloxy)-4-methyl-3-(4,4,5,5-tetramethyl-1,3,2-dioxaborolan-2-yl) aniline (0.933 g, 2.75 mmol), RuPhos-Pd-G3 (0.088 g, 0.11 mmol), 2-RuPhos (0.099 g, 0.21 mmol) and K$_2$CO$_3$ (0.585 g, 4.23 mmol) in 1,4-dioxane (35 mL) and water (7 mL) was stirred at 100° C. for 2 h. Additional RuPhos-Pd-G3 (0.088 g, 0.11 mmol), RuPhos (0.099 g, 0.21 mmol) and K$_2$CO$_3$ (0.585 g, 4.23 mmol) were added and the reaction mixture stirred at 100° C. for further 2 h. The solvent was removed in vacuo to afford crude product. This was purified by flash silica chromatography (40% EtOAc in petroleum ether) to afford tert-butyl (4aR)-10-[3-amino-2-(benzyloxy)-6-methylphenyl]-11-chloro-9-fluoro-1,2,4a,5-tetrahydropyrazino[1',2':4,5][1,4]oxazino[2,3-c]quinoline-3(4H)-carboxylate (0.57 g, 45%) as a pale yellow solid; $^1$H NMR (300 MHz, CDCl$_3$, 30° C.) 1.51 (9H, s), 2.15 (3H, s), 3.23-3.87 (5H, m), 3.87-3.93 (2H, m), 4.32 (2H, s), 4.49-4.65 (2H, m), 6.87-7.32 (6H, m), 7.33-7.51 (1H, m), 7.80 (1H, s), 8.59 (1H, s); m/z: ES$^+$ [M+H]$^+$=605.

tert-Butyl (4aR)-10-(3-amino-2-hydroxy-6-methylphenyl)-11-chloro-9-fluoro-1,2,4a,5-tetrahydropyrazino[1',2':4,5][1,4]oxazino[2,3-c]quinoline-3(4H)-carboxylate

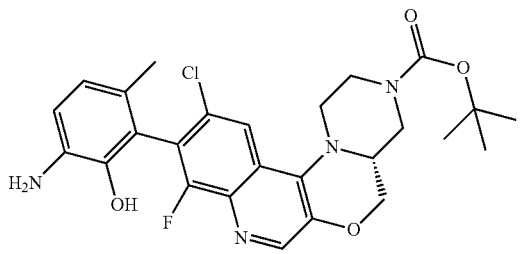 [SMILES: Cc1ccc(N)c(O)c1-c1c(Cl)cc2c3c(cnc2c1F)OC[C@H]1CN(C(=O)OC(C)(C)C)CCN31]

10% Pd/C (100 mg, 0.94 mmol) and tert-butyl (4aR)-10-[3-amino-2-(benzyloxy)-6-methylphenyl]-11-chloro-9-fluoro-1,2,4a,5-tetrahydropyrazino[1',2':4,5][1,4]oxazino[2,3-c]quinoline-3(4H)-carboxylate (350 mg, 0.58 mmol) in MeOH (10 mL) was stirred under an atmosphere of hydrogen at rt overnight. The reaction mixture was filtered through CELITE™ and the filtrate concentrated in vacuo to afford tert-butyl (4aR)-10-(3-amino-2-hydroxy-6-methylphenyl)-11-chloro-9-fluoro-1,2,4a,5-tetrahydropyrazino[1',2':4,5][1,4]oxazino[2,3-c]quinoline-3(4H)-carboxylate (297 mg, 100%) as a pale yellow solid; $^1$H NMR (300 MHz, CDCl$_3$, 30° C.) 1.51 (9H, s), 2.07 (3H, s), 3.21-3.38 (2H, m), 3.49-3.65 (2H, m), 3.65-3.72 (1H, m), 3.72-3.91 (2H, m), 4.30 (2H, s), 6.71-6.81 (2H, m), 7.84 (1H, d), 8.53 (1H, d); m/z: ES$^+$ [M+H]$^+$=515.

tert-Butyl (4aR)-11-chloro-9-fluoro-10-(6-methyl-2-oxo-2,3-dihydro-1,3-benzoxazol-7-yl)-1,2,4a,5-tetrahydropyrazino[1',2':4,5][1,4]oxazino[2,3-c]quinoline-3(4H)-carboxylate

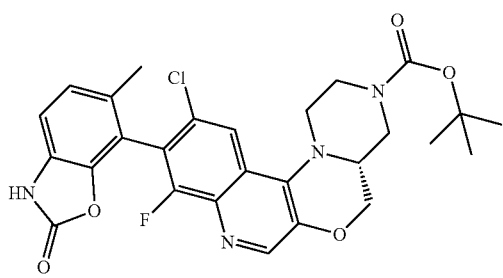 [SMILES: Cc1ccc2[nH]c(=O)oc2c1-c1c(Cl)cc2c3c(cnc2c1F)OC[C@H]1CN(C(=O)OC(C)(C)C)CCN31]

Bis(trichloromethyl) carbonate (32.3 mg, 0.11 mmol) was added portionwise to tert-butyl (4aR)-10-(3-amino-2-hydroxy-6-methylphenyl)-11-chloro-9-fluoro-1,2,4a,5-tetrahydropyrazino[1',2':4,5][1,4]oxazino[2,3-c]quinoline-3(4H)-carboxylate (160 mg, 0.31 mmol) and NEt$_3$ (0.087 mL, 0.62 mmol) in THF (10 mL) at 0° C. The resulting mixture was stirred at rt for 2 h. The solvent was removed in vacuo to afford crude product. This was purified by flash silica chromatography (40 to 100% EtOAc in petroleum ether) to afford tert-butyl (4aR)-11-chloro-9-fluoro-10-(6-methyl-2-oxo-2,3-dihydro-1,3-benzoxazol-7-yl)-1,2,4a,5-tetrahydropyrazino[1',2':4,5][1,4]oxazino[2,3-c]quinoline-3(4H)-carboxylate (300 mg, >100%) as a yellow solid; $^1$H NMR (300 MHz, CDCl$_3$, 30° C.) 1.51 (9H, s), 2.07 (3H, d), 2.18 (2H, d), 3.64 (7H, m), 4.31 (2H, m), 7.10 (2H, m), 7.88 (1H, s), 8.62 (1H, s); m/z: ES$^+$ [M+H]$^+$=541.

7-[(4aR)-11-Chloro-9-fluoro-1,2,3,4,4a,5-hexahydropyrazino[1',2':4,5][1,4]oxazino[2,3-c]quinolin-10-yl]-6-methyl-1,3-benzoxazol-2(3H)-one Atropisomer 1 and 2

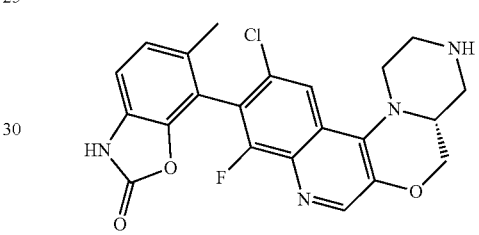

TFA (2 mL, 25.96 mmol) was added to tert-butyl (4aR)-11-chloro-9-fluoro-10-(6-methyl-2-oxo-2,3-dihydro-1,3-benzoxazol-7-yl)-1,2,4a,5-tetrahydropyrazino[1',2':4,5][1,4]oxazino[2,3-c]quinoline-3(4H)-carboxylate (300 mg, 0.55 mmol) in DCM (10 mL). The resulting solution was stirred at rt for 2 h. The solvent was removed in vacuo. The residue was purified by C18-flash chromatography (5 to 40% MeCN in water (0.05% TFA)) to afford crude atropisomer 1 as a TFA salt and crude atropisomer 2 as a TFA salt. Crude atropisomer 1 TFA salt was then purified further by SCX (7M NH$_3$/MeOH) to afford atropisomer 1 of 7-[(4aR)-11-chloro-9-fluoro-1,2,3,4,4a,5-hexahydropyrazino[1',2':4,5][1,4]oxazino[2,3-c]quinolin-10-yl]-6-methyl-1,3-benzoxazol-2(3H)-one (74 mg, 30%) as a pale yellow solid; $^1$H NMR (300 MHz, DMSO, 30° C.) 2.11 (3H, s), 3.05 (2H, m), 3.18 (3H, m), 3.43 (2H, m), 4.35 (1H, m), 4.46 (1H, m), 7.16 (2H, m), 7.97 (1H, s), 8.60 (1H, s); m/z: ES$^+$ [M+H]$^+$=441. Crude atropisomer 2 TFA salt was purified by the same method to give atropisomer 2 of 7-[(4aR)-11-chloro-9-fluoro-1,2,3,4,4a,5-hexahydropyrazino[1',2':4,5][1,4]oxazino[2,3-c]quinolin-10-yl]-6-methyl-1,3-benzoxazol-2(3H)-one (88 mg, 36%) as a pale yellow solid; $^1$H NMR (300 MHz, DMSO, 30° C.) 2.10 (3H, s), 2.98 (1H, m), 3.09 (2H, m), 3.19 (3H, m), 3.46 (1H, m), 4.32 (1H, m), 4.51 (1H, m), 7.16 (2H, m), 7.98 (1H, s), 8.60 (1H, s); m/z: ES$^+$ [M+H]$^+$=441.

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-1,3-benzoxazol-2(3H)-one (Atropisomer 1, Compound 47)

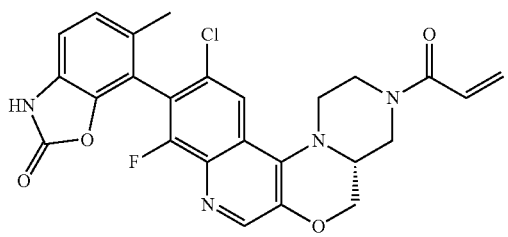 [SMILES: C=CC(=O)N1CCN2c3c(cnc4c(F)c(-c5c(C)ccc6[nH]c(=O)oc56)c(Cl)cc34)OC[C@H]2C1]

A solution of acryloyl chloride (15.19 mg, 0.17 mmol) in DMF (0.7 mL) was added dropwise to a stirred solution of atropisomer 1 of 7-[(4aR)-11-chloro-9-fluoro-1,2,3,4,4a,5-hexahydropyrazino[1',2':4,5][1,4]oxazino[2,3-c]quinolin-10-yl]-6-methyl-1,3-benzoxazol-2(3H)-one (74 mg, 0.17 mmol) and DIPEA (0.059 mL, 0.34 mmol) in DMF (2 mL) at −10° C. The resulting solution was stirred at −10° C. for 30 min. The crude reaction mixture was purified by C18-flash chromatography (5 to 50% MeCN in water (0.1% formic acid)) to afford crude product. This was purified by preparative HPLC (Column: Xselect CSH OBD Column 30*150 mm 5 m n; Mobile Phase A: Water (0.1% formic acid), Mobile Phase B: MeCN; Flow rate: 60 mL/min; Gradient: 25% B to 48% B in 7 min; 254/220 nm) to afford atropisomer 1 of 7-[(4aR)-11-chloro-9-fluoro-3-(prop-2-enoyl)-1,2,3,4,4a,5-hexahydropyrazino[1',2':4,5][1,4]oxazino[2,3-c]quinolin-10-yl]-6-methyl-1,3-benzoxazol-2(3H)-one (36 mg, 43%) as a white solid; $^1$H NMR (400 MHz, CD$_3$CN, 30° C.) 2.18 (3H, s), 3.29 (1H, m), 3.49 (1H, m), 3.69 (3H, m), 3.96 (1H, m), 4.35 (3H, m), 5.76 (1H, m), 6.24 (1H, d), 6.75 (1H, m), 7.15 (1H, d), 7.21 (1H, d), 8.07 (1H, s), 8.58 (1H, s), 9.06 (1H, br.s); m/z: ES$^+$ [M+H]$^+$=495.

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-1,3-benzoxazol-2(3H)-one (Atropisomer 2, Compound 48)

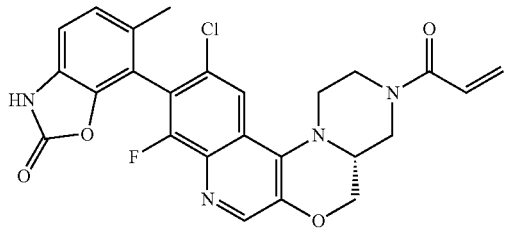 [SMILES: C=CC(=O)N1CCN2c3c(cnc4c(F)c(-c5c(C)ccc6[nH]c(=O)oc56)c(Cl)cc34)OC[C@H]2C1]

A solution of acryloyl chloride (18.07 mg, 0.20 mmol) in DMF (0.9 mL) was added dropwise to a stirred solution of atropisomer 2 of 7-[(4aR)-11-chloro-9-fluoro-1,2,3,4,4a,5-hexahydropyrazino[1',2':4,5][1,4]oxazino[2,3-c]quinolin-10-yl]-6-methyl-1,3-benzoxazol-2(3H)-one (88 mg, 0.20 mmol) and DIPEA (0.07 mL, 0.40 mmol) in DMF (2 mL) at −10° C. The resulting solution was stirred at −10° C. for 30 min. The crude reaction mixture was purified by C18-flash chromatography (5 to 50% MeCN in water (0.1% formic acid)) to afford crude product. This was purified by preparative HPLC (Column: Xselect CSH OBD Column 30*150 mm 5 m n; Mobile Phase A: Water (0.1% formic acid), Mobile Phase B: MeCN; Flow rate: 60 mL/min; Gradient: 25% B to 50% B in 7 min; 254/220 nm) to afford atropisomer 2 of 7-[(4aR)-11-chloro-9-fluoro-3-(prop-2-enoyl)-1,2,3,4,4a,5-hexahydropyrazino[1',2':4,5][1,4]oxazino[2,3-c]quinolin-10-yl]-6-methyl-1,3-benzoxazol-2(3H)-one (44 mg, 45%) as a white solid; $^1$H NMR (400 MHz, CD$_3$CN, 30° C.) 2.18 (3H, s), 3.26 (1H, m), 3.47 (1H, m), 3.64 (2H, m), 3.90 (2H, m), 4.34 (3H, m), 5.75 (1H, m), 6.24 (1H, d), 6.75 (1H, dd), 7.15 (1H, d), 7.21 (1H, d), 8.07 (1H, s), 8.58 (1H, s), 9.13 (1H, brs); m/z: ES$^+$ [M+H]$^+$=495.

tert-Butyl (4aR)-11-chloro-9-fluoro-6-methyl-10-(5-methyl-1H-indazol-4-yl)-5-oxo-1,2,4,4a,5,6-hexahydro-3H-pyrazino[1',2':4,5]pyrazino[2,3-c]quinoline-3-carboxylate

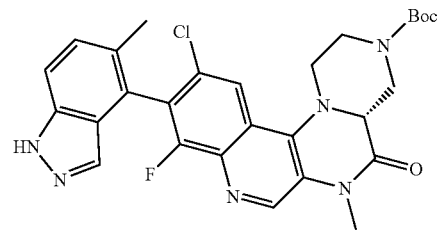 [SMILES: Cc1ccc2[nH]ncc2c1-c1c(Cl)cc2c3c(cnc2c1F)N(C)C(=O)[C@H]1CN(C(=O)OC(C)(C)C)CCN31]

RuPhos-Pd-G3 (134 mg, 0.16 mmol) was added to a mixture of tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (800 mg, 1.60 mmol), (5-methyl-1H-indazol-4-yl)boronic acid (338 mg, 1.92 mmol), K$_2$CO$_3$ (442 mg, 3.20 mmol) and RuPhos (74.7 mg, 0.16 mmol) in 1,4-dioxane/H$_2$O (20 mL, 4:1 ratio) at rt. The resulting suspension was stirred at 100° C. for 1 h. The solvent was removed in vacuo and the residue purified by flash C18-flash chromatography (0 to 100%, MeCN in water (0.1% formic acid)) to give crude product as a pale yellow solid. This was purified by preparative chiral-H PLC (Column: CHIRALPAK IC, 2*25 cm, 5 m; Mobile Phase A: Hex:DCM=3:1 (10 mM NH$_3$-MeOH)-HPLC, Mobile Phase B: EtOH-HPLC; Flow rate: 16 mL/min; Gradient: 50 B to 50 B in 23 min; 220/254 nm) to give atropisomer 1 of tert-butyl (4aR)-11-chloro-9-fluoro-6-methyl-10-(5-methyl-1H-indazol-4-yl)-5-oxo-1,2,4,4a,5,6-hexahydro-3H-pyrazino[1',2':4,5]pyrazino[2,3-c]quinoline-3-carboxylate (339 mg, 43%); m/z: ES$^+$ [M+H]$^+$=551. This was followed by atropisomer 2 of tert-butyl (4aR)-11-chloro-9-fluoro-6-methyl-10-(5-methyl-1H-indazol-4-yl)-5-oxo-1,2,4,4a,5,6-hexahydro-3H-pyrazino[1',2':4,5]pyrazino[2,3-c]quinoline-3-carboxylate (274 mg, 35%) as a pale yellow solid; m/z: ES$^+$ [M+H]$^+$=551.

(4aR)-11-Chloro-9-fluoro-6-methyl-10-(5-methyl-1H-indazol-4-yl)-2,3,4,4a-tetrahydro-1H-pyrazino[1',2':4,5]pyrazino[2,3-c]quinolin-5(6H)-one Atropisomer 1

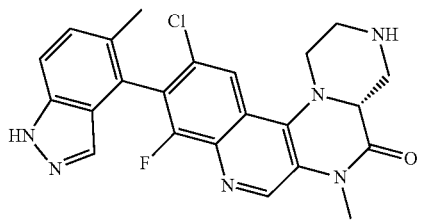 [SMILES: Cc1ccc2[nH]ncc2c1-c1c(Cl)cc2c3c(cnc2c1F)N(C)C(=O)[C@H]1CNCCN31]

4M HCl in 1,4-dioxane (8 mL, 32 mmol) was added to atropisomer 1 of tert-butyl (4aR)-11-chloro-9-fluoro-6-methyl-10-(5-methyl-1H-indazol-4-yl)-5-oxo-1,2,4,4a,5,6-hexahydro-3H-pyrazino[1',2':4,5]pyrazino[2,3-c]quinoline-3-carboxylate (320 mg, 0.58 mmol) in MeOH (8 mL) at rt. The resulting mixture was stirred at rt for 1 h. The solvent was removed in vacuo. The crude product obtained was purified by SCX (7M $NH_3$/MeOH) to afford atropisomer 1 of (4aR)-11-chloro-9-fluoro-6-methyl-10-(5-methyl-1H-indazol-4-yl)-2,3,4,4a-tetrahydro-1H-pyrazino[1',2':4,5]pyrazino[2,3-c]quinolin-5(6H)-one (216 mg, 82%) as a white solid; $^1$H NMR (300 MHz, DMSO, 30° C.) 2.17 (3H, s), 2.58-2.76 (1H, m), 2.90 (1H, d), 2.95-3.10 (2H, m), 3.16 (1H, d), 3.54 (3H, s), 3.68 (2H, d), 7.41 (1H, d), 7.56 (1H, s), 7.60 (1H, d), 8.13 (1H, s), 9.02 (1H, s), 13.18 (1H, s); m/z: ES$^+$ [M+H]$^+$=451.

(4aR)-11-Chloro-9-fluoro-6-methyl-10-(5-methyl-1H-indazol-4-yl)-3-(prop-2-enoyl)-2,3,4,4a-tetrahydro-1H-pyrazino[1',2':4,5]pyrazino[2,3-c]quinolin-5(6H)-one (Atropisomer 1, Compound 49)

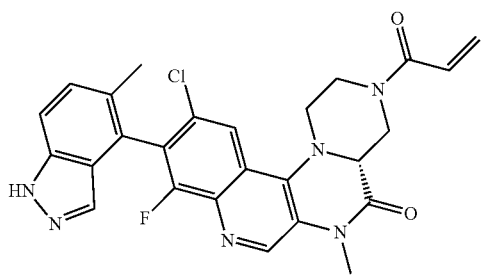 [SMILES: C=CC(=O)N1CCN2c3c(cnc4c(F)c(-c5c(C)ccc6[nH]ncc56)c(Cl)cc34)N(C)C(=O)[C@H]2C1]

Acryloyl chloride (16 mg, 0.18 mmol) was added to atropisomer 1 of (4aR)-11-chloro-9-fluoro-6-methyl-10-(5-methyl-1H-indazol-4-yl)-2,3,4,4a-tetrahydro-1H-pyrazino[1',2':4,5]pyrazino[2,3-c]quinolin-5(6H)-one (80 mg, 0.18 mmol) and DIPEA (0.062 mL, 0.35 mmol) in DMF (3 mL) at −10° C. The resulting mixture was stirred at rt for 1 h. The reaction mixture was purified by flash C18-flash chromatography (30 to 60% MeCN in water (0.05% $NH_4HCO_3$)) to give atropisomer 1 of (4aR)-11-chloro-9-fluoro-6-methyl-10-(5-methyl-1H-indazol-4-yl)-3-(prop-2-enoyl)-2,3,4,4a-tetrahydro-1H-pyrazino[1',2':4,5]pyrazino[2,3-c]quinolin-5(6H)-one (66 mg, 74%) as a white solid; $^1$H NMR (300 MHz, DMSO, 30° C.) 2.18 (3H, s), 2.60-2.92 (1H, m), 3.14-3.32 (1H, m), 3.35-3.43 (1H, m), 3.51 (3H, s), 3.57-3.71 (1H, m), 3.93-4.57 (2H, m), 4.68-5.25 (1H, m), 5.77 (1H, d), 6.16 (1H, dd), 6.75-7.14 (1H, m), 7.41 (1H, d), 7.52-7.65 (2H, m), 8.23 (1H, s), 9.04 (1H, s), 13.19 (1H, s); m/z: ES$^+$ [M+H]$^+$=505.

(4aR)-11-Chloro-9-fluoro-6-methyl-10-(5-methyl-1H-indazol-4-yl)-2,3,4,4a-tetrahydro-1H-pyrazino[1',2':4,5]pyrazino[2,3-c]quinolin-5(6H)-one Atropisomer 2

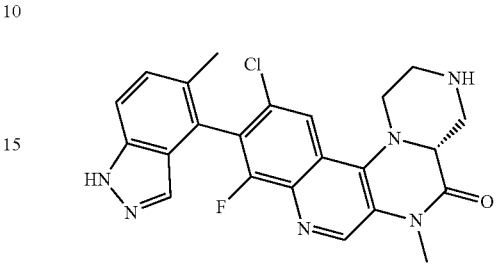

4M HCl in 1,4-dioxane (8 mL) was added to atropisomer 2 of tert-butyl (4aR)-11-chloro-9-fluoro-6-methyl-10-(5-methyl-1H-indazol-4-yl)-5-oxo-1,2,4,4a,5,6-hexahydro-3H-pyrazino[1',2':4,5]pyrazino[2,3-c]quinoline-3-carboxylate (270 mg, 0.49 mmol) in MeOH (8 mL) at rt. The resulting mixture was stirred at rt for 1 h. The solvent was removed in vacuo. The crude product was purified by SCX (7M $NH_3$/MeOH) to afford atropisomer 2 of (4aR)-11-chloro-9-fluoro-6-methyl-10-(5-methyl-1H-indazol-4-yl)-2,3,4,4a-tetrahydro-1H-pyrazino[1',2':4,5]pyrazino[2,3-c]quinolin-5(6H)-one (208 mg, 94%) as an orange solid; $^1$H NMR (300 MHz, DMSO, 30° C.) 2.16 (3H, s), 2.64-2.73 (1H, m), 2.85-3.06 (3H, m), 3.54 (3H, s), 3.68 (2H, d), 4.06-4.16 (1H, m), 7.41 (1H, d), 7.53-7.64 (2H, m), 8.14 (1H, s), 9.02 (1H, s), 13.18 (1H, s); m/z: ES$^+$ [M+H]$^+$=451.

(4aR)-11-Chloro-9-fluoro-6-methyl-10-(5-methyl-1H-indazol-4-yl)-3-(prop-2-enoyl)-2,3,4,4a-tetrahydro-1H-pyrazino[1',2':4,5]pyrazino[2,3-c]quinolin-5(6H)-one (Atropisomer 2, Compound 50)

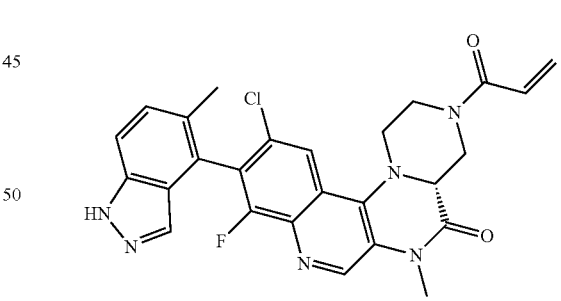

Acryloyl chloride (16.06 mg, 0.18 mmol) was added to atropisomer 2 of (4aR)-11-chloro-9-fluoro-6-methyl-10-(5-methyl-1H-indazol-4-yl)-2,3,4,4a-tetrahydro-1H-pyrazino[1',2':4,5]pyrazino[2,3-c]quinolin-5(6H)-one (80 mg, 0.18 mmol) and DIPEA (0.062 mL, 0.35 mmol) in DMF (3 mL) at −10° C. The resulting mixture was stirred at rt for 1 h. The reaction mixture was purified by C18-flash chromatography (0 to 100% MeCN in water (0.1% $NH_4HCO_3$)) to afford atropisomer 2 of (4aR)-11-chloro-9-fluoro-6-methyl-10-(5-methyl-1H-indazol-4-yl)-3-(prop-2-enoyl)-2,3,4,4a-tetrahydro-1H-pyrazino[1',2':4,5]pyrazino[2,3-c]quinolin-5(6H)-one (63 mg, 70%) as a white solid; $^1$H NMR (300

MHz, DMSO, 30° C.) 2.17 (3H, s), 2.62-2.96 (1H, m), 3.14-3.29 (1H, m), 3.36-3.45 (1H, m), 3.51 (3H, s), 3.57-3.70 (1H, m), 3.91-4.57 (2H, m), 4.70-5.25 (1H, m), 5.78 (1H, d), 6.16 (1H, dd), 6.72-7.20 (1H, m), 7.41 (1H, d), 7.54-7.65 (2H, m), 8.23 (1H, s), 9.04 (1H, s), 13.19 (1H, s); m/z: ES+ [M+H]+=505.

tert-Butyl (4aR)-11-chloro-10-(2-chloro-6-hydroxyphenyl)-9-fluoro-6-methyl-5-oxo-1,2,4,4a,5,6-hexahydro-3H-pyrazino[1',2':4,5]pyrazino[2,3-c]quinoline-3-carboxylate Atropisomer 1 and 2

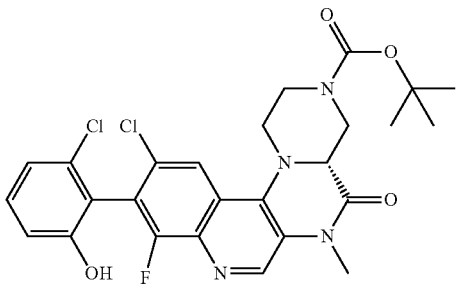 [SMILES: CN1C(=O)[C@H]2CN(C(=O)OC(C)(C)C)CCN2c2c1cnc1c(F)c(-c3c(O)cccc3Cl)c(Cl)cc21]

RuPhos-Pd-G3 (50.2 mg, 0.06 mmol) was added to tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (300 mg, 0.6 mmol), (2-chloro-6-hydroxyphenyl)boronic acid (517 mg, 3 mmol), K₂CO₃ (166 mg, 1.2 mmol) and RuPhos (28 mg, 0.06 mmol) in 1,4-dioxane/H₂O (15 mL, 4:1 ratio) at rt. The resulting suspension was stirred at 100° C. for 1 h. The solvent was removed in vacuo. The crude product was purified by flash C18-flash chromatography (0 to 100% MeCN in water (0.1% formic acid)) to afford an orange solid. This was purified by preparative chiral-HPLC (Column: CHIRALPAK IC, 2*25 cm, 5 m; Mobile Phase A: Hex:DCM=3:1 (10 mM NH₃-MeOH)-HPLC, Mobile Phase B: EtOH-HPLC; Flow rate: 20 mL/min; Gradient: 15 B to 15 B in 18 min; 220/254 nm) to afford atropisomer 1 of tert-butyl (4aR)-11-chloro-10-(2-chloro-6-hydroxyphenyl)-9-fluoro-6-methyl-5-oxo-1,2,4,4a,5,6-hexahydro-3H-pyrazino[1',2': 4,5]pyrazino[2,3-c]quinoline-3-carboxylate (64 mg, 28%) as a white solid; ¹H NMR (300 MHz, DMSO, 30° C.) 1.46 (9H, s), 2.61-2.79 (1H, m), 3.14-3.31 (3H, m), 3.51 (3H, s), 3.82-4.03 (2H, m), 4.76 (1H, d), 6.99 (1H, d), 7.09 (1H, d), 7.35 (1H, t), 8.08 (1H, s), 9.00 (1H, s), 10.18 (1H, s); m/z: ES+ [M+H]+=547. This was followed by atropisomer 2 of tert-butyl (4aR)-11-chloro-10-(2-chloro-6-hydroxyphenyl)-9-fluoro-6-methyl-5-oxo-1,2,4,4a,5,6-hexahydro-3H-pyrazino[1',2':4,5]pyrazino[2,3-c]quinoline-3-carboxylate (100 mg, 44%) as a yellow solid; ¹H NMR (300 MHz, DMSO, 30° C.) 1.46 (9H, s), 2.62-2.77 (1H, m), 3.20-3.31 (3H, m), 3.51 (3H, s), 3.78-4.00 (2H, m), 4.76 (1H, d), 6.99 (1H, d), 7.09 (1H, d), 7.35 (1H, t), 8.08 (1H, s), 9.00 (1H, s), 10.18 (1H, s); m/z: ES+ [M+H]+=547.

(4aR)-11-Chloro-10-(2-chloro-6-hydroxyphenyl)-9-fluoro-6-methyl-2,3,4,4a-tetrahydro-1H-pyrazino[1',2':4,5]pyrazino[2,3-c]quinolin-5(6H)-one Atropisomer 1

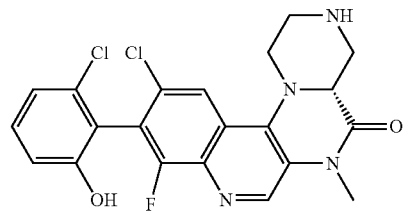 [SMILES: CN1C(=O)[C@H]2CNCCN2c2c1cnc1c(F)c(-c3c(O)cccc3Cl)c(Cl)cc21]

4M HCl in 1,4-dioxane (4 mL, 16.00 mmol) was added to atropisomer 1 of tert-butyl (4aR)-11-chloro-10-(2-chloro-6-hydroxyphenyl)-9-fluoro-6-methyl-5-oxo-1,2,4,4a,5,6-hexahydro-3H-pyrazino[1',2':4,5]pyrazino[2,3-c]quinoline-3-carboxylate (57 mg, 0.1 mmol) in MeOH (4 mL) at rt. The resulting mixture was stirred at rt for 30 min. The solvent was removed in vacuo. The crude product was purified by SCX (7M NH₃/MeOH) to afford atropisomer 1 of (4aR)-11-chloro-10-(2-chloro-6-hydroxyphenyl)-9-fluoro-6-methyl-2,3,4,4a-tetrahydro-1H-pyrazino[1',2':4,5]pyrazino[2,3-c]quinolin-5(6H)-one (45 mg, 97%) as a white solid; ¹H NMR (300 MHz, DMSO, 30° C.) 2.57-2.75 (1H, m), 2.85-2.93 (1H, m), 2.94-3.06 (2H, m), 3.07-3.15 (1H, m), 3.53 (3H, s), 3.61-3.72 (2H, m), 6.99 (1H, d), 7.09 (1H, d), 7.35 (1H, t), 8.05 (1H, s), 8.99 (1H, s), 10.25 (1H, s); m/z: ES+ [M+H]+=447.

(4aR)-11-Chloro-10-(2-chloro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one (Atropisomer 1, Compound 51)

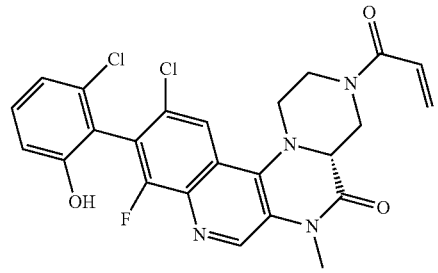 [SMILES: C=CC(=O)N1CCN2c3c(cnc4c(F)c(-c5c(O)cccc5Cl)c(Cl)cc34)N(C)C(=O)[C@H]2C1]

Acryloyl chloride (7.5 mg, 0.08 mmol) was added to atropisomer 1 of (4aR)-11-chloro-10-(2-chloro-6-hydroxyphenyl)-9-fluoro-6-methyl-2,3,4,4a-tetrahydro-1H-pyrazino[1',2':4,5]pyrazino[2,3-c]quinolin-5(6H)-one (37 mg, 0.08 mmol) and DIPEA (0.029 mL, 0.17 mmol) in DMF (3 mL) at −10° C. The resulting mixture was stirred at rt for 1 h. The reaction mixture was purified by C18-flash chromatography (0 to 100% MeCN in water (0.1% NH₄HCO₃)) to afford atropisomer 1 of (4aR)-11-chloro-10-(2-chloro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5 (6H)-one (25 mg, 61%) as a white solid; ¹H NMR (300 MHz, DMSO, 30° C.) 2.60-2.84 (1H, m), 3.11-3.27 (1H, m), 3.35-3.38 (1H, m), 3.50 (3H, s), 3.55-3.70 (1H, m), 3.94-4.53 (2H, m), 4.73-5.21 (1H, m), 5.77 (1H, d), 6.15 (1H, dd), 6.95-7.14 (3H, m), 7.35 (1H, t), 8.14 (1H, s), 9.01 (1H, s), 10.20 (1H, s); m/z: ES+ [M+H]+=501.

(4aR)-11-Chloro-10-(2-chloro-6-hydroxyphenyl)-9-fluoro-6-methyl-2,3,4,4a-tetrahydro-1H-pyrazino[1',2':4,5]pyrazino[2,3-c]quinolin-5(6H)-one Atropisomer 2

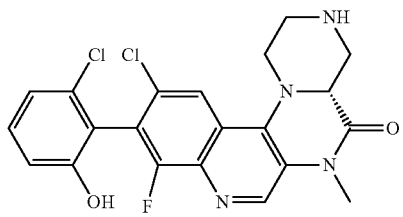 [SMILES: CN1C(=O)[C@H]2CNCCN2c2c1cnc1c(F)c(-c3c(O)cccc3Cl)c(Cl)cc21]

4M HCl in 1,4-dioxane (4 mL, 16.00 mmol) was added to atropisomer 2 of tert-butyl (4aR)-11-chloro-10-(2-chloro-6-hydroxyphenyl)-9-fluoro-6-methyl-5-oxo-1,2,4,4a,5,6-hexahydro-3H-pyrazino[1',2':4,5]pyrazino[2,3-c]quinoline-3-carboxylate (96 mg, 0.18 mmol) in MeOH (4 mL) at rt. The resulting mixture was stirred at rt for 30 min. The solvent was removed in vacuo. The crude product was purified by SCX (7M NH3/MeOH) to afford atropisomer 2 of (4aR)-11-chloro-10-(2-chloro-6-hydroxyphenyl)-9-fluoro-6-methyl-2,3,4,4a-tetrahydro-1H-pyrazino[1',2':4,5]pyrazino[2,3-c]quinolin-5(6H)-one (71 mg, 91%) as a white solid; 1H NMR (300 MHz, DMSO, 30° C.) 2.60-2.71 (1H, m), 2.82-2.94 (1H, m), 2.94-3.05 (2H, m), 3.05-3.17 (1H, m), 3.53 (3H, s), 3.58-3.73 (2H, m), 6.99 (1H, d), 7.09 (1H, d), 7.35 (1H, t), 8.04 (1H, s), 8.99 (1H, s), 10.15 (1H, s); m/z: ES+ [M+H]+=447.

(4aR)-11-Chloro-10-(2-chloro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one (Atropisomer 2, Compound 52)

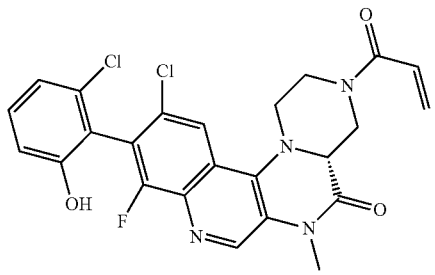 [SMILES: C=CC(=O)N1CCN2c3c(cnc4c(F)c(-c5c(O)cccc5Cl)c(Cl)cc34)N(C)C(=O)[C@H]2C1]

Acryloyl chloride (12.1 mg, 0.13 mmol) was added to atropisomer 2 of ((4aR)-11-chloro-10-(2-chloro-6-hydroxyphenyl)-9-fluoro-6-methyl-2,3,4,4a-tetrahydro-1H-pyrazino[1',2':4,5]pyrazino[2,3-c]quinolin-5(6H)-one (60 mg, 0.13 mmol) and DIPEA (0.047 mL, 0.27 mmol) in DMF (3 mL) at −10° C. The resulting mixture was stirred at rt for 1 h. The crude reaction mixture was purified by flash C18-flash chromatography (0 to 100% MeCN in water (0.1% NH4HCO3)) to afford a white solid. This was purified by C18-flash chromatography (0 to 100% MeCN in water (0.05% formic acid)) to afford atropisomer 2 of (4aR)-11-chloro-10-(2-chloro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one (40 mg, 60%) as a white solid; 1H NMR (300 MHz, DMSO, 30° C.) 2.63-2.75 (1H, m), 3.13-3.26 (1H, m), 3.33-3.39 (1H, m), 3.50 (3H, s), 3.56-3.68 (1H, m), 3.92-4.50 (2H, m), 4.73-5.10 (1H, m), 5.77 (1H, d), 6.15 (1H, dd), 6.89-7.17 (3H, m), 7.35 (1H, t), 8.13 (1H, s), 9.01 (1H, s), 10.21 (1H, s); m/z: ES+ [M+H]+=501.

tert-Butyl (4aR)-11-chloro-9-fluoro-10-(2-methoxy-6-methylphenyl)-6-methyl-5-oxo-1,2,4,4a,5,6-hexahydro-3H-pyrazino[1',2':4,5]pyrazino[2,3-c]quinoline-3-carboxylate

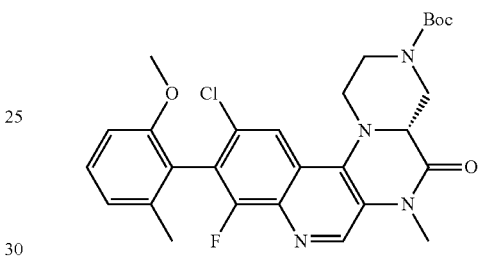

RuPhos-Pd-G3 (50.2 mg, 0.06 mmol) was added to a mixture of tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (300 mg, 0.60 mmol), (2-methoxy-6-methylphenyl)boronic acid (100 mg, 0.6 mmol), K2CO3 (166 mg, 1.2 mmol) and RuPhos (28 mg, 0.06 mmol) in 1,4-dioxane/H2O (15 mL, 4:1 ratio) at rt. The resulting suspension was stirred at 100° C. for 1 h. The solvent was removed in vacuo. The residue obtained was purified by C18-flash chromatography (0 to 100%, MeCN in water (0.1% formic acid)) to give an orange solid. This was purified by preparative chiral-HPLC (Column: CHIRAL-PAK IE, 2*25 cm, 5 m; Mobile Phase A: Hex (8 mmol/L NH3.MeOH)-HPLC, Mobile Phase B: IPA-HPLC; Flow rate: 13 mL/min; Gradient: 50 B to 50 B in 36 min; 220/254 nm) to afford atropisomer 1 of tert-butyl (4aR)-11-chloro-9-fluoro-10-(2-methoxy-6-methylphenyl)-6-methyl-5-oxo-1,2,4,4a,5,6-hexahydro-3H-pyrazino[1',2':4,5]pyrazino[2,3-c]quinoline-3-carboxylate (81 mg, 26%) as a white solid; 1H NMR (300 MHz, DMSO, 30° C.) 1.46 (9H, s), 2.02 (3H, s), 2.64-2.77 (1H, m), 3.22-3.28 (2H, m), 3.50 (3H, s), 3.68 (3H, s), 3.77-3.91 (2H, m), 4.34 (1H, d), 4.76 (1H, d), 6.97-7.06 (2H, m), 7.39 (1H, t), 8.08 (1H, s), 8.99 (1H, s); m/z: ES+ [M+H]+=541. This was followed by atropisomer 2 of tert-butyl (4aR)-11-chloro-9-fluoro-10-(2-methoxy-6-methylphenyl)-6-methyl-5-oxo-1,2,4,4a,5,6-hexahydro-3H-pyrazino[1',2':4,5]pyrazino[2,3-c]quinoline-3-carboxylate (119 mg, 37%) as a pale yellow solid; 1H NMR (300 MHz, DMSO, 30° C.) 1.46 (9H, s), 2.00 (3H, s), 2.66-2.80 (1H, m), 3.22-3.33 (3H, m), 3.51 (3H, s), 3.69 (3H, s), 3.85-3.98 (2H, m), 4.76 (1H, d), 6.96-7.07 (2H, m), 7.39 (1H, t), 8.09 (1H, s), 8.99 (1H, s); m/z: ES+ [M+H]+=541.

(4aR)-11-Chloro-9-fluoro-10-(2-hydroxy-6-methyl-phenyl)-6-methyl-2,3,4,4a-tetrahydro-1H-pyrazino[1',2':4,5]pyrazino[2,3-c]quinolin-5(6H)-one Atropisomer 1

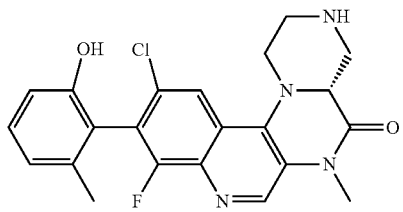 [SMILES: Cc1cccc(O)c1-c1c(Cl)cc2c3c(cnc2c1F)N(C)C(=O)[C@H]1CNCCN31]

1M Boron tribromide in DCM (2 mL, 2 mmol) was added to atropisomer 1 of tert-butyl 11-chloro-9-fluoro-10-(2-methoxy-6-methylphenyl)-6-methyl-5-oxo-1,2,4,4a,5,6-hexahydro-3H-pyrazino[1',2':4,5]pyrazino[2,3-c]quinoline-3-carboxylate (73 mg, 0.13 mmol) in DCM (6 mL) at 0° C. The resulting suspension was stirred at rt for 1.5 h. Additional 1M boron tribromide in DCM (2 mL, 2.00 mmol) was added and the mixture stirred at rt for another 1 h. The reaction mixture was quenched with MeOH (2 mL) and the solvent removed in vacuo. The crude product was purified by SCX (7M NH$_3$/MeOH) to afford atropisomer 1 of (4aR)-11-chloro-9-fluoro-10-(2-hydroxy-6-methylphenyl)-6-methyl-2,3,4,4a-tetrahydro-1H-pyrazino[1',2':4,5]pyrazino[2,3-c]quinolin-5(6H)-one (37 mg, 64%) as a white solid; $^1$H NMR (300 MHz, DMSO, 30° C.) 1.96 (3H, s), 2.59-2.71 (1H, m), 2.85-3.08 (3H, m), 3.14 (1H, d), 3.53 (3H, s), 3.63-3.72 (2H, m), 6.83 (2H, d), 7.19 (1H, t), 8.05 (1H, d), 8.98 (1H, s), 9.48 (1H, s; m/z: ES$^+$ [M+H]$^+$=427.

(4aR)-11-Chloro-9-fluoro-10-(2-hydroxy-6-methyl-phenyl)-6-methyl-3-(prop-2-enoyl)-2,3,4,4a-tetrahydro-1H-pyrazino[1',2':4,5]pyrazino[2,3-c]quinolin-5(6H)-one (Atropisomer 1, Compound 53)

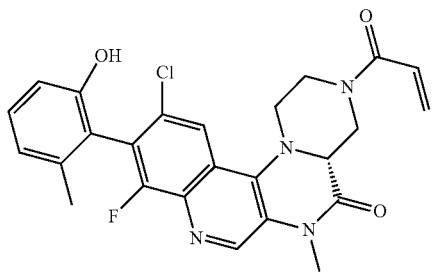 [SMILES: C=CC(=O)N1CCN2c3c(cnc4c(F)c(-c5c(C)cccc5O)c(Cl)cc34)N(C)C(=O)[C@H]2C1]

Acryloyl chloride (7 mg, 0.08 mmol) was added to atropisomer 1 of (4aR)-11-chloro-9-fluoro-10-(2-hydroxy-6-methylphenyl)-6-methyl-2,3,4,4a-tetrahydro-1H-pyrazino[1',2':4,5]pyrazino[2,3-c]quinolin-5(6H)-one (33 mg, 0.08 mmol) and DIPEA (0.027 mL, 0.15 mmol) in DMF (3 mL) at −10° C.

The resulting mixture was stirred at rt for 1 h. The reaction mixture was purified by C18-flash chromatography (0 to 100% MeCN in water (0.05% formic acid)) to afford atropisomer 1 of (4aR)-11-chloro-9-fluoro-10-(2-hydroxy-6-methylphenyl)-6-methyl-3-(prop-2-enoyl)-2,3,4,4a-tetrahydro-1H-pyrazino[1',2':4,5]pyrazino[2,3-c]quinolin-5(6H)-one (24 mg, 65%) as a white solid; $^1$H NMR (300 MHz, DMSO, 30° C.) 1.97 (3H, s), 2.62-2.77 (1H, m), 3.14-3.26 (1H, m), 3.34-3.40 (1H, m), 3.50 (3H, s), 3.62 (1H, d), 3.94-4.53 (2H, m), 4.72-5.22 (1H, m), 5.77 (1H, d), 6.15 (1H, dd), 6.83 (2H, d), 7.00-7.15 (1H, m), 7.20 (1H, t), 8.13 (1H, s), 8.99 (1H, s), 9.53 (1H, s); m/z: ES$^+$ [M+H]$^+$=481.

(4aR)-11-Chloro-9-fluoro-10-(2-hydroxy-6-methyl-phenyl)-6-methyl-2,3,4,4a-tetrahydro-1H-pyrazino[1',2':4,5]pyrazino[2,3-c]quinolin-5(6H)-one Atropisomer 2

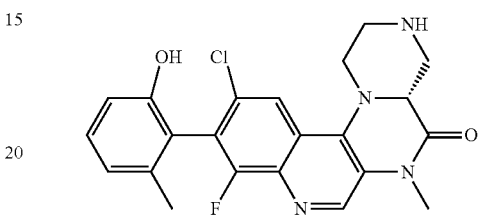

1M Boron tribromide in DCM (2 mL, 2 mmol) was added to atropisomer 2 of tert-butyl 11-chloro-9-fluoro-10-(2-methoxy-6-methylphenyl)-6-methyl-5-oxo-1,2,4,4a,5,6-hexahydro-3H-pyrazino[1',2':4,5]pyrazino[2,3-c]quinoline-3-carboxylate (115 mg, 0.21 mmol) in DCM (6 mL) at 0° C. The resulting suspension was stirred at rt for 1.5 h. Additional 1M boron tribromide in DCM (2 mL, 2 mmol) was added and the mixture stirred at rt for another 1 h. The reaction mixture was quenched with MeOH (2 mL) and the solvent removed in vacuo. The crude product was purified by SCX (7M NH$_3$/MeOH) to afford atropisomer 2 of (4aR)-11-chloro-9-fluoro-10-(2-hydroxy-6-methylphenyl)-6-methyl-2,3,4,4a-tetrahydro-1H-pyrazino[1',2':4,5]pyrazino[2,3-c]quinolin-5(6H)-one (51 mg, 56%) as a white solid; $^1$H NMR (300 MHz, DMSO, 30° C.) 2.00 (3H, s), 2.59-2.70 (1H, m), 2.86-3.08 (3H, m), 3.13 (1H, d), 3.53 (3H, s), 3.63-3.72 (2H, m), 6.74-7.04 (2H, m), 7.19 (1H, t), 8.04 (1H, s), 8.98 (1H, s), 9.46 (1H, s); m/z: ES$^+$ [M+H]$^+$=427.

(4aR)-11-Chloro-9-fluoro-10-(2-hydroxy-6-methyl-phenyl)-6-methyl-3-(prop-2-enoyl)-2,3,4,4a-tetrahydro-1H-pyrazino[1',2':4,5]pyrazino[2,3-c]quinolin-5(6H)-one (Atropisomer 2, Compound 54)

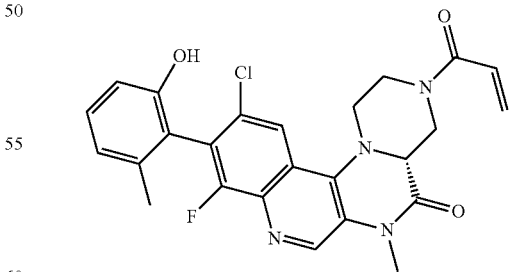

Acryloyl chloride (8.69 mg, 0.10 mmol) was added to (4aR)-11-chloro-9-fluoro-10-(2-hydroxy-6-methylphenyl)-6-methyl-2,3,4,4a-tetrahydro-1H-pyrazino[1',2':4,5]pyrazino[2,3-c]quinolin-5(6H)-one (41 mg, 0.1 mmol) and DIPEA (0.034 mL, 0.19 mmol) in DMF (3 mL) at −10° C. The resulting mixture was stirred at rt for 1 h. The crude reaction mixture was purified by C18-flash chromatography (0 to 100% MeCN in water (0.05% formic acid)) to afford (4aR)-11-chloro-9-fluoro-10-(2-hydroxy-6-methylphenyl)-6-methyl-3-(prop-2-enoyl)-2,3,4,4a-tetrahydro-1H-pyrazino[1',2':4,5]pyrazino[2,3-c]quinolin-5(6H)-one (30 mg, 64%) as a white solid; ¹H NMR (300 MHz, DMSO, 30° C.) 1.99 (3H, s), 2.59-2.75 (1H, m), 3.10-3.25 (1H, m), 3.34-3.41 (1H, m), 3.50 (3H, s), 3.63 (1H, d), 3.90-4.51 (2H, m), 4.72-5.21 (1H, m), 5.77 (1H, d), 6.15 (1H, dd), 6.83 (2H, d), 6.98-7.16 (1H, m), 7.20 (1H, t), 8.12 (1H, s), 8.99 (1H, s), 9.51 (1H, s); m/z: ES⁺ [M+H]⁺=481.

tert-Butyl (4aR)-11-chloro-9-fluoro-10-(2-methoxynaphthalen-1-yl)-6-methyl-5-oxo-1,2,4,4a,5,6-hexahydro-3H-pyrazino[1',2':4,5]pyrazino[2,3-c]quinoline-3-carboxylate

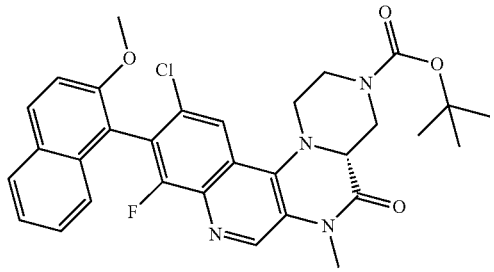 [SMILES: COc1ccc2ccccc2c1-c1c(Cl)cc2c3c(cnc2c1F)N(C)C(=O)[C@H]1CN(C(=O)OC(C)(C)C)CCN31]

RuPhos-Pd-G3 (134 mg, 0.16 mmol), RuPhos (74.7 mg, 0.16 mmol) and tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (800 mg, 1.6 mmol), (2-methoxynaphthalen-1-yl)boronic acid (485 mg, 2.4 mmol) and K₂CO₃ (442 mg, 3.2 mmol) in 1,4-dioxane/H₂O (5 mL, 4:1 ratio) were sealed into a microwave tube. The reaction mixture was heated at 100° C. for 30 min in the microwave reactor then cooled to rt. The solvent was removed in vacuo. The crude product was purified by flash silica chromatography (0 to 20% EtOAc in petroleum ether) to afford tert-butyl (4aR)-11-chloro-9-fluoro-10-(2-methoxynaphthalen-1-yl)-6-methyl-5-oxo-1,2,4,4a,5,6-hexahydro-3H-pyrazino[1',2':4,5]pyrazino[2,3-c]quinoline-3-carboxylate (900 mg, 97%) as a yellow solid; ¹H NMR (300 MHz, DMSO, 30° C.) 1.44 (9H, s), 3.26 (3H, s), 3.50 (3H, s), 3.82-3.91 (5H, m), 3.95-4.08 (1H, m), 4.76 (1H, d), 7.12-7.18 (1H, m), 7.34-7.44 (2H, m), 7.63 (1H, d), 7.93-8.02 (1H, m), 8.09-8.18 (2H, m), 9.00 (1H, s); m/z: ES⁺ [M+H]⁺=557.

(4aR)-11-Chloro-9-fluoro-10-(2-hydroxynaphthalen-1-yl)-6-methyl-2,3,4,4a-tetrahydro-1H-pyrazino[1',2':4,5]pyrazino[2,3-c]quinolin-5(6H)-one Atropisomer 1 and 2

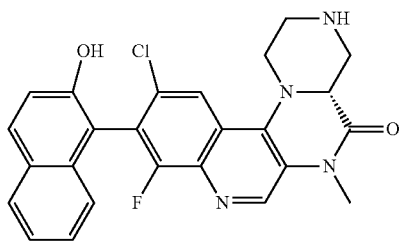 [SMILES: CN1C(=O)[C@H]2CNCCN2c2c1cnc1c(F)c(-c3c(O)ccc4ccccc34)c(Cl)cc21]

1M Boron tribromide in DCM (8.23 mL, 8.23 mmol) was added dropwise to tert-butyl (4aR)-11-chloro-9-fluoro-10-(2-methoxynaphthalen-1-yl)-6-methyl-5-oxo-1,2,4,4a,5,6-hexahydro-3H-pyrazino[1',2':4,5]pyrazino[2,3-c]quinoline-3-carboxylate (950 mg, 1.65 mmol) in DCM (3 mL). The resulting mixture was stirred at 0° C. for 2 h. The solvent was removed in vacuo. The residue was purified by C18-flash chromatography (0 to 40% MeOH in water (0.1% NH₄HCO₃)) to afford crude product as a yellow solid. This was purified by preparative chiral-HPLC (Column: Chiralpak IC, 2*25 cm, 5 m; Mobile Phase A: MTBE (10 mM NH₃-MeOH)-HPLC, Mobile Phase B: EtOH-HPLC; Flow rate: 20 mL/min; Gradient: 30 B to 30 B in 24 min; 254/220 nm) to give atropisomer 1 of (4aR)-11-chloro-9-fluoro-10-(2-hydroxynaphthalen-1-yl)-6-methyl-2,3,4,4a-tetrahydro-1H-pyrazino[1',2':4,5]pyrazino[2,3-c]quinolin-5(6H)-one (210 mg, 43%); m/z: ES⁺ [M+H]⁺=463. This was followed by atropisomer 2 of (4aR)-11-chloro-9-fluoro-10-(2-hydroxynaphthalen-1-yl)-6-methyl-2,3,4,4a-tetrahydro-1H-pyrazino[1',2':4,5]pyrazino[2,3-c]quinolin-5(6H)-one (160 mg, 33%) as a yellow gum; m/z: ES⁺ [M+H]⁺=463.

(4aR)-11-Chloro-9-fluoro-10-(2-hydroxynaphthalen-1-yl)-6-methyl-3-(prop-2-enoyl)-2,3,4,4a-tetrahydro-1H-pyrazino[1',2':4,5]pyrazino[2,3-c]quinolin-5(6H)-one (Atropisomer 1, Compound 55)

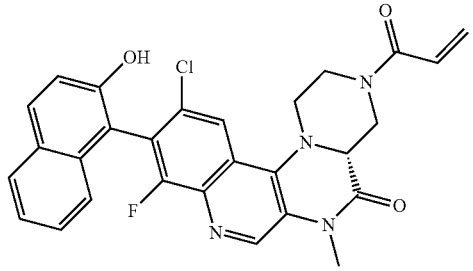 [SMILES: C=CC(=O)N1CCN2c3c(cnc4c(F)c(-c5c(O)ccc6ccccc56)c(Cl)cc34)N(C)C(=O)[C@H]2C1]

Acryloyl chloride (21.5 mg, 0.24 mmol) was added dropwise to atropisomer 1 of (4aR)-11-chloro-9-fluoro-10-(2-hydroxynaphthalen-1-yl)-6-methyl-2,3,4,4a-tetrahydro-1H-pyrazino[1',2':4,5]pyrazino[2,3-c]quinolin-5(6H)-one (110 mg, 0.24 mmol) and DIPEA (0.083 mL, 0.48 mmol) in DMF (2 mL). The resulting mixture was stirred at 0° C. for 2 h. The crude reaction mixture was purified by C18-flash chromatography (0 to 40% MeCN in water (0.1% NH₄HCO₃)) to afford atropisomer 1 of (4aR)-11-chloro-9-fluoro-10-(2-hydroxynaphthalen-1-yl)-6-methyl-3-(prop-2-enoyl)-2,3,4,4a-tetrahydro-1H-pyrazino[1',2':4,5]pyrazino[2,3-c]quinolin-5(6H)-one (56 mg, 46%) as a white solid; ¹H NMR (300 MHz, DMSO, 30° C.) 2.69 (1H, t), 3.23 (1H, t), 3.36-3.42 (1H, m), 3.51 (3H, s), 3.57-3.69 (1H, m), 3.92-4.53 (2H, m), 4.80 (1H, d), 5.72-5.82 (1H, m), 6.10-6.22 (1H, m), 7.01-7.16 (2H, m), 7.26-7.41 (3H, m), 7.86-7.99 (2H, m), 8.20 (1H, s), 9.02 (1H, s), 9.96 (1H, s); m/z: ES⁺ [M+H]⁺=517.

(4aR)-11-Chloro-9-fluoro-10-(2-hydroxynaphthalen-1-yl)-6-methyl-3-(prop-2-enoyl)-2,3,4,4a-tetrahydro-1H-pyrazino[1',2':4,5]pyrazino[2,3-c]quinolin-5(6H)-one (Atropisomer 2, Compound 56)

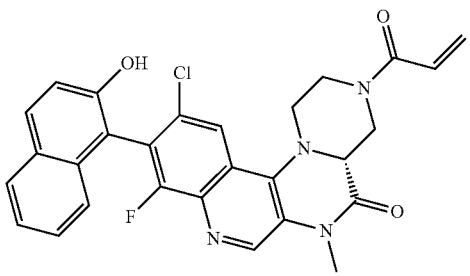 [SMILES: C=CC(=O)N1CCN2c3c(cnc4c(F)c(-c5c(O)ccc6ccccc56)c(Cl)cc34)N(C)C(=O)[C@H]2C1]

Acryloyl chloride (31.3 mg, 0.35 mmol) was added dropwise to atropisomer 2 of (4aR)-11-chloro-9-fluoro-10-(2-hydroxynaphthalen-1-yl)-6-methyl-2,3,4,4a-tetrahydro-1H-pyrazino[1',2':4,5]pyrazino[2,3-c]quinolin-5(6H)-one (160 mg, 0.35 mmol) and DIPEA (0.121 mL, 0.69 mmol) in DMF (2 mL). The resulting mixture was stirred at 0° C. for 2 h. The crude reaction mixture was purified by C18-flash chromatography (0 to 40% MeCN in water (0.1% NH$_4$HCO$_3$)) to afford crude product. This was purified by preparative HPLC (Column: XBridge Prep OBD C18 Column 19*250 mm, 5 m; Mobile Phase A: Water (10 mmol/L NH$_4$HCO$_3$), Mobile Phase B: MeCN; Flow rate: 25 mL/min; Gradient: 35% B to 70% B in 8 min; 254/220 nm) to give atropisomer 2 of (4aR)-11-chloro-9-fluoro-10-(2-hydroxynaphthalen-1-yl)-6-methyl-3-(prop-2-enoyl)-2,3,4,4a-tetrahydro-1H-pyrazino[1',2':4,5]pyrazino[2,3-c]quinolin-5(6H)-one (35 mg, 20%) as a light yellow solid; $^1$H NMR (300 MHz, DMSO, 30° C.) 2.71 (1H, t), 3.20 (1H, t), 3.35-3.45 (1H, m), 3.51 (3H, s), 3.64 (1H, d), 3.98 (1H, d), 4.47 (1H, d), 4.80 (1H, d), 5.77 (1H, d), 6.10-6.22 (1H, m), 7.01-7.16 (2H, m), 7.26-7.41 (3H, m), 7.85-7.99 (2H, m), 8.19 (1H, s), 9.01 (1H, s), 9.94 (1H, s); m/z: ES$^+$ [M+H]$^+$=517.

tert-Butyl (4aR)-11-chloro-10-(2,3-difluoro-6-methoxyphenyl)-9-fluoro-6-methyl-5-oxo-1,2,4,4a,5,6-hexahydro-3H-pyrazino[1',2':4,5]pyrazino[2,3-c]quinoline-3-carboxylate Atropisomers 1 and 2

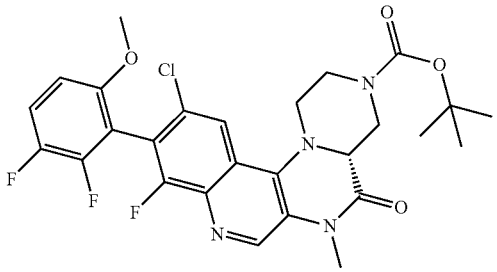 [SMILES: COc1ccc(F)c(F)c1-c1c(Cl)cc2c3c(cnc2c1F)N(C)C(=O)[C@H]1CN(C(=O)OC(C)(C)C)CCN31]

RuPhos-Pd-G3 (84 mg, 0.1 mmol) was added to tert-butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (500 mg, 1 mmol), (2,3-difluoro-6-methoxyphenyl)boronic acid (188 mg, 1 mmol), K$_2$CO$_3$ (277 mg, 2 mmol) and RuPhos (46.7 mg, 0.1 mmol) in 1,4-dioxane/H$_2$O (20 mL, 4:1 ratio) at rt. The resulting suspension was stirred at 100° C. for 1 h. Additional (2,3-difluoro-6-methoxyphenyl)boronic acid (188 mg, 1 mmol), K$_2$CO$_3$ (277 mg, 2 mmol), RuPhos (46.7 mg, 0.1 mmol) and RuPhos-Pd-G3 (84 mg, 0.1 mmol) were added and the reaction mixture heated for a further 1.5 h. The solvent was removed in vacuo. The residue obtained was purified by flash silica chromatography (0 to 100% EtOAc in petroleum ether) to afford crude product as a yellow solid. This was purified by preparative chiral-HPLC (Column: CHIRAL ART Cellulose-SB S-5 m, 2*25 cm, 5 m; Mobile Phase A: Hex (8 mmol/L NH$_3$.MeOH)-HPLC, Mobile Phase B: EtOH-HPLC; Flow rate: 20 mL/min; Gradient: 50 B to 50 B in 15 min; 220/254 nm) to give atropisomer 1 of tert-butyl (4aR)-11-chloro-10-(2,3-difluoro-6-methoxyphenyl)-9-fluoro-6-methyl-5-oxo-1,2,4,4a,5,6-hexahydro-3H-pyrazino[1',2':4,5]pyrazino[2,3-c]quinoline-3-carboxylate (93 mg, 42%); $^1$H NMR (300 MHz, DMSO, 30° C.) 1.46 (9H, s), 2.64-2.79 (1H, m), 3.17-3.30 (3H, m), 3.51 (3H, s), 3.77 (3H, s), 3.82-4.00 (2H, m), 4.75 (1H, d), 7.09 (1H, d), 7.56-7.72 (1H, m), 8.13 (1H, s), 9.02 (1H, s); m/z: ES$^+$ [M+H]$^+$=563. This was followed by atropisomer 2 of tert-butyl (4aR)-11-chloro-10-(2,3-difluoro-6-methoxyphenyl)-9-fluoro-6-methyl-5-oxo-1,2,4,4a,5,6-hexahydro-3H-pyrazino[1',2':4,5]pyrazino[2,3-c]quinoline-3-carboxylate (73 mg, 33%); $^1$H NMR (300 MHz, DMSO, 30° C.) 1.46 (9H, s), 2.63-2.77 (1H, m), 3.18-3.30 (3H, m), 3.51 (3H, s), 3.77 (3H, s), 3.82-3.99 (2H, m), 4.75 (1H, d), 7.08 (1H, d), 7.56-7.72 (1H, m), 8.12 (1H, s), 9.02 (1H, s); m/z: ES$^+$ [M+H]$^+$=563.

(4aR)-11-Chloro-10-(2,3-difluoro-6-hydroxyphenyl)-9-fluoro-6-methyl-2,3,4,4a-tetrahydro-1H-pyrazino[1',2':4,5]pyrazino[2,3-c]quinolin-5(6H)-one Atropisomer 1

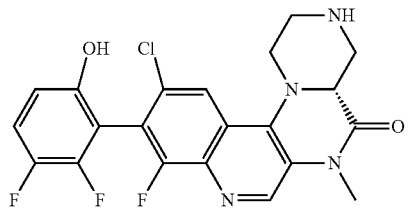 [SMILES: CN1C(=O)[C@H]2CNCCN2c2c1cnc1c(F)c(-c3c(O)ccc(F)c3F)c(Cl)cc21]

1M boron tribromide in DCM (3 mL, 3.00 mmol) was added to atropisomer 1 of tert-butyl (4aR)-11-chloro-10-(2,3-difluoro-6-methoxyphenyl)-9-fluoro-6-methyl-5-oxo-1,2,4,4a,5,6-hexahydro-3H-pyrazino[1',2':4,5]pyrazino[2,3-c]quinoline-3-carboxylate (85 mg, 0.15 mmol) in DCM (3 mL) at 0° C. The resulting suspension was stirred at rt for 2 h. The solvent was removed in vacuo. The crude product obtained was purified by SCX (7M NH$_3$/MeOH) to afford atropisomer 1 of (4aR)-11-chloro-10-(2,3-difluoro-6-hydroxyphenyl)-9-fluoro-6-methyl-2,3,4,4a-tetrahydro-1H-pyrazino[1',2':4,5]pyrazino[2,3-c]quinolin-5(6H)-one (50 mg, 74%) as a white solid; $^1$H NMR (300 MHz, DMSO, 30° C.) 2.59-2.71 (1H, m), 2.88-3.17 (4H, m), 3.53 (3H, s), 3.69 (2H, d), 6.85 (1H, d), 7.34-7.51 (1H, m), 8.09 (1H, s), 9.02 (1H, s), 10.24; m/z: ES$^+$ [M+H]$^+$=449.

(4aR)-11-Chloro-10-(2,3-difluoro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one (Atropisomer 1, Compound 57)

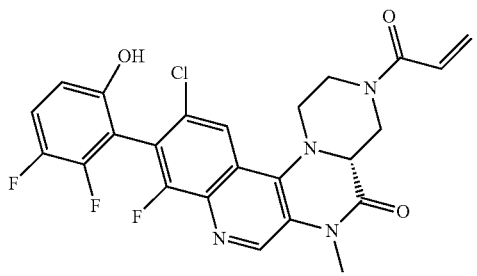 [SMILES: C=CC(=O)N1CCN2c3c(cnc4c(F)c(-c5c(O)ccc(F)c5F)c(Cl)cc34)N(C)C(=O)[C@H]2C1]

Acryloyl chloride (2.3 mg, 0.03 mmol) was added to atropisomer 1 of (4aR)-11-chloro-10-(2,3-difluoro-6-hydroxyphenyl)-9-fluoro-6-methyl-2,3,4,4a-tetrahydro-1H-pyrazino[1',2':4,5]pyrazino[2,3-c]quinolin-5(6H)-one (45 mg, 0.1 mmol) and DIPEA (0.035 mL, 0.20 mmol) in DMF (3 mL) at −10° C. The resulting mixture was stirred at rt for 30 min. The crude reaction mixture was purified by C18-flash chromatography (0 to 100% MeCN in water (0.05% formic acid)) to afford atropisomer 1 of (4aR)-11-chloro-10-(2,3-difluoro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one (24 mg, 47%) as a white solid; $^1$H NMR (300 MHz, DMSO, 30° C.) 2.63-2.81 (1H, m), 3.11-3.27 (1H, m), 3.34-3.40 (1H, m), 3.50 (3H, s), 3.57-3.73 (1H, m), 3.84-4.52 (2H, m), 4.70-5.31 (1H, m), 5.77 (1H, d), 6.15 (1H, d), 6.84 (1H, d), 6.96-7.18 (1H, m), 7.38-7.54 (1H, m), 8.17 (1H, s), 9.03 (1H, s), 10.27 (1H, s); m/z: ES$^+$ [M+H]$^+$=503.

(4aR)-11-Chloro-10-(2,3-difluoro-6-hydroxyphenyl)-9-fluoro-6-methyl-2,3,4,4a-tetrahydro-1H-pyrazino[1',2':4,5]pyrazino[2,3-c]quinolin-5(6H)-one Atropisomer 2

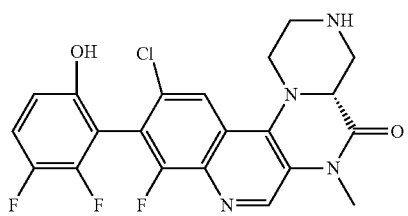

1M boron tribromide in DCM (3 mL, 3.00 mmol) was added to atropisomer 2 of tert-butyl (4aR)-11-chloro-10-(2,3-difluoro-6-methoxyphenyl)-9-fluoro-6-methyl-5-oxo-1,2,4,4a,5,6-hexahydro-3H-pyrazino[1',2':4,5]pyrazino[2,3-c]quinoline-3-carboxylate (70 mg, 0.12 mmol) in DCM (3 mL) at 0° C. The resulting suspension was stirred at rt for 2 h. The solvent was removed in vacuo. The crude product was purified by SCX (7M NH$_3$/MeOH) to afford atropisomer 2 of (4aR)-11-chloro-10-(2,3-difluoro-6-hydroxyphenyl)-9-fluoro-6-methyl-2,3,4,4a-tetrahydro-1H-pyrazino[1',2':4,5]pyrazino[2,3-c]quinolin-5(6H)-one (43 mg, 77%) as a white solid; $^1$H NMR (300 MHz, DMSO, 30° C.) 2.78-2.91 (1H, m), 3.16-3.21 (1H, m), 3.36-3.52 (3H, m), 3.59 (3H, s), 3.99 (1H, d), 4.15 (1H, d), 6.84 (1H, d), 7.33-7.55 (1H, m), 8.19 (1H, s), 9.08 (1H, s), 10.24 (1H, s); m/z: ES$^+$ [M+H]$^+$=449.

(4aR)-11-Chloro-10-(2,3-difluoro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one (Atropisomer 2, Compound 58)

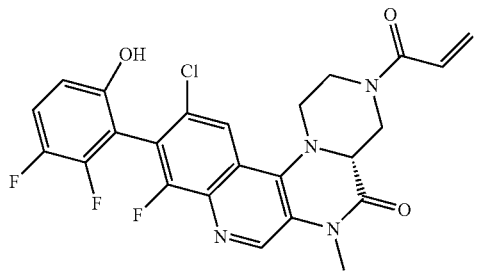 [SMILES: C=CC(=O)N1CCN2c3c(cnc4c(F)c(-c5c(O)ccc(F)c5F)c(Cl)cc34)N(C)C(=O)[C@H]2C1]

Acryloyl chloride (7.7 mg, 0.08 mmol) was added to atropisomer 2 of (4aR)-11-chloro-10-(2,3-difluoro-6-hydroxyphenyl)-9-fluoro-6-methyl-2,3,4,4a-tetrahydro-1H-pyrazino[1',2':4,5]pyrazino[2,3-c]quinolin-5(6H)-one (38 mg, 0.08 mmol) and DIPEA (0.03 mL, 0.17 mmol) in DMF (3 mL) at −10° C. The resulting mixture was stirred at rt for 30 min. The crude reaction mixture was purified by C18-flash chromatography (0 to 100% MeCN in water (0.05% formic acid)) to afford atropisomer 2 of (4aR)-11-chloro-10-(2,3-difluoro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one (16 mg, 38%) as a white solid; $^1$H NMR (300 MHz, DMSO, 30° C.) 2.61-2.75 (1H, m), 3.13-3.27 (1H, m), 3.35-3.42 (1H, m), 3.50 (3H, s), 3.56-3.69 (1H, m), 3.86-4.55 (2H, m), 4.68-5.09 (1H, m), 5.77 (1H, d), 6.15 (1H, dd), 6.84 (1H, d), 6.97-7.17 (1H, m), 7.35-7.51 (1H, m), 8.16 (1H, s), 9.03 (1H, s), 10.31 (1H, s); m/z: ES$^+$ [M+H]$^+$=503.

3-Bromo-4-chloro-5-fluoroaniline

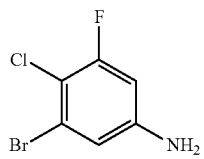

N-Chlorosuccinimide (25.3 g, 189.46 mmol) was added to 3-bromo-5-fluoroaniline (30 g, 157.88 mmol) in DMF (500 mL) at 25° C. The resulting solution was stirred at 25° C. for 16 h. The solvent was removed in vacuo. The crude product obtained was purified by flash silica chromatography (0 to 20% EtOAc in petroleum ether) to afford 3-bromo-4-chloro-5-fluoroaniline (14.9 g, 42%) as a brown solid; $^1$H NMR (400 MHz, DMSO, 30° C.) 5.81 (2H, s), 6.51 (1H, dd), 6.77 (1H, dd); m/z: ES$^+$ [M+H]$^+$=224.

5-[(3-Bromo-4-chloro-5-fluoroanilino)methylidene]-2,2-dimethyl-1,3-dioxane-4,6-dione

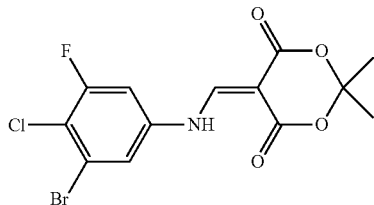 [SMILES: CC1(C)OC(=O)C(=CNc2cc(F)c(Cl)c(Br)c2)C(=O)O1]

5-(Methoxymethylidene)-2,2-dimethyl-1,3-dioxane-4,6-dione (14.83 g, 79.66 mmol) was added to 3-bromo-4-chloro-5-fluoroaniline (14.9 g, 66.38 mmol) in EtOH (350 mL) at rt. The resulting solution was stirred at 80° C. for 16 h. The reaction mixture was filtered at rt. The solid obtained was washed with water (200 mL×2) and dried under vacuum to afford 5-[(3-bromo-4-chloro-5-fluoroanilino)methylidene]-2,2-dimethyl-1,3-dioxane-4,6-dione (24 g, 95%) as a white solid; $^1$H NMR (400 MHz, DMSO, 30° C.) 1.68 (6H, s), 7.89 (1H, dd), 8.02 (1H, dd), 8.60 (1H, d), 11.21 (1H, d); m/z: ES$^+$ [M+H]$^+$=378.

7-Bromo-6-chloro-5-fluoroquinolin-4-ol

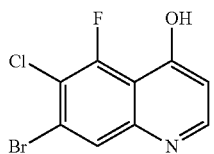 [SMILES: Oc1ccnc2cc(Br)c(Cl)c(F)c12]

5-[(3-Bromo-4-chloro-5-fluoroanilino)methylidene]-2,2-dimethyl-1,3-dioxane-4,6-dione (22 g, 58.11 mmol) was added to diphenyl ether (250 mL) at 260° C. The resulting solution was stirred at 260° C. for 90 min. The reaction mixture was cooled to rt, heptane (200 mL) added and the resulting mixture was filtered. The solid collected was washed with heptane then diethyl ether and dried on the filter to afford 7-bromo-6-chloro-5-fluoroquinolin-4-ol (13 g, 81%) as a brown solid; $^1$H NMR (400 MHz, DMSO, 30° C.) 6.05 (1H, dd), 7.52 (1H, d), 7.82-7.97 (1H, m), 11.88 (1H, s); m/z: ES$^+$ [M+H]$^+$=276.

7-Bromo-6-chloro-5-fluoro-3-nitroquinolin-4-ol

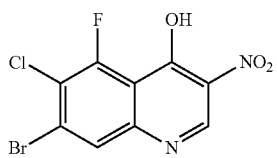

Fuming nitric acid (9.27 ml, 141.05 mmol) was added dropwise to 7-bromo-6-chloro-5-fluoroquinolin-4-ol (13 g, 47.02 mmol) in propionic acid (200 ml, 2672.82 mmol) at 120° C. and reaction mixture stirred at 120° C. for 2 h. The resulting solution was cooled to rt, water (150 mL) added and the resulting mixture filtered. The solid collected was washed with water (150 mL×2) and diethyl ether (100 mL) then dried to give 7-bromo-6-chloro-5-fluoro-3-nitroquinolin-4-ol (8.36 g, 55%) as a pale solid; $^1$H NMR (400 MHz, DMSO, 30° C.) 7.68 (1H, d), 9.18 (1H, d), 13.02 (1H, s); m/z: ES$^+$ [M+H]$^+$=321.

7-Bromo-4,6-dichloro-5-fluoro-3-nitroquinoline

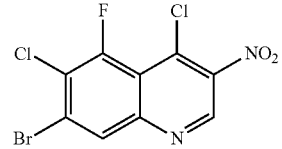

7-Bromo-6-chloro-5-fluoro-3-nitroquinolin-4-ol (8.36 g, 26 mmol) was added to Phosphorus(V) oxychloride (130 mL) and DMF (0.012 mL) at rt. The resulting solution was stirred at 120° C. for 2 h. The reaction mixture was quenched at rt with sat. NaHCO$_3$ (50 mL) and extracted with EtOAc (100 mL×3). The organic layer was dried (Na$_2$SO$_4$), filtered and concentrated in vacuo to afford crude product. This was purified by flash silica chromatography (0 to 20% EtOAc in petroleum ether) to afford 7-bromo-4,6-dichloro-5-fluoro-3-nitroquinoline (5.8 g, 66%) as a pale yellow solid; $^1$H NMR (400 MHz, DMSO, 30° C.) 7.76 (1H, d), 9.15 (1H, d); m/z: ES$^+$ [M+H]$^+$=339.

1-tert-Butyl 3-methyl (3R)-4-(7-bromo-6-chloro-5-fluoro-3-nitroquinolin-4-yl)piperazine-1,3-dicarboxylate

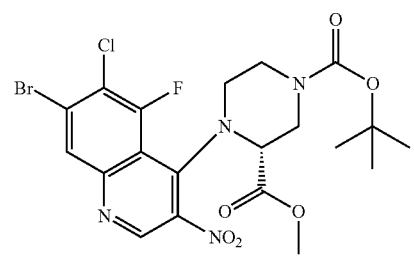 [SMILES: COC(=O)[C@H]1CN(C(=O)OC(C)(C)C)CCN1c1c([N+](=O)[O-])cnc2cc(Br)c(Cl)c(F)c12]

1-tert-Butyl 3-methyl (3R)-piperazine-1,3-dicarboxylate (5.03 g, 20.59 mmol) was added to 7-bromo-4,6-dichloro-5-fluoro-3-nitroquinoline (3.5 g, 10.30 mmol) and DIPEA (7.19 mL, 41.19 mmol) in THF (50 mL) at rt. The resulting solution was stirred at 80° C. for 16 h. The solvent was removed in vacuo. The crude product obtained was purified by flash silica chromatography (0 to 20% EtOAc in petroleum ether) to afford 1-tert-butyl 3-methyl (3R)-4-(7-bromo-6-chloro-5-fluoro-3-nitroquinolin-4-yl)piperazine-1,3-dicarboxylate (1.75 g, 31%) as a red solid; $^1$H NMR (300 MHz, DMSO, 30° C.) 1.45 (9H, s), 3.31 (3H, d), 3.37-3.45 (2H, m), 3.47-3.55 (2H, m), 3.68-3.82 (2H, m), 4.20-4.30 (1H, m), 8.45 (1H, d), 9.10 (1H, s); m/z: ES$^+$ [M+H]$^+$=547.

tert-Butyl (4aR)-10-bromo-11-chloro-12-fluoro-5-oxo-1,2,4,4a,5,6-hexahydro-3H-pyrazino[1',2':4,5]pyrazino[2,3-c]quinoline-3-carboxylate

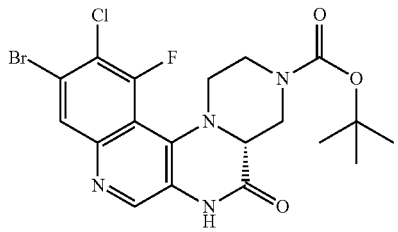 [SMILES: CC(C)(C)OC(=O)N1CCN2c3c(cnc4cc(Br)c(Cl)c(F)c34)NC(=O)[C@H]2C1]

Iron (0.867 g, 15.52 mmol) was added to 1-tert-butyl 3-methyl (3R)-4-(7-bromo-6-chloro-5-fluoro-3-nitroquinolin-4-yl)piperazine-1,3-dicarboxylate (1.7 g, 3.10 mmol) in glacial acetic acid (20 mL) at 25° C. The resulting solution was stirred at 80° C. for 1 h. The reaction mixture was filtered through CELITE™ The filtrate was concentrated in vacuo. The crude product obtained was purified by flash silica chromatography (0 to 50% EtOAc in petroleum ether) to afford tert-butyl (4aR)-10-bromo-11-chloro-12-fluoro-5-oxo-1,2,4,4a,5,6-hexahydro-3H-pyrazino[1',2':4,5]pyrazino[2,3-c]quinoline-3-carboxylate (1.4 g, 93%) as a pale yellow solid; $^1$H NMR (300 MHz, DMSO, 30° C.) 1.43 (9H, s), 2.57-3.14 (2H, m), 3.19-3.39 (2H, m), 3.69-4.09 (2H, m), 4.55-4.75 (1H, m), 7.91-8.28 (1H, m), 8.53-8.75 (1H, m), 10.83-11.13 (1H, m); m/z: ES$^+$ [M+H]$^+$=485.

tert-Butyl (4aR)-10-bromo-11-chloro-12-fluoro-6-methyl-5-oxo-1,2,4,4a,5,6-hexahydro-3H-pyrazino[1',2':4,5]pyrazino[2,3-c]quinoline-3-carboxylate

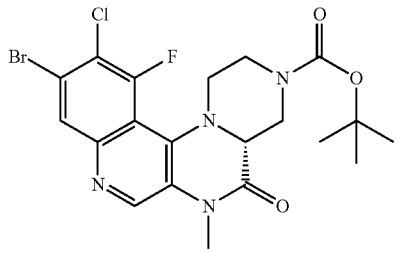

2-(tert-Butylimino)-N,N-diethyl-1,3-dimethyl-1,3,2λ$^5$-diazaphosphinan-2-amine (0.847 g, 3.09 mmol) was added to tert-butyl (4aR)-10-bromo-11-chloro-12-fluoro-5-oxo-1,2,4,4a,5,6-hexahydro-3H-pyrazino[1',2':4,5]pyrazino[2,3-c]quinoline-3-carboxylate (1 g, 2.06 mmol) and iodomethane (0.386 mL, 6.18 mmol) in DCM (10 mL) at 0° C. The resulting solution was stirred at 0° C. for 30 min. The solvent was removed in vacuo. The residue obtained was purified by flash silica chromatography (20 to 50% EtOAc in petroleum ether) to afford crude product. This was purified by preparative chiral-HPLC (Column: EnantioPak A1-52.12*25 cm, 5 ⬚ m. % Solvent A: CO$_2$: 55. % Solvent B: MeOH-Preparative: 45) to afford tert-butyl (4aR)-10-bromo-11-chloro-12-fluoro-6-methyl-5-oxo-1,2,4,4a,5,6-hexahydro-3H-pyrazino[1',2':4,5]pyrazino[2,3-c]quinoline-3-carboxylate (0.603 g, 59%) as a pale yellow solid; $^1$H NMR (300 MHz, DMSO, 30° C.) 1.45 (9H, s), 2.98-3.26 (2H, m), 3.28-3.38 (2H, m), 3.48 (3H, s), 3.77-4.05 (2H, m), 4.71 (1H, d), 8.32 (1H, d), 9.00 (1H, s); m/z: ES$^+$ [M+H]$^+$=499.

tert-Butyl (4aR)-11-chloro-12-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate

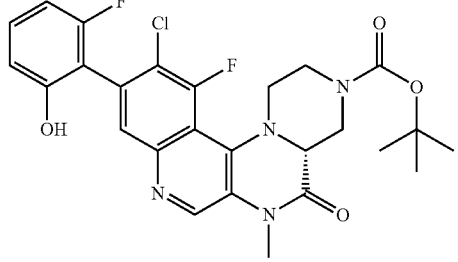

(2-Fluoro-6-hydroxyphenyl)boronic acid (94 mg, 0.60 mmol) was added to tert-butyl (4aR)-10-bromo-11-chloro-12-fluoro-6-methyl-5-oxo-1,2,4,4a,5,6-hexahydro-3H-pyrazino[1',2':4,5]pyrazino[2,3-c]quinoline-3-carboxylate (200 mg, 0.4 mmol), tetrakis(triphenylphosphine)palladium (0) (46 mg, 0.04 mmol) and K$_2$CO$_3$ (111 mg, 0.8 mmol) in 1,4-dioxane (2 mL) and water (0.5 mL) at rt. The resulting solution was stirred at 100° C. for 1 h. The crude reaction mixture was purified by C18-flash chromatography (0 to 60% MeCN in water (0.1% formic acid)) to afford tert-butyl (4aR)-11-chloro-12-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (174 mg, 82%) as a pale yellow solid; $^1$H NMR (400 MHz, DMSO, 30° C.) 1.45 (9H, s), 2.99-3.22 (2H, m), 3.24-3.37 (2H, m), 3.50 (3H, s), 3.79-4.02 (2H, m), 4.74 (1H, d), 6.67-6.94 (2H, m), 7.18-7.42 (1H, m), 7.82 (1H, d), 8.99 (1H, s), 10.14 (1H, s); m/z: ES$^+$ [M+H]$^+$=531.

(4aR)-11-Chloro-12-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one

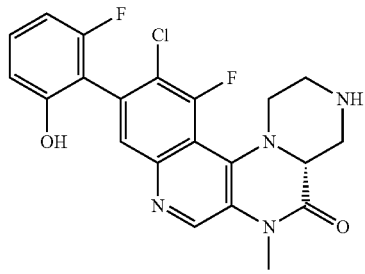 [SMILES: CN1C(=O)[C@H]2CNCCN2c2c1cnc1cc(-c3c(O)cccc3F)c(Cl)c(F)c21]

tert-Butyl (4aR)-11-chloro-12-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (164 mg, 0.31 mmol) was added to TFA (0.5 mL) and DCM (5 mL) at rt. The resulting solution was stirred at rt for 1 h. The solvent was removed in vacuo to afford crude product. This was purified by SCX (7M NH$_3$/MeOH) to afford ((4aR)-11-chloro-12-fluoro-10-(2-fluoro-6-hydroxyphenyl)-6-methyl-2,3,4,4a-tetrahydro-1H-pyrazino[1',2':4,5]

pyrazino[2,3-c]quinolin-5(6H)-one (116 mg, 87%) as a white solid; ¹H NMR (400 MHz, DMSO, 30° C.) 2.55-2.70 (1H, m), 2.79-2.92 (2H, m), 2.94-3.01 (1H, m), 3.12-3.21 (1H, m), 3.27-3.30 (1H, m), 3.52 (3H, s), 3.55-3.60 (1H, m), 3.65 (1H, d), 6.65-6.94 (2H, m), 7.23-7.42 (1H, m), 7.80 (1H, d), 8.98 (1H, s), 10.07 (1H, s); m/z: ES⁺ [M+H]⁺=431.

(4aR)-11-Chloro-12-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (Compound 59)

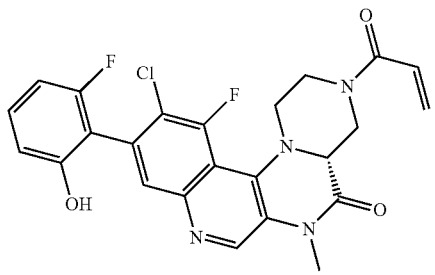 [SMILES: C=CC(=O)N1CCN2c3c(cnc4cc(-c5c(O)cccc5F)c(Cl)c(F)c34)N(C)C(=O)[C@H]2C1]

Acryloyl chloride (28.9 mg, 0.32 mmol) was added to (4aR)-11-chloro-12-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (106 mg, 0.25 mmol) and DIPEA (0.064 mL, 0.37 mmol) in DMF (2 mL) at 0° C. The resulting solution was stirred at 0° C. for 30 min. The crude reaction mixture was purified by C18-flash chromatography (0 to 50% MeCN in water (0.1% NH₄HCO₃)) to afford (4aR)-11-chloro-12-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (54 mg, 45%) as a white solid; ¹H NMR (400 MHz, DMSO, 30° C.) 2.61-2.74 (1H, m), 3.00-3.08 (1H, m), 3.35-3.44 (1H, m), 3.49 (3H, s), 3.56-3.64 (1H, m), 3.88-4.00 (1H, m), 4.42-4.52 (1H, m), 4.72-5.21 (1H, m), 5.49-5.90 (1H, m), 6.08-6.22 (1H, m), 6.75-6.88 (2H, m), 7.01-7.12 (1H, m), 7.28-7.37 (1H, m), 7.83 (1H, s), 9.00 (1H, s), 10.11 (1H, s); m/z: ES⁺ [M+H]⁺=485.

3-Bromo-4,5-dichloroaniline

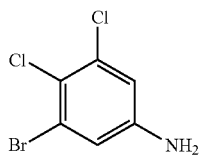

3-Bromo-5-chloroaniline (20 g, 96.87 mmol) was added dropwise to N-chlorosuccinimide (12.93 g, 96.87 mmol) in DMF (100 mL) at rt. The resulting solution was stirred at rt for 16 h. The solvent was removed in vacuo. The crude product obtained was purified by flash silica chromatography (5 to 10% EtOAc in petroleum ether) to afford 3-bromo-4,5-dichloroaniline (8 g, 34%) as a brown solid; ¹H NMR (300 MHz, DMSO, 30° C.) 6.02 (2H, s), 6.83 (1H, d), 6.94 (1H, d); m/z: ES⁺ [M+H]⁺=242.

5-[(3-Bromo-4,5-dichloroanilino)methylidene]-2,2-dimethyl-1,3-dioxane-4,6-dione

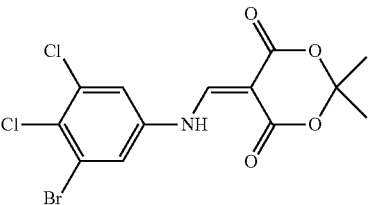 [SMILES: CC1(C)OC(=O)C(=CNc2cc(Cl)c(Cl)c(Br)c2)C(=O)O1]

5-(Methoxymethylidene)-2,2-dimethyl-1,3-dioxane-4,6-dione (8.35 g, 44.83 mmol) was added to 3-bromo-4,5-dichloroaniline (9 g, 37.36 mmol) in EtOH (200 mL) at rt. The resulting solution was stirred at 90° C. for 4 h. The reaction mixture was filtered and the solid collected washed with water (200 mL×2) to afford 5-[(3-bromo-4,5-dichloroanilino)methylidene]-2,2-dimethyl-1,3-dioxane-4,6-dione (11 g, 75%) as a pale yellow solid; ¹H NMR (400 MHz, DMSO, 30° C.) 1.70 (6H, s), 7.83 (1H, d), 8.25 (1H, d), 8.80-8.92 (1H, m), 11.59 (1H, d); m/z: ES⁺ [M+H]⁺=394.

7-Bromo-5,6-dichloroquinolin-4(1H)-one

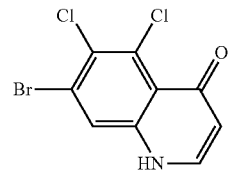

5-[(3-Bromo-4,5-dichloroanilino)methylidene]-2,2-dimethyl-1,3-dioxane-4,6-dione (7 g, 17.72 mmol) was added to DOWTHERM™ A (100 mL) at 210° C. The resulting solution was stirred at 210° C. for 40 min then cooled to rt and added to heptane (200 mL). The resulting suspension was filtered and the solid collected was washed with heptane then diethyl ether then dried on the filter to afford 7-bromo-5,6-dichloroquinolin-4(1H)-one (8.66 g, >100%) as a brown solid that was used without further purification; ¹H NMR (400 MHz, DMSO, 30° C.) 6.10-6.20 (1H, m), 7.68-7.78 (1H, m), 7.79-7.83 (1H, m), 11.37 (1H, s); m/z: ES⁺ [M+H]⁺=292.

7-Bromo-5,6-dichloro-3-nitroquinolin-4-ol

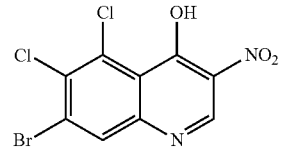

Fuming nitric acid (3.73 ml, 83.57 mmol) was added dropwise to 7-bromo-5,6-dichloroquinolin-4(1H)-one (8.16 g, 27.86 mmol) in propionic acid (130 ml, 1737.33 mmol) at 120° C. The resulting solution was stirred at 120° C. for 2 h. The reaction mixture was cooled to rt, water (70 mL) added and the resulting suspension filtered. The solid collected was washed with water (30 mL×2) and diethyl ether (30 mL) then dried to afford 7-bromo-5,6-dichloro-3-nitroquinolin-4-ol (6.33 g, 67%) as a pale solid; ¹H NMR (400 MHz, DMSO, 30° C.) 7.99 (1H, d), 8.77 (1H, d), 12.37 (1H, s); m/z: ES⁺ [M+H]⁺=337.

7-Bromo-4,5,6-trichloro-3-nitroquinoline

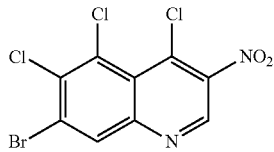 [SMILES: O=[N+]([O-])c1cnc2cc(Br)c(Cl)c(Cl)c2c1Cl]

7-Bromo-5,6-dichloro-3-nitroquinolin-4-ol (2.78 g, 8.23 mmol) was added to phosphorus(V) oxychloride (50 mL) and DMF (0.013 mL) at 25° C. The resulting solution was stirred at 120° C. for 2 h. The solvent was removed in vacuo. The residue obtained was quenched with sat. NaHCO₃ (50 mL) and extracted with DCM (100 mL×3). The organic layer was dried (Na₂SO₄), filtered and concentrated in vacuo to afford crude product. This was purified by flash silica chromatography (0 to 20% EtOAc in petroleum ether) to afford 7-bromo-4,5,6-trichloro-3-nitroquinoline (2.48 g, 85%) as a pale yellow solid; ¹H NMR (400 MHz, DMSO, 30° C.) 7.91-8.07 (1H, m), 8.79 (1H, d); m/z: ES⁺ [M+H]⁺=337.

1-tert-Butyl 3-methyl (3R)-4-(7-bromo-5,6-dichloro-3-nitroquinolin-4-yl)piperazine-1,3-dicarboxylate

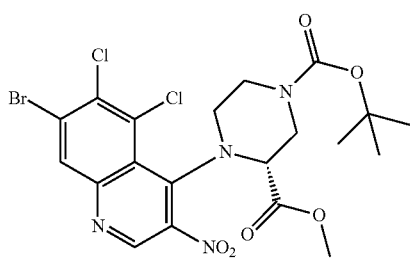 [SMILES: COC(=O)[C@H]1CN(C(=O)OC(C)(C)C)CCN1c1c([N+](=O)[O-])cnc2cc(Br)c(Cl)c(Cl)c12]

DIPEA (5.15 mL, 29.46 mmol) was added to 7-bromo-4,5,6-trichloro-3-nitroquinoline (3.5 g, 9.82 mmol) and 1-(tert-butyl) 3-methyl (R)-piperazine-1,3-dicarboxylate (4.8 g, 19.64 mmol) in THF (50 mL) at rt. The resulting solution was stirred at 80° C. for 2 days. The solvent was removed in vacuo. The crude product obtained was purified by flash silica chromatography (0 to 20% EtOAc in petroleum ether) to afford 1-tert-butyl 3-methyl (3R)-4-(7-bromo-5,6-dichloro-3-nitroquinolin-4-yl)piperazine-1,3-dicarboxylate (1.95 g, 35%) as a red solid; ¹H NMR (400 MHz, DMSO, 30° C.) 1.44 (9H, s), 3.25-3.32 (3H, m), 3.50-3.60 (2H, m), 3.75-3.85 (2H, m), 3.98-4.04 (1H, m), 4.12-4.22 (2H, m), 7.80-7.95 (1H, m), 9.07 (1H, d); m/z: ES⁺ [M+H]⁺=563.

tert-Butyl (4aR)-10-bromo-11,12-dichloro-5-oxo-1,2,4,4a,5,6-hexahydro-3H-pyrazino[1',2':4,5]pyrazino[2,3-c]quinoline-3-carboxylate

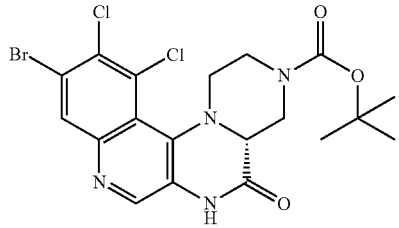 [SMILES: CC(C)(C)OC(=O)N1CCN2c3c(cnc4cc(Br)c(Cl)c(Cl)c34)NC(=O)[C@H]2C1]

Iron (0.940 g, 16.84 mmol) was added to 1-tert-butyl 3-methyl (3R)-4-(7-bromo-5,6-dichloro-3-nitroquinolin-4-yl)piperazine-1,3-dicarboxylate (1.9 g, 3.37 mmol) in glacial acetic acid (17 mL) at rt. The resulting solution was stirred at 80° C. for 1 h. The reaction mixture was filtered through CELITE™ The solvent was removed in vacuo. The crude product obtained was purified by flash silica chromatography (20 to 50% EtOAc in petroleum ether) to afford tert-butyl (4aR)-10-bromo-11,12-dichloro-5-oxo-1,2,4,4a,5,6-hexahydro-3H-pyrazino[1',2':4,5]pyrazino[2,3-c]quinoline-3-carboxylate (0.875 g, 52%) as a yellow solid; ¹H NMR (400 MHz, DMSO, 30° C.) 1.43 (9H, s), 2.98-3.15 (2H, m), 3.17-3.42 (2H, m), 3.71-3.95 (2H, m), 4.70 (1H, d), 8.07 (1H, d), 8.74 (1H, d), 11.04 (1H, s); m/z: ES⁺ [M+H]⁺=501.

tert-Butyl (4aR)-10-bromo-11,12-dichloro-6-methyl-5-oxo-1,2,4,4a,5,6-hexahydro-3H-pyrazino[1',2':4,5]pyrazino[2,3-c]quinoline-3-carboxylate

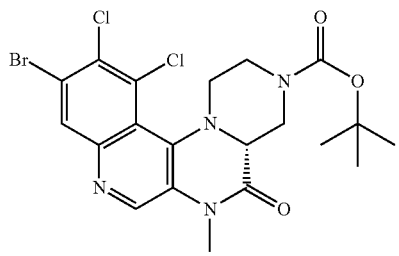 [SMILES: CN1C(=O)[C@H]2CN(C(=O)OC(C)(C)C)CCN2c2c1cnc1cc(Br)c(Cl)c(Cl)c21]

2-(tert-Butylimino)-N,N-diethyl-1,3-dimethyl-1,3,2λ⁵-diazaphosphinan-2-amine (1352 mg, 4.93 mmol) was added to tert-butyl (4aR)-10-bromo-11,12-dichloro-5-oxo-1,2,4,4a,5,6-hexahydro-3H-pyrazino[1',2':4,5]pyrazino[2,3-c]quinoline-3-carboxylate (825 mg, 1.64 mmol) and iodomethane (0.308 mL, 4.93 mmol) in DCM (10 mL) at 0° C. The resulting solution was stirred at 0° C. for 30 min. The solvent was removed in vacuo. The residue obtained was purified by flash silica chromatography (20 to 50% EtOAc in petroleum ether) to afford crude product. This was purified by preparative chiral-HPLC (Column: CHIRALCEL OJ-H2*25 cm, 5 ᵯ m Chiral-P (OJ-H). injection Volume (mg, ml): 1.5 ml. % Solvent A: CO₂: 75. % Solvent B: IPA:MeCN=1:1 (2 mM NH₃-MeOH)) to afford tert-butyl (4aR)-10-bromo-11,12-dichloro-6-methyl-5-oxo-1,2,4,4a,5,6-hexahydro-3H-pyrazin o[1',2':4,5]pyrazino[2,3-c]quinoline-3-carboxylate (410 mg, 48%) as a pale yellow solid; ¹H NMR (400 MHz, DMSO, 30° C.) 1.44 (9H, s), 2.53-2.70 (2H, m), 2.98-3.37

(2H, m), 3.49 (3H, s), 3.72-3.99 (2H, m), 4.72 (1H, d), 8.03 (1H, s), 9.08 (1H, s); m/z: ES⁺ [M+H]⁺=515.

tert-Butyl (4aR)-11,12-dichloro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate

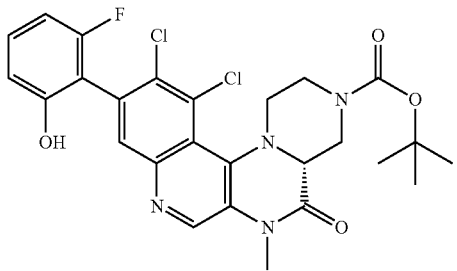 [SMILES: CN1C(=O)[C@H]2CN(C(=O)OC(C)(C)C)CCN2c2c1cnc1cc(-c3c(O)cccc3F)c(Cl)c(Cl)c21]

Tetrakis(triphenylphosphine)palladium(0) (44.8 mg, 0.04 mmol) was added to tert-butyl (4aR)-10-bromo-11,12-dichloro-6-methyl-5-oxo-1,2,4,4a,5,6-hexahydro-3H-pyrazino[1',2':4,5]pyrazino[2,3-c]quinoline-3-carboxylate (200 mg, 0.39 mmol), (2-fluoro-6-hydroxyphenyl)boronic acid (91 mg, 0.58 mmol) and K₂CO₃ (107 mg, 0.77 mmol) in 1,4-dioxane (4 mL) and water (1 mL) at rt. The resulting solution was stirred at 100° C. for 1 h. The solvent was removed in vacuo. The crude product obtained was purified by flash silica chromatography (0 to 50% EtOAc in petroleum ether) to afford tert-butyl (4aR)-11,12-dichloro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (200 mg, 94%) as a pale yellow solid; ¹H NMR (400 MHz, DMSO, 30° C.) 1.44 (9H, d), 2.71-2.78 (3H, m), 3.04-3.28 (2H, m), 3.38-3.60 (2H, m), 3.79-4.02 (2H, m), 4.65-4.80 (1H, m), 6.71-6.88 (2H, m), 7.27-7.32 (1H, m), 7.61-7.65 (1H, m), 9.09-9.13 (1H, m), 10.10-10.20 (1H, m); m/z: ES⁺ [M+H]⁺=547.

(4aR)-11,12-dichloro-10-(2-fluoro-6-hydroxyphenyl)-6-methyl-2,3,4,4a-tetrahydro-1H-pyrazino[1',2':4,5]pyrazino[2,3-c]quinolin-5(6H)-one

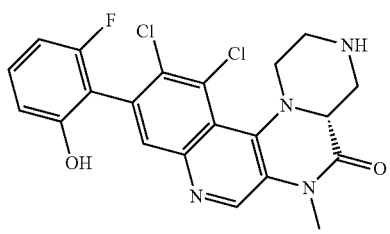 [SMILES: CN1C(=O)[C@H]2CNCCN2c2c1cnc1cc(-c3c(O)cccc3F)c(Cl)c(Cl)c21]

tert-Butyl (4aR)-11,12-dichloro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (180 mg, 0.33 mmol) was added to DCM (5 mL) and TFA (0.5 mL) at rt. The resulting solution was stirred at rt for 1 h. The solvent was removed in vacuo to afford crude product. This was purified by SCX (7M NH₃/MeOH) to afford (4aR)-11,12-dichloro-10-(2-fluoro-6-hydroxyphenyl)-6-methyl-2,3,4,4a-tetrahydro-1H-pyrazino[1',2':4,5]pyrazino[2,3-c]quinolin-5(6H)-one (114 mg, 77%) as a white solid; ¹H NMR (400 MHz, DMSO, 30° C.) 2.54-2.70 (1H, m), 2.80-2.90 (2H, m), 2.93-3.04 (2H, m), 3.06-3.13 (1H, m), 3.30 (3H, s), 3.60-3.74 (2H, m), 6.73-6.90 (2H, m), 7.27-7.35 (1H, m), 7.57-7.63 (1H, m), 9.10 (1H, d), 10.11 (1H, s); m/z: ES⁺ [M+H]⁺=447.

(4aR)-11,12-Dichloro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (Compound 60)

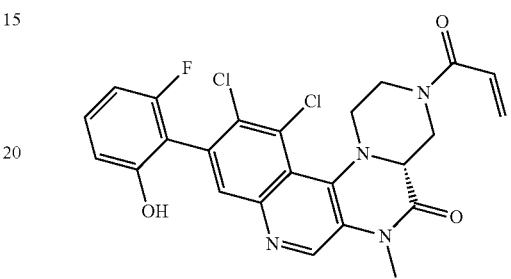

Acryloyl chloride (31.5 mg, 0.35 mmol) was added to (4aR)-11,12-dichloro-10-(2-fluoro-6-hydroxyphenyl)-6-methyl-2,3,4,4a-tetrahydro-1H-pyrazino[1',2':4,5]pyrazino[2,3-c]quinolin-5(6H)-one (103.8 mg, 0.23 mmol) and DIPEA (0.061 mL, 0.35 mmol) in DMF (2 mL) at 0° C. The resulting solution was stirred at 0° C. for 30 min. The crude reaction mixture was purified by C18-flash chromatography (0 to 60% MeCN in water (0.1% NH₄HCO₃)) to afford crude product. This was purified by preparative chiral-HPLC (Column: XBridge Prep OBD C18 Column 19*250 mm, 5 m; Mobile Phase A: Water (10 mmolL/L NH₄HCO₃), Mobile Phase B: MeCN; Flow rate: 25 mL/min; Gradient: 35% B to 58% B in 8 min; 254/220 nm) to afford (4aR)-11,12-dichloro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (32 mg, 28%) as a white solid; ¹H NMR (300 MHz, DMSO, 30° C.) 2.59-2.70 (1H, m), 3.03-3.17 (1H, m), 3.28-3.33 (1H, m), 3.52 (3H, s), 3.55-3.64 (1H, m), 3.88-4.54 (2H, m), 4.68-5.30 (1H, m), 5.61-5.85 (1H, m), 6.07-6.20 (1H, m), 6.73-6.90 (2H, m), 6.99-7.15 (1H, m), 7.25-7.40 (1H, m), 7.66 (1H, s), 9.13 (1H, s), 10.16 (1H, s); m/z: ES⁺ [M+H]⁺=501.

2-Bromo-3-[(4-methoxyphenyl)methoxy]benzaldehyde

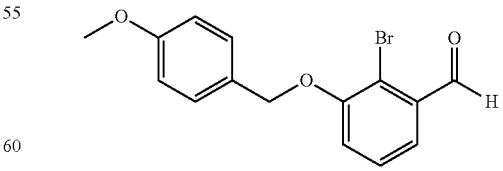

1-(Chloromethyl)-4-methoxybenzene (4.28 g, 27.36 mmol) was added to 2-bromo-3-hydroxybenzaldehyde (5 g, 24.87 mmol), K₂CO₃ (6.88 g, 49.75 mmol) and potassium iodide (0.826 g, 4.97 mmol) in DMF (50 mL) at rt. The resulting mixture was stirred at rt overnight. The reaction mixture was diluted with EtOAc (150 mL), washed sequentially with water (100 mL) and brine (100 mL×2). The organic layer was dried (Na₂SO₄) and concentrated in vacuo to afford crude product. This was purified by flash silica chromatography (0 to 100% EtOAc in petroleum ether) to afford 2-bromo-3-[(4-methoxyphenyl)methoxy]benzaldehyde (7.8 g, 98%) as a white solid; ¹H NMR (300 MHz, DMSO, 30° C.) 3.77 (3H, s), 5.21 (2H, s), 6.94-7.04 (2H, m), 7.41-7.56 (5H, m), 10.29 (1H, s); m/z: ES⁺ [M+H]⁺=321.

2-Bromo-1-(difluoromethyl)-3-[(4-methoxyphenyl)methoxy]benzene

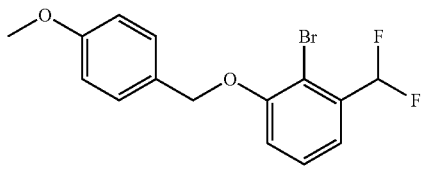 [SMILES: COc1ccc(COc2cccc(C(F)F)c2Br)cc1]

(Diethylamino)sulfur trifluoride (4.11 mL, 31.14 mmol) was added to 2-bromo-3-[(4-methoxyphenyl)methoxy]benzaldehyde (4 g, 12.45 mmol) in DCM (50 mL) at 0° C. The resulting suspension was stirred at rt overnight. The reaction mixture was quenched with sat. NaHCO₃ (100 mL) diluted with DCM (200 mL), washed sequentially with sat. NaHCO₃ (100 mL) and brine (200 mL). The organic layer was dried (Na₂SO₄) and concentrated in vacuo to afford crude product as a pale yellow oil. This was purified by flash silica chromatography (0 to 50% EtOAc in petroleum ether) to afford 2-bromo-1-(difluoromethyl)-3-[(4-methoxyphenyl)methoxy]benzene (3.65 g, 85%) as a white solid; ¹H NMR (300 MHz, DMSO, 30° C.) 3.77 (3H, s), 5.18 (2H, s), 6.92-7.55 (8H, m).

2-{2-(Difluoromethyl)-6-[(4-methoxyphenyl)methoxy]phenyl}-4,4,5,5-tetramethyl-1,3,2-dioxaborolane

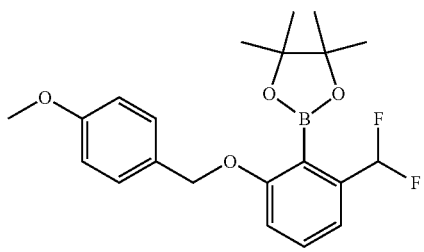 [SMILES: COc1ccc(COc2cccc(C(F)F)c2B2OC(C)(C)C(C)(C)O2)cc1]

2.5 M n-Butyllithium solution in hexanes (2.8 mL, 6.99 mmol) was added to 2-bromo-1-(difluoromethyl)-3-[(4-methoxyphenyl)methoxy]benzene (2 g, 5.83 mmol) in THF (30 mL) at −78° C. The resulting mixture was stirred at −78° C. for 1 h then 4,4,5,5-tetramethyl-2-[(propan-2-yl)oxy]-1,3,2-dioxaborolane (1.193 g, 6.41 mmol) was added and the reaction mixture stirred overnight at rt. The reaction mixture was quenched with sat. NH₄Cl (100 mL), diluted with EtOAc (200 mL), washed sequentially with sat. NH₄Cl (200 mL) and brine (200 mL×2). The organic layer was dried (Na₂SO₄) and concentrated in vacuo to afford crude product. This was purified by flash C18-flash chromatography (0 to 100% EtOAc in petroleum ether) to afford 2-{2-(difluoromethyl)-6-[(4-methoxyphenyl)methoxy]phenyl}-4,4,5,5-tetramethyl-1,3,2-dioxaborolane (1.02 g, 45%) as a white solid; ¹H NMR (300 MHz, DMSO, 30° C.) 1.21 (12H, s), 3.76 (3H, s), 5.04 (2H, s), 6.72-6.98 (3H, m), 7.09-7.23 (2H, m), 7.36-7.53 (3H, m).

tert-Butyl (4aR)-11-chloro-10-{2-(difluoromethyl)-6-[(4-methoxyphenyl)methoxy]phenyl}-9-fluoro-6-methyl-5-oxo-1,2,4,4a,5,6-hexahydro-3H-pyrazino[1',2':4,5]pyrazino[2,3-c]quinoline-3-carboxylate

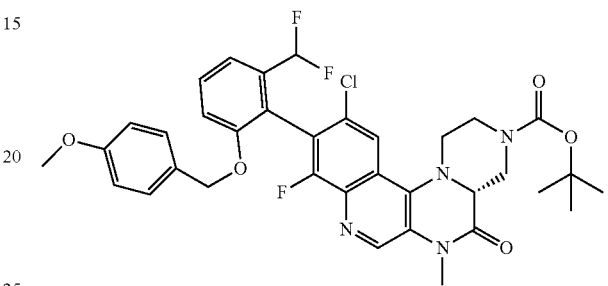

tert-Butyl (4aR)-10-bromo-11-chloro-9-fluoro-6-methyl-5-oxo-1,2,4,4a,5,6-hexahydro-3H-pyrazino[1',2':4,5]pyrazino[2,3-c]quinoline-3-carboxylate (300 mg, 0.6 mmol), 2-{2-(difluoromethyl)-6-[(4-methoxyphenyl)methoxy]phenyl}-4,4,5,5-tetramethyl-1,3,2-dioxaborolane (305 mg, 0.78 mmol), K₂CO₃ (166 mg, 1.2 mmol), RuPhos (28 mg, 0.06 mmol) and RuPhos-Pd-G3 (50.2 mg, 0.06 mmol) were suspended in 1,4-dioxane/H₂O (15 mL, 4:1 ratio) and sealed into a microwave tube. The reaction mixture was heated at 100° C. for 45 min in the microwave reactor and cooled to rt. The solvent was removed in vacuo. The crude product obtained was purified by flash silica chromatography (30 to 70% EtOAc in petroleum ether) to afford tert-butyl (4aR)-11-chloro-10-{2-(difluoromethyl)-6-[(4-methoxyphenyl)methoxy]phenyl}-9-fluoro-6-methyl-5-oxo-1,2,4,4a,5,6-hexahydro-3H-pyrazino[1',2':4,5]pyrazino[2,3-c]quinoline-3-carboxylate (350 mg, 85%) as a yellow solid; ¹H NMR (300 MHz, DMSO, 30° C.) 1.46 (9H, s), 2.65-2.79 (1H, m), 3.19-3.34 (3H, m), 3.50 (3H, s), 3.68 (3H, s), 3.80-3.99 (3H, m), 4.76 (1H, d), 5.07 (2H, s), 6.42-7.27 (4H, m), 7.37 (1H, d), 7.44 (1H, t), 7.54-7.70 (1H, m), 8.08 (1H, d), 8.99 (1H, s); m/z: ES⁺ [M+H]⁺=683.

(4aR)-11-Chloro-10-[2-(difluoromethyl)-6-hydroxyphenyl]-9-fluoro-6-methyl-2,3,4,4a-tetrahydro-1H-pyrazino[1',2':4,5]pyrazino[2,3-c]quinolin-5(6H)-one.1HCl

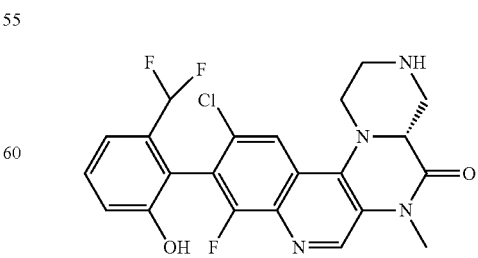

4M HCl in 1,4-dioxane (4 mL, 16.00 mmol) was added to tert-butyl (4aR)-11-chloro-10-{2-(difluoromethyl)-6-[(4- methoxyphenyl)methoxy]phenyl}-9-fluoro-6-methyl-5-oxo-1,2,4,4a,5,6-hexahydro-3H-pyrazino[1',2':4,5]pyrazino[2,3-c]quinoline-3-carboxylate (340 mg, 0.5 mmol) in MeOH (4 mL) at rt. The resulting mixture was stirred at 60° C. for 1 h. The solvent was removed in vacuo to afford (4aR)-11-chloro-10-[2-(difluoromethyl)-6-hydroxyphenyl]-9-fluoro-6-methyl-2,3,4,4a-tetrahydro-1H-pyrazino[1',2':4,5]pyrazino[2,3-c]quinolin-5(6H)-one.1HCl (275 mg, >100%) as a white solid that was used without further purification; $^1$H NMR (300 MHz, DMSO, 30° C.) 2.89-3.03 (1H, m), 3.17-3.24 (1H, m), 3.36-3.54 (2H, m), 3.59 (3H, s), 3.64-3.76 (1H, m), 3.99 (1H, d), 4.22-4.31 (1H, m), 6.36-6.96 (2H, m), 7.22 (1H, s), 7.37 (1H, d), 7.48 (1H, t), 8.17 (1H, s), 9.05 (1H, s); m/z: ES$^+$ [M+H]$^+$=463.

(4aR)-11-Chloro-10-[2-(difluoromethyl)-6-hydroxyphenyl]-9-fluoro-6-methyl-3-(prop-2-enoyl)-2,3,4,4a-tetrahydro-1H-pyrazino[1',2':4,5]pyrazino[2,3-c]quinolin-5(6H)-one (Atropisomer 1, Compound 61; Atropisomer 2, Compound 62)

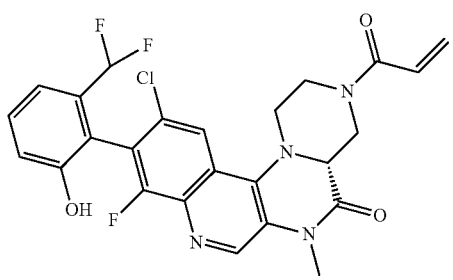 [SMILES: C=CC(=O)N1CCN2c3c(cnc4c(F)c(-c5c(O)cccc5C(F)F)c(Cl)cc34)N(C)C(=O)[C@H]2C1]

Acryloyl chloride (40.8 mg, 0.45 mmol) was added to (4aR)-11-chloro-10-[2-(difluoromethyl)-6-hydroxyphenyl]-9-fluoro-6-methyl-2,3,4,4a-tetrahydro-1H-pyrazino[1',2':4,5]pyrazino[2,3-c]quinolin-5(6H)-one.1HCl (250 mg, 0.5 mmol) and DIPEA (0.262 mL, 1.50 mmol) in DMF (5 mL) at −10° C. The resulting mixture was stirred at rt for 1 h. The crude reaction mixture was purified by C18-flash chromatography (0 to 100% MeCN in water (0.05% formic acid)) to afford crude product as a white solid. This was purified by preparative chiral-HPLC (Column: CHIRALPAK IC, 2*25 cm, 5 ? m; Mobile Phase A: Hex:DCM=3:1 (10 mM NH$_3$-MEOH)-HPLC, Mobile Phase B: EtOH-HPLC; Flow rate: 16 mL/min; Gradient: 50 B to 50 B in 16 min; 220/254 nm) to afford atropisomer 1 of (4aR)-11-chloro-10-[2-(difluoromethyl)-6-hydroxyphenyl]-9-fluoro-6-methyl-3-(prop-2-enoyl)-2,3,4,4a-tetrahydro-1H-pyrazino[1',2':4,5]pyrazino[2,3-c]quinolin-5(6H)-one (26 mg, 23%) as a white solid; $^1$H NMR (300 MHz, DMSO, 30° C.) 2.60-2.72 (1H, m), 3.21 (1H, t), 3.34-3.39 (1H, m), 3.50 (3H, s), 3.56-3.67 (1H, m), 3.89-4.10 (1H, m), 4.39-4.52 (1H, m), 4.71-4.84 (1H, m), 5.64-5.82 (1H, m), 6.15 (1H, dd), 6.40-6.78 (1H, m), 7.00-7.13 (1H, m), 7.15-7.23 (2H, m), 7.38-7.56 (1H, m), 8.11 (1H, s), 9.00 (1H, s), 10.10 (1H, s); m/z: ES$^+$ [M+H]$^+$=517. This was followed by atropisomer 2 of (4aR)-11-chloro-10-[2-(difluoromethyl)-6-hydroxyphenyl]-9-fluoro-6-methyl-3-(prop-2-enoyl)-2,3,4,4a-tetrahydro-1H-pyrazino[1',2':4,5]pyrazino[2,3-c]quinolin-5(6H)-one (27 mg, 23%) as a white solid; $^1$H NMR (300 MHz, DMSO, 30° C.) 2.62-2.72 (1H, m), 3.21 (1H, t), 3.28-3.31 (1H, m), 3.50 (3H, s), 3.55-3.68 (1H, m), 3.89-4.07 (1H, m), 4.39-4.51 (1H, m), 4.72-4.84 (1H, m), 5.66-5.81 (1H, m), 6.15 (1H, dd), 6.43-6.77 (1H, m), 7.01-7.13 (1H, m), 7.14-7.26 (2H, m), 7.38-7.57 (1H, m), 8.11 (1H, s), 9.00 (1H, s), 10.06 (1H, s); m/z: ES$^+$ [M+H]$^+$=517.

tert-Butyl (2R,5R)-4-(7-bromo-6,8-difluoro-3-nitroquinolin-4-yl)-5-(hydroxymethyl)-2-methylpiperazine-1-carboxylate

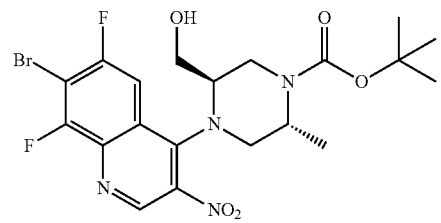 [SMILES: C[C@@H]1CN(c2c([N+](=O)[O-])cnc3c(F)c(Br)c(F)cc23)[C@@H](CO)CN1C(=O)OC(C)(C)C]

DIPEA (1.517 mL, 8.68 mmol) was added to 7-bromo-4-chloro-6,8-difluoro-3-nitroquinoline (702 mg, 2.17 mmol) and tert-butyl (2R,5R)-5-(hydroxymethyl)-2-methylpiperazine-1-carboxylate (500 mg, 2.17 mmol) in THF (8 mL) at 25° C. The resulting solution was stirred at 80° C. for 4 h. The solvent was removed in vacuo. The crude product was purified by flash silica chromatography (10 to 50% EtOAc in petroleum ether) to afford tert-butyl (2R,5R)-4-(7-bromo-6,8-difluoro-3-nitroquinolin-4-yl)-5-(hydroxymethyl)-2-methylpiperazine-1-carboxylate (861 mg, 77%) as a yellow solid; $^1$H NMR (400 MHz, DMSO, 30° C.) 1.21 (3H, d), 1.44 (9H, s), 2.84-3.00 (1H, m), 3.27-3.34 (1H, m), 3.47-3.68 (2H, m), 3.70-3.84 (2H, m), 3.97-4.08 (1H, m), 4.21-4.33 (1H, m), 4.64 (1H, t), 7.92 (1H, dd), 9.02 (1H, s); m/z: ES$^+$ [M+H]$^+$=517.

tert-Butyl (2R,4aR)-10-bromo-9,11-difluoro-2-methyl-1,2,4a,5-tetrahydropyrazino[1',2':4,5][1,4]oxazino[2,3-c]quinoline-3(4H)-carboxylate

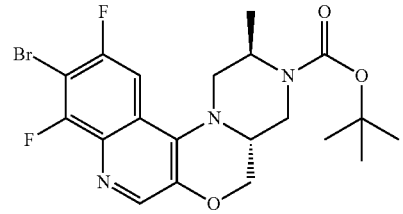 [SMILES: C[C@@H]1CN2c3c(cnc4c(F)c(Br)c(F)cc34)OC[C@H]2CN1C(=O)OC(C)(C)C]

1M Lithium bis(trimethylsilyl)amide in THF (2.409 mL, 2.41 mmol) was added to tert-butyl (2R,5R)-4-(7-bromo-6,8-difluoro-3-nitroquinolin-4-yl)-5-(hydroxymethyl)-2-methylpiperazine-1-carboxylate (831 mg, 1.61 mmol) in DMF (5 mL) at rt. The resulting solution was stirred at 120° C. for 6 h. The crude reaction mixture was purified by C18-flash chromatography (0 to 70% MeCN in water (0.1% NH$_4$HCO$_3$)) to afford tert-butyl (2R,4aR)-10-bromo-9,11-difluoro-2-methyl-1,2,4a,5-tetrahydropyrazino[1',2':4,5][1,4]oxazino[2,3-c]quinoline-3(4H)-carboxylate (120 mg, 16%) as a brown solid; $^1$H NMR (400 MHz, DMSO, 30° C.) 1.43 (9H, s), 1.50 (3H, d), 2.97-3.12 (1H, m), 3.24-3.30 (1H, m), 3.31-3.38 (2H, m), 3.93-4.01 (1H, m), 4.22-4.27 (1H, m), 4.32-4.37 (2H, m), 7.45 (1H, dd), 8.58 (1H, s); m/z: ES$^+$ [M+H]$^+$=470.

tert-Butyl (2R,4aR)-9,11-difluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate Atropisomer 1 and 2

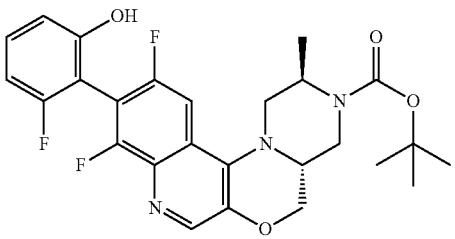 [SMILES: C[C@@H]1CN2c3c(cnc4c(F)c(-c5c(O)cccc5F)c(F)cc34)OC[C@H]2CN1C(=O)OC(C)(C)C]

(2-Fluoro-6-hydroxyphenyl)boronic acid (72.9 mg, 0.47 mmol) was added to tert-butyl (2R,4aR)-10-bromo-9,11-difluoro-2-methyl-1,2,4a,5-tetrahydropyrazino[1',2':4,5][1,4]oxazino[2,3-c]quinoline-3(4H)-carboxylate (110 mg, 0.23 mmol), K$_2$CO$_3$ (64.6 mg, 0.47 mmol), RuPhos (11 mg, 0.02 mmol) and RuPhos-Pd-G3 (19.6 mg, 0.02 mmol) in 1,4-dioxane (2 mL) and water (0.5 mL, 4:1 ratio) at 25° C. The resulting solution was stirred at 100° C. for 4 h. The crude reaction mixture was purified by C18-flash chromatography (0 to 70% MeCN in water (0.1% formic acid)) to afford crude product as a pale yellow solid. This was purified by preparative chiral-HPLC (Column: CHIRALPAK IC, 2*25 cm, 5 m; Mobile Phase A: Hex (8 mmol/L NH$_3$.MeOH)-HPLC, Mobile Phase B: EtOH-HPLC; Flow rate: 20 mL/min; Gradient: 30 B to 30 B in 10 min; 254/220 nm) to afford atropisomer 1 of tert-butyl (2R,4aR)-9,11-difluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (40 mg, 34%) as a white solid; $^1$H NMR (400 MHz, MeOD, 30° C.) 1.51 (9H, s), 1.65 (3H, d), 3.09-3.17 (1H, m), 3.36-3.41 (1H, m), 3.47-3.55 (1H, m), 3.74-3.82 (1H, m), 4.09-4.18 (1H, m), 4.29-4.36 (1H, m), 4.42-4.53 (2H, m), 6.70-6.82 (2H, m), 7.27-7.37 (1H, m), 7.51 (1H, d), 8.48 (1H, s); m/z: ES$^+$ [M+H]$^+$=502. This was followed by atropisomer 2 of tert-butyl (2R,4aR)-9,11-difluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (38 mg, 32%) as a white solid; $^1$H NMR (400 MHz, MeOD, 30° C.) 1.51 (9H, s), 1.65 (3H, d), 3.09-3.17 (1H, m), 3.35-3.42 (1H, m), 3.47-3.55 (1H, m), 3.73-3.83 (1H, m), 4.09-4.18 (1H, m), 4.29-4.37 (1H, m), 4.39-4.53 (2H, m), 6.69-6.84 (2H, m), 7.27-7.37 (1H, m), 7.51 (1H, dd), 8.48 (1H, s); m/z: ES$^+$ [M+H]$^+$=502.

2-[(2R,4aR)-9,11-Difluoro-2-methyl-1,2,3,4,4a,5-hexahydropyrazino[1',2':4,5][1,4]oxazino[2,3-c]quinolin-10-yl]-3-fluorophenol Atropisomer 1

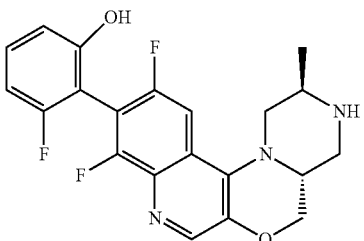

TFA (0.3 mL, 3.89 mmol) was added to atropisomer 1 of tert-butyl (2R,4aR)-9,11-difluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (35 mg, 0.07 mmol) in DCM (3 mL) at rt. The resulting solution was stirred at rt for 1 h. The solvent was removed in vacuo to afford crude product. This was purified by SCX (7M NH$_3$/MeOH) to afford atropisomer 1 of 2-[(2R,4aR)-9,11-difluoro-2-methyl-1,2,3,4,4a,5-hexahydropyrazino[1',2':4,5][1,4]oxazino[2,3-c]quinolin-10-yl]-3-fluorophenol (26 mg, 93%) as a white solid; $^1$H NMR (400 MHz, MeOD, 30° C.) 1.43 (3H, d), 3.34-3.42 (2H, m), 3.56-3.69 (2H, m), 3.93-4.05 (1H, m), 4.26-4.36 (1H, m), 4.38-4.49 (2H, m), 6.67-6.86 (2H, m), 7.27-7.41 (1H, m), 7.57 (1H, d), 8.43 (1H, s); m/z: ES$^+$ [M+H]$^+$=402.

1-[(2R,4aR)-9,11-Difluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one (Atropisomer 1, Compound 63)

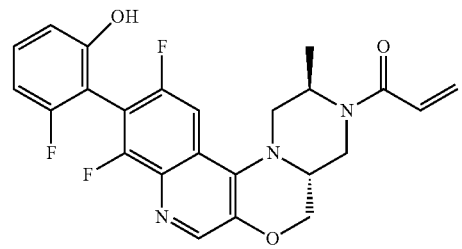 [SMILES: C=CC(=O)N1C[C@@H]2COc3cnc4c(F)c(-c5c(O)cccc5F)c(F)cc4c3N2C[C@H]1C]

A solution of acryloyl chloride (7.9 mg, 0.09 mmol) in DMF (0.5 mL) was added dropwise to a stirred solution of atropisomer 1 of 2-[(2R,4aR)-9,11-difluoro-2-methyl-1,2,3,4,4a,5-hexahydropyrazino[1',2':4,5][1,4]oxazino[2,3-c]quinolin-10-yl]-3-fluorophenol (35 mg, 0.09 mmol) and DIPEA (22.5 mg, 0.17 mmol) in DMF (0.5 mL) at 0° C. The resulting solution was stirred at 0° C. for 30 min. The reaction mixture was quenched with water (1 mL). The crude reaction mixture was purified by C18-flash chromatography (0 to 25% MeCN in water (0.1% formic acid)) to afford atropisomer 1 of 1-[(2R,4aR)-9,11-difluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one (13 mg, 32%) as a white solid; $^1$H NMR (400 MHz, MeOD, 30° C.) 1.66-1.86 (3H, m), 3.06-3.18 (1H, m), 3.40-3.63 (2H, m), 3.64-3.83 (1H, m), 3.99-4.71 (4H, m), 5.81 (1H, d), 6.27 (1H, dd), 6.69-6.87 (3H, m), 7.27-7.37 (1H, m), 7.52 (1H, d), 8.48 (1H, s); m/z: ES$^+$ [M+H]$^+$=456.

2-[(2R,4aR)-9,11-Difluoro-2-methyl-1,2,3,4,4a,5-hexahydropyrazino[1',2':4,5][1,4]oxazino[2,3-c]quinolin-10-yl]-3-fluorophenol Atropisomer 2

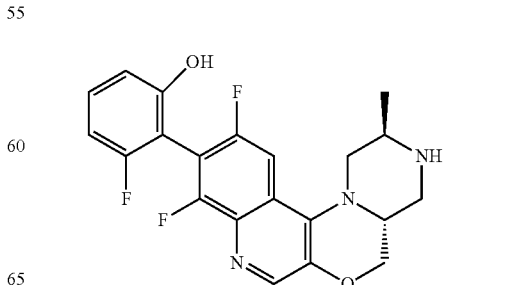

TFA (0.3 mL, 3.89 mmol) was added to atropisomer 2 of tert-butyl (2R,4aR)-9,11-difluoro-10-(2-fluoro-6-hydroxyphenyl)-2-methyl-1,2,4a,5-tetrahydropyrazino[1',2':4,5][1,4]oxazino[2,3-c]quinoline-3(4H)-carboxylate (33 mg, 0.07 mmol) in DCM (3 mL) at 25° C. The resulting solution was stirred at rt for 1 h. The solvent was removed in vacuo to afford crude product. This was purified by SCX (7M NH$_3$/MeOH) to afford atropisomer 2 of 2-[(2R,4aR)-9,11-difluoro-2-methyl-1,2,3,4,4a,5-hexahydropyrazino[1',2':4,5][1,4]oxazino[2,3-c]quinolin-10-yl]-3-fluorophenol (25 mg, 95%) as a white solid; $^1$H NMR (400 MHz, MeOD, 30° C.) 1.42 (3H, d), 3.20-3.30 (2H, m), 3.54-3.66 (2H, m), 3.83-3.98 (1H, m), 4.22-4.31 (1H, m), 4.37-4.51 (2H, m), 6.67-6.87 (2H, m), 7.28-7.40 (1H, m), 7.50-7.56 (1H, m), 8.41 (1H, s); m/z: ES+ [M+H]$^+$=402.

1-[(2R,4aR)-9,11-Difluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one (Atropisomer 2, Compound 64)

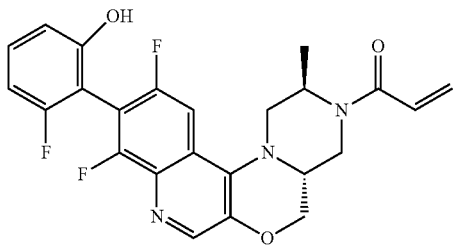 [SMILES: C=CC(=O)N1C[C@@H]2COc3cnc4c(F)c(-c5c(O)cccc5F)c(F)cc4c3N2C[C@H]1C]

A solution of acryloyl chloride (6.8 mg, 0.07 mmol) in DMF (0.5 mL) was added dropwise to a stirred solution of atropisomer 2 of 2-[(2R,4aR)-9,11-difluoro-2-methyl-1,2,3,4,4a,5-hexahydropyrazino[1',2':4,5][1,4]oxazino[2,3-c]quinolin-10-yl]-3-fluorophenol (30 mg, 0.07 mmol) and DIPEA (9.7 mg, 0.07 mmol) in DMF (2 mL) at 0° C. The resulting solution was stirred at 0° C. for 30 min. The reaction mixture was quenched with water (1 mL). The crude reaction mixture was purified by C18-flash chromatography (0 to 25% MeCN in water (0.1% formic acid)) to afford atropisomer 2 of 1-[(2R,4aR)-9,11-difluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one (19 mg, 54%) as a white solid; $^1$H NMR (400 MHz, MeOD, 30° C.) 1.62-1.88 (3H, m), 3.12-3.19 (1H, m), 3.40-3.66 (2H, m), 3.70-3.83 (1H, m), 4.08-4.69 (4H, m), 5.82 (H, d), 6.28 (1H, dd), 6.69-6.88 (3H, m), 7.27-7.38 (1H, m), 7.53 (1H, d), 8.49 (1H, s); m/z: ES$^+$ [M+H]$^+$=456.

4-Iodo-5-methyl-1H-benzimidazole

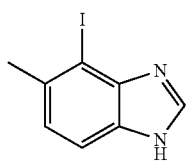

N-Iodosuccinimide (3.75 g, 16.65 mmol) was added to 5-methyl-1H-benzimidazole (2 g, 15.13 mmol) in TFA (10 mL). The resulting mixture was stirred at 80° C. for 1 h. The solvent was removed in vacuo. The residue obtained was diluted with EtOAc (100 mL) and washed with sat. NaHCO$_3$ (50 mL×2) and brine (50 mL). The organic layer was dried (Na$_2$SO$_4$) and concentrated in vacuo to afford crude product. This was purified by flash silica chromatography (0 to 5% MeOH in DCM) to afford 4-iodo-5-methyl-1H-benzimidazole (0.92 g, 24%) as a white solid; $^1$H NMR (300 MHz, CDCl$_3$, 30° C.) 2.59 (3H, s), 7.21 (1H, d), 7.55 (1H, d), 8.08 (1H, s); m/z: ES$^+$ [M+H]$^+$=259.

4-Iodo-5-methyl-1-(oxan-2-yl)-1H-benzimidazole

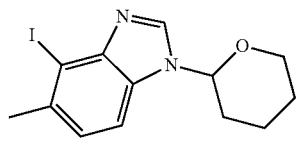

4-Methylbenzenesulfonic acid hydrate (67.8 mg, 0.36 mmol) was added to 4-iodo-5-methyl-1H-benzimidazole (920 mg, 3.57 mmol) and 3,4-dihydro-2H-pyran (1.63 mL, 17.83 mmol) in THF (10 mL). The resulting mixture was stirred at 80° C. overnight. The solvent was removed in vacuo. The crude product obtained was purified by flash silica chromatography (10 to 50% EtOAc in petroleum ether) to afford 4-iodo-5-methyl-1-(oxan-2-yl)-1H-benzimidazole (1.05 g, 86%) as a white solid; $^1$H NMR (300 MHz, DMSO, 30° C.) 1.53-1.65 (2H, m), 1.64-1.82 (1H, m), 1.92-2.05 (2H, m), 2.10-2.25 (1H, m), 2.50 (3H, s), 3.64-3.80 (1H, m), 3.91-4.04 (1H, m), 5.64 (1H, dd), 7.24 (1H, d), 7.56 (1H, d), 8.41 (1H, s); m/z: ES$^+$ [M+H]$^+$=343.

[(4aR)-3-(tert-Butoxycarbonyl)-11-chloro-1,2,3,4,4a,5-hexahydropyrazino[1',2':4,5][1,4]oxazino[2,3-c]quinolin-10-yl]boronic acid

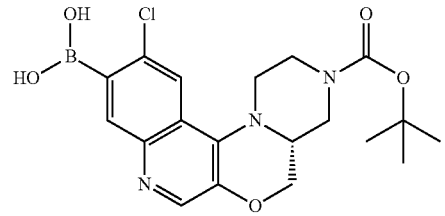 [SMILES: CC(C)(C)OC(=O)N1CCN2c3c(cnc4cc(B(O)O)c(Cl)cc34)OC[C@H]2C1]

Bis(triphenylphosphine)palladium(II) dichloride (0.309 g, 0.44 mmol) was added to tert-butyl (4aR)-10-bromo-11-chloro-1,2,4a,5-tetrahydropyrazino[1',2':4,5][1,4]oxazino[2,3-c]quinoline-3(4H)-carboxylate (2 g, 4.40 mmol), 5,5,5',5'-tetramethyl-2,2'-bi-1,3,2-dioxaborinane (1.99 g, 8.8 mmol) and potassium acetate (0.863 g, 8.8 mmol) in 1,4-dioxane (30 mL) at rt. The resulting suspension was stirred at 100° C. for 16 h. The solvent was removed in vacuo. The crude product obtained was purified by C18-flash chromatography (0 to 100%, MeCN in water) to afford [(4aR)-3-(tert-butoxycarbonyl)-11-chloro-1,2,3,4,4a,5-hexahydropyrazino[1',2':4,5][1,4]oxazino[2,3-c]quinolin-10-yl]boronic acid (1.4 g, 76%) as a yellow solid; $^1$H NMR (300 MHz, DMSO, 30° C.) 1.44 (9H, s), 2.00 (1H, s), 3.08-3.55 (4H, m), 3.59-3.88 (3H, m), 4.14-4.29 (1H, m), 4.35 (1H, d), 7.89 (1H, s), 8.51 (2H, d); m/z: ES$^+$ [M+H]$^+$=420.

tert-Butyl (4aR)-11-chloro-10-[5-methyl-1-(oxan-2-yl)-1H-benzimidazol-4-yl]-1,2,4a,5-tetrahydropyrazino[1',2':4,5][1,4]oxazino[2,3-c]quinoline-3(4H)-carboxylate

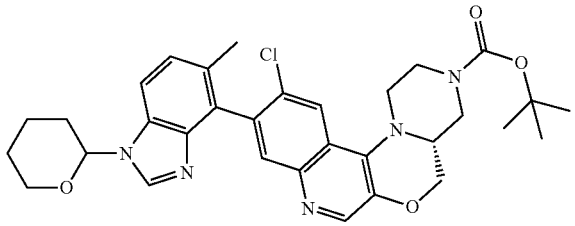 [SMILES: Cc1ccc2c(ncn2C2CCCCO2)c1-c1cc2ncc3c(c2cc1Cl)N1CCN(C(=O)OC(C)(C)C)C[C@@H]1CO3]

RuPhos-Pd-G3 (50 mg, 0.06 mmol) was added to [(4aR)-3-(tert-butoxycarbonyl)-11-chloro-1,2,3,4,4a,5-hexahydropyrazino[1',2':4,5][1,4]oxazino[2,3-c]quinolin-10-yl]boronic acid (250 mg, 0.6 mmol), 4-iodo-5-methyl-1-(oxan-2-yl)-1H-benzimidazole (408 mg, 1.19 mmol), K$_2$CO$_3$ (165 mg, 1.19 mmol) and RuPhos (27.8 mg, 0.06 mmol) in 1,4-dioxane/H$_2$O (5 mL, 4:1 ratio) at rt. The resulting suspension was stirred at 80° C. for 2 h. The solvent was removed in vacuo. The crude product obtained was purified by C18-flash chromatography (70 to 80% MeOH in water (0.1% NH$_4$HCO$_3$)) to afford tert-butyl (4aR)-11-chloro-10-[5-methyl-1-(oxan-2-yl)-1H-benzimidazol-4-yl]-1,2,4a,5-tetrahydropyrazino[1',2':4,5][1,4]oxazino[2,3-c]quinoline-3(4H)-carboxylate (220 mg, 63%) as a yellow solid; $^1$H NMR (300 MHz, DMSO, 30° C.) 1.45 (9H, s), 1.62 (2H, s), 1.97 (2H, d), 2.18 (3H, d), 3.17 (2H, d), 3.51 (2H, s), 4.30 (9H, d), 5.69 (1H, d), 7.27 (1H, d), 7.64 (1H, d), 7.78 (1H, d), 8.11 (1H, s), 8.25 (1H, s), 8.56 (1H, s); m/z: ES$^+$ [M+H]$^+$=590.

(4aR)-11-Chloro-10-(5-methyl-1H-benzimidazol-4-yl)-1,2,3,4,4a,5-hexahydropyrazino[1',2':4,5][1,4]oxazino[2,3-c]quinoline

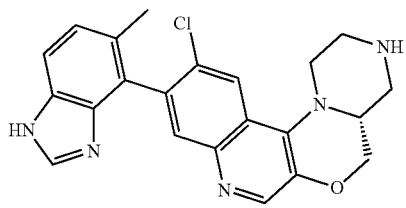 [SMILES: Cc1ccc2[nH]cnc2c1-c1cc2ncc3c(c2cc1Cl)N1CCNC[C@@H]1CO3]

A mixture of tert-butyl (4aR)-11-chloro-10-[5-methyl-1-(oxan-2-yl)-1H-benzimidazol-4-yl]-1,2,4a,5-tetrahydropyrazino[1',2':4,5][1,4]oxazino[2,3-c]quinoline-3(4H)-carboxylate (210 mg, 0.36 mmol) in 4M HCl in MeOH (5 mL, 20 mmol) was stirred at 80° C. for 3 h. The solvent was removed in vacuo. The crude product was purified by SCX (7M NH$_3$/MeOH) to afford (4aR)-11-chloro-10-(5-methyl-1H-benzimidazol-4-yl)-1,2,3,4,4a,5-hexahydropyrazino[1',2':4,5][1,4]oxazino[2,3-c]quinoline (140 mg, 97%) as a yellow solid; $^1$H NMR (300 MHz, DMSO, 30° C.). 2.17 (3H, d), 3.38-3.52 (2H, m), 3.52 (2H, s), 3.66 (2H, s), 4.38 (2H, s), 4.51 (1H, d), 7.08-7.34 (3H, m), 8.06 (1H, s), 8.18 (1H, s), 8.58 (1H, s); m/z: ES$^+$ [M+H]$^+$=406.

11-[(4aR)-11-Chloro-10-(5-methyl-1H-benzimidazol-4-yl)-1,2,4a,5-tetrahydropyrazino[1',2':4,5][1,4]oxazino[2,3-c]quinolin-3(4H)-yl]prop-2-en-1-one (Atropisomer 1, Compound 65; Atropisomer 2, Compound 66)

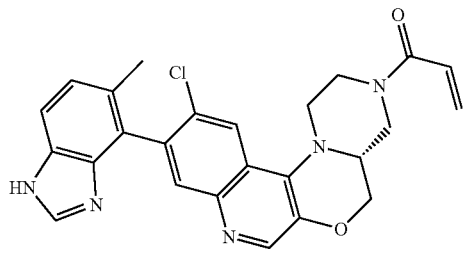 [SMILES: C=CC(=O)N1CCN2c3c(cnc4cc(-c5c(C)ccc6[nH]cnc56)c(Cl)cc34)OC[C@H]2C1]

A mixture of acryloyl chloride (27.5 mg, 0.30 mmol) in DMF (3 mL) was added to a stirred mixture of (4aR)-11-chloro-10-(5-methyl-1H-benzimidazol-4-yl)-1,2,3,4,4a,5-hexahydropyrazino[1',2':4,5][1,4]oxazino[2,3-c]quinoline (130 mg, 0.32 mmol) and DIPEA (0.112 mL, 0.64 mmol) in DMF (3 mL) at 0° C. The resulting mixture was stirred at 0° C. for 40 min then concentrated in vacuo to afford crude product. This was purified by preparative HPLC (Column: XBridge Prep OBD C18 Column 30×150 mm 5 m; Mobile Phase A: Water (0.05% NH$_4$OH), Mobile Phase B: MeCN; Flow rate: 60 mL/min; Gradient: 35% B to 37% B in 7 min; 254; 220 nm) to afford atropisomer 1 of 11-[(4aR)-11-chloro-10-(5-methyl-1H-benzimidazol-4-yl)-1,2,4a,5-tetrahydropyrazino[1',2':4,5][1,4]oxazino[2,3-c]quinolin-3(4H)-yl]prop-2-en-1-one (20 mg, 14%) as a white solid; $^1$H NMR (300 MHz, DMSO, 30° C.) 2.18 (3H, s), 3.45-3.98 (6H, m), 4.00-4.51 (4H, m), 5.75-5.79 (1H, d), 6.17-6.23 (1H, d), 6.88 (1H, s), 7.17-7.20 (1H, d), 7.56-7.58 (1H, d), 7.84 (1H, s), 8.06 (1H, s), 8.17 (1H, s), 8.57 (1H, s); m/z: ES$^+$ [M+H]$^+$=460; This was followed by atropisomer 2 of 11-[(4aR)-11-chloro-10-(5-methyl-1H-benzimidazol-4-yl)-1,2,4a,5-tetrahydropyrazino[1',2':4,5][1,4]oxazino[2,3-c]quinolin-3(4H)-yl]prop-2-en-1-one (23 mg, 16%) as a white solid; $^1$H NMR (300 MHz, DMSO, 30° C.) 2.18 (3H, s), 3.45-3.98 (6H, m), 4.00-4.51 (4H, m), 5.75-5.79 (1H, d), 6.17-6.23 (1H, d), 6.88 (1H, s), 7.17-7.20 (1H, d), 7.56-7.58 (1H, d), 7.84 (1H, s), 8.06 (1H, s), 8.17 (1H, s), 8.57 (1H, s); m/z: ES$^+$ [M+H]$^+$=460.

3-Iodo-4-methyl-2-(methylamino)benzoic acid

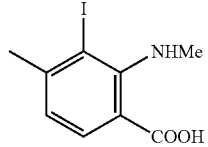

Glacial acetic acid (0.155 mL, 2.71 mmol) was added to 2-amino-3-iodo-4-methylbenzoic acid (1.5 g, 5.41 mmol) and formaldehyde (0.496 mL, 5.41 mmol) in MeOH (30 mL) at rt. The resulting suspension was stirred at rt for 16 h. The reaction mixture was diluted with EtOAc (100 mL) then washed with water (50 mL×3), dried (Na$_2$SO$_4$) and concentrated in vacuo. The residue obtained was dissolved DCM (20 mL) and sodium cyanoborohydride (0.68 g, 10.8 mmol)

added at rt. The resulting suspension was stirred at rt for 1 h and then concentrated in vacuo. The crude product was purified by C18-flash chromatography (20 to 100%, MeCN in water) to afford 3-iodo-4-methyl-2-(methylamino)benzoic acid (0.45 g, 29%) as a white solid; $^1$H NMR (300 MHz, DMSO, 30° C.) 2.44 (3H, s), 2.50 (1H, s), 2.76-2.95 (3H, m), 6.96 (1H, d), 7.69 (1H, d); m/z: ES$^+$ [M+H]$^+$=292.

7-Iodo-1,6-dimethyl-1,3-dihydro-2H-benzimidazol-2-one

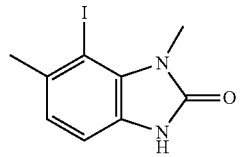

Diphenyl phosphorazidate (0.279 mL, 1.29 mmol) was added to 3-iodo-4-methyl-2-(methylamino)benzoic acid (250 mg, 0.86 mmol) and NEt$_3$ (0.359 mL, 2.58 mmol) in DMA (4 mL) at rt. The resulting mixture was stirred at 80° C. for 4 h. The crude reaction mixture was purified by C18-flash chromatography (0 to 50% water (0.1% TFA) in MeCN) to afford 7-iodo-1,6-dimethyl-1,3-dihydro-2H-benzimidazol-2-one (120 mg, 49%) as a yellow solid; $^1$H NMR (300 MHz, DMSO, 30° C.) 2.40 (3H, s), 3.63 (3H, s), 6.88 (1H, d), 7.01 (1H, d), 11.01 (1H, s); m/z: ES$^+$ [M+H]$^+$=289.

tert-Butyl (4aR)-11-chloro-10-(3,5-dimethyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate

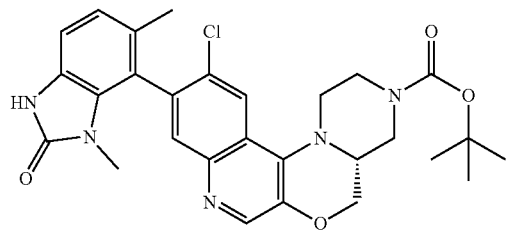 [SMILES: Cc1ccc2[nH]c(=O)n(C)c2c1-c1cc2ncc3c(c2cc1Cl)N1CCN(C(=O)OC(C)(C)C)C[C@@H]1CO3]

RuPhos-Pd-G3 (39.8 mg, 0.05 mmol) was added to 7-iodo-1,6-dimethyl-1,3-dihydro-2H-benzimidazol-2-one, [(4aR)-3-(tert-butoxycarbonyl)-11-chloro-1,2,3,4,4a,5-hexahydropyrazino[1',2':4,5][1,4]oxazino[2,3-c]quinolin-10-yl]boronic acid (200 mg, 0.48 mmol), K$_2$CO$_3$ (132 mg, 0.95 mmol) and RuPhos (22.2 mg, 0.05 mmol) in 1,4-dioxane/H$_2$O (15 mL, 4:1 ratio) at rt. The resulting suspension was stirred at 100° C. for 1.5 h and then concentrated in vacuo. The crude product was purified by C18-flash chromatography (0 to 100% MeCN in water (0.1% NH$_4$HCO$_3$)) to afford tert-butyl (4aR)-11-chloro-10-(3,5-dimethyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate (165 mg, 65%) as a white solid; $^1$H NMR (300 MHz, DMSO, 30° C.) 1.45 (9H, s), 1.96 (3H, d), 2.60 (3H, d), 3.23-3.92 (7H, m), 4.22-4.28 (1H, m), 4.39 (1H, d), 6.97 (2H, s), 7.92 (1H, d), 8.14 (1H, d), 8.58 (1H, d), 10.96 (1H, s); m/z: ES$^+$ [M+H]$^+$=536.

7-[(4aR)-11-Chloro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one.1HCl

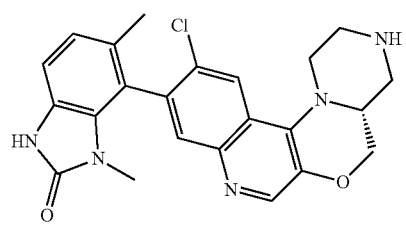 [SMILES: Cc1ccc2[nH]c(=O)n(C)c2c1-c1cc2ncc3c(c2cc1Cl)N1CCNC[C@@H]1CO3]

4M HCl in 1,4-dioxane (4 mL, 16 mmol) was added tert-butyl (4aR)-11-chloro-10-(3,5-dimethyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate (162 mg, 0.3 mmol) in MeOH (4 mL) at rt. The resulting mixture was stirred at rt for 1 h. The solvent was removed in vacuo to afford 7-[(4aR)-11-chloro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one.1HCl (174 mg, >100%) as a pale yellow solid that was used without further purification; $^1$H NMR (300 MHz, DMSO, 30° C.) 1.97 (3H, d), 2.64 (3H, d), 3.20-3.63 (4H, m), 4.03-4.60 (5H, m), 7.02 (2H, d), 8.18 (1H, s), 8.41 (1H, d), 8.82 (1H, s), 11.08 (1H, s); m/z: ES$^+$ [M+H]$^+$=436.

7-[(4aR)-11-Chloro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (Atropisomer 1, Compound 67; Atropisomer 2, Compound 68)

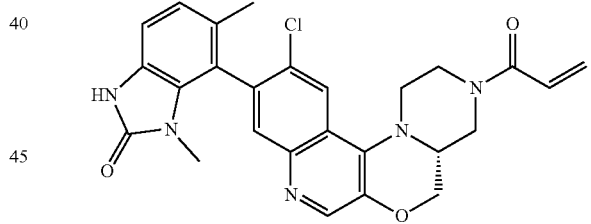

Acryloyl chloride (28.7 mg, 0.32 mmol) was added to 7-[(4aR)-11-chloro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one.1HCl (150 mg, 0.32 mmol) and DIPEA (0.166 mL, 0.95 mmol) in DMF (3 mL) at −10° C. The resulting mixture was stirred to rt for 1 h. The crude reaction mixture was purified by C18-flash chromatography (0 to 100%, MeCN in water (0.05% NH$_4$HCO$_3$)) to give a solid. This was purified by preparative chiral-HPLC (Column: CHIRALPAK IG, 20*250 mm, 5 μm; Mobile Phase A: MTBE-HPLC, Mobile Phase B: EtOH-HPLC; Flow rate: 18 mL/min; Gradient: 50 B to 50 B in 14 min; 220/254 nm) to afford atropisomer 1 of 7-[(4aR)-11-chloro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (51 mg, 33%) as a white solid; $^1$H NMR (300 MHz, DMSO, 30° C.) 1.98 (3H, s), 2.58 (3H, s), 3.08-3.30 (1H, m), 3.40-3.73 (3H, m), 3.75-4.29 (4H, m), 4.30-4.49 (1H, m), 5.77 (1H, d), 6.19 (1H, d), 6.74-7.09 (3H, m), 7.93 (1H, s), 8.19 (1H, s), 8.59 (1H, s), 10.95 (1H, s); m/z: ES+ [M+H]+=490. This was followed by atropisomer 2 of 7-[(4aR)-11-chloro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (43 mg, 28%) as a white solid; ¹H NMR (300 MHz, DMSO, 30° C.) 1.95 (3H, s), 2.63 (3H, s), 3.39-3.64 (3H, m), 3.66-4.30 (5H, m), 4.32-4.50 (1H, m), 5.77 (1H, d), 6.20 (1H, dd), 6.73-7.01 (3H, m), 7.92 (1H, s), 8.18 (1H, s), 8.58 (1H, s), 10.95 (1H, s); m/z: ES+ [M+H]+=490.

8-Bromo-7-methylisoquinoline

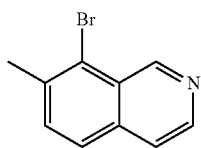

2,2-Diethoxyethan-1-amine (2.68 g, 20.1 mmol) was added dropwise to 2-bromo-3-methylbenzaldehyde (4 g, 20.1 mmol) in toluene (12 mL) at rt. The resulting suspension was stirred at 100° C. for 16 h. After cooling to rt the solvent was removed in vacuo. The residue obtained was dissolved in DCM (16 mL) and aluminium trichloride (8.84 g, 66.32 mmol) added portionwise to the solution at rt. The resulting suspension was stirred at rt for 3 h. The reaction mixture was poured into ice (100 mL), extracted with DCM (50 mL×3), the organic layer was dried (Na₂SO₄) and concentrated in vacuo. The crude product was purified by flash silica chromatography (0 to 20% EtOAc in petroleum ether) to afford 8-bromo-7-methylisoquinoline (1.56 g, 35%) as a yellow solid; m/z: ES+ [M+H]+=222.

8-Bromo-7-methyl-2-oxo-2λ⁵-isoquinoline

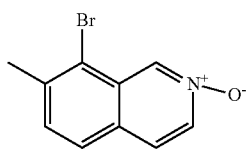

3-Chloroperbenzoic acid (2.078 g, 8.43 mmol) was added to 8-bromo-7-methylisoquinoline (1.56 g, 7.02 mmol) in chloroform (80 mL) at 0° C. The resulting solution was stirred at rt for 2 h. The reaction mixture was diluted with DCM (200 mL), washed with sat. NaHCO₃ (100 mL), dried (Na₂SO₄) and concentrated in vacuo to afford 8-bromo-7-methyl-2-oxo-2λ⁵-isoquinoline (1.6 g, 96%) as a pale yellow solid; m/z: ES+ [M+H]+=238.

8-Bromo-7-methylisoquinolin-1(2H)-one

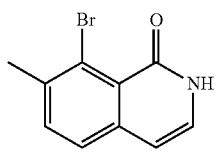

Acetic anhydride (11.73 mL, 124.33 mmol) was added to 8-bromo-7-methyl-2-oxo-2λ⁵-isoquinoline (1.6 g, 6.72 mmol) at rt. The resulting solution was stirred at 100° C. for 3 h then cooled to rt and concentrated in vacuo. The residue was diluted with aq. NaOH (20 mL, 20.00 mmol) and then heated at 100° C. for 1 h. The reaction mixture was acidified with 0.5M citric acid to pH 6 at rt. The aqueous layer was extracted with DCM (50 mL×3) and the combined organic layers dried (Na₂SO₄) and concentrated in vacuo. The crude product was purified by flash silica chromatography (30 to 50% EtOAc in petroleum ether) to afford 8-bromo-7-methylisoquinolin-1(2H)-one (0.42 g, 26%) as a brown solid; ¹H NMR (300 MHz, DMSO, 30° C.) 2.46 (3H, s), 6.50 (1H, d), 7.13 (1H, dd), 7.53 (1H, d), 7.60 (1H, d), 11.20 (1H, s); m/z: ES+ [M+H]+=238.

8-Bromo-7-methyl-2-{[2-(trimethylsilyl)ethoxy]methyl}isoquinolin-1(2H)-one

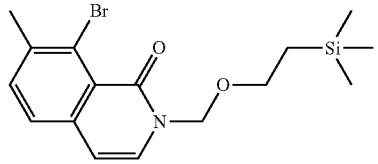

Sodium hydride (121 mg, 5.04 mmol) was added to 8-bromo-7-methylisoquinolin-1(2H)-one (400 mg, 1.68 mmol) in THF (10 mL) at 0° C. The mixture was stirred at 0° C. for 20 min then 2-(trimethylsilyl)ethoxymethyl chloride (840 mg, 5.04 mmol) was added to the mixture. The resulting suspension was stirred at rt for 16 h. The reaction mixture was quenched with water (1 mL). The reaction mixture was diluted with EtOAc (100 mL) and washed sequentially with sat. NH₄Cl (100 mL) then brine (100 mL×2). The organic layer was dried (Na₂SO₄) and concentrated in vacuo to afford crude product. This was purified by flash silica chromatography (0 to 50% EtOAc in petroleum ether) to afford 8-bromo-7-methyl-2-{[2-(trimethylsilyl)ethoxy]methyl}isoquinolin-1(2H)-one (303 mg, 49%) as a white solid; ¹H NMR (300 MHz, DMSO, 30° C.) 0.00 (9H, s), 0.86-0.98 (2H, m), 2.52 (3H, s), 3.57-3.69 (2H, m), 5.34 (2H, s), 6.63 (1H, d), 7.51 (1H, d), 7.59 (1H, d), 7.69 (1H, d); m/z: ES+ [M+H]+=368.

tert-Butyl (4aR)-11-chloro-10-(7-methyl-1-oxo-2-{[2-(trimethylsilyl)ethoxy]methyl}-1,2-dihydroisoquinolin-8-yl)-1,2,4a,5-tetrahydropyrazino[1',2':4,5][1,4]oxazino[2,3-c]quinoline-3(4H)-carboxylate Atropisomer 1 and 2

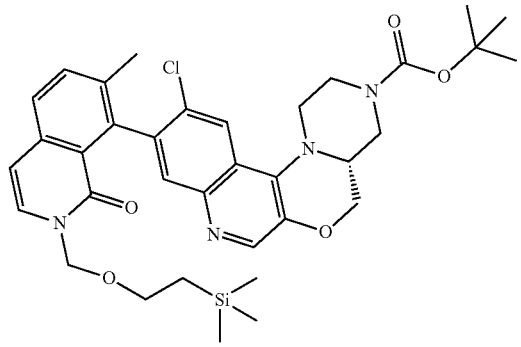 [SMILES: Cc1ccc2ccn(COCC[Si](C)(C)C)c(=O)c2c1-c1cc2ncc3c(c2cc1Cl)N1CCN(C(=O)OC(C)(C)C)C[C@@H]1CO3]

RuPhos-Pd-G3 (49.8 mg, 0.06 mmol) was added to 8-bromo-7-methyl-2-{[2-(trimethylsilyl)ethoxy]methyl}isoquinolin-1(2H)-one (219 mg, 0.60 mmol), [(4aR)-3-(tert-butoxycarbonyl)-11-chloro-1,2,3,4,4a,5-hexahydropyrazino[1',2':4,5][1,4]oxazino[2,3-c]quinolin-10-yl]boronic acid (250 mg, 0.6 mmol), $K_2CO_3$ (165 mg, 1.19 mmol) and RuPhos (27.8 mg, 0.06 mmol) in 1,4-dioxane/$H_2O$ (10 mL, 4:1 ratio) at rt. The resulting suspension was stirred at 100° C. for 1 h. The solvent was removed in vacuo and the crude product obtained purified by C18-flash chromatography (0 to 100%, MeCN in water (0.1% HCOOH)) to afford a white solid. The solid was purified by preparative chiral-HPLC (Column: CHIRALPAK IE, 2*25 cm, 5 m; Mobile Phase A: MTBE-HPLC, Mobile Phase B: MeOH (8 mmol/L $NH_3$.MeOH)-HPLC; Flow rate: 20 mL/min; Gradient: 50 B to 50 B in 10 min; 254/220 nm) to afford atropisomer 1 of tert-butyl (4aR)-11-chloro-10-(7-methyl-1-oxo-2-{[2-(trimethylsilyl)ethoxy]methyl}-1,2-dihydroisoquinolin-8-yl)-1,2,4a,5-tetrahydropyrazino[1',2':4,5][1,4]oxazino[2,3-c]quinoline-3(4H)-carboxylate (46 mg, 12%, 100% d.e.) as a yellow solid; $^1$H NMR (300 MHz, DMSO, 30° C.) 0.00 (9H, s), 0.88 (2H, dd), 1.54 (9H, s), 2.08 (3H, s), 3.47-3.97 (9H, m), 4.28-4.53 (2H, m), 5.17 (1H, d), 5.26 (1H, d), 6.75 (1H, d), 7.51 (1H, d), 7.67 (1H, s), 7.72-7.87 (2H, m), 8.11 (1H, s), 8.62 (1H, s); m/z: ES$^+$ [M+H]$^+$=663. This was followed by atropisomer 2 of tert-butyl (4aR)-11-chloro-10-(7-methyl-1-oxo-2-{[2-(trimethylsilyl)ethoxy]methyl}-1,2-dihydroisoquinolin-8-yl)-1,2,4a,5-tetrahydropyrazino[1',2':4,5][1,4]oxazino[2,3-c]quinoline-3(4H)-carboxylate (47 mg, 12%, 100% d.e.) as a yellow solid; $^1$H NMR (300 MHz, DMSO, 30° C.) 0.00 (9H, s), 0.82-0.94 (2H, m), 1.55 (9H, s), 2.12 (3H, s), 3.45-3.98 (9H, m), 4.24-4.58 (2H, m), 5.16 (1H, d), 5.26 (1H, d), 6.75 (1H, d), 7.51 (1H, d), 7.66 (1H, s), 7.72-7.87 (2H, m), 8.09 (1H, s), 8.60 (1H, s); m/z: ES+ [M+H]+=663.

8-[(4aR)-11-Chloro-1,2,3,4,4a,5-hexahydropyrazino[1',2':4,5][1,4]oxazino[2,3-c]quinolin-10-yl]-7-methylisoquinolin-1(2H)-one Atropisomer 1

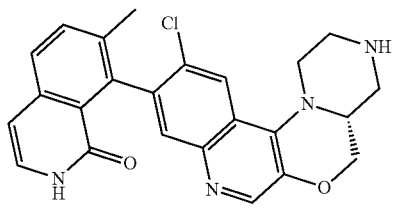 [SMILES: Cc1ccc2cc[nH]c(=O)c2c1-c1cc2ncc3c(c2cc1Cl)N1CCNC[C@@H]1CO3]

TFA (3 mL, 38.94 mmol) was added to atropisomer 1 of tert-butyl (4aR)-11-chloro-10-(7-methyl-1-oxo-2-{[2-(trimethylsilyl)ethoxy]methyl}-1,2-dihydroisoquinolin-8-yl)-1,2,4a,5-tetrahydropyrazino[1',2':4,5][1,4]oxazino[2,3-c]quinoline-3(4H)-carboxylate (46 mg, 0.07 mmol) in DCM (6 mL) at rt. The resulting mixture was stirred at rt for 1 h then concentrated in vacuo to afford atropisomer 1 of 8-[(4aR)-11-chloro-1,2,3,4,4a,5-hexahydropyrazino[1',2':4,5][1,4]oxazino[2,3-c]quinolin-10-yl]-7-methylisoquinolin-1(2H)-one (72 mg, >100%) as a pale yellow solid that was used without further purification; m/z: ES+ [M+H]+=433.

8-[(4aR)-11-Chloro-3-(prop-2-enoyl)-1,2,3,4,4a,5-hexahydropyrazino[1',2':4,5][1,4]oxazino[2,3-c]quinolin-10-yl]-7-methylisoquinolin-1(2H)-one (Atropisomer 1, Compound 69)

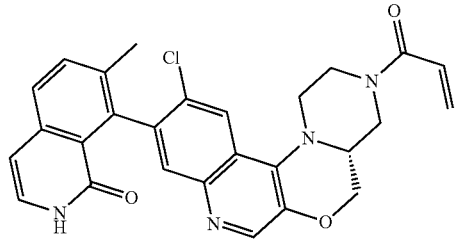 [SMILES: C=CC(=O)N1CCN2c3c(cnc4cc(-c5c(C)ccc6cc[nH]c(=O)c56)c(Cl)cc34)OC[C@H]2C1]

Acryloyl chloride (14.92 mg, 1.16 mmol) was added to atropisomer 1 of 8-[(4aR)-11-chloro-1,2,3,4,4a,5-hexahydropyrazino[1',2':4,5][1,4]oxazino[2,3-c]quinolin-10-yl]-7-methylisoquinolin-1(2H)-one (60 mg, 0.11 mmol) and DIPEA (0.077 mL, 0.44 mmol) in DMF (3 mL) at −10° C. The resulting mixture was stirred at rt for 1 h. The crude reaction mixture was purified by C18-flash chromatography (0 to 100% MeCN in water (0.05% $NH_4HCO_3$)) to afford atropisomer 1 of 8-[(4aR)-11-chloro-3-(prop-2-enoyl)-1,2,3,4,4a,5-hexahydropyrazino[1',2':4,5][1,4]oxazino[2,3-c]quinolin-10-yl]-7-methylisoquinolin-1(2H)-one (13 mg, 24%) as a white solid; $^1$H NMR (300 MHz, DMSO, 30° C.) 1.99 (3H, s), 3.39-3.87 (3H, m), 3.90-4.50 (6H, m), 5.78 (1H, d), 6.20 (1H, d), 6.56 (1H, d), 6.86-6.92 (1H, m), 7.10 (1H, t), 7.58 (1H, s), 7.60-7.73 (2H, m), 8.03 (1H, s), 8.51 (1H, s), 10.78 (1H, d); m/z: ES$^+$ [M+H]$^+$=487.

8-[(4aR)-11-Chloro-1,2,3,4,4a,5-hexahydropyrazino[1',2':4,5][1,4]oxazino[2,3-c]quinolin-10-yl]-7-methylisoquinolin-1(2H)-one Atropisomer 2

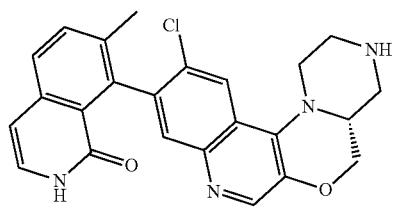 [SMILES: Cc1ccc2cc[nH]c(=O)c2c1-c1cc2ncc3c(c2cc1Cl)N1CCNC[C@@H]1CO3]

TFA (3 mL, 38.94 mmol) was added to atropisomer 2 of tert-butyl (4aR)-11-chloro-10-(7-methyl-1-oxo-2-{[2-(trimethylsilyl)ethoxy]methyl}-1,2-dihydroisoquinolin-8-yl)-1,2,4a,5-tetrahydropyrazino[1',2':4,5][1,4]oxazino[2,3-c]quinoline-3(4H)-carboxylate (47 mg, 0.07 mmol) in DCM (6 mL) at rt. The resulting mixture was stirred at rt for 1 h then concentrated in vacuo to afford atropisomer 2 of 8-[(4aR)-11-chloro-1,2,3,4,4a,5-hexahydropyrazino[1',2':4,5][1,4]oxazino[2,3-c]quinolin-10-yl]-7-methylisoquinolin-1(2H)-one (50 mg, >100%) as a pale yellow solid that was used without further purification; m/z: ES$^+$ [M+H]$^+$=433.

8-[(4aR)-11-Chloro-3-(prop-2-enoyl)-1,2,3,4,4a,5-hexahydropyrazino[1',2':4,5][1,4]oxazino[2,3-c]quinolin-10-yl]-7-methylisoquinolin-1(2H)-one (Atropisomer 2, Compound 70)

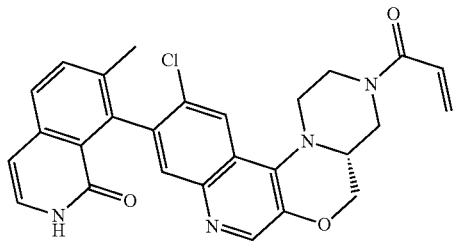 [SMILES: C=CC(=O)N1CCN2c3c(cnc4cc(-c5c(C)ccc6cc[nH]c(=O)c56)c(Cl)cc34)OC[C@H]2C1]

Acryloyl chloride (9.95 mg, 0.11 mmol) was added to atropisomer 2 of 8-[(4aR)-11-chloro-1,2,3,4,4a,5-hexahydropyrazino[1',2':4,5][1,4]oxazino[2,3-c]quinolin-10-yl]-7-methylisoquinolin-1(2H)-one (40 mg, 0.07 mmol) and DIPEA (0.051 mL, 0.29 mmol) in DMF (3 mL) at −10° C. The resulting mixture was stirred at rt for 1 h. The crude reaction mixture was purified by C18-flash chromatography (0 to 100%, MeCN in water (0.05% NH$_4$HCO$_3$)) to afford atropisomer 2 of 8-[(4aR)-11-chloro-3-(prop-2-enoyl)-1,2,3,4,4a,5-hexahydropyrazino[1',2':4,5][1,4]oxazino[2,3-c]quinolin-10-yl]-7-methylisoquinolin-1(2H)-one (13 mg, 37%) as a white solid; $^1$H NMR (300 MHz, DMSO, 30° C.) 2.01 (3H, s), 3.40-3.74 (3H, m), 3.76-4.48 (6H, m), 5.77 (1H, d), 6.20 (1H, d), 6.56 (1H, d), 6.86 (1H, br s), 7.09 (1H, t), 7.57 (1H, s), 7.60-7.73 (2H, m), 8.03 (1H, s), 8.51 (1H, s), 10.81 (1H, d); m/z: ES$^+$ [M+H]$^+$=487.

4-Iodo-5-methyl-1,3-dihydro-2H-benzimidazol-2-one

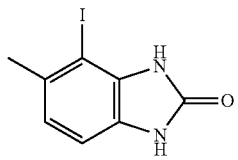

Diphenyl phosphorazidate (0.585 mL, 2.71 mmol) was added to 3-iodo-4-methyl-2-nitrobenzoic acid (500 mg, 1.8 mmol) and NEt$_3$ (0.755 mL, 5.41 mmol) in DMA (8 mL) at rt. The resulting mixture was stirred at 80° C. for 3 h. The crude product was purified by C18-flash chromatography (0 to 100% MeCN in water (0.05% TFA)) to afford 4-iodo-5-methyl-1,3-dihydro-2H-benzimidazol-2-one (450 mg, 91%) as a brown solid; $^1$H NMR (300 MHz, DMSO, 30° C.) 2.34 (3H, s), 6.81 (1H, d), 6.91 (1H, d), 10.62 (1H, s), 10.79 (1H, s); m/z: ES$^+$ [M+H]$^+$=275.

tert-Butyl (4aR)-11-chloro-10-(5-methyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate Atropisomer 1 and 2

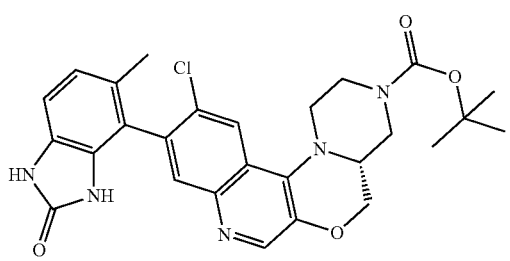 [SMILES: Cc1ccc2[nH]c(=O)[nH]c2c1-c1cc2ncc3c(c2cc1Cl)N1CCN(C(=O)OC(C)(C)C)C[C@@H]1CO3]

RuPhos-Pd-G3 (49.8 mg, 0.06 mmol) was added to 4-iodo-5-methyl-1,3-dihydro-2H-benzimidazol-2-one (163 mg, 0.6 mmol), [(4aR)-3-(tert-butoxycarbonyl)-11-chloro-1,2,3,4,4a,5-hexahydropyrazino[1',2':4,5][1,4]oxazino[2,3-c]quinolin-10-yl]boronic acid (250 mg, 0.6 mmol), K$_2$CO$_3$ (165 mg, 1.19 mmol), RuPhos (27.8 mg, 0.06 mmol) in 1,4-dioxane/H$_2$O (10 mL, 4:1 ratio) at rt. The resulting suspension was stirred at 100° C. for 1 h and then concentrated in vacuo. The residue was purified by C18-flash chromatography (0 to 100% MeCN in water (0.1% NH$_4$HCO$_3$)) to afford crude product as a yellow solid. This was purified by preparative chiral-HPLC (Column: CHIRAL ART Cellulose-SB, 2*25 cm, 5 m; Mobile Phase A: MTBE-HPLC, Mobile Phase B: EtOH-HPLC; Flow rate: 20 mL/min; Gradient: 20 B to 20 B in 8 min; 220/254 nm) to afford atropisomer 1 of tert-butyl (4aR)-11-chloro-10-(5-methyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate (50 mg, 16%); $^1$H NMR (300 MHz, DMSO, 30° C.) 1.45 (9H, s), 2.02 (3H, s), 3.19-3.26 (1H, m), 3.39-3.92 (6H, m), 4.25 (1H, t), 4.31-4.44 (1H, m), 6.83-6.96 (2H, m), 7.78 (1H, s), 8.09 (1H, s), 8.56 (1H, s), 10.27 (1H, s), 10.59 (1H, s); m/z: ES$^+$ [M+H]$^+$=522. This was followed by atropisomer 2 of tert-butyl (4aR)-11-chloro-10-(5-methyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate (49 mg, 16%) as a white solid; $^1$H NMR (300 MHz, DMSO, 30° C.) 1.45 (9H, s), 2.01 (3H, s), 3.13-3.31 (1H, m), 3.37-3.90 (6H, m), 4.19-4.44 (2H, m), 6.83-6.96 (2H, m), 7.78 (1H, s), 8.10 (1H, s), 8.56 (1H, s), 10.27 (1H, s), 10.59 (1H, s); m/z: ES$^+$ [M+H]$^+$=522.

4-[(4aR)-11-Chloro-1,2,3,4,4a,5-hexahydropyrazino[1',2':4,5][1,4]oxazino[2,3-c]quinolin-10-yl]-5-methyl-1,3-dihydro-2H-benzimidazol-2-one Atropisomer 1

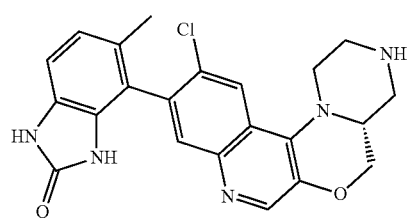 [SMILES: Cc1ccc2[nH]c(=O)[nH]c2c1-c1cc2ncc3c(c2cc1Cl)N1CCNC[C@@H]1CO3]

4M HCl in 1,4-dioxane (4 mL, 16 mmol) was added to atropisomer 1 of tert-butyl (4aR)-11-chloro-10-(5-methyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate (48 mg, 0.09 mmol) in MeOH (4 mL) at rt. The resulting mixture was stirred at rt for 1 h. The solvent was removed in vacuo to afford atropisomer 1 of 4-[(4aR)-11-chloro-1,2,3,4,4a,5-hexahydropyrazino[1',2':4,5][1,4]oxazino[2,3-c]quinolin-10-yl]-5-methyl-1,3-dihydro-2H-benzimidazol-2-one (54 mg, >100%) as a yellow solid that was used without further purification; $^1$H NMR (300 MHz, DMSO, 30° C.) 2.06 (3H, s), 3.19-3.38 (2H, m), 3.43-4.63 (7H, m), 6.94 (2H, s), 7.99 (1H, s), 8.36 (1H, s), 8.81 (1H, s), 10.37 (1H, s), 10.71 (1H, s); m/z: ES$^+$ [M+H]$^+$=422.

4-[(4aR)-11-Chloro-3-(prop-2-enoyl)-1,2,3,4,4a,5-hexahydropyrazino[1',2':4,5][1,4]oxazino[2,3-c]quinolin-10-yl]-5-methyl-1,3-dihydro-2H-benzimidazol-2-one (Atropisomer 1, Compound 71)

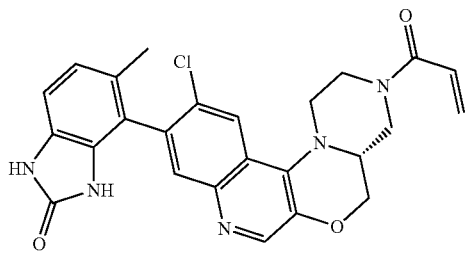 [SMILES: C=CC(=O)N1CCN2c3c(cnc4cc(-c5c(C)ccc6[nH]c(=O)[nH]c56)c(Cl)cc34)OC[C@H]2C1]

Acryloyl chloride (8 mg, 0.09 mmol) was added to atropisomer 1 of 4-[(4aR)-11-chloro-1,2,3,4,4a,5-hexahydropyrazino[1',2':4,5][1,4]oxazino[2,3-c]quinolin-10-yl]-5-methyl-1,3-dihydro-2H-benzimidazol-2-one (44 mg, 0.09 mmol) and DIPEA (0.047 mL, 0.27 mmol) in DMF (3 mL) at −10° C. The resulting mixture was stirred at rt for 1 h. The crude reaction mixture was purified by C18-flash chromatography (0 to 100% MeCN in water (0.05% NH$_4$HCO$_3$)) to afford atropisomer 1 of 4-[(4aR)-11-chloro-3-(prop-2-enoyl)-1,2,3,4,4a,5-hexahydropyrazino[1',2':4,5][1,4]oxazino[2,3-c]quinolin-10-yl]-5-methyl-1,3-dihydro-2H-benzimidazol-2-one (30 mg, 70%) as a white solid; $^1$H NMR (300 MHz, DMSO, 30° C.) 2.02 (3H, s), 3.49-4.49 (9H, m), 5.77 (1H, d), 6.20 (1H, d), 6.83-6.96 (3H, m), 7.78 (1H, s), 8.13 (1H, s), 8.56 (1H, s), 10.26 (1H, s), 10.60 (1H, s); m/z: ES$^+$ [M+H]$^+$=476.

4-[(4aR)-11-Chloro-1,2,3,4,4a,5-hexahydropyrazino[1',2':4,5][1,4]oxazino[2,3-c]quinolin-10-yl]-5-methyl-1,3-dihydro-2H-benzimidazol-2-one Atropisomer 2

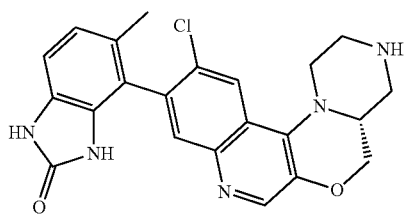 [SMILES: Cc1ccc2[nH]c(=O)[nH]c2c1-c1cc2ncc3c(c2cc1Cl)N1CCNC[C@@H]1CO3]

4M HCl in 1,4-dioxane (4 mL, 16 mmol) was added to atropisomer 2 of tert-butyl (4aR)-11-chloro-10-(5-methyl-2-oxo-2,3-dihydro-1H-benzimidazol-4-yl)-1,2,4a,5-tetrahydropyrazino[1',2':4,5][1,4]oxazino[2,3-c]quinoline-3(4H)-carboxylate (47 mg, 0.09 mmol) in MeOH (4 mL) at rt. The resulting mixture was stirred at rt for 1 h. The solvent was removed in vacuo to afford atropisomer 2 of 4-[(4aR)-11-Chloro-1,2,3,4,4a,5-hexahydropyrazino[1',2':4,5][1,4]oxazino[2,3-c]quinolin-10-yl]-5-methyl-1,3-dihydro-2H-benzimidazol-2-one (50 mg, >100%) as a yellow solid that was used without further purification; $^1$H NMR (300 MHz, DMSO, 30° C.) 2.05 (3H, s), 3.42-4.50 (9H, m), 6.94 (2H, s), 7.99 (1H, s), 8.33 (1H, s), 8.81 (1H, s), 10.36 (1H, s), 10.71 (1H, s); m/z: ES$^+$ [M+H]$^+$=422.

4-[(4aR)-11-Chloro-3-(prop-2-enoyl)-1,2,3,4,4a,5-hexahydropyrazino[1',2':4,5][1,4]oxazino[2,3-c]quinolin-10-yl]-5-methyl-1,3-dihydro-2H-benzimidazol-2-one (Atropisomer 2, Compound 72)

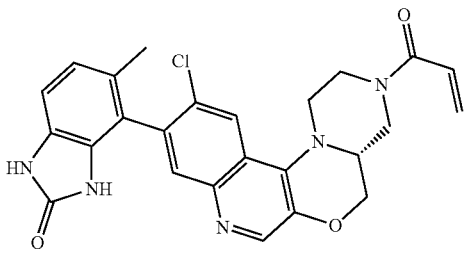 [SMILES: C=CC(=O)N1CCN2c3c(cnc4cc(-c5c(C)ccc6[nH]c(=O)[nH]c56)c(Cl)cc34)OC[C@H]2C1]

Acryloyl chloride (7.7 mg, 0.08 mmol) was added to atropisomer 2 of 4-[(4aR)-11-chloro-1,2,3,4,4a,5-hexahydropyrazino[1',2':4,5][1,4]oxazino[2,3-c]quinolin-10-yl]-5-methyl-1,3-dihydro-2H-benzimidazol-2-one (42 mg, 0.08 mmol) and DIPEA (0.044 mL, 0.25 mmol) in DMF (3 mL) at −10° C. The resulting mixture was stirred at rt for 1 h. The crude reaction mixture was purified by C18-flash chromatography (0 to 100% MeCN in water (0.05% NH$_4$HCO$_3$)) to afford atropisomer 2 of 4-[(4aR)-11-chloro-3-(prop-2-enoyl)-1,2,3,4,4a,5-hexahydropyrazino[1',2':4,5][1,4]oxazino[2,3-c]quinolin-10-yl]-5-methyl-1,3-dihydro-2H-benzimidazol-2-one (30 mg, 75%) as a white solid; $^1$H NMR (300 MHz, DMSO, 30° C.) 2.01 (3H, s), 3.16-3.28 (1H, m), 3.40-4.50 (8H, m), 5.77 (1H, d), 6.20 (1H, dd), 6.78-6.96 (3H, m), 7.78 (1H, s), 8.14 (1H, s), 8.56 (1H, s), 10.26 (1H, s), 10.59 (1H, s). m/z: ES$^+$ [M+H]$^+$=476.

tert-Butyl (4aS)-11-chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinoline-3-carboxylate Atropisomer 1 and 2

Tetrakis(triphenylphosphine)palladium(0) (66 mg, 0.06 mmol) was added to tert-butyl (4aS)-10-bromo-11-chloro-6-(2-(dimethylamino)ethyl)-1,2,4,4a,5,6-hexahydro-3H-pyrazino[1',2':4,5]pyrazino[2,3-c]quinoline-3-carboxylate (300 mg, 0.57 mmol), (5-methyl-1H-indazol-4-yl)boronic acid (101 mg, 0.57 mmol) and K$_2$CO$_3$ (158 mg, 1.14 mmol) in 1,4-dioxane/H$_2$O (15 mL, 4:1 ratio) at rt. The resulting suspension was stirred at 100° C. for 1 h. The solvent was removed in vacuo. The residue obtained was purified by C18-flash chromatography (0 to 100%, MeCN in water (0.1% HCOOH)) to afford crude product as an orange solid. This was purified by preparative chiral-HPLC (Column:

Chiralpak ID-2, 2*25 cm, 5 m; Mobile Phase A: MTBE (0.1% DEA)-HPLC, Mobile Phase B: EtOH-HPLC; Flow rate: 17 mL/min; Gradient: 20 B to 20 B in 13 min; 220/254 nm) to afford atropisomer 1 of tert-butyl (4aS)-11-chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinoline-3-carboxylate (113 mg, 34%) as a yellow solid; ¹H NMR (300 MHz, DMSO, 30° C.) 1.46 (9H, s), 2.18 (3H, s), 2.21 (6H, s), 2.39-2.50 (1H, m), 2.52-2.60 (1H, m), 2.69-2.93 (3H, m), 3.06-3.37 (2H, m), 3.38-3.56 (2H, m), 3.66 (1H, t), 3.75-4.09 (3H, m), 7.34 (1H, d), 7.46 (1H, s), 7.51 (1H, dd), 7.71 (1H, s), 8.04 (1H, s), 8.73 (1H, s), 13.11 (1H, s); m/z: ES⁺ [M+H]⁺=576. This was followed by atropisomer 2 of tert-butyl (4aS)-11-chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinoline-3-carboxylate (117 mg, 36%) as a yellow solid; ¹H NMR (300 MHz, DMSO, 30° C.) 1.46 (9H, s), 2.16 (3H, s), 2.21 (6H, s), 2.37-2.50 (1H, m), 2.52-2.58 (1H, m), 2.71-2.89 (3H, m), 3.07-3.39 (2H, m), 3.39-3.56 (2H, m), 3.66 (1H, t), 3.77-3.89 (1H, m), 3.90-4.08 (2H, m), 7.34 (1H, d), 7.51 (2H, d), 7.71 (1H, s), 8.04 (1H, s), 8.72 (1H, s), 13.10 (1H, s); m/z: ES⁺ [M+H]⁺=576.

2-[(4aR)-11-Chloro-10-(5-methyl-1H-indazol-4-yl)-1,2,3,4,4a,5-hexahydro-6H-pyrazino[1',2':4,5]pyrazino[2,3-c]quinolin-6-yl]-N,N-dimethylethan-1-amine Atropisomer 1

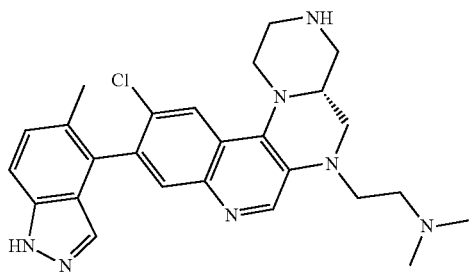 [SMILES: Cc1ccc2[nH]ncc2c1-c1cc2ncc3c(c2cc1Cl)N1CCNC[C@@H]1CN3CCN(C)C]

4M HCl in 1,4-dioxane (4 mL, 16.00 mmol) was added to atropisomer 1 of tert-butyl (4aS)-11-chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinoline-3-carboxylate (110 mg, 0.19 mmol) in MeOH (4 mL) at rt. The resulting suspension was stirred at rt for 1 h. The solvent was removed in vacuo. The crude product was purified SCX (7M NH₃/MeOH) to afford atropisomer 1 of 2-[(4aR)-11-chloro-10-(5-methyl-1H-indazol-4-yl)-1,2,3,4,4a,5-hexahydro-6H-pyrazino[1',2':4,5]pyrazino[2,3-c]quinolin-6-yl]-N,N-dimethylethan-1-amine (89 mg, 98%) as a yellow solid; ¹H NMR (300 MHz, DMSO, 30° C.) 2.18 (3H, s), 2.49 (6H, s), 2.79-2.95 (3H, m), 3.21-3.29 (1H, m), 3.38-3.51 (6H, m), 3.59-4.16 (3H, m), 7.34 (1H, d), 7.41-7.57 (2H, m), 7.74 (1H, s), 8.05 (1H, s), 8.79 (1H, s), 13.12 (1H, s); m/z: ES⁺ [M+H]⁺=476.

1-[(4aS)-11-Chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinolin-3-yl]prop-2-en-1-one (Atropisomer 1, Compound 73)

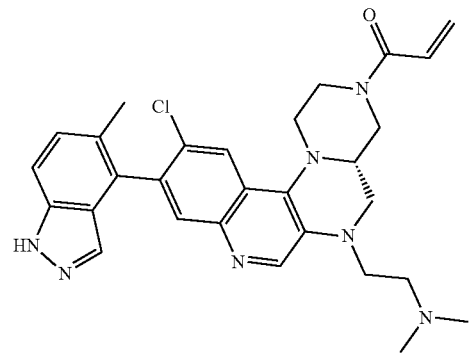 [SMILES: C=CC(=O)N1CCN2c3c(cnc4cc(-c5c(C)ccc6[nH]ncc56)c(Cl)cc34)N(CCN(C)C)C[C@H]2C1]

Acryloyl chloride (14 mg, 0.16 mmol) was added to atropisomer 1 of 2-[(4aR)-11-chloro-10-(5-methyl-1H-indazol-4-yl)-1,2,3,4,4a,5-hexahydro-6H-pyrazino[1',2':4,5]pyrazino[2,3-c]quinolin-6-yl]-N,N-dimethylethan-1-amine (68 mg, 0.14 mmol) and DIPEA (0.05 mL, 0.29 mmol) in DMF (3 mL) at −10° C. The resulting mixture was stirred at rt for 1 h. The reaction mixture was purified by C18-flash chromatography (0 to 100% MeCN in water (0.05% NH₄HCO₃)) to afford crude product as a yellow solid. This was purified by preparative HPLC (Column: XBridge Prep OBD C18 Column 30×150 mm 5 m; Mobile Phase A: Water (0.05% NH₄OH), Mobile Phase B: MeCN; Flow rate: 60 mL/min; Gradient: 37% B to 38% B in 7 min; 254; 220 nm) to afford atropisomer 1 of 1-[(4aS)-11-chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinolin-3-yl]prop-2-en-1-one (21 mg, 27%) as a pale yellow solid; ¹H NMR (300 MHz, DMSO, 30° C.) 2.19 (9H, d), 2.35-2.47 (2H, m), 2.77-2.93 (1H, m), 3.15-3.31 (2H, m), 3.35-3.63 (4H, m), 3.65-3.89 (2H, m), 4.04-4.31 (1H, m), 4.46 (1H, dd), 5.76 (1H, d), 6.19 (1H, d), 6.78-6.94 (1H, m), 7.34 (1H, d), 7.43-7.56 (2H, m), 7.72 (1H, s), 8.07 (1H, s), 8.72 (1H, s), 13.09 (1H, s); m/z: ES⁺ [M+H]⁺=530.

2-[(4aR)-11-Chloro-10-(5-methyl-1H-indazol-4-yl)-1,2,3,4,4a,5-hexahydro-6H-pyrazino[1',2':4,5]pyrazino[2,3-c]quinolin-6-yl]-N,N-dimethylethan-1-amine Atropisomer 2

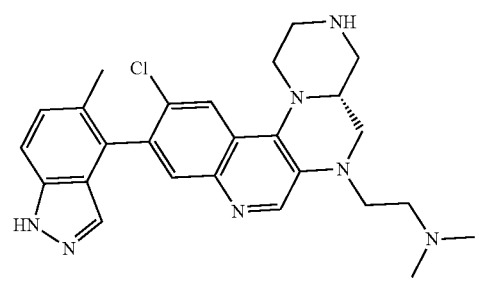 [SMILES: Cc1ccc2[nH]ncc2c1-c1cc2ncc3c(c2cc1Cl)N1CCNC[C@@H]1CN3CCN(C)C]

4M HCl in 1,4-dioxane (4 mL, 16.00 mmol) was added to atropisomer 2 of tert-butyl (4aS)-11-chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinoline-3-carboxylate (114 mg, 0.2 mmol) in MeOH (4 mL) at rt. The resulting suspension was stirred at rt for 1 h. The solvent was removed in vacuo. The crude product obtained was purified by SCX (7M NH$_3$/MeOH) to afford atropisomer 2 of 2-[(4aR)-11-chloro-10-(5-methyl-1H-indazol-4-yl)-1,2,3,4,4a,5-hexahydro-6H-pyrazino[1',2':4,5]pyrazino[2,3-c]quinolin-6-yl]-N,N-dimethylethan-1-amine (84 mg, 90%) as a yellow solid; $^1$H NMR (300 MHz, DMSO, 30° C.) 2.16 (3H, s), 2.46 (6H, s), 2.71-3.14 (3H, m), 3.25-3.29 (1H, m), 3.35-3.52 (5H, m), 3.59-4.17 (4H, m), 7.34 (1H, d), 7.44-7.57 (2H, m), 7.74 (1H, s), 8.05 (1H, s), 8.77 (1H, s), 13.11 (1H, s); m/z: ES$^+$ [M+H]$^+$=476.

1-[(4aS)-11-Chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinolin-3-yl]prop-2-en-1-one (Atropisomer 2, Compound 74)

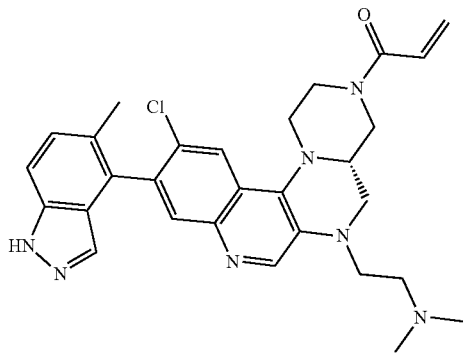 [SMILES: C=CC(=O)N1CCN2c3c(cnc4cc(-c5c(C)ccc6[nH]ncc56)c(Cl)cc34)N(CCN(C)C)C[C@H]2C1]

Acryloyl chloride (14 mg, 0.16 mmol) was added to atropisomer 2 of 2-[(4aR)-11-chloro-10-(5-methyl-1H-indazol-4-yl)-1,2,3,4,4a,5-hexahydro-6H-pyrazino[1',2':4,5]pyrazino[2,3-c]quinolin-6-yl]-N,N-dimethylethan-1-amine (69 mg, 0.14 mmol) and DIPEA (0.051 mL, 0.29 mmol) in DMF (3 mL) at −10° C.

The resulting mixture was stirred at rt for 1 h. The crude reaction mixture was purified by C18-flash chromatography (0 to 100%, MeCN in water (0.05% NH$_4$HCO$_3$) to afford crude product as a yellow solid. This was purified by preparative HPLC (Column: XBridge Prep OBD C18 Column 30×150 mm 5 m; Mobile Phase A: Water (0.05% NH$_3$H$_2$O), Mobile Phase B: MeCN; Flow rate: 60 mL/min; Gradient: 37% B to 38% B in 7 min; 254; 220 nm) to afford atropisomer 2 of 1-[(4aS)-11-chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinolin-3-yl]prop-2-en-1-one (23 mg, 29%) as a pale yellow solid; $^1$H NMR (300 MHz, DMSO, 30° C.) 2.18 (9H, d), 2.37-2.49 (2H, m), 2.79-2.90 (1H, m), 3.17-3.31 (2H, m), 3.35-3.63 (4H, m), 3.65-3.88 (2H, m), 4.18 (1H, dd), 4.45 (1H, dd), 5.77 (1H, d), 6.20 (1H, d), 6.83-6.95 (1H, m), 7.34 (1H, d), 7.51 (2H, d), 7.71 (1H, s), 8.07 (1H, s), 8.72 (1H, s), 13.09 (1H, s); m/z: ES$^+$ [M+H]$^+$=530.

5-[(3-Chloro-4-iodoanilino)methylidene]-2,2-dimethyl-1,3-dioxane-4,6-dione

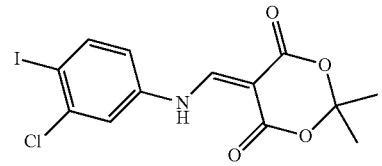 [SMILES: CC1(C)OC(=O)C(=CNc2ccc(I)c(Cl)c2)C(=O)O1]

5-(Methoxymethylene)-2,2-dimethyl-1,3-dioxane-4,6-dione (21.15 g, 113.62 mmol) was added to 3-chloro-4-iodoaniline (24 g, 94.69 mmol) in EtOH (450 mL). The resulting solution was stirred at 80° C. overnight. The reaction mixture was filtered and the solid collected washed with diethyl ether (400 mL) to afford 5-[(3-chloro-4-iodoanilino)methylidene]-2,2-dimethyl-1,3-dioxane-4,6-dione (37 g, 96%) as a white solid; $^1$H NMR (400 MHz, DMSO, 30° C.) 1.67 (6H, s), 7.34 (1H, dd), 7.90-7.98 (2H, m), 8.57 (1H, s), 11.20 (1H, s).

7-Chloro-6-iodoquinolin-4-ol

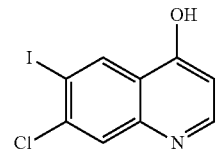 [SMILES: Oc1ccnc2cc(Cl)c(I)cc12]

5-[(3-Chloro-4-iodoanilino)methylidene]-2,2-dimethyl-1,3-dioxane-4,6-dione (37 g, 90.8 mmol) was added to stirring DOWTHERM™ A (320 mL) at 210° C. and the reaction mixture stirred for 40 min at 210° C. The reaction mixture was cooled to rt and added to heptane (200 mL). The resulting suspension was filtered and the solid collected washed with heptane then diethyl ether and dried on the filter to afford 7-chloro-6-iodoquinolin-4-ol (26.2 g, 94%) as a brown solid; $^1$H NMR (400 MHz, DMSO, 30° C.) 1.67 (6H, s), 7.34 (1H, dd), 7.90-7.98 (2H, m), 8.57 (1H, s), 11.20 (1H, s); m/z: ES$^+$ [M+H]$^+$=306.

7-Chloro-6-iodo-3-nitroquinolin-4-ol

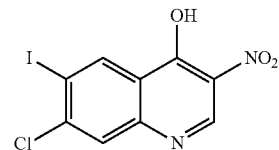

7-Chloro-6-iodoquinolin-4-ol (26.2 g, 85.76 mmol) was added to propionic acid (220 mL) and the mixture then heated at 125° C. Fuming nitric acid (7.67 mL, 171.52 mmol) was then added dropwise and the solution stirred for further 2 h at 125° C. The reaction mixture was cooled to rt, water (220 mL) was added and the resulting suspension filtered. The solid collected was washed with water (100 mL×2) and diethyl ether (100 mL) then dried to afford 7-chloro-6-iodo-3-nitroquinolin-4-ol (23.6 g, 79%); m/z: ES$^+$ [M+H]$^+$=351.

4,7-Dichloro-6-iodo-3-nitroquinoline

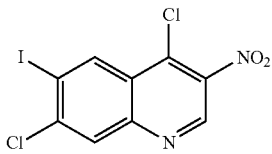 [SMILES: O=[N+]([O-])c1cnc2cc(Cl)c(I)cc2c1O]

Phosphorus(V) oxychloride (23.40 ml, 251.07 mmol) was added to 7-chloro-6-iodo-3-nitroquinolin-4-ol (22 g, 62.77 mmol) in toluene (250 ml) at rt. The mixture was then heated to 100° C. with stirring, at which point DMF (1.5 mL) was added and the mixture heated at 105° C. overnight. The reaction mixture was allowed to cool to rt and concentrated in vacuo to give the crude product. This was purified by flash silica chromatography (0 to 25% EtOAc in petroleum ether) to afford 4,7-dichloro-6-iodo-3-nitroquinoline (21 g, 91%) as a pale yellow solid; m/z: ES$^+$ [M+H]$^+$=369.

tert-Butyl (3R)-4-(7-chloro-6-iodo-3-nitroquinolin-4-yl)-3-(hydroxymethyl)piperazine-1-carboxylate

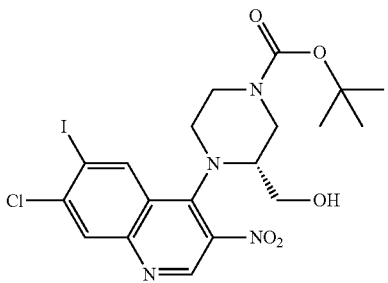 [SMILES: CC(C)(C)OC(=O)N1CCN(c2c([N+](=O)[O-])cnc3cc(Cl)c(I)cc23)[C@@H](CO)C1]

DIPEA (10.41 mL, 59.63 mmol) was added to 4,7-dichloro-6-iodo-3-nitroquinoline (10 g, 27.1 mmol) and tert-butyl (3R)-3-(hydroxymethyl)piperazine-1-carboxylate (10.55 g, 48.79 mmol) in IPA (200 mL). The resulting mixture was stirred at 80° C. for 4 h. The solvent was removed in vacuo. The crude product was purified by flash silica chromatography (0 to 80% EtOAc in petroleum ether) to afford tert-butyl (3R)-4-(7-chloro-6-iodo-3-nitroquinolin-4-yl)-3-(hydroxymethyl)piperazine-1-carboxylate (6.2 g, 42%) as a yellow solid; m/z: ES$^+$ [M+H]$^+$=549.

tert-Butyl (4aR)-10-chloro-11-iodo-1,2,4a,5-tetrahydropyrazino[1',2':4,5][1,4]oxazino[2,3-c]quinoline-3(4H)-carboxylate

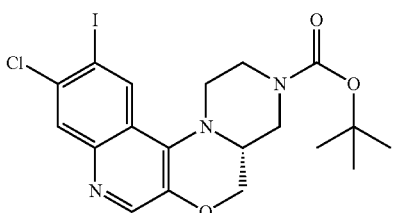

1M Lithium bis(trimethylsilyl)amide in THF (10.2 mL, 10.2 mmol) was added slowly to tert-butyl (3R)-4-(7-chloro-6-iodo-3-nitroquinolin-4-yl)-3-(hydroxymethyl)piperazine-1-carboxylate (5.6 g, 10.2 mmol) in NMP (30 mL) at rt and the reaction mixture heated at 130° C. for 3 h. The reaction mixture was cooled to rt, partitioned between water (2 L) and EtOAc (1 L) then the organic layer washed with brine (500 mL) and concentrated in vacuo to afford crude product. This was purified by flash silica chromatography (0 to 20% EtOAc in petroleum ether) to afford tert-butyl (4aR)-10-chloro-11-iodo-1,2,4a,5-tetrahydropyrazino[1',2':4,5][1,4]oxazino[2,3-c]quinoline-3(4H)-carboxylate (1.4 g, 27%) as a pale yellow solid; $^1$H NMR (400 MHz, DMSO, 30° C.) 1.43 (9H, s), 3.19-3.21 (1H, m), 3.36-3.57 (2H, m), 3.69-3.78 (2H, m), 3.98-4.11 (1H, m), 4.15-4.21 (1H, m), 4.31-4.38 (1H, m), 8.06 (1H, d), 8.50 (2H, d), 9.13-9.22 (1H, m); m/z: ES$^+$ [M+H]$^+$=502.

tert-Butyl (4aR)-10-chloro-11-[(trimethylsilyl)ethynyl]-1,2,4a,5-tetrahydropyrazino[1',2':4,5][1,4]oxazino[2,3-c]quinoline-3(4H)-carboxylate

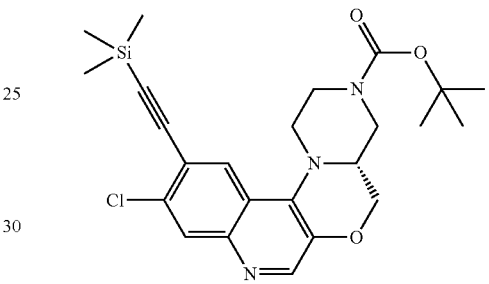

Tetrakis(triphenylphosphine)palladium(0) (184 mg, 0.16 mmol) was added to tert-butyl (4aR)-10-chloro-11-iodo-1,2,4a,5-tetrahydropyrazino[1',2':4,5][1,4]oxazino[2,3-c]quinoline-3(4H)-carboxylate (800 mg, 1.59 mmol), ethynyltrimethylsilane (783 mg, 7.97 mmol) and NEt$_3$ (0.444 mL, 3.19 mmol) in THF (15 mL) at 20° C. The resulting mixture was stirred at 60° C. for 16 h. The solvent was removed in vacuo. The crude product obtained was purified by flash silica chromatography (0 to 90% EtOAc in petroleum ether) to afford tert-butyl (4aR)-10-chloro-11-[(trimethylsilyl)ethynyl]-1,2,4a,5-tetrahydropyrazino[1',2':4,5][1,4]oxazino[2,3-c]quinoline-3(4H)-carboxylate (430 mg, 57%) as a yellow solid; $^1$H NMR (400 MHz, DMSO, 30° C.) 0.28 (9H, d), 1.43 (9H, d), 3.37 (1H, s), 3.44 (1H, s), 3.55 (2H, s), 3.67 (2H, s), 4.03 (1H, q), 4.17 (1H, dt), 4.34 (1H, d), 7.48 (1H, s), 8.06 (1H, d), 8.52 (1H, s); m/z: ES$^+$ [M+H]$^+$=472.

tert-Butyl (4aR)-11-ethynyl-10-(5-methyl-1H-indazol-4-yl)-1,2,4a,5-tetrahydropyrazino[1',2':4,5][1,4]oxazino[2,3-c]quinoline-3(4H)-carboxylate

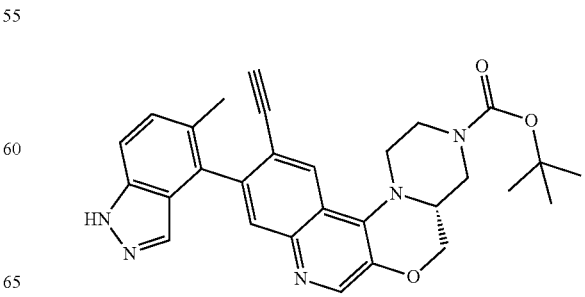

XPhos-Pd-G2 (41.7 mg, 0.05 mmol) was added to tert-butyl (4aR)-10-chloro-11-[(trimethylsilyl)ethynyl]-1,2,4a,5-tetrahydropyrazino[1',2':4,5][1,4]oxazino[2,3-c]quinoline-3(4H)-carboxylate (250 mg, 0.53 mmol), (5-methyl-1H-indazol-4-yl)boronic acid (140 mg, 0.79 mmol) and $K_2CO_3$ (146 mg, 1.06 mmol) in 1,4-dioxane/water (15 mL, 4:1 ratio) at 20° C. and sealed into a microwave tube. The reaction was heated to 140° C. for 1 h in the microwave reactor and cooled to rt. The solvent was removed in vacuo to afford crude product. This was purified by flash silica chromatography (0 to 100% EtOAc in petroleum ether) to afford tert-butyl (4aR)-11-ethynyl-10-(5-methyl-1H-indazol-4-yl)-1,2,4a,5-tetrahydropyrazino[1',2':4,5][1,4]oxazino[2,3-c]quinoline-3(4H)-carboxylate (130 mg, 50%) as a yellow solid; m/z: ES+ [M+H]+=496.

(4aR)-11-Ethynyl-10-(5-methyl-1H-indazol-4-yl)-1,2,3,4,4a,5-hexahydropyrazino[1',2':4,5][1,4]oxazino[2,3-c]quinoline

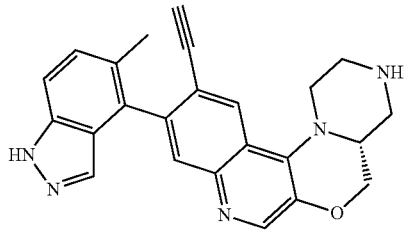 [SMILES: C#Cc1cc2c3c(cnc2cc1-c1c(C)ccc2[nH]ncc12)OC[C@H]1CNCCN31]

4M HCl in 1,4-dioxane (0.5 mL) was added to tert-butyl (4aR)-11-ethynyl-10-(5-methyl-1H-indazol-4-yl)-1,2,4a,5-tetrahydropyrazino[1',2':4,5][1,4]oxazino[2,3-c]quinoline-3(4H)-carboxylate (130 mg, 0.26 mmol) in MeOH (0.5 mL) at rt. The resulting mixture was stirred at rt for 1 h. The solvent was removed in vacuo to afford (4aR)-11-ethynyl-10-(5-methyl-1H-indazol-4-yl)-1,2,3,4,4a,5-hexahydropyrazino[1',2':4,5][1,4]oxazino[2,3-c]quinoline (150 mg, >100%) as a yellow oil that was used without further purification; $^1$H NMR (400 MHz, DMSO, 30° C.) 2.22 (3H, d), 3.21-3.31 (1H, m), 3.37-3.53 (1H, m), 3.60 (1H, br s), 3.60-3.74 (1H, m), 4.10-4.25 (2H, m), 4.28-4.51 (4H, m), 7.36 (1H, dd), 7.57-7.67 (1H, m), 8.02 (1H, s), 8.44 (1H, d), 8.80 (1H, d), 9.70 (1H, s), 9.98 (1H, s); m/z: ES+ [M+H]+=396.

1-[(4aR)-11-Ethynyl-10-(5-methyl-1H-indazol-4-yl)-1,2,4a,5-tetrahydropyrazino[1',2':4,5][1,4]oxazino[2,3-c]quinolin-3(4H)-yl]prop-2-en-1-one (Atropisomer 1, Compound 75; Atropisomer 2, Compound 76)

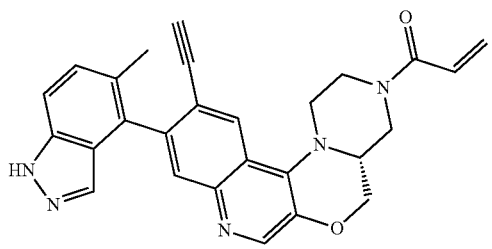 [SMILES: C#Cc1cc2c3c(cnc2cc1-c1c(C)ccc2[nH]ncc12)OC[C@H]1CN(C(=O)C=C)CCN31]

Acryloyl chloride (29.2 mg, 0.32 mmol) was added dropwise to (4aR)-11-ethynyl-10-(5-methyl-1H-indazol-4-yl)-1,2,3,4,4a,5-hexahydropyrazino[1',2':4,5][1,4]oxazino[2,3-c]quinoline (116 mg, 0.27 mmol) and DIPEA (0.188 mL, 1.07 mmol) in DMF (2 mL) at −20° C. The resulting mixture was stirred at −20° C. for 1 h. The crude reaction mixture was purified by C18-flash chromatography (0 to 50% MeCN in water (0.1% $NH_4HCO_3$)) to afford crude product as a white solid. This was purified by preparative chiral-HPLC (Column: CHIRALPAK IG-03, 2.0 cm I.D*25 cm L (5 μm); Mobile Phase A: MTBE (10 mM $NH_3$-MeOH)-HPLC, Mobile Phase B: EtOH-HPLC; Flow rate: 15 mL/min; Gradient: 50 B to 50 B in 15 min; 254/220 nm) to afford atropisomer 1 of 1-[(4aR)-11-ethynyl-10-(5-methyl-1H-indazol-4-yl)-1,2,4a,5-tetrahydropyrazino[1',2':4,5][1,4]oxazino[2,3-c]quinolin-3(4H)-yl]prop-2-en-1-one (11 mg, 37%) as a white solid; $^1$H NMR (400 MHz, DMSO, 30° C.) 2.21 (3H, s), 3.49 (1H, s), 3.60 (1H, s), 3.63 (1H, s), 3.77 (1H, s), 3.94 (2H, s), 4.09 (2H, s), 4.23 (1H, s), 4.38 (1H, d), 5.77 (1H, s), 6.19 (1H, d), 6.87 (1H, s), 7.33 (1H, d), 7.41-7.68 (2H, m), 7.78 (1H, s), 8.25 (1H, s), 8.56 (1H, s), 13.05 (1H, s); m/z: ES+ [M+H]+=450. This was followed by atropisomer 2 of 1-[(4aR)-11-ethynyl-10-(5-methyl-1H-indazol-4-yl)-1,2,4a,5-tetrahydropyrazino[1',2':4,5][1,4]oxazino[2,3-c]quinolin-3(4H)-yl]prop-2-en-1-one (11 mg, 38%) as a white solid; $^1$H NMR (400 MHz, DMSO, 30° C.) 2.19 (3H, s), 3.48 (2H, s), 3.61 (2H, d), 3.78 (1H, s), 3.94 (1H, s), 4.06 (2H, s), 4.23 (1H, s), 4.36 (1H, s), 5.77 (1H, s), 6.19 (1H, d), 6.87 (1H, s), 7.33 (1H, d), 7.45-7.53 (2H, m), 7.78 (1H, s), 8.25 (1H, s), 8.56 (1H, s), 13.05 (1H, s); m/z: ES+ [M+H]+=450.

tert-Butyl (4aR)-11-chloro-9-fluoro-10-[5-methyl-1-(oxan-2-yl)-1H-benzimidazol-4-yl]-1,2,4a,5-tetrahydropyrazino[1',2':4,5][1,4]oxazino[2,3-c]quinoline-3(4H)-carboxylate

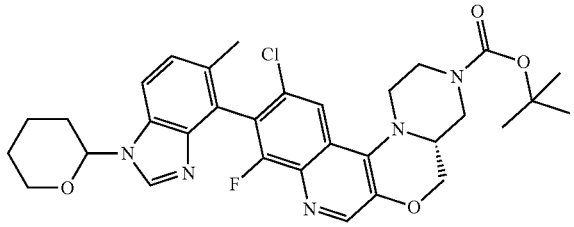 [SMILES: Cc1ccc2c(ncn2C2CCCCO2)c1-c1c(Cl)cc2c3c(cnc2c1F)OC[C@H]1CN(C(=O)OC(C)(C)C)CCN31]

RuPhos-Pd-G3 (0.177 g, 0.21 mmol) was added in one portion [5-methyl-1-(oxan-2-yl)-1H-benzimidazol-4-yl]boronic acid (1.375 g, 5.29 mmol), tert-butyl (4aR)-10-bromo-11-chloro-9-fluoro-1,2,4a,5-tetrahydropyrazino[1',2':4,5][1,4]oxazino[2,3-c]quinoline-3(4H)-carboxylate (1 g, 2.12 mmol), $K_2CO_3$ (0.731 g, 5.29 mmol) and RuPhos (0.099 g, 0.21 mmol) in 1,4-dioxane/$H_2O$ (25 mL, 4:1 ratio) at 25° C. The resulting solution was stirred at 100° C. for 2 h. The solvent was removed in vacuo. The resulting residue was purified by flash silica chromatography (0 to 7% EtOAc in petroleum ether) to afford crude product. This was purified by C18-flash chromatography (0 to 60% MeCN in water) to afford tert-butyl (4aR)-11-chloro-9-fluoro-10-[5-methyl-1-(oxan-2-yl)-1H-benzimidazol-4-yl]-1,2,4a,5-tetrahydropyrazino[1',2':4,5][1,4]oxazino[2,3-c]quinoline-3(4H)-carboxylate (0.5 g, 39%) as a yellow solid; m/z: ES+ [M+H]+=608.

(4aR)-11-Chloro-9-fluoro-10-(5-methyl-1H-benz-
imidazol-4-yl)-1,2,3,4,4a,5-hexahydropyrazino[1',2':
4,5][1,4]oxazino[2,3-c]quinoline

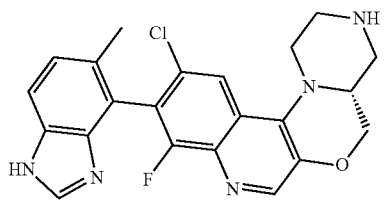 [SMILES: Cc1ccc2[nH]cnc2c1-c1c(Cl)cc2c3c(cnc2c1F)OC[C@H]1CNCCN31]

4M HCl in MeOH (4 mL, 16 mmol) was added in one portion to tert-butyl (4aR)-11-chloro-9-fluoro-10-[5-methyl-1-(oxan-2-yl)-1H-benzimidazol-4-yl]-1,2,4a,5-tetrahydro-pyrazino[1',2':4,5][1,4]oxazino[2,3-c]quinoline-3(4H)-car-boxylate (500 mg, 0.82 mmol) in MeOH (4 mL) at rt and reaction mixture stirred at 60° C. for 16 h. The solvent was removed in vacuo.

The crude product was purified by SCX (7M NH$_3$/MeOH) to afford (4aR)-11-chloro-9-fluoro-10-(5-methyl-1H-benz-imidazol-4-yl)-1,2,3,4,4a,5-hexahydropyrazino[1',2':4,5][1,4]oxazino[2,3-c]quinoline (260 mg, 75%) as a pale yellow gum; $^1$H NMR (400 MHz, DMSO, 30° C.) 2.27 (3H, d), 3.23-3.40 (2H, m), 3.39-3.61 (2H, m), 3.67-3.99 (3H, m), 4.33-4.46 (1H, m), 4.53-4.66 (1H, m), 7.66 (1H, d), 7.87-7.98 (1H, m), 8.16 (1H, s), 8.62-8.70 (1H, m), 9.62 (1H, s), 9.88-10.00 (1H, m); m/z: ES$^+$ [M+H]$^+$=424.

1-[(4aR)-11-Chloro-9-fluoro-10-(5-methyl-1H-benz-
imidazol-4-yl)-1,2,4a,5-tetrahydropyrazino[1',2':4,5]
[1,4]oxazino[2,3-c]quinolin-3(4H)-yl]prop-2-en-1-
one (Atropisomer 1, Compound 77; Atropisomer 2,
Compound 78)

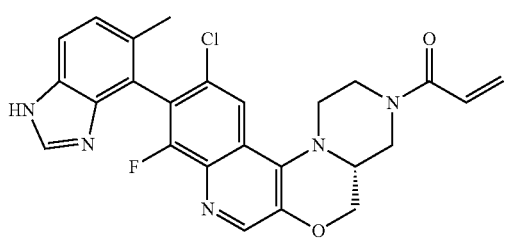 [SMILES: C=CC(=O)N1CCN2c3c(cnc4c(F)c(-c5c(C)ccc6[nH]cnc56)c(Cl)cc34)OC[C@H]2C1]

A mixture of acryloyl chloride (0.047 mL, 0.58 mmol) in DMF (5 mL) was added dropwise to a stirred mixture of (4aR)-11-chloro-9-fluoro-10-(5-methyl-1H-benzimidazol-4-yl)-1,2,3,4,4a,5-hexahydropyrazino[1',2':4,5][1,4]oxazino[2,3-c]quinoline (245 mg, 0.58 mmol) and DIPEA (0.202 mL, 1.16 mmol) in DMF (5 mL) at 0° C. The resulting mixture was stirred at 0° C. for 30 min. The crude reaction mixture was purified by C18-flash chromatography (35% MeCN in water) to afford crude product. This was purified by preparative chiral-HPLC (Column: CHIRAL ART Cel-lulose-SB S-5 ⌀ m, 2*25 cm, 5 ⌀ m; Mobile Phase A: MTBE (10 mM NH$_3$-MeOH)-HPLC, Mobile Phase B: EtOH-HPLC; Flow rate: 20 mL/min; Gradient: 30 B to 30 B in 13 min; 220/254 nm) to afford atropisomer 1 of 1-[(4aR)-11-chloro-9-fluoro-10-(5-methyl-1H-benzimidazol-4-yl)-1,2,4a,5-tetrahydropyrazino[1',2':4,5][1,4]oxazino[2,3-c]quino-lin-3(4H)-yl]prop-2-en-1-one (34 mg, 12%) as a white solid; $^1$H NMR (400 MHz, DMSO, 30° C.) 2.19 (3H, s), 3.38-3.55 (1H, m), 3.55-3.68 (2H, m), 3.69-3.91 (1H, m), 3.90-4.04 (1H, m), 4.02-4.21 (2H, m), 4.21-4.33 (1H, m), 4.33-4.53 (1H, m), 5.59-5.79 (1H, m), 6.20 (1H, d), 6.87 (1H, s), 7.23 (1H, d), 7.55-7.78 (1H, m), 7.89-8.09 (2H, m), 8.61 (1H, s), 11.92-12.53 (1H, m); m/z: ES$^+$ [M+H]$^+$=478. This was followed by atropisomer 2 of 1-[(4aR)-11-chloro-9-fluoro-10-(5-methyl-1H-benzimidazol-4-yl)-1,2,4a,5-tetrahydro-pyrazino[1',2':4,5][1,4]oxazino[2,3-c]quinolin-3(4H)-yl] prop-2-en-1-one (56 mg, 20%) as a white solid; $^1$H NMR (400 MHz, DMSO, 30° C.) 2.17 (3H, s), 3.36-4.63 (9H, m), 5.59-5.82 (1H, d), 6.20 (1H, d), 6.78-6.98 (1H, m), 7.20 (1H, d), 7.41-7.83 (1H, m), 7.88-8.25 (2H, m), 8.61 (1H, s), 11.88-12.60 (1H, m); m/z: ES$^+$ [M+H]$^+$=478.

3-Bromo-2-chloro-4-fluoroaniline

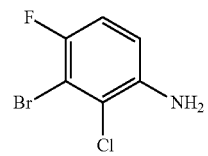

N-Chlorosuccinimide (1.335 g, 10.00 mmol) was added to 3-bromo-4-fluoroaniline (1.9 g, 10 mmol) in DMF (20 mL). The resulting mixture was stirred at 60° C. for 3 h. The reaction mixture was diluted with EtOAc (50 mL) and washed with brine (50 mL). The organic layer was dried (Na$_2$SO$_4$) and concentrated in vacuo to afford crude product. This was purified by flash silica chromatography (0 to 15% EtOAc in petroleum ether) to afford 3-bromo-2-chloro-4-fluoroaniline (1.1 g, 49%) as a yellow solid; $^1$H NMR (400 MHz, DMSO, 30° C.) 5.50 (2H, s), 6.82 (1H, dd), 7.08 (1H, t); m/z: ES$^+$ [M+H]$^+$=224.

5-[(3-Bromo-2-chloro-4-fluoroanilino)methylidene]-
2,2-dimethyl-1,3-dioxane-4,6-dione

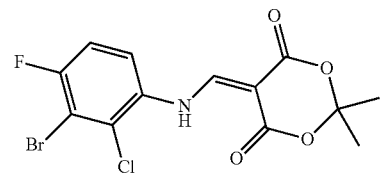 [SMILES: CC1(C)OC(=O)C(=CNc2ccc(F)c(Br)c2Cl)C(=O)O1]

5-(Methoxymethylene)-2,2-dimethyl-1,3-dioxane-4,6-di-one (10.2 g, 54.8 mmol) was added to 3-bromo-2-chloro-4-fluoroaniline (12.3 g, 54.8 mmol) in ethanol (200 mL). The resulting mixture was stirred at 80° C. overnight. The reaction mixture was cooled to rt and filtered. The solid obtained was washed with EtOH (100 mL) and dried under vacuum to afford 5-[(3-bromo-2-chloro-4-fluoroanilino) methylidene]-2,2-dimethyl-1,3-dioxane-4,6-dione (17 g, 82%) as a yellow solid; $^1$H NMR (400 MHz, DMSO, 30° C.) 1.69 (6H, s), 7.53 (1H, dd), 8.01 (1H, dd), 8.70 (1H, d), 11.54 (1H, d); m/z: ES$^+$ [M+H]$^+$=378.

7-Bromo-8-chloro-6-fluoroquinolin-4-ol

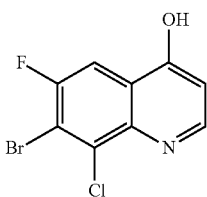 [SMILES: Oc1ccnc2c(Cl)c(Br)c(F)cc12]

5-[(3-Bromo-2-chloro-4-fluoroanilino)methylidene]-2,2-dimethyl-1,3-dioxane-4,6-dione (17 g, 44.9 mmol) was added to DOWTHERM™ A (200 mL) at 230° C. The resulting mixture was stirred at 230° C. for 40 min. The reaction mixture was cooled to rt and filtered. The solid collected was washed with diethyl ether (500 mL) and dried under vacuum to afford 7-bromo-8-chloro-6-fluoroquinolin-4-ol (12 g, 97%) as a yellow solid; $^1$H NMR (400 MHz, DMSO, 30° C.) 6.13 (1H, d), 7.76-7.92 (2H, m), 11.54 (1H, s); m/z: ES$^+$ [M+H]$^+$=276.

7-Bromo-8-chloro-6-fluoro-3-nitroquinolin-4-ol

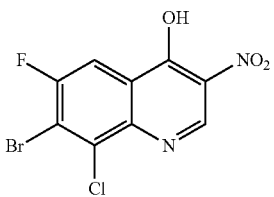 [SMILES: O=[N+]([O-])c1cnc2c(Cl)c(Br)c(F)cc2c1O]

Fuming nitric acid (8.73 mL, 97.65 mmol) was added to 7-bromo-8-chloro-6-fluoroquinolin-4-ol (9 g, 32.55 mmol) in propionic acid (150 mL) at 125° C. The resulting mixture was stirred at 125° C. for 2 h. The reaction mixture was cooled to rt then poured into ice water. The resulting mixture was filtered and the solid collected washed with water (300 mL) and dried under vacuum to afford 7-bromo-8-chloro-6-fluoro-3-nitroquinolin-4-ol (8.9 g, 85%) as a yellow solid; $^1$H NMR (400 MHz, DMSO, 30° C.) 8.00 (1H, d), 8.83 (1H, s), 12.65 (1H, s); m/z: ES$^+$ [M+H]$^+$=321.

7-Bromo-4,8-dichloro-6-fluoro-3-nitroquinoline

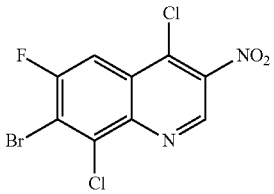 [SMILES: O=[N+]([O-])c1cnc2c(Cl)c(Br)c(F)cc2c1Cl]

Phosphorus(V) oxychloride (7.65 mL, 82.12 mmol) was added to 7-bromo-8-chloro-6-fluoro-3-nitroquinolin-4-ol (8.8 g, 27.37 mmol) in toluene (150 mL) and DMF (0.5 mL). The resulting mixture was stirred at 100° C. overnight. The reaction mixture was concentrated in vacuo, dissolved in DCM (250 mL) and washed sequentially with sat. NaHCO$_3$ (250 mL), brine (250 mL) and water (250 mL). The organic layer was dried (Na$_2$SO$_4$) and concentrated in vacuo to afford 7-bromo-4,8-dichloro-6-fluoro-3-nitroquinoline (8.5 g, 91%) as a yellow solid; $^1$H NMR (400 MHz, DMSO, 30° C.) 8.37 (1H, d), 9.49 (1H, s); m/z: ES$^+$ [M+H]$^+$=339.

1-tert-Butyl 3-methyl (3R)-4-(7-bromo-8-chloro-6-fluoro-3-nitroquinolin-4-yl)piperazine-1,3-dicarboxylate

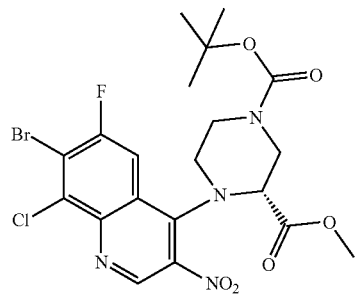 [SMILES: COC(=O)[C@H]1CN(C(=O)OC(C)(C)C)CCN1c1c([N+](=O)[O-])cnc2c(Cl)c(Br)c(F)cc12]

DIPEA (1.541 mL, 8.83 mmol) was added to 7-bromo-4,8-dichloro-6-fluoro-3-nitroquinoline (1 g, 2.94 mmol) and 1-tert-butyl 3-methyl (3R)-piperazine-1,3-dicarboxylate (1.078 g, 4.41 mmol) in MeCN (15 mL). The resulting mixture was stirred at 80° C. for 3 h. The solvent was removed in vacuo. The crude product was purified by flash silica chromatography (0 to 15% EtOAc in petroleum ether) to afford 1-tert-butyl 3-methyl (3R)-4-(7-bromo-8-chloro-6-fluoro-3-nitroquinolin-4-yl)piperazine-1,3-dicarboxylate (1 g, 62%) as a yellow solid; $^1$H NMR (400 MHz, DMSO, 30° C.) 1.44 (9H, s), 3.16-3.31 (2H, m), 3.53 (3H, s), 3.55-3.66 (1H, m), 3.75-3.91 (2H, m), 3.95-4.14 (1H, m), 4.26-4.37 (1H, m), 8.19 (1H, d), 9.18 (1H, s); m/z: ES$^+$ [M+H]$^+$=547.

tert-Butyl (4aR)-10-bromo-9-chloro-11-fluoro-5-oxo-1,2,4,4a,5,6-hexahydro-3H-pyrazino[1',2':4,5]pyrazino[2,3-c]quinoline-3-carboxylate

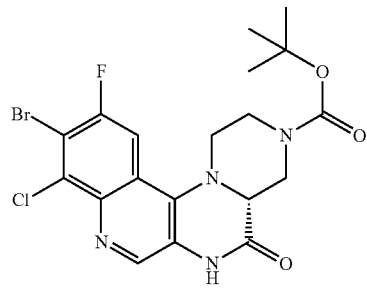 [SMILES: CC(C)(C)OC(=O)N1CCN2c3c(cnc4c(Cl)c(Br)c(F)cc34)NC(=O)[C@H]2C1]

Iron (484 mg, 8.67 mmol) was added 1-tert-butyl 3-methyl (3R)-4-(7-bromo-8-chloro-6-fluoro-3-nitroquinolin-4-yl)piperazine-1,3-dicarboxylate (950 mg, 1.73 mmol) in glacial acetic acid (15 mL) at 25° C. The resulting mixture was stirred at 60° C. for 1 h. The mixture was filtered through CELITE™. The solvent was removed in vacuo. The crude product obtained was purified by flash silica chromatography (0 to 25% EtOAc in petroleum ether) to afford tert-butyl (4aR)-10-bromo-9-chloro-11-fluoro-5-oxo-1,2,4,4a,5,6-hexahydro-3H-pyrazino[1',2':4,5]pyrazino[2,3-c]quinoline-3-carboxylate (750 mg, 89%) as a yellow solid; $^1$H NMR (400 MHz, DMSO, 30° C.) 1.44 (9H, s), 2.57-2.76 (1H, m), 3.08-3.29 (3H, m), 3.75-3.97 (2H, m), 4.70 (1H, d), 7.94 (1H, d), 8.66 (1H, s), 11.02 (1H, s); m/z: ES+ [M+H]+=485.

tert-Butyl (4aR)-10-bromo-9-chloro-11-fluoro-6-methyl-5-oxo-1,2,4,4a,5,6-hexahydro-3H-pyrazino[1',2':4,5]pyrazino[2,3-c]quinoline-3-carboxylate

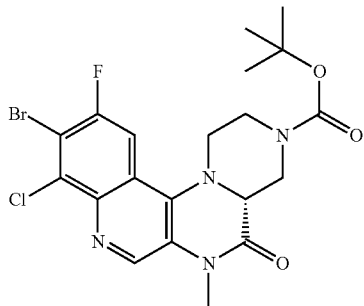 [SMILES: CN1C(=O)[C@H]2CN(C(=O)OC(C)(C)C)CCN2c2c1cnc1c(Cl)c(Br)c(F)cc21]

2-(tert-Butylimino)-N,N-diethyl-1,3-dimethyl-1,3,2λ5-diazaphosphinan-2-amine (1186 mg, 4.32 mmol) was added to tert-butyl (4aR)-10-bromo-9-chloro-11-fluoro-5-oxo-1,2,4,4a,5,6-hexahydro-3H-pyrazino[1',2':4,5]pyrazino[2,3-c]quinoline-3-carboxylate (700 mg, 1.44 mmol) and iodomethane (0.27 mL, 4.32 mmol) in DCM (6 mL) at 0° C. The resulting mixture was stirred at 0° C. for 30 min. The crude reaction mixture was purified by flash silica chromatography (15 to 25% EtOAc in petroleum ether) to afford tert-butyl (4aR)-10-bromo-9-chloro-11-fluoro-6-methyl-5-oxo-1,2,4,4a,5,6-hexahydro-3H-pyrazino[2,3-c]quinoline-3-carboxylate (720 mg, 100%) as a yellow solid; 1H NMR (400 MHz, DMSO, 30° C.) 1.45 (9H, s), 2.57-2.72 (1H, m), 3.12-3.29 (3H, m), 3.48 (3H, s), 3.78-4.00 (2H, m), 4.74 (1H, d), 7.99 (1H, d), 9.02 (1H, s); m/z: ES+ [M+H]+=499.

tert-Butyl (4aR)-9-chloro-11-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate Atropisomer 1 and 2

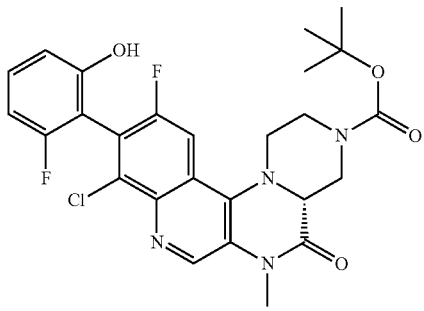 [SMILES: CN1C(=O)[C@H]2CN(C(=O)OC(C)(C)C)CCN2c2c1cnc1c(Cl)c(-c3c(O)cccc3F)c(F)cc21]

Tetrakis(triphenylphosphine)palladium(0) (92 mg, 0.08 mmol) was added to tert-butyl (4aR)-10-bromo-9-chloro-11-fluoro-6-methyl-5-oxo-1,2,4,4a,5,6-hexahydro-3H-pyrazino[1',2':4,5]pyrazino[2,3-c]quinoline-3-carboxylate (400 mg, 0.8 mmol), (2-fluoro-6-hydroxyphenyl)boronic acid (250 mg, 1.6 mmol) and Na2CO3 (212 mg, 2 mmol) in 1,4-dioxane (10 mL) and water (2 mL). The resulting mixture was stirred at 100° C. for 3 h. The reaction mixture was concentrated in vacuo, dissolved in DCM (50 mL), and washed with water (50 mL×2). The organic layer was dried (Na2SO4), concentrated in vacuo, and purified by flash silica chromatography (25 to 50% EtOAc in petroleum ether) to afford crude product. This was purified by preparative chiral-HPLC (Column: CHIRAL IC, 2*25 cm, 5 m; Mobile Phase A: CO2:50, Mobile Phase B: IPA (8 mmol/L NH3.MeOH)-HPLC: 50; Flow rate: 40 mL/min; 254 nm) to afford atropisomer 1 of tert-butyl (4aR)-9-chloro-11-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (150 mg, 35%) as a yellow solid; 1H NMR (400 MHz, DMSO, 30° C.) 1.45 (9H, s), 2.59-2.74 (1H, m), 3.14-3.28 (3H, m), 3.51 (3H, s), 3.80-4.00 (2H, m), 4.76 (1H, d), 6.76-6.90 (2H, m), 7.30-7.41 (1H, m), 7.91 (1H, d), 9.02 (1H, s), 10.19 (1H, s); m/z: ES+ [M+H]+=531. This was followed by atropisomer 2 of tert-butyl (4aR)-9-chloro-11-fluoro-10-(2-fluoro-6-hydroxyphenyl)-6-methyl-5-oxo-1,2,4,4a, 5,6-hexahydro-3H-pyrazino[1',2':4,5]pyrazino[2,3-c]quinoline-3-carboxylate (155 mg, 37%) as a yellow solid; 1H NMR (400 MHz, DMSO, 30° C.) 1.45 (9H, s), 2.57-2.76 (1H, m), 3.11-3.30 (3H, m), 3.51 (3H, s), 3.78-4.06 (2H, m), 4.77 (1H, d), 6.75-6.90 (2H, m), 7.29-7.41 (1H, m), 7.90 (1H, d), 9.02 (1H, s), 10.19 (1H, s) m/z: ES+ [M+H]+=531.

(4aR)-9-Chloro-11-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one Atropisomer 1

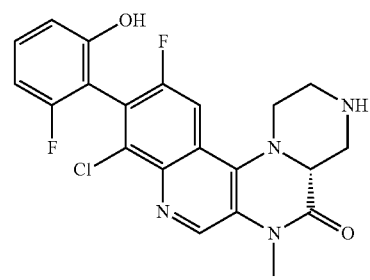 [SMILES: CN1C(=O)[C@H]2CNCCN2c2c1cnc1c(Cl)c(-c3c(O)cccc3F)c(F)cc21]

TFA (1 mL, 12.98 mmol) was added to atropisomer 1 of tert-butyl (4aR)-9-chloro-11-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (155 mg, 0.29 mmol) in DCM (4 mL). The resulting mixture was stirred at rt for 2 h. The solvent was removed in vacuo. The crude product obtained was purified by SCX (7M NH3/MeOH) to afford atropisomer 1 of (4aR)-9-chloro-11-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (120 mg, 95%) as a yellow solid; 1H NMR (400 MHz, DMSO, 30° C.) 2.83-2.96 (1H, m), 3.17-3.27 (1H, m), 3.35-3.58 (3H, m), 3.59 (3H, s), 4.05 (1H, d), 4.20-4.27 (1H, m), 6.75-6.93 (2H, m), 7.28-7.42 (1H, m), 8.02 (1H, d), 9.10 (1H, s), 10.15-10.35 (1H, m); m/z: ES+ [M+H]+=431.

(4aR)-9-Chloro-11-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (Atropisomer 1, Compound 79)

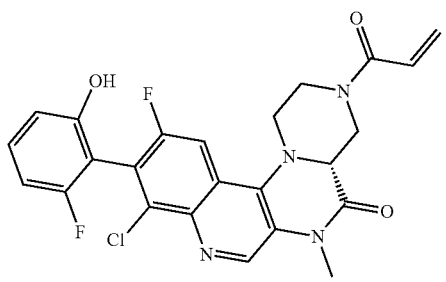 [SMILES: C=CC(=O)N1CCN2c3c(cnc4c(Cl)c(-c5c(O)cccc5F)c(F)cc34)N(C)C(=O)[C@H]2C1]

Acryloyl chloride (0.024 mL, 0.29 mmol) was added to atropisomer 1 of (4aR)-9-chloro-11-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (120 mg, 0.28 mmol) and DIPEA (0.073 mL, 0.42 mmol) in DMF (4 mL) at 0° C. The resulting mixture was stirred at 0° C. for 1 h. The crude reaction mixture was purified by C18-flash chromatography (0 to 50% MeCN in water (0.1% $NH_4CO_3$)) to afford atropisomer 1 of (4aR)-9-chloro-11-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (24 mg, 17%) as a yellow solid; $^1$H NMR (400 MHz, DMSO, 30° C.) 2.56-2.72 (1H, m), 3.06-3.29 (1H, m), 3.30-3.32 (1H, m), 3.50 (3H, s), 3.53-3.64 (1H, m), 3.86-4.09 (1H, m), 4.44 (1H, d), 4.78 (1H, d), 5.62-5.81 (1H, m), 6.15 (1H, dd), 6.71-6.93 (2H, m), 6.99-7.14 (1H, m), 7.26-7.45 (1H, m), 7.96 (1H, d), 9.03 (1H, s), 10.23 (1H, s); m/z: $ES^+$ $[M+H]^+$=485.

(4aR)-9-Chloro-11-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one Atropisomer 2

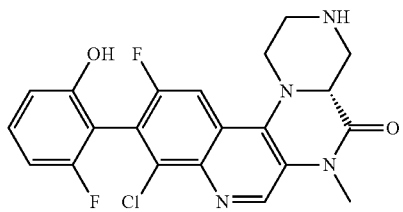 [SMILES: CN1C(=O)[C@H]2CNCCN2c2c1cnc1c(Cl)c(-c3c(O)cccc3F)c(F)cc21]

TFA (1 mL, 12.98 mmol) was added to atropisomer 2 of tert-butyl (4aR)-9-chloro-11-fluoro-10-(2-fluoro-6-hydroxyphenyl)-6-methyl-5-oxo-1,2,4,4a,5,6-hexahydro-3H-pyrazino[1',2':4,5]pyrazino[2,3-c]quinoline-3-carboxylate (150 mg, 0.28 mmol) in DCM (4 mL). The resulting mixture was stirred at rt for 2 h. The solvent was removed in vacuo. The crude product obtained was purified by SCX (7M $NH_3$/MeOH) to afford atropisomer 2 of (4aR)-9-chloro-11-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (120 mg, 99%) as a yellow solid; $^1$H NMR (400 MHz, DMSO, 30° C.) 2.83-2.94 (1H, m), 3.17-3.25 (1H, m), 3.35-3.57 (3H, m), 3.59 (3H, s), 4.05 (1H, d), 4.20-4.28 (1H, m), 6.77-6.93 (2H, m), 7.28-7.42 (1H, m), 8.02 (1H, d), 9.10 (1H, s), 10.17-10.31 (1H, m); m/z: $ES^+$ $[M+H]^+$=431.

(4aR)-9-Chloro-11-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (Atropisomer 2, Compound 80)

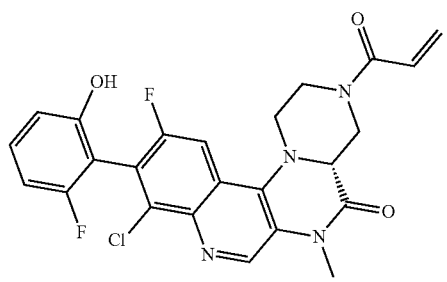 [SMILES: C=CC(=O)N1CCN2c3c(cnc4c(Cl)c(-c5c(O)cccc5F)c(F)cc34)N(C)C(=O)[C@H]2C1]

Acryloyl chloride (0.024 mL, 0.29 mmol) was added to atropisomer 2 of (4aR)-9-chloro-11-fluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one (120 mg, 0.28 mmol) and DIPEA (0.073 mL, 0.42 mmol) in DMF (4 mL) at 0° C. The resulting mixture was stirred at 0° C. for 1 h. The crude reaction mixture was purified by C18-flash chromatography (0 to 50% MeCN in water (0.1% $NH_4CO_3$)) to afford atropisomer 2 of (4aR)-9-chloro-11-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one (45 mg, 33%) as a yellow solid; $^1$H NMR (400 MHz, DMSO, 30° C.) 2.54-2.70 (1H, m), 3.05-3.26 (1H, m), 3.27-3.31 (1H, m), 3.50 (3H, s), 3.53-3.65 (1H, m), 3.86-4.11 (1H, m), 4.45 (1H, d), 4.78 (1H, d), 5.65-5.82 (1H, m), 6.11-6.20 (1H, m), 6.76-6.90 (2H, m), 6.99-7.14 (1H, m), 7.31-7.42 (1H, m), 7.97 (1H, d), 9.03 (1H, s), 10.23 (1H, s); m/z: $ES^+$ $[M+H]^+$=485.

tert-Butyl (2R,4aR)-11-chloro-9-fluoro-10-(2-fluoro-6-methoxyphenyl)-2-methyl-1,2,4a,5-tetrahydropyrazino[1',2':4,5][1,4]oxazino[2,3-c]quinoline-3(4H)-carboxylate

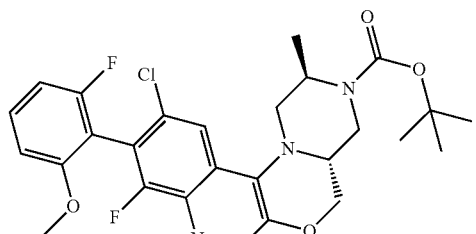

tert-Butyl (2R,4aR)-10-bromo-11-chloro-9-fluoro-2-methyl-1,2,4a,5-tetrahydropyrazino[1',2':4,5][1,4]oxazino[2,3-c]quinoline-3(4H)-carboxylate (200 mg, 0.41 mmol) was added to a mixture of (2-fluoro-6-methoxyphenyl)boronic acid (105 mg, 0.62 mmol), $K_2CO_3$ (114 mg, 0.82 mmol), RuPhos (38 mg, 0.08 mmol) and RuPhos-Pd-G3 (69 mg, 0.08 mmol) in 1,4-dioxane (8 mL) and water (2 mL, 4:1 ratio) at rt. The resulting mixture was stirred at 100° C. for 1.5 h then allowed to cool. This was concentrated in vacuo and then purified by C18-flash chromatography (0 to 60% MeCN in water (0.1% NH$_4$HCO$_3$)) to afford tert-butyl (2R,4aR)-11-chloro-9-fluoro-10-(2-fluoro-6-methoxyphenyl)-2-methyl-1,2,4a,5-tetrahydropyrazino[1',2':4,5][1,4]oxazino[2,3-c]quinoline-3(4H)-carboxylate (160 mg, 73%) as a yellow solid; $^1$H NMR (400 MHz, CDCl$_3$, 30° C.) 1.52 (9H, s), 1.58 (3H, d), 3.45-3.55 (2H, m), 3.63-3.70 (1H, m), 3.73-3.86 (4H, m), 4.05-4.18 (1H, m), 4.20-4.31 (1H, m), 4.34-4.45 (2H, m), 6.79-6.93 (2H, m), 7.39-7.55 (1H, m), 7.93 (1H, s), 8.79 (1H, s); m/z: ES$^+$ [M+H]$^+$=532.

2-[(2R,4aS)-11-Chloro-9-fluoro-2-methyl-2,3,4,4a,5,6-hexahydro-1H-benzo[h]pyrazino[1,2-a][1,6]naphthyridin-10-yl]-3-fluorophenol

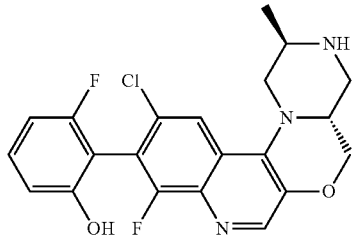 [SMILES: C[C@@H]1CN2c3c(cnc4c(F)c(-c5c(O)cccc5F)c(Cl)cc34)OC[C@H]2CN1]

1M Boron tribromide in DCM (0.846 mL, 0.85 mmol) was added to a solution tert-butyl (2R,4aR)-11-chloro-9-fluoro-10-(2-fluoro-6-methoxyphenyl)-2-methyl-1,2,4a,5-tetrahydropyrazino[1',2':4,5][1,4]oxazino[2,3-c]quinoline-3(4H)-carboxylate (150 mg, 0.28 mmol) in DCM (8 mL) at rt. The resulting solution was stirred at rt for 2 h. The solvent was removed in vacuo and the crude product obtained was purified by SCX (7M NH$_3$/MeOH) to afford 2-[(2R,4aS)-11-chloro-9-fluoro-2-methyl-2,3,4,4a,5,6-hexahydro-1H-benzo[h]pyrazino[1,2-a][1,6]naphthyridin-10-yl]-3-fluorophenol (115 mg, 98%) as a tan solid; $^1$H NMR (400 MHz, MeOD, 30° C.) 1.17 (3H, d), 2.85-3.05 (3H, m), 3.05-3.21 (1H, m), 3.53-3.67 (1H, m), 4.05-4.35 (3H, m), 6.65-6.75 (1H, m), 6.79 (1H, d), 7.25-7.36 (1H, m), 7.82 (1H, s), 8.31 (1H, s).; m/z: ES$^+$ [M+H]$^+$=418.

1-[(2R,4aS)-11-Chloro-9-fluoro-10-(2-fluoro-6-hydroxyphenyl)-2-methyl-1,2,4,4a,5,6-hexahydro-3H-benzo[h]pyrazino[1,2-a][1,6]naphthyridin-3-yl]prop-2-en-1-one (Atropisomer 1, Compound 81; Atropisomer 2, Compound 82)

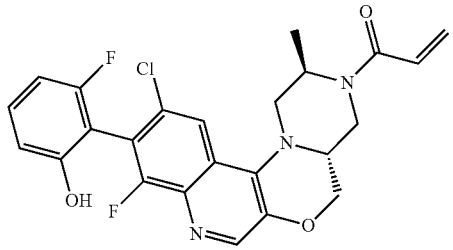 [SMILES: C=CC(=O)N1C[C@@H]2COc3cnc4c(F)c(-c5c(O)cccc5F)c(Cl)cc4c3N2C[C@H]1C]

Acryloyl chloride (22.85 mg, 0.25 mmol) was added to a solution of 2-[(2R,4aS)-11-chloro-9-fluoro-2-methyl-2,3,4,4a,5,6-hexahydro-1H-benzo[h]pyrazino[1,2-a][1,6]naphthyridin-10-yl]-3-fluorophenol (105 mg, 0.25 mmol) and DIPEA (65 mg, 0.50 mmol) in THF (10 mL) at 0° C. The resulting solution was stirred at 0° C. for 1 h. The crude reaction mixture was purified by C18-flash chromatography (0 to 60% MeCN in water (0.1% NH$_4$HCO$_3$)) to afford crude product as a white solid. This was purified by preparative chiral-HPLC (CHIRALPAK IG, 2.0 cm I.D*25 cm L (5 μm); Mobile Phase A: Hex-HPLC, Mobile Phase B: IPA-HPLC; Flow rate: 15 mL/min; Gradient: 50 B to 50 B in 17 min; 220/254 nm) to afford atropisomer 1 of 1-[(2R,4aS)-11-chloro-9-fluoro-10-(2-fluoro-6-hydroxyphenyl)-2-methyl-1,2,4,4a,5,6-hexahydro-3H-benzo[h]pyrazino[1,2-a][1,6]naphthyridin-3-yl]prop-2-en-1-one (27 mg, 34%) as a white solid; $^1$H NMR (400 MHz, DMSO, 30° C.) 1.54-1.61 (3H, m), 3.01-3.11 (1H, m), 3.40-3.97 (3H, m), 4.12-4.88 (4H, m), 5.74 (1H, dd), 6.16 (1H, dd), 6.61-7.00 (3H, m), 7.25-7.42 (1H, m), 7.83 (1H, s), 8.63 (1H, s), 10.18 (1H, s); m/z: ES$^+$ [M+H]$^+$=472. This was followed by atropisomer 2 of 1-[(2R,4aS)-11-chloro-9-fluoro-10-(2-fluoro-6-hydroxyphenyl)-2-methyl-1,2,4,4a,5,6-hexahydro-3H-benzo[h]pyrazino[1,2-a][1,6]naphthyridin-3-yl]prop-2-en-1-one (22 mg, 27%); $^1$H NMR (400 MHz, DMSO, 30° C.) 1.55-1.64 (3H, m), 3.01-3.09 (1H, m), 3.38-3.99 (3H, m), 4.51-4.60 (4H, m), 5.75 (1H, dd), 6.16 (1H, dd), 6.67-6.98 (3H, m), 7.22-7.45 (1H, m), 7.83 (1H, s), 8.63 (1H, s), 10.15 (1H, s); m/z: ES$^+$ [M+H]$^+$=472.

tert-Butyl (3R)-3-({[tert-butyl(dimethyl)silyl]oxy}methyl)piperazine-1-carboxylate

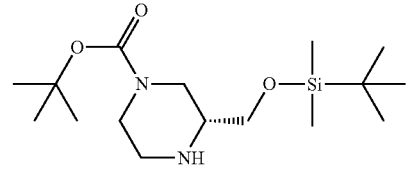 [SMILES: CC(C)(C)OC(=O)N1CCN[C@@H](CO[Si](C)(C)C(C)(C)C)C1]

NEt$_3$ (12.9 mL, 92.47 mmol) was added to tert-butyl (3R)-3-(hydroxymethyl)piperazine-1-carboxylate (10 g, 46.24 mmol), tert-butylchlorodimethylsilane (10.45 g, 69.35 mmol) and 4-dimethylaminopyridine (0.282 g, 2.31 mmol) in DCM (200 mL) at rt. The resulting suspension was stirred at rt for 16 h. The solvent was removed in vacuo. The crude product obtained was purified by flash silica chromatography (0 to 9% MeOH in DCM) to afford tert-butyl (3R)-3-({[tert-butyl(dimethyl)silyl]oxy}methyl)piperazine-1-carboxylate (15 g, 98%) as a pale yellow gum; $^1$H NMR (300 MHz, DMSO, 30° C.) 0.05 (6H, s), 0.89 (9H, s), 1.40 (9H, s), 2.27 (1H, s), 2.41 (1H, s), 2.48-2.54 (2H, m), 2.71 (1H, s), 2.78-2.90 (1H, m), 3.33-3.57 (2H, m), 3.74 (1H, d), 3.86-3.96 (1H, m).

7-Bromo-6-chloro-5-methoxy-3-nitroquinolin-4-ol

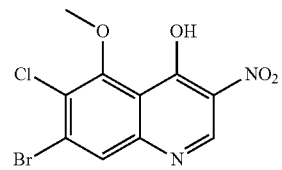

Sodium methoxide (7.51 g, 41.68 mmol) was added to 7-bromo-6-chloro-5-fluoro-3-nitroquinolin-4-ol (2.68 g, 8.34 mmol) in MeOH (40 mL) at rt. The resulting mixture was stirred at 80° C. for 1 h. The solvent was removed in vacuo, water (200 mL) added and the mixture filtered. The solid collected was washed with water (100 mL×2) and diethyl ether (100 mL) then dried under vacuum to give 7-bromo-6-chloro-5-methoxy-3-nitroquinolin-4-ol (2.6 g, 94%) as a yellow solid; m/z: ES$^+$ [M+H]$^+$=333.

7-Bromo-4,6-dichloro-5-methoxy-3-nitroquinoline

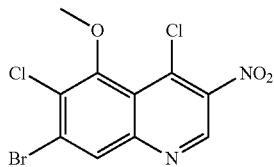 [SMILES: COc1c(Cl)c(Br)cc2ncc([N+](=O)[O-])c(Cl)c12]

DMF (0.608 µl, 6.52 µmol) was added to 7-bromo-6-chloro-5-methoxy-3-nitroquinolin-4-ol (2.59 g, 7.77 mmol) in phosphorus(V) oxychloride (40 mL) at rt. The resulting mixture was stirred at 120° C. for 2 h. The solvent was removed in vacuo and the residue obtained quenched with sat. NaHCO$_3$ (50 mL) then extracted with EtOAc (50 mL×3). The organic layer was dried (Na$_2$SO$_4$) and concentrated in vacuo to afford 7-bromo-4,6-dichloro-5-methoxy-3-nitroquinoline (2.38 g, 87%) as yellow solid; $^1$H NMR (400 MHz, DMSO, 30° C.) 3.98 (3H, s), 7.34 (1H, s), 9.08 (1H, s); m/z: ES$^+$ [M+H]$^+$=351.

tert-Butyl (3R)-4-(7-bromo-6-chloro-5-methoxy-3-nitroquinolin-4-yl)-3-({[tert-butyl(dimethyl)silyl]oxy}methyl)piperazine-1-carboxylate

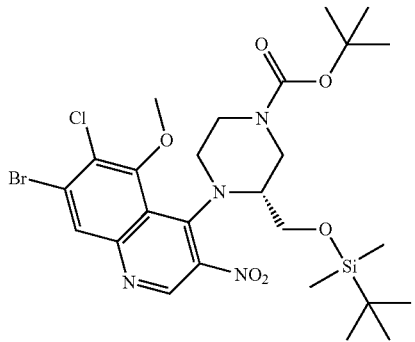 [SMILES: COc1c(Cl)c(Br)cc2ncc([N+](=O)[O-])c(N3CCN(C(=O)OC(C)(C)C)C[C@@H]3CO[Si](C)(C)C(C)(C)C)c12]

DIPEA (8.96 mL, 51.28 mmol) was added to 7-bromo-4,6-dichloro-5-methoxy-3-nitroquinoline (3.61 g, 10.26 mmol) and tert-butyl (3R)-3-({[tert-butyl(dimethyl)silyl]oxy}methyl)piperazine-1-carboxylate (5.09 g, 15.39 mmol) in IPA (40 mL) at rt. The resulting solution was stirred at 100° C. for 1 h. The solvent was removed in vacuo. The crude product obtained was purified by flash silica chromatography (0 to 20% EtOAc in petroleum ether) to afford tert-butyl (3R)-4-(7-bromo-6-chloro-5-methoxy-3-nitroquinolin-4-yl)-3-({[tert-butyl(dimethyl)silyl]oxy}methyl)piperazine-1-carboxylate (1.63 g, 25%) as a yellow solid; $^1$H NMR (400 MHz, DMSO, 30° C.) 0.23 (6H, d), 0.58 (9H, s), 1.43 (9H, s), 3.05 (1H, d), 3.21-3.39 (2H, m), 3.56 (2H, d), 3.80 (3H, s), 3.84-4.04 (4H, m), 8.27 (1H, s), 8.91 (1H, s); m/z: ES$^+$ [M+H]$^+$=645.

tert-Butyl (3R)-4-(7-bromo-6-chloro-5-methoxy-3-nitroquinolin-4-yl)-3-(hydroxymethyl)piperazine-1-carboxylate

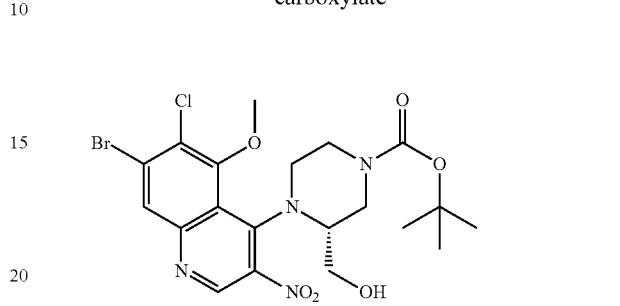

Tetra-n-butylammonium fluoride (6.27 mL, 6.27 mmol) was added to tert-butyl (3R)-4-(7-bromo-6-chloro-5-methoxy-3-nitroquinolin-4-yl)-3-({[tert-butyl(dimethyl)silyl]oxy}methyl)piperazine-1-carboxylate (1.62 g, 2.51 mmol) in THF (6.3 mL) at rt. The resulting solution was stirred at rt for 1 h.

The solvent was removed in vacuo. The crude product obtained was purified by flash silica chromatography (0 to 4% MeOH in DCM) to give tert-butyl (3R)-4-(7-bromo-6-chloro-5-methoxy-3-nitroquinolin-4-yl)-3-(hydroxymethyl)piperazine-1-carboxylate (1.21 g, 91%) as a yellow solid; m/z: ES$^+$ [M+H]$^+$=531.

tert-Butyl (4aR)-10-bromo-11-chloro-12-hydroxy-1,2,4a,5-tetrahydropyrazino[1',2':4,5][1,4]oxazino[2,3-c]quinoline-3(4H)-carboxylate

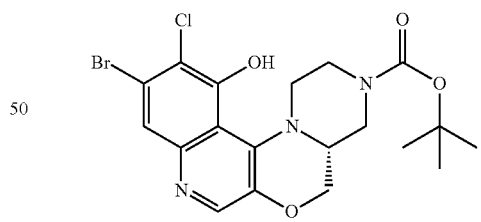

1M Lithium bis(trimethylsilyl)amide in THF (4.51 mL, 4.51 mmol) was added to tert-butyl (3R)-4-(7-bromo-6-chloro-5-methoxy-3-nitroquinolin-4-yl)-3-(hydroxymethyl)piperazine-1-carboxylate (800 mg, 1.5 mmol) in NMP (5 mL) at rt. The resulting solution was stirred at 120° C. for 16 h. The crude reaction mixture was purified by C18-flash chromatography (0 to 70% MeCN in water (0.1% NH$_4$HCO$_3$)) to afford tert-butyl (4aR)-10-bromo-11-chloro-12-hydroxy-1,2,4a,5-tetrahydropyrazino[1',2':4,5][1,4]oxazino[2,3-c]quinoline-3(4H)-carboxylate (120 mg, 17%) as a brown solid; m/z: ES$^+$ [M+H]$^+$=472.

tert-Butyl (4aR)-10-bromo-11-chloro-12-methoxy-1,2,4a,5-tetrahydropyrazino[1',2':4,5][1,4]oxazino[2,3-c]quinoline-3(4H)-carboxylate

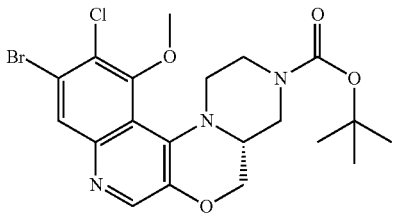 [SMILES: COc1c(Cl)c(Br)cc2ncc3c(c12)N1CCN(C(=O)OC(C)(C)C)C[C@@H]1CO3]

Iodomethane (36 mg, 0.25 mmol) was added to tert-butyl (4aR)-10-bromo-11-chloro-12-hydroxy-1,2,4a,5-tetrahydropyrazino[1',2':4,5][1,4]oxazino[2,3-c]quinoline-3(4H)-carboxylate (120 mg, 0.25 mmol) and K$_2$CO$_3$ (71 mg, 0.51 mmol) in DMF (2 mL). The resulting mixture was stirred at rt for 4 h.

The reaction mixture was purified by C18-flash chromatography (2 to 80% MeOH in water) to afford tert-butyl (4aR)-10-bromo-11-chloro-12-methoxy-1,2,4a,5-tetrahydropyrazino[1',2':4,5][1,4]oxazino[2,3-c]quinoline-3(4H)-carboxylate (80 mg, 65%) as a yellow solid; $^1$H NMR (400 MHz, DMSO, 30° C.) 1.43 (9H, s), 3.35-3.52 (2H, m), 3.54-3.88 (5H, m), 3.86-4.80 (5H, m), 7.93-8.21 (1H, m), 8.31-8.65 (1H, m); m/z: ES$^+$ [M+H]$^+$=484.

tert-Butyl (4aR)-11-chloro-10-(2-fluoro-6-hydroxyphenyl)-12-methoxy-1,2,4a,5-tetrahydropyrazino[1',2':4,5][1,4]oxazino[2,3-c]quinoline-3(4H)-carboxylate

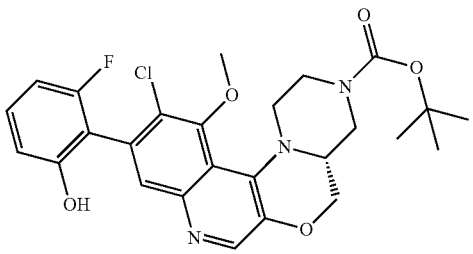 [SMILES: COc1c(Cl)c(-c2c(O)cccc2F)cc2ncc3c(c12)N1CCN(C(=O)OC(C)(C)C)C[C@@H]1CO3]

tert-Butyl (4aR)-10-bromo-11-chloro-12-methoxy-1,2,4a,5-tetrahydropyrazino[1',2':4,5][1,4]oxazino [2,3-c]quinoline-3(4H)-carboxylate (56 mg, 0.36 mmol), (2-fluoro-6-hydroxyphenyl)boronic acid (56.3 mg, 0.36 mmol), Na$_2$CO$_3$ (38.3 mg, 0.36 mmol) and tetrakis(triphenylphosphine)palladium(0) (33 mg, 0.03 mmol) was added to a mixture of degassed water (1.5 mL) and 1,4-dioxane (6 mL, 4:1 ratio). The reaction mixture was then stirred at 100° C. for 1 h. The solvent was removed in vacuo and the crude product purified by C18-flash chromatography (30 to 60% MeOH in water (0.1% NH$_4$OH)) to afford tert-butyl (4aR)-11-chloro-10-(2-fluoro-6-hydroxyphenyl)-12-methoxy-1,2,4a,5-tetrahydropyrazino[1',2':4,5][1,4]oxazino[2,3-c]quinoline-3(4H)-carboxylate (30 mg, 40%) as a yellow solid; $^1$H NMR (400 MHz, DMSO, 30° C.) 1.45 (9H, s), 3.00-4.92 (12H, m), 6.34-7.09 (2H, m), 7.18-7.47 (1H, m), 7.66 (1H, s), 8.65 (1H, s), 10.23 (1H, s); m/z: ES$^+$ [M+H]$^+$=516.

2-[(4aR)-1111-Chloro-12-methoxy-1,2,3,4,4a,5-hexahydropyrazino[1',2':4,5][1,4]oxazino[2,3-c]quinolin-10-yl]-3-fluorophenol

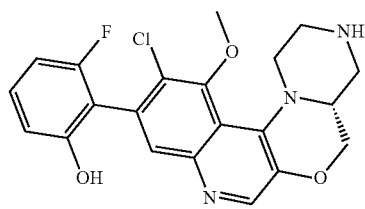 [SMILES: COc1c(Cl)c(-c2c(O)cccc2F)cc2ncc3c(c12)N1CCNC[C@@H]1CO3]

A mixture of tert-butyl (4aR)-11-chloro-10-(2-fluoro-6-hydroxyphenyl)-12-methoxy-1,2,4a,5-tetrahydropyrazino[1',2':4,5][1,4]oxazino[2,3-c]quinoline-3(4H)-carboxylate (30 mg, 0.06 mmol) and 2M HCl in MeOH (5 mL, 10 mmol) was stirred at rt for 1 h. The solvent was removed in vacuo. The crude product was purified by SCX (7M NH$_3$/MeOH) to afford 2-[(4aR)-11-chloro-12-methoxy-1,2,3,4,4a,5-hexahydropyrazino[1',2':4,5][1,4]oxazino[2,3-c]quinolin-10-yl]-3-fluorophenol (10 mg, 41%) as a yellow solid; m/z: ES$^+$ [M+H]$^+$=416.

1-[(4aR)-11-Chloro-10-(2-fluoro-6-hydroxyphenyl)-12-methoxy-1,2,4a,5-tetrahydropyrazino[1',2':4,5][1,4]oxazino[2,3-c]quinolin-3(4H)-yl]prop-2-en-1-one (Compound 83)

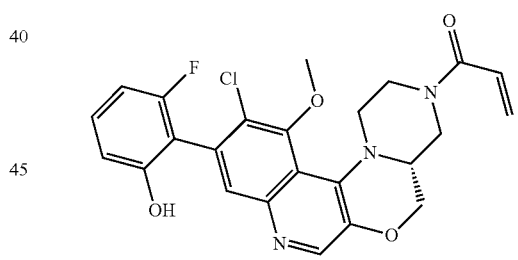

A solution of acryloyl chloride (1.96 mg, 0.02 mmol) in DMF (1 mL) was added to a solution of 2-[(4aR)-11-chloro-12-methoxy-1,2,3,4,4a,5-hexahydropyrazino[1',2':4,5][1,4]oxazino[2,3-c]quinolin-10-yl]-3-fluorophenol (10 mg, 0.02 mmol) and DIPEA (8.40 µl, 0.05 mmol) in DMF (2 mL) at 0° C. The resulting solution was stirred at 0° C. for 1 h. The crude reaction mixture was purified by C18-flash chromatography (0 to 65% MeOH in water (0.1% NH$_4$OH)) to afford 1-[(4aR)-11-chloro-10-(2-fluoro-6-hydroxyphenyl)-12-methoxy-1,2,4a,5-tetrahydropyrazino[1',2':4,5][1,4]oxazino[2,3-c]quinolin-3(4H)-yl]prop-2-en-1-one (6.5 mg, 58%) as a white solid; $^1$H NMR (400 MHz, DMSO, 30° C.) 2.91-2.96 (1H, m), 3.28-3.33 (1H, m), 3.46-3.64 (3H, m), 3.82 (3H, s), 3.93-4.72 (4H, m), 5.76 (1H, d), 6.18 (1H, dd), 6.68-6.77 (1H, m), 6.77-6.91 (2H, m), 7.20-7.31 (1H, m), 7.61 (1H, s), 8.47-8.52 (1H, m), 10.10 (1H, br s); m/z: ES$^+$ [M+H]$^+$=470.

6-Amino-2-bromo-3-methylbenzoic acid

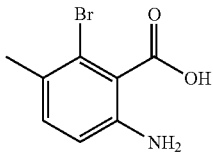

Hydrogen peroxide (40 ml, 391.60 mmol) was added to a solution of 4-bromo-5-methyl-1H-indole-2,3-dione (20 g, 83.31 mmol) in 2M NaOH (400 ml) at rt. The resulting solution was stirred at rt for 2 h. Sodium sulfite (48 g) was then added and the mixture was stirred for another 0.5 h at rt. The reaction mixture was extracted with EtOAc (200 mL) and the aqueous layer pH adjusted to pH 4 with concentrated HCl. A precipitate was collected by filtration, washed with water (300 ml) and dried under vacuum to afford 6-amino-2-bromo-3-methylbenzoic acid (12.4 g, 65%) as a pale yellow solid; $^1$H NMR (400 MHz, MeOD, 30° C.) 2.29 (3H, s), 6.70 (1H, d), 7.07 (1H, d); m/z: ES$^+$ [M+H]$^+$=230.

2-Bromo-6-{[(4-methoxyphenyl)methyl]amino}-3-methylbenzoic acid

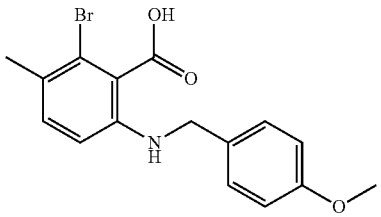

Glacial acetic acid (0.62 mL, 10.87 mmol) was added dropwise to 6-amino-2-bromo-3-methylbenzoic acid (5 g, 21.73 mmol) and 4-methoxybenzaldehyde (3.55 g, 26.08 mmol) in DCM (100 mL) at rt. After 1 h sodium triacetoxyborohydride (9.21 g, 43.47 mmol) was added. The resulting mixture was stirred at rt for 3 h. The reaction mixture was diluted with DCM (400 mL), washed with sat. NH$_4$Cl (500 mL×2), water (500 mL×2), dried (Na$_2$SO$_4$) and concentrated in vacuo to afford 2-bromo-6-{[(4-methoxyphenyl)methyl]amino}-3-methylbenzoic acid (8 g, >100%) as a brown solid, that was used without further purification; $^1$H NMR (400 MHz, DMSO, 30° C.) 2.19 (3H, s), 3.17 (1H, s), 3.71 (3H, s), 4.25 (2H, s), 6.48 (1H, d), 6.84-6.89 (2H, m), 7.05 (1H, d), 7.21-7.25 (2H, m); m/z: ES$^+$ [M+H]$^+$=340.

4-Bromo-1-[(4-methoxyphenyl)methyl]-5-methyl-1,3-dihydro-2H-benzimidazol-2-one

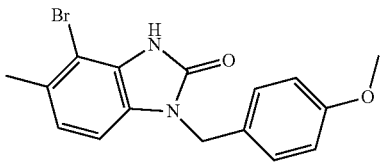

Diphenyl phosphorazidate (7.31 mL, 33.84 mmol) was added to 2-bromo-6-{[(4-methoxyphenyl)methyl]amino}-3-methylbenzoic acid (7.9 g, 22.56 mmol) and NEt$_3$ (9.43 mL, 67.67 mmol) in DMA (150 mL). The resulting mixture was stirred at 80° C. for 4 h. The reaction mixture was poured into ice water and a precipitate collected by filtration, washed with water (100 mL) and dried under vacuum to afford 4-bromo-1-[(4-methoxyphenyl)methyl]-5-methyl-1,3-dihydro-2H-benzimidazol-2-one (7.2 g, 92%) as a yellow solid; $^1$H NMR (400 MHz, DMSO, 30° C.) 2.31 (3H, s), 3.70 (3H, s), 4.91 (2H, s), 6.84-6.99 (4H, m), 7.25 (2H, d), 11.23 (1H, s); m/z: ES$^+$ [M+H]$^+$=347.

1-[(4-Methoxyphenyl)methyl]-5-methyl-4-(4,4,5,5-tetramethyl-1,3,2-dioxaborolan-2-yl)-1,3-dihydro-2H-benzimidazol-2-one

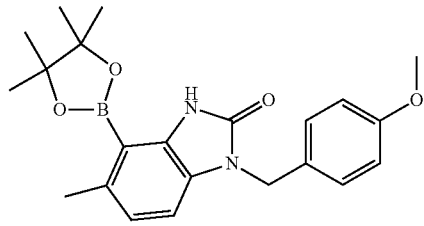

[1,1'-Bis(diphenylphosphino)ferrocene]dichloropalladium(II), complex with DCM (0.47 g, 0.58 mmol) was added to 4-bromo-1-[(4-methoxyphenyl)methyl]-5-methyl-1,3-dihydro-2H-benzimidazol-2-one (2 g, 5.76 mmol), 4,4,4',4',5,5,5',5'-octamethyl-2,2'-bi-1,3,2-dioxaborolane (3.66 g, 14.4 mmol) and potassium acetate (1.41 g, 14.4 mmol) in 1,4-dioxane (40 mL). The resulting mixture was stirred at 100° C. for 3 h. The reaction mixture was concentrated in vacuo, dissolved in EtOAc (100 mL) and washed with water (100 mL×2). The organic layer was dried (Na$_2$SO$_4$) and concentrated in vacuo to afford crude product. This was purified by flash silica chromatography (0 to 50% EtOAc in petroleum ether) to afford 1-[(4-methoxyphenyl)methyl]-5-methyl-4-(4,4,5,5-tetramethyl-1,3,2-dioxaborolan-2-yl)-1,3-dihydro-2H-benzimidazol-2-one (1.6 g, 71%) as a yellow solid; $^1$H NMR (400 MHz, DMSO, 30° C.) 1.33 (12H, s), 2.41 (3H, s), 3.70 (3H, s), 4.92 (2H, s), 6.77 (1H, d), 6.87 (2H, d), 6.99 (1H, d), 7.23 (2H, d), 9.68 (1H, s); m/z: ES$^+$ [M+H]$^+$=395.

tert-Butyl (4aR)-11-chloro-9-fluoro-10-{1-[(4-methoxyphenyl)methyl]-5-methyl-2-oxo-2,3-dihydro-1H-benzimidazol-4-yl}-1,2,4a,5-tetrahydropyrazino[1',2':4,5][1,4]oxazino[2,3-c]quinoline-3(4H)-carboxylate

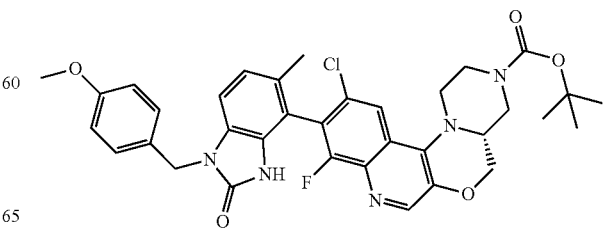

RuPhos-Pd-G3 (88 mg, 0.11 mmol) and RuPhos (49.4 mg, 0.11 mmol) were added to tert-butyl (R)-4-(7-bromo-6-chloro-8-fluoro-3-nitroquinolin-4-yl)-3-(hydroxymethyl)piperazine-1-carboxylate (500 mg, 1.06 mmol), 1-[(4-methoxyphenyl)methyl]-5-methyl-4-(4,4,5,5-tetramethyl-1,3,2-dioxaborolan-2-yl)-1,3-dihydro-2H-benzimidazol-2-one (834 mg, 2.12 mmol) and K$_2$CO$_3$ (365 mg, 2.64 mmol) in 1,4-dioxane (10 mL) and water (2 mL). The resulting mixture was stirred at 100° C. for 40 min. The solvent was removed in vacuo. The crude product obtained was purified by flash silica chromatography (0 to 9% EtOAc in petroleum ether) to afford tert-butyl (4aR)-11-chloro-9-fluoro-10-{1-[(4-methoxyphenyl)methyl]-5-methyl-2-oxo-2,3-dihydro-1H-benzimidazol-4-yl}-1,2,4a,5-tetrahydropyrazino[1',2':4,5][1,4]oxazino[2,3-c]quinoline-3(4H)-carboxylate (500 mg, 72%) as a yellow solid; $^1$H NMR (400 MHz, DMSO, 30° C.) 1.45 (9H, s), 1.96 (3H, d), 3.15-3.20 (1H, m), 3.20-3.25 (1H, m), 3.41-3.55 (2H, m), 3.60-3.70 (1H, m), 3.72-3.91 (5H, m), 4.18-4.32 (1H, m), 4.34-4.48 (1H, m), 5.01 (2H, s), 6.91-7.06 (3H, m), 7.10 (1H, d), 7.34 (2H, d), 7.92 (1H, s), 8.60 (1H, s), 10.79 (1H, s); m/z: ES$^+$ [M+H]$^+$=660.

tert-Butyl (4aR)-11-chloro-9-fluoro-10-{1-[(4-methoxyphenyl)methyl]-3,5-dimethyl-2-oxo-2,3-dihydro-1H-benzimidazol-4-yl}-1,2,4a,5-tetrahydropyrazino[1',2':4,5][1,4]oxazino[2,3-c]quinoline-3(4H)-carboxylate Atropisomer 1 and 2

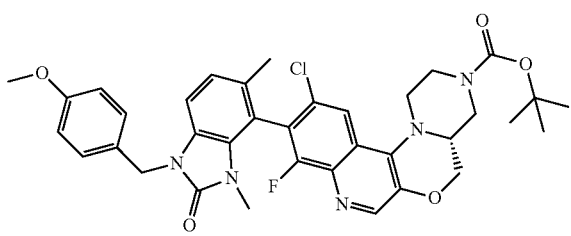 [SMILES: COc1ccc(Cn2c(=O)n(C)c3c(-c4c(Cl)cc5c6c(cnc5c4F)OC[C@H]4CN(C(=O)OC(C)(C)C)CCN64)c(C)ccc32)cc1]

tert-Butyl (4aR)-11-chloro-9-fluoro-10-{1-[(4-methoxyphenyl)methyl]-5-methyl-2-oxo-2,3-dihydro-1H-benzimidazol-4-yl}-1,2,4a,5-tetrahydropyrazino[1',2':4,5][1,4]oxazino[2,3-c]quinoline-3(4H)-carboxylate (480 mg, 0.73 mmol) was added to N,N-dimethylformamide dimethyl acetal (10 mL, 74.69 mmol). The resulting mixture was stirred at 100° C. for 4 h. The crude reaction mixture was purified by C18-flash chromatography (0 to 60% MeCN in water) to afford crude product. This was purified by preparative chiral-HPLC (Column: CHIRAL IC, 2*25 cm, 5 μm; Mobile Phase A: CO$_2$:50, Mobile Phase B: IPA (8 mmol/L NH$_3$.MeOH)-HPLC: 50; Flow rate: 40 mL/min; 254 nm) to afford atropisomer 1 of tert-butyl (4aR)-11-chloro-9-fluoro-10-{1-[(4-methoxyphenyl)methyl]-3,5-dimethyl-2-oxo-2,3-dihydro-1H-benzimidazol-4-yl}-1,2,4a,5-tetrahydropyrazino[1',2':4,5][1,4]oxazino[2,3-c]quinoline-3(4H)-carboxylate (170 mg, 35%) as a yellow solid; $^1$H NMR (400 MHz, DMSO, 30° C.) 1.44 (9H, s), 1.96 (3H, s), 2.77 (3H, s), 3.21-3.58 (5H, m), 3.60-3.70 (1H, m), 3.72 (3H, s), 3.75-3.79 (1H, m), 4.18-4.32 (1H, m), 4.34-4.48 (1H, m), 5.01 (2H, d), 6.91 (2H, d), 7.06 (1H, d), 7.20 (1H, d), 7.34 (2H, d), 8.01 (1H, s), 8.60 (1H, s); m/z: ES$^+$ [M+H]$^+$=674. This was followed by atropisomer 2 of tert-butyl (4aR)-11-chloro-9-fluoro-10-{1-[(4-methoxyphenyl)methyl]-3,5-dimethyl-2-oxo-2,3-dihydro-1H-benzimidazol-4-yl}-1,2,4a,5-tetrahydropyrazino[1',2':4,5][1,4]ox-azino[2,3-c]quinoline-3(4H)-carboxylate (150 mg, 31%) as a yellow solid; $^1$H NMR (400 MHz, DMSO, 30° C.) 1.44 (9H, s), 1.99 (3H, s), 2.73 (3H, s), 3.19-3.29 (1H, m), 3.34-3.67 (5H, m), 3.72 (3H, s), 3.79-3.87 (1H, m), 4.20-4.33 (1H, m), 4.36-4.45 (1H, m), 5.01 (2H, s), 6.91 (2H, d), 7.06 (1H, d), 7.20 (1H, d), 7.33 (2H, d), 8.02 (1H, s), 8.61 (1H, s); m/z: ES$^+$ [M+H]$^+$=674.

7-[(4aR)-11-Chloro-9-fluoro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one Atropisomer 1

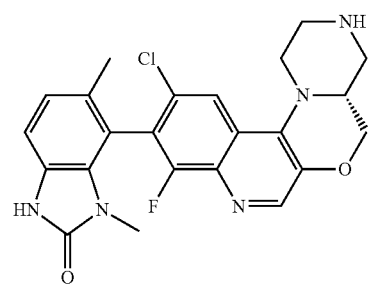 [SMILES: Cc1ccc2[nH]c(=O)n(C)c2c1-c1c(Cl)cc2c3c(cnc2c1F)OC[C@H]1CNCCN31]

Trifluoromethanesulfonic acid (0.025 mL, 0.28 mmol) was added in one portion to atropisomer 1 of tert-butyl (4aR)-11-chloro-9-fluoro-10-{1-[(4-methoxyphenyl)methyl]-3,5-dimethyl-2-oxo-2,3-dihydro-1H-benzimidazol-4-yl}-1,2,4a,5-tetrahydropyrazino[1',2':4,5][1,4]oxazino[2,3-c]quinoline-3(4H)-carboxylate (160 mg, 0.24 mmol) in TFA (4 mL). The resulting mixture was stirred at 80° C. for 3 h. The solvent was removed in vacuo. The crude product obtained was purified by SCX (7M NH$_3$/MeOH) to afford atropisomer 1 of 7-[(4aR)-11-chloro-9-fluoro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (100 mg, 93%) as a yellow solid; $^1$H NMR (400 MHz, DMSO, 30° C.) 1.96 (3H, s), 2.69 (3H, s), 2.86-3.48 (8H, m), 4.18-4.32 (1H, m), 4.34-4.48 (1H, m) 7.01 (2H, s), 7.95 (1H, d), 8.58 (1H, s), 10.95 (1H, br s); m/z: ES$^+$ [M+H]$^+$=454.

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (Atropisomer 1, Compound 84)

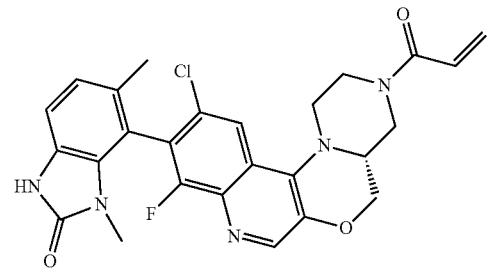 [SMILES: C=CC(=O)N1CCN2c3c(cnc4c(F)c(-c5c(C)ccc6[nH]c(=O)n(C)c56)c(Cl)cc34)OC[C@H]2C1]

Acryloyl chloride (0.018 mL, 0.22 mmol) was added to atropisomer 1 of 7-[(4aR)-11-chloro-9-fluoro-1,2,3,4,4a,5-hexahydropyrazino[1',2':4,5][1,4]oxazino[2,3-c]quinolin- 10-yl]-1,6-dimethyl-1,3-dihydro-2H-benzimidazol-2-one (100 mg, 0.22 mmol) and DIPEA (0.077 mL, 0.44 mmol) in DMF (5 mL) at 0° C. The resulting solution was stirred at 0° C. for 1 h. The crude reaction mixture was purified by C18-flash chromatography (0 to 50% MeCN in water (0.1% NH$_4$HCO$_3$)) to afford atropisomer 1 of 7-[(4aR)-11-chloro-9-fluoro-3-(prop-2-enoyl)-1,2,3,4,4a,5-hexahydropyrazino [1',2':4,5][1,4]oxazino[2,3-c]quinolin-10-yl]-1,6-dimethyl-1,3-dihydro-2H-benzimidazol-2-one (50 mg, 45%) as a white solid; $^1$H NMR (300 MHz, DMSO, 30° C.) 1.97 (3H, s), 2.70 (3H, s), 3.35-4.59 (9H, m), 5.77 (1H, d), 6.19 (1H, dd), 6.75-6.97 (1H, m), 7.02 (2H, s), 8.05 (1H, s), 8.61 (1H, s), 11.00 (1H, s); m/z: ES$^+$ [M+H]$^+$=508.

7-[(4aR)-11-Chloro-9-fluoro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one Atropisomer 2

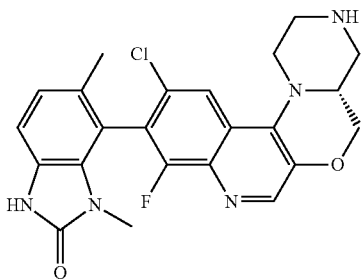 [SMILES: Cc1ccc2[nH]c(=O)n(C)c2c1-c1c(Cl)cc2c3c(cnc2c1F)OC[C@H]1CNCCN31]

Trifluoromethanesulfonic acid (0.025 mL, 0.28 mmol) was added in one portion to atropisomer 2 of tert-butyl (4aR)-11-chloro-9-fluoro-10-{1-[(4-methoxyphenyl)methyl]-3,5-dimethyl-2-oxo-2,3-dihydro-1H-benzimidazol-4-yl}-1,2,4a,5-tetrahydropyrazino[1',2':4,5][1,4]oxazino[2,3-c]quinoline-3(4H)-carboxylate (150 mg, 0.22 mmol) in TFA (4 mL). The resulting mixture was stirred at 80° C. for 3 h. The solvent was removed in vacuo. The crude product was purified by SCX (7M NH$_3$/MeOH) to afford atropisomer 2 of 7-[(4aR)-11-chloro-9-fluoro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (100 mg, 99%) as a yellow solid; $^1$H NMR (400 MHz, DMSO, 30° C.) 1.99 (3H, s), 2.64 (3H, s), 2.86-3.50 (8H, m), 4.18-4.32 (1H, m), 4.34-4.48 (1H, m), 7.02 (2H, s), 7.96 (1H, d), 8.59 (1H, s), 10.95 (1H, br s); m/z: ES$^+$ [M+H]$^+$=454.

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (Atropisomer 2, Compound 85)

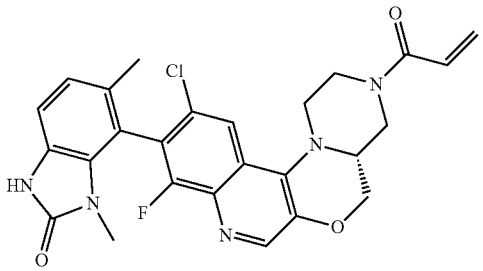 [SMILES: C=CC(=O)N1CCN2c3c(cnc4c(F)c(-c5c(C)ccc6[nH]c(=O)n(C)c56)c(Cl)cc34)OC[C@H]2C1]

Acryloyl chloride (0.018 mL, 0.22 mmol) was added to atropisomer 2 of 7-[(4aR)-11-chloro-9-fluoro-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one (100 mg, 0.22 mmol) and DIPEA (0.077 mL, 0.44 mmol) in DMF (5 mL) at 0° C. The resulting solution was stirred at 0° C. for 1 h. The reaction mixture was purified by C18-flash chromatography (0 to 50% MeCN in water (0.1% NH$_4$HCO$_3$)) to afford atropisomer 2 of 7-[(4aR)-11-chloro-9-fluoro-3-(prop-2-enoyl)-1,2,3,4,4a,5-hexahydropyrazino [1',2':4,5][1,4]oxazino[2,3-c]quinolin-10-yl]-1,6-dimethyl-1,3-dihydro-2H-benzimidazol-2-one (53 mg, 47%) as a white solid; $^1$H NMR (300 MHz, DMSO, 30° C.) 2.00 (3H, s), 2.65 (3H, s), 3.40-4.54 (9H, m), 5.76 (1H, d), 6.19 (1H, d), 6.77-6.96 (1H, m), 7.03 (2H, s), 8.06 (1H, s), 8.62 (1H, s), 11.01 (1H, s); m/z: ES$^+$ [M+H]$^+$=508.

7-Bromo-6-iodo-2,3-dihydro-1H-isoindol-1-one

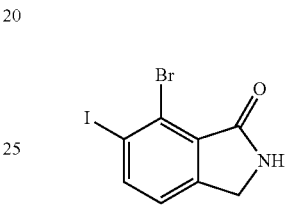

7-Bromo-2,3-dihydro-1H-isoindol-1-one (10 g, 47.16 mmol) was added to concentrated H$_2$SO$_4$ (80 mL) at 0° C. and the resulting solution stirred at 0° C. for 0.5 h. N-Iodosuccinimide (15.92 g, 70.74 mmol) was then added and the reaction mixture stirred at 0° C. for 2 h. The reaction mixture was poured on to ice and a precipitate collected by filtration. The solid collected was washed with sat. aq. sodium sulfite (200 ml), water (200 ml) and dried under vacuum to afford crude product as a brown solid. The crude product was triturated with MeOH and the solid obtained dried under vacuum to afford 7-bromo-6-iodo-2,3-dihydro-1H-isoindol-1-one (4.3 g, 27%) as white solid; $^1$H NMR (400 MHz, DMSO, 30° C.) 4.27 (2H, s), 7.37 (1H, d), 8.11 (1H, d), 8.74 (1H, s); m/z: ES$^+$ [M+H]$^+$=340.

7-Bromo-6-methyl-2,3-dihydro-1H-isoindol-1-one

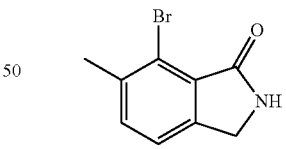

Bis(triphenylphosphine)palladium(II) dichloride (1.66 g, 2.37 mmol) was added to a solution of 7-bromo-6-iodo-2,3-dihydro-1H-isoindol-1-one (4 g, 11.84 mmol), 2,4,6-trimethyl-1,3,5,2,4,6-trioxatriborinane (0.743 g, 5.92 mmol) and K$_2$CO$_3$ (3.27 g, 23.67 mmol) in toluene (40 mL) and water (20 mL) at rt. The resulting solution was stirred at 100° C. for 4 h. After standard workup, the crude product was purified by C18-flash chromatography (0 to 60% MeCN in water (0.1% TFA)) to afford white solid. This was purified by preparative chiral-HPLC (Column: Enantiocel-C1, 5*25 cm, 5 Mm; Mobile Phase A: CO$_2$:70, Mobile Phase B: MeOH-Preparative: 30; Flow rate: 150 mL/min; 220 nm) to give 7-bromo-6-methyl-2,3-dihydro-1H-isoindol-1-one (0.52 g, 35%) as a yellow solid; $^1$H NMR (400 MHz, DMSO, 30° C.) 1.68 (3H, s), 4.05 (2H, s), 6.62 (1H, d), 6.72 (1H, d); m/z: ES$^+$ [M+H]$^+$=226.

6-Methyl-7-(4,4,5,5-tetramethyl-1,3,2-dioxaborolan-2-yl)-2,3-dihydro-1H-isoindol-1-one

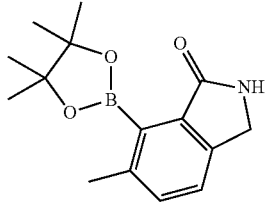 [SMILES: Cc1ccc2c(c1B1OC(C)(C)C(C)(C)O1)C(=O)NC2]

Bis(triphenylphosphine)palladium(II) dichloride (155 mg, 0.22 mmol) was added to 7-bromo-6-methyl-2,3-dihydro-1H-isoindol-1-one (500 mg, 2.21 mmol), 4,4,4',4',5,5,5',5'-octamethyl-2,2'-bi-1,3,2-dioxaborolane (2247 mg, 8.85 mmol) and potassium acetate (434 mg, 4.42 mmol) in 1,4-dioxane (2 mL) at rt. The resulting suspension was stirred at 130° C. for 2 h. After standard work up, the crude product was purified by C18-flash chromatography (0 to 50% MeOH in water) to afford 6-methyl-7-(4,4,5,5-tetramethyl-1,3,2-dioxaborolan-2-yl)-2,3-dihydro-1H-isoindol-1-one as a white solid; $^1$H NMR (400 MHz, DMSO, 30° C.) 1.35 (12H, s), 2.36 (3H, s), 3.17 (1H, d), 3.31 (1H, s), 7.29-7.41 (2H, m), 8.36 (1H, s); m/z: ES$^+$ [M+H]$^+$=274.

tert-Butyl (4aR)-10-bromo-11-chloro-9-fluoro-1,2,4a,5-tetrahydropyrazino[1',2':4,5][1,4]oxazino[2,3-c]quinoline-3(4H)-carboxylate 1M Lithium bis(trimethylsilyl)amide in THF (19.24 mL, 19.24 mmol) was added slowly to tert-butyl (R)-4-(7-bromo-6-chloro-8-fluoro-3-nitroquinolin-4-yl)-3-(hydroxymethyl)piperazine-1-carboxylate (10 g, 19.24 mmol) in NMP (120 mL) at rt and the reaction mixture heated at 130° C. for 6 h. The reaction mixture was cooled to rt, partitioned between water (1 L) and EtOAc (1 L), washed with water (1 L) and brine (500 mL) and concentrated in vacuo. The crude product was purified by flash silica chromatography (0 to 20% EtOAc in petroleum ether) to afford tert-butyl (4aR)-10-bromo-11-chloro-9-fluoro-1,2,4a,5-tetrahydropyrazino[1',2':4,5][1,4]oxazino[2,3-c]quinoline-3(4H)-carboxylate (3.06 g, 34%) as a pale yellow solid; $^1$H NMR (400 MHz, CDCl$_3$, 30° C.) 1.51 (9H, s), 3.25 (1H, td), 3.39 (1H, s), 3.42-3.61 (2H, m), 3.72 (1H, m), 3.93 (2H, m), 4.27-4.35 (2H, m), 7.85 (1H, d), 8.58 (1H, s); m/z: ES$^+$ [M+H]$^+$=474.

tert-Butyl (4aR)-11-chloro-9-fluoro-10-(5-methyl-3-oxo-2,3-dihydro-1H-isoindol-4-yl)-1,2,4a,5-tetrahydropyrazino[1',2':4,5][1,4]oxazino[2,3-c]quinoline-3(4H)-carboxylate Xphos-Pd-G2 (77 mg, 0.09 mmol), RuPhos (42.7 mg, 0.09 mmol), tert-butyl (4aR)-10-bromo-11-chloro-9-fluoro-1,2,4a,5-tetrahydropyrazino[1',2':4,5][1,4]oxazino[2,3-c]quinoline-3(4H)-carboxylate (433 mg, 0.92 mmol), 6-methyl-7-(4,4,5,5-tetramethyl-1,3,2-dioxaborolan-2-yl)-2,3-dihydro-1H-isoindol-1-one (250 mg, 0.92 mmol) and K$_2$CO$_3$ (253 mg, 1.83 mmol) in 1,4-dioxane/H$_2$O (1.0 mL, 4:1 ratio) were sealed into a microwave tube. The reaction mixture was heated to 100° C. for 30 min in the microwave reactor and then cooled to rt. The solvent was removed in vacuo. The crude product was purified by flash silica chromatography (30 to 100% EtOAc in petroleum ether) to afford tert-butyl (4aR)-11-chloro-9-fluoro-10-(5-methyl-3-oxo-2,3-dihydro-1H-isoindol-4-yl)-1,2,4a,5-tetrahydropyrazino[1',2':4,5][1,4]oxazino[2,3-c]quinoline-3(4H)-carboxylate (250 mg, 51%) as a brown solid; m/z: ES$^+$ [M+H]$^+$=539

7-(11-Chloro-9-fluoro-1,2,3,4,4a,5-hexahydropyrazino[1',2':4,5][1,4]oxazino[2,3-c]quinolin-10-yl)-6-methyl-2,3-dihydro-1H-isoindol-1-one Atropisomer 1 and 2

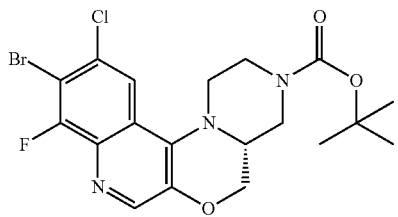 [SMILES: CC(C)(C)OC(=O)N1CCN2c3c(cnc4c(F)c(Br)c(Cl)cc34)OC[C@H]2C1]

4M HCl in 1,4-dioxane (2 mL, 8 mmol) was added to tert-butyl (4aR)-11-chloro-9-fluoro-10-(5-methyl-3-oxo-2,3-dihydro-1H-isoindol-4-yl)-1,2,4a,5-tetrahydropyrazino[1',2':4,5][1,4]oxazino[2,3-c]quinoline-3(4H)-carboxylate (245 mg, 0.45 mmol) in MeOH (3 mL) at rt. The resulting solution was stirred at rt for 1 h and the solvent was removed in vacuo. The crude product was purified by C18-flash chromatography (0 to 30% MeCN in MeOH (0.1% NH$_4$OH)) to afford atropisomer 1 of 7-(11-chloro-9-fluoro-1,2,3,4,4a,5-hexahydropyrazino[1',2':4,5][1,4]oxazino[2,3-c]quinolin-10-yl)-6-methyl-2,3-dihydro-1H-isoindol-1-one (15 mg, 8%) as a yellow solid; $^1$H NMR (400 MHz, DMSO, 30° C.) 1.01-1.10 (1H, m), 2.09 (3H, d), 2.96-3.27 (5H, m), 3.38-3.53 (1H, m), 4.08 (1H, d), 4.30-4.41 (3H, m), 4.44-4.55 (1H, m), 7.55-7.65 (2H, m), 7.87 (1H, s), 8.45 (1H, d), 8.56 (1H, s). m/z: ES⁺ [M+H]⁺=439. This was followed by atropisomer 2 of 7-(11-chloro-9-fluoro-1,2,3,4,4a,5-hexahydropyrazino[1',2':4,5][1,4]oxazino[2,3-c]quinolin-10-yl)-6-methyl-2,3-dihydro-1H-isoindol-1-one (10 mg, 5%) as a yellow solid; m/z: ES⁺ [M+H]⁺=439.

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-2,3-dihydro-1H-isoindol-1-one (Atropisomer 1, Compound 86)

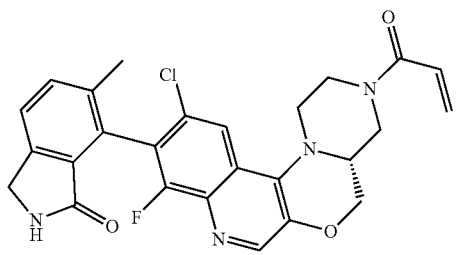 [SMILES: C=CC(=O)N1CCN2c3c(cnc4c(F)c(-c5c(C)ccc6c5C(=O)NC6)c(Cl)cc34)OC[C@H]2C1]

Acryloyl chloride (1.86 mg, 0.02 mmol) in DMF (0.15 mL) was added to atropisomer 1 of 7-(11-chloro-9-fluoro-1,2,3,4,4a,5-hexahydropyrazino[1',2':4,5][1,4]oxazino[2,3-c]quinolin-10-yl)-6-methyl-2,3-dihydro-1H-isoindol-1-one (10 mg, 0.02 mmol) and DIPEA (7.96 µl, 0.05 mmol) in DMF (2 mL) at −20° C. The resulting solution was stirred at −20° C. for 1 h. The crude reaction mixture was purified by C18-flash chromatography (0 to 40% MeCN in water (0.1% NH₄OH)) to afford atropisomer 1 of 7-[(4aR)-11-chloro-9-fluoro-3-(prop-2-enoyl)-1,2,3,4,4a,5-hexahydropyrazino[1',2':4,5][1,4]oxazino[2,3-c]quinolin-10-yl]-6-methyl-2,3-dihydro-1H-isoindol-1-one (8 mg, 71%) as a white solid; ¹H NMR (300 MHz, DMSO, 30° C.) 2.10 (3H, s), 3.06-3.28 (1H, m), 3.33-4.03 (5H, m), 4.04-4.29 (2H, m), 4.29-4.50 (3H, m), 5.74 (1H, d), 6.17 (1H, d), 6.66-6.99 (1H, m), 7.52-7.65 (2H, m), 7.92 (1H, d), 8.45 (1H, s), 8.55 (1H, s). m/z: ES⁺ [M+H]⁺=493.

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-2,3-dihydro-1H-isoindol-1-one (Atropisomer 2, Compound 87)

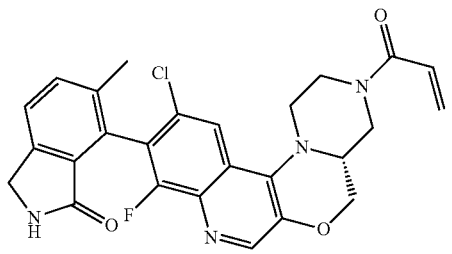 [SMILES: C=CC(=O)N1CCN2c3c(cnc4c(F)c(-c5c(C)ccc6c5C(=O)NC6)c(Cl)cc34)OC[C@H]2C1]

Acryloyl chloride (1.86 mg, 0.02 mmol) in DMF (0.15 mL) was added to atropisomer 2 of 7-(11-chloro-9-fluoro-1,2,3,4,4a,5-hexahydropyrazino[1',2':4,5][1,4]oxazino[2,3-c]quinolin-10-yl)-6-methyl-2,3-dihydro-1H-isoindol-1-one (10 mg, 0.02 mmol) and DIPEA (7.96 µl, 0.05 mmol) in DMF (2 mL) at −20° C. The resulting solution was stirred at −20° C. for 1 h. The reaction mixture was purified by C18-flash chromatography (0 to 40% MeCN in water (0.1% NH₄OH)) to afford product then further purified by preparative HPLC (Column: SunFire C18 OBD Prep Column, 100 Å, 5 µm, 19 mm×250 mm; Mobile Phase A: Water (0.1% formic acid), Mobile Phase B: MeCN; Flow rate: 25 mL/min; Gradient: 28% B to 43% B in 6 min; 254/220 nm) to afford atropisomer 2 of 7-[(4aR)-11-chloro-9-fluoro-3-(prop-2-enoyl)-1,2,3,4,4a,5-hexahydropyrazino[1',2':4,5][1,4]oxazino[2,3-c]quinolin-10-yl]-6-methyl-2,3-dihydro-1H-isoindol-1-one (6.5 mg, 58%) as a white solid; ¹H NMR (300 MHz, DMSO, 30° C.) 2.06 (3H, s), 3.34-3.46 (1H, m), 3.48-3.62 (2H, m), 3.61-4.29 (5H, m), 4.30-4.49 (3H, m), 5.74 (1H, d), 6.17 (1H, d), 6.72-6.99 (1H, m), 7.52-7.65 (2H, m), 7.92 (1H, d), 8.45 (1H, s), 8.55 (1H, s). m/z: ES⁺ [M+H]⁺=493.

1-tert-Butyl 3-methyl (3R)-4-[6-chloro-8-fluoro-7-(2-fluoro-6-methoxyphenyl)-3-nitroquinolin-4-yl]piperazine-1,3-dicarboxylate

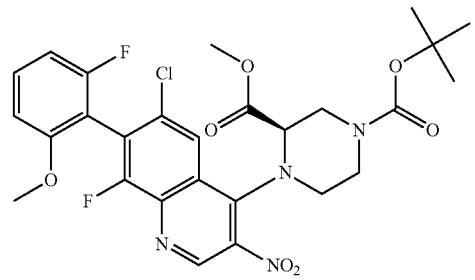 [SMILES: COC(=O)[C@H]1CN(C(=O)OC(C)(C)C)CCN1c1c([N+](=O)[O-])cnc2c(F)c(-c3c(F)cccc3OC)c(Cl)cc12]

To a deoxygenated solution of 4,6-dichloro-8-fluoro-7-(2-fluoro-6-methoxyphenyl)-3-nitroquinoline (1 g, 2.60 mmol) and DIPEA (0.48 mL, 2.86 mmol) in dry THF (30 mL) was added 1-(tert-butyl) 3-methyl piperazine-1,3-dicarboxylate (0.67 g, 2.73 mmol) at rt. The reaction mixture was heated at 65° C. for 21 h. Further 1-(tert-butyl) 3-methyl piperazine-1,3-dicarboxylate (0.32 g, 0.5 eq) and DIPEA (0.23 mL, 0.5 eq) were added and the reaction mixture continued heating at 65° C. for a further 18 h. The reaction allowed to cool and stirred at rt for 24 h. Further 1-(tert-butyl) 3-methyl piperazine-1,3-dicarboxylate (0.32 g, 0.5 eq) and DIPEA (0.23 mL, 0.5 eq) were added and the reaction mixture continued heating at 65° C. for a further 2 h. The reaction mixture allowed to cool, concentrated in vacuo, the residue dissolved in DCM and washed with 1 M citric acid. The organic layer was collected and the aqueous was washed further with DCM. The combined organics were washed with brine, dried (phase separator) and concentrated in vacuo to give crude material as brown oil. This was purified by flash silica chromatography (0 to 100% EtOAc in heptane) to afford 1-tert-butyl 3-methyl (3R)-4-[6-chloro-8-fluoro-7-(2-fluoro-6-methoxyphenyl)-3-nitroquinolin-4-yl]piperazine-1,3-dicarboxylate (1.01 g, 66%) as a brown foam; ¹H NMR (400 MHz, DMSO, 30° C.) 1.44 (9H, s), 3.27-3.35 (2H, m), 3.57 (3H, s), 3.61-3.69 (1H, m), 3.73 (1H, dt), 3.79 (3H, d), 3.81-3.92 (1H, m), 4.06-4.2 (1H, m), 4.35-4.43 (1H, m), 7.04 (1H, t), 7.11 (1H, dd), 7.55-7.63 (1H, m), 8.31-8.35 (1H, m), 9.16 (1H, d); m/z: ES⁺ [M+H]⁺ 593.

tert-Butyl (4aR)-11-chloro-9-fluoro-10-(2-fluoro-6-methoxyphenyl)-5-oxo-1,2,4,4a,5,6-hexahydro-3H-pyrazino[1',2':4,5]pyrazino[2,3-c]quinoline-3-carboxylate

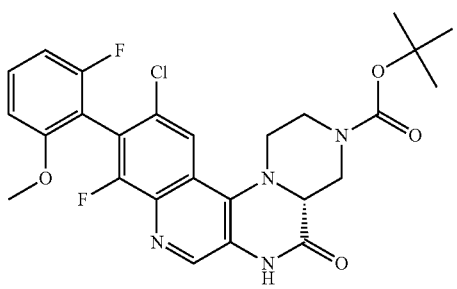 [SMILES: COc1cccc(F)c1-c1c(Cl)cc2c3c(cnc2c1F)NC(=O)[C@H]1CN(C(=O)OC(C)(C)C)CCN31]

To a stirred solution of 1-tert-butyl 3-methyl (3R)-4-[6-chloro-8-fluoro-7-(2-fluoro-6-methoxyphenyl)-3-nitroquinolin-4-yl]piperazine-1,3-dicarboxylate (1.01 g, 1.64 mmol) in acetic acid (20 mL) at rt was added iron powder (0.32 g, 5.75 mmol) and the resultant reaction mixture stirred at 80° C. for 90 min. The reaction mixture was allowed to cool to rt, filtered through CELITE™, washing with DCM and MeOH. The filtrate was concentrated in vacuo, re-dissolved in DCM and made basic with aq. sat. NaHCO₃ to pH 8. The resulting mixture was filtered through a pad of CELITE™. The filtrate was separated and the aqueous layer extracted with further DCM. The combined organics layers were dried (phase separator) and concentrated in vacuo to afford tert-butyl (4aR)-11-chloro-9-fluoro-10-(2-fluoro-6-methoxyphenyl)-5-oxo-1,2,4,4a,5,6-hexahydro-3H-pyrazino[1',2':4,5]pyrazino[2,3-c]quinoline-3-carboxylate (0.85 g, 97%) as a brown solid; $^1$H NMR (400 MHz, DMSO, 30° C.) 1.45 (9H, s), 2.68-2.79 (1H, m), 3.21-3.29 (3H, m), 3.77 (3H, d), 3.81-3.95 (2H, m), 4.70 (1H, d), 7.00 (1H, td), 7.07 (1H, dd), 7.55 (1H, q), 8.04 (1H, s), 8.65 (1H, s), 11.02 (1H, s); m/z: ES⁺ [M+H]⁺ 531.

(4aR)-11-Chloro-9-fluoro-10-(2-fluoro-6-hydroxyphenyl)-2,3,4,4a-tetrahydro-1H-pyrazino[1',2':4,5]pyrazino[2,3-c]quinolin-5(6H)-one Atropisomer 1 and 2

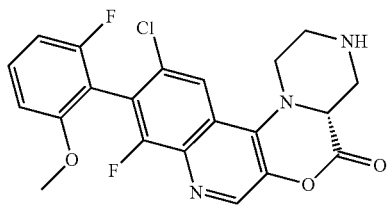 [SMILES: COc1cccc(F)c1-c1c(Cl)cc2c3c(cnc2c1F)OC(=O)[C@H]1CNCCN31]

tert-Butyl (4aR)-11-chloro-9-fluoro-10-(2-fluoro-6-methoxyphenyl)-5-oxo-1,2,4,4a,5,6-hexahydro-3H-pyrazino[1',2':4,5]pyrazino[2,3-c]quinoline-3-carboxylate (0.83 g, 1.56 mmol) was dissolved in DCM (12 mL) and the mixture was cooled to 0° C. before tribromoborane (12.50 mL, 12.46 mmol) was added dropwise. The mixture was stirred for 2 h in the ice bath (0° C.-15° C. over this time), then allowed to warm to rt and stirred overnight. The mixture was quenched by addition of water and MeOH then purified by SCX (1M NH₃/MeOH) to afford crude material as a brown solid. This was purified using SFC (Chiralpak IC, 30×250 mm, 5 μm Mobile phase: 45% MeOH+0.1% NH3/55% scCO₂ Flow rate: 90 ml/min BPR: 120 bar Column temperature: 40 deg C. UV max 265 nm.) to afford atropisomer 1 of (4aR)-11-chloro-9-fluoro-10-(2-fluoro-6-hydroxyphenyl)-2,3,4,4a-tetrahydro-1H-pyrazino[1',2':4,5]pyrazino[2,3-c]quinolin-5(6H)-one, atropisomer 2 (0.19 g, 29%, 99% d.e.) as a brown solid; $^1$H NMR (400 MHz, DMSO, 30° C.) 2.6-2.67 (1H, m), 2.85-3.04 (3H, m), 3.09 (1H, d), 3.57-3.66 (2H, m), 6.79 (1H, t), 6.85 (1H, d), 7.29-7.4 (1H, m), 7.99 (1H, d), 8.64 (1H, s), 10.18 (1H, s), 10.98 (1H, s); m/z: ES⁺ [M]⁺417. This was followed by atropisomer 2 of (4aR)-11-chloro-9-fluoro-10-(2-fluoro-6-hydroxyphenyl)-2,3,4,4a-tetrahydro-1H-pyrazino[1',2':4,5]pyrazino[2,3-c]quinolin-5(6H)-one (0.22 g, 34%, 94% d.e.) as a brown solid; $^1$H NMR (400 MHz, DMSO, 30° C.) 2.59-2.66 (1H, m), 2.84-3.03 (3H, m), 3.09 (1H, d), 3.55-3.59 (1H, m), 3.62 (1H, d), 6.79 (1H, t), 6.84 (1H, d), 7.27-7.38 (1H, m), 7.98 (1H, d), 8.64 (1H, s), 10.14 (1H, s), 10.97 (1H, s); m/z: ES⁺ [M]⁺417.

(4aR)-11-Chloro-9-fluoro-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one (Atropisomer 1, Compound 88)

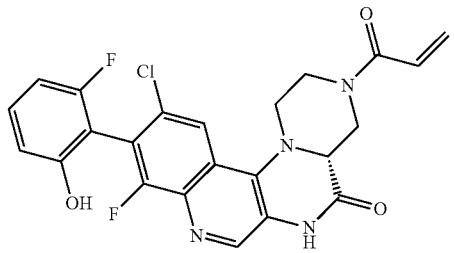 [SMILES: C=CC(=O)N1CCN2c3c(cnc4c(F)c(-c5c(O)cccc5F)c(Cl)cc34)NC(=O)[C@H]2C1]

To a solution of atropisomer 1 of (4aR)-11-chloro-9-fluoro-10-(2-fluoro-6-hydroxyphenyl)-2,3,4,4a-tetrahydro-1H-pyrazino[1',2':4,5]pyrazino[2,3-c]quinolin-5(6H)-one (220 mg, 0.53 mmol) and pyridine (85 μL, 1.06 mmol) in DCM (4 mL) and IPA (1 mL) at 0° C. was added acryloyl chloride (43 μL, 0.53 mmol) and the reaction mixture stirred at 0° C. for 20 min. Further acryloyl chloride (43 μL, 0.53 mmol) was added and the reaction mixture stirred at 0° C. for a further 10 min. Further acryloyl chloride (43 μL, 0.53 mmol) was added and the reaction mixture stirred at 0° C. for a further 15 min, then allowed to warm to rt for 1 h. Further acryloyl chloride (43 μL, 0.53 mmol) was added and the reaction mixture stirred at rt for a further 20 min. DCM was removed in vacuo, 1M NH₃/MeOH (2 mL) was added and the crude solution was purified by preparative HPLC (Waters XSelect CSH C18 ODB column, 5μ silica, 30 mm diameter, 100 mm length), using water (containing 1% NH₃) and MeCN as eluents, to afford atropisomer 1 of (4aR)-11-chloro-9-fluoro-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one (56 mg, 23%, 99% d.e.) as a white solid; $^1$H NMR (400 MHz, DMSO, 30° C.) 2.63-2.72 (1H, m), 3.14-3.24 (1H, m), 3.33-3.37 (1H, m), 3.61 (1H, d), 3.93 (1H, s), 4.41 (1H, d), 4.74 (1H, d), 5.75 (1H, d), 6.14 (1H, dd), 6.78 (1H, t), 6.84 (1H, d), 6.97-7.09 (1H, m), 7.33 (1H, q), 8.06 (1H, s), 8.65 (1H, s); m/z: ES⁺ [M+H]⁺ 471.

(4aR)-11-Chloro-9-fluoro-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one (Atropisomer 2, Compound 89)

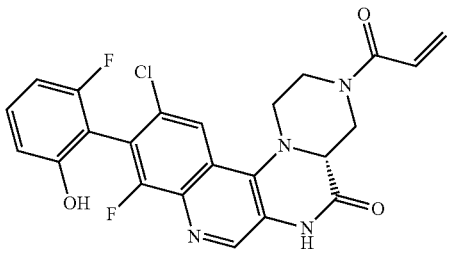 [SMILES: C=CC(=O)N1CCN2c3c(cnc4c(F)c(-c5c(O)cccc5F)c(Cl)cc34)NC(=O)[C@H]2C1]

To a stirring solution of atropisomer 2 of (4aR)-11-chloro-9-fluoro-10-(2-fluoro-6-hydroxyphenyl)-2,3,4,4a-tetrahydro-1H-pyrazino[1',2':4,5]pyrazino[2,3-c]quinolin-5(6H)-one (190 mg, 0.46 mmol) and pyridine (73.4 µL, 0.91 mmol) in DCM (4 mL) and 2-propanol (1 mL) at 0° C. was added acryloyl chloride (37 µL, 0.46 mmol) and the reaction mixture stirred at 0° C. for 15 min. Further acryloyl chloride (37 µL, 0.46 mmol) was added and the reaction mixture stirred at 0° C. for a further 15 min. Further acryloyl chloride (19 µL, 0.23 mmol) was added and the reaction mixture stirred at 0° C. for a further 15 min. Reaction mixture then allowed to warm to rt. DCM was removed in vacuo, 1M NH$_3$/MeOH (2 mL) was added and the crude solution was purified by preparative HPLC (Waters XSelect CSH C18 ODB column, 5µ silica, 30 mm diameter, 100 mm length), using water (containing 1% NH$_3$) and MeCN as eluents, to afford atropisomer 2 of (4aR)-11-chloro-9-fluoro-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one (65 mg, 30%, 98% d.e.) as a white solid; $^1$H NMR (400 MHz, DMSO, 30° C.) 2.61-2.72 (1H, m), 3.04-3.3 (1H, m), 3.33-3.37 (1H, m), 3.60 (1H, d), 3.94 (1H, s), 4.41 (1H, s), 4.74 (1H, d), 5.75 (1H, d), 6.14 (1H, dd), 6.77 (1H, t), 6.84 (1H, d), 6.97-7.09 (1H, m), 7.33 (1H, q), 8.07 (1H, s), 8.65 (1H, s); m/z: ES$^+$ [M+H]$^+$ 471.

7-Bromo-4,6-dichloro-3-nitroquinoline

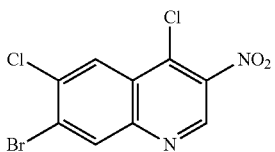 [SMILES: O=[N+]([O-])c1cnc2cc(Br)c(Cl)cc2c1Cl]

Phosphoric trichloride (6.12 mL, 65.90 mmol) was added to 7-bromo-6-chloro-3-nitroquinolin-4(1H)-one (5 g, 16.47 mmol) in toluene (45 mL). DMF (0.20 mL) was added and the mixture was heated at 105° C. for 3 h, then allowed to cool to rt. The reaction mixture was concentrated in vacuo then taken up in DCM (200 mL) and poured into ice-cold aq. sat. NaHCO$_3$ (200 mL). The aqueous layer was extracted with DCM (200 mL). The combined organic layers were washed with water (100 mL), brine (100 mL), dried (phase separator) and concentrated in vacuo to afford 7-bromo-4,6-dichloro-3-nitroquinoline (4.97 g, 94%) as a beige solid; $^1$H NMR (400 MHz, DMSO, 30° C.) 8.59 (1H, s), 8.70 (1H, s), 9.42 (1H, s).

1-tert-Butyl 3-methyl (3R)-4-(7-bromo-6-chloro-3-nitroquinolin-4-yl)piperazine-1,3-dicarboxylate

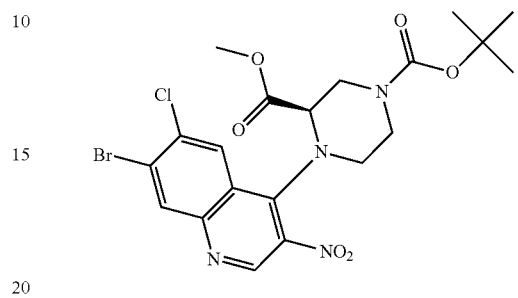

To a solution of 7-bromo-4,6-dichloro-3-nitroquinoline (4.97 g, 15.44 mmol) in THF (100 mL) was added 1-tert-butyl 3-methyl (3R)-piperazine-1,3-dicarboxylate (4.9 g, 20.07 mmol) followed by DIPEA (8.07 mL, 46.31 mmol) and reaction mixture heated at reflux overnight. Further 1-tert-butyl 3-methyl (3R)-piperazine-1,3-dicarboxylate (0.943 g, 0.25 eq) was added, along with further DIPEA (1.35 mL, 0.5 eq) and the reaction mixture heated at reflux for a further 24 h. The reaction mixture was partially concentrated and partitioned between water and EtOAc. Layers were separated, the organic layer washed with water and the combined aqueous layers were back extracted with EtOAc. The combined organic layers were dried (phase separator) and concentrated in vacuo to afford crude material as a dark brown oil. This was purified by flash silica chromatography (0 to 18% EtOAc in heptane) to afford 1-tert-butyl 3-methyl (3R)-4-(7-bromo-6-chloro-3-nitroquinolin-4-yl)piperazine-1,3-dicarboxylate (5.2 g, 64%) as an orange foam; $^1$H NMR (400 MHz, DMSO, 30° C.) 1.44 (9H, s), 3.29 (2H, s), 3.5-3.58 (3H, m), 3.6-3.69 (1H, m), 3.73 (1H, dd), 3.78-3.9 (1H, m), 4.02-4.2 (1H, m), 4.3-4.38 (1H, m), 8.49 (1H, s), 8.52 (1H, s), 9.11 (1H, s); m/z: ES$^+$ [M+H]$^+$ 529, 531.

tert-Butyl (4aR)-10-bromo-11-chloro-5-oxo-1,2,4,4a,5,6-hexahydro-3H-pyrazino[1',2':4,5]pyrazino[2,3-c]quinoline-3-carboxylate

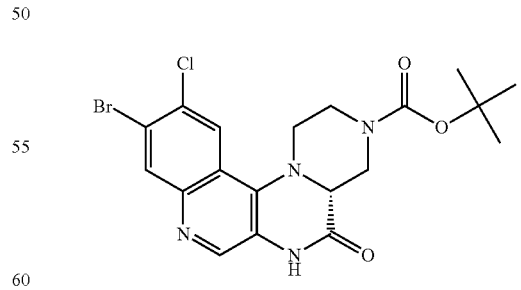

To a stirred solution of 1-tert-butyl 3-methyl (3R)-4-(7-bromo-6-chloro-3-nitroquinolin-4-yl)piperazine-1,3-dicarboxylate (3.98 g, 7.50 mmol) in acetic acid (30 mL) at rt was added iron powder (1.47 g, 26.26 mmol) and the resultant reaction mixture stirred at 80° C. for 1 h. The reaction mixture was allowed to cool to rt, diluted with EtOAc and filtered through CELITE™, washing with EtOAc, MeOH and DCM. The filtrate was concentrated in vacuo, then the residue slurried in diethyl ether overnight and filtered to afford a beige solid. The solid was redissolved in EtOAc (500 mL) and washed with sat. aq. NaHCO₃ (400 mL) and brine (200 mL). The combined aqueous layers were back extracted with EtOAc, then DCM (400 mL) the combined organic extracts were dried (phase separator) and concentrated in vacuo to afford tert-butyl (4aR)-10-bromo-11-chloro-5-oxo-1,2,4,4a,5,6-hexahydro-3H-pyrazino[1',2':4,5]pyrazino[2,3-c]quinoline-3-carboxylate (3.47 g, 99%) as a yellow solid; ¹H NMR (400 MHz, DMSO, 30° C.) 1.44 (9H, s), 2.63-2.75 (2H, m), 3.2-3.28 (2H, m), 3.74-3.95 (2H, m), 4.68 (1H, d), 8.22 (1H, s), 8.38 (1H, s), 8.60 (1H, s), 10.94 (1H, s); m/z: ES⁺ [M+H]⁺ 467, 469 tert-Butyl (4aR)-10-bromo-11-chloro-6-ethyl-5-oxo-1,2,4,4a,5,6-hexahydro-3H-pyrazino[1',2':4,5]pyrazino[2,3-c]quinoline-3-carboxylate

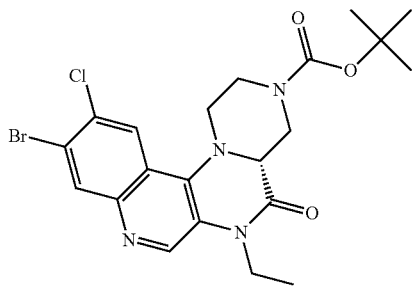 [SMILES: CCN1C(=O)[C@H]2CN(C(=O)OC(C)(C)C)CCN2c2c1cnc1cc(Br)c(Cl)cc21]

To a stirred suspension of tert-butyl (4aR)-10-bromo-11-chloro-5-oxo-1,2,4,4a,5,6-hexahydro-3H-pyrazino[1',2':4,5]pyrazino[2,3-c]quinoline-3-carboxylate (700 mg, 1.5 mmol) and K₂CO₃ (414 mg, 2.99 mmol) in acetone (15 mL) at rt was added iodoethane (2.41 mL, 29.93 mmol). The resultant suspension was heated at 50° C. overnight. Further iodoethane (2.41 mL, 29.93 mmol) was added and the reaction mixture heated at 50° C. for 4 h. Further K₂CO₃ (414 mg, 2.99 mmol) was added and the reaction mixture heated at 50° C. for 90 min. Further iodoethane (2.41 mL, 29.93 mmol) and K₂CO₃ (414 mg, 2.99 mmol) were added and the reaction mixture heated at 50° C. for 30 min before the reaction mixture was allowed to cool and left stirring at rt for 72 h. The reaction mixture was combined with another smaller batch (50 mg scale), concentrated in vacuo and the crude residue dissolved in DCM, washed with water and brine. The aqueous layers were back extracted with DCM and the combined organic layers were dried (phase separator) and concentrated in vacuo to afford the crude product as a dark red oil. The crude product was slurried in diethyl ether and then concentrated in vacuo to give tert-butyl (4aR)-10-bromo-11-chloro-6-ethyl-5-oxo-1,2,4,4a,5,6-hexahydro-3H-pyrazino[1',2':4,5]pyrazino[2,3-c]quinoline-3-carboxylate (829 mg, 100%, across the two batches) as an orange foam; ¹H NMR (400 MHz, DMSO, 30° C.) 1.19 (3H, t), 1.45 (9H, s), 2.56-2.65 (1H, m), 3.16-3.28 (3H, m), 3.76-3.97 (2H, m), 4.02-4.22 (2H, m), 4.72 (1H, d), 8.27 (1H, s), 8.44 (1H, s), 8.99 (1H, s); m/z: ES⁺ [M+H]⁺ 495, 497.

tert-Butyl (4aR)-11-chloro-6-ethyl-10-(2-fluoro-6-hydroxyphenyl)-5-oxo-1,2,4,4a,5,6-hexahydro-3H-pyrazino[1',2':4,5]pyrazino[2,3-c]quinoline-3-carboxylate

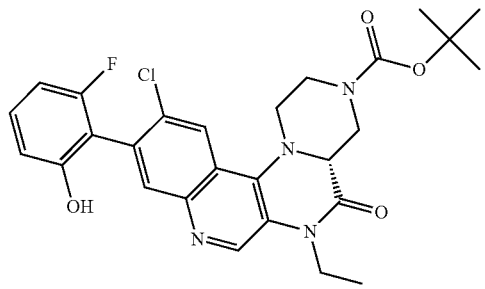 [SMILES: CCN1C(=O)[C@H]2CN(C(=O)OC(C)(C)C)CCN2c2c1cnc1cc(-c3c(O)cccc3F)c(Cl)cc21]

RuPhos (73.3 mg, 0.16 mmol) and RuPhos Pd G3 (131 mg, 0.16 mmol) were added to a degassed mixture of tert-butyl (4aR)-10-bromo-11-chloro-6-ethyl-5-oxo-1,2,4,4a,5,6-hexahydro-3H-pyrazino[1',2':4,5]pyrazino[2,3-c]quinoline-3-carboxylate (829 mg, 1.57 mmol), (2-fluoro-6-hydroxyphenyl)boronic acid (490 mg, 3.14 mmol) and K₂CO₃ (652 mg, 4.72 mmol) in dioxane (10 ml) and water (2.5 ml) and the reaction mixture stirred at 80° C. for 24 h. The reaction was allowed to cool then diluted with EtOAc and water. The organic layer was washed with aq. sat. NaHCO₃ (100 mL) and brine (100 mL). The combined aqueous was back extracted with EtOAc (×2). All organic fractions were then combined, dried (phase separator) and concentrated in vacuo to afford crude material as a brown oil. This was purified by flash silica chromatography (0 to 100% EtOAc in heptane) to afford tert-butyl (4aR)-11-chloro-6-ethyl-10-(2-fluoro-6-hydroxyphenyl)-5-oxo-1,2,4,4a,5,6-hexahydro-3H-pyrazino[1',2':4,5]pyrazino[2,3-c]quinoline-3-carboxylate (546 mg, 66%) as a brown solid; ¹H NMR (400 MHz, DMSO, 30° C.) 1.20 (3H, t), 1.46 (9H, s), 2.57-2.66 (1H, m), 3.14-3.28 (3H, m), 3.84 (1H, s), 3.93 (1H, s), 4.1-4.2 (2H, m), 4.75 (1H, d), 6.77 (1H, t), 6.83 (1H, d), 7.25-7.33 (1H, m), 7.93 (1H, d), 8.21 (1H, s), 8.99 (1H, s), 10.01 (1H, s); m/z: ES⁺ [M+H]⁺ 527

(4aR)-11-Chloro-6-ethyl-10-(2-fluoro-6-hydroxyphenyl)-2,3,4,4a-tetrahydro-1H-pyrazino[1',2':4,5]pyrazino[2,3-c]quinolin-5(6H)-one

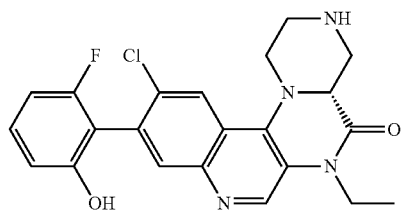 [SMILES: CCN1C(=O)[C@H]2CNCCN2c2c1cnc1cc(-c3c(O)cccc3F)c(Cl)cc21]

tert-Butyl (4aR)-11-chloro-6-ethyl-10-(2-fluoro-6-hydroxyphenyl)-5-oxo-1,2,4,4a,5,6-hexahydro-3H-pyrazino[1',2':4,5]pyrazino[2,3-c]quinoline-3-carboxylate (546 mg, 0.98 mmol) was dissolved in MeOH (4 mL) at rt before HCl (4M in dioxane, 2 mL) was added and the resultant solution stirred at rt for 2 h. The reaction mixture was purified by SCX (1M NH₃/MeOH) to afford (4aR)-11-chloro-6-ethyl-10-(2-fluoro-6-hydroxyphenyl)-2,3,4,4a-tetrahydro-1H- pyrazino[1',2':4,5]pyrazino[2,3-c]quinolin-5(6H)-one (341 mg, 81%) as an orange solid; $^1$H NMR (400 MHz, DMSO, 30° C.) 1.17-1.26 (3H, m), 2.53-2.62 (1H, m), 2.86-2.95 (1H, m), 2.96-3.06 (2H, m), 3.07-3.14 (1H, m), 3.56-3.61 (1H, m), 3.66 (1H, d), 4.11-4.28 (2H, m), 6.77 (1H, t), 6.84 (1H, d), 7.30 (1H, td), 7.92 (1H, d), 8.18 (1H, s), 8.99 (1H, s), 10.00 (1H, s); m/z: ES$^+$ [M+H]$^+$ 427.

(4aR)-11-Chloro-6-ethyl-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one (Compound 90)

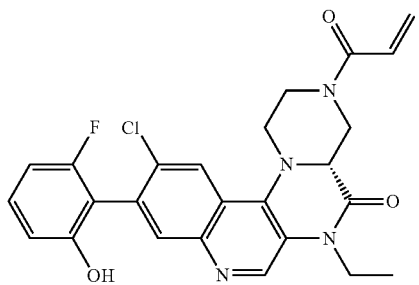 [SMILES: C=CC(=O)N1CCN2c3c(cnc4cc(-c5c(O)cccc5F)c(Cl)cc34)N(CC)C(=O)[C@H]2C1]

To a solution (4aR)-11-chloro-6-ethyl-10-(2-fluoro-6-hydroxyphenyl)-2,3,4,4a-tetrahydro-1H-pyrazino[1',2':4,5]pyrazino[2,3-c]quinolin-5(6H)-one (341 mg, 0.80 mmol) and pyridine (129 µL, 1.60 mmol) in DCM (6 mL) and IPA (2 mL) at 0° C. was added acryloyl chloride (65 µL, 0.80 mmol) and the reaction mixture stirred at 0° C. for 20 min. Further acryloyl chloride (65 µL, 0.80 mmol) was added and the reaction mixture stirred at 0° C. for a further 10 min. Further acryloyl chloride (33 µL, 0.40 mmol) was added and the reaction mixture stirred at 0° C. for a further 10 min. Reaction mixture then allowed to warm to rt and concentrated in vacuo to afford crude material as a brown foam. The crude product was purified by preparative LCMS (Waters XSelect CSH C18 ODB column, 5µ silica, 30 mm diameter, 100 mm length), using water (containing 1% NH$_3$) and MeCN as eluents, to afford (4aR)-11-chloro-6-ethyl-10-(2-fluoro-6-hydroxyphenyl)-3-(prop-2-enoyl)-2,3,4,4a-tetrahydro-1H-pyrazino[1',2':4,5]pyrazino[2,3-c]quinolin-5 (6H)-one (131 mg, 34.1%) as a yellow solid; $^1$H NMR (400 MHz, DMSO, 30° C.) 1.13-1.22 (3H, m), 2.55-2.64 (1H, m), 3.13-3.24 (1H, m), 3.29-3.37 (1H, m), 3.61 (1H, d), 3.93 (1H, s), 4.08-4.2 (2H, m), 4.46 (1H, d), 4.76 (1H, d), 5.75 (1H, d), 6.14 (1H, dd), 6.76 (1H, t), 6.83 (1H, d), 6.99-7.15 (1H, m), 7.24-7.34 (1H, m), 7.94 (1H, d), 8.26 (1H, s), 9.00 (1H, s), 10.05 (1H, s); m/z: ES$^+$ [M+H]$^+$ 481.

5-{[(5-Bromo-4,6-dimethylpyridin-3-yl)amino]methylidene}-2,2-dimethyl-1,3-dioxane-4,6-dione

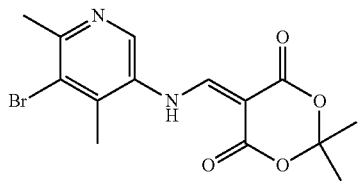 [SMILES: Cc1ncc(NC=C2C(=O)OC(C)(C)OC2=O)c(C)c1Br]

A mixture of trimethoxymethane (16.32 ml, 149.2 mmol) and 2,2-dimethyl-1,3-dioxane-4,6-dione (8.24 g, 57.19 mmol) in ethanol (100 ml) was heated at 90° C. for 90 min, then cooled to 70° C. over 1 h. 5-Bromo-4,6-dimethylpyridin-3-amine (10 g, 49.73 mmol) was slowly added over a period of 10 min and the reaction mixture was heated for a further 1 h, then allowed to cool to rt. The resulting precipitate was filtered, washed with ethanol and diethyl ether and dried under vacuum to afford 5-{[(5-bromo-4,6-dimethylpyridin-3-yl)amino]methylidene}-2,2-dimethyl-1,3-dioxane-4,6-dione (12.21 g, 69%) as a yellow solid; $^1$H NMR (400 MHz, DMSO, 30° C.) 1.68 (6H, s), 2.39 (3H, s), 2.62 (3H, s), 8.43 (1H, s), 8.57 (1H, s), 11.19 (1H, s); m/z: ES$^+$ [M+H]$^+$ 355.1.

7-Bromo-6,8-dimethyl-1,5-naphthyridin-4-ol

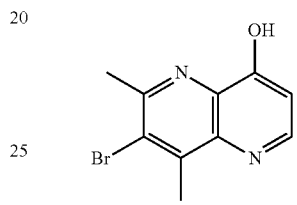

5-{[(5-Bromo-4,6-dimethylpyridin-3-yl)amino]methylidene}-2,2-dimethyl-1,3-dioxane-4,6-dione (12.21 g, 34.38 mmol) was slowly added to DOWTHERM™ A (150 ml, 34.38 mmol) over a period of 5 min at 230° C. The reaction was maintained at 230° C. for 10 min before being cooled to 40° C. over a period of 90 min. The precipitate that formed was filtered off and washed with heptane and diethyl ether, and dried in a vacuum oven to afford 7-bromo-6,8-dimethyl-1,5-naphthyridin-4-ol (7.04 g, 81%) as a brown solid; $^1$H NMR (400 MHz, DMSO, 100° C.) 2.74 (3H, s), 2.78 (3H, s), 6.65 (1H, s), 8.19 (1H, s); m/z: ES$^+$ [M+H]$^+$ 253.1.

7-Bromo-6,8-dimethyl-3-nitro-1,5-naphthyridin-4-ol

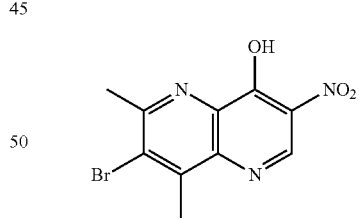

A mixture of 7-bromo-6,8-dimethyl-1,5-naphthyridin-4-ol (7.04 g, 23.64 mmol) and fuming nitric acid (20 ml, 23.64 mmol) was heated at 80° C. for 4 h. The reaction cooled to 50° C., further fuming nitric acid (10 ml) was added and reaction mixture heated for a further 1 h at 80° C. The reaction mixture was cooled to rt overnight and then poured slowly over ice and adjusted to pH 2 with 50% aq. NaOH. The resulting precipitate was filtered and washed with water, then diethyl ether and dried in a vacuum oven to afford 7-bromo-6,8-dimethyl-3-nitro-1,5-naphthyridin-4-ol (6.18 g, 88%) as a yellow solid; $^1$H NMR (400 MHz, DMSO, 100° C.) 2.71 (3H, s), 2.79 (3H, s), 8.86 (1H, s); m/z: ES$^+$ [M+H]$^+$ 298.1.

3-Bromo-8-chloro-2,4-dimethyl-7-nitro-1,5-naphthyridine

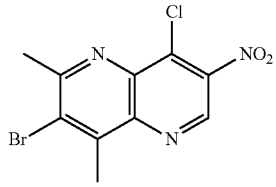 [SMILES: Cc1nc2c(Cl)c([N+](=O)[O-])cnc2c(C)c1Br]

Phosphoric trichloride (1.40 ml, 15.10 mmol) was added to 7-bromo-6,8-dimethyl-3-nitro-1,5-naphthyridin-4-ol (3.00 g, 10.06 mmol) in DMF (30 ml) at rt. The reaction mixture was left to stir at rt overnight, then added to ice water and a solid crashed out of solution which was filtered off, washed with water and diethyl ether and dried under vacuum to afford 3-bromo-8-chloro-2,4-dimethyl-7-nitro-1,5-naphthyridine (2.95 g, 93%) as a beige solid; $^1$H NMR (400 MHz, DMSO, 30° C.) 2.90 (3H, s), 2.91 (3H, s), 9.45 (1H, s).

1-tert-Butyl 3-methyl (3R)-4-(7-bromo-6,8-dimethyl-3-nitro-1,5-naphthyridin-4-yl)piperazine-1,3-dicarboxylate

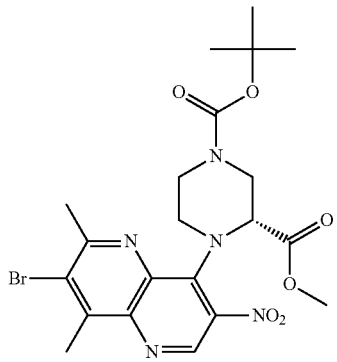 [SMILES: COC(=O)[C@H]1CN(C(=O)OC(C)(C)C)CCN1c1c([N+](=O)[O-])cnc2c(C)c(Br)c(C)nc12]

DIPEA (1.79 ml, 10.25 mmol) was added to a solution of 3-bromo-8-chloro-2,4-dimethyl-7-nitro-1,5-naphthyridine (2.95 g, 9.32 mmol) and 1-tert-butyl 3-methyl (3R)-piperazine-1,3-dicarboxylate (2.39 g, 9.79 mmol) in THF (40 ml). The resultant brown solution was heated at 65° C. for 24 h. The reaction mixture was concentrated in vacuo, the residue re-dissolved in ethyl acetate and washed with water (×2) and brine. The aqueous layer was back extracted with ethyl acetate and the combined organics dried (phase separator) and concentrated in vacuo to afford crude material as a brown foam. This was purified by flash silica chromatography (0 to 100% ethyl acetate in heptane) to afford 1-tert-butyl 3-methyl (3R)-4-(7-bromo-6,8-dimethyl-3-nitro-1,5-naphthyridin-4-yl)piperazine-1,3-dicarboxylate (4.13 g, 85%) as a yellow solid; $^1$H NMR (400 MHz, DMSO, 30° C.) 1.42 (9H, s), 2.74 (3H, s), 2.82 (3H, s), 3.09-3.15 (1H, m), 3.24 (1H, s), 3.55 (1H, d), 3.67 (3H, s), 3.73-3.84 (1H, m), 3.88 (1H, s), 4.37 (1H, d), 5.59 (1H, s), 9.04 (1H, s); m/z: ES$^+$ [M+H]$^+$ 523.9.

tert-Butyl (8aR)-3-bromo-2,4-di methyl-8-oxo-7,8,8a,9,11,12-hexahydro-10H-pyrazino[1',2':4,5]pyrazino[2,3-c][1,5]naphthyridine-10-carboxylate

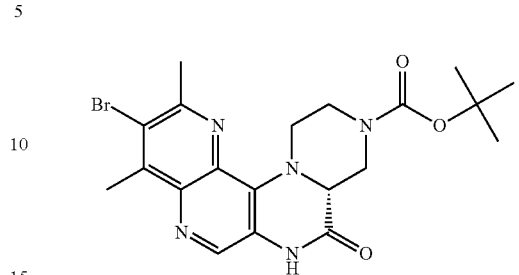

To a solution of 1-tert-butyl 3-methyl (3R)-4-(7-bromo-6,8-dimethyl-3-nitro-1,5-naphthyridin-4-yl)piperazine-1,3-dicarboxylate (4.13 g, 7.88 mmol) in acetic acid (30 ml) at rt was added iron powder (1.1 g, 19.69 mmol) and the resultant solution heated at 75° C. for 2 h. The reaction mixture was cooled to 30° C. and 1.0M citric acid (50 ml) was added. The resulting suspension was stirred at rt for 1 h, the solid collected by filtration, washed with water and dried under vacuum to afford tert-butyl (8aR)-3-bromo-2,4-dimethyl-8-oxo-7,8,8a,9,11,12-hexahydro-10H-pyrazino[1',2':4,5]pyrazino[2,3-c][1,5]naphthyridine-10-carboxylate (1.71 g, 47%) as a yellow solid; $^1$H NMR (400 MHz, DMSO, 100° C.) 1.44 (9H, s), 2.76 (6H, d), 3.15 (2H, dt), 3.34 (1H, t), 3.93 (1H, d), 4.09 (1H, d), 4.21 (1H, d), 6.08 (1H, d), 8.33 (1H, s), 10.62 (1H, s); m/z: ES$^+$ [M+H]$^+$ 462.3.

tert-Butyl (8aR)-3-bromo-2,4,7-trimethyl-8-oxo-7,8,8a,9,11,12-hexahydro-10H-pyrazino[1',2':4,5]pyrazino[2,3-c][1,5]naphthyridine-10-carboxylate

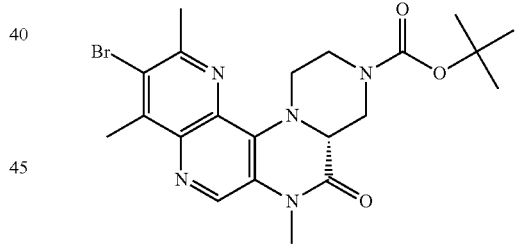

To a yellow suspension of tert-butyl (8aR)-3-bromo-2,4-dimethyl-8-oxo-7,8,8a,9,11,12-hexahydro-10H-pyrazino[1',2':4,5]pyrazino[2,3-c][1,5]naphthyridine-10-carboxylate (1.71 g, 3.70 mmol) and K$_2$CO$_3$ (1.02 g, 7.40 mmol) in acetone (25 ml) at rt was added iodomethane (2.30 ml, 36.99 mmol). The resultant suspension was heated at 40° C. for 18 h. Further K$_2$CO$_3$ (0.50 g) and iodomethane (2.30 ml) were added and reaction continued heating at 40° C. for additional 24 h. The reaction mixture was concentrated in vacuo and the crude residue dissolved in DCM and water added. The phases were separated, the organic layer washed with water and brine. The aqueous layers were back extracted with DCM and the combined organic layers dried (phase separator) and concentrated in vacuo to afford the crude product as an orange solid. This was suspended in diethyl ether and was then concentrated in vacuo to give tert-butyl (8aR)-3-bromo-2,4,7-trimethyl-8-oxo-7,8,8a,9,11,12-hexahydro-10H-pyrazino[1',2':4,5]pyrazino[2,3-c][1,5]naphthyridine- 10-carboxylate (1.35 g, 77%) as an orange solid; $^1$H NMR (400 MHz, DMSO, 30° C.) 1.44 (9H, s), 2.52-2.53 (1H, m), 2.76 (3H, s), 2.80 (3H, s), 3.08-3.19 (1H, m), 3.36-3.43 (1H, m), 3.44 (3H, s), 3.89 (1H, d), 4.12 (1H, s), 4.19 (1H, dd), 5.84 (1H, s), 8.62 (1H, s); m/z: ES$^+$ [M+H]$^+$ 476.3.

tert-Butyl (8aR)-3-(2-fluoro-6-hydroxyphenyl)-2,4,7-trimethyl-8-oxo-7,8,8a,9,11,12-hexahydro-10H-pyrazino[1',2':4,5]pyrazino[2,3-c][1,5]naphthyridine-10-carboxylate (Atropisomer 1 and Atropisomer 2)

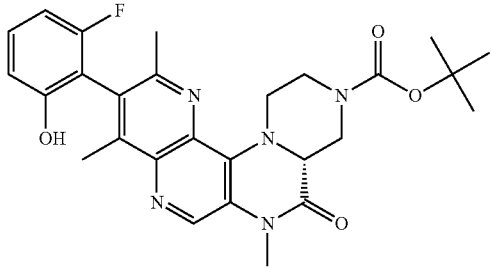 [SMILES: Cc1nc2c3c(cnc2c(C)c1-c1c(O)cccc1F)N(C)C(=O)[C@H]1CN(C(=O)OC(C)(C)C)CCN31]

A mixture of tert-butyl (8aR)-3-bromo-2,4,7-trimethyl-8-oxo-7,8,8a,9,11,12-hexahydro-10H-pyrazino[1',2':4,5]pyrazino[2,3-c][1,5]naphthyridine-10-carboxylate (1.35 g, 2.84 mmol), (2-fluoro-6-hydroxyphenyl)boronic acid (0.89 g, 5.68 mmol) and K$_2$CO$_3$ (2.36 g, 17.04 mmol) in 2-methyl tetrahydrofuran (18 ml) and water (6 ml) was degassed. Ruphos Pd G3 (0.24 g, 0.28 mmol) and RuPhos (0.13 g, 0.28 mmol) were added and the reaction mixture heated at 60° C. for 4 h. The reaction mixture was cooled to rt, diluted with 2-methyl tetrahydrofuran (20 ml) and filtered through CELITE™, washing with 2-methyl tetrahydrofuran (50 ml). The solution was washed with water (100 ml). The aqueous was extracted with further 2-methyl tetrahydrofuran (50 ml), and the combined organics were washed with brine (100 ml), dried (MgSO$_4$) and concentrated in vacuo to give crude material as a brown oil.

This was combined with a smaller crude batch for purification from an identical reaction (0.636 g reaction scale) and purified by flash silica chromatography (0 to 100% ethyl acetate in heptane) to afford the title product, as a mixture of atropisomers, as an orange foam (1.52 g). The atropisomers were separated using supercritical fluid chromatography (SFC) (Column: Chiralpak OD, 20×250 mm, 5 micron; Mobile phase A: 25% MeOH (+0.1% NH3)/Mobile Phase B: scCO2; flow rate: 60 ml/min; BPR: 120 bar; Column temperature: 40° C.) to afford atropisomer 1 of tert-butyl (8aR)-3-(2-fluoro-6-hydroxyphenyl)-2,4,7-trimethyl-8-oxo-7,8,8a,9,11,12-hexahydro-10H-pyrazino[1',2':4,5]pyrazino[2,3-c][1,5]naphthyridine-10-carboxylate (0.53 g, 1.04 mmol, 25%) as a yellow solid; $^1$H NMR (400 MHz, DMSO, 30° C.) 1.43 (9H, s), 2.34 (3H, s), 2.39 (3H, s), 2.51-2.53 (1H, m), 3.18-3.25 (1H, m), 3.4-3.5 (4H, m), 3.89 (1H, d), 4.03-4.15 (1H, m), 4.15-4.21 (1H, m), 5.94 (1H, s), 6.78-6.84 (1H, m), 6.87 (1H, d), 7.32 (1H, td), 8.65 (1H, s), 9.97 (1H, s). m/z: ES$^+$ [M+H]$^+$ 508.4. This was followed by atropisomer 2 of tert-butyl (8aR)-3-(2-fluoro-6-hydroxyphenyl)-2,4,7-trimethyl-8-oxo-7,8,8a,9,11,12-hexahydro-10H-pyrazino[1',2':4,5]pyrazino[2,3-c][1,5]naphthyridine-10-carboxylate (0.62 mg, 1.21 mmol, 29%) as a yellow solid; $^1$H NMR (400 MHz, DMSO, 30° C.) 1.44 (9H, s), 2.35 (3H, s), 2.39 (3H, s), 2.52-2.53 (1H, m), 3.19-3.26 (1H, m), 3.39-3.45 (1H, m), 3.47 (3H, s), 3.89 (1H, d), 4.03-4.15 (1H, m), 4.16-4.22 (1H, m), 6.00 (1H, s), 6.78-6.85 (1H, m), 6.87 (1H, d), 7.33 (1H, td), 8.65 (1H, s), 9.98 (1H, s); m/z: ES$^+$ [M+H]$^+$ 508.5.

(8aR)-3-(2-Fluoro-6-hydroxyphenyl)-2,4,7-trimethyl-9,10,11,12-tetrahydro-7H-pyrazino[1',2':4,5]pyrazino[2,3-c][1,5]naphthyridin-8(8aH)-one (Atropisomer 1)

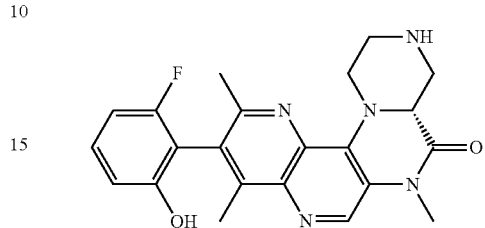

Atropisomer 1 of tert-butyl (8aR)-3-(2-fluoro-6-hydroxyphenyl)-2,4,7-trimethyl-8-oxo-7,8,8a,9,11,12-hexahydro-10H-pyrazino[1',2':4,5]pyrazino[2,3-c][1,5]naphthyridine-10-carboxylate (0.53 g, 1.04 mmol) was dissolved in MeOH (8 ml) at rt before HCl (4M in dioxane) (2.70 ml, 10.80 mmol) was added and the resultant solution stirred at rt overnight. The reaction mixture was purified by SCX (1M NH$_3$/MeOH) to afford atropisomer 1 of (8aR)-3-(2-fluoro-6-hydroxyphenyl)-2,4,7-trimethyl-9,10,11,12-tetrahydro-7H-pyrazino[1',2':4,5]pyrazino[2,3-c][1,5]naphthyridin-8(8aH)-one (0.41 g, 98%) as an orange solid; $^1$H NMR (400 MHz, DMSO, 30° C.) 2.31 (3H, s), 2.38 (3H, s), 2.51-2.53 (1H, m), 2.78-2.97 (3H, m), 3.16 (1H, dd), 3.33-3.38 (1H, m), 3.43 (3H, s), 4.08 (1H, dd), 5.93 (1H, dt), 6.77-6.83 (1H, m), 6.87 (1H, d), 7.32 (1H, td), 8.59 (1H, s), 9.96 (1H, s); m/z: ES$^+$ [M+H]$^+$ 408.0.

(8aR)-3-(2-Fluoro-6-hydroxyphenyl)-2,4,7-trimethyl-10-(prop-2-enoyl)-9,10,11,12-tetrahydro-7H-pyrazino[1',2':4,5]pyrazino[2,3-c][1,5]naphthyridin-8(8aH)-one (Atropisomer 1, Compound 91)

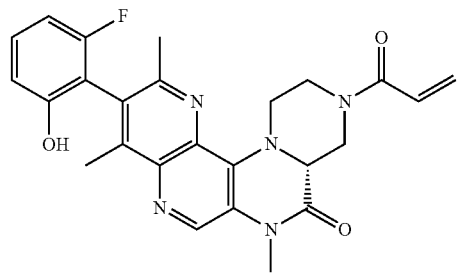 [SMILES: C=CC(=O)N1CCN2c3c(cnc4c(C)c(-c5c(O)cccc5F)c(C)nc34)N(C)C(=O)[C@H]2C1]

To a stirred solution of atropisomer 1 of (8aR)-3-(2-fluoro-6-hydroxyphenyl)-2,4,7-trimethyl-9,10,11,12-tetrahydro-7H-pyrazino[1',2':4,5]pyrazino[2,3-c][1,5]naphthyridin-8(8aH)-one (0.41 g, 1.02 mmol) and DIPEA (0.230 ml, 1.32 mmol) in DCM (10 ml) at 0° C. was added acryloyl chloride (0.161 mL, 2.03 mmol) dropwise and the reaction mixture was stirred at 0° C. for 15 min. The reaction mixture was diluted with DCM and quenched at 0° C. with water. The layers were separated, the organic phase was washed with water and brine, dried (phase separator) and concentrated in vacuo to give a yellow solid. This was dissolved in cold 7M NH$_3$ in MeOH (6 mL) and was stirred at rt for 1 h.

The solvent was removed in vacuo to afford crude material as a yellow sticky foam. This was dissolved in a mixture of MeCN/water and purified by reverse phase C18 chromatography using water (containing 1% NH₃) and MeCN as eluents, to afford atropisomer 1 of (8aR)-3-(2-fluoro-6-hydroxyphenyl)-2,4,7-trimethyl-10-(prop-2-enoyl)-9,10,11, 12-tetrahydro-7H-pyrazino[1',2':4,5]pyrazino[2,3-c][1,5] naphthyridin-8(8aH)-one (0.28 g, 60%) as a yellow solid; $^1$H NMR (400 MHz, DMSO, 100° C.) 2.37 (3H, s), 2.43 (3H, s), 2.51-2.53 (1H, m), 3.44-3.53 (4H, m), 3.71 (1H, ddd), 4.03-4.13 (1H, m), 4.16 (1H, dd), 4.31-4.46 (1H, m), 5.63-5.82 (2H, m), 6.12 (1H, dd), 6.75-6.85 (2H, m), 6.87-6.91 (1H, m), 7.32 (1H, td), 8.67 (1H, s), 9.47 (1H, s); m/z: ES⁺ [M+H]⁺ 462.1

(8aR)-3-(2-Fluoro-6-hydroxyphenyl)-2,4,7-trimethyl-9,10,11,12-tetrahydro-7H-pyrazino[1',2':4,5] pyrazino[2,3-c][1,5]naphthyridin-8(8aH)-one (Atropisomer 2)

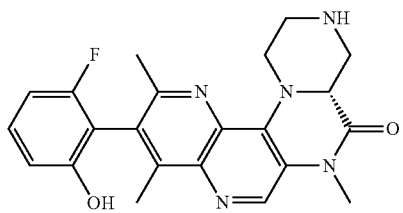 [SMILES: Cc1nc2c3c(cnc2c(C)c1-c1c(O)cccc1F)N(C)C(=O)[C@H]1CNCCN31]

Atropisomer 2 of tert-Butyl (8aR)-3-(2-fluoro-6-hydroxyphenyl)-2,4,7-trimethyl-8-oxo-7,8,8a,9,11,12-hexahydro-10H-pyrazino[1',2':4,5]pyrazino[2,3-c][1,5]naphthyridine-10-carboxylate (0.62 g, 1.2 mmol) was dissolved in MeOH (8 ml) at rt before HCl (4M in dioxane; 3.15 ml, 12.6 mmol) was added and the resultant solution stirred at rt overnight. The reaction mixture was purified by SCX (1M NH₃/MeOH) to afford atropisomer 2 of (8aR)-3-(2-fluoro-6-hydroxyphenyl)-2,4,7-trimethyl-9,10,11,12-tetrahydro-7H-pyrazino[1',2':4,5]pyrazino[2,3-c][1,5]naphthyridin-8 (8aH)-one (0.51 g, >100%) as an orange solid that was used without further purification; $^1$H NMR (400 MHz, DMSO, 30° C.) 2.31 (3H, s), 2.37 (3H, s), 2.51-2.53 (1H, m), 2.78-2.96 (3H, m), 3.14-3.2 (1H, m), 3.32-3.37 (1H, m), 3.43 (3H, s), 4.07 (1H, dd), 5.94 (1H, dt), 6.77-6.84 (1H, m), 6.86 (1H, d), 7.32 (1H, td), 8.59 (1H, s), 9.95 (1H, s); m/z: ES⁺ [M+H]⁺ 408.2.

(8aR)-3-(2-Fluoro-6-hydroxyphenyl)-2,4,7-trimethyl-10-(prop-2-enoyl)-9,10,11,12-tetrahydro-7H-pyrazino[1',2':4,5]pyrazino[2,3-c][1,5]naphthyridin-8(8aH)-one (Atropisomer 2, Compound 92)

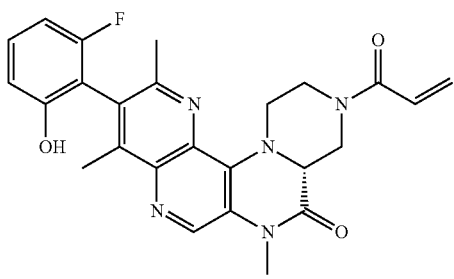 [SMILES: C=CC(=O)N1CCN2c3c(cnc4c(C)c(-c5c(O)cccc5F)c(C)nc34)N(C)C(=O)[C@H]2C1]

To a stirred solution of atropisomer 2 of (8aR)-3-(2-fluoro-6-hydroxyphenyl)-2,4,7-trimethyl-9,10,11,12-tetrahydro-7H-pyrazino[1',2':4,5]pyrazino[2,3-c][1,5]naphthyridin-8(8aH)-one (0.51 g, 1.24 mmol) and DIPEA (0.28 ml, 1.61 mmol) in DCM (10 ml) at 0° C. was added acryloyl chloride (0.20 ml, 2.48 mmol) dropwise and the reaction mixture was stirred at 0° C. for 15 min. The reaction mixture was diluted with DCM and quenched at 0° C. with water. The layers were separated, the organic phase washed with water and brine, dried (phase separator) and concentrated in vacuo to give an orange foam. This was dissolved in cold 7M NH₃ in MeOH (6 ml) and stirred at rt for 1 hour. Solvent removed in vacuo to afford crude material as a yellow sticky foam. This was dissolved in a mixture of MeCN/water and purified by reverse phase chromatography, using water (containing 1% NH₃) and MeCN as eluents, to afford atropisomer 2 of (8aR)-3-(2-fluoro-6-hydroxyphenyl)-2,4,7-trimethyl-10-(prop-2-enoyl)-9,10,11,12-tetrahydro-7H-pyrazino [1',2':4,5]pyrazino[2,3-c][1,5]naphthyridin-8(8aH)-one (0.34 g, 59%) as a yellow solid; $^1$H NMR (400 MHz, DMSO, 100° C.) 2.38 (3H, s), 2.43 (3H, s), 2.51-2.52 (1H, m), 3.44-3.53 (4H, m), 3.70 (1H, ddd), 4.08 (1H, ddd), 4.15 (1H, dd), 4.3-4.48 (1H, m), 5.66-5.83 (2H, m), 6.12 (1H, dd), 6.75-6.84 (2H, m), 6.89 (1H, dt), 7.32 (1H, td), 8.67 (1H, s), 9.35-9.65 (1H, m); m/z: ES⁺ [M+H]⁺ 462.1.

The invention claimed is:
1. A compound of Formula (I):

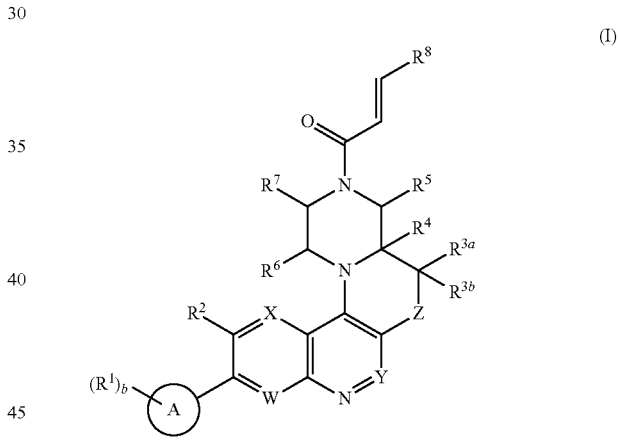

wherein:
A is selected from $C_6$-$C_{10}$ aryl, monocyclic heteroaryl and bicyclic heteroaryl;
$R^1$ is in each instance independently selected from F, Cl, Br, OH, CN, $C_1$-$C_4$ alkyl, $C_1$-$C_4$ alkoxy, $C_1$-$C_3$ fluoroalkyl, $C_1$-$C_3$ fluoroalkoxy, acetylenyl, $NR^9R^{10}$, $C(O)NR^{11}R^{12}$, $CH_2R^{13}$ and $N=S(O)Me_2$;
b is 0, 1, 2 or 3;
W is $CR^{14}$ or N;
X is $CR^{15}$ or N;
Y is CH or N;
Z is O or $NR^{16}$;
$R^2$ is H, CN, F, Cl, Br, $C_1$-$C_4$ alkyl, $C_1$-$C_4$ alkoxy, $C_1$-$C_3$ fluoroalkyl, $C_1$-$C_2$ fluoroalkoxy or acetylenyl;
$R^{3a}$ and $R^{3b}$ are each independently selected from H or Me or, in the case where Z is $NR^{16}$, can also together be =O;
$R^4$, $R^5$, $R^6$ and $R^7$ are each independently selected from H or Me;
$R^8$ is H or $CH_2NMe_2$;

$R^9$ is H, $C_1$-$C_4$ alkyl, C(O)$C_1$-$C_3$ alkyl or $CO_2C_1$-$C_3$ alkyl;
$R^{10}$, $R^{11}$ and $R^{12}$ are each independently selected from H and $C_1$-$C_4$ alkyl; or
$R^9$ and $R^{10}$ together, or $R^{11}$ and $R^{12}$ together, form a 4-, 5-, 6- or 7-membered saturated heterocycle optionally incorporating O, NH or N($C_1$-$C_4$ alkyl) group;
$R^{13}$ is OH, CN, $NR^{17}R^{18}$, C(O)$NR^{19}R^{20}$ or $SO_2C_1$-$C_3$alkyl;
$R^{14}$ and $R^{15}$ are each independently selected from H, F, Cl, MeO and Me;
$R^{16}$ is H, $C_1$-$C_3$ fluoroalkyl or $CH_2R^{21}$;
$R^{17}$, $R^{18}$, $R^{19}$ and $R^{20}$ are each independently selected from H and $C_1$-$C_4$ alkyl or $R^{17}$ and $R^{18}$ together, or $R^{19}$ and $R^{20}$ together, form a 4-, 5-, 6- or 7-membered saturated heterocycle optionally incorporating O, NH or N($C_1$-$C_4$ alkyl) group;
$R^{21}$ is selected from the group consisting of:
H;
$C_1$-$C_3$ alkyl optionally substituted with 1 or 2 substituents selected from hydroxy, $C_1$-$C_3$ alkoxy, halo, $NR^{22}R^{23}$, C(O)$NR^{24}R^{25}$, $SO_2Me$, heteroaryl, $C_{3-7}$cycloalkyl or heterocyclyl, wherein said heteroaryl or $C_3$-$C_7$cycloalkyl is optionally further substituted with $C_1$-$C_4$ alkyl, hydroxy, halo, cyano, or $C_1$-$C_4$ alkoxy and said heterocyclyl is optionally further substituted with $C_1$-$C_4$ alkyl, hydroxy, halo, C(O)Me, $C_1$-$C_3$ alkoxy, $C_1$-$C_3$fluoroalkyl, $C_3$-$C_7$cycloalkyl, heterocyclyl or heteroaryl and wherein $R^{22}$, $R^{23}$, $R^{24}$ and $R^{25}$ are in each instance independently selected from H and $C_1$-$C_4$ alkyl;
$C_3$-$C_7$cycloalkyl optionally substituted with $C_1$-$C_4$ alkyl, hydroxy or halo;
heterocyclyl optionally substituted with $C_1$-$C_4$ alkyl, hydroxy, halo, C(O)Me, $C_1$-$C_3$ alkoxy, $C_1$-$C_3$ fluoroalkyl, $C_3$-$C_7$ cycloalkyl, $CH_2$cyclopropyl, heterocyclyl or heteroaryl; and
heteroaryl optionally substituted with $C_1$-$C_4$ alkyl, hydroxy, halo, cyano or $C_1$-$C_4$ alkoxy;
or a pharmaceutically acceptable salt thereof.

2. A compound according to claim 1, or a pharmaceutically acceptable salt thereof, wherein X is $CR^{15}$.

3. A compound according to claim 1, or a pharmaceutically acceptable salt thereof, wherein W is $CR^{14}$.

4. A compound according to claim 1, or a pharmaceutically acceptable salt thereof, wherein Y is CH.

5. A compound according to claim 1, or a pharmaceutically acceptable salt thereof, wherein Y is N.

6. A compound according to claim 1, or a pharmaceutically acceptable salt thereof, wherein A is selected from phenyl or 1H-pyridin-2-one.

7. A compound according to claim 1, or a pharmaceutically acceptable salt thereof, wherein A is selected from:

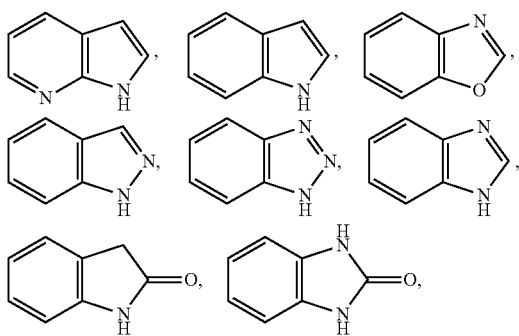

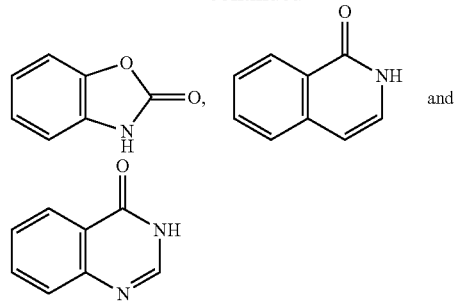

and the corresponding compounds in which the NH group is replaced by a N($C_1$-$C_4$)alkyl group.

8. A compound according to claim 1, or a pharmaceutically acceptable salt thereof, wherein Z is O.

9. A compound according to claim 1, or a pharmaceutically acceptable salt thereof, wherein Z is $NR^{16}$.

10. A compound according to claim 9, or a pharmaceutically acceptable salt thereof, wherein $R^{3a}$ and $R^{3b}$ are independently selected from H and Me.

11. A compound according to claim 9, or a pharmaceutically acceptable salt thereof, wherein $R^{3a}$ and $R^{3b}$ together are =O.

12. A compound according to claim 9, or a pharmaceutically acceptable salt thereof, wherein $R^{21}$ is selected from H and $C_1$-$C_3$ alkyl optionally substituted with 1 or 2 substituents selected from hydroxy, $C_1$-$C_3$ alkoxy, halo, $NR^{22}R^{23}$, C(O)$NR^{24}R^{25}$, $SO_2Me$ and $C_1$-$C_4$ alkoxy.

13. A compound according to claim 9, or a pharmaceutically acceptable salt thereof, wherein $R^{16}$ is Me.

14. A compound according to claim 1, or a pharmaceutically acceptable salt thereof, having the Formula (In)

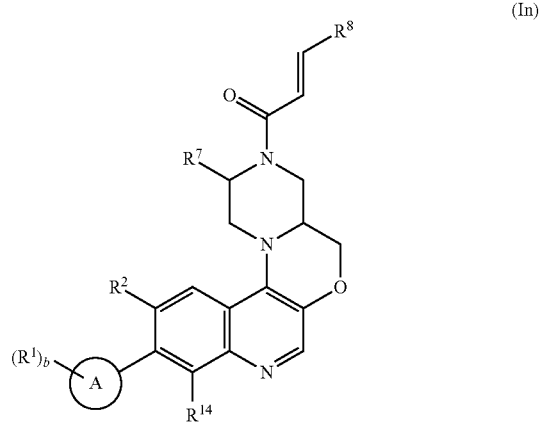

wherein:
A is selected from phenyl and bicyclic heteroaryl;
$R^1$ is in each instance independently selected from F, Cl, Br, OH, CN, $C_1$-$C_4$ alkyl, $C_1$-$C_2$ alkoxy or $C_1$-$C_2$ fluoroalkyl;
b is 0, 1, 2 or 3;
$R^2$ is CN, F, Cl, Me, Et, $CF_3$, MeO or acetylenyl;
$R^7$ is H or Me;

R⁸ is H or CH₂NMe₂; and
R¹⁴ is F, Cl, MeO and Me; or
Formula (Io)

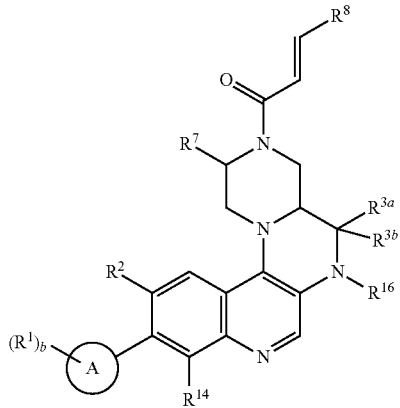

(Io)

wherein:
A is selected from phenyl and bicyclic heteroaryl;
R¹ is in each instance independently selected from F, Cl, Br, OH, CN, $C_1$-$C_4$ alkyl, $C_1$-$C_2$ alkoxy or $C_1$-$C_2$ fluoroalkyl;
b is 0, 1, 2 or 3;
R² is CN, F, Cl, Me, Et, CF₃, MeO or acetylenyl;
$R^{3a}$ and $R^{3b}$ are each independently selected from H or Me or together are =O;
R⁷ is H or Me;
R⁸ is H or CH₂NMe₂;
R¹⁴ is F, Cl, MeO and Me; and
R¹⁶ is H or Me; or
Formula (Ip)

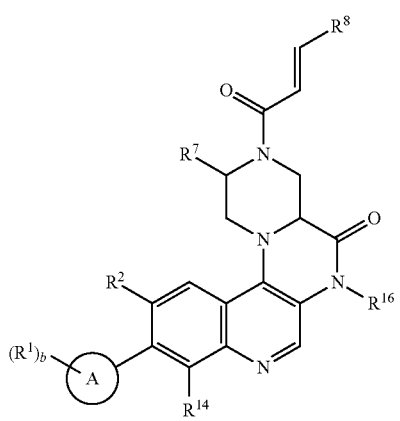

(Ip)

wherein:
A is selected from phenyl and bicyclic heteroaryl;
R¹ is in each instance independently selected from F, Cl, Br, OH, CN, $C_1$-$C_4$ alkyl, $C_1$-$C_2$ alkoxy or $C_1$-$C_2$ fluoroalkyl;
b is 0, 1, 2 or 3;
R² is CN, F, Cl, Me, Et, CF₃, MeO or acetylenyl;
R⁷ is H or Me;
R⁸ is H or CH₂NMe₂;
R¹⁴ is F, Cl, MeO and Me; and
R¹⁶ is H or Me.

15. A compound according to claim 14 wherein A is phenyl.

16. A compound according to claim 14 wherein A is selected from:

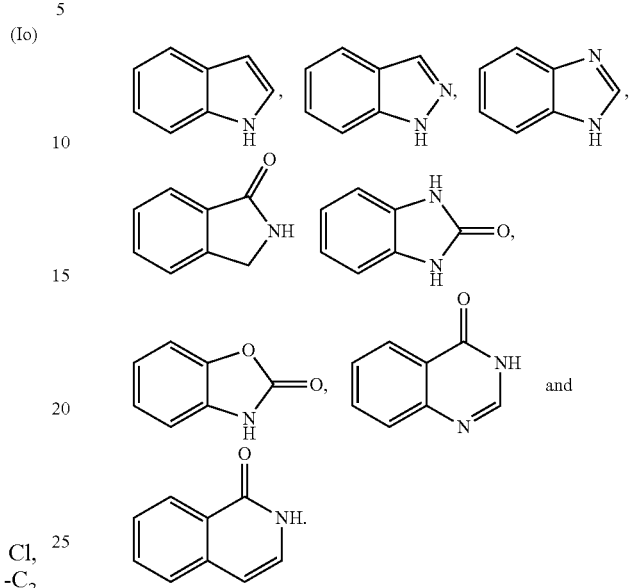

17. A compound according to claim 1, or pharmaceutically acceptable salt thereof, selected from:
1-((4aR)-11-Chloro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one;
1-((4aR)-11-Chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one;
1-((4aS)-11-Chloro-10-(5-methyl-1H-indazol-4-yl)-1,2,4a,5-tetrahydropyrazino[1',2':4,5][1,4]oxazino[2,3-c]quinolin-3(4H)-yl)prop-2-en-1-one;
1-((4aR)-11-Chloro-9-fluoro-10-(2-fluoro-6-hydroxyphenyl)-1,2,4a,5-tetrahydropyrazino[1',2':4,5][1,4]oxazino[2,3-c]quinolin-3(4H)-yl)prop-2-en-1-one;
(2E)-1-[(4aR)-11-Chloro-10-(2-fluoro-6-hydroxyphenyl)-1,2,4a,5-tetrahydropyrazino[1',2':4,5][1,4]oxazino[2,3-c]quinolin-3(4H)-yl]-4-(dimethylamino)but-2-en-1-one;
1-((4aR)-11-Chloro-10-(2-fluoro-6-hydroxyphenyl)-1,2,4a,5-tetrahydropyrazino[1',2':4,5][1,4]oxazino[2,3-c]cinnolin-3(4H)-yl)prop-2-en-1-one;
1-((4aS)-11-Chloro-6-(2-(dimethylamino)ethyl)-10-(2-fluoro-6-hydroxyphenyl)-1,2,4,4a,5,6-hexahydro-3H-pyrazino[1',2':4,5]pyrazino[2,3-c]quinolin-3-yl)prop-2-en-1-one;
1-[(2R,4aR)-11-Chloro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one;
1-((4aS)-11-Chloro-10-(2-fluoro-6-hydroxyphenyl)-1,2,4,4a,5,6-hexahydro-3H-pyrazino[1',2':4,5]pyrazino[2,3-c]quinolin-3-yl)prop-2-en-1-one;
1-((4aS)-11-Chloro-10-(2-fluoro-6-hydroxyphenyl)-6-methyl-1,2,4,4a,5,6-hexahydro-3H-pyrazino[1',2':4,5]pyrazino[2,3-c]quinolin-3-yl)prop-2-en-1-one;
(4aR)-3-Acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one;
(4aS)-3-Acryloyl-11-chloro-10-(2-fluoro-6-hydroxyphenyl)-6-methyl-2,3,4,4a-tetrahydro-1H-pyrazino[1',2':4,5]pyrazino[2,3-c]quinolin-5(6H)-one;

(4aR)-11-chloro-9-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one;

(2R,4aR)-11-Chloro-9-fluoro-10-(2-fluoro-6-hydroxyphenyl)-2,6-dimethyl-3-(prop-2-enoyl)-2,3,4,4a-tetrahydro-1H-pyrazino[1',2':4,5]pyrazino[2,3-c]quinolin-5(6H)-one;

1-[(4aR)-11-Chloro-10-(2-fluoro-6-hydroxyphenyl)-9-methoxy-1,2,4a,5-tetrahydropyrazino[1',2':4,5][1,4]oxazino[2,3-c]quinolin-3(4H)-yl]prop-2-en-1-one;

(4aR)-11-Chloro-9-fluoro-6-methyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one;

(2R,4aR)-11-Chloro-9-fluoro-2,6-dimethyl-10-(5-methyl-1H-benzimidazol-4-yl)-3-(prop-2-enoyl)-2,3,4,4a-tetrahydro-1H-pyrazino[1',2':4,5]pyrazino[2,3-c]quinolin-5(6H)-one;

(2R,4aR)-11-Chloro-3-[(2E)-4-(dimethylamino)but-2-enoyl]-9-fluoro-10-(2-fluoro-6-hydroxyphenyl)-2,6-dimethyl-2,3,4,4a-tetrahydro-1H-pyrazino[1',2':4,5]pyrazino[2,3-c]quinolin-5(6H)-one;

(2R,4aR)-11-Chloro-9-fluoro-10-(2-fluoro-6-hydroxyphenyl)-2-methyl-3-(prop-2-enoyl)-2,3,4,4a-tetrahydro-1H-pyrazino[1',2':4,5]pyrazino[2,3-c]quinolin-5(6H)-one;

11-Chloro-10-(2-fluoro-6-hydroxyphenyl)-4a,6-dimethyl-3-(prop-2-enoyl)-2,3,4,4a-tetrahydro-1H-pyrazino[1',2':4,5]pyrazino[2,3-c]quinolin-5(6H)-one;

(4aR)-11-Chloro-9-fluoro-10-[2-fluoro-6-(hydroxymethyl)phenyl]-6-methyl-3-(prop-2-enoyl)-2,3,4,4a-tetrahydro-1H-pyrazino[1',2':4,5]pyrazino[2,3-c]quinolin-5(6H)-one;

(2E)-1-[(2R,4aR)-11-Chloro-9-fluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]-4-(dimethylamino)but-2-en-1-one;

1-[(4aR)-11-Chloro-10-(2-fluoro-6-hydroxyphenyl)-9-methyl-1,2,4a,5-tetrahydropyrazino[1',2':4,5][1,4]oxazino[2,3-c]quinolin-3(4H)-yl]prop-2-en-1-one;

1-[(2R,4aR)-11-Chloro-10-(2-fluoro-6-hydroxyphenyl)-2,9-dimethyl-1,2,4a,5-tetrahydropyrazino[1',2':4,5][1,4]oxazino[2,3-c]quinolin-3(4H)-yl]prop-2-en-1-one;

(4aR)-3-Acryloyl-9,11-difluoro-10-(2-fluoro-6-hydroxyphenyl)-6-methyl-2,3,4,4a-tetrahydro-1H-pyrazino[1',2':4,5]pyrazino[2,3-c]quinolin-5(6H)-one;

(4aR)-3-Acryloyl-10-(2-fluoro-6-hydroxyphenyl)-6,9,11-trimethyl-2,3,4,4a-tetrahydro-1H-pyrazino[1',2':4,5]pyrazino[2,3-c]quinolin-5(6H)-one;

8-[(4aR)-11-Chloro-3-(prop-2-enoyl)-1,2,3,4,4a,5-hexahydropyrazino[1',2':4,5][1,4]oxazino[2,3-c]quinolin-10-yl]-7-fluoroisoquinolin-1(2H)-one;

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-1,3-benzoxazol-2(3H)-one;

(4aR)-11-Chloro-9-fluoro-6-methyl-10-(5-methyl-1H-indazol-4-yl)-3-(prop-2-enoyl)-2,3,4,4a-tetrahydro-1H-pyrazino[1',2':4,5]pyrazino[2,3-c]quinolin-5(6H)-one;

(4aR)-11-Chloro-10-(2-chloro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one;

(4aR)-11-Chloro-9-fluoro-10-(2-hydroxy-6-methylphenyl)-6-methyl-3-(prop-2-enoyl)-2,3,4,4a-tetrahydro-1H-pyrazino[1',2':4,5]pyrazino[2,3-c]quinolin-5(6H)-one;

(4aR)-11-Chloro-9-fluoro-10-(2-hydroxynaphthalen-1-yl)-6-methyl-3-(prop-2-enoyl)-2,3,4,4a-tetrahydro-1H-pyrazino[1',2':4,5]pyrazino[2,3-c]quinolin-5(6H)-one;

(4aR)-11-Chloro-10-(2,3-difluoro-6-hydroxyphenyl)-9-fluoro-6-methyl-3-(prop-2-enoyl)-2,3,4,4a-tetrahydro-1H-pyrazino[1',2':4,5]pyrazino[2,3-c]quinolin-5(6H)-one;

(4aR)-11-Chloro-12-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one;

(4aR)-11,12-Dichloro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one;

(4aR)-11-Chloro-10-[2-(difluoromethyl)-6-hydroxyphenyl]-9-fluoro-6-methyl-3-(prop-2-enoyl)-2,3,4,4a-tetrahydro-1H-pyrazino[1',2':4,5]pyrazino[2,3-c]quinolin-5(6H)-one;

1-[(2R,4aR)-9,11-Difluoro-10-(2-fluoro-6-hydroxyphenyl)-2-methyl-1,2,4a,5-tetrahydropyrazino[1',2':4,5][1,4]oxazino[2,3-c]quinolin-3(4H)-yl]prop-2-en-1-one;

11-[(4aR)-11-Chloro-10-(5-methyl-1H-benzimidazol-4-yl)-1,2,4a,5-tetrahydropyrazino[1',2':4,5][1,4]oxazino[2,3-c]quinolin-3(4H)-yl]prop-2-en-1-one;

7-[(4aR)-11-Chloro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one;

8-[(4aR)-11-Chloro-3-(prop-2-enoyl)-1,2,3,4,4a,5-hexahydropyrazino[1',2':4,5][1,4]oxazino[2,3-c]quinolin-10-yl]-7-methylisoquinolin-1(2H)-one;

4-[(4aR)-11-Chloro-3-(prop-2-enoyl)-1,2,3,4,4a,5-hexahydropyrazino[1',2':4,5][1,4]oxazino[2,3-c]quinolin-10-yl]-5-methyl-1,3-dihydro-2H-benzimidazol-2-one;

1-[(4aS)-11-Chloro-6-[2-(dimethylamino)ethyl]-10-(5-methyl-1H-indazol-4-yl)-1,2,4,4a,5,6-hexahydro-3H-pyrazino[1',2':4,5]pyrazino[2,3-c]quinolin-3-yl]prop-2-en-1-one;

1-[(4aR)-11-Ethynyl-10-(5-methyl-1H-indazol-4-yl)-1,2,4a,5-tetrahydropyrazino[1',2':4,5][1,4]oxazino[2,3-c]quinolin-3(4H)-yl]prop-2-en-1-one;

1-[(4aR)-11-Chloro-9-fluoro-10-(5-methyl-1H-benzimidazol-4-yl)-1,2,4a,5-tetrahydropyrazino[1',2':4,5][1,4]oxazino[2,3-c]quinolin-3(4H)-yl]prop-2-en-1-one;

(4aR)-9-Chloro-11-fluoro-10-(2-fluoro-6-hydroxyphenyl)-6-methyl-3-(prop-2-enoyl)-2,3,4,4a-tetrahydro-1H-pyrazino[1',2':4,5]pyrazino[2,3-c]quinolin-5(6H)-one;

1-[(2R,4aS)-11-Chloro-9-fluoro-10-(2-fluoro-6-hydroxyphenyl)-2-methyl-1,2,4,4a,5,6-hexahydro-3H-benzo[h]pyrazino[1,2-a][1,6]naphthyridin-3-yl]prop-2-en-1-one;

1-[(4aR)-11-Chloro-10-(2-fluoro-6-hydroxyphenyl)-12-methoxy-1,2,4a,5-tetrahydropyrazino[1',2':4,5][1,4]oxazino[2,3-c]quinolin-3(4H)-yl]prop-2-en-1-one;

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-1,6-dimethyl-1,3-dihydro-2H-benzimidazol-2-one;

7-[(4aR)-11-Chloro-9-fluoro-3-(prop-2-enoyl)-1,2,3,4,4a,5-hexahydropyrazino[1',2':4,5][1,4]oxazino[2,3-c]quinolin-10-yl]-6-methyl-2,3-dihydro-1H-isoindol-1-one;

(4aR)-11-Chloro-9-fluoro-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one;

(4aR)-11-Chloro-6-ethyl-10-(2-fluoro-6-hydroxyphenyl)-3-(prop-2-enoyl)-2,3,4,4a-tetrahydro-1H-pyrazino[1',2':4,5]pyrazino[2,3-c]quinolin-5(6H)-one; and (8aR)-3-(2-Fluoro-6-hydroxyphenyl)-2,4,7-trimethyl-10-(prop-2-enoyl)-9,10,11,12-tetrahydro-7H-pyrazino[1',2':4,5]pyrazino[2,3-c][1,5]naphthyridin-8(8aH)-one;

and each individual stereoisomer, for example atropisomer, thereof.

18. A pharmaceutical composition comprising a compound according to claim 1, or a pharmaceutically acceptable salt thereof, and a pharmaceutically acceptable excipient.

\* \* \* \* \*